(12) United States Patent
Hoffman

(10) Patent No.: US 12,297,444 B2
(45) Date of Patent: May 13, 2025

(54) AAV-BASED GENE THERAPIES FOR TREATMENT OF AUTOIMMUNE DISEASES

(71) Applicant: University of Florida Research Foundation, Incorporated, Gainesville, FL (US)

(72) Inventor: Brad E. Hoffman, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 677 days.

(21) Appl. No.: 17/229,790

(22) Filed: Apr. 13, 2021

(65) Prior Publication Data

US 2021/0324410 A1    Oct. 21, 2021

Related U.S. Application Data

(60) Provisional application No. 63/010,014, filed on Apr. 14, 2020.

(51) Int. Cl.
| | |
|---|---|
| C12N 15/86 | (2006.01) |
| A61K 9/00 | (2006.01) |
| A61K 38/17 | (2006.01) |
| A61P 25/28 | (2006.01) |
| C12N 7/00 | (2006.01) |

(52) U.S. Cl.
CPC ............ *C12N 15/86* (2013.01); *A61K 9/0019* (2013.01); *A61K 38/1774* (2013.01); *A61P 25/28* (2018.01); *C12N 7/00* (2013.01); *C12N 2750/14143* (2013.01); *C12N 2750/14171* (2013.01)

(58) Field of Classification Search
CPC ...................... C12N 15/86; C12N 7/00; C12N 2750/14143; C12N 2750/14171; A61K 9/0019; A61K 38/1774; A61P 25/28
See application file for complete search history.

(56) References Cited

U.S. PATENT DOCUMENTS

| | | | |
|---|---|---|---|
| 6,630,348 | B1 | 10/2003 | Lee et al. |
| 8,329,637 | B2 | 12/2012 | Roncarolo et al. |
| 8,647,822 | B2 | 2/2014 | Sekaly et al. |
| 9,816,108 | B2 | 11/2017 | Boye et al. |
| 2002/0151509 | A1 | 10/2002 | Snyder et al. |
| 2003/0130221 | A1 | 7/2003 | High et al. |
| 2009/0304726 | A1 | 12/2009 | Solomon et al. |
| 2014/0010861 | A1 | 1/2014 | Bancel et al. |
| 2014/0308247 | A1 | 10/2014 | Roeth et al. |
| 2016/0287685 | A1 | 10/2016 | De Haan |
| 2017/0043036 | A1 | 2/2017 | Hoffman |
| 2020/0138978 | A1 | 5/2020 | Hoffman |
| 2023/0263909 | A1 | 8/2023 | Hoffman |
| 2023/0381342 | A1 | 11/2023 | Hoffman |

FOREIGN PATENT DOCUMENTS

| | | | | |
|---|---|---|---|---|
| EP | 1193272 | A1 | 4/2002 | |
| EP | 21787606.9 | | 11/2024 | |
| JP | 2002-320490 | A | 11/2002 | |
| WO | WO 1995/06727 | A2 | 3/1995 | |
| WO | WO-2007140971 | A2 * | 12/2007 | ......... G01N 33/6896 |
| WO | WO 2010/055413 | A1 | 5/2010 | |
| WO | WO 2012/122025 | A2 | 9/2012 | |
| WO | WO 2013/045488 | A1 | 4/2013 | |
| WO | 2020/102172 | A2 | 5/2020 | |
| WO | 2021/102182 | A1 | 5/2021 | |
| WO | 2021/211640 | A1 | 10/2021 | |

OTHER PUBLICATIONS

Perera, J. D. R., et al., "Peptide nucleic acids and their role in gene regulation and editing," Biopolymers 112(12):e23460. doi: 10.1002/bip.23460. Epub Jun. 15, 2021. (Year: 2021).*
GenBank Accession U64564.1, Human myelin/oligodendrocyte glycoprotein-25.1kD (Mog) mRNA. PRI Aug. 15, 2001 (Year: 2001).*
Supplementary European Search Report for Application No. EP 15782332.9 mailed Nov. 23, 2017.
International Search Report and Written Opinion mailed Jul. 28, 2015 for Application No. PCT/US2015/027598.
International Preliminary Report on Patentability mailed Nov. 3, 2016 for Application No. PCT/US2015/027598.
Invitation to Pay Additional Fees mailed Jul. 15, 2021 for Application No. PCT/US2021/27129.
International Search Report and Written Opinion mailed Sep. 24, 2021 for Application No. PCT/US2021/27129.
Battaglia et al., Rapamycin promotes expansion of functional CD4+CD25+FOXP3+ regulatory T cells of both healthy subjects and type 1 diabetic patients. J Immunol. Dec. 15, 2006;177(12):8338-47. doi: 10.4049/jimmunol.177.12.8338.
Cao et al., Induction and role of regulatory CD4+CD25+ T cells in tolerance to the transgene product following hepatic in vivo gene transfer. Blood.Aug. 15, 2007; 110(4):1132-1140.
Cooper et al., Improved induction of immune tolerance to factor IX by hepatic AAV-8 gene transfer. Hum Gene Ther. Jul. 2009;20(7):767-76. doi: 10.1089/hum.2008.161.

(Continued)

*Primary Examiner* — Tracy Vivlemore
*Assistant Examiner* — Eric J Rogers
(74) *Attorney, Agent, or Firm* — Wolf, Greenfield & Sacks, P.C.

(57) ABSTRACT

Disclosed are AAV viral-based vector compositions useful in delivering a variety of nucleic acid segments, including those encoding therapeutic polypeptides to selected mammalian host cells for use in therapeutic autoimmune modalities, including, for example, the in vivo induction of immunological tolerance via a liver-directed AAV-based gene therapeutic regimen for treating and/or ameliorating autoimmune disorders such as multiple sclerosis. Further disclosed are nucleic acid segments encoding therapeutic polypeptides that have been codon-optimized for expression in human cells.

14 Claims, 62 Drawing Sheets

Specification includes a Sequence Listing.

(56) References Cited

OTHER PUBLICATIONS

Fissolo et al., Treatment with MOG-DNA vaccines induces CD4+ CD25+FoxP3+ regulatory T cells and up-regulates genes with neuroprotective functions in experimental autoimmune encephalomyelitis. J Neuroinflammation. Jun. 22, 2012;9:139. doi: 10.1186/1742-2094-9-139.
Hoffman et al., Coaxing the liver into preventing autoimmune disease in the brain. Journal of Clinical Investigation. Oct. 2008;118(10):3271-3273.
Hoffman et al., Immunology of hepatic gene transfer. In: Herzog, R (ed). Immunology of Gene Therapy. Chapter 8. Wiley-Blackwell. 2008. 44 pages. Pre-publication.
Hoffman et al., Muscle as a target for supplementary factor IX gene transfer. Hum Gene Ther. Jul. 2007;18(7):603-13.
Hoffman, AAV Immunotherapy Induces Functional Antigen Specific Regulatory T-Cells to a Neuroantigen: A Potential Treatment for MS. Molecular Therapy. May 2015;23(Suppl.1):S209.
Keeler et al., Gene Therapy-Induced Antigen-Specific Tregs Inhibit Neuro-inflammation and Reverse Disease in a Mouse Model of Multiple Sclerosis. Molecular Therapy. Jan. 2018;26(1):1-11.
Kerlero et al., Predominance of the autoimmune response to myelin oligodendrocyte glycoprotein (MOG) in multiple sclerosis: reactivity to the extracellular domain of MOG is directed against three main regions. Eur J Immunol. Nov. 1997;27(11):3059-69. doi: 10.1002/eji.1830271144.
Kozlowski et al., Adeno-associated viral delivery of a metabolically regulated insulin transgene to hepatocytes. Mol Cell Endocrinol. Jul. 15, 2007;273(1-2):6-15. Epub May 3, 2007.
Luth et al., Ectopic expression of neural autoantigen in mouse liver suppresses experimental autoimmune neuroinflammation by inducing antigen-specific Tregs. J Clin Invest. Oct. 2008;118(10):3403-10. doi: 10.1172/JCI32132.
Manno et al., Successful transduction of liver in hemophilia by AAV-Factor IX and limitations imposed by the host immune response. Nat Med. Mar. 2006; 12(3):342-7. doi: 10.1038/nm1358. Epub Feb. 12, 2006. Erratum in: Nat Med. May 2006;12(5):592. Rasko, John [corrected to Rasko, John JE]; Rustagi, Pradip K [added].
Mingozzi et al., CD8(+) T-cell responses to adeno-associated virus capsid in humans. Nat Med. Apr. 2007;13(4):419-22. doi: 10.1038/nm1549. Epub Mar. 18, 2007.
Palaschak et al., Re-Establishing Immune Tolerance to Neuroantigens by AAV Gene Therapy. Molecular Therapy. May 2014;22(Suppl. 1):S304.
Stephens et al., Curing CNS autoimmune disease with myelin-reactive Foxp3+ Treg. Eur J Immunol. Apr. 2009;39(4):1108-17. doi: 10.1002/eji.200839073.
Wang et al., Adeno-associated virus vector as a platform for gene therapy delivery. Nat Rev Drug Discov. May 2019;18(5):358-378. doi: 10.1038/s41573-019-0012-9.
Xiao et al., Efficient long-term gene transfer into muscle tissue of immunocompetent mice by adeno-associated virus vector. J Virol. Nov. 1996;70(11):8098-108. doi: 10.1128/JVI.70.11.8098-8108. 1996.
Zhang et al., TGF-beta-induced myelin peptide-specific regulatory T cells mediate antigen-specific suppression of induction of experimental autoimmune encephalomyelitis. J Immunol. Jun. 15, 2010;184(12):6629-36. doi: 10.4049/jimmunol.0904044. Epub May 7, 2010.
Ziegler et al., AAV2 vector harboring a liver-restricted promoter facilitates sustained expression of therapeutic levels of alpha-galactosidase A and the induction of immune tolerance in Fabry mice. Mol Ther. Feb. 2004;9(2):231-40. doi: 10.1016/j.ymthe.2003. 11.015.
International Preliminary Report on Patentability mailed Oct. 27, 2022 for Application No. PCT/US2021/027129.
International Search Report and Written Opinion mailed Aug. 16, 2021 for Application No. PCT/US2021/027167.
International Preliminary Report on Patentability mailed Oct. 27, 2022 for Application No. PCT/US2021/027167.
Ko et al., Targeting MOG expression to dendritic cells delays onset of experimental autoimmune disease. Autoimmunity. May 2011;44(3):177-87. doi: 10.3109/08916934.2010.515274. Epub Oct. 1, 2010.
Korn et al., Myelin-specific regulatory T cells accumulate in the CNS but fail to control autoimmune inflammation. Nat Med. Apr. 2007;13(4):423-31. doi: 10.1038/nm1564. Epub Mar. 25, 2007. Author Manuscript, 18 pages.
Lalive et al., Antibody response in MOG(35-55) induced EAE. J Neuroimmunol. Dec. 15, 2011;240-241:28-33. doi: 10.1016/j.jneuroim.2011.09.005. Epub Oct. 10, 2011.
Martino et al., Tolerance induction to cytoplasmic beta-galactosidase by hepatic AAV gene transfer: implications for antigen presentation and immunotoxicity. PLoS One. Aug. 4, 2009;4(8):e6376. doi: 10.1371/journal.pone.0006376.
Marusic et al., Tolerance induction and autoimmune encephalomyelitis amelioration after administration of myelin basic protein-derived peptide. J Exp Med. Aug. 18, 1997;186(4):507-15. doi: 10.1084/jem.186.4.507.
Moghimi et al., Induction of tolerance to factor VIII by transient co-administration with rapamycin. J Thromb Haemost. Aug. 2011;9(8):1524-33. doi: 10.1111/j.1538-7836.2011.04351.x.
Varrin-Doyer et al., MOG transmembrane and cytoplasmic domains contain highly stimulatory T-cell epitopes in MS. Neurol Neuroimmunol Neuroinflamm. Aug. 14, 2014;1(2):e20. doi: 10.1212/NXI. 0000000000000020.
Zhang et al., Infusion of Sulfosuccinimidyl-4-[N-maleimidomethyl]cyclohexane-1-carboxylate-Conjugated MOG35-55-Coupled Spleen Cells Effectively Prevents and Reverses Experimental Autoimmune Encephalomyelitis in Mice. J Immunol Res. 2015;2015:129682. doi: 10.1155/2015/129682. Epub Jul. 14, 2015.
Partial Supplementary European Search Report for Application No. EP 21788164.8 mailed Jul. 30, 2024.
Partial Supplementary European Search Report for Application No. EP 21787606.9 mailed Nov. 19, 2024.
Extended European Search Report for Application No. EP 21787606.9 mailed Feb. 10, 2025.
Cote et al., MBP-Specific Gene-Immunotherapy Prevents and Reverses Severe Disease in a Mouse Model of Multiple Sclerosis. Molecular Therapy, Apr. 28, 2020;28(4S1):96-97.

\* cited by examiner

Used to study pathogenesis of autoimmunity, CNS inflammation, demyelination, cell trafficking and tolerance induction.

Characterized by paralysis, CNS inflammation and demyelination, mediated by myelin-specific CD4+ T cells, but CD8+ cells and B cells also play a role in some models of EAE.

Several neuro proteins or peptides are used to induce EAE including:

Myelin Basic Protein (MBP)
Proteolipid Protein (PLP)
Myelin Oligodendrocyte Glycoprotein (MOG)

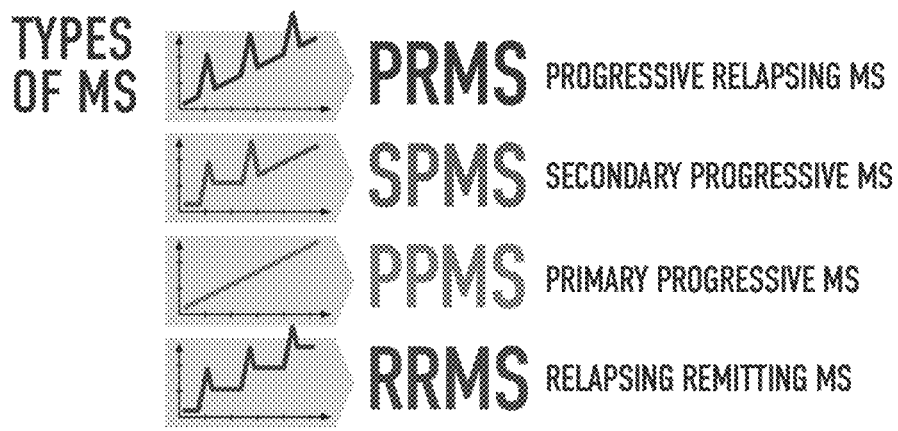

FIG. 1

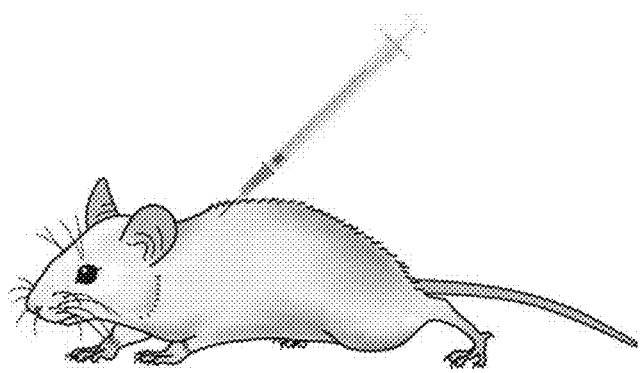

FIG. 2A

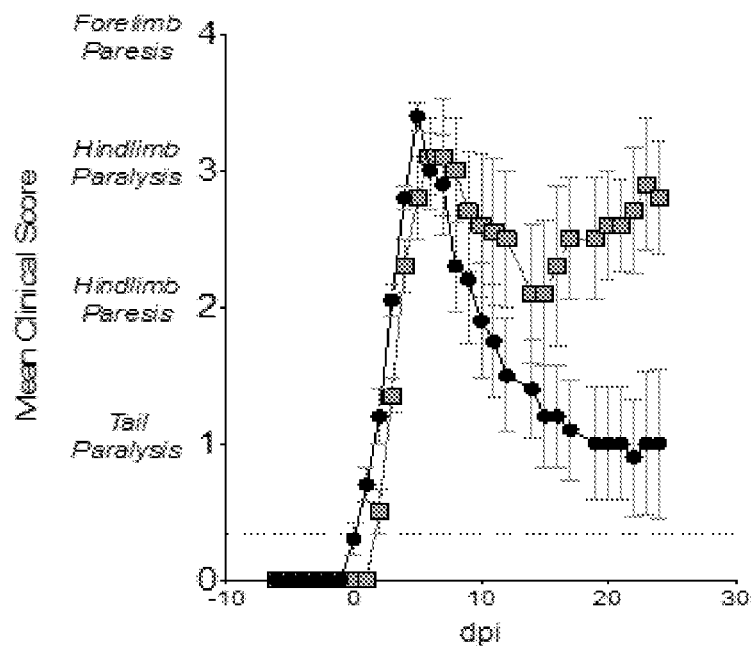
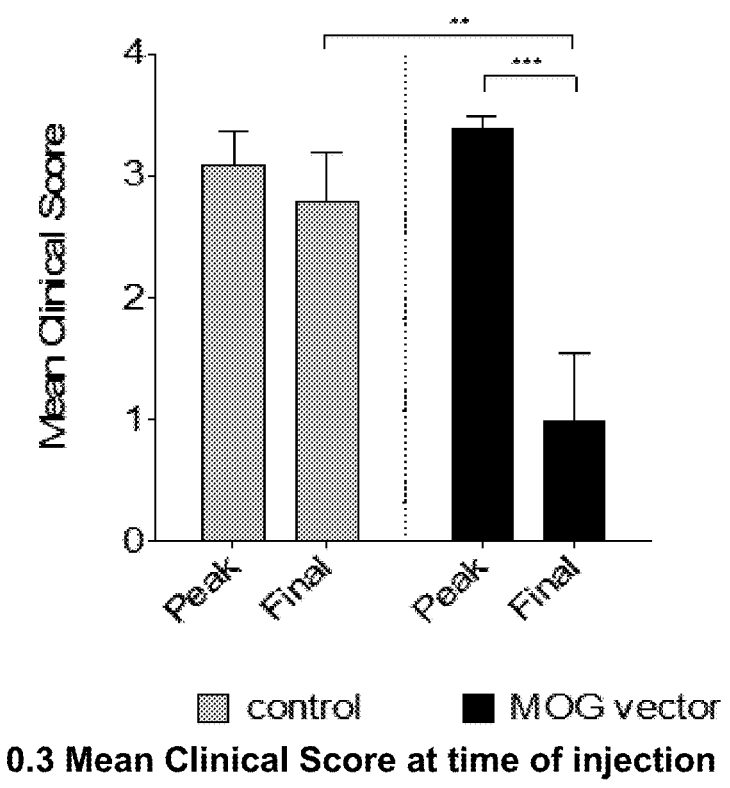
FIG. 13A

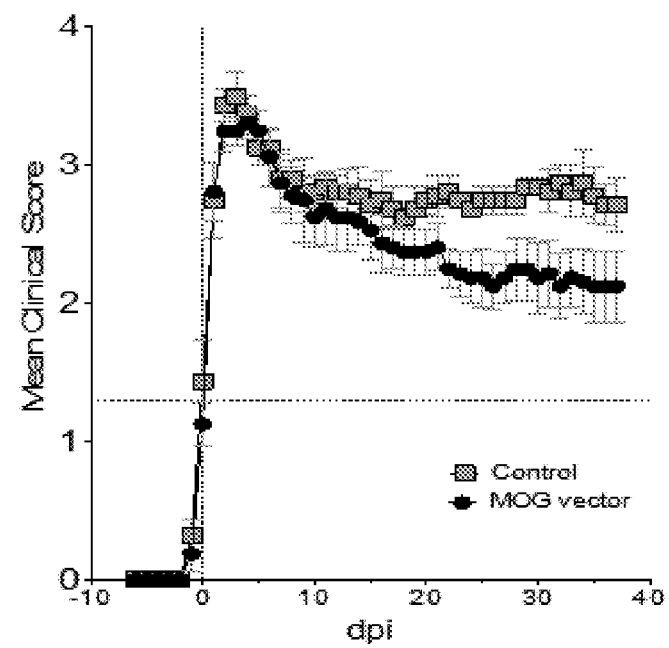
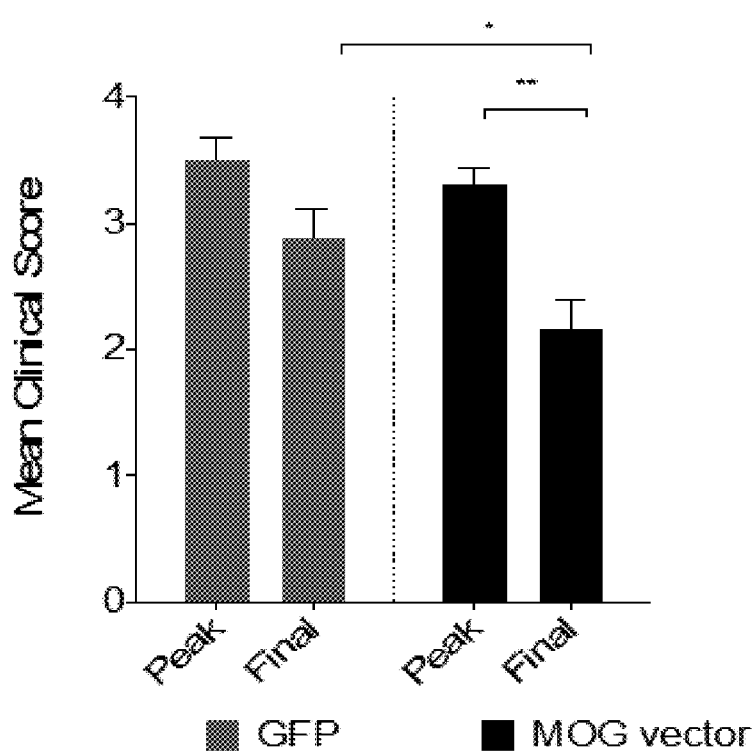
1.3 Mean Clinical Score at time of injection
FIG. 13C

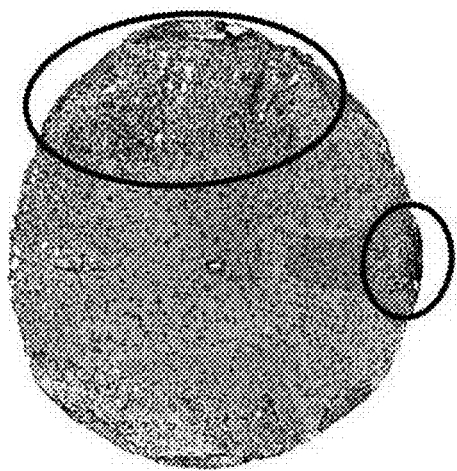 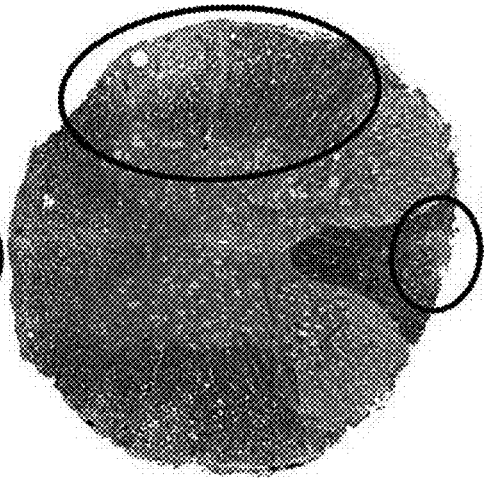
FIG. 14A  FIG. 14B
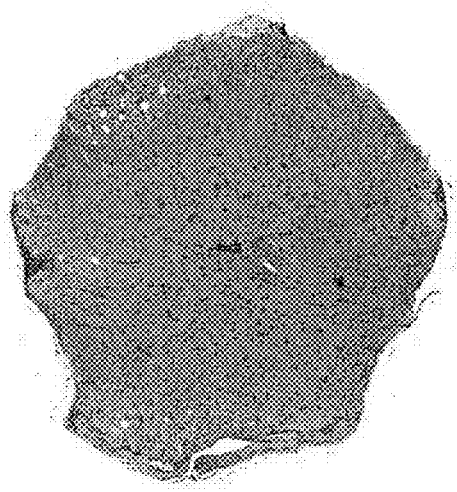 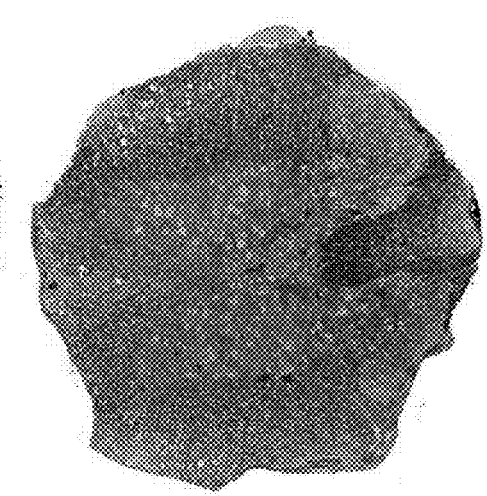
FIG. 15A  FIG. 15B

Gated on Live CD4+

Gated on Live CD4+FoxP3+CD25+ (Tregs)

MOG Tetramer        Control Tetramer

SEQUENCE LISTING

<160> NUMBER OF SEQ ID NOS: 150

<210> SEQ ID NO 1
<211> LENGTH: 195
<212> TYPE: PRT
<213> ORGANISM: Mus musculus

<400> SEQUENCE: 1

Met Gly Asn His Ser Gly Lys Arg Glu Leu Ser Ala Glu Lys Ala Ser
1               5                   10                  15

Lys Asp Gly Glu Ile His Arg Gly Glu Ala Gly Lys Lys Arg Ser Val
            20                  25                  30

Gly Lys Leu Ser Gln Thr Ala Ser Glu Asp Ser Asp Val Phe Gly Glu
            35                  40                  45

Ala Asp Ala Ile Gln Asn Asn Gly Thr Ser Ala Glu Asp Thr Ala Val
50                  55                  60

Thr Asp Ser Lys His Thr Ala Asp Pro Lys Asn Asn Trp Gln Gly Ala
65                  70                  75                  80

His Pro Ala Asp Pro Gly Asn Arg Pro His Leu Ile Arg Leu Phe Ser
            85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Pro Thr Ala Ala Ser
            115                 120                 125

Gly Gly Leu Asp Val Met Ala Ser Gln Lys Arg Pro Ser Gln Arg Ser
            130                 135                 140

Lys Tyr Leu Ala Thr Ala Ser Thr Met Asp His Ala Arg His Gly Phe
145                 150                 155                 160

Leu Pro Arg His Arg Asp Thr Gly Ile Leu Asp Ser Ile Gly Arg Phe
            165                 170                 175

Phe Ser Gly Asp Arg Gly Ala Pro Lys Arg Gly Ser Gly Lys Val Ser
            180                 185                 190

Ser Glu Pro
        195

<210> SEQ ID NO 2
<211> LENGTH: 248
<212> TYPE: PRT
<213> ORGANISM: Mus musculus

<400> SEQUENCE: 2

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
            50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
            85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
            115                 120                 125

Gln His Gln Ala His Ser Leu Glu Arg Val Cys His Cys Leu Gly Lys
            130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
            165                 170                 175

```
Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
    210                 215                 220

Leu Ser Ile Cys Lys Thr Ala Glu Phe Gln Met Thr Phe His Leu Phe
225                 230                 235                 240

Ile Ala Ala Phe Val Gly Ala Ala
                245

<210> SEQ ID NO 3
<211> LENGTH: 247
<212> TYPE: PRT
<213> ORGANISM: Mus musculus

<400> SEQUENCE: 3

Met Ala Cys Leu Trp Ser Phe Ser Leu Pro Ser Cys Phe Leu Ser Leu
1               5                   10                  15

Leu Leu Leu Leu Leu Gln Leu Ser Cys Ser Tyr Ala Gly Gln Phe
            20                  25                  30

Arg Val Ile Gly Pro Gly Tyr Pro Ile Arg Ala Leu Val Gly Asp Glu
        35                  40                  45

Ala Glu Leu Pro Cys Arg Ile Ser Pro Gly Lys Asn Ala Thr Gly Met
    50                  55                  60

Glu Val Gly Trp Tyr Arg Ser Pro Phe Ser Arg Val Val His Leu Tyr
65                  70                  75                  80

Arg Asn Gly Lys Asp Gln Asp Ala Glu Gln Ala Pro Glu Tyr Arg Gly
                85                  90                  95

Arg Thr Glu Leu Leu Lys Glu Thr Ile Ser Glu Gly Lys Val Thr Leu
            100                 105                 110

Arg Ile Gln Asn Val Arg Phe Ser Asp Glu Gly Gly Tyr Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Asn Pro Gly Val Leu Thr Leu Ile Ala
145                 150                 155                 160

Leu Val Pro Thr Ile Leu Leu Gln Val Ser Val Gly Leu Val Phe Leu
                165                 170                 175

Phe Leu Gln His Arg Leu Arg Gly Lys Leu Arg Ala Glu Val Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
    210                 215                 220

Ile Ile Cys Tyr Asn Trp Leu His Arg Arg Leu Ala Gly Gln Phe Leu
225                 230                 235                 240

Glu Glu Leu Arg Asn Pro Leu
                245

<210> SEQ ID NO 4
<211> LENGTH: 13
<212> TYPE: PRT
<213> ORGANISM: Artificial sequence
<220> FEATURE:
<223> OTHER INFORMATION: Synthetic
```

<400> SEQUENCE: 4

His Cys Leu Gly Lys Trp Leu Gly His Pro Asp Lys Phe
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic

<400> SEQUENCE: 5

Asn Thr Trp Thr Cys Gln Ser Ile Ala Phe Pro
1               5                   10

<210> SEQ ID NO 6
<211> LENGTH: 21
<212> TYPE: PRT
<213> ORGANISM: Artificial sequence
<220> FEATURE:
<223> OTHER INFORMATION: Synthetic

<400> SEQUENCE: 6

Met Glu Val Gly Trp Tyr Arg Ser Pro Phe Ser Arg Val Val His Leu
1               5                   10                  15

Tyr Arg Asn Gly Lys
            20

<210> SEQ ID NO 7
<211> LENGTH: 15
<212> TYPE: PRT
<213> ORGANISM: Artificial sequence
<220> FEATURE:
<223> OTHER INFORMATION: Synthetic

<400> SEQUENCE: 7

Asp Glu Gly Gly Tyr Thr Cys Phe Phe Arg Asp His Ser Tyr Gln
1               5                   10                  15

<210> SEQ ID NO 8
<211> LENGTH: 744
<212> TYPE: DNA
<213> ORGANISM: Mus musculus

<400> SEQUENCE: 8

| | | | | | |
|---|---|---|---|---|---|
| atggcctgtt | tgtggagctt | ctctttgccc | agctgcttcc | tctcccttct | cctcctcctt | 60 |
| ctcctccagt | tgtcatgcag | ctatgcagga | caattcagag | tgataggacc | agggtatccc | 120 |
| atccgggctt | tagttgggga | tgaagcagag | ctgccgtgcc | gcatctctcc | tgggaaaaat | 180 |
| gccacgggca | tggaggtggg | ttggtaccgt | tctcccttct | caagagtggt | tcacctctac | 240 |
| cgaaatggca | aggaccaaga | tgcagagcaa | gcacctgaat | accggggacg | cacagagctt | 300 |
| ctgaaagaga | ctatcagtga | gggaaaggtt | acccttagga | ttcagaacgt | gagattctca | 360 |
| gatgaaggag | gctacacctg | cttcttcaga | gaccactctt | accaagaaga | ggcagcaatg | 420 |
| gagttgaaag | tggaagatcc | cttctattgg | gtcaaccccg | tgtgctgac | tctcatcgca | 480 |
| cttgtgccta | cgatcctcct | gcaggtctct | gtaggccttg | tattcctctt | cctgcagcac | 540 |
| agactgagag | aaaacttcg | tgcagaagta | gagaatctcc | atcggacttt | tgatcctcac | 600 |
| ttcctgaggg | tgcccgctg | gaagataaca | ctgtttgtta | ttgtgcctgt | tcttggaccc | 660 |
| ctggttgcct | tgatcatctg | ctacaactgg | ctgcaccgaa | gactggcagg | acagtttctt | 720 |

-continued gaagagctaa gaaaccccct ttga 744

<210> SEQ ID NO 9
<211> LENGTH: 247
<212> TYPE: PRT
<213> ORGANISM: Mus musculus

<400> SEQUENCE: 9

Met Ala Cys Leu Trp Ser Phe Ser Trp Pro Ser Cys Phe Leu Ser Leu
1               5                   10                  15

Leu Leu Leu Leu Leu Gln Leu Ser Cys Ser Tyr Ala Gly Gln Phe
            20                  25                  30

Arg Val Ile Gly Pro Gly Tyr Pro Ile Arg Ala Leu Val Gly Asp Glu
        35                  40                  45

Ala Glu Leu Pro Cys Arg Ile Ser Pro Gly Lys Asn Ala Thr Gly Met
    50                  55                  60

Glu Val Gly Trp Tyr Arg Ser Pro Phe Ser Arg Val Val His Leu Tyr
65                  70                  75                  80

Arg Asn Gly Lys Asp Gln Asp Ala Glu Gln Ala Pro Glu Tyr Arg Gly
                85                  90                  95

Arg Thr Glu Leu Leu Lys Glu Thr Ile Ser Glu Gly Lys Val Thr Leu
            100                 105                 110

Arg Ile Gln Asn Val Arg Phe Ser Asp Glu Gly Gly Tyr Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Asn Pro Gly Val Leu Thr Leu Ile Ala
145                 150                 155                 160

Leu Val Pro Thr Ile Leu Leu Gln Val Ser Val Gly Leu Val Phe Leu
                165                 170                 175

Phe Leu Gln His Arg Leu Arg Gly Lys Leu Arg Ala Glu Val Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
    210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 10
<211> LENGTH: 834
<212> TYPE: DNA
<213> ORGANISM: Mus musculus

<400> SEQUENCE: 10
atgggcttgt tagagtgttg tgctagatgt ctggtagggg cccccttttgc ttccctggtg 60 gccactggat tgtgtttctt tggagtggca ctgttctgtg gatgtggaca tgaagctctc 120
actggtacag aaaagctaat tgagacctat ttctccaaaa actaccagga ctatgagtat 180
ctcattaatg tgattcatgc tttccagtat gtcatctatg aactgcctc tttcttcttc 240 ctttatgggg ccctcctgct ggctgagggc ttctacacca ccggcgctgt caggcagatc 300
tttggcgact acaagaccac catctgcggc aagggcctga gcgcaacggt aacaggggc 360

-continued

```
cagaagggga ggggttccag aggccaacat caagctcatt ctttggagcg ggtgtgtcat    420
tgtttgggaa atggctagg acatcccgac aagtttgtgg gcatcaccta tgccctgact    480
gttgtatggc tcctggtgtt tgcctgctcg gctgtacctg tgtacattta cttcaatacc    540
tggaccacct gtcagtctat tgccttccct agcaagacct ctgccagtat aggcagtctc    600
tgcgctgatg ccagaatgta tggtgttctc ccatggaatg ctttccctgg caaggtttgt    660
ggctccaacc ttctgtccat ctgcaaaaca gctgagttcc aaatgacctt ccacctgttt    720
attgctgcgt tgtgggtgc tgcggccaca ctagtttccc tgctcacctt catgattgct    780
gccacttaca acttcgccgt ccttaaactc atgggccgag caccaagtt ctga          834
```

<210> SEQ ID NO 11
<211> LENGTH: 277
<212> TYPE: PRT
<213> ORGANISM: Unknown
<220> FEATURE:
<223> OTHER INFORMATION: Mus musculus or Homo sapiens

<400> SEQUENCE: 11

```
Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val
    50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
    210                 215                 220

Leu Ser Ile Cys Lys Thr Ala Glu Phe Gln Met Thr Phe His Leu Phe
225                 230                 235                 240

Ile Ala Ala Phe Val Gly Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275
```

<210> SEQ ID NO 12
<211> LENGTH: 588
<212> TYPE: DNA
<213> ORGANISM: Mus musculus

<400> SEQUENCE: 12

| | | | | | |
|---|---|---|---|---|---|
| atgggaaacc | actctggaaa | gagagaatta | tctgctgaga | aggccagtaa | ggatggagag | 60 |
| attcaccgag | gagaggctgg | aaagaagaga | agcgtgggca | agctttctca | gacgcctca | 120 |
| gaggacagtg | atgtgttttgg | ggaggcagat | gcgatccaga | acaatgggac | ctcggctgag | 180 |
| gacacggcgg | tgacagactc | caagcacaca | gcagacccaa | agaataactg | gcaaggcgcc | 240 |
| cacccagctg | acccagggaa | ccgcccccac | ttgatccgcc | tcttttcccg | agatgccccg | 300 |
| ggaagggagg | acaacacctt | caaagacagg | ccctcagagt | ccgacgagct | tcagaccatc | 360 |
| caagaagacc | ccacagcagc | ttccggaggc | ctggatgtga | tggcatcaca | gaagagaccc | 420 |
| tcacagcgat | ccaagtacct | ggccacagca | agtaccatgg | accatgccag | gcatggcttc | 480 |
| ctcccaaggc | acagagacac | gggcatcctt | gactccatcg | ggcgcttctt | tagcggtgac | 540 |
| aggggtgcgc | ccaagcgggg | ctctggcaag | gtgagctccg | agccgtag | | 588 |

<210> SEQ ID NO 13
<211> LENGTH: 915
<212> TYPE: DNA
<213> ORGANISM: Homo sapiens

<400> SEQUENCE: 13

| | | | | | |
|---|---|---|---|---|---|
| atgggaaacc | acgcaggcaa | acgagaatta | aatgccgaga | aggccagtac | gaatagtgaa | 60 |
| actaacagag | gagaatctga | aaaaaagaga | aacctgggtg | aactttcacg | gacaaccca | 120 |
| gaggacaacg | aagtgttcgg | agaggcagat | gcgaaccaga | acaatgggac | ctcctctcag | 180 |
| gacacagcgg | tgactgactc | caagcgcaca | gcggacccga | agaatgcctg | gcaggatgcc | 240 |
| cacccagctg | acccagggag | ccgcccccac | ttgatccgcc | tcttttcccg | agatgccccg | 300 |
| gggagggagg | acaacacctt | caaagacagg | ccctctgagt | ccgacgagct | ccagaccatc | 360 |
| caagaagaca | gtgcagccac | ctccgagagc | ctggatgtga | tggcgtcaca | gaagagaccc | 420 |
| tcccagaggc | acggatccaa | gtacctggcc | acagcaagta | ccatggacca | tgccaggcat | 480 |
| ggcttcctcc | caaggcacag | agacacgggc | atccttgact | ccatcgggcg | cttctttggc | 540 |
| ggtgacaggg | gtgcgcccaa | gcggggctct | ggcaaggact | cacaccaccc | ggcaagaact | 600 |
| gctcactacg | gctccctgcc | ccagaagtca | cacggccgga | cccaagatga | aaaccccgta | 660 |
| gtccacttct | tcaagaacat | tgtgacgcct | cgcacaccac | ccccgtcgca | gggaaagggg | 720 |
| agaggactgt | ccctgagcag | atttagctgg | ggggccgaag | gccagagacc | aggatttggc | 780 |
| tacggaggca | gagcgtccga | ctataaatcg | gctcacaagg | gattcaaggg | agtcgatgcc | 840 |
| cagggcacgc | tttccaaaat | ttttaagctg | ggaggaagag | atagtcgctc | tggatcaccc | 900 |
| atggctagac | gctga | | | | | 915 |

<210> SEQ ID NO 14
<211> LENGTH: 744
<212> TYPE: DNA
<213> ORGANISM: Homo sapiens

<400> SEQUENCE: 14

| | | | | | |
|---|---|---|---|---|---|
| atggcaagct | tatcgagacc | ctctctgccc | agctgcctct | gctccttcct | cctcctcctc | 60 |

-continued

| | |
|---|---:|
| ctcctccaag tgtcttccag ctatgcaggg cagttcagag tgataggacc aagacaccct | 120 |
| atccgggctc tggtcgggga tgaagtggaa ttgccatgtc gcatatctcc tgggaagaac | 180 |
| gctacaggca tggaggtggg gtggtaccgc ccccccttct ctagggtggt tcatctctac | 240 |
| agaaatggca aggaccaaga tggagaccag gcacctgaat atcggggccg gacagagctg | 300 |
| ctgaaagatg ctattggtga gggaaaggtg actctcagga tccggaatgt aaggttctca | 360 |
| gatgaaggag gtttcacctg cttcttccga gatcattctt accaagagga ggcagcaatg | 420 |
| gaattgaaag tagaagatcc tttctactgg gtgagccctg gagtgctggt tctcctcgcg | 480 |
| gtgctgcctg tgctcctcct gcagatcact gttggcctcg tcttcctctg cctgcagtac | 540 |
| agactgagag gaaaacttcg agcagagata gagaatctcc accggacttt tgatccccac | 600 |
| tttctgaggg tgccctgctg gaagataacc ctgtttgtaa ttgtgccggt tcttggaccc | 660 |
| ttggttgcct tgatcatctg ctacaactgg ctacatcgaa gactagcagg gcaattcctt | 720 |
| gaagagctac gaaatccctt ctga | 744 |

<210> SEQ ID NO 15
<211> LENGTH: 247
<212> TYPE: PRT
<213> ORGANISM: Homo sapiens

<400> SEQUENCE: 15

Met Ala Ser Leu Ser Arg Pro Ser Leu Pro Cys Leu Cys Ser Phe
1               5                   10                  15

Leu Leu Leu Leu Leu Gln Val Ser Ser Ser Tyr Ala Gly Gln Phe
                20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Val Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
    210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 16
<211> LENGTH: 903
<212> TYPE: DNA
<213> ORGANISM: Homo sapiens

<400> SEQUENCE: 16

```
atgggcaacc acgccggtaa gagagaactg aacgccgaaa aggcctctac aaactccgag      60
acaaatagag gagaaagcga gaagaagcgg aacctgggcg agctgagcag aaccacatct     120
gaagataacg aggtgttcgg cgaagccgac gccaaccaga caacggcac aagcagccaa      180
gatacagccg tcaccgactc caagagaaca gctgacccca gaatgcctg gcaggacgcc      240
caccccgccg atccagggag ccggccccac ctgatcagac tgttctcccg ggatgcccct     300
ggcagagagg acaatacctt caaggacaga ccttctgagt ctgatgaact ccagaccatt     360
caggaggaca gcgctgctac cagcgagagc ctggacgtga tggccagcca gaaacggcct     420
agccaaagac acggctccaa gtacctggcc accgctagca ccatggacca cgccagacac     480
ggctttctgc ccagacatag agacaccggc atcctggaca gcatcggcag gttcttcgga     540
ggcgaccggg gcgctcctaa gcggggatct ggaaaagaca gccaccaccc tgctagaacc     600
gcccactacg gcagcctgcc tcagaagtcc cacggccgga cccaggatga aacccgtg       660
gtgcacttct ttaaaaacat cgtgacccct cggaccccac ctcctagcca gggcaagggc     720
cgcggactga gcctgagcag attcagctgg ggcgccgagg ccagagacc cggctttggc     780
tatggcggca gagccagcga ctacaagagc gcccataagg gcttcaaagg cgtggacgcc     840
cagggaacac tgtctaagat cttcaagctg ggcggaagag attctcggag cggcagccct     900
atg                                                                   903
```

<210> SEQ ID NO 17
<211> LENGTH: 304
<212> TYPE: PRT
<213> ORGANISM: Homo sapiens

<400> SEQUENCE: 17

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

```
Gly Phe Leu Pro Arg His Arg Asp Thr Gly Ile Leu Asp Ser Ile Gly
                165                 170                 175

Arg Phe Gly Gly Asp Arg Gly Ala Pro Lys Arg Gly Ser Gly Lys
        180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
        210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
        275                 280                 285

Lys Leu Gly Gly Arg Asp Ser Arg Ser Gly Ser Pro Met Ala Arg Arg
    290                 295                 300

<210> SEQ ID NO 18
<211> LENGTH: 910
<212> TYPE: DNA
<213> ORGANISM: Homo sapiens

<400> SEQUENCE: 18
atggggaatc atgctggtaa gcgcgagctg aatgctgaaa aagcaagtac aaactccgaa      60
accaatcgag gagagagtga aaagaaacga aaccttggtg aactgagtcg gaccacctcc     120
gaggataacg aggttttcgg cgaggcggac gcgaatcaaa acaatggtac ttcatcacag     180
gacacggcgg tcactgattc caaacgaacg gcagacccga agaatgcctg caagatgca      240 catccggctg atcccggtag ccggccccac ctgataaggc ttttctcccg agacgcgccg     300
ggcagggagg acaatacatt taaagatcgc cctagcgaaa gtgacgagtt gcagaccata     360
caagaagatt cagcagcaac cagtgaatcc ctggatgtta tggcatctca gaagaggccg     420
agccagcgac acggtagcaa atacctcgcg acggcgagta cgatggacca tgcacgccat     480
ggctttcttc ctcgccatag ggacacaggt atactcgatt ccataggacg attctttgga     540
ggggatcggg tgctcctaa acgaggttct ggtaaagatt cccatcaccc tgctcgcacc     600
gcacattacg ggagcctccc gcaaaagtca cacggacgca cccaggatga aaccccgtc     660 gtgcatttct ttaaaaatat agttactcca cgaactccac caccgagtca aggcaaaggc     720
agggccctta gcctgtcaag attcagctgg ggtgctgagg ccagagacc aggatttgga     780 tatggaggta gggcgtctga ttacaagtcc gcccacaagg gtttcaaagg ggtggatgct     840
caagggacat tgtcaaaaat tttcaagttg ggcggacggg actctcgaag cggatcccca     900
atggcccgac                                                            910

<210> SEQ ID NO 19
<211> LENGTH: 197
<212> TYPE: PRT
<213> ORGANISM: Homo sapiens

<400> SEQUENCE: 19

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
```

```
              20                  25                  30
His Arg Asp Thr Gly Ile Leu Asp Ser Ile Gly Arg Phe Phe Gly Gly
         35                  40                  45

Asp Arg Gly Ala Pro Lys Arg Gly Ser Gly Lys Val Pro Trp Leu Lys
 50                  55                  60

Pro Gly Arg Ser Pro Leu Pro Ser His Ala Arg Ser Gln Pro Gly Leu
 65                  70                  75                  80

Cys Asn Met Tyr Lys Asp Ser His His Pro Ala Arg Thr Ala His Tyr
                 85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 20
<211> LENGTH: 910
<212> TYPE: DNA
<213> ORGANISM: Homo sapiens

<400> SEQUENCE: 20
atgggaaatc acgctggaaa acgggagttg aacgccgaaa aagcctctac caatagcgaa      60
accaatcgcg gagagtcaga gaaaaagaga acctgggtg agctgagtcg cactacgagt     120
gaagataacg aagtcttcgg tgaggcggac gcgaatcaaa ataatgggac tagcagccaa     180
gacacggccg tcacagatag caaacgcaca gcagatccca agaatgcttg caagacgca      240 catccggccg accccgggtc tagaccccac ctgattcggc tctttagccg cgacgcacct     300
ggaagggagg ataacacctt taaggatcgg cctagtgaat ctgatgagct tcagaccata     360
caagaagaca gcgccgccac ctcagaatca cttgacgtca tggcttcaca aaagcgcccc     420
tcacaaaggc atggctccaa atacttggct acagcaagca cgatggacca tgctcggcac     480
ggcttccttc cccgccaccg ggacaccggc atactcgaca gcatagggcg cttttttcggt    540 ggagacaggg gagctcccaa gcggggtagt ggtaaggatt ctcatcatcc cgcccgaacc     600
gcgcactatg gatcacttcc tcagaaatcc catggcagga ctcaagacga aaacccggtt     660
gtgcactttt tcaagaacat tgtaaccccct cggactccgc cgccgagcca gggtaaagga    720
cgaggcttgt ccctctcaag attctcatgg gggcagagg acagcgcccc ggggtttggc     780 tacggggggtc gggcgagcga ctacaaatca gcccacaaag ggtttaaggg ggtggatgca     840
cagggaacct tgtcaaaaat ttttaaactc ggaggacgag acagtaggag cggttctccc     900
atggcgcggc                                                            910

<210> SEQ ID NO 21
<211> LENGTH: 186
<212> TYPE: PRT
```

<213> ORGANISM: Homo sapiens

<400> SEQUENCE: 21

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
        35                  40                  45
Asp Arg Gly Ala Pro Lys Arg Gly Ser Gly Lys Val Pro Trp Leu Lys
    50                  55                  60
Pro Gly Arg Ser Pro Leu Pro Ser His Ala Arg Ser Gln Pro Gly Leu
65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
            100                 105                 110
Val Val His Phe Phe Lys Asn Ile Val Thr Pro Arg Thr Pro Pro Pro
        115                 120                 125
Ser Gln Gly Lys Gly Ala Glu Gly Gln Arg Pro Gly Phe Gly Tyr Gly
    130                 135                 140
Gly Arg Ala Ser Asp Tyr Lys Ser Ala His Lys Gly Phe Lys Gly Val
145                 150                 155                 160
Asp Ala Gln Gly Thr Leu Ser Lys Ile Phe Lys Leu Gly Gly Arg Asp
                165                 170                 175
Ser Arg Ser Gly Ser Pro Met Ala Arg Arg
            180                 185

<210> SEQ ID NO 22
<211> LENGTH: 516
<212> TYPE: DNA
<213> ORGANISM: Homo sapiens

<400> SEQUENCE: 22
atggcgtcac agaagagacc ctcccagagg cacggatcca agtacctggc cacagcaagt    60
accatggacc atgccaggca tggcttcctc ccaaggcaca gagacacggg catccttgac   120
tccatcgggc gcttctttgg cggtgacagg ggtgcgccca gcggggctc tggcaaggac    180
tcacaccacc cggcaagaac tgctcactac ggctccctgc cccagaagtc acacggccgg   240
acccaagatg aaaaccccgt agtccacttc ttcaagaaca ttgtgacgcc tcgcacacca   300
cccccgtcgc agggaaaggg gagaggactg tccctgagca gatttagctg ggggggccgaa   360
ggccagagac aggatttggg ctacggaggc agagcgtccg actataaatc ggctcacaag   420
ggattcaagg gagtcgatgc ccagggcacg ctttccaaaa tttttaagct gggaggaaga   480
gatagtcgct ctggatcacc catggctaga cgctga                              516

<210> SEQ ID NO 23
<211> LENGTH: 171
<212> TYPE: PRT
<213> ORGANISM: Homo sapiens

<400> SEQUENCE: 23

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 24
<211> LENGTH: 910
<212> TYPE: DNA
<213> ORGANISM: Homo sapiens

<400> SEQUENCE: 24

```
atgggcaatc acgccggcaa gcgagaactg aacgcggaga aggcttctac taattccgaa      60
actaacaggg gcgagtcaga aaagaaacgg aatctcgggg agttgtcaag gacgacgagc     120
gaggacaaca aagtcttcgg cgaggcagac gccaaccaga taacggtac gtcaagccaa      180
gacacggccg tcactgattc caaacgaact gccgatccaa agaacgcatg caggatgca      240
catcctgcgg atcctggcag tcgaccgcat cttattcgcc tgttctcaag agatgcccca    300
ggaagagaag ataatacatt taaggatcga ccgtccgagt ctgatgagct gcagacgatc    360
caagaagaca gcgcggcaac gtctgagtct ctcgacgtga tggcttctca aaaacggccc   420
tcacaaaggc atggttctaa atacctcgct actgcgagca cgatggatca cgctagacat    480
gggttccttc cccggcatag agacacagga attctggata gtataggcag gttcttcggc    540
ggcgatagag gtgcgccaaa gagggcctct ggaaaggatt ctcaccaccc ggcccggaca    600
gctcactatg gtagtttgcc ccagaagtca catggtagga cgcaagacga aaacccgta    660
gttcattttt ttaaaaacat cgtcactccc aggaccccac cgccgtcaca aggaaaagga    720
cggggcctgt ctctttctag attctcttgg ggggcagagg ggcaacgccc tggctttggg    780
tacggtgggc gagcttctga ctacaagtcc gctcataagg gtttcaaagg ggtcgatgct   840
cagggcacgc tgtcaaagat attcaagctg ggaggacggg acagtcgctc tggcagccct    900
atggcacgaa                                                            910
```

<210> SEQ ID NO 25
<211> LENGTH: 160
<212> TYPE: PRT
<213> ORGANISM: Homo sapiens

<400> SEQUENCE: 25

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
 50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Ser Gln Gly Lys Gly Ala Glu Gly Gln Arg
            100                 105                 110

Pro Gly Phe Gly Tyr Gly Gly Arg Ala Ser Asp Tyr Lys Ser Ala His
        115                 120                 125

Lys Gly Phe Lys Gly Val Asp Ala Gln Gly Thr Leu Ser Lys Ile Phe
130                 135                 140

Lys Leu Gly Gly Arg Asp Ser Arg Ser Gly Ser Pro Met Ala Arg Arg
145                 150                 155                 160

<210> SEQ ID NO 26
<211> LENGTH: 911
<212> TYPE: DNA
<213> ORGANISM: Homo sapiens

<400> SEQUENCE: 26
atgggcaatc atgcagggaa acgcgaactg aacgcagaaa aagcctccac aaacagtgag      60
actaatcgag gagaaagcga gaagaagcga aacttgggcg aattgtcacg aaccacatca     120
gaggacaatg aagtattcgg ggaagctgac gccaaccaga acaacggcac ctccagccaa     180
gatacagctg taaccgattc taaacggaca gcagaccccaa agaatgcttg caagatgca    240 caccctgccg acccagggtc tagaccacac ctcattagac tttctcccg agatgcgcct     300 gggcgagagg ataatacctt taaagaccga ccctccgaat ccgacgagct gcaaacaatt     360
caggaggaca gtgcggcgac cagtgagtca ctcgacgtga tggcctctca aaagcggcca    420
tcacagcgac atggatccaa atatcttgca accgcgtcta ccatggacca tgctcgacat    480
ggttttttgc ctcgccatag ggacacaggg attcttgact caatagggcg ttttttcggg     540
ggcgacagag gggcacctaa acgaggctca ggtaaagaca gtcatcatcc ggcacgaact     600
gcgcactacg gctccctgcc acaaaagtct cacggccgaa cacaagacga aacccagtg     660 gtgcacttct ttaaaaatat cgttaccccc cgaacgccac cgccatcaca aggtaaggga    720
cgaggcttgt cactgtcacg cttcagctgg ggggcagaag ggcaacgccc cggtttcgga    780
tatggtggaa gagcatcaga ctataaaagc gcgcacaaag gattcaaagg tgtcgacgcc    840
caggggacac tctctaagat ctttaagctg ggaggtcggg attcacgatc aggatcccct    900
atggcacgga g                                                         911

<210> SEQ ID NO 27
<211> LENGTH: 197
<212> TYPE: PRT
<213> ORGANISM: Homo sapiens

<400> SEQUENCE: 27

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu

```
              20                  25                  30
Gly Glu Leu Ser Arg Thr Thr Ser Glu Asp Asn Glu Val Phe Gly Glu
             35                  40                  45

Ala Asp Ala Asn Gln Asn Asn Gly Thr Ser Ser Gln Asp Thr Ala Val
 50                  55                  60

Thr Asp Ser Lys Arg Thr Ala Asp Pro Lys Asn Ala Trp Gln Asp Ala
 65                  70                  75                  80

His Pro Ala Asp Pro Gly Ser Arg Pro His Leu Ile Arg Leu Phe Ser
                 85                  90                  95

Arg Asp Ala Pro Gly Arg Glu Asp Asn Thr Phe Lys Asp Arg Pro Ser
                100                 105                 110

Glu Ser Asp Glu Leu Gln Thr Ile Gln Glu Asp Ser Ala Ala Thr Ser
                115                 120                 125

Glu Ser Leu Asp Val Met Ala Ser Gln Lys Arg Pro Ser Gln Arg His
                130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Gly Gly Asp Arg Gly Ala Pro Lys Arg Gly Ser Gly Lys
                180                 185                 190

Val Ser Ser Glu Glu
        195

<210> SEQ ID NO 28
<211> LENGTH: 594
<212> TYPE: DNA
<213> ORGANISM: Homo sapiens

<400> SEQUENCE: 28
atgggaaacc acgcaggcaa acgagaatta aatgccgaga aggccagtac gaatagtgaa      60
actaacagag gagaatctga aaaaaagaga aacctgggtg aactttcacg acaacctca     120 gaggacaacg aagtgttcgg agaggcagat gcgaaccaga acaatgggac ctcctctcag    180
gacacagcgg tgactgactc caagcgcaca gcggacccga gaatgcctg gcaggatgcc    240 cacccagctg acccagggag ccgccccac ttgatccgcc tcttttccg agatgccccg     300 gggagggagg acaacacctt caagacagg ccctctgagt ccgacgagct ccagaccatc    360
caagaagaca gtgcagccac ctccgagagc ctggatgtga tggcgtcaca gaagagaccc   420
tcccagaggc acgatccaa gtacctggcc acagcaagta ccatggacca tgccaggcat    480
ggcttcctcc caaggcacag agacacgggc atccttgact ccatcgggcg cttctttggc   540
ggtgacaggg gtgcgcccaa gcggggctct ggcaaggtga gctctgagga gtag         594

<210> SEQ ID NO 29
<211> LENGTH: 594
<212> TYPE: DNA
<213> ORGANISM: Homo sapiens

<400> SEQUENCE: 29
atgggcaacc acgccggcaa gcgcgagctg aacgccgaga aggcctctac aaacagcgaa      60
accaatagag gcgaatccga aaaaaagcgg aacctgggcg agctgagcag aaccacctcc    120
gaagataacg aggtgttcgg cgaggccgat gctaatcaga acaacggcac ctctagccaa    180
gatacagccg tcaccgacag caagagaaca gccgacccca gaacgcctg gcaggacgct    240
```

```
catcctgctg atcctggcag cagaccccac ctgatcagac tgttcagccg ggacgcccct    300
ggaagagagg acaacacctt caaggaccgg ccatctgaaa gcgacgagct ccagaccatc    360
caggaggaca gcgccgctac atctgagagc ctggacgtga tggccagcca gaagaggcct    420
agccagcggc acggcagcaa gtacctggcc acagccagca ccatggacca cgccagacac    480
ggcttcctgc ccagacacag agataccggc atcctggata gcatcggcag attttttcgga    540 ggcgacagag gagcccctaa gcggggatct ggcaaagtgt ccagcgagga atga          594
```

<210> SEQ ID NO 30
<211> LENGTH: 594
<212> TYPE: DNA
<213> ORGANISM: Homo sapiens

<400> SEQUENCE: 30

```
atggggaacc atgcgggtaa aagggagttg aacgccgaaa aagcgtccac aaactctgaa     60
actaatcggg gtgagtcaga gaaaaaaagg aatctgggcg aactttctag aacaacaagc    120
gaagacaacg aagttttcgg cgaagcggat gcgaatcaga caacgggac ctcttctcag    180 gatactgcag taacggatag caagcgcaca gccgatccga gaatgcctg caagacgcc    240 cacccagccg atcctgggtc acgcccacac ctcattagac tgttcagccg cgatgcgcca    300
ggccgagagg ataatacctt taaggatcga ccctccgaga gcgatgagtt gcaaacaatc    360
caggaggata gcgcggcaac gtcagagtct ctcgatgtaa tggcctctca agagagacct    420
tcacaacgac atggaagcaa gtatctcgcc acagcgagca ctatggatca cgcgcgacat    480
ggcttccttc ccaggcacag ggataccgga atactcgata gcattggaag gttttttggt    540
ggggataggg gtgccccaaa acggggttcc ggtaaggttt cctccgaaga atag           594
```

<210> SEQ ID NO 31
<211> LENGTH: 242
<212> TYPE: PRT
<213> ORGANISM: Homo sapiens

<400> SEQUENCE: 31

```
Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val
    50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Phe Val Gly Ile Thr Tyr Ala Leu Thr Val Val Trp
        115                 120                 125

Leu Leu Val Phe Ala Cys Ser Ala Val Pro Val Tyr Ile Tyr Phe Asn
    130                 135                 140

Thr Trp Thr Thr Cys Gln Ser Ile Ala Phe Pro Ser Lys Thr Ser Ala
145                 150                 155                 160

Ser Ile Gly Ser Leu Cys Ala Asp Ala Arg Met Tyr Gly Val Leu Pro
```

```
              165                 170                 175
Trp Asn Ala Phe Pro Gly Lys Val Cys Gly Ser Asn Leu Leu Ser Ile
            180                 185                 190

Cys Lys Thr Ala Glu Phe Gln Met Thr Phe His Leu Phe Ile Ala Ala
            195                 200                 205

Phe Val Gly Ala Ala Ala Thr Leu Val Ser Leu Leu Thr Phe Met Ile
            210                 215                 220

Ala Ala Thr Tyr Asn Phe Ala Val Leu Lys Leu Met Gly Arg Gly Thr
225                 230                 235                 240

Lys Phe

<210> SEQ ID NO 32
<211> LENGTH: 594
<212> TYPE: DNA
<213> ORGANISM: Homo sapiens

<400> SEQUENCE: 32
atgggtaatc acgcagggaa gcgggagctg aatgcggaga aagcctctac taactctgaa      60
acgaacagag gagagagcga aaaaaaacgc aacctgggag agctgtctag gacgacgtct     120
gaggacaatg aagtctttgg tgaggccgac gctaatcaaa ataacggtac ttccagccag     180
gatactgcgg taaccgattc caagcggact gccgatccaa aaaacgcttg gcaggacgca     240
cacccagcag accctggctc ccgcccacac cttatccgac tcttttctcg ggacgcacca     300
ggacgggaag acaacacttt caaagatcga ccatctgagt ccgacgagct gcaaactatc     360
caggaagatt ccgcggccac gtctgagtca ctggacgtta tggcctcaca aaagaggcca     420
agtcaaagac atgggtccaa atatcttgct acagcgtcaa ctatggatca tgcccgccat     480
ggttttttgc cgcgccatcg agataccggg attcttgaca gtatcggtcg cttttttgga     540
ggagaccggg gtgctcctaa gagaggatct ggcaaagtct ccagtgagga atag          594

<210> SEQ ID NO 33
<211> LENGTH: 594
<212> TYPE: DNA
<213> ORGANISM: Homo sapiens

<400> SEQUENCE: 33
atgggcaacc acgctggaaa acgggagttg aacgccgaga agcgtctac aaacagtgaa       60 accaaccggg gcgaatcaga aaagaagcgc aaccttggcg aactttcccg gacgacttct     120
gaggataatg aagtattcgg ggaagcagat gctaatcaaa ataacgggac tagctcacaa     180
gacactgccg tcaccgacag caaacgcact gcggacccaa agaatgcttg gcaagacgca     240 cacccctgcag accctgggag caggcctcac ttgattaggc ttttctctcg ggacgcgcca     300
ggccgagaag acaatacgtt caaagacaga cctagtgaaa gcgatgagct tcaaaccatt     360
caggaagact ctgcggctac cagtgagagc cttgatgtaa tggcatccca gaaaaggcca     420
tctcagaggc acggttcaaa atacctggcc actgcatcta caatggacca tgctagacat     480
gggttcctcc cgaggcatag agacactgga atactcgatt ctatagggcg gttctttgga     540
ggtgaccgcg gcgcacctaa gcggggttcc gggaaggtct caagtgagga gtag          594

<210> SEQ ID NO 34
<211> LENGTH: 594
<212> TYPE: DNA
<213> ORGANISM: Homo sapiens

<400> SEQUENCE: 34
```

```
atgggaaacc acgcaggaaa gcgggaactt aacgccgaga aagcttccac taactctgaa    60
acgaatcggg gtgagtccga gaaaaagcgg aacctcggtg agctgagtag gaccacctcc   120
gaagataacg aagtcttcgg ggaggcggac gcaaaccaga taacggaac  ctcaagccag   180
gatactgcgg ttacagatag caaacgcaca gcggatccca agaacgcctg gcaagacgcg   240
catccggcag atccgggcag tcggcctcat cttatacgac ttttcagtcg cgacgcccca   300
gggcgagaag acaatacgtt caaggaccgc ccttccgagt ccgacgaact tcagactatt   360
caagaagaca gtgctgccac ttccgaatcc ctcgacgtta tggcctcaca agagaccg    420
agtcaaagac atggatcaaa gtatcttgct acggcaagta cgatggatca cgcgagacat   480
ggatttctcc ccaggcatcg cgatacgggc atattggact ctattggccg gttttttggg   540
ggtgataggg gggctccgaa acgcgggtcc ggcaaggtgt cttcagaaga gtga          594
```

<210> SEQ ID NO 35
<211> LENGTH: 222
<212> TYPE: PRT
<213> ORGANISM: Homo sapiens

<400> SEQUENCE: 35

Met Asp Tyr Glu Tyr Leu Ile Asn Val Ile His Ala Phe Gln Tyr Val
1               5                   10                  15
Ile Tyr Gly Thr Ala Ser Phe Phe Leu Tyr Gly Ala Leu Leu Leu
            20                  25                  30
Ala Glu Gly Phe Tyr Thr Thr Gly Ala Val Arg Gln Ile Phe Gly Asp
        35                  40                  45
Tyr Lys Thr Thr Ile Cys Gly Lys Gly Leu Ser Ala Thr Val Thr Gly
    50                  55                  60
Gly Gln Lys Gly Arg Gly Ser Arg Gly Gln His Gln Ala His Ser Leu
65                  70                  75                  80
Glu Arg Val Cys His Cys Leu Gly Lys Trp Leu Gly His Pro Asp Lys
                85                  90                  95
Phe Val Gly Ile Thr Tyr Ala Leu Thr Val Val Trp Leu Leu Val Phe
            100                 105                 110
Ala Cys Ser Ala Val Pro Val Tyr Ile Tyr Phe Asn Thr Trp Thr Thr
        115                 120                 125
Cys Gln Ser Ile Ala Phe Pro Ser Lys Thr Ser Ala Ser Ile Gly Ser
    130                 135                 140
Leu Cys Ala Asp Ala Arg Met Tyr Gly Val Leu Pro Trp Asn Ala Phe
145                 150                 155                 160
Pro Gly Lys Val Cys Gly Ser Asn Leu Leu Ser Ile Cys Lys Thr Ala
                165                 170                 175
Glu Phe Gln Met Thr Phe His Leu Phe Ile Ala Ala Phe Val Gly Ala
            180                 185                 190
Ala Ala Thr Leu Val Ser Leu Leu Thr Phe Met Ile Ala Ala Thr Tyr
        195                 200                 205
Asn Phe Ala Val Leu Lys Leu Met Gly Arg Gly Thr Lys Phe
    210                 215                 220

<210> SEQ ID NO 36
<211> LENGTH: 9
<212> TYPE: PRT
<213> ORGANISM: Artificial sequence
<220> FEATURE:
<223> OTHER INFORMATION: Synthetic

<400> SEQUENCE: 36

Gly Arg Val Arg Val Asn Ser Ala Tyr
1               5

<210> SEQ ID NO 37
<211> LENGTH: 14
<212> TYPE: PRT
<213> ORGANISM: Artificial sequence
<220> FEATURE:
<223> OTHER INFORMATION: Synthetic

<400> SEQUENCE: 37

Asn Thr Trp Thr Thr Cys Gln Ser Ile Ala Phe Pro Ser Lys
1               5                   10

<210> SEQ ID NO 38
<211> LENGTH: 888
<212> TYPE: DNA
<213> ORGANISM: Homo sapiens

<400> SEQUENCE: 38

| | | | | | |
|---|---|---|---|---|---|
| atggcaagct | tatcgagacc | ctctctgccc | agctgcctct | gctccttcct | cctcctcctc | 60 |
| ctcctccaag | tgtcttccag | ctatgcaggg | cagttcagag | tgataggacc | aagacaccct | 120 |
| atccgggctc | tggtcgggga | tgaagtggaa | ttgccatgtc | gcatatctcc | tgggaagaac | 180 |
| gctacaggca | tggaggtggg | gtggtaccgc | ccccccttct | ctagggtggt | tcatctctac | 240 |
| agaaatggca | aggaccaaga | tggagaccag | gcacctgaat | atcggggccg | gacagagctg | 300 |
| ctgaaagatg | ctattggtga | gggaaaggtg | actctcagga | tccggaatgt | aaggttctca | 360 |
| gatgaaggag | gtttcacctg | cttcttccga | gatcattctt | accaagagga | ggcagcaatg | 420 |
| gaattgaaag | tagaagatcc | tttctactgg | gtgagccctg | gagtgctggt | tctcctcgcg | 480 |
| gtgctgcctg | tgctcctcct | gcagatcact | gttggcctcg | tcttcctctg | cctgcagtac | 540 |
| agactgagag | gaaaacttcg | agcagagata | gagaatctcc | accggacttt | tgatccccac | 600 |
| tttctgaggg | tgccctgctg | gaagataacc | ctgtttgtaa | ttgtgccggt | tcttggaccc | 660 |
| ttggttgcct | tgatcatctg | ctacaactgg | ctacatcgaa | gactagcagg | gcaattcctt | 720 |
| gaagagctac | gtaagttctc | ttctctctgt | tataagcaga | gaataaaaag | ccaggaaagg | 780 |
| gagacagaag | caacaagagg | aagaggcggg | ctattgaggg | atcacattcc | cagaggaaag | 840 |
| gaggagctgg | agagcctggg | tggagggaag | actcctcctg | ggaggtag | | 888 |

<210> SEQ ID NO 39
<211> LENGTH: 888
<212> TYPE: DNA
<213> ORGANISM: Homo sapiens

<400> SEQUENCE: 39

| | | | | | |
|---|---|---|---|---|---|
| atggccagcc | tgagcagacc | tagcctgccc | agctgcctgt | gctcattcct | gctgctgctg | 60 |
| ctgctgcagg | tgtcctctag | ctacgccggc | cagttcagag | tgatcggccc | tagacaccct | 120 |
| atccgggccc | tggttggaga | tgaggtggaa | ctgccttgta | gaatcagccc | cggcaaaaac | 180 |
| gccacaggca | tggaagtggg | ctggtataga | ccccccttt | ctagagtggt | gcacctgtac | 240 |
| agaaacggca | aggaccagga | cggcgatcag | gcccctgagt | acagaggcag | aacagagctg | 300 |
| ctgaaggacg | ccatcggcga | gggcaaggtg | accctgagaa | tcagaaatgt | gcggttcagc | 360 |
| gacgagggcg | gcttcacctg | cttcttccgg | gaccacagct | accaggagga | agccgctatg | 420 |
| gaactgaaag | tggaagatcc | tttctactgg | gtcagccctg | gcgtgctggt | gctgcttgct | 480 |

```
gtgctgcctg tgctcttgct gcaaatcacc gtgggtcttg tgttcctgtg tctgcagtac    540
cggctgagag gcaagctgag agccgagatc gagaacctgc acagaacctt cgaccccac    600 ttcctgcggg tgccctgctg gaagatcaca ctgttcgtga tagttccagt gctgggacct    660
ctggtcgccc tgatcatctg ctacaactgg ctgcaccgga gactggccgg acagtttctg    720
gaagaactga gaaagttcag cagcctgtgc tacaagcaga gaatcaagag ccaggagcgg    780
gaaaccgagg ccaccagagg cagaggaggc ctgctccgcg accacatccc cagaggcaag    840
gaagagctcg agagcctggg cggaggaaaa acacctccag gcagatga              888
```

<210> SEQ ID NO 40
<211> LENGTH: 888
<212> TYPE: DNA
<213> ORGANISM: Homo sapiens

<400> SEQUENCE: 40

```
atggcaagcc tctcacgacc aagtctgccc tcttgcctgt gttctttcct tctcctgctt     60
ctcttgcagg tgtcctctag ttatgcgggt cagtttaggg ttattggtcc tagacatccg    120
atacgggctt tggtaggtga cgaggtcgaa ctgccgtgtc ggataagtcc tgataagaac    180
gccacgggca tggaagttgg ttggtaccgc ccgccattct ccagagtggt gcatctgtac    240
aggaatggaa aggatcagga cggtgatcaa gcaccagagt atcgcggtag gaccgaactc    300
ctgaaagatg caatagggga aggaaaggta actttgcgca ttcgaaatgt tcgattttca    360
gacgagggtg ggttcacctg ttttttttagg gatcacagtt atcaggaaga agcagctatg    420
gaactgaagg tagaagatcc gttttattgg gtgtctccag gcgtcctggt tctcttggca    480
gtacttccgg tgctgttgtt gcaaatcacc gtaggtctcg tctttctgtg tctgcaatac    540
aggctgcgcg gaaagctgcg gcggagatt gagaacctgc ataggacgtt cgacccacac    600
ttcctgaggg ttccctgctg gaagatcaca ctctttgtta ttgtcccggt gctcggcccc    660
cttgttgctc ttatcatttg ttataactgg cttcaccgga ggcttgccgg gcagttcttg    720
gaggagctta gaaaatttag ttctctctgc tataaacagc ggattaagtc acaggaacgc    780
gagacagaag cgactagggg cagagggggc ctgcttaggg accatattcc gagggtaaa    840 gaagagctgg aatcccttgg tggtggtaag acacctccag gaaggtag              888
```

<210> SEQ ID NO 41
<211> LENGTH: 888
<212> TYPE: DNA
<213> ORGANISM: Homo sapiens

<400> SEQUENCE: 41

```
atggcttccc tttcacgacc gtccttgcct tcttgcctgt gctccttctt gttgctcctt     60
cttttgcagg tgagttccag ttatgctggt caatttagag tcattggccc acgccacccg    120
atacgcgcgc tggtgggaga tgaggtagag ctcccctgcc gcatatcccc gggcaaaaat    180
gcgaccggca tggaggtagg ctggtataga ccgccgttct cccgagtggt acacctttat    240
cgcaacggta aagaccaaga cggggatcag gccccagaat atagaggtcg gacgaactg    300 ctgaaagacg cgattggaga aggcaaagtc acacttagaa tccgcaacgt cagatttca    360 gatgaaggcg gttttacctg cttttttcaga gatcactctt atcaggagga ggccgctatg    420
gagcttaaag tggaagaccc ttttattgg gtctctcctg gcgtgttggt tttgcttgct    480
gtccttccgg ttcttctgct ccagataact gtcggacttg tttttctgtg tcttcaatac    540
```

| | |
|---|---|
| cgactccgag ggaaactccg agctgaaata gagaacctgc atcggacctt tgaccctcat | 600 |
| ttccttcgcg tgccttgctg gaaaattacc ttgtttgtaa ttgttcccgt actcgggcct | 660 |
| ctcgtagcac tgatcatatg ctataactgg ctccatagga gactcgcggg gcaattcttg | 720 |
| gaagagcttc ggaagttttc tagtctctgt tacaagcaac gaatcaagtc caagaaagg | 780 |
| gaaacggaag ccacgagagg acgcggcggg ctcctgagag atcatatccc gagggtaaa | 840 |
| gaagagctcg aaagccttgg tggaggtaag actccgccgg gtcgatag | 888 |

<210> SEQ ID NO 42
<211> LENGTH: 888
<212> TYPE: DNA
<213> ORGANISM: Homo sapiens

<400> SEQUENCE: 42

| | |
|---|---|
| atggcgtctt tgtcacgccc ttcactccct tcatgcctgt gcagcttcct tctgctcctg | 60 |
| ctccttcaag tctcatcctc atatgcaggc cagtttagag tgatcggacc acgccaccca | 120 |
| atccgcgctc tggttggcga cgaagtagag ttgccatgca gaattagccc cggcaaaaat | 180 |
| gcgactggca tggaagtagg atggtaccgc ccgccctttt caagagttgt tcatttgtat | 240 |
| agaaatggta aggaccaaga tggcgatcaa gctcctgaat atcgcggacg gaccgagttg | 300 |
| cttaaggatg ccatcgggga agggaaggta acattgagga ttcggaacgt acgatttagt | 360 |
| gacgaggggg gattcacatg cttctttcgg gaccattcct atcaagagga ggcggccatg | 420 |
| gagcttaaag ttgaggatcc cttctactgg gtttcacccg gagtcttggt cctccttgcg | 480 |
| gtcctcccag ttcttcttct ccagataaca gtgggtcttg tattctctg ccttcaatat | 540 |
| aggcttagag gaaaactcag ggcggaaata gaaaatctgc accgcacctt cgacccgcat | 600 |
| ttcttgcggg taccttgttg gaagataacg ctcttcgtca tcgttcctgt gctgggcct | 660 |
| ttggttgcgc tgattatttg ttataactgg cttcatagac ggctggcagg acagttcctg | 720 |
| gaagagcttc gcaagttctc cagtttgtgc tataagcaaa ggataaaaag tcaagagcgc | 780 |
| gaaaccgaag ctacgcgcgg acgaggcggt ctgcttcgag atcatattcc aagagggaag | 840 |
| gaggagctgg agtctttggg cggtggaaag actccacccg aaggtag | 888 |

<210> SEQ ID NO 43
<211> LENGTH: 744
<212> TYPE: DNA
<213> ORGANISM: Homo sapiens

<400> SEQUENCE: 43

| | |
|---|---|
| atggcaagct tatcaagacc ctctctgccc agctgcctct gctccttcct cctcctcctc | 60 |
| ctcctccaag tgtcttccag ctatgcaggg cagttcagag tgataggacc aagacaccct | 120 |
| atccgggctc tggtcgggga tgaagtggaa ttgccatgtc gcatatctcc tgggaagaac | 180 |
| gctacaggca tggaggtggg gtggtaccgc cccccttct ctagggtggt tcatctctac | 240 |
| agaaatggca aggaccaaga tggagaccag gcacctgaat atcggggccg acagagctg | 300 |
| ctgaaagatg ctattggtga gggaaaggtg actctcagga tccggaatgt aaggttctca | 360 |
| gatgaaggag gtttcacctg cttcttccga gatcattctt accaagagga ggcagcaatg | 420 |
| gaattgaaag tagaagatcc tttctactgg gtgagccctg gagtgctggt tctcctcgcg | 480 |
| gtgctgcctg tgctcctcct gcagatcact gttggcctca tcttcctctg cctgcagtac | 540 |
| agactgagag gaaaacttcg agcagagata gagaatctcc accggacttt tgatccccac | 600 |
| tttctgaggg tgcctgctg gaagataacc ctgtttgtaa ttgtgccggt tcttggaccc | 660 |

```
ttggttgcct tgatcatctg ctacaactgg ctacatcgaa gactagcagg gcaattcctt    720
gaagagctac gaaatcccct ctga                                          744
```

<210> SEQ ID NO 44
<211> LENGTH: 744
<212> TYPE: DNA
<213> ORGANISM: Homo sapiens

<400> SEQUENCE: 44

```
atggccagcc tgagccggcc ttctctgcct agctgcctgt gcagcttcct gttactgctg    60
ctgctgcaag tgtcttctag ctacgccgga cagtttagag tgatcggccc agacaccct   120 atccgggccc tggtcggaga tgaggtggaa ctgccttgca gaatcagccc tggcaagaac   180
gccacaggca tggaagtggg ctggtacaga ccccccttca gcagagtggt gcacctgtac   240
cggaacggca aggaccagga cggcgatcag gcccctgagt acagaggcag aaccgagctg   300
cttaaagacg ccatcggcga gggcaaggtt acactgagaa tcagaaatgt gcggttcagc   360
gacgagggcg gcttcacctg cttcttccgg gaccacagct accaggagga agccgctatg   420
gaactgaagg tcgaggaccc tttctactgg gtgtcccctg gagtgctggt gctgttggct   480
gtgctgcccg tgctgctcct gcagatcacc gtgggactga tcttcctctg tctgcagtac   540
cggctgcggg gcaaactgag agccgagatc gagaacctgc accggacctt cgaccccac   600 ttcctgcggg tgccttgttg aagatcaca ctgttcgtga tcgtgccagt gctgggccct   660
ctggtggccc tgatcatctg ctacaactgg ctgcacagaa gactggccgg ccagttcctg   720
gaagagctga gaaaccccct ctga                                           744
```

<210> SEQ ID NO 45
<211> LENGTH: 744
<212> TYPE: DNA
<213> ORGANISM: Homo sapiens

<400> SEQUENCE: 45

```
atggctagcc tgagtagacc gagtctcccg tcatgtctgt gttcattcct tcttctgctc    60
ctcctccagg taagtagtag ctatgcaggt caatttaggg tgataggtcc ccgacaccct   120
attcgagcgt tggtaggaga tgaagtagaa ctcccgtgtc gcatcagccc cggcaagaac   180
gccaccggca tggaagtggg atggtatcga ccgccgtttt caagagttgt ccatctgtat   240
aggaatggca agatcagga cggggaccaa gcacccgaat acaggggacg cacagaactt   300
cttaaagatg cgataggaga gggtaaagtt acgttgagaa ttcgcaacgt gcggtttagt   360
gatgaaggtg gcttcacgtg cttcttccgc gatcacagtt accaagaaga agccgcgatg   420
gaactcaagg tcgaagatcc gttctactgg gtcagccctg gtgtactggt tttgttggcc   480
gtgttgcctg tattgttgct tcaaatcacg gttggtttga tttttctctg tctccagtac   540
cgactgagag ggaagttgcg ggccgagatt gagaacctcc ataggaacctt cgacccacac   600 ttcctgcgag tcccttgctg gaaaataaca ctcttcgtca ttgtgccggt tttggggccc   660
ctggtagctt tgataatttg ttacaactgg ctccatcgca gactggcagg ccaattcctg   720
gaggaactgc gaaacccgtt ttga                                          744
```

<210> SEQ ID NO 46
<211> LENGTH: 744
<212> TYPE: DNA
<213> ORGANISM: Homo sapiens

<400> SEQUENCE: 46

| | | | | | |
|---|---|---|---|---|---|
| atggcgtctc | tgtcacggcc | ttcactgcct | tcttgcctgt | gtagctttct | cttgcttctc | 60 |
| cttctgcaag | tatcttcatc | ctatgcggga | cagttccgag | tcattggacc | acggcacccg | 120 |
| atccgcgcac | ttgtaggaga | tgaagtcgag | ctgccttgcc | ggatctcccc | tgggaaaaac | 180 |
| gccacaggga | tggaagtggg | ctggtaccgc | ccccccttca | gcagggtcgt | ccatctgtat | 240 |
| cgaaacggga | agaccagga | cggagaccag | gcccccgaat | atcggggtag | aacggaattg | 300 |
| ctcaaggacg | cgatcggcga | aggcaaggtt | acgttgcgga | taaggaatgt | acgatttagt | 360 |
| gacgaaggag | gatttacctg | cttttttagg | gaccatagtt | accaagaaga | ggcggcaatg | 420 |
| gagcttaagg | ttgaggaccc | attttattgg | gtaagccccg | gcgttctcgt | acttctggcc | 480 |
| gtactcccag | tgctcctcct | tcagatcact | gttggcctca | tattcctgtg | tttgcagtac | 540 |
| cggctccgag | gtaagctgcg | ggcggaaatc | gaaaacttgc | atagaacctt | cgatccccat | 600 |
| ttcctccgag | tgccttgttg | gaagattact | ttgttcgtca | tagtccctgt | ccttgggcct | 660 |
| cttgtagcat | tgataatctg | ctataattgg | ttgcataggc | gccttgccgg | acaattcctc | 720 |
| gaggagctcc | gaaatccatt | ctga | | | | 744 |

<210> SEQ ID NO 47
<211> LENGTH: 744
<212> TYPE: DNA
<213> ORGANISM: Homo sapiens

<400> SEQUENCE: 47

| | | | | | |
|---|---|---|---|---|---|
| atggcgtctc | tgtctcgacc | ttccctccca | tcatgtctgt | gttccttcct | cctgctcctg | 60 |
| cttcttcaag | tttcctcttc | ttacgcggga | caatttagag | tgatcggacc | gcgacatccc | 120 |
| attcgcgcgt | tggtcgggga | tgaagtcgag | ttgccgtgcc | ggatcagtcc | cggtaaaaac | 180 |
| gctaccggaa | tggaagtggg | ttggtatcga | cctcctttct | cccgcgtcgt | acacctctat | 240 |
| cgaaatggta | aagatcagga | cggggaccag | gcccccgagt | atcgcggaag | aacggaactc | 300 |
| cttaaagatg | ctataggaga | aggtaaagtt | acgcttcgga | tcagaaacgt | gcgcttctca | 360 |
| gatgaggggg | gatttacatg | cttctttagg | gaccactctt | atcaagagga | agctgcgatg | 420 |
| gagctcaaag | ttgaggaccc | attttattgg | gtctctccgg | gcgttttggt | attgttggca | 480 |
| gtactccctg | ttttgcttct | ccaaattacg | gtcggtctta | tattcctgtg | tctgcagtat | 540 |
| cgcttgcgcg | gcaagttgag | agctgagatc | gagaacttgc | acaggacctt | cgacccgcac | 600 |
| tttctgaggg | taccgtgttg | gaagataaca | ctgtttgtta | tcgtacctgt | tctcggaccg | 660 |
| cttgtagccc | tcattatctg | ctataactgg | ctgcacaggc | gcttggcggg | acaattcttg | 720 |
| gaggagttgc | gaaacccatt | ttga | | | | 744 |

<210> SEQ ID NO 48
<211> LENGTH: 627
<212> TYPE: DNA
<213> ORGANISM: Homo sapiens

<400> SEQUENCE: 48

| | | | | | |
|---|---|---|---|---|---|
| atggcaagct | tatcaagacc | ctctctgccc | agctgcctct | gctccttcct | cctcctcctc | 60 |
| ctcctccaag | tgtcttccag | ctatgcaggg | cagttcagag | tgataggacc | aagacaccct | 120 |
| atccgggctc | tggtcgggga | tgaagtggaa | ttgccatgtc | gcatatctcc | tgggaagaac | 180 |
| gctacaggca | tggaggtggg | gtggtaccgc | ccccccttct | ctagggtggt | tcatctctac | 240 |
| agaaatggca | aggaccaaga | tggagaccag | gcacctgaat | atcggggccg | gacagagctg | 300 |

-continued

```
ctgaaagatg ctattggtga gggaaaggtg actctcagga tccggaatgt aaggttctca    360
gatgaaggag gtttcacctg cttcttccga gatcattctt accaagagga ggcagcaatg    420
gaattgaaag tagaagatcc tttctactgg gtgagccctg gagtgctggt tctcctcgcg    480
gtgctgcctg tgctcctcct gcagatcact gttggcctca tcttcctctg cctgcagtac    540
agactgagag gaaaacttcg agcagagata gagaatctcc accggacttt tgggcaattc    600
cttgaagagc tacgaaatcc cttctga                                         627
```

<210> SEQ ID NO 49
<211> LENGTH: 627
<212> TYPE: DNA
<213> ORGANISM: Homo sapiens

<400> SEQUENCE: 49

```
atggccagcc tgagcagacc ctctctgcct agctgcctgt gcagcttcct gctgctgctg    60
ctgcttcaag tgtccagctc ttacgccggc cagttcagag tgatcggccc tagacacccc   120
atccgggccc tggtgggcga tgaggtggaa ctgccgtgca gaatcagccc cggcaaaaac   180
gccaccggca tggaagtggg atggtacaga cctccttttta gccgggtggt gcacctgtac   240
agaaacggca aggaccagga cggcgaccag gcccctgagt accggggcag aaccgagctg   300
cttaaagacg ccatcggaga aggcaaggtg accctgcgga tcagaaacgt gcggttcagt   360
gatgagggcg gattcacctg cttcttccgg gaccacagct accaggagga gccgctatg    420 gaactgaagg ttgaggaccc cttctactgg gtcagccctg gagtgctggt cctgctggcc   480
gtgctgcctg tgctgctgct gcagatcaca gtgggcctga tcttcctgtg tctgcagtac   540
cggctgagag gcaagctgag ggctgaaatc gagaacctgc acagaacatt cggccagttt   600
ctggaagagc tgagaaatcc tttctga                                        627
```

<210> SEQ ID NO 50
<211> LENGTH: 627
<212> TYPE: DNA
<213> ORGANISM: Homo sapiens

<400> SEQUENCE: 50

```
atggcgagtt tgtcacggcc ctctctgcca tcatgtctgt gctcattcct tctgctgttg    60
ttgcttcagg tgtcaagttc ttacgccggt cagttcaggg taatcgggcc gaggcatcct   120
ataagagcct tggttggaga tgaagtggag cttccttgcc gcatttcccc tggtaagaat   180
gcgacgggaa tggaagtggg atggtataga cctccattct cacgcgttgt tcatctctac   240
agaaatggca aagaccaaga cggggaccag gccccggagt atcgggtcg cacggaactc    300 cttaaagacg ccataggaga ggggaaagta actttgagga tacgcaacgt acgcttcagc   360
gatgaaggtg ggtttacatg cttcttccgc gatcatagtt accaggagga ggcggcgatg   420
gagcttaaag tcgaggatcc gttctactgg gtgagcccag gtgttctggt tctcctcgct   480
gtactgcctg tgctgcttct tcagataaca gtaggtttga ttttttctgtg cttgcagtac   540 cggctgagag gcaaattgcg agcggagatc gaaaacttgc atcgaacctt cggacagttt   600
ttggaagagc ttagaaaccc tttctga                                        627
```

<210> SEQ ID NO 51
<211> LENGTH: 627
<212> TYPE: DNA
<213> ORGANISM: Homo sapiens

<400> SEQUENCE: 51

```
atggcatctc tgagtcggcc tagcctgcca tcttgtctgt gctctttct tttgcttttg      60
ttgttgcaag tgtcctcaag ttacgctgga caattcagag ttatcggacc ccgccaccca    120
atcagggcgc tcgtcggaga cgaggtgaaa cttccgtgtc gcatttctcc aggcaaaaac    180
gcaacgggga tggaagtcgg ttggtacagg cctcccttt cccgggtggt acatctttat    240
aggaatggaa aagaccaaga cggagaccaa gcaccggaat atcgaggccg acagagctg    300
ctcaaagacg caatcgggga ggggaaggtc actctgagga tccgaaacgt ccgattcagc    360
gacgaggggg ggtttacatg cttttttcagg gatcacagct atcaggaaga gcggctatg    420
gaattgaagg ttgaagaccc atttactgg gtatcacccg gagtgctggt gctcctggcg    480
gtcctccccg tattgctcct gcaaataacc gttgggttga ttttcctctg ccttcaatac    540
cgattgcgcg ggaaactgag ggcagaaatt gaaaatcttc atcggacctt cgggcagttt    600
ctggaagagc ttagaaaccc ctttttga                                      627
```

<210> SEQ ID NO 52
<211> LENGTH: 627
<212> TYPE: DNA
<213> ORGANISM: Homo sapiens

<400> SEQUENCE: 52

```
atggcttcac tttcacgccc gtcacttcct tcctgtctct gttcattcct tttgttgttg      60
ctcctccaag tcagtagttc ttacgcaggt caatttaggg ttataggtcc caggcatccc    120
ataagagcgt tggtgggaga cgaggtagag cttccttgca ggatctctcc tggaaaaaat    180
gccacgggca tggaagtcgg atggtatcga ccccccattct cacgcgtggt tcacctctac    240
cgcaacggaa aggaccagga tggcgaccag gctccagagt atcgcggccg aacggaattg    300
ctgaaggacg cgatcggcga gggaaaagtg acgctgagga ttcgaaatgt tcgattttca    360
gatgaggggg gtttcacatg cttctttcgc gaccattctt atcaggagga ggctgccatg    420
gaactcaagg tggaggaccc ttttttattgg gtcagccccg gcgtacttgt tctcttggcg    480
gtactgccag tacttctgct ccagatcact gtaggattga tatttctctg tctccaatat    540
cgactcaggg gtaagctgcg ggctgaaatt gaaaatttgc acagaacttt tgggcagttc    600
ctggaggaac tcagaaaccc tttctga                                       627
```

<210> SEQ ID NO 53
<211> LENGTH: 675
<212> TYPE: DNA
<213> ORGANISM: Homo sapiens

<400> SEQUENCE: 53

```
atggcaagct tatcaagacc ctctctgccc agctgcctct gctccttcct cctcctcctc      60
ctcctccaag tgtcttccag ctatgcaggg cagttcagag tgataggacc aagacaccct    120
atccgggctc tggtcgggga tgaagtggaa ttgccatgtc gcatatctcc tgggaagaac    180
gctacaggca tggaggtggg gtggtaccgc cccccttct ctagggtggt tcatctctac    240
agaaatggca aggaccaaga tggagaccag gcacctgaat atcggggccg acagagctg    300
ctgaaagatg ctattggtga gggaaaggtg actctcagga tccggaatgt aaggttctca    360
gatgaaggag gtttcacctg cttcttccga gatcattctt accaagagga ggcagcaatg    420
gaattgaaag tagaagatcc tttctactgg gtgagccctg gagtgctggt tctcctcgcg    480
gtgctgcctg tgctcctcct gcagatcact gttggcctca tcttcctctg cctgcagtac    540
```

```
agactgagag gaaaacttcg agcagagata gagaatctcc accggacttt tgagtccttt    600
ggtgttctag acccccaggt taaggaacca aaaaagacag ggcaattcct tgaagagcta    660
cgaaatccct tctga                                                    675
```

<210> SEQ ID NO 54
<211> LENGTH: 675
<212> TYPE: DNA
<213> ORGANISM: Homo sapiens

<400> SEQUENCE: 54

```
atggccagct tgtctagacc tagcctgccc agctgcctgt gcagcttcct gctgctgctg     60
ctgctgcagg tgtccagcag ctacgccggc cagttcagag tgatcggccc tagacacccc    120
atccgggccc tggtgggcga cgaggtcgag ctgccgtgca gaatctctcc aggcaagaac    180
gccacaggaa tggaagtggg ctggtacaga ccccccttca gcagagtggt gcacctgtac    240
cggaacggca aggaccagga cggcgatcag gcccctgagt accgaggaag aacagagctg    300
ctcaaggacg ccatcggcga gggcaaagtg acactgagaa tcagaaacgt gcggttcagt    360
gatgagggcg gcttcacctg cttcttccgg gaccacagct accaggagga agccgctatg    420
gaactgaagg tggaagatcc tttctactgg gtcagccctg gcgtgctggt cctgctggcc    480
gtgctgcctg tgctgctgct gcaaatcacc gtgggtctta tcttcctgtg tctgcagtac    540
agactgagag gcaagctgag agccgagatc gagaacctgc acagaacctt cgagagcttt    600
ggcgtgctgg gcccccaggt taaggaaccc aagaagaccg gacagtttct ggaagagctg    660
cggaatcctt tctga                                                    675
```

<210> SEQ ID NO 55
<211> LENGTH: 675
<212> TYPE: DNA
<213> ORGANISM: Homo sapiens

<400> SEQUENCE: 55

```
atggcaagtc tttcaaggcc gagcctccct tcttgtttgt gtagtttcct cctgctgctg     60
ctcctccagg tttcatcctc ttacgctgga caattccgcg taatcggccc tcggcatcct    120
attcgagcac tcgtaggtga tgaagttgag ttgccgtgta gaatatctcc aggcaagaac    180
gcgactggga tggaggttgg atggtatcgc cccccattct cacgcgtcgt tcatctttat    240
aggaatggga aggatcagga cggggatcaa gcacctgagt accggggtag gactgagctc    300
ttgaaggacg cgattggtga gggtaaggtt actcttagga ttagaaatgt acggttctcc    360
gacgaaggtg ggttcacttg cttcttccgc gaccactcat accaggagga agcggcgatg    420
gaattgaagg tcgaggatcc gttctactgg gtgtcacctg gtgtcctggt cttgcttgca    480
gttctcccag ttctcttgct gcagatcacg gtcggtttga tcttcctctg cttgcaatac    540
cgcctccgcg ggaaactccg cgcggaaatc gaaaacctgc acaggacatt gaaagtttc     600 ggggtacttg gaccccaggt gaaggagccc aaaaaaacgg gacagttctt ggaggaactg    660
cgaaacccct tctga                                                    675
```

<210> SEQ ID NO 56
<211> LENGTH: 675
<212> TYPE: DNA
<213> ORGANISM: Homo sapiens

<400> SEQUENCE: 56

```
atggcctctt tgtctcggcc gagtttgcca tcctgtctgt gttcttttct tctcctgctt      60
ctgctgcagg taagcagttc atacgcagga cagttccggg ttattggacc gcgccatcca     120
atccgggcct tggtaggtga cgaggtggaa ttgccatgcc gcatcagtcc ggggaagaac     180
gcgacaggaa tggaggtagg atggtacaga ccgcccttt  ctcgagttgt gcatctgtac     240
cgcaacggca aagatcaaga cggggaccaa gcacccgagt accgaggtag gactgagctt     300
ttgaaagatg ccatcgggga ggggaaagtt actctgcgca tccgaaacgt gcgcttttcc     360
gatgaaggcg gtttcacttg tttctttaga gaccattcct accaagaaga agccgctatg     420
gaattgaaag tagaagatcc attctattgg gtttctccag cgtccttgt  tctgcttgca     480
gttcttcccg tactcctgct tcaaattacg gttggcctca tatttctttg tctccaatat     540
cgacttcggg gcaaacttcg cgccgaaata gagaatctcc ataggacgtt tgaatctttt     600
ggggtactcg ggccgcaggt gaaagagcca aaaaagaccg gtcaatttct cgaagagctc     660
aggaatccct tttga                                                     675

<210> SEQ ID NO 57
<211> LENGTH: 675
<212> TYPE: DNA
<213> ORGANISM: Homo sapiens

<400> SEQUENCE: 57
atggcgtccc ttagccggcc ttcccttcct tcctgcctct gttcctttct gcttttgctt      60
ttgttgcaag tttctagcag ctatgctgga caatttcgcg tcatcggccc aagacaccca     120
attagggccc tcgtcgggga tgaagtggag cttccgtgca ggattagtcc tgggaagaac     180
gctactggta tggaagttgg atggtatagg ccccgttca  gcagggtcgt ccacctctat     240
cggaacggga aagatcaaga tggagatcag gcgcccgaat acagaggtcg gactgagttg     300
ctcaaagatg caatcggtga aggcaaggtc actctgagaa ttcggaacgt gcgattttcc     360
gacgaaggcg gatttacctg cttttttagg gatcattcat atcaggaaga ggcggcgatg     420
gagctcaagg ttgaagatcc cttctattgg gtttctccgg gcgtttttggt tttgctggcc    480
gttttgcctg tactccttct ccagatcact gttggactga tattcttgtg tctccagtat     540
cgactgagag gtaaactccg cgcagagata gagaatttgc ataggacatt cgagagcttt     600
ggagtacttg gccctcaggt caaagaaccg aaaaagaccg gacagttctt ggaagagctg     660
agaaatccct tctga                                                     675

<210> SEQ ID NO 58
<211> LENGTH: 396
<212> TYPE: DNA
<213> ORGANISM: Homo sapiens

<400> SEQUENCE: 58
atggcaagct tatcaagacc ctctctgccc agctgcctct gctccttcct cctcctcctc      60
ctcctccaag tgtcttccag ctatgcagat cctttctact gggtgagccc tggagtgctg     120
gttctcctcg cggtgctgcc tgtgctcctc ctgcagatca ctgttggcct catcttcctc     180
tgcctgcagt acagactgag aggaaaaactt cgagcagaga tagagaatct ccaccggact     240
tttgatcccc actttctgag ggtgccctgc tggaagataa ccctgtttgt aattgtgccg     300
gttcttggac ccttggttgc cttgatcatc tgctacaact ggctacatcg aagactagca     360
gggcaattcc ttgaagagct acgaaatccc ttctga                              396
```

-continued

```
<210> SEQ ID NO 59
<211> LENGTH: 396
<212> TYPE: DNA
<213> ORGANISM: Homo sapiens

<400> SEQUENCE: 59
atggccagcc tgagcagacc tagcctgcct tcttgtctgt gcagcttcct gctgctgctg    60
ctgctgcagg tgtccagcag ctacgccgac cctttctact gggtgtctcc aggcgtgctg   120
gtgctgctcg ccgtgcttcc tgtgctgctg ctgcagatca ccgtgggcct gatcttcctc   180
tgcctgcaat acagactgag aggcaagctg cgggccgaga tcgagaacct gcacagaacc   240
ttcgaccccc acttcctgag agtgccgtgc tggaagatca cactgttcgt gatcgtgccc   300
gtgcttggac ctctggtcgc cctgatcatc tgctacaact ggctgcaccg gagactggcc   360
ggccagttcc tggaagagct gcgaaacccc ttctga                              396

<210> SEQ ID NO 60
<211> LENGTH: 396
<212> TYPE: DNA
<213> ORGANISM: Homo sapiens

<400> SEQUENCE: 60
atggcgagtc tctcaaggcc gtctttgccg tcttgtcttt gcagcttttt gttgcttttg    60
ctgctccaag tatcatcaag ttacgcggac cctttttatt gggtttcacc tggcgtactt   120
gtgctgttgg cggtcctccc agtattgctg ttgcaaatca cggtgggtct tatatttctt   180
tgcttgcaat accgcttgcg gggtaagctc agggctgaaa tagaaaactt gcatcgcaca   240
ttcgacccgc atttttctccg cgtgccgtgt tggaaaatta cgctcttcgt tatcgtgcca   300
gtacttggac tcttgtcgc gctcatcatc tgctataact ggcttcaccg ccgccttgcc   360
ggtcagttcc ttgaagaatt gagaaatccc ttttga                              396

<210> SEQ ID NO 61
<211> LENGTH: 396
<212> TYPE: DNA
<213> ORGANISM: Homo sapiens

<400> SEQUENCE: 61
atggcaagcc tcagcaggcc tagtttgcca tcatgccttt gttcttttct cttgttgctg    60
ctgctccaag tcagtagctc ttatgcagat ccctttttatt gggtctcccc aggtgtactt   120
gttttgttgg cggtgttgcc ggttctgttg ctgcaaatta cagtagggtt gatatttctg   180
tgtttgcagt atcgcctgcg gggggaagctg agagctgaaa tagagaactt gcataggacc   240
ttcgatccac actttctcag agtcccttgt tggaaaatta cgctgttcgt tatcgtgccc   300
gtgctcggcc ccttggtagc cttgataatt tgctataact ggcttcatcg cagacttgct   360
ggtcagttct tggaggagct tcgcaatcct ttttga                              396

<210> SEQ ID NO 62
<211> LENGTH: 396
<212> TYPE: DNA
<213> ORGANISM: Homo sapiens

<400> SEQUENCE: 62
atggctagtc tgtcccgacc ttccttgcca agttgcctgt gttctttttct cctgctgctt    60 ctcctccaag tctcaagctc atacgcagac ccgttctact gggtgagccc cggcgtactt   120
gtgctgttgg cagttttgcc ggtactgctc cttcagataa cagtcgggtt gattttcctc   180
```

```
tgccttcaat accgcttgag agggaaactc cgcgccgaga tcgaaaacct tcaccggacc    240
ttcgatcccc actttcttag ggtaccctgc tggaagataa ctttgttcgt cattgtaccc    300
gtcctgggac cgttggttgc gttgattata tgttataact ggctgcaccg caggttggcg    360
ggacagtttc tggaagagct ccgcaatccg ttttga                              396
```

<210> SEQ ID NO 63
<211> LENGTH: 327
<212> TYPE: DNA
<213> ORGANISM: Homo sapiens

<400> SEQUENCE: 63

```
atggcaagct tatcaagacc ctctctgccc agctgcctct gctccttcct cctcctcctc    60
ctcctccaag tgtcttccag ctatgcagat cctttctact gggtgagccc tggagtgctg    120
gttctcctcg cggtgctgcc tgtgctcctc ctgcagatca ctgttggcct catcttcctc    180
tgcctgcagt acagactgag aggaaaactt cgagcagaga tagaatctcc caccggact    240 tttgagtcct ttggtgttct aggaccccag gttaaggaac caaaaaagac agggcaattc    300
cttgaagagc tacgaaatcc cttctga                                         327
```

<210> SEQ ID NO 64
<211> LENGTH: 327
<212> TYPE: DNA
<213> ORGANISM: Homo sapiens

<400> SEQUENCE: 64

```
atggccagct tgtctagacc tagcctgccc agctgcctgt gcagctttct gctgctgctg    60
ctgcttcaag tgtccagcag ctacgccgat cctttctact gggtcagccc cggcgtgctc    120
gtgctgctgg ccgtgctgcc tgtgctgctg ctgcagatca ccgtgggcct gatcttcctg    180
tgtctgcaat acagactgag aggcaagctg agagccgaga tcgagaacct gcacagaacc    240
ttcgagagct tcggcgtgtt gggccctcag gtgaaggaac ccaagaagac aggccagttc    300
ctggaagagc tgcggaaccc cttctga                                         327
```

<210> SEQ ID NO 65
<211> LENGTH: 327
<212> TYPE: DNA
<213> ORGANISM: Homo sapiens

<400> SEQUENCE: 65

```
atggcttccc tctcaagacc cagcctccca agctgccttt gctcattcct gttgctcttg    60
ctcctgcaag tctcatcctc ttacgctgac ccctttact gggtcagtcc gggcgtcctc    120
gtattgttgg ccgtgctgcc tgtactcctt cttcaaatca cagtgggcct tatatttctc    180
tgtctgcaat accggctccg aggcaaattg cgggccgaga tagaaaattt gcacaggaca    240
tttgaatcat tcggcgtcct cggcccacag gtgaaagagc ccaaaaaaac gggacaattt    300
ctcgaggaat tgaggaatcc tttctga                                         327
```

<210> SEQ ID NO 66
<211> LENGTH: 327
<212> TYPE: DNA
<213> ORGANISM: Homo sapiens

<400> SEQUENCE: 66

```
atggcaagtt tgtcacggcc ctctctgccg agctgtttgt gtagctttct cctgttgttg    60
ctgttgcagg ttagctccag ctatgcagat cccttctatt gggtttcacc tggggtgctg    120
```

| | |
|---|---|
| gttctcctgg cggtgcttcc tgttttgctg ctccagatta ccgtaggact gattttctc | 180 |
| tgcctccaat accggttgcg aggcaagctc agagcagaaa ttgagaatct ccacaggaca | 240 |
| ttcgagtcct tcggggtgct tgggcctcag gtcaaggaac cgaaaaagac aggtcagttc | 300 |
| cttgaggagc tgcgaaatcc tttttga | 327 |

<210> SEQ ID NO 67
<211> LENGTH: 327
<212> TYPE: DNA
<213> ORGANISM: Homo sapiens

<400> SEQUENCE: 67

| | |
|---|---|
| atggctagtc tcagccgacc aagcctgcct tcctgtcttt gttctttcct tctgttgctg | 60 |
| ttgttgcagg tgtccagctc ttatgctgat ccttttact gggtatcccc tggagtcttg | 120 |
| gttctcctcg ccgtacttcc ggtgctcttg ttgcagatca cggtagggct tatatttctt | 180 |
| tgcttgcaat accgattgcg gggcaaactg cgagctgaaa tagaaaacct ccacagaact | 240 |
| ttcgagtcat ttggcgtgct cggaccgcag gtcaaggagc ctaagaaaac tggtcagttc | 300 |
| ctcgaagagc tgcgcaaccc gttctga | 327 |

<210> SEQ ID NO 68
<211> LENGTH: 621
<212> TYPE: DNA
<213> ORGANISM: Homo sapiens

<400> SEQUENCE: 68

| | |
|---|---|
| atggcaagct tatcaagacc ctctctgccc agctgcctct gctccttcct cctcctcctc | 60 |
| ctcctccaag tgtcttccag ctatgcaggg cagttcagag tgataggacc aagacaccct | 120 |
| atccgggctc tggtcgggga tgaagtggaa ttgccatgtc gcatatctcc tgggaagaac | 180 |
| gctacaggca tggaggtggg gtggtaccgc ccccccttct ctagggtggt tcatctctac | 240 |
| agaaatggca aggaccaaga tggagaccag gcacctgaat atcggggccg gacagagctg | 300 |
| ctgaaagatg ctattggtga gggaaaggtg actctcagga tccggaatgt aaggttctca | 360 |
| gatgaaggag gtttcacctg cttcttccga gatcattctt accaagagga ggcagcaatg | 420 |
| gaattgaaag tagaagatcc tttctactgg gtgagccctg gagtgctggt tctcctcgcg | 480 |
| gtgctgcctg tgctcctcct gcagatcact gttggcctca tcttcctctg cctgcagtac | 540 |
| agactgagag gaaaacttcg agcagagata gagaatctcc accggacttt tgtcttccac | 600 |
| ctggaagccc tctctggcta a | 621 |

<210> SEQ ID NO 69
<211> LENGTH: 621
<212> TYPE: DNA
<213> ORGANISM: Homo sapiens

<400> SEQUENCE: 69

| | |
|---|---|
| atggccagcc tgagcagacc tagcctgcca tcttgtctgt gcagcttcct gctgctgctg | 60 |
| ctgctgcagg tgtccagcag ctacgccggc cagttccggg tgatcggtcc tagacacccc | 120 |
| atcagagccc tggtcggaga tgaggtggaa ctgccgtgca gaatcagccc cggcaagaac | 180 |
| gccacaggca tggaagtggg ctggtaccgg cctcctttta gcagagtggt gcacctgtac | 240 |
| agaaacggca agaccaggga cggcgatcag gcccctgagt accggggcag aaccgagctg | 300 |
| ctcaaggacg ccatcggcga gggcaaggtg accctgagaa tccggaacgt gcggttcagc | 360 |

```
gacgagggcg gatttacctg cttcttcaga gatcactctt atcaggagga agccgctatg    420
gaactgaagg ttgaggaccc cttctactgg gtcagccctg gcgtgctggt gctgctggcc    480
gtgctgcctg tgctcctgct gcagatcaca gtgggcctga tcttcctgtg tctgcaatac    540
agactgagag gcaagctgcg ggccgagatc gagaacctgc accggacctt cgtgttccac    600
ctggaagctc tgtccggctg a                                              621

<210> SEQ ID NO 70
<211> LENGTH: 621
<212> TYPE: DNA
<213> ORGANISM: Homo sapiens

<400> SEQUENCE: 70
atggcgagtc ttagtcgccc gagtcttccg tcatgtcttt gttctttcct tcttcttttg     60
ctcttgcaag ttagctctag ctacgccggg caattcaggg ttatagggcc taggcatcca    120
atacgagcat tggttgggga cgaagtagaa ctgccgtgta ggataagccc tggcaaaaac    180
gctactggga tggaagtcgg gtggtatcga ccgccattca gccgagttgt gcacctttac    240
agaaacggaa aagaccaaga cggcgatcaa gctcccgaat atagaggaag gaccgaactg    300
ctgaaggacg ccatagggga aggtaaggtg acgctgagga tcagaaacgt gaggtttagt    360
gacgaaggag gtttcacgtg cttttttcgg gaccattctt atcaggagga agctgcgatg    420
gagttgaaag ttgaagaccc gttttactgg gtgagtcctg gggtgctcgt tctcttggcg    480
gtcctcccgg tacttctgtt gcagataacc gtcggtctca tatttctctg ccttcagtac    540
cgcttgaggg gcaagctccg ggcagaaata gagaacttgc atcggacgtt tgttttcat     600 ttggaggcgc tgtctggata a                                              621

<210> SEQ ID NO 71
<211> LENGTH: 621
<212> TYPE: DNA
<213> ORGANISM: Homo sapiens

<400> SEQUENCE: 71
atggcttctc tttctagacc ctcttttgcca agttgtcttt gctctttct tctcctcctc     60 ctgctgcagg ttagcagctc ctatgctggt cagttccgag taataggtcc tagacatccg    120
attcgagcgc tcgttggcga tgaagttgaa cttcccgta gaataagccc cggtaaaaac    180
gcgacaggca tggaggtcgg gtggtatcgc ccccgttct ctagagtggt gcatctttat    240
cggaatggaa aggatcaaga tggtgaccaa gcacctgagt atagaggccg cacagaactc    300
ctcaaagacg cgataggcga aggaaaagtc accctccgaa tacgaaacgt gcggttttct    360
gatgaaggtg gtttcacgtg ttttttcaga gaccatagtt atcaagaaga agctgcaatg    420
gagctcaagg ttgaagaccc tttctattgg gtaagcccag gagttttggt tctgcttgcg    480
gtccttccgg tactgctcct ccagattacc gtggggctta tattcctctg tctccagtat    540
aggttgaggg gcaagctcag agcagaaata gagaatttgc atcgcacatt cgtgtttcac    600
ctggaggcgt tgagtggata a                                              621

<210> SEQ ID NO 72
<211> LENGTH: 621
<212> TYPE: DNA
<213> ORGANISM: Homo sapiens

<400> SEQUENCE: 72
atggcgagtc tttcacgccc atctttgcct tcctgcttgt gtagtttcct gctccttctt     60
```
ctgcttcagg ttagcagttc ttatgcaggg caatttcgcg ttatcgggcc cagacaccca    120
attcgggccc ttgttggaga tgaggttgaa ctcccgtgca ggataagtcc aggaaaaaat    180
gctacgggga tggaagtcgg atggtatagg ccgcccttct ccagggtagt acatctgtat    240
agaaacggca aggaccaaga tggagatcag gccccagagt acaggggggcg cacagagctg    300 cttaaagacg ctattggaga gggcaaagtg acccttcgga tacgaaatgt acgctttagc    360
gatgagggcg ggttcacctg tttctttcgc gaccactctt atcaagagga ggcggctatg    420
gagctcaagg ttgaagaccc tttctactgg gtaagcccag gcgtgcttgt tttgctggct    480
gtcctgcccg tgcttttgct ccagatcact gtaggtctga tatttctctg tttgcaatat    540
cgattgagag ggaaactgcg cgctgaaatc gaaaacttgc accggacctt cgtctttcac    600
ttggaagcct tgtctggtta a                                              621

<210> SEQ ID NO 73
<211> LENGTH: 759
<212> TYPE: DNA
<213> ORGANISM: Homo sapiens

<400> SEQUENCE: 73
atggcaagct tatcaagacc ctctctgccc agctgcctct gctccttcct cctcctcctc     60
ctcctccaag tgtcttccag ctatgcaggg cagttcagag tgataggacc aagacaccct    120
atccgggctc tggtcgggga tgaagtggaa ttgccatgtc gcatatctcc tgggaagaac    180
gctacaggca tggaggtggg gtggtaccgc ccccccttct ctagggtggt tcatctctac    240
agaaatggca aggaccaaga tggagaccag gcacctgaat atcggggccg gacagagctg    300
ctgaaagatg ctattggtga gggaaaggtg actctcagga tccggaatgt aaggttctca    360
gatgaaggag gtttcacctg cttcttccga gatcattctt accaagagga ggcagcaatg    420
gaattgaaag tagaagatcc tttctactgg gtgagccctg gagtgctggt tctcctcgcg    480
gtgctgcctg tgctcctcct gcagatcact gttggcctca tcttcctctg cctgcagtac    540
agactgagag gaaaacttcg agcagagata gagaatctcc accggacttt tgatccccac    600
tttctgaggg tgccctgctg aagataaacc ctgtttgtaa ttgtgccggt tcttggaccc    660
ttggttgcct tgatcatctg ctacaactgg ctacatcgaa gactagcagg gcaattcctt    720
gaagagctac tcttccacct ggaagccctc tctggctaa                           759

<210> SEQ ID NO 74
<211> LENGTH: 759
<212> TYPE: DNA
<213> ORGANISM: Homo sapiens

<400> SEQUENCE: 74
atggccagcc tgtctagacc tagcctgcct tcatgcctgt gcagcttcct gctgctcctg     60
ttgctgcagg tgtccagctc ttacgccgga cagttccggg tgatcgggcc tagacacccc    120
atcagagccc tggtgggcga cgaggtggaa ctgccctgca gaatcagccc tgggaagaac    180
gccaccggca tggaagtggg atggtaccgg cctcctttca gcagagtggt gcacctgtac    240
agaaacggca aagaccagga cggcgatcag gcccctgagt accggggcag aacagagctg    300
ctgaaggacg ccatcggcga gggcaaggtg acactgcgga tccggaacgt gcggttcagt    360
gatgagggag gcttcacctg cttcttcaga gatcacagct accaggagga agccgccatg    420
gaactgaaag tcgaggaccc cttctactgg gtctcccctg gcgtgctggt tctgctggcc    480

| | |
|---|---:|
| gtgctgcctg tgctgctgct gcagatcacc gtgggcctga tcttcctgtg tctgcaatac | 540 |
| agactgagag gcaagctgcg ggccgagatc gagaacctgc acagaacctt cgaccctcac | 600 |
| ttcctgagag tgccttgctg aagatcacc ctgtttgtga tcgtgcccgt gctgggcccc | 660 |
| ctggtcgccc tgatcatctg ctacaactgg ctgcaccgga gactggctgg ccagtttctc | 720 |
| gaggaactgc tgttccacct ggaagctctg agcggctga | 759 |

<210> SEQ ID NO 75
<211> LENGTH: 759
<212> TYPE: DNA
<213> ORGANISM: Homo sapiens

<400> SEQUENCE: 75

| | |
|---|---:|
| atggcgtcat tgtcccggcc gagtcttcct agttgcctct gcagttttct tttgcttctg | 60 |
| ctgttgcaag tcagcagcag ctacgccggg cagtttagag tgattggccc aagacatccc | 120 |
| attagggcac tggtgggaga cgaggtcgaa cttccgtgta aataagtcc cggaaaaaac | 180 |
| gctacaggta tggaggtggg ctggtatcgc ccgccattca gtcgcgtagt gcatctctat | 240 |
| agaaacggca aggatcagga tggcgaccag gcccctgagt accgaggccg gaccgaactg | 300 |
| ctgaaagacg caataggcga aggcaaggta acgctcagaa taaggaacgt gcggtttagc | 360 |
| gacgagggcg gctttacatg ctttttccgc gatcattcat accaggagga agcagcaatg | 420 |
| gagcttaaag tcgaagatcc tttttattgg gtaagcccag gtgtactggt tctgcttgct | 480 |
| gtacttccgg ttctcctgct tcaaattacg gtcgggctta tctttctctg ccttcaatac | 540 |
| agattgcgag gaaaactcag gcggagatc gaaaaccttc accgaacatt tgacccgcac | 600 |
| tttctcaggg tgccctgctg gaagatcaca cttttgtta tagtccccgt gttgggtccg | 660 |
| cttgtggcac tgataatctg ttataactgg ttgcacagaa ggctcgcagg acaattcttg | 720 |
| gaggaattgc ttttccacct tgaggcgttg tccggctaa | 759 |

<210> SEQ ID NO 76
<211> LENGTH: 759
<212> TYPE: DNA
<213> ORGANISM: Homo sapiens

<400> SEQUENCE: 76

| | |
|---|---:|
| atggcgtctc tttctcgacc aagccttcct tcatgtctct gcagcttttt gcttctgctt | 60 |
| ctccttcagg tcagctcatc ctacgcagga cagtttcgcg tgattggtcc cagacaccca | 120 |
| atccgagcat tggtgggcga tgaggtcgag ctccccctgta ggatcagccc tggaaaaaat | 180 |
| gcaacaggaa tggaagtagg ctggtatagg ccgccatttt ctcgcgttgt gcatctctac | 240 |
| cgcaatggta aagaccagga tggagaccag gctccagagt accgagggag gaccgaactg | 300 |
| ctgaaagatg ccatcggtga gggaaaagtt acgcttagaa taaggaatgt ccgattctct | 360 |
| gacgaaggtg gcttcacctg cttctttcga gaccatagtt accaggaaga ggcggctatg | 420 |
| gaactcaaag ttgaagaccc attttactgg gtctctccgg gcgtactcgt attgctggcc | 480 |
| gttctcccag ttctccttct gcaaattaca gttgggttga tcttttttgtg tctccaatat | 540 |
| cggcttagag gcaaattgag agcagagata gaaaaccttc accggacttt tgatcctcat | 600 |
| ttccttcgag ttccgtgttg gaaaattacc ctctttgtga ttgttccggt gttgggccca | 660 |
| ttggtcgctc ttattatctg ttacaattgg ctgcacagac gactggcagg tcagttcctg | 720 |
| gaagaactgc tgttccacct ggaggcattg tctggctaa | 759 |

<210> SEQ ID NO 77
<211> LENGTH: 759
<212> TYPE: DNA
<213> ORGANISM: Homo sapiens

<400> SEQUENCE: 77

| | | | | | |
|---|---|---|---|---|---|
| atggcttcat | tgtcacggcc | gtccctcccc | tcatgtcttt | gtagtttcct | tttgctgctt | 60 |
| cttttgcagg | tttcctcttc | ctacgcagga | cagttccgcg | tcatagggcc | aaggcacccg | 120 |
| attcgcgcac | tggtaggcga | tgaagtggaa | ctcccgtgcc | ggatctcacc | cggcaagaac | 180 |
| gccactggga | tggaagttgg | ttggtatagg | ccccgttttt | ctagggtggt | acacttgtac | 240 |
| cgcaacggaa | aagaccaaga | tggcgaccag | gcaccagagt | accggggtag | aactgaactc | 300 |
| ctgaaggacg | caatagggga | gggtaaggta | acgctgagga | taaggaatgt | gcgattctca | 360 |
| gatgaaggcg | gatttacttg | tttctttagg | gaccactcct | accaggagga | agcagccatg | 420 |
| gagcttaagg | tcgaggaccc | cttctattgg | gtatcccctg | gtgtcctcgt | gcttctggcc | 480 |
| gtacttccgg | tattgctctt | gcaaattacg | gtggggttga | ttttcctttg | tcttcaatac | 540 |
| aggctccggg | gaaaacttcg | agctgagatc | gagaatttgc | atcgcacttt | tgacccgcac | 600 |
| tttctccgag | tgccatgctg | gaaaattaca | ctcttcgtga | tagtacctgt | cttgggccca | 660 |
| tggtggcgc | tcattatctg | ttataattgg | ctgcatagac | gactcgccgg | gcagtttctc | 720 |
| gaagagcttt | tgtttcacct | tgaagccctg | agcggctaa | | | 759 |

<210> SEQ ID NO 78
<211> LENGTH: 690
<212> TYPE: DNA
<213> ORGANISM: Homo sapiens

<400> SEQUENCE: 78

| | | | | | |
|---|---|---|---|---|---|
| atggcaagct | tatcaagacc | ctctctgccc | agctgcctct | gctccttcct | cctcctcctc | 60 |
| ctcctccaag | tgtcttccag | ctatgcaggg | cagttcagag | tgataggacc | aagacaccct | 120 |
| atccgggctc | tggtcgggga | tgaagtggaa | ttgccatgtc | gcatatctcc | tgggaagaac | 180 |
| gctacaggca | tggaggtggg | gtggtaccgc | cccccttct | ctagggtggt | tcatctctac | 240 |
| agaaatggca | aggaccaaga | tggagaccag | gcacctgaat | atcggggccg | acagagctg | 300 |
| ctgaaagatg | ctattggtga | gggaaaggtg | actctcagga | tccggaatgt | aaggttctca | 360 |
| gatgaaggag | gtttcacctg | cttcttccga | gatcattctt | accaagagga | ggcagcaatg | 420 |
| gaattgaaag | tagaagatcc | tttctactgg | gtgagccctg | gagtgctggt | tctcctcgcg | 480 |
| gtgctgcctg | tgctcctcct | gcagatcact | gttggcctca | tcttcctctg | cctgcagtac | 540 |
| agactgagag | gaaaacttcg | agcagagata | gagaatctcc | accggacttt | tgagtccttt | 600 |
| ggtgttctag | accccaggt | taaggaacca | aaaaagacag | ggcaattcct | tgaagagcta | 660 |
| ctcttccacc | tggaagccct | ctctggctaa | | | | 690 |

<210> SEQ ID NO 79
<211> LENGTH: 690
<212> TYPE: DNA
<213> ORGANISM: Homo sapiens

<400> SEQUENCE: 79

| | | | | | |
|---|---|---|---|---|---|
| atggccagcc | tgtctagacc | cagcctgcct | agctgcctgt | gcagctttct | gctgctgctg | 60 |
| ctgctgcagg | tgtctagctc | ttacgccggc | cagttccggg | tgatcggccc | tagacacccc | 120 |
| atccgggccc | tggtgggaga | tgaggtggaa | ctgccgtgca | gaatcagccc | tggaaagaac | 180 |

```
gccacaggca tggaagtggg ctggtataga cctccttta gcagagtggt gcacctgtac      240
agaaatggca aggatcagga cggcgaccag gcccctgagt accggggcag aaccgagctg      300
ctgaaggacg ccatcggaga aggcaaggtg acactgcgga tcagaaacgt gcggttcagc      360
gacgagggcg gcttcacctg cttcttcaga gatcacagct accaggagga agccgctatg      420
gaactgaaag tcgaggaccc cttctactgg gtgtcccctg gcgtgctcgt gctgctggcc      480
gtgctgcctg tgctgctgct gcaaatcacc gtgggcctga tcttcctgtg tctgcagtac      540
agactgagag gcaaactgag agccgagatc gagaacctgc accggacctt cgagagcttc      600
ggcgtgttgg gcccccaggt taaggaacct aagaagaccg ccagtttcct ggaagagctg      660
ctcttccacc tggaagctct gagcggctga                                        690

<210> SEQ ID NO 80
<211> LENGTH: 690
<212> TYPE: DNA
<213> ORGANISM: Homo sapiens

<400> SEQUENCE: 80
atggcatcct tgtctcgccc gagcctcccg agttgcctct gttccttcct tctcctcctc      60
ttgctccagg tcagttcaag ttatgcaggc cagttccggg tcatcggacc acgacacccc     120
atcagggcct tggtaggaga cgaagtagag ttgccatgtc gcatctcacc tggtaaaaat     180
gcgaccggga tggaagtcgg ttggtatcga ccaccgttct ccagggtcgt gcatttgtat     240
aggaacggta aggatcagga tggtgaccag gccccagagt acagggtcg cacggaactc     300 ttgaaagacg cgattgggga aggaaaggtt actttgcgga tccggaatgt cagatttcc     360 gatgagggag gctttacgtg ttttttcgg gatcacagtt accaggaaga agcggcaatg      420
gaactcaagg tagaagaccc cttttattgg gtctctcctg gagtattggt cctgctggca      480
gttcttcctg tacttctctt gcagatcacg gtgggactca tttttctgtg tttgcagtat      540
cgacttcgag gaaagctccg agcagagatt gagaatcttc accggacctt tgagagtttt      600
ggggttcttg gtcctcaggt gaaggaacca aaaaaaacgg gcaattttct tgaggaattg      660
ctcttccact tggaagctct ctctggttaa                                        690

<210> SEQ ID NO 81
<211> LENGTH: 690
<212> TYPE: DNA
<213> ORGANISM: Homo sapiens

<400> SEQUENCE: 81
atggcaagtc tttcaagacc ctctctccca agttgtctgt gctcattcct tctgttgctt      60
ttgctccagg taagctccag ctatgcgggg cagttcaggg taattggccc cgacatccg     120 attcgagcac tcgttggcga tgaagttgaa ctcccttgcc gcataagccc cggtaaaaac     180
gcgacaggga tggaagtcgg gtggtatcgg cctccgtttt caagggttgt tcatctctac     240
aggaacggta aggaccaaga tggggatcag gcgcctgagt accgaggcag aaccgaactg     300
ctcaaagacg ccatcggaga agggaaggtg acactgcgga taagaaatgt tcggttcagt      360
gatgagggag gtttacctg tttctttagg gatcatagct accaagaaga ggcagccatg      420
gaactcaagg ttgaagatcc gttctactgg gtttcaccgg gtgttctggt cctcttggcc      480
gtcctcccgg tgttgcttct gcagataact gtcggtctca tctttctctg tcttcaatat      540
aggttgaggg gaaaacttcg cgccgaaatt gagaatctgc atcgcacttt cgagagtttc      600
ggggttctcg gccgcaagt gaaagagcct aagaagactg ggcaatttct tgaggagttg      660
```

```
ctgtttcacc tcgaggcatt gtcaggataa                                      690
```

<210> SEQ ID NO 82
<211> LENGTH: 690
<212> TYPE: DNA
<213> ORGANISM: Homo sapiens

<400> SEQUENCE: 82

```
atggcatctc tctctcgccc gagccttcca tcctgcttgt gctctttct gctcctcctg      60
cttcttcaag tgtctagctc atacgcagga cagtttcggg ttataggtcc gaggcacccg    120
atccgagccc tcgtgggcga tgaggtcgaa ctcccgtgtc gcatcagtcc aggaaaaaac    180
gcgacaggga tggaggttgg gtggtaccgg ccgccattct caagagtagt tcacctttac    240
aggaatggca aagaccagga tggtgatcaa gctccagaat accgaggtag gactgagttg    300
ttgaaggatg cgataggga aggaaaagtg accctgcgga ttagaaacgt gcgattcagt    360
gatgaaggag gattcacatg cttctttagg gatcactctt accaagagga agccgcgatg    420
gagttgaagg tcgaagaccc cttttattgg gtttctcctg gcgtgcttgt actgttggca    480
gtccttccag tcttgctgct tcagataacg gttggtctga tatttctttg tcttcaatac    540
cggctcagag gaaaactgcg cgctgagata gagaatttgc acagaacatt cgagtcattt    600
ggagttctgg gtccgcaagt caaagaaccc aagaaaactg ggcagttcct tgaggaattg    660
ctctttcacc tggaagcgct ctcagggtaa                                      690
```

<210> SEQ ID NO 83
<211> LENGTH: 642
<212> TYPE: DNA
<213> ORGANISM: Homo sapiens

<400> SEQUENCE: 83

```
atggcaagct tatcaagacc ctctctgccc agctgcctct gctccttcct cctcctcctc      60
ctcctccaag tgtcttccag ctatgcaggg cagttcagag tgataggacc aagacacccct   120
atccgggctc tggtcgggga tgaagtggaa ttgccatgtc gcatatctcc tgggaagaac    180
gctacaggca tggaggtggg gtggtaccgc cccccttct ctagggtggt tcatctctac      240
agaaatggca aggaccaaga tggagaccag gcacctgaat atcggggccg gacagagctg    300
ctgaaagatg ctattggtga gggaaggtg actctcagga tccggaatgt aaggttctca    360
gatgaaggag gtttcacctg cttcttccga gatcattctt accaagagga ggcagcaatg    420
gaattgaaag tagaagatcc tttctactgg gtgagccctg gagtgctggt tctcctcgcg    480
gtgctgcctg tgctcctcct gcagatcact gttggcctca tcttcctctg cctgcagtac    540
agactgagag gaaaacttcg agcagagata gagaatctcc accggacttt tgggcaattc    600
cttgaagagc tactcttcca cctggaagcc ctctctggct aa                        642
```

<210> SEQ ID NO 84
<211> LENGTH: 642
<212> TYPE: DNA
<213> ORGANISM: Homo sapiens

<400> SEQUENCE: 84

```
atggccagcc tgagccggcc tagcctgccc agctgcctgt gcagcttcct gctgctgctg      60
ctgctgcagg tgtccagcag ctacgccgga cagtttagag tgatcggtcc tagacacccc    120
atccgggccc tggtgggcga tgaggtggaa ctgccgtgca gaatcagccc tggaaagaac    180
```

| | | |
|---|---|---|
| gccaccggca tggaagtggg atggtacaga ccccccttta gcagagtggt gcacctgtac | 240 | |
| cggaacggca aggatcagga cggcgaccag gcccctgagt accggggcag aacagagctg | 300 | |
| ctgaaggacg ccatcggcga gggcaaagtg acactgcgga tcagaaacgt gcggttcagc | 360 | |
| gacgagggag gcttcacctg cttcttcaga gatcactctt atcaggagga agccgctatg | 420 | |
| gaactcaagg tcgaggaccc cttctactgg gtgtctcctg gcgtgctggt cctgctggcc | 480 | |
| gtgctgcctg tgctgctgct tcaaatcacc gtgggcctga tcttcctctg tctgcagtac | 540 | |
| agactgagag gcaagctgag agccgagatc gagaacctgc acagaacctt cggccagttc | 600 | |
| ctggaagagc tgctcttcca cctggaagct ctgtccggct ga | 642 | |

<210> SEQ ID NO 85
<211> LENGTH: 642
<212> TYPE: DNA
<213> ORGANISM: Homo sapiens

<400> SEQUENCE: 85

| | | |
|---|---|---|
| atggcatcac tcagtagacc ctctctgcca tcatgcttgt gctctttcct tttgctgctg | 60 | |
| ctgttgcaag tctcttcatc ttatgcgggc cagtttcggg taataggtcc tagacacccc | 120 | |
| atccgggctc tggtgggcga tgaagtagag ttgccttgcc ggatctcacc gggaaaaaac | 180 | |
| gctacaggta tggaggtggg ttggtatcgg ccgccgttca gccgcgttgt gcatctgtac | 240 | |
| cgaaatggta aagatcaaga cggcgatcag gccccggagt accggggtcg cacagaactg | 300 | |
| ctcaaggacg ctatcgggga gggcaaagtc acactcagaa tacggaatgt cagattctct | 360 | |
| gatgaaggtg gattccacctg tttcttttcga gatcatagtt accaagaaga agctgcaatg | 420 | |
| gaactgaagg tcgaagatcc gttctattgg gtttcaccgg gcgtcctcgt cttgctggcc | 480 | |
| gtactgccag tattgttgct ccaaataacg gttggtctca ttttcttgtg tctccaatat | 540 | |
| agattgcggg gaaagctccg agcagaaatt gagaacctcc atagaacatt cggcaattc | 600 | |
| ctcgaagaac ttctctttca cttggaggcg ttgagcggtt aa | 642 | |

<210> SEQ ID NO 86
<211> LENGTH: 642
<212> TYPE: DNA
<213> ORGANISM: Homo sapiens

<400> SEQUENCE: 86

| | | |
|---|---|---|
| atggcgtctc ttagtcgccc tagcttgcct tcctgtctgt gctcatttct ccttcttctt | 60 | |
| cttttgcagg tgtcttcttc ttacgccggg cagtttaggg tgatcggtcc aagacatccg | 120 | |
| ataagagccc tcgttggtga cgaagtagag ctgccctgtc gcatctcccc aggaaaaaac | 180 | |
| gccaccggta tggaggttgg gtggtaccga ccgccttta gtcgagtagt ccatctctac | 240 | |
| agaaatggca aagatcagga tggggatcaa gcccctgaat accgagggag gacagagctt | 300 | |
| ctcaaggacg ccattgggga gggtaaagtc acgcttcgaa tcaggaacgt gagattcagt | 360 | |
| gatgagggcg gatttacttg tttcttcagg gatcactctt atcaggaaga agccgccatg | 420 | |
| gagctgaaag tcgaagaccc tttctactgg gttagccccg gagtgctggt gcttctcgcc | 480 | |
| gtacttccgg tccttttgct ccagataaca gttggtctga tctttctttg ccttcaatat | 540 | |
| aggctcaggg gaaaattgcg agccgaaatc gaaaatcttc ataggacatt cggacaattc | 600 | |
| ttggaagaat tgcttttttca tcttgaggcc cttttccggat aa | 642 | |

<210> SEQ ID NO 87
<211> LENGTH: 642

```
<212> TYPE: DNA
<213> ORGANISM: Homo sapiens

<400> SEQUENCE: 87
atggcttctc tcagtcggcc ctctcttccg tcctgcctct gttcctttct tttgctcttg    60
ctgcttcagg tgagtagctc atacgccggc caattccggg tcatcggacc tcggcatcca   120
atcagggcgt tggttggaga tgaggtagag ttgccttgca ggataagtcc tggcaagaat   180
gcgaccggaa tggaagtggg ttggtataga ccccctttt cacgggtagt acacttgtat    240
aggaacggca agaccagga cggcgaccag gcgcccgagt atcgaggtcg aaccgaattg    300
ctcaaagatg cgatcggaga gggaaaagta acccttcgca tacggaatgt gcggttctct   360
gatgaagggg gcttcacgtg cttctttcgg gaccatagtt atcaggaaga ggccgcaatg   420
gagcttaagg ttgaggaccc tttctactgg gtatccccag gcgtattggt attgcttgcc   480
gtgctccctg tgcttctcct gcaaattacg gtgggtctta ttttcctttg cctgcaatac   540
cggcttcgcg ggaaacttag agcagaaatt gaaaatctgc accgcacttt cggccaattc   600
ctggaagaat tgctgtttca cctggaagcc ctctcaggtt aa                      642

<210> SEQ ID NO 88
<211> LENGTH: 888
<212> TYPE: DNA
<213> ORGANISM: Homo sapiens

<400> SEQUENCE: 88
atggcaagct tatcaagacc ctctctgccc agctgcctct gctccttcct cctcctcctc   60
ctcctccaag tgtcttccag ctatgcaggg cagttcagag tgataggacc aagacaccct   120
atccgggctc tggtcgggga tgaagtggaa ttgccatgtc gcatatctcc tgggaagaac   180
gctacaggca tggaggtggg gtggtaccgc ccccccttct ctagggtggt tcatctctac   240
agaaatggca aggaccaaga tggagaccag gcacctgaat atcggggccg acagagctg    300
ctgaaagatg ctattggtga gggaaaggtg actctcagga tccggaatgt aaggttctca   360
gatgaaggag gtttcacctg cttcttccga gatcattctt accaagagga ggcagcaatg   420
gaattgaaag tagaagatcc tttctactgg gtgagccctg gagtgctggt tctcctcgcg   480
gtgctgcctg tgctcctcct gcagatcact gttggcctca tcttcctctg cctgcagtac   540
agactgagag gaaaacttcg agcagagata gagaatctcc accggacttt tgatccccac   600
tttctgaggg tgccctgctg gaagataacc ctgtttgtaa ttgtgccggt tcttggaccc   660
ttggttgcct tgatcatctg ctacaactgg ctacatcgaa gactagcagg gcaattcctt   720
gaagagctac gtaagttctc ttctctctgt tataagcaga gaataaaaag ccaggaaagg   780
gagacagaag caacaagagg aagaggcggg ctattgaggg atcacattcc cagaggaaag   840
gaggagctgg agagcctggg tggagggaag actcctcctg ggaggtag                888

<210> SEQ ID NO 89
<211> LENGTH: 888
<212> TYPE: DNA
<213> ORGANISM: Homo sapiens

<400> SEQUENCE: 89
atggccagct tgtctagacc cagcctgcct agctgcctgt gcagcttcct gctgctgctg    60
cttctgcaag tgtcttctag ctacgccgga cagttcagag ttatcggccc tagacacccc   120
atccgggccc tggtcggcga tgaggttgag ctgccctgta gaatcagccc tggcaaaaac   180
```

```
gccaccggca tggaagtggg ctggtacaga cctccttta gcagagtggt gcacctgtac    240
agaaacggca aggatcagga cggcgaccag gcccctgagt accggggcag aacagagctg    300
ctgaaagacg ccatcggaga aggcaaggtg accctgcgga tcagaaatgt gcggttcagc    360
gacgagggcg gcttcacatg cttcttccgg gaccacagct accaggagga agctgctatg    420
gaactgaagg tcgaggaccc tttctactgg gtgtcccctg agtgctggt gctgctggcc    480 gtgctgcctg tgctgctgct gcagatcacc gtgggtctta tcttcctgtg cctgcagtac    540
cggctgcggg gcaagctgag agccgagatc gagaacctgc acagaacctt cgaccccac    600 ttcctgaggg tgccttgctg aagatcacc ctgttcgtga tcgtgccgt gctgggacct    660 ctggtggccc tgatcatctg ctacaactgg ctgcaccgga ctggccgg ccagtttctt    720 gaggaactga gaaagttcag cagcctgtgt acaagcaga gaatcaagag ccaggagaga    780
gagacagagg ccacaagagg ccggggaggc ctgctcagag atcacatccc cagaggcaaa    840
gaggaactcg agagcctggg cggaggcaag acccctccag gcagatga              888

<210> SEQ ID NO 90
<211> LENGTH: 888
<212> TYPE: DNA
<213> ORGANISM: Homo sapiens

<400> SEQUENCE: 90
atggcttcat tgagtaggcc ctctcttcct tcctgtctgt gttcatttct gctgcttctt     60
ctcctccaag tgagttcctc ctatgcgggc caatttcggg ttatagggcc tcgacacccg    120
atccgagccc tcgtaggaga cgaagttgag cttccatgtc gcataagtcc ggggaaaaat    180
gccacaggaa tggaagttgg atggtataga cctccttta gccgcgttgt gcacctctac    240
agaaacggaa aagaccagga tggggatcaa gcgccggagt atcgaggtcg gactgaactg    300
ctgaaagatg caataggga aggtaaggtc acgcttagaa ttcggaatgt gcgcttctcc    360
gatgaaggtg gcttcacttg cttttttccga gaccacagct accaggagga ggcagcgatg    420
gagcttaaag tcgaagatcc gttttactgg gtatcacctg gggtcttggt tcttctcgct    480
gtccttccgg tgctgttgct tcaaatcacc gtcggattga tttttctttg tctccagtac    540
cgcctccgcg gcaagctcag agctgaaatt gaaaacctcc ataggacttt tgatcccac    600 ttccttcggg tgccatgctg gaaaataaca ttgttcgtta tcgttccggt gcttggcccg    660
ctcgtcgcct tgattatctg ctacaactgg ctgcacaggc gcctggcggg tcaattcttg    720
gaggagctca gaaatttag ttccctgtgc tacaagcaaa ggataaaatc tcaagaacgg    780
gagaccgaag caacacgggg tcgaggtggg ctgttgcggg accatatccc cagaggtaaa    840
gaggaacttg aaagtcttgg tggcgggaag acaccccgg gtaggtag                 888

<210> SEQ ID NO 91
<211> LENGTH: 888
<212> TYPE: DNA
<213> ORGANISM: Homo sapiens

<400> SEQUENCE: 91
atggcttccc tctctcgccc gagtctccct agttgtcttt gctcctttct cttgctgctc     60
ttgttgcaag tctcatcttc ttacgccggg cagtttaggg taatcggccc gcggcacccg    120
atacgcgctc ttgttgggga tgaggtagag ttgccgtgta ggatttcccc tggtaaaaac    180
gctactggta tggaagtagg atggtataga ccccgtttta gccgggtagt ccatctttac    240
cgaaacggaa aagatcaaga tggtgaccaa gcgccggaat accgcggccg aactgagttg    300
```

```
ctgaaagacg caatcggtga gggtaaagtt accctcagaa ttagaaacgt cagattttcc    360
gatgaggggg gcttcacctg ttttttcagg gaccatagtt accaagagga agcagctatg    420
gagctgaagg tagaagatcc gttctattgg gtaagtccag gtgtattggt gctgctcgcc    480
gtattgcctg ttctcctcct ccaaattacg gtggggttga tattcttgtg cttgcagtat    540
aggttgcgag gtaagctccg agccgagatc gagaatctcc acaggacgtt tgaccctcac    600
ttccttcgag taccatgctg gaagataacc ctcttcgtta ttgttcctgt tttgggcccc    660
ctcgtcgctc tcataatctg ctacaattgg ctgcatagga gacttgctgg gcagttcctg    720
gaagaactcc ggaaatttag cagtttgtgt tacaagcaga ggataaaatc tcaagagagg    780
gagaccgaag caaccagggg ccgggggtggc cttttgaggg atcacattcc gcgaggaaaa    840
gaggagctcg aaagccttgg gggcggaaag accccgccgg gtagatag                 888
```

\<210\> SEQ ID NO 92
\<211\> LENGTH: 888
\<212\> TYPE: DNA
\<213\> ORGANISM: Homo sapiens

\<400\> SEQUENCE: 92

```
atggcaagtt tgtcccgccc ttcattgcct agctgtctgt gttctttttct ccttttgctg    60 cttcttcagg ttagtagtag ttacgccggg cagtttcgcg tgatcgggcc aagacatcct    120
atacgcgcat tggtaggtga cgaagtcgaa ctcccatgca gaatctcccc tggaaaaaac    180
gcgaccggga tggaggtggg ctggtaccga ccccccttct ctcgggtggt ccatttgtac    240
cggaacggta agaccaagat gggaccag gctcccgagt accggggcg aactgagttg        300 cttaaagacg caattggaga gggtaaagta acgttgcgga ttagaaatgt gagattttcc    360
gatgaaggtg gatttacgtg tttctttcga gaccattcct atcaggaaga agctgccatg    420
gagttgaaag tggaggatcc attttactgg gttagtccag gcgtgctcgt acttctggct    480
gttctgcccg tacttcttct gcaaatcacc gtaggtctta tctttctgtg tttgcagtat    540
aggcttcgag gcaagctcag ggctgaaata gagaatctcc ataggacatt tgaccctcac    600
tttctgcggg tgcctgttg gaagatcacc ttgttcgtaa tcgtgccagt cctttggacca   660 ttggtagcac tcataatatg ttacaattgg ctccataggc gactggccgg acaattcttg    720
gaggaactgc gcaagttcag cagcttgtgt tataaacaac gaattaaatc ccaggagaga    780
gagacggaag caactagagg tcgaggcggc ctgctccgag atcacatacc gagaggtaaa    840
gaagaattgg agtcacttgg tggaggaaaa acgcccccgg gtcggtag                  888
```

\<210\> SEQ ID NO 93
\<211\> LENGTH: 483
\<212\> TYPE: DNA
\<213\> ORGANISM: Homo sapiens

\<400\> SEQUENCE: 93

```
atggcatcac aaaaaagacc cagtcagcgc cacggcagta agtacctggc tacagcgagt    60
acgatggatc acgctcgaca cgggttcttg ccgcggcatc gagacacagg cattttggat    120
tctatcggga ggttttttcgg tggggaccga ggtgctccga agcgcggcag cggcaaggac    180
agtcatcatc cggcgagaac cgcgcactat ggcagtttgc cgcaaaaaag tcacggtaga    240
acccaagacg agaatcctgt tgttcacttt ttcaaaaaca ttgtgacgcc acgaacacca    300
cccccgtctc aagggaaggg tgcggaaggc cagcgccctg gtttcggata cggaggccgg    360
```

| | |
|---|---|
| gcttcagatt acaaatccgc tcataaaggg ttcaagggtg tggatgccca ggggactttg | 420 |
| tctaaaattt tcaaattggg aggacgggat tcaagatcag gctccccaat ggcccgacgg | 480 |
| tga | 483 |

<210> SEQ ID NO 94
<211> LENGTH: 834
<212> TYPE: DNA
<213> ORGANISM: Homo sapiens

<400> SEQUENCE: 94

| | |
|---|---|
| atgggactgc tggaatgctg cgcccggtgc ctggttggag ccccttttcgc cagcctggtg | 60 |
| gccacaggcc tgtgcttctt cggagtggcc cttttctgcg gttgtggaca cgaggccctg | 120 |
| accggcacgg aaaagctgat cgagacatat ttcagcaaga actaccagga ctacgagtac | 180 |
| ctgatcaacg tgatccacgc cttttcagtac gtgatctacg gcaccgccag cttcttcttt | 240 |
| ctgtacggcg ccctgctgct ggccgagggc ttctacacca ccggcgccgt gcggcagatc | 300 |
| ttcggcgact acaagaccac aatctgcggc aagggcctga cgccacagt gaccggcggc | 360 |
| cagaaaggca gaggcagcag aggacaacac caggcccact ctctcgagag agtgtgccac | 420 |
| tgcctgggaa agtggctggg ccaccctgat aagttcgtgg gaatcaccta cgccctgacc | 480 |
| gtggtgtggc tgctggtgtt cgcttgttct gctgttcctg tgtacatcta cttcaacacc | 540 |
| tggaccacct gccagagcat cgccttcccc agcaaaacca gcgcctctat aggaagcctc | 600 |
| tgtgccgacg ccagaatgta cggcgtgctg ccttggaacg cctttccagg caaagtgtgt | 660 |
| ggcagcaacc tgctctccat ctgcaagacc gccgaattcc agatgacctt ccacctgttc | 720 |
| atcgccgctt ttgtgggcgc tgccgctaca ctggtcagcc tgctgacatt catgatcgcc | 780 |
| gccacctaca acttcgccgt gctgaagctg atgggcagag gcacaaagtt ctga | 834 |

<210> SEQ ID NO 95
<211> LENGTH: 834
<212> TYPE: DNA
<213> ORGANISM: Homo sapiens

<400> SEQUENCE: 95

| | |
|---|---|
| atgggactgc tggagtgctg cgcccggtgc ctggttggag ccccttttcgc cagcctggtg | 60 |
| gccacaggcc tgtgcttctt cggagtggcc cttttctgcg gttgtggaca cgaggccctg | 120 |
| accggcacgg aaaagctgat cgagacatat ttcagcaaga actaccagga ctacgagtac | 180 |
| ctgatcaacg tgatccacgc cttttcagtac gtgatctacg gcaccgccag cttcttcttt | 240 |
| ctgtacggcg ccctgctgct ggccgagggc ttctacacca ccggcgccgt gcggcagatc | 300 |
| ttcggcgact acaagaccac aatctgcggc aagggcctga cgccacagt gaccggcggc | 360 |
| cagaaaggca gaggcagcag aggacaacac caggcccact ctctcgagag agtgtgccac | 420 |
| tgcctgggaa agtggctggg ccaccctgat aagttcgtgg gaatcaccta cgccctgacc | 480 |
| gtggtgtggc tgctggtgtt cgcttgttct gctgttcctg tgtacatcta cttcaacacc | 540 |
| tggaccacct gccagagcat cgccttcccc agcaaaacca gcgcctctat aggaagcctc | 600 |
| tgtgccgacg ccagaatgta cggcgtgctg ccttggaacg cctttccagg caaagtgtgt | 660 |
| ggcagcaacc tgctctccat ctgcaagacc gccgaattcc agatgacctt ccacctgttc | 720 |
| atcgccgctt ttgtgggcgc tgccgctaca ctggtcagcc tgctgacatt catgatcgcc | 780 |
| gccacctaca acttcgccgt gctgaagctg atgggcagag gcacaaagtt ctga | 834 |

<210> SEQ ID NO 96
<211> LENGTH: 834
<212> TYPE: DNA
<213> ORGANISM: Homo sapiens

<400> SEQUENCE: 96

| | | | | | |
|---|---|---|---|---|---|
| atgggctcc | ttgagtgttg | cgcgcgatgt | cttgttgggg | cgccatttgc | gagcctcgta | 60 |
| gccacgggac | tctgcttttt | cggcgtggca | ctcttttgtg | gctgtgggca | cgaggccctg | 120 |
| actggcactg | aaaagctcat | agagacttat | ttcagcaaga | attaccaaga | ctacgaatac | 180 |
| ctcatcaatg | tgattcacgc | gtttcagtat | gttatttatg | gaaccgcgtc | cttttttcttt | 240 |
| ctgtacgggg | ctttgctcct | tgctgaaggc | ttttacacta | cggggctgt | ccggcagata | 300 |
| tttggagact | ataagactac | catttgcgga | aagggattga | gcgctaccgt | tacagggggc | 360 |
| cagaaagggc | gaggatcacg | aggccaacat | caggcgcact | ctctggaaag | agtatgccat | 420 |
| tgcctgggta | agtggctggg | acatccagat | aaatttgtag | gaataaccta | tgccctcact | 480 |
| gttgtgtggt | tgcttgtttt | tgcctgttct | gccgtacctg | tttatatcta | tttcaacacc | 540 |
| tggacaactt | gccaatctat | agcctttccc | tccaagacat | ctgccagcat | cggctctctg | 600 |
| tgcgctgatg | ccaggatgta | tggcgtcttg | ccttggaatg | ccttccctgg | gaaagtatgt | 660 |
| gggtcaaacc | ttctgagcat | ttgtaaaacg | gcagagtttc | agatgacgtt | tcatcttttt | 720 |
| atagcggcgt | tcgttggcgc | cgctgctacg | ctcgtttccc | ttctcacttt | tatgatagct | 780 |
| gcaacgtata | attttgcggt | tttgaagctc | atgggccgag | gcactaaatt | ttga | 834 |

<210> SEQ ID NO 97
<211> LENGTH: 834
<212> TYPE: DNA
<213> ORGANISM: Homo sapiens

<400> SEQUENCE: 97

| | | | | | |
|---|---|---|---|---|---|
| atgggtctcc | ttgagtgttg | tgctcggtgt | cttgtcggtg | cacccttcgc | gtccttggtg | 60 |
| gcgacaggtc | tgtgcttttt | cggtgtggca | ctgttttgtg | gttgcgggca | cgaggctctg | 120 |
| acaggtacgg | agaaactgat | cgagacttac | ttctctaaaa | attaccaaga | ttacgagtac | 180 |
| ctcataaacg | taattcacgc | attccagtac | gtcatatacg | ggactgcgtc | ttttttcttc | 240 |
| ttgtacggcg | ccttgctcct | tgcggaaggg | ttttatacta | ccggggcagt | acgacagatt | 300 |
| ttcggcgatt | acaaaacaac | aatctgcgga | aagggactga | gtgcaaccgt | taccggaggc | 360 |
| caaaaaggac | ggggttcaag | aggccaacac | caggcacaca | gcctggagcg | ggtatgccac | 420 |
| tgcttgggga | agtggctcgg | gcatcctgac | aagtttgttg | gaataactta | tgccttgacc | 480 |
| gtcgtctggc | tgctcgtctt | tgcctgtagc | gcagttccag | tgtacatcta | cttcaacaca | 540 |
| tggaccactt | gccagtccat | cgcgttccca | tcaaagacaa | gcgcgtcaat | cgggtcactg | 600 |
| tgcgcagatg | cccgcatgta | cggagtgttg | ccctggaacg | ccttccccgg | gaaagtatgc | 660 |
| ggaagcaatc | tcttgtctat | ttgtaagaca | gcggaattcc | agatgacatt | ccactttttt | 720 |
| atcgcagcgt | ttgtcggcgc | cgccgcgacg | cttgtctctt | tgttgacatt | tatgattgcc | 780 |
| gcgacataca | attttgctgt | gctgaagttg | atgggcagag | gcacgaaatt | ctga | 834 |

<210> SEQ ID NO 98
<211> LENGTH: 834
<212> TYPE: DNA
<213> ORGANISM: Homo sapiens

<400> SEQUENCE: 98

| | | |
|---|---|---|
| atggggctct tggagtgctg tgccagatgc ctcgttggtg ccccatttgc aagcctggtg | 60 | |
| gcaaccggac tctgcttctt tggtgtagca ctgttttgcg gctgtggtca tgaggctctc | 120 | |
| acgggaacag aaaaattgat cgaaacttat ttctccaaga attaccagga ctatgagtac | 180 | |
| ctcataaacg tcatccatgc atttcagtat gtgatttatg ggaccgctag ttttttttt | 240 | |
| ctttacggcg ccctccttct cgccgaagga ttttatacga ccggtgcggt ccgacaaatc | 300 | |
| ttcggagact ataaaactac tatttgtggc aaaggactct cagctaccgt tacgggcgga | 360 | |
| cagaagggcc gaggatcccg cgggcaacac caggcgcact cttggaaag agtctgccat | 420 | |
| tgccttggaa agtggctggg gcacccagat aagttcgtag gcataactta cgccctcact | 480 | |
| gtagtatggt tgctggtttt cgcatgctca gcggtcccag tctacattta ttttaacacc | 540 | |
| tggactacgt gtcaatcaat agcctttccg tccaaaacgt cagcatccat aggttccctg | 600 | |
| tgcgcggacg cgagaatgta tggggtgctg ccgtggaacg cttttcctgg taaggtttgc | 660 | |
| gggagcaatc tgctcagcat ttgtaaaact gcagagttcc agatgacgtt ccatttgttc | 720 | |
| atcgctgcgt ttgtggggc ggcagcgaca ctcgtatccc tgctcacctt tatgattgcc | 780 | |
| gcaacgtata actttgcggt tcttaagctt atgggccggg ggacaaagtt ctga | 834 | |

<210> SEQ ID NO 99
<211> LENGTH: 834
<212> TYPE: DNA
<213> ORGANISM: Homo sapiens

<400> SEQUENCE: 99

| | | |
|---|---|---|
| atggggctct tggagtgctg tgccagatgc ctcgttggtg ccccatttgc aagcctggtg | 60 | |
| gcaaccggac tctgcttctt tggtgtagca ctgttttgcg gctgtggtca tgaggctctc | 120 | |
| acgggaacag aaaaattgat cgaaacttat ttctccaaga attaccagga ctatgagtac | 180 | |
| ctcataaacg tcatccatgc atttcagtat gtgatttacg ggaccgctag ttttttttt | 240 | |
| ctttacggcg ccctccttct cgccgaagga ttttatacga ccggtgcggt ccgacaaatc | 300 | |
| ttcggagact ataaaactac tatttgtggc aaaggactct cagctaccgt tacgggcgga | 360 | |
| cagaagggcc gaggatcccg cgggcaacac caggcgcact cttggaaag agtctgccat | 420 | |
| tgccttggaa agtggctggg gcacccagat aagttcgtag gcataactta cgccctcact | 480 | |
| gtagtatggt tgctggtttt cgcatgctca gcggtcccag tctacattta ttttaacacc | 540 | |
| tggactacgt gtcaatcaat agcctttccg tccaaaacgt cagcatccat aggttccctg | 600 | |
| tgcgcggacg cgagaatgta tggggtgctg ccgtggaacg cttttcctgg taaggtttgc | 660 | |
| gggagcaatc tgctcagcat ttgtaaaact gcagagttcc agatgacgtt ccatttgttc | 720 | |
| atcgctgcgt ttgtggggc ggcagcgaca ctcgtatccc tgctcacctt tatgattgcc | 780 | |
| gcaacgtata actttgcggt tcttaagctt atgggccggg ggacaaagtt ctga | 834 | |

<210> SEQ ID NO 100
<211> LENGTH: 834
<212> TYPE: DNA
<213> ORGANISM: Homo sapiens

<400> SEQUENCE: 100

| | | |
|---|---|---|
| atgggcttgt tagagtgctg tgcaagatgt ctggtagggg ccccctttgc ttccctggtg | 60 | |
| gccactggat tgtgtttctt tggggtggca ctgttctgtg gctgtggaca tgaagccctc | 120 | |
| actggcacag aaaagctaat tgagacctat ttctccaaaa actaccaaga ctatgagtat | 180 | |
| ctcatcaatg tgatccatgc cttccagtat gtcatctatg gaactgcctc tttcttcttc | 240 | |

```
ctttatgggg ccctcctgct ggctgagggc ttctacacca ccggcgcagt caggcagatc    300
tttggcgact acaagaccac catctgcggc aagggcctga gcgcaacggt aacagggggc    360
cagaagggga ggggttccag aggccaacat caagctcatt ctttggagcg ggtgtgtcat    420
tgtttgggaa aatggctagg acatcccgac aagtttgtgg gcatcaccta tgccctgacc    480
gttgtgtggc tcctggtgtt tgcctgctct gctgtgcctg tgtacattta cttcaacacc    540
tggaccacct gccagtctat tgccttcccc agcaagacct ctgccagtat aggcagtctc    600
tgtgctgatg ccagaatgta tggtgttctc ccatggaatg cttttccctgg caaggtttgt    660 ggctccaacc ttctgtccat ctgcaaaaca gctgagttcc aaatgacctt ccacctgttt    720
attgctgcat ttgtggggGC tgcagctaca ctggtttccc tgctcacctt catgattgct    780
gccacttaca actttgccgt ccttaaactc atgggccgag gcaccaagtt ctga         834
```

<210> SEQ ID NO 101
<211> LENGTH: 834
<212> TYPE: DNA
<213> ORGANISM: Homo sapiens

<400> SEQUENCE: 101

```
atgggcctgc tggaatgctg cgcccggtgc ctggtgggcg ccccttttcgc cagcctggtg    60 gccacaggac tgtgcttctt cggcgtggcc ctgttctgcg gctgcggcca cgaggccctg    120
accggcacag agaagctgat cgagacatat ttcagcaaga actaccagga ctacgagtac    180
ctgatcaacg tgatccacgc cttccaatac gtgatctacg gcaccgcctc tttttttcttc    240 ctgtacggcg ctctgctgct ggccgagggc ttctacacca ccggcgccgt gcggcagatc    300
ttcggcgact acaagaccac aatctgcggc aaaggcctgt ctgccaccgt tacaggcggc    360
cagaagggca gaggcagtag aggacagcac caggcccaca gcctggaaag agtgtgccac    420
tgcctgggca gtggctggg acatcctgat aagttcgtgg gcatcaccta cgccctgacc    480
gtggtgtggc tgctggtctt tgcctgcagc gccgtgcctg tgtacatcta cttcaacacc    540
tggaccacct gtcagagcat cgcctttcct agcaagacca cgccagcat cggcagcctc    600 tgtgctgatg ccagaatgta cggagtgctg ccttggaacg ccttccccgg caaggtgtgt    660
ggcagcaacc tgctgagcat ttgtaaaacc gccgaattcc agatgacatt ccacctgttt    720
atcgccgctt ttgtgggagc cgctgctaca ctggtttctc tgctcacctt catgatcgct    780
gccacctaca acttcgccgt gctgaagctg atgggaagag gcactaagtt ctga          834
```

<210> SEQ ID NO 102
<211> LENGTH: 834
<212> TYPE: DNA
<213> ORGANISM: Homo sapiens

<400> SEQUENCE: 102

```
atgggcctgc tggagtgctg cgcccggtgc ctggtgggcg ccccttttcgc cagcctggtg    60 gccacaggac tgtgcttctt cggcgtggcc ctgttctgcg gctgcggcca cgaggccctg    120
accggcacag agaagctgat cgagacatat ttcagcaaga actaccagga ctacgagtac    180
ctgatcaacg tgatccacgc cttccaatac gtgatctacg gcaccgcctc tttttttcttc    240 ctgtacggcg ctctgctgct ggccgagggc ttctacacca ccggcgccgt gcggcagatc    300
ttcggcgact acaagaccac aatctgcggc aaaggcctgt ctgccaccgt tacaggcggc    360
cagaagggca gaggcagtag aggacagcac caggcccaca gcctggaaag agtgtgccac    420
```

```
tgcctgggca agtggctggg acatcctgat aagttcgtgg gcatcaccta cgccctgacc    480
gtggtgtggc tgctggtctt tgcctgcagc gccgtgcctg tgtacatcta cttcaacacc    540
tggaccacct gtcagagcat cgcctttcct agcaagacca gcgccagcat cggcagcctc    600
tgtgctgatg ccagaatgta cggagtgctg ccttggaacg ccttccccgg caaggtgtgt    660
ggcagcaacc tgctgagcat ttgtaaaacc gccgaattcc agatgacatt ccacctgttt    720
atcgccgctt ttgtgggagc cgctgctaca ctggtttctc tgctcacctt catgatcgct    780
gccacctaca acttcgccgt gctgaagctg atgggaagag gcactaagtt ctga           834

<210> SEQ ID NO 103
<211> LENGTH: 834
<212> TYPE: DNA
<213> ORGANISM: Homo sapiens

<400> SEQUENCE: 103
atggggctct tggagtgctg cgccaggtgt ctcgtcggag cgccatttgc ctccttggtg     60
gcaacgggac tttgcttttt cggcgtagcc ctgttttgcg ggtgcggcca tgaagcgttg    120
accggcactg agaagctgat agaaacctat ttctcaaaaa attatcaaga ctacgagtat    180
cttatcaacg tcattcacgc cttcaatat gtgatctacg gtacggctag cttcttttc     240
ctgtatggtg cgctgttgct cgctgaagga ttttacacga caggtgccgt tcggcaaatt    300
tttggcgatt ataaaacgac aatttgtgga aaaggcctct cagctaccgt gactggcggc    360
caaaaaggcc ggggtagcag gggtcagcat caagcacatt ccctcgaacg agtgtgccac    420
tgccttggaa agtggttggg caccccgat aaattcgtgg ggataaccta cgctcttact     480
gttgtttggc tgctcgtgtt cgcctgctct gctgtacctg tgtatatcta ctttaataca    540
tggaccacgt gccaaagtat tgcctttcct agtaagacat ctgcttctat ggatcactc     600
tgcgctgatg cacggatgta tggcgttttg ccgtggaatg ctttccctgg taaagtgtgt    660
ggttccaatc tgttgagtat ttgtaaaaca gcagagttcc agatgacgtt ccacctgttt    720
atcgctgctt ttgttggtgc agcggccacg cttgtcagcc tgttgacttt tatgatagct    780
gctacctaca actttgcggt actcaagctc atggggcgag gcacaaagtt ttga           834

<210> SEQ ID NO 104
<211> LENGTH: 834
<212> TYPE: DNA
<213> ORGANISM: Homo sapiens

<400> SEQUENCE: 104
atggggcttc tcgagtgctg cgctcgctgt ctggttggcg caccttttgc aagccttgta     60
gcgactggct tgtgtttttt cggtgtggca ttgttttgcg ggtgcggtca cgaggcgttg    120
acaggtactg agaagctgat cgagacttac ttctctaaaa attatcaaga ttacgaatac    180
ctgattaacg tgatacacgc tttccagtat gtaatctacg gcacagcgag cttttttcttt   240
ctttatggcg cactgctgct cgcggaagga ttctatacta ctggggcggt tcggcagatc    300
tttggtgatt acaaaacaac aatttgcggt aaaggtcttt ccgcaacagt cactggcggg    360
cagaaggggc gaggaagccg ggggcaacat caggcacact ccttgaaag agtatgccat     420
tgtttgggga atggctggg ccacccggac aaatttgtcg gtatcacata cgcgcttact     480
gttgtttggt tgttggtatt tgcttgttca gctgtcccag tctatatcta ttttaacacc    540
tggaccactt gccaatctat cgcattccct tcaaagacct ctgcgtccat aggctctctt    600
tgtgcagatg ctagaatgta cggcgtattg ccttggaatg cattcccagg taaagtttgc    660
```

```
ggtagtaacc tgcttagcat ttgcaagact gctgaattcc agatgacatt ccacctcttt      720
attgccgcat ttgtaggtgc tgctgccaca ctcgtgtctc tcctgacttt tatgattgcg      780
gcaacgtata acttcgcagt tttgaagctg atggggaggg gtactaaatt ctga            834
```

<210> SEQ ID NO 105
<211> LENGTH: 834
<212> TYPE: DNA
<213> ORGANISM: Homo sapiens

<400> SEQUENCE: 105

```
atggggcttc tcgagtgctg cgctcgctgt ctggttggcg caccttttgc aagccttgta       60
gcgactggct tgtgtttttt cggtgtggca ttgttttgcg ggtgcggtca cgaggcgttg      120
acaggtactg agaagctgat cgagacttac ttctctaaaa attatcaaga ttacgaatac      180
ctgattaacg tgatacacgc tttccagtat gtaatctacg gcacagcgag cttttctttt     240
ctttacggcg cactgctgct cgcggaagga ttctatacta ctggggcggt tcggcagatc      300
tttggtgatt acaaaacaac aatttgcggt aaaggtcttt ccgcaacagt cactggcggg      360
cagaaggggc gaggaagccg ggggcaacat caggcacact ccttggaaag agtatgccat      420
tgtttgggga atggctgggc cacccggac aaatttgtcg gtatcacata cgcgcttact      480
gttgtttggt tgtggtatt tgcttgttca gctgtcccag tctatatcta ttttaacacc      540
tggaccactt gccaatctat cgcattccct tcaaagacct ctgcgtccat aggctctctt      600
tgtgcagatg ctagaatgta cggcgtattg ccttggaatg cattcccagg taaagtttgc      660
ggtagtaacc tgcttagcat ttgcaagact gctgaattcc agatgacatt ccacctcttt      720
attgccgcat ttgtaggtgc tgctgccaca ctcgtgtctc tcctgacttt tatgattgcg      780
gcaacgtata acttcgcagt tttgaagctg atggggaggg gtactaaatt ctga            834
```

<210> SEQ ID NO 106
<211> LENGTH: 834
<212> TYPE: DNA
<213> ORGANISM: Homo sapiens

<400> SEQUENCE: 106

```
atgggcctcc ttgagtgctg tgccaggtgt cttgtagggg ctcccttgc ttcactggtt        60 gctacgggtc tgtgcttttt tggtgtcgca ctgttttgcg ggtgtggaca cgaagccttg      120
actggtacgg aaaagctcat agagacttat ttctccaaaa actaccaaga ctacgagtac      180
ttgataaatg ttattcacgc gttccagtat gttatctatg gacggcaag cttctttttc      240 ctgtacggcg cgttgttgtt ggcagaggga ttctacacta cgggcgcggt aagacagatc      300
ttcggggatt ataagactac tatttgcggg aaggcctca cgccaccgt taccggcggt       360 caaaagggta gagggtctcg cggtcagcac caagcccata gtcttgaacg ggtctgtcat      420
tgcctcggaa atggcttgg tcacccagac aagtttgtgg aattaccta gcgctcact        480 gtggtatggc tgcttgtctt cgcttgctca gcagtccctg tgtatatcta tttcaacacg      540
tggaccacat gccagagtat agcattccca agtaagacga gcgcgtccat cggcagtttg      600
tgtgctgacg cgaggatgta cggcgttctc ccttggaatg catttccggg aaaagtgtgt      660
ggatcaaatt tgcttagcat ttgcaagaca gcggaattcc aaatgacatt ccacctgttc      720 attgcgcgt tctgcggagc agctgccacc cttgttagtc ttctgacctt catgatcgcc      780
gctacctata acttcgcagt cctcaagttg atgggccggg gtactaagtt ttga            834
```

<210> SEQ ID NO 107
<211> LENGTH: 729
<212> TYPE: DNA
<213> ORGANISM: Homo sapiens

<400> SEQUENCE: 107

```
atgggcttgt tagagtgctg tgcaagatgt ctggtagggg ccccctttgc ttccctggtg      60
gccactggat tgtgtttctt tggggtggca ctgttctgtg ctgtggaca tgaagccctc     120
actggcacag aaaagctaat tgagacctat ttctccaaaa actaccaaga ctatgagtat    180
ctcatcaatg tgatccatgc cttccagtat gtcatctatg gaactgcctc tttcttcttc    240
ctttatgggg ccctcctgct ggctgagggc ttctacacca ccggcgcagt caggcagatc    300
tttggcgact acaagaccac catctgcggc aagggcctga gcgcaacgtt tgtgggcatc    360
acctatgccc tgaccgttgt gtggctcctg gtgtttgcct gctctgctgt gcctgtgtac    420
atttacttca acacctggac cacctgccag tctattgcct tccccagcaa gacctctgcc    480
agtataggca gtctctgtgc tgatgccaga atgtatggtg ttctcccatg gaatgctttc    540
cctggcaagg tttgtggctc caaccttctg tccatctgca aaacagctga gttccaaatg    600
accttccacc tgtttattgc tgcatttgtg ggggctgcag ctacactggt ttccctgctc    660
accttcatga ttgctgccac ttacaacttt gccgtcctta aactcatggg ccgaggcacc    720
aagttctga                                                            729
```

<210> SEQ ID NO 108
<211> LENGTH: 729
<212> TYPE: DNA
<213> ORGANISM: Homo sapiens

<400> SEQUENCE: 108

```
atgggcctgc tggaatgctg cgcccggtgc ctggtgggcg ccccctttcgc ttctctggtc    60
gccaccggcc tctgttttttt cggcgtggcc ctgttctgcg ttgtggcca cgaggccctg    120
accggcacag agaagctgat cgagacatat ttcagcaaga actaccagga ctacgagtac    180
ctgatcaacg tgatccacgc cttccaatac gtgatctacg gcaccgccag cttcttcttc    240
ctgtacggcg ctctgctgct ggccgagggc ttctacacca ccggagctgt tagacagatc    300
ttcggagatt acaagaccac aatctgcgga aagggcctga gcgccacatt cgtgggcatc    360
acctacgccc tgacagtggt gtggctgctg gtctttgctt gtagcgccgt ccccgtgtac    420
atctacttca acacctggac cacatgccag agcatcgcct tccccagcaa gaccagcgcc    480
tctatcggca gcctgtgcgc cgacgccaga atgtacggcg tgctgccttg gaacgccttt    540
cctggaaaag tgtgcggctc taatctgctc agcatctgca agacagccga attccagatg    600
accttccacc tgtttatcgc cgcttttgtg ggagccgctg ctacactggt gtccctgctg    660
accttcatga tcgccgccac ctacaacttc gccgtgctga agctgatggg cagaggcacc    720
aagttctga                                                            729
```

<210> SEQ ID NO 109
<211> LENGTH: 729
<212> TYPE: DNA
<213> ORGANISM: Homo sapiens

<400> SEQUENCE: 109

```
atgggcctgc tggagtgctg cgcccggtgc ctggtgggcg ccccctttcgc ttctctggtc    60
gccaccggcc tctgttttttt cggcgtggcc ctgttctgcg ttgtggcca cgaggccctg    120
```

```
accggcacag agaagctgat cgagacatat ttcagcaaga actaccagga ctacgagtac    180
ctgatcaacg tgatccacgc cttccaatac gtgatctacg gcaccgccag cttcttcttc    240
ctgtacggcg ctctgctgct ggccgagggc ttctacacca ccggagctgt tagacagatc    300
ttcggagatt acaagaccac aatctgcgga aagggcctga cgccacatt cgtgggcatc    360 acctacgccc tgacagtggt gtggctgctg gtctttgctt gtagcgccgt ccccgtgtac    420
atctacttca cacctggac cacatgccag agcatcgcct tccccagcaa gaccagcgcc    480
tctatcggca gcctgtgcgc cgacgccaga atgtacggcg tgctgccttg aacgccttt    540 cctggaaaag tgtgcggctc taatctgctc agcatctgca agacagccga attccagatg    600
accttccacc tgtttatcgc cgcttttgtg ggagccgctg ctacactggt gtccctgctg    660
accttcatga tcgccgccac ctacaacttc gccgtgctga agctgatggg cagaggcacc    720
aagttctga                                                           729

<210> SEQ ID NO 110
<211> LENGTH: 729
<212> TYPE: DNA
<213> ORGANISM: Homo sapiens

<400> SEQUENCE: 110
atgggtttgt tggagtgctg cgctcggtgc ctggtggggg caccgtttgc gagcttggtt     60
gcaaccggtc tctgcttttt cggggtagca cttttttgcg ggtgtggaca tgaggctttg    120
accggaacgg aaaaacttat tgagacctac ttcagtaaga attatcagga ctacgagtat    180
ctgattaatg taattcacgc atttcagtac gtgatatatg gtacagcttc ctttttttt    240 ctgtacggag cattgctgtt ggcagaagga ttctacacga cggggggcggt acgacagatc    300 ttcggggact ataagacaac catctgtgga aaaggcttga gtgctacttt cgtaggcatt    360
acttacgcct tgacggtagt gtggctcttg gttttcgctt gttctgcagt gccagtttac    420
atctacttca atacttggac gacgtgtcaa tcaatagcgt tccctagtaa gacaagtgcc    480
agcattggta gtttgtgcgc ggacgctcgc atgtacggag ttctcccttg gaacgccttt    540
cccggcaagg tctgtgggtc taacctgctc agcatatgta agaccgcaga attccaaatg    600
acatttcatt tgttcatcgc tgcctttgtg ggtgccgctg ccaccctggt gtcccttctt    660 acgttatga tagcagcaac gtacaatttt gcagtattga aactcatggg gcggggcact    720
aagttctga                                                          729

<210> SEQ ID NO 111
<211> LENGTH: 729
<212> TYPE: DNA
<213> ORGANISM: Homo sapiens

<400> SEQUENCE: 111
atggggctcc ttgagtgctg tgcccggtgc ctggtcggtg ctcccttcgc ttcacttgtt     60
gccactggac tctgcttttt tggagtcgcc ttgttttgtg gttgtgggca cgaggcgctc    120
acaggcaccg agaagcttat agaaacttac ttcagcaaga actatcaaga ctatgaatac    180
cttatcaatg ttattcacgc gtttcagtac gtaatttatg gaaccgcctc cttcttttc    240 ctgtacgggg ccttgttgct tgctgagggc ttctacacaa ctggggccgt ccgccagatc    300
ttcggtgact acaaaacgac aatttgcggt aagggccttt ccgctacttt tgttggtatc    360
acttatgcgc tgacagtcgt atggcttctt gtatttgcgt gtagcgccgt acctgtttat    420
```

| | |
|---|---|
| atctacttca acacgtggac tacctgccaa tctatagcgt tcccatcaaa gaccagtgct | 480 |
| agtatcgggt ccctgtgtgc tgacgccaga atgtacggtg tacttccttg gaatgctttc | 540 |
| ccaggtaaag tatgcggctc aaatctgctc agtatatgta agacggccga gtttcagatg | 600 |
| actttccatc tgttcattgc ggcgttcgtc ggcgcagcgg ctactctggt ctcacttctg | 660 |
| acgtttatga tagctgccac ttataacttt gcggttctca agttgatggg tcgcggtacg | 720 |
| aagttttga | 729 |

<210> SEQ ID NO 112
<211> LENGTH: 729
<212> TYPE: DNA
<213> ORGANISM: Homo sapiens
<400> SEQUENCE: 112

| | |
|---|---|
| atggggcttc ttgagtgttg cgccaggtgt ctcgttggcg ctcccttcgc gagccttgtc | 60 |
| gccaccggct tgtgtttctt tggagttgct ttgttctgtg ctgcggcca tgaggctctt | 120 |
| accgggactg aaaagctgat tgaaacgtat ttcagcaaga actaccaaga ctacgagtac | 180 |
| ctgataaacg taatccatgc gtttcagtac gtaatatatg gtaccgcatc tttcttcttc | 240 |
| ttgtacgggg cgctgctcct ggcagaggga ttttacacta caggtgctgt gcgacaaatt | 300 |
| ttcggagatt ataaaacaac aatttgcgga aagggtctta gtgctacgtt cgttgggata | 360 |
| acgtacgcgc tgacagtcgt atggctgctt gtctttgcgt gtagcgccgt tccggtgtat | 420 |
| atatatttta atacgtggac aacgtgtcaa tccattgctt ttccgagcaa aacttccgct | 480 |
| tctatcggat ccctgtgtgc cgacgcgaga atgtacggag ttcttccctg gaacgccttt | 540 |
| ccgggcaagg tgtgtggttc aaccttcttc tctatatgta aaacagcgga gttccaaatg | 600 |
| actttccatc tttttatagc cgcattcgta ggagcagctg caactctggt ttccttgctg | 660 |
| acattcatga tcgcagctac ttataacttt gcagtcttga aacttatggg acgcggaact | 720 |
| aaatttga | 729 |

<210> SEQ ID NO 113
<211> LENGTH: 483
<212> TYPE: DNA
<213> ORGANISM: Homo sapiens
<400> SEQUENCE: 113

| | |
|---|---|
| atggcatcac agaagaggcc tagtcaaagg cacggttcta aatatcttgc cacagcatct | 60 |
| actatggacc acgcacgaca cggcttttg ccacgacaca gggatacggg gatcttggac | 120 |
| tccattggtc gatttttcgg cggtgataga ggagcgccca aaagaggttc cggaaaagat | 180 |
| agccaccatc ccgcaaggac tgcccattat ggaagccttc ctcagaaaag ccacgggagg | 240 |
| actcaggacg aaaacccagt tgttcacttc tttaagaata tagtgacgcc acggaccct | 300 |
| ccgccgagcc aagggaaggg cgcagagggc caacgaccag gatttgggta tggcggcaga | 360 |
| gcaagtgact ataagagcgc tcataaggc ttcaaggcg tcgacgcgca ggggaccttg | 420 |
| tctaaaatct ttaagttggg tggaagagat agccggtctg gcagtccgat ggctcggcgc | 480 |
| tga | 483 |

<210> SEQ ID NO 114
<211> LENGTH: 834
<212> TYPE: DNA
<213> ORGANISM: Homo sapiens
<400> SEQUENCE: 114

-continued

```
atgggactgc tggaatgctg cgcccggtgc ctggtgggcg ccccttttcgc cagcctggtg    60 gccaccggcc tgtgcttctt tggcgtggcc ctgttctgcg gctgcggaca cgaggccctg   120
acaggcaccg agaagctgat cgagacatat ttcagcaaga actaccagga ctacgagtac   180
ctgatcaacg tgatccacgc ctttcagtac gtgatctacg gaaccgccag cttcttcttc   240
ctgtacggcg ctctgctgct ggccgaaggc ttctacacca ccggcgctgt tagacagatc   300
ttcggcgact acaagacaac catctgtgga aaaggactga cgccaccgt gaccggcggc    360 caaaagggcc ggggctctag aggccagcac caggcccact ctctggaaag agtgtgccac   420
tgcctgggca atggctggg ccaccctgat aagttcgtgg gcatcaccta cgccctgacc    480
gtggtgtggc tgcttgtttt cgcctgcagc gccgtgccag tgtacatcta cttcaacacc   540
tggaccacat gccagagcat cgcctttcct agcaagacca cgcctctat cggcagcctg    600 tgtgccgacg ccagaatgta cggcgtgctg ccttggaacg ccttccccgg caaggtgtgt   660
ggcagcaacc tgctttctat ctgcaagacc gccgagttcc agatgacctt ccacctgttc   720
atcgccgctt ttgtgggagc cgccgccaca ctggtcagcc tgctgacctt catgatcgcc   780
gctacataca acttcgccgt gctgaagctg atgggcagag gcaccaagtt ctga         834
```

<210> SEQ ID NO 115
<211> LENGTH: 834
<212> TYPE: DNA
<213> ORGANISM: Homo sapiens

<400> SEQUENCE: 115

```
atgggactgc tggagtgctg cgcccggtgc ctggtgggcg ccccttttcgc cagcctggtg   60 gccaccggcc tgtgcttctt tggcgtggcc ctgttctgcg gctgcggaca cgaggccctg   120
acaggcaccg agaagctgat cgagacatat ttcagcaaga actaccagga ctacgagtac   180
ctgatcaacg tgatccacgc ctttcagtac gtgatctacg gaaccgccag cttcttcttc   240
ctgtacggcg ctctgctgct ggccgaaggc ttctacacca ccggcgctgt tagacagatc   300
ttcggcgact acaagacaac catctgtgga aaaggactga cgccaccgt gaccggcggc    360 caaaagggcc ggggctctag aggccagcac caggcccact ctctggaaag agtgtgccac   420
tgcctgggca atggctggg ccaccctgat aagttcgtgg gcatcaccta cgccctgacc    480
gtggtgtggc tgcttgtttt cgcctgcagc gccgtgccag tgtacatcta cttcaacacc   540
tggaccacat gccagagcat cgcctttcct agcaagacca cgcctctat cggcagcctg    600 tgtgccgacg ccagaatgta cggcgtgctg ccttggaacg ccttccccgg caaggtgtgt   660
ggcagcaacc tgctttctat ctgcaagacc gccgagttcc agatgacctt ccacctgttc   720
atcgccgctt ttgtgggagc cgccgccaca ctggtcagcc tgctgacctt catgatcgcc   780
gctacataca acttcgccgt gctgaagctg atgggcagag gcaccaagtt ctga         834
```

<210> SEQ ID NO 116
<211> LENGTH: 834
<212> TYPE: DNA
<213> ORGANISM: Homo sapiens

<400> SEQUENCE: 116

```
atgggacttt tggagtgttg cgccagatgc ctggtcggtg ccccgtttgc aagccttgtt    60
gccactggct tgtgcttctt cggtgtagca ttgttctgcg ggtgtggcca tgaggctctg   120
acaggtacag agaagttgat tgaaacatac ttttccaaga actaccaaga ctacgaatat   180
```

```
ctgattaacg ttatacatgc cttccaatat gtaatctatg ggaccgctag cttttttcttc    240
ctttatggag ctttgctcct ggccgagggt ttttacacga cgggtgcggt tcgacagatt    300
tttggagact ataagactac gatttgtggt aaaggactca gcgcgaccgt gacgggtgga    360
caaaaaggtc gcggttctcg ggtcaacac caagctcact ctcttgaacg agtttgtcac    420
tgtttgggaa aatggctcgg ccatcccgat aaatttgtgg gcataactta cgctcttacg    480
gtggtatggc tcctggtctt tgcgtgctcc gctgtcccg tatatatcta tttcaacaca    540
tggactacgt gccaatccat cgcttttccc agcaagacga gtgcgtctat aggttcactt    600
tgcgctgatg cgaggatgta cggcgtgctc ccctggaatg cttttcctgg caaagtttgt    660
ggttctaatc ttctgagtat ttgcaaaaca gcagaatttc agatgacctt ccatttgttt    720
atagccgctt ttgtgggtgc agctgctaca ctcgtgagcc ttcttacgtt catgattgct    780
gcaacataca attttgctgt actcaaactc atgggcagag gcaccaaatt ctga          834
```

<210> SEQ ID NO 117
<211> LENGTH: 834
<212> TYPE: DNA
<213> ORGANISM: Homo sapiens
<400> SEQUENCE: 117

```
atgggtctcc ttgagtgctg cgccaggtgc cttgttggag ctccgttcgc cagtctggta     60
gccactgggt tgtgcttctt cggcgtcgcc ttgttctgcg gatgtgggca cgaggcgctt    120
actggtaccg agaaattgat cgagacatac ttttcaaaga attatcaaga ctatgaatac    180
ctgataaatg tgattcacgc atttcaatac gtgatatacg gcacagcctc tttctttttt    240
ctgtacgggg ctctccttct cgctgaaggc ttctacacga ctggggcagt cagacaaatc    300
tttggcgatt acaagacgac tatatgtggg aagggcctgt cagccaccgt gaccgggggg    360
cagaagggca ggggctcaag agggcagcat caagctcatt cacttgagcg ggtttgccat    420
tgcttgggga aatggctggg ccatccagat aaattcgtcg gtatcactta tgctcttaca    480
gtagtgtggc tgcttgtatt cgcttgtagt gcagtccccg tgtacattta tttcaacacc    540
tggaccacct gtcagtctat cgcgtttccc tccaagacgt cagcatccat cgggagtctg    600
tgtgcggacg caagaatgta cggcgttttg ccctggaatg cgtttccggg caaagtgtgc    660
gggtctaatt tgctttctat ttgcaagacc gctgagttcc agatgacttt tcacttgttt    720
attgcggcct ttgtgggggc tgccgcgacg ctggtctctt tgctcacatt tatgatagca    780
gctacgtata atttcgcggt cttgaaactg atggggagag gcacgaaatt ctga          834
```

<210> SEQ ID NO 118
<211> LENGTH: 834
<212> TYPE: DNA
<213> ORGANISM: Homo sapiens
<400> SEQUENCE: 118

```
atgggcttgc tcgaatgttg tgcgaggtgc ctcgttggcg ctccatttgc atcacttgta     60
gcaacaggcc tctgttttttt tggtgtcgcg ctcttttgtg gctgtggaca tgaagcgctc    120
acgggtacag agaagctcat agaaacctac ttcagcaaaa attaccagga ttacgaatac    180
ctgatcaacg tcatccacgc cttcaatac gtgatctatg ggaccgcgag cttttttcttc    240
ctttatgggg cgcttctgct cgcggaaggt ttttacacta cgggcgcggt ccgacagata    300
ttcggtgact ataagacgac aatatgtgga aaaggtcttt cagccacagt cacgggggcc    360
caaaagggcc gagggtcaag gggtcagcac caggcccatt cacttgaacg ggtatgtcat    420
```

```
tgtttgggca agtggttggg gcacccagat aagtttgtcg gcataaccta tgctctgacg    480
gttgtttggc tcctggtttt cgcttgttct gcggtcccgg tttatatcta ctttaacacc    540
tggacaacct gtcaatctat agcatttcca agtaagacgt cagctagcat cggttccctg    600
tgtgctgacg ccagaatgta cggtgttttg ccctggaacg cctttcctgg aaaagtctgt    660
ggttctaatc tgttgtcaat ttgcaagaca gcggagttcc agatgacgtt ccatctcttt    720
attgccgcct tcgttggggc ggcggcgacc ttggtttctc ttctgacctt tatgatagct    780
gcaacttata actttgccgt actgaaactg atgggaaggg ggaccaaatt ctga          834
```

<210> SEQ ID NO 119
<211> LENGTH: 834
<212> TYPE: DNA
<213> ORGANISM: Homo sapiens

<400> SEQUENCE: 119

```
atgggcttgc tcgaatgttg tgcgaggtgc ctcgttggcg ctccatttgc atcacttgta     60
gcaacaggcc tctgtttttt tggtgtcgcg ctcttttgtg gctgtggaca tgaagcgctc    120
acgggtacag agaagctcat agaaacctac ttcagcaaaa attaccagga ttacgaatac    180
ctgatcaacg tcatccacgc cttcaatac gtgatctacg ggaccgcgag cttttttcttc    240 ctttatgggg cgcttctgct cgcggaaggt ttttacacta cgggcgcggt ccgacagata    300
ttcggtgact ataagacgac aatatgtgga aaaggtcttt cagccacagt cacaggggc     360 caaaagggcc gagggtcaag gggtcagcac caggcccatt cacttgaacg ggtatgtcat    420
tgtttgggca agtggttggg gcacccagat aagtttgtcg gcataaccta tgctctgacg    480
gttgtttggc tcctggtttt cgcttgttct gcggtcccgg tttatatcta ctttaacacc    540
tggacaacct gtcaatctat agcatttcca agtaagacgt cagctagcat cggttccctg    600
tgtgctgacg ccagaatgta cggtgttttg ccctggaacg cctttcctgg aaaagtctgt    660
ggttctaatc tgttgtcaat ttgcaagaca gcggagttcc agatgacgtt ccatctcttt    720
attgccgcct tcgttggggc ggcggcgacc ttggtttctc ttctgacctt tatgatagct    780
gcaacttata actttgccgt actgaaactg atgggaaggg ggaccaaatt ctga          834
```

<210> SEQ ID NO 120
<211> LENGTH: 669
<212> TYPE: DNA
<213> ORGANISM: Homo sapiens

<400> SEQUENCE: 120

```
atggactatg agtatctcat caatgtgatc catgccttcc agtatgtcat ctatggaact     60
gcctctttct tcttccttta tggggccctc ctgctggctg agggcttcta caccaccggc    120
gcagtcaggc agatctttgg cgactacaag accaccatct gcggcaaggg cctgagcgca    180
acggtaacag ggggccagaa ggggaggggt tccagaggcc aacatcaagc tcattctttg    240
gagcgggtgt gtcattgttt gggaaaatgg ctaggacatc ccgacaagtt tgtgggcatc    300
acctatgccc tgaccgttgt gtggctcctg gtgtttgcct gctctgctgt gcctgtgtac    360
atttacttca acacctggac cacctgccag tctattgcct tccccagcaa gacctctgcc    420
agtataggca gtctctgtgc tgatgccaga atgtatggtg ttctcccatg gaatgctttc    480
cctggcaagg tttgtggctc caaccttctg tccatctgca aaacagctga gttccaaatg    540
accttccacc tgtttattgc tgcatttgtg ggggctgcag ctacactggt ttccctgctc    600
```

| acctt catga ttgctgccac ttacaacttt gccgtcctta aactcatggg ccgaggcacc | 660 |
|---|---|
| aagttctga | 669 |

<210> SEQ ID NO 121
<211> LENGTH: 669
<212> TYPE: DNA
<213> ORGANISM: Homo sapiens

<400> SEQUENCE: 121

| atggactacg agtacctgat caacgtgatc cacgcctttc agtacgtgat ctacggcacc | 60 |
|---|---|
| gcctccttct tcttcctgta cggcgccctg ctgctggccg agggcttcta caccaccggc | 120 |
| gctgtgcggc agatcttcgg cgactacaag accacaatct gcggcaaggg cctgtctgcc | 180 |
| acagtgaccg gcggccagaa aggcagaggc tctagaggcc aacaccaggc ccactctctg | 240 |
| gaaagagtgt gccactgcct gggcaaatgg ctgggccacc tgataagtt cgtgggcatc | 300 |
| acatacgccc tgaccgtggt gtggctgctc gtgttcgcct gcagcgccgt ccccgtgtac | 360 |
| atctacttca cacctggac cacctgtcag agcatcgcct tccccagcaa gacaagcgcc | 420 |
| agcatcggca gcctgtgcgc cgacgccaga atgtacggcg tgctgccttg gaacgccttt | 480 |
| cctggcaagg tgtgtggcag caacctgctg agcatttgca agaccgccga gttccagatg | 540 |
| accttccacc tgttcatcgc cgccttcgtg ggagccgctg ccaccctggt gtccctgctg | 600 |
| acattcatga tcgccgctac atacaacttc gccgtgctga agctgatggg cagagggacc | 660 |
| aagttctga | 669 |

<210> SEQ ID NO 122
<211> LENGTH: 669
<212> TYPE: DNA
<213> ORGANISM: Homo sapiens

<400> SEQUENCE: 122

| atggattacg aataccttat taacgtcatt cacgccttcc aatatgtcat ttatggaact | 60 |
|---|---|
| gcttccttct ttttcttgta tggggcactg ttgttggctg aggggtttta tacgacgggc | 120 |
| gcggttaggc aaatctttgg cgattataaa acaacaatct gtggtaaggg gttgagtgca | 180 |
| acagtaactg gaggtcaaaa aggcagaggt tctcgcggtc agcatcaagc gcactccctg | 240 |
| gagcgcgttt gtcattgctt ggggaaatgg ctcggccacc ctgataaatt tgtaggtatt | 300 |
| acctacgcac tgacagttgt ttggcttctg gttttcgctt gtagcgcagt gcccgtctat | 360 |
| atctacttca acacatggac tacttgccag agtatagctt ttccctctaa gacttccgct | 420 |
| tctattggtt ctttgtgcgc ggacgccaga atgtatgggg tgctcccgtg gaatgcattc | 480 |
| ccgggcaaag tttgcgggtc aaacttgttg tcaatttgta agaccgctga gtttcagatg | 540 |
| acattccacc tgttcatcgc tgctttcgtg ggtgctgccg ccacattggt aagcctcctg | 600 |
| actttcatga ttgctgctac ctacaacttt gcagttctga aacttatggg gcgcggaacc | 660 |
| aagttctga | 669 |

<210> SEQ ID NO 123
<211> LENGTH: 669
<212> TYPE: DNA
<213> ORGANISM: Homo sapiens

<400> SEQUENCE: 123

| atggattacg aatacttgat aaatgtaatt catgcgttcc agtatgtgat atacggaacg | 60 |
|---|---|
| gcgagctttt tctttcttta tggggcgttg ctgttggctg agggcttttt a tactaccggc | 120 |

```
gctgtgcgcc agattttttgg ggattacaag acgactatct gcggaaaagg tctttcagcc    180
actgtcacgg gaggccagaa aggtagaggc tccagaggcc agcaccaagc tcattcactg    240
gagcgagttt gtcattgttt gggcaaatgg cttggtcacc cggataagtt cgtcggtatc    300
acctatgcgc ttaccgtagt ctggcttttg gtcttcgctt gtagtgcggt acctgtttat    360
atttatttca atacctggac cacatgtcag tcaatagcgt tcccctctaa gacttctgcg    420
tccattggca gcctttgtgc tgacgcccgc atgtatggtg tcttgccatg gaacgcattt    480
ccaggcaagg tttgtgggtc caatctcctc tcaatctgta aaaccgccga gtttcaaatg    540
acgtttcacc ttttcatagc ggcatttgtt ggtgcggcgg cgacactcgt gtctctgctc    600
acatttatga ttgccgccac ttacaacttc gccgtactga agttgatggg gcgcggaacc    660
aaattttga                                                            669

<210> SEQ ID NO 124
<211> LENGTH: 669
<212> TYPE: DNA
<213> ORGANISM: Homo sapiens

<400> SEQUENCE: 124
atggattacg aatacttgat aaatgtaatt catgcgttcc agtatgtgat atacggaacg     60
gcgagctttt tctttcttta cggggcgttg ctgttggctg agggctttta tactaccggc    120
gctgtgcgcc agattttttgg ggattacaag acgactatct gcggaaaagg tctttcagcc    180
actgtcacgg gaggccagaa aggtagaggc tccagaggcc agcaccaagc tcattcactg    240
gagcgagttt gtcattgttt gggcaaatgg cttggtcacc cggataagtt cgtcggtatc    300
acctatgcgc ttaccgtagt ctggcttttg gtcttcgctt gtagtgcggt acctgtttat    360
atttatttca atacctggac cacatgtcag tcaatagcgt tcccctctaa gacttctgcg    420
tccattggca gcctttgtgc tgacgcccgc atgtatggtg tcttgccatg gaacgcattt    480
ccaggcaagg tttgtgggtc caatctcctc tcaatctgta aaaccgccga gtttcaaatg    540
acgtttcacc ttttcatagc ggcatttgtt ggtgcggcgg cgacactcgt gtctctgctc    600
acatttatga ttgccgccac ttacaacttc gccgtactga agttgatggg gcgcggaacc    660
aaattttga                                                            669

<210> SEQ ID NO 125
<211> LENGTH: 669
<212> TYPE: DNA
<213> ORGANISM: Homo sapiens

<400> SEQUENCE: 125
atggattacg aatacttgat caacgtaatc catgcctttc aatacgttat atacggtacg     60
gcatcattct ttttttttgta tggcgcccct ctccttgctg aaggtttcta cacaacgggt    120
gctgtgaggc agatatttgg ggattacaaa accaccattt gtggcaaagg actctcagca    180
acggtgaccg ggggtcagaa aggtcgcggc tctcggggac aacaccaggc tcacagtctc    240
gaaagagttt gtcactgcct cgggaagtgg cttggtcacc ccgataagtt tgttggaata    300 acgtatcgc tcaccgtcgt atggctgttg gtcttcgcat gttcagcggt cccagtgtat    360
atatacttca atacctggac cacctgccag tctatagcat tcccttccaa gacctccgcg    420 tccataggt cactctgtgc tgatgctcga atgtacgggg ttcttccgtg gaatgctttt    480
cctgggaaag tgtgcgggtc taacctgctc tcaatctgca agacagccga gtttcagatg    540
```

```
acattccatc tgttcatcgc cgcgttcgtt ggcgccgcgg caacattggt gtctttgttg    600
acatttatga tagccgcaac ctacaacttt gctgtcttga agctcatggg tcggggcacg    660
aagttctga                                                            669

<210> SEQ ID NO 126
<211> LENGTH: 483
<212> TYPE: DNA
<213> ORGANISM: Homo sapiens

<400> SEQUENCE: 126
atggcttctc aaaaacgacc ctcacaacgc cacggttcaa atacctggc gacggccagc      60 accatggatc atgcacggca tggcttcttg ccaaggcatc gggacaccgg cattctcgac    120
tcaattggaa ggttttttgg aggggatcga ggcgccccca agcgcggatc tgggaaggac    180
tcccatcacc ctgcccgcac cgctcactat ggctctttgc cacaaaaatc ccatggccgc    240
acccaagatg aaaatccagt ggtccatttt tttaagaaca tagtgacgcc ccgaaccccc    300
ccaccgtccc aaggtaaagg agcagaaggc caacgaccag gattcggata cggggtcgg    360 gcaagtgatt ataagtctgc ccataagggt tttaaggggg tagacgctca aggtacgctg    420
agcaaaattt ttaaacttgg tggccgcgat tctaggagcg ggtcaccgat ggcgaggagg    480
tga                                                                  483

<210> SEQ ID NO 127
<211> LENGTH: 831
<212> TYPE: DNA
<213> ORGANISM: Homo sapiens

<400> SEQUENCE: 127
atgggactgc ttgagtgctg cgcccggtgc ctggtgggcg ccccttcgc ctctctggtt      60 gccaccggcc tgtgtttttt cggcgtggcc ctgttctgcg gttgtggaca cgaggccctg    120
accggcacag agaagctgat cgagacatat tcagcaaga actaccagga ctacgagtac    180
ctgatcaacg tgatccacgc ctttcagtac gtgatctacg gcaccgccag cttcttcttc    240
ctgtacggcg ccctgctgct ggccgaaggc ttctacacca ccggcgctgt tagacagatc    300
ttcggagatt ataagaccac aatctgcggc aaaggcctga gcgccaccgt gacaggcgga    360
cagaagggcc ggggcagtag aggccagcac caggcccaca gcctggaaag agtgtgccac    420
tgcctgggca gtggctggg acatcctgat aagttcgtgg gcatcaccta cgcccttaca    480
gtggtgtggc tgctggtgtt cgcctgcagc gccgtgcccg tgtacatcta cttcaacacc    540
tggaccacct gccagagcat cgccttcccc agcaagacca cgccagcat cggctctctg    600 tgcgccgacg ccagaatgta cggcgtgctg ccttggaacg ccttcccagg aaaggtgtgt    660
ggcagcaacc tgttgtctat ttgtaaaacc gccgagttcc agatgacctt ccacctgttt    720
atcgccgctt ttgtgggcgc cgctgctaca ctggtcagcc tgctgacatt catgatcgcc    780
gccacctaca acttcgccgt gctgaagctg atgggcagag caccaagtt c              831

<210> SEQ ID NO 128
<211> LENGTH: 831
<212> TYPE: DNA
<213> ORGANISM: Homo sapiens

<400> SEQUENCE: 128
atgggcctgc ttgagtgttg tgcaaggtgt ctggtcggag cacctttgc gtctctggtt      60 gcgacgggct tgtgcttctt cggggtggcg ttgttctgtg ggtgtgggca cgaagccctc    120
```

```
acgggtactg agaagctgat agaaacctat ttcagtaaaa actatcaaga ttatgagtat    180
ctcattaacg tcatccacgc gtttcaatat gttatctacg ggacggcgag cttttttcttc   240
ctctatggag ccctttttgct ggctgagggc ttttatacaa ccggtgctgt caggcagatc   300
ttcggcgatt acaagacgac aatctgcggg aaaggtctgt ccgctactgt aacaggaggg    360
caaaagggggc ggggtagtcg cggacaacac caggcgcatt ccctggagcg cgtatgtcac   420
tgcctgggca gtggcttgg acacccagac aagttcgtag gaatcacgta cgctttgaca    480
gtggtgtggc ttctggtatt cgcgtgcagc gccgtgcctg tctacatata cttcaatacg    540
tggactactt gtcagtccat agcttccct agtaagacct ctgcgagcat aggctccctt    600
tgtgcagatg caagaatgta tggggtactc ccttggaatg cgtttcctgg gaaagtatgt    660
ggtagtaatc ttctcagtat atgtaaaaca gcggagttcc agatgacgtt tcatctcttt    720
attgctgctt ttgtaggtgc agctgcaaca ctcgtgtccc tccttacgtt tatgatcgct    780
gctacctaca atttcgccgt attgaaactt atggggcggg gcacaaaatt t            831
```

```
<210> SEQ ID NO 129
<211> LENGTH: 831
<212> TYPE: DNA
<213> ORGANISM: Homo sapiens

<400> SEQUENCE: 129
atgggcctcc tggagtgctg cgccaggtgc ctcgtaggag caccctttgc ttccttggtt    60
gctacaggct tgtgcttttt cggggttgca ttgttttgcg gatgtgggca cgaggctttg    120
accgggacgg aaaagttgat tgaaacttat ttctcaaaaa attaccagga ctatgaatat    180
ctgataaacg taatacatgc attccagtat gtgatctacg gtactgcatc attctttttt    240
ctgtacggtg ccctccttct ggctgagggc ttttatacaa ctggagccgt gcgacaaatt    300
tttggagatt acaagaccac gatttgcgga aaagggctgt ccgctactgt gacaggaggc    360
cagaaggggc gaggctctcg cggacaacac caggcacata gcttggaacg agtatgtcac    420
tgcctcggca aatggcttgg gcaccccgat aagtttgttg ggatcacgta tgcactgacg    480
gtcgtctggc ttctggtatt tgcctgttca gcggtgccag tatatatata ctttaatacc    540
tggactacct gtcagtctat cgcctttccg agtaagacga gtgcctcaat cggctcactc    600
tgcgctgatg ctcgaatgta cggggttctg ccgtggaacg cctttccggg caaggtttgt    660
ggttcaaact tgcttctat ttgtaaaaca gcagaattcc agatgacatt tcatcttttc     720
atcgctgctt ttgtgggcgc cgcggcgaca ttggtatctc tgttgacatt catgatagct    780
gcaacatata acttcgccgt tctgaagttg atgggacggg gaacaaagtt c             831
```

```
<210> SEQ ID NO 130
<211> LENGTH: 831
<212> TYPE: DNA
<213> ORGANISM: Homo sapiens

<400> SEQUENCE: 130
atgggactcc ttgaatgctg cgcgcggtgc ctcgtcggtg caccgttcgc ttcactggtt    60
gcaaccggcc tctgtttctt tggcgttgca ttgttctgcg ggtgtgggca tgaagctttg    120
actggcacgg agaagctcat tgaaacctat tttagcaaga actatcagga ctacgagtac    180
cttataaacg tgattcacgc cttccaatac gttatatacg gaaccgcttc ttttttttc     240
ctttatggtg cgcttttgtt ggccgagggc ttctatacaa ccggtgcagt acgccaaatc    300
```

```
ttcggcgatt ataagacgac gatctgtggc aagggctga gtgcaaccgt gactggcggc    360
caaaaaggcc gcggtagtcg gggacaacat caagcacata gtctggaacg agtatgtcac    420
tgtctcggca agtggttggg acatcctgat aagttcgttg gtattacata tgccctgaca    480
gtcgtttggc tcctcgtctt tgcttgtagt gctgtgccgg tgtacatcta tttcaatacc    540
tggacgacgt gtcagtctat cgcgttcccg tcaaaaacgt ccgcaagcat aggttcactt    600
tgtgccgatg ctaggatgta cggagttttg ccatggaatg cgtttcctgg gaaagtgtgt    660
ggctccaacc ttctctcaat ctgtaagacc gccgaattcc aaatgacatt ccatctcttt    720
atcgcagcct ttgtcggtgc cgccgctacc ctcgtgagtc ttttgacatt catgatcgcg    780
gccacataca acttcgcagt ccttaagctc atgggcaggg cactaaatt c              831

<210> SEQ ID NO 131
<211> LENGTH: 594
<212> TYPE: DNA
<213> ORGANISM: Homo sapiens

<400> SEQUENCE: 131
atggcgtcac agaagagacc ctcccagagg cacggatcca agtacctggc cacagcaagt     60
accatggacc atgccaggca tggcttcctc ccaaggcaca gagacacggg catccttgac    120
tccatcgggc gcttctttgg cggtgacagg ggtgcgccca gcggggctc tggcaaggta    180 ccctggctaa agccgggccg gagccctctg ccctctcatg cccgcagcca gcctgggctg    240
tgcaacatgt acaaggactc acaccacccg gcaagaactg ctcactacgg ctccctgccc    300
cagaagtcac acgccggac ccaagatgaa aaccccgtag tccacttctt caagaacatt    360
gtgacgcctc gcacaccacc cccgtcgcag ggaaagggga gaggactgtc cctgagcaga    420
tttagctggg gggccgaagg ccagagacca ggatttggct acggaggcag agcgtccgac    480
tataaatcgg ctcacaaggg attcaaggga gtcgatgccc agggcacgct tccaaaatt    540 tttaagctgg gaggaagaga tagtcgctct ggatcaccca tggctagacg ctga          594

<210> SEQ ID NO 132
<211> LENGTH: 594
<212> TYPE: DNA
<213> ORGANISM: Homo sapiens

<400> SEQUENCE: 132
atggcctctc agaagcggcc cagccagcgg cacggttcta agtacctggc cacagctagc     60
accatggacc acgccagaca cggcttcctg ccaagacaca gagataccgg catcctggac    120
agcatcggcc gcttcttcgg cggagataga ggcgccccta gagaggctc aggcaaggtg    180 ccctggctga gcctggcag aagccctctg cctagccacg ccagaagcca gcctggcctg    240
tgcaatatgt acaaggacag ccaccacccc gccagaacag cccactacgg cagcctgcct    300
cagaaaagcc acgccggac acaggatgaa aaccccgtcg tgcacttctt caagaacatc    360
gtgaccccta gaaccctcc accttcccaa ggaaaaggca gaggcctgtc cctcagcaga    420
ttcagctggg gagctgaggg ccagagacct ggatttggct acggcggacg ggccagcgac    480
tataagtccg cccataaggg ctttaagggc gtggacgccc agggcaccct gagcaagatc    540
ttcaaactgg gcggccggga ctctagatct ggcagcccca tggctaggcg gtga          594

<210> SEQ ID NO 133
<211> LENGTH: 594
<212> TYPE: DNA
<213> ORGANISM: Homo sapiens
```

<400> SEQUENCE: 133

```
atggcgtcac agaagcgacc ttctcagagg cacggaagca agtatctcgc gacggccagt      60
accatggatc acgccaggca tggcttcttg cctagacacc gagatactgg gattcttgac     120
tctataggtc ggttttttgg tggcgaccgc ggtgctccaa aaagaggtag cggtaaggta     180
ccctggctga aaccgggtag atccccactg ccgagccatg ccaggtccca acctggcctg     240
tgcaacatgt ataagactc tcatcatccc gctcgcactg cccattacgg agccttccc      300
caaaaatcac acgtcgcac tcaagacgaa aacccggttg tacactttttt caaaaatata     360
gtgaccctc ggactccccc accgtcccag gggaaaggga gaggcctttc actttcaaga     420
tttagctggg gcgcggaagg ccaacgcccg ggttttggat acgtgggag ggcctctgat     480
tacaaatccg cccacaaagg cttcaaaggg gtggatgccc aaggcaccct ttccaaaata     540
tttaagctcg gaggacggga ctctaggtct gggtctccta tggcgcgacg ctga          594
```

<210> SEQ ID NO 134
<211> LENGTH: 594
<212> TYPE: DNA
<213> ORGANISM: Homo sapiens

<400> SEQUENCE: 134

```
atggcttcac aaaaacgccc aagtcaacgg cacggcagca aatacctggc gacagcttcc      60
actatggatc atgcgcgaca tggatttctt cccaggcata gggatacagg tatccttgac     120
agtatcggaa gattcttcgg cggtgatcgg ggagcccta agagagggag tggtaaagta     180
ccctggctga aacctggccg gagtcccctt cctagtcacg ccaggtctca acctggggttg    240
tgtaatatgt acaaggatag tcatcacccc gctcgaaccg cccactacgg ctcttttgccg    300
caaaagtcac acgccggac tcaggacgaa aaccctgtcg tgcacttctt taaaaacatc      360
gtcacgccaa gaacaccacc accaagtcaa ggaaaggggc gcggtctcag cctgtctcga    420
ttctcatggg gggccgaggg gcagcgaccc ggcttcggct acggggtcg ggcatccgat     480
tataagtccg cccacaaagg gtttaaggg gtggacgccc aaggcactct gtccaaaatc      540
tttaaattgg gtgggcgaga ttcccgaagc ggttccccga tggcgagaag gtga           594
```

<210> SEQ ID NO 135
<211> LENGTH: 594
<212> TYPE: DNA
<213> ORGANISM: Homo sapiens

<400> SEQUENCE: 135

```
atggcgagtc aaaaaagacc gtcacagcga catgggtcca agtatctcgc tactgcttcc      60
acaatggacc atgcgaggca tgggttcctc ccgagacatc gagataccgg gatactcgat     120
tcaataggca ggttttttgg cggcgatagg ggcgctccga aacgaggatc tggaaaagtg     180
ccttggttga aaccggggag atcccccttg ccgtctcacg cacgctctca acccggtctt     240
tgcaatatgt ataaggactc tcatcaccca gcaaggaccg cccactacgg ctccctcccg     300
caaaaaagcc acggacggac ccaggacgag aatcctgtcg tacactttttt caaaaacatt     360
gtgacacctc ggacgccacc tccctcccag ggaaagggtc gaggcctctc tctctcccga     420
ttctcctggg gggcagaggg tcagagaccg ggttttggtt atggtggacg ggcatccgat     480
tacaagtcag cgcacaaagg attcaaaggg gtggacgctc aaggcacgct gtcaaaaatt     540
tttaaactgg gaggacgcga cagtagaagt ggtagcccca tggcaaggcg ctga           594
```

<210> SEQ ID NO 136
<211> LENGTH: 594
<212> TYPE: DNA
<213> ORGANISM: Homo sapiens

<400> SEQUENCE: 136

| | | | | | |
|---|---|---|---|---|---|
| atggcgagtc | aaaaaagacc | gtctcagagg | cacgggagca | agtacctggc | gacagcctcc | 60 |
| acaatggacc | acgccagaca | cggcttcttg | cccagacacc | gagataccgg | tatattggac | 120 |
| tcaatcggaa | gattttttcg | gggcgacaga | gaagcgccta | agcggggtc | cggaaaagtt | 180 |
| ccttggctca | aacccggacg | gagcccactt | cctagtcacg | cacggagtca | acctgggctg | 240 |
| tgtaatatgt | acaaagactc | acatcaccct | gcgcggacag | cccactacgg | aagtcttcca | 300 |
| cagaagtctc | acgggcgcac | ccaagacgaa | aatcccgtgg | tccacttctt | caagaatatc | 360 |
| gttaccccaa | gaaccccgcc | accatctcaa | gggaaaggga | gaggtctgtc | cctttctcga | 420 |
| ttcagttggg | gtgcagaagg | tcagagacca | ggatttggct | atggtggacg | cgcttctgat | 480 |
| tacaaatccg | cccataaagg | gtttaagggt | gtggacgcgc | aagtacgct | ctcaaagatc | 540 |
| ttcaaattgg | gtggacgcga | ttcaagatca | ggaagtccta | tggcgaggcg | ctga | 594 |

<210> SEQ ID NO 137
<211> LENGTH: 561
<212> TYPE: DNA
<213> ORGANISM: Homo sapiens

<400> SEQUENCE: 137

| | | | | | |
|---|---|---|---|---|---|
| atggcgtcac | agaagagacc | ctcccagagg | cacggatcca | agtacctggc | cacagcaagt | 60 |
| accatggacc | atgccaggca | tggcttcctc | ccaaggcaca | gagacacggg | catccttgac | 120 |
| tccatcgggc | gcttctttgg | cggtgacagg | ggtgcgccca | agcggggctc | tgcaaggta | 180 |
| ccctggctaa | agccgggccg | gagccctctg | ccctctcatg | cccgcagcca | gcctgggctg | 240 |
| tgcaacatgt | acaaggactc | acaccacccg | gcaagaactg | ctcactacgg | ctccctgccc | 300 |
| cagaagtcac | acggccggac | ccaagatgaa | aaccccgtag | tccacttctt | caagaacatt | 360 |
| gtgacgcctc | gcacaccacc | cccgtcgcag | ggaaagggg | ccgaaggcca | gagaccagga | 420 |
| tttggctacg | gaggcagagc | gtccgactat | aaatcggctc | acaagggatt | caagggagtc | 480 |
| gatgcccagg | gcacgctttc | caaaattttt | aagctgggag | gaagagatag | tcgctctgga | 540 |
| tcacccatgg | ctagacgctg | a | | | | 561 |

<210> SEQ ID NO 138
<211> LENGTH: 561
<212> TYPE: DNA
<213> ORGANISM: Homo sapiens

<400> SEQUENCE: 138

| | | | | | |
|---|---|---|---|---|---|
| atggctagcc | agaagagacc | tagccagaga | catggcagca | agtacctggc | caccgccagc | 60 |
| accatggacc | acgccagaca | cggctttctg | cctagacacc | gggacaccgg | catcctggac | 120 |
| agcatcggca | gattcttcgg | cggagataga | ggcgccccta | agcggggctc | tgcaaagtg | 180 |
| ccttggctga | agcccggccg | gagcccctg | cccagccacg | ccaggtccca | acctggcctg | 240 |
| tgcaatatgt | acaaggacag | ccaccacccc | gccagaaccg | cccactacgg | cagcctccct | 300 |
| cagaaaagcc | acggcagaac | acaggacgag | aaccccgtgg | tccacttctt | caagaacatc | 360 |
| gtgacacctc | ggacacctcc | accttctcag | ggaaaaggcg | ctgaaggcca | gcggcctggc | 420 |
| ttcggctacg | gaggacgggc | ctctgattat | aagtccgccc | acaagggatt | taagggcgtg | 480 |

```
gacgctcagg gcaccctgtc taagatcttc aagctgggcg aagagatag cagaagcggc    540 tccccaatgg cccgcagatg a                                              561
```

<210> SEQ ID NO 139
<211> LENGTH: 561
<212> TYPE: DNA
<213> ORGANISM: Homo sapiens

<400> SEQUENCE: 139

```
atggctagcc aaaaacggcc aagccaacga catgggtcaa atatctggc aactgcttca     60 accatggatc acgcccgaca tggattttg cccagacatc gagacaccgg gattctcgat    120
agcataggcc gattcttcgg cggtgaccga ggcgctccaa aacgcggttc tggtaaggtt   180
ccctggttga agccgggtcg ctcacctctt ccatcccacg cacgctccca acccggtctg   240
tgtaatatgt ataaggattc acatcaccct gcacgcacgg cgcattatgg aagcctgcca   300
cagaagtccc acgacgaac acaagacgag aatcctgtgg tccatttctt caagaatatc    360
gtgacgccaa gaacaccccc tcctagtcag ggcaaaggtg ccgaagggca gcggcctgga   420
ttcgggtatg gtgggagagc ttctgactac aagtccgctc acaaaggatt taagggcgtg   480
gatgcccaag gcacactttc taagattttt aaattggggg gccgcgactc ccgctctgga   540
tcaccgatgg cacgccgctg a                                              561
```

<210> SEQ ID NO 140
<211> LENGTH: 561
<212> TYPE: DNA
<213> ORGANISM: Homo sapiens

<400> SEQUENCE: 140

```
atggcctctc aaaaacgacc aagtcagagg catggtagca ataccctcgc acagctagt     60 acgatggacc acgctaggca tggtttcctt cctcgccacc gggatacagg aatccttgac   120
agtataggtc ggttctttgg cggagataga ggtgcccta aacgcggttc agggaaggtc    180
ccctggttga agcccggccg gtctcccctg cccagtcacg ctcgaagtca gccggggttg   240
tgcaacatgt acaaggacag ccatcatccg gcacgcacgg cacattatgg ctctctccct   300
cagaaatccc atggccgaac tcaggatgaa aatccagtag tacatttttt taagaacata   360
gtaacgccta gaactccccc gccgtcccaa ggtaaagggg ccgaggggca agacccggc    420 tttggttacg gaggacgagc gagcgattac aaatcagccc ataaggagtt caagggcgta   480
gatgcacaag gacgcttag caaaattttc aaacttggag aagagacag tagatcaggg    540 tctccaatgg ctcgaagatg a                                              561
```

<210> SEQ ID NO 141
<211> LENGTH: 561
<212> TYPE: DNA
<213> ORGANISM: Homo sapiens

<400> SEQUENCE: 141

```
atggctagcc aaaagagacc atcacaaaga cacggttcaa aatatctcgc aacggcgtct    60
actatggacc acgcccgcca cgggtttctg cctcgccatc gagatacagg aattctcgat   120
tccataggta gattcttcgg cggggataga ggcgcaccaa agcgaggaag cgggaaagta   180
ccatggctga aaccaggaag aagtcccttg ccgagccacg ccagaagtca gcccggcctt   240
tgcaatatgt ataaggatag tcatcatcct gcccgcacgg cacactacgg gagtctcccg   300
```

| | |
|---|---|
| cagaagtctc acggccgaac ccaagacgaa aaccccgttg ttcactttttt caaaaatata | 360 |
| gtcacaccgc gcactcctcc cccaagccaa ggaaaggggg ctgaaggcca gaggcctggc | 420 |
| tttggatacg gcggcagagc ctccgactac aaaagtgccc ataagggttt caaaggggta | 480 |
| gatgctcagg gaacactttc caagatattc aagctgggcg ggcgagacag tcgatctgga | 540 |
| agcccgatgg cacgacggtg a | 561 |

<210> SEQ ID NO 142
<211> LENGTH: 561
<212> TYPE: DNA
<213> ORGANISM: Homo sapiens

<400> SEQUENCE: 142

| | |
|---|---|
| atggcgagtc aaaagagacc tagccagaga cacggctcaa aatatctcgc cacagcatca | 60 |
| acgatggacc acgccaggca cgggtttctc ccgagacacc gcgacaccgg gatactggat | 120 |
| agcattggtc gattttttgg aggagaccgc ggtgctccta agcgcgggtc aggtaaagtt | 180 |
| ccctggctca aacccggcag gagtccattg ccgtcccatg cacgctctca gcctggcctc | 240 |
| tgtaatatgt ataaggactc acatcacccg gctcggaccg cccattacgg cagtcttccg | 300 |
| cagaagagtc acggtcggac tcaagatgag aaccctgtag tccattttttt caagaacatt | 360 |
| gtcactccgc ggacacctcc cccaagccag ggaagggag ccgaagggca agacccggt | 420 |
| tttggctatg gcgggcgagc atcagactat aagtcagctc acaaaggttt taagggcgtc | 480 |
| gacgcccaag ggactcttag taaaattttc aaactgggag ggcgagacag tcgcagtgga | 540 |
| tcacctatgg cccgacgatg a | 561 |

<210> SEQ ID NO 143
<211> LENGTH: 514
<212> TYPE: DNA
<213> ORGANISM: Homo sapiens

<400> SEQUENCE: 143

| | |
|---|---|
| atggcgtcac agaagagacc ctcccagagg cacggatcca agtacctggc cacagcaagt | 60 |
| accatggacc atgccaggca tggcttcctc ccaaggcaca gagacacggg catccttgac | 120 |
| tccatcgggc gcttctttgg cggtgacagg ggtgcgccca agcggggctc tggcaaggac | 180 |
| tcacaccacc cggcaagaac tgctcactac ggctccctgc cccagaagtc acacggccgg | 240 |
| acccaagatg aaaaccccgt agtccacttc ttcaagaaca ttgtgacgcc tcgcacacca | 300 |
| cccccgtcgc agggaaaggg gagaggactg tccctgagca gatttagctg gggggccgaa | 360 |
| ggccagagac caggatttgg ctacggaggc agagcgtccg actataaatc ggctcacaag | 420 |
| ggattcaagg gagtcgatgc ccagggcacg cttttccaaaa ttttttaagct gggaggaaga | 480 |
| gatagtcgct ctggatcacc catggctaga cgct | 514 |

<210> SEQ ID NO 144
<211> LENGTH: 511
<212> TYPE: DNA
<213> ORGANISM: Homo sapiens

<400> SEQUENCE: 144

| | |
|---|---|
| atggcttctc agaaaagacc tagccaaaga cacggcagca agtacctggc caccgcctcc | 60 |
| accatggacc acgccagaca cggctttctg ccaagacacc gggacaccgg catcctggac | 120 |
| agcatcggcc gcttctttgg tggagataga ggcgccccta agcggggatc tggcaaggac | 180 |
| agccaccacc ccgccagaac cgctcactac ggctccctgc ctcagaagtc ccacggaaga | 240 |

```
acccaggacg agaaccccgt ggtccacttc ttcaagaaca tcgtgacacc cagaacacct      300
cctccatctc agggcaaagg caggggcctg agcctcagcc ggttcagctg gggcgctgaa      360
ggccagcggc ctggcttcgg ctacggcgga cgggccagcg attataagag cgcccataag      420
ggcttcaaag gcgtggacgc ccagggaaca ctgtctaaga tcttcaagct gggcggcaga      480
gatagcagaa gcggcagccc tatggcccgg a                                    511

<210> SEQ ID NO 145
<211> LENGTH: 515
<212> TYPE: DNA
<213> ORGANISM: Homo sapiens

<400> SEQUENCE: 145
atggcaagtc agaagcgccc gtcccaaagg cacggaagta agtacctcgc tacagcttca       60
accatggatc atgcaagaca cggctttctc ccaagacatc gcgacactgg tatcctcgat      120
agcataggac gattttttcgg gggtgacaga ggggcgccca aaagaggttc tggcaaagac      180
tcacatcacc ctgcaagaac agctcactat gggagcctgc ctcaaaagag ccacggaagg      240
acacaggacg aaaatccagt ggtgcatttc tttaaaaata tagtgacacc acgaaccccca     300 ccgccttcac agggaaaagg tcggggcctt tcactctcaa gattttcttg gggagcggag      360
ggccagcgcc cagggtttgg atacggaggc gcgctagtg attataagtc cgcacacaaa       420
ggtttcaaag gtgtagatgc ccaaggtact ttgagcaaaa tctttaaatt gggcgggcgc      480
gactcaagga gcggctcccc tatggcacgc agatg                                515

<210> SEQ ID NO 146
<211> LENGTH: 514
<212> TYPE: DNA
<213> ORGANISM: Homo sapiens

<400> SEQUENCE: 146
atggcaagcc agaagcgccc ttcccagcgc cacgggagta aatatctcgc aacagcaagt       60
actatggatc atgctcgcca cggctttctg ccccgacacc gcgacacagg aattttggac      120
tccatcggcc gcttttttgg tggggacaga ggagcaccca agcgcggtag tgcaaggac       180 tctcaccacc ccgcaagaac cgctcactat ggtagccttc ctcaaaaatc tcatggccgg      240
acgcaggatg aaaatccagt agtgcatttc ttcaagaata tcgtaacgcc aagaaccccg      300
ccgccttctc aaggaaaggg gcgaggtctg tctcttagcc gcttcagctg gggtgccgaa      360
ggacagaggc cgggctttgg atatggggggg agagcttcag actataagag cgcccacaaa     420
ggttttaagg gtgtggacgc ccaaggtact ctctcaaaaa tcttcaaact gggggggacgc     480 gatagtcggt ccggcagccc catgcccga agat                                  514

<210> SEQ ID NO 147
<211> LENGTH: 512
<212> TYPE: DNA
<213> ORGANISM: Homo sapiens

<400> SEQUENCE: 147
atggcaagcc agaagagacc gagccagaga catggaagta agtatttggc tacagcgagc       60
accatggatc atgcccgcca cggattcctc ccgagacata gagacacggg gatcctcgac      120
tctataggcc ggttctttgg gggagatagg ggtgccccca gcggggtag cggaaaagat       180 agccatcatc cggcccgcac tgcgcattac ggctcccttc cacaaaagtc acacgggcgg      240
```

```
acccaagacg agaatccggt ggttcatttt tttaagaaca tagtcacgcc taggacacca    300
ccgccgagtc aaggaaaagg acggggactc agccttagtc ggttttcctg gggagctgag    360
gggcaaaggc cgggctttgg ctatggcggt cgagcttcag attacaagag tgcacataaa    420
gggtttaagg gagttgatgc tcaaggaacc ctcagtaaaa tcttcaagtt gggtgggcgg    480
gattccaggt caggatcacc catggccagg ag                                  512

<210> SEQ ID NO 148
<211> LENGTH: 516
<212> TYPE: DNA
<213> ORGANISM: Homo sapiens

<400> SEQUENCE: 148
atggcttctc agaagcgccc tagccaacgc cacggctcca agtacttggc aacggcttct     60
accatggacc acgctaggca tggcttttg cctagacacc gagacacggg gattctcgat    120
tctataggga ggttctttgg gggggaccgg ggtgctccca agcggggtc cggaaaggat     180 agccaccacc cggctaggac ggctcattat ggtagcttgc cgcaaaagag tcatggtcgc    240
actcaggatg agaatcccgt agtccacttt tttaagaaca tcgtcacacc acggacgccc    300
ccgccttcac aagggaaagg tagggggcctc tcactctctc ggttcagctg gggtgccgag    360
ggacaacgac ctggttttgg ttacggaggg cgggctagtg attataagtc tgcgcataaa    420
ggctttaagg gtgtggacgc gcaaggcaca ctttcaaaga tttttaagct cggaggtcga    480
gattctcgat caggtagccc tatggcaaga cgctga                             516

<210> SEQ ID NO 149
<211> LENGTH: 483
<212> TYPE: DNA
<213> ORGANISM: Homo sapiens

<400> SEQUENCE: 149
atggcgtcac agaagagacc ctcccagagg cacggatcca agtacctggc cacagcaagt     60
accatggacc atgccaggca tggcttcctc ccaaggcaca gagacacggg catccttgac    120
tccatcgggc gcttctttgg cggtgacagg ggtgcgccca gcggggctc tggcaaggac    180 tcacaccacc cggcaagaac tgctcactac ggctccctgc cccagaagtc acacggccgg    240
acccaagatg aaaaccccgt agtccacttc ttcaagaaca ttgtgacgcc tcgcacacca    300
cccccgtcgc agggaaaggg ggccgaaggc cagagaccag gatttggcta cggaggcaga    360
gcgtccgact ataaatcggc tcacaaggga ttcaagggag tcgatgccca gggcacgctt    420
tccaaaattt ttaagctggg aggaagagat agtcgctctg gatcacccat ggctagacgc    480
tga                                                                 483

<210> SEQ ID NO 150
<211> LENGTH: 483
<212> TYPE: DNA
<213> ORGANISM: Homo sapiens

<400> SEQUENCE: 150
atggcttccc aaaagcggcc ttctcagcgg cacggcagca agtacctggc cacagccagc     60
acaatggacc acgccagaca cggcttcctg ccccggcacc gggacaccgg catcctggac    120
tccatcggca gattcttcgg cggagataga ggagcccta agagaggctc cggaaaggac    180
agccaccacc ccgccagaac cgccactac ggctctctgc cacagaaaag ccacggccgg    240
acccaggacg agaaccccgt ggtgcacttc tttaagaaca tcgtgacccc tagaacccct    300
```

```
ccacctagcc agggcaaggg tgctgaaggc cagagacctg gctttggcta cggcggaagg    360
gcctctgatt ataagagcgc ccataagggc ttcaaaggcg tcgacgccca gggaacactg    420
agcaaaatct tcaagctggg cggcagagat agcagaagcg gcagccctat ggctcgcaga    480
tga                                                                 483
```

AAV-BASED GENE THERAPIES FOR TREATMENT OF AUTOIMMUNE DISEASES

RELATED APPLICATIONS

This application claims the benefit of the filing date of U.S. Provisional Application No. 63/010,014, filed Apr. 14, 2020, the entire contents of which are incorporated by reference.

FIELD OF THE INVENTION

The present invention relates generally to the fields of molecular biology and virology, and in particular to the development of gene therapy vectors and methods for treatment of autoimmune diseases, such as multiple sclerosis (MS).

BACKGROUND OF THE INVENTION

Multiple Sclerosis (MS). MS is a multifocal demyelinating disease with progressive neurodegeneration caused by an autoimmune response to self-antigens in a genetically susceptible individual. Depending on where in the CNS the damage occurs, symptoms may include problems with muscle control, balance, vision, or speech. It is estimated that MS affects 250,000 to 350,000 people in the US alone. MS is an autoimmune disease that develops (in part) from a failure of central and peripheral tolerance mechanisms (particularly regulatory T cells, i.e., Tregs) to maintain self-tolerance and control potentially pathogenic autoreactive lymphocytes.[2,3] It is characterized by chronic lymphocyte infiltration and inflammation of the CNS, resulting in demyelination.

Gene Therapy. Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

Recombinant adeno-associated virus (rAAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). rAAV vectors have also generated long-term clinical benefit in humans when targeted to immune-privileged sites, e.g., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and CD8⁺ T cell responses against the viral capsid. Adaptive responses to the transgene product have also been reported in animal models (Manno et al., 2006; Mingozzi et al., 2007; Muruve et al., 2008; Vandenberghe and Wilson, 2007; Mingozzi and High, 2007).

In its normal "wild type" form, AAV DNA is packaged into the viral capsid as a single-stranded molecule about 4600 nucleotides (nt) in length. Following infection of the cell by the virus, the molecular machinery of the cell converts the single-stranded DNA into a double-stranded form. Only this double-stranded DNA form can be transcribed by cellular enzymes into RNA, which is then translated into polypeptides by additional cellular pathways.

BRIEF SUMMARY OF THE INVENTION

The present disclosure provides viral vector-based gene therapy methods for treating and/or ameliorating one or more of symptoms of autoimmune disease in human subjects. In particular, the present disclosure provides recombinant AAV (rAAV)-based gene therapy methods for tolerization of immune cells that are implicated in autoimmune disease, such as multiple sclerosis (MS). The development of such vectors, and compositions comprising them, provides a major advancement in medicine, and particularly in the development of a gene therapy-based treatment modality for MS.

The present disclosure overcomes these and other limitations of the prior art by providing novel AAV nucleic acid vectors that are optimized for liver-directed expression of neuroproteins (including, without limitation, myelin oligodendrocyte glycoprotein (MOG), proteolipid protein (PLP), and myelin basic protein (MBP)), or functional fragments thereof, including vectors that are optimized for expression in human cells. The disclosed vectors have enhanced immune tolerance-inducement properties that may abrogate the need for identifying HLA- and/or MHC-specific epitopes required for inducing antigen-specific Tregs. In some embodiments, the present disclosure permits each patient undergoing treatment to generate his/her own unique antigen-specific Tregs, which makes the treatment more universally applicable and more clinically feasible than existing technologies.

Two million people worldwide are living with MS. Diagnosis generally occurs at the ages of 20 to 40, but documented cases of MS in children as young as two have been reported. Schilder's disease, a variant of MS, is a rare progressive demyelinating disorder that usually begins in childhood. While there is currently no cure for MS, there are various MS treatment options which have been shown to decrease the severity and frequency of relapses and delay disease progression in numerous studies. The development of protocols that stimulate Treg numbers and/or their function has become a significant focus in treating autoimmune disease. In fact, many of the beneficial effects associated with currently FDA approved immune-modulators used in the treatment of MS are associated with restored Treg homeostasis.[2,4,5]

AAV gene therapy has been proven to be a powerful new tool for the treatment of a broad spectrum of diseases, including restoration of vision in patients with Leber congenital amaurosis by retinal gene transfer, and treatment of hemophilia B by hepatic gene therapy.[6,7] According to aspects of the disclosure, it has been demonstrated that hepatic gene therapy transfer with AAV vectors can reliably induce a robust, antigen-specific immune tolerance to a variety of proteins in experimental animals, even when the antigen is subsequently expressed in a highly immunogenic manner in other organs. Together, these results demonstrate that liver-directed gene therapy can abrogate potentially cytotoxic CD8⁺ T cell responses.[1,8-13] Importantly, it has also been shown that this protocol can even eliminate pre-existing antibodies.[1] This finding is quite significant since there is an increasing body of evidence that B cells and auto-antibodies may play a pathogenic role in demyelinating disease.[14,15] Others have shown that transgenic mice or transient transfection by plasmid or adenovirus vectors expressing myelin basic protein could prevent the onset of Experimental autoimmune encephalomyelitis (EAE) disease in mice.[16,17] Suppression was dependent on hepatic gene expression and was mediated by induction of antigen-specific Tregs. In contrast, aspects of the disclosure relate to treatment of certain autoimmune conditions, e.g., MS, utilizing AAV delivery of nucleic acids encoding one or more host proteins to the liver.

Hepatocyte-restricted transgene expression from an optimized AAV vector can reliably induce immune tolerance to various therapeutic proteins (e.g., mediated by antigen-specific $CD4^+CD25^+FoxP3^+$ Tregs). The process suppresses antibody formation and cytotoxic $CD8^+$ T cell response against the transgene product. Hepatic transgene expression is maintained even when the antigen is subsequently expressed in a highly immunogenic manner in other organs. The process efficiently and rapidly reverses pre-existing high antibody titers, and provides long-term correction of haemostasis in a murine hemophilia B model. Importantly, the method does not require protein to be secreted to be functional.

In some embodiments, advantageously, the novel rAAV nucleic acid vectors, expression constructs, and infectious virions and viral particles comprising them as disclosed herein have an improved efficiency in transducing one or more mammalian liver cells to provide persistent expression of one or more genes of interest.

In some embodiments, the improved rAAV nucleic acid vectors provided herein transduce mammalian cells with sufficient transduction efficiency to suppress the immune response associated with MS in patients, and thus abrogate CNS inflammation, and immune-mediated damage that occurs in MS patients. Unlike current therapies, this gene-therapy based approach represents a persistent, long-term treatment that reduces the clinical disability experienced by MS patients. The present invention also concerns rAAV nucleic acid vectors, comprising a polynucleotide that comprises a promoter, an enhancer, a post-transcriptional regulatory sequence, a polyadenylation signal, or any combination thereof, operably linked to the nucleic acid segment that encodes the selected transgene of interest.

Some embodiments contemplate a recombinant adeno-associated viral (rAAV) vector comprising a polynucleotide that comprises a first nucleic acid segment that is at least 95%, at least 98%, at least 99%, or at least 99.5% identical to any one of the sequences of SEQ ID NOs: 13, 16, 18, 20, 24, 26, 28-30, 32-34, 39-150. In some embodiments, the first nucleic acid segment of the rAAV vector encodes a first therapeutic molecule that comprises a neuropeptide selected from a myelin basic protein (MBP), a myelin oligodendrocyte glycoprotein (MOG), and a proteolipid protein (PLP). In some embodiments, the first therapeutic molecule is a MOG encoded by any one of the nucleotide sequences of SEQ ID NOs: 39-92. In some embodiments, the first therapeutic molecule is a PLP encoded by any one of the nucleotide sequences of SEQ ID NOs: 93-126, and 127-130. In some embodiments, the first therapeutic molecule is a MBP encoded by any one of the nucleotide sequences of SEQ ID NOs: 13, 16, 18, 20, 24, 26, 28-30, 32-34, 93, 113, 126, 131-150.

In some embodiments, the first nucleic acid segment of the rAAV vector is operably linked to a promoter that is capable of expressing the therapeutic molecule in a mammalian liver cell. In some embodiments, the promoter is a hepatocyte-specific promoter. In some embodiments, the hepatocyte-specific promoter comprises an albumin promoter, a human ai-antitrypsin promoter, a transthyretin (TTR) promoter, a hepatic combinatorial bundle (HCB) promoter, or an apolipoprotein E (apoE) promoter. In some embodiments, the hepatocyte-specific promoter comprises a hepatic combinatorial bundle (HCB) promoter. In some embodiments, the hepatocyte-specific promoter comprises a human apolipoprotein E (hapoE) promoter.

In some embodiments, the polynucleotide further comprises an enhancer, a post-transcriptional regulatory sequence, a polyadenylation signal, or any combination thereof, operably linked to the first nucleic acid segment. In some embodiments, the polynucleotide comprises AAV2 inverted terminal repeat sequences (ITRs).

In some embodiments, the polynucleotide comprises a second nucleic acid segment encoding a second therapeutic molecule. In some embodiments, the second therapeutic molecule is a MBP or a PLP if the first therapeutic molecule is MOG. In some embodiments, the second therapeutic molecule is a MBP or a MOG if the first therapeutic molecule is PLP. In some embodiments, the second therapeutic molecule is a PLP or a MOG if the first therapeutic molecule is MBP.

In some embodiments, the second nucleotide sequence or the second autoimmune disease therapeutic molecule of interest is not necessary for the full therapeutic function of the rAAV.

In some embodiments, the polynucleotide comprises a third nucleic acid segment encoding a third therapeutic molecule. In some embodiments, the third therapeutic molecule is a MOG, if the first and second therapeutic molecules comprise a MBP and a PLP. In some embodiments, the third therapeutic molecule is a PLP, if the first and second therapeutic molecules comprise a MBP and a MOG. In some embodiments, the third therapeutic molecule is a MBP, if the first and second therapeutic molecule comprises a MOG and a PLP. In some embodiments, the polynucleotide encodes a MOG, a MBP, and a PLP. In some embodiments, the second therapeutic molecule and/or the third therapeutic molecule is encoded by any one of the sequences of SEQ ID NOs: 13, 16, 18, 20, 24, 26, 28-30, 32-34, 39-93, and 100-150. In some embodiments, the MOG, the PLP, and/or the MBP comprises a full-length polypeptide.

The present disclosure further provides compositions and formulations that include one or more of the proteins, nucleic acid segments, viral vectors, host cells, or viral particles of the present invention, together with one or more pharmaceutically-acceptable buffers, diluents, or excipients. Such compositions may be included in one or more diagnostic or therapeutic kits for diagnosing, preventing, treating or ameliorating one or more symptoms of a mammalian inflammatory disease, such as autoimmune disease, and in particular, for delivery of a therapeutic agent for the treatment of MS in a human.

The present disclosure further includes a method for providing a mammal (e.g., a human) in need thereof with a diagnostically- or therapeutically-effective amount of a selected therapeutic agent, the method comprising administering to a cell, tissue or organ of a mammal in need thereof an amount of one or more of the disclosed rAAV nucleic acid vectors. In some embodiments, administration is continued for a time which is effective to provide the mammal with a diagnostically- or a therapeutically-effective amount of the selected therapeutic agent.

In some embodiments, an rAAV vector of the present disclosure is used to treat an autoimmune disease. In some embodiments, the autoimmune disease is selected from multiple sclerosis, disseminated sclerosis, encephalomyelitis disseminata, optic neuritis, celiac disease, diabetes, Graves' disease, Hashimoto's disease, hyperthyroidism, or an allergic disease. In some embodiments, the autoimmune disease is multiple sclerosis.

The present disclosure further provides a method for diagnosing, preventing, treating, and/or ameliorating at least one symptom of a disease, a disorder, a dysfunction, an injury, an abnormal condition, and/or trauma in a mammal (e.g., a human). In an overall and general sense, the method includes at least the step of administering to the mammal in need thereof one or more of the disclosed rAAV nucleic acid vectors, in an amount and for a time sufficient to diagnose, prevent, treat or ameliorate the one or more symptoms of the disease, disorder, dysfunction, injury, abnormal condition, or trauma in the mammal.

BRIEF DESCRIPTION OF THE DRAWINGS

The following drawings form part of the present specification and are included to demonstrate certain aspects of the present invention. The present disclosure may be better understood by reference to the following description taken in conjunction with the accompanying drawings, in which like reference numerals identify like elements, and in which:

FIG. 1 describes aspects of an experimental autoimmune encephalomyelitis (EAE) murine model employed in the present study as an animal model for MS.

FIG. 2A and FIG. 2B show a mouse model and mean clinical score criteria for the EAE study.

FIG. 4A shows the Western blot analysis from protein extracted from liver, while FIG. 4B shows the analysis of transcriptional levels using real-time RT-PCR.

In FIG. 5A, five female mice were injected subcutaneously with antigen in complete Freund's adjuvant (Ag/CFA) emulsion. Mean clinical score (±standard error of measurement (SEM)) was recorded starting at day 12. In FIG. 5B, five female C57BL/6 mice were injected subcutaneously with MOG/CFA emulsion. Mean clinical score (±SEM) was recorded.

FIG. 6A: Mean clinical score, FIG. 6B: anti-MOG IgG1, FIG. 6C: anti-MOG IgG2c.

FIG. 13A, FIG. 13B, and FIG. 13C show mean clinical score (MCS) in EAE-induced C57BL/6 mice that received AAV8-MOG or control vector after the mice reached a specific MCS. FIG. 13A shows MCS in EAE-induced C57BL/6 mice that received AAV8-MOG or control vector after the mice reached a MCS of about 0.3. FIG. 13B shows mean clinical score (MCS) in EAE-induced C57BL/6 mice that received AAV8-MOG or control vector after the mice reached a MCS of about 0.8. FIG. 13C shows mean clinical score (MCS) in EAE-induced C57BL/6 mice that received AAV8-MOG or control vector after the mice reached a MCS of about 1.3. Bar graphs show statistical significance between final scores and peak-to-final scores throughout.

FIG. 14A and FIG. 14B show serial sections of spinal cord from an EAE induced female mouse ~35 days after receiving control vector (MCS=4.0). FIG. 14A is a hematoxylin and eosin (H&E) stain showing areas of high inflammatory infiltration. FIG. 14B is a Luxol fast blue stain showing areas of demyelination. Circled areas highlight the co-localization of inflammation and loss of myelin.

FIG. 15A and FIG. 15B show serial sections of spinal cord from an EAE induced female mouse ~35 days after receiving AAV-MOG vector (MCS=1.25). FIG. 15A is a hematoxylin and eosin stain showing diminished infiltration. FIG. 15B is a Luxol fast blue stain which shows that the section has less areas of demyelination as a result of the suppression of the inflammation.

FIG. 19A shows a Western blot analysis from protein extracted from liver of mice injected with AAV-MBP. FIG. 19B shows analysis of transcriptional levels of RNA obtained from the liver of mice treated with AAV-MBP or control by real-time RT-PCR.

FIG. 20A shows Western blot analysis from liver lysates obtained from mice injected with AAV8.MOG 200 days after EAE or control (AAV8.GFP; lane C). Lane M is a molecular size marker in kDa. FIG. 20B shows real-time qPCR analysis to estimate the transgene copy number from liver lysates (±SD) (n=4). FIG. 20C shows representative flow cytometry analysis of freshly isolated splenocytes from FOXP3$^{gfp+}$ reporter mice tolerized with AAV8.MOG vector that were stained ex vivo with MOG/I-A$^b$ or h.CLIP/I-A$^b$ (control) tetramers. FIG. 20D shows statistical comparison of I-A$^b$ MOG and I-A$^b$ h.CLIP (control) tetramer populations of CD4$^+$CD25$^+$ FOXP3$^+$ Tregs from mice that received AAV.MOG vector (n=8; U=0; p=0.0002, two-tailed Mann-Whitney U test). FIG. 20E and FIG. 20F show an in vitro Treg suppression assay. FIG. 20E shows FOXP3$^{gfp+}$ Tregs isolated from mice after being tolerized with AAV.MOG were co-cultured at indicated concentrations with MOG-specific 2D2 T cells in the presence of 1 μg/μL MOG$_{35-55}$ peptide. FIG. 20F shows the mean % suppression of Tregs (n=3; 1:160 versus 1:10: t=9.753, df=3.967, p=0.0006; 1:40 versus 1:10:t=4.565, df=2.705, p=0.0246, unpaired t test with Welch's correction; experiment was repeated twice). Data are presented with mean values as indicated; error bars show ±SD. *p<0.05; ***p<0.001.

FIG. 21A shows the experimental scheme and initial timeline in days. FIG. 21B shows MCS (±SEM) of AAV8.MOG-treated mice and control mice (n=5 per group; ****p<0.0001, two-tailed t test, Mann-Whitney test). Experiments were reproduced at least twice. FIG. 21C shows anti-MOG$_{35-55}$ titers measured via ELISA (mean±SEM) (n=3 per group). FIG. 21D shows IgG2c antibody titers measured via ELISA (mean±SEM) (n=3 per group). FIG. 21E shows the frequency of CD4$^+$CD25$^+$FOXP3$^+$ Tregs (mean±SD) present in blood at 5 weeks after vector administration (n=6 group; U=4; p=0.0260, two-tailed Mann-Whitney U test). FIG. 21F shows plasma alanine aminotransferase (ALT) enzyme levels (IU/L) from age-matched naive control mice and vector-treated mice at 105 days post-injection (n=10 per group).

FIG. 22A shows the experimental scheme and initial timeline in days. FIG. 22B shows MCS (±SEM) of AAV8.MOG-treated mice and control mice (n=9-10 per group; p<0.0001, two-tailed t test, Mann-Whitney test). Right panel: blow-out-treated mice showing only 2 of 10 developed relapsing-remitting EAE. FIG. 22C shows the survival curve of mice (p>0.0001, log rank [Mantel-Cox] test). FIG. 22D shows plasma ALT levels (IU/L) from age-matched naive control mice and vector treated at various time points. Dashed line is time of re-challenge.

FIG. 23A shows MCS 0.3, loss of tail tonality (n=5; final control versus final AAV8.MOG: q=0.9342, degrees of freedom (D.F.) 12, p<0.0001; peak AAV8.MOG versus final AAV8.MOG: q=10.74, D.F. 12, p<0.0001). FIG. 23B shows MCS 0.8, tail paralysis (n=9-10; final control versus final AAV8.MOG: q=9.042, D.F. 30, p<0.0001; peak AAV8.MOG versus final AAV8.MOG: t=8.627, D.F. 30, p<0.0001). FIG. 23C shows MCS 1.3, tail paralysis with hind-leg paresis (n=5; final control versus final AAV8.MOG: q=4.358, D.F. 12, p=0.0412; peak AAV8.MOG versus final AAV8.MOG: q=6.9, D.F. 124, p=0.0019). Dashed line indicates MCS at time of treatment. Statistical analysis was determined using two-way ANOVA Tukey's multiple comparisons test. Gray symbols in the top panels of FIGS. 23A-23C represent non-responding mice. *p<0.05; p<0.01; *p<0.001; ****p<0.0001. FIG. 23D shows representative histological images of two different regions of spinal cord demonstrating multiple foci of inflammation in the white matter of control mice (H&E staining, top row) and serial section of spinal cord from the same mouse showing multifocal demyelination associated with the areas of inflammation (Luxol fast blue (LFB) staining, bottom row). In contrast, despite having reached a higher peak clinical score, there was an absence of infiltrates in the CNS of AAV8.MOG-treated mice. Certain regions of the spinal cord sections are magnified at right.

FIGS. 24A-24C show that mice developed neurological symptoms. FIG. 24A shows MCS 1.4, tail paralysis with hind-leg paresis (n=10; final control versus final AAV8.MOG: q=12.03, D.F. 34, p<0.0001; peak AAV8.MOG versus final AAV8.MOG: q=9.95, D.F. 34, p<0.0001). FIG. 24B shows MCS 3.0, hind-leg paralysis (n=7-8; final control versus final AAV8.MOG: q=11, D.F. 14, p<0.0001; peak AAV8.MOG versus final AAV8.MOG: q=8.085, D.F. 14, p=0.0003). FIG. 24C shows MCS 3.5, hind-leg paralysis with forearm paresis (n=5; final control versus final AAV8.MOG: q=7.439, D.F. 12, p=0.0010; peak AAV8.MOG versus final AAV8.MOG: q=7.123, D.F. 12, p=0.0014). Mice were intravenously injected with either AAV8.MOG and rapamycin (rapa) or rapamycin alone (control). Clinical scores (mean±SEM) were recorded. Graphical representation of peak and endpoint MCS are shown above group statistics. Dashed lines indicate MCS at time of treatment. Arrows indicate time of vector and rapamycin injections. Data are representative of at least two repeat experiments. FIG. 24D shows a representative FACS analysis of CD25$^{hi}$FOXP3$^+$ Tregs in blood (isolated from mice in group A) after rapamycin treatment. FIG. 24E shows the percentage of Tregs (mean±SEM) (post-rapa control versus post-rapa AAV8.MOG: n=3, t=3.996, df=4, p=0.0162, unpaired two-tailed Student's t test) and FIG. 24F shows activated CD44$^+$ Tregs obtained from peripheral blood at the indicated times (post-rapa control versus post-rapa AAV8.mog: n=3, q=5.368, df=8, p=0.0219; pre-rapa AAV8.MOG versus post-rapa AAV8.MOG: n=3, q=7.698, df=8, p=0.0027, two-way ANOVA Tukey's multiple comparisons test) (pre-EAE=naive mice; pre-Rapa=day 0; post-Rapa=day 10). FIG. 24G shows plasma alanine aminotransferase (ALT) activity from AAV8.MOG-treated and control mice following rapamycin treatment with MCS 3.0 (n=10). FIG. 24H shows plasma alanine aminotransferase (ALT) activity from AAV8.MOG-treated and control mice following rapamycin treatment with MCS 3.5 (n=10). Statistical analysis was determined for the responders by two-way ANOVA with Tukey's multiple comparisons test. Plots indicated with gray symbols and smaller circles in the top panels of FIGS. 24A-24C indicate non-responding mice. *p<0.05; p<0.01; *p<0.001; ****p<0.0001.

FIG. 28D shows areas of inflammation (left) and demyelination (right) in control subjects (top) and subjects treated with AAV.MOG (bottom).

FIG. 29B shows Western Blot analysis from liver tissue demonstrating the expression of mPLP at end point. FIG. 29C shows that treated mice had significantly lower αPLP IgG than control mice at various timepoints. Histological analysis was performed on spinal cords at endpoint. LFB stain represents myelin, and the H&E stain shows inflammation (FIG. 29D). H&E is the combination of two histological stains: hematoxylin and eosin. The hematoxylin stains cell nuclei blue, and eosin stains the extracellular matrix and cytoplasm pink. Timing of treatment in FIG. 29B corresponds to an initial moderate/severe disease, whereas treatment in FIG. 29C corresponds to the remittance of the initial disease. In all timelines, AAV.PLP established overt protection and preventing disease relapse.

FIG. 31A shows that vector-treated mice were protected and failed to develop disease induced with $PLP_{139-151}$ peptide, whereas the control mice developed EAE. FIG. 31B shows the evaluation of liver inflammation at various time points via analysis of ALT levels.

FIG. 41A shows that DBA ($H2^q$) mice receiving the AAV.MOG gene-immunotherapy ($MOG_{79-96}$) showed virtually no signs of disease onset nor cellular infiltration or demyelination within the CNS (hallmarks of EAE) when compared to mice receiving AAV.null. FIG. 41B shows that DBA ($H2^q$) mice receiving the AAV.MOG gene-immunotherapy ($MOG_{79-9}6$) had significant reductions in neurological impairment (clinical disease score) (p<0.05), cellular infiltration, and demyelination as compared to controls receiving AAV.null.

DETAILED DESCRIPTION

Figure 2B:
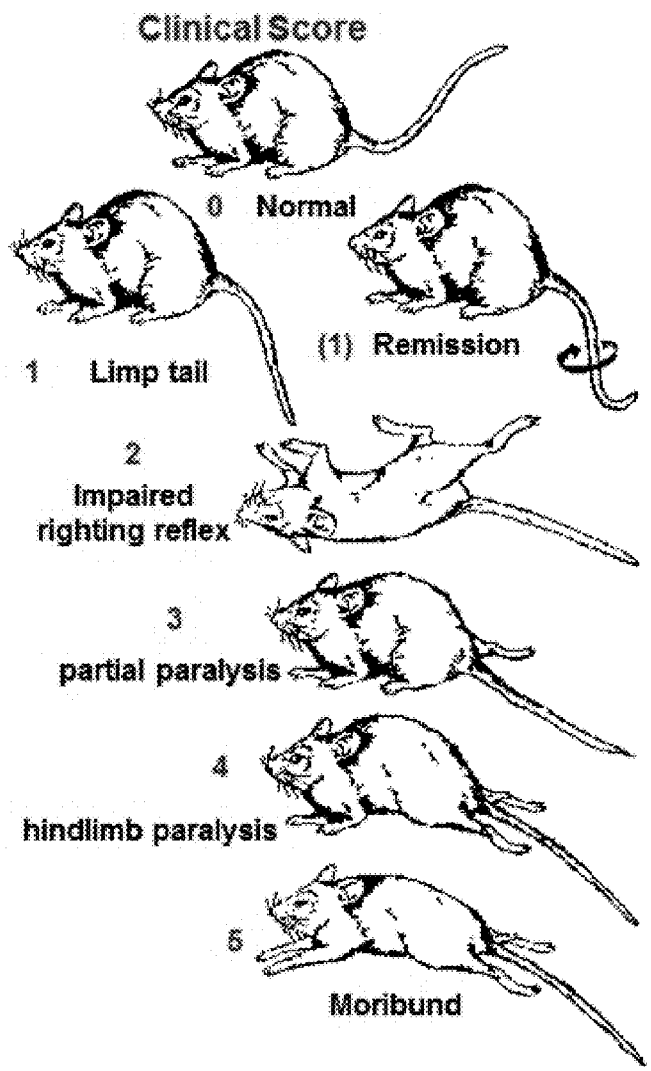
Figure 3:
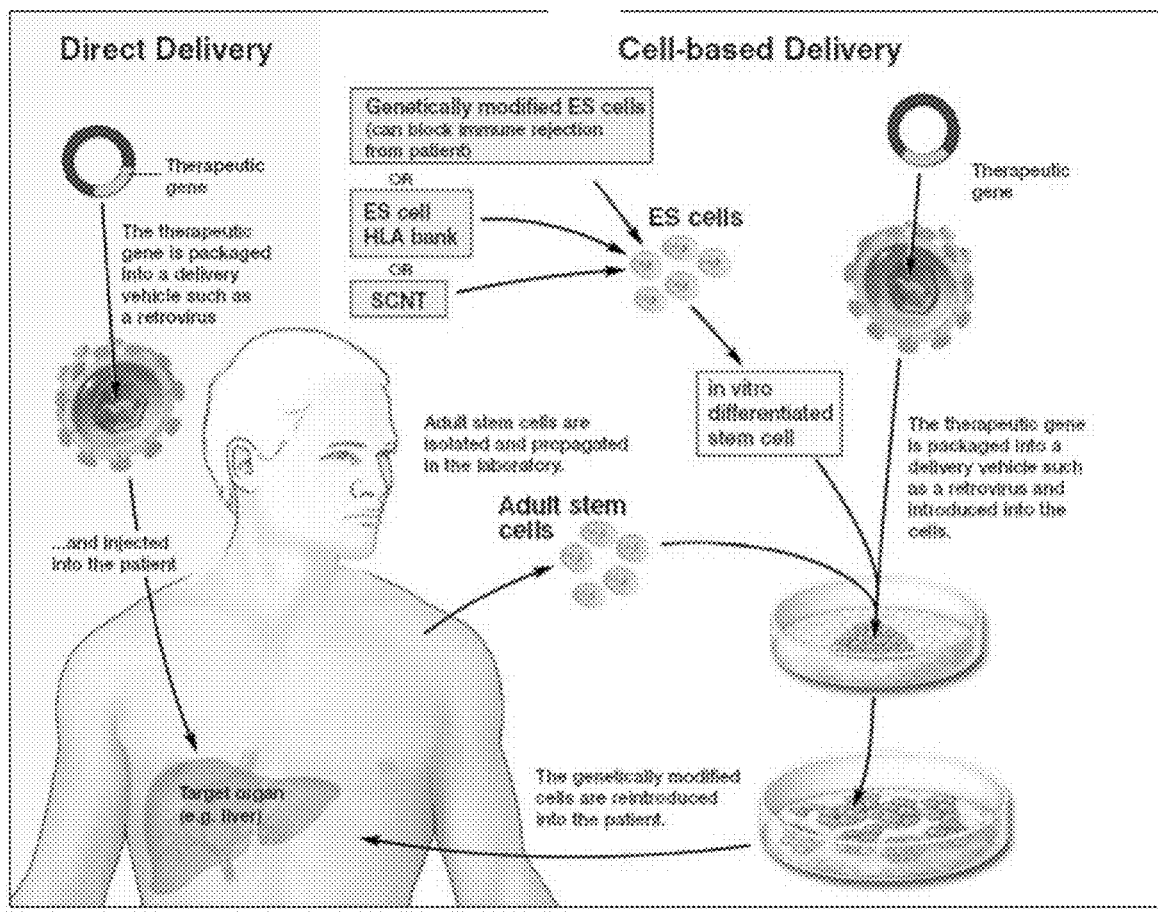
FIG. 3 shows a comparison of exemplary methods of the present invention as contrasted with the cell-based delivery methods of the prior art.

The present disclosure provides recombinant AAV vectors having enhanced tolerization properties. In particular embodiments, the rAAV vectors encode therapeutic peptides, such as MOG, MBP, and/or PLP. The therapeutic peptides encoded in the disclosed vectors are useful for induction of immunological tolerance. Accordingly, the disclosed vectors are particularly useful for the in vivo induction of immunological tolerance via a liver-directed AAV-based gene therapeutic regimen for treating and/or ameliorating autoimmune disorders such as multiple sclerosis. In particular embodiments, the disclosed rAAV vectors are codon-optimized for expression in mammalian cells, such as human cells. Further disclosed are rAAV particles and pharmaceutical compositions comprising the disclosed rAAV vectors, and methods of administering to subjects in need thereof the disclosed rAAV particles and compositions. Further provided herein are methods for preventing an autoimmune disease (e.g., MS) or inhibiting progression of the disease in a mammal (e.g., a human), the method comprising administering to the mammal any one of the disclosed rAAV vectors, as well as uses of these vectors as medicaments.

In some embodiments, a rAAV nucleic acid vector described herein comprises inverted terminal repeat sequences (ITRs), such as those derived from a wild-type AAV genome, such as the AAV2 genome. In some embodiments, the rAAV nucleic acid vector further comprises a polynucleotide that includes a first nucleic acid segment (also referred to as a heterologous nucleic acid molecule or a transgene) operably linked to a promoter and optionally, other regulatory elements, wherein the ITRs flank the first nucleic acid segment. In some embodiments, the ITRs comprise AAV2 ITRs. In some embodiments, the ITRs comprise AAV8 ITRs. Thus, in some embodiments, the polynucleotide further comprises an enhancer, a post-transcriptional regulatory sequence, a polyadenylation signal, or any combination thereof, operably linked to the first nucleic acid segment.

In some embodiments, the polynucleotide of the rAAV nucleic acid vector further comprises a second nucleic acid segment (also referred to as a second heterologous nucleic acid molecule or a transgene) operably linked to a promoter and optionally, other regulatory elements. The ITRs flank the polynucleotide comprising the first and second nucleic acid segments. In some embodiments, the ITRs are AAV2 or AAV8 ITRs. Thus, in some embodiments, the polynucleotide further comprises an enhancer, a post-transcriptional regulatory sequence, a polyadenylation signal, or any combination thereof, operably linked to the first and/or second nucleic acid segment.

In some embodiments, the polynucleotide of the rAAV nucleic acid vector further comprises a third nucleic acid segment (also referred to as a third heterologous nucleic acid molecule or a transgene) operably linked to a promoter and optionally, other regulatory elements. The ITRs flank the nucleic acid segment comprising the first, second and third nucleic acid segments. In some embodiments, the ITRs are AAV2 or AAV8 ITRs. Thus, in some embodiments, the polynucleotide further comprises an enhancer, a post-transcriptional regulatory sequence, a polyadenylation signal, or any combination thereof, operably linked to the first, second and/or third nucleic acid segment.

In some embodiments, the promoter is a mammalian cell-specific or a mammalian tissue-specific promoter. In some embodiments, the promoter is a promoter that is capable of expressing the nucleic acid segment in one or more cells of a mammalian liver, such as human hepatocyte cells. In some embodiments, the promoter is a hepatocyte-specific promoter. Exemplary hepatocyte-specific promoters and enhancer elements include, e.g., albumin, human al-antitrypsin (hAAT), transthyretin (TTR), hepatic combinatorial bundle (HCB) promoter, and apolipoprotein E (apoE) promoters or enhancer elements. In some embodiments, the hepatocyte-specific promoter comprises a hepatic combinatorial bundle (HCB) promoter. In some embodiments, the hepatocyte-specific promoter comprises a human apolipoprotein E (hapoE) promoter.

In some embodiments, the rAAV nucleic acid vector comprises a polynucleotide that comprises a first nucleic acid segment (or sequence) that has a nucleotide sequence is at least 95%, at least 98%, at least 99%, or at least 99.5% identical to any one of the sequences of SEQ ID NOs: 8, 10, 12, 13, 14, 16, 18, 20, 22, 24, 26, 28-30, 32-34, or 38-150. In some embodiments, the rAAV nucleic acid vector comprises a polynucleotide that comprises a first nucleic acid sequence that is at least 95%, at least 98%, at least 99%, or at least 99.5% identical to any one of the sequences of SEQ ID NOs: 13, 16, 18, 20, 24, 26, 28-30, 32-34, 38-150.

In some embodiments, the first nucleic acid sequence encodes a first autoimmune disease therapeutic molecule of interest (e.g., an "autoimmune therapeutic molecule"). As used herein, an autoimmune therapeutic molecule includes any antigen (such as a protein, fragment thereof, or a peptide) that contributes to initiation and/or progression of an autoimmune disease. Exemplary autoimmune therapeutic molecules include myelin basic protein (MBP, e.g., for multiple sclerosis), proteolipid protein (PLP, e.g., for multiple sclerosis), myelin oligodendrocyte glycoprotein (MOG, e.g., for multiple sclerosis), myelin-associated glycoprotein (MAG, e.g., for Anti-MAG Peripheral Neuropathy), insulin (e.g., for type 1 diabetes), islet-specific glucose-6-phosphatase catalytic subunit-related protein (IGRP, e.g., for type 1 diabetes), Preproinsulin (e.g., for type 1 diabetes), Glutamic decarboxylase (GAD, e.g., for type 1 diabetes), tyrosine phosphatase like autoantigen (e.g., for type 1 diabetes), insulinoma antigen-2 (e.g., for type 1 diabetes), Islet cell antigen (e.g., for type 1 diabetes), thyroid stimulating hormone (TSH) receptor (e.g., for Graves' disease), thyrotropin receptor (e.g., for Graves' disease), Aggrecan (e.g., for rheumatoid arthritis), CD4+T cell epitope (GRVRVN-SAY (SEQ ID NO: 36), e.g., for proteoglycan induced arthritis (PGIA) or rheumatoid arthritis), or acetylcholine receptor (e.g., for Myasthenia gravis). In some embodiments, the autoimmune therapeutic molecule of interest is a human protein, such as human myelin basic protein (MBP), a human proteolipid protein (PLP), or a human myelin oligodendrocyte glycoprotein (MOG).

In some embodiments, the first nucleic acid sequence encodes a first autoimmune disease therapeutic molecule of interest, such as a mammalian myelin basic protein (MBP), proteolipid protein (PLP), or myelin oligodendrocyte glycoprotein (MOG). In some embodiments, the first nucleic acid sequence encodes a human MBP, a human MOG, or a human PLP. In particular embodiments, the full-length MBP, MOG, and/or PLP is encoded in the polynucleotide.

In some embodiments, the first therapeutic molecule is encoded by any one of SEQ ID NOs: 13, 16, 18, 20, 24, 26, 28-30, 32-34, 39-93, and 100-150. In some embodiments, where the first therapeutic molecule is MOG, the first therapeutic molecule is encoded by any one of SEQ ID NOs: 39-92. In some embodiments, where the first therapeutic molecule is PLP, the first therapeutic molecule is encoded by any one of SEQ ID NOs: 100-112, 114-125, and 127-130. In some embodiments, where the first therapeutic molecule is MBP, the first therapeutic molecule is encoded by any one of SEQ ID NOs: 13, 16, 18, 20, 24, 26, 28-30, 32-34, 93, 113, 126, and 131-150.

In some embodiments, the polynucleotide encodes a second nucleic acid sequence encoding a second autoimmune disease therapeutic molecule of interest, such as a mammalian myelin basic protein (MBP), proteolipid protein (PLP), or myelin oligodendrocyte glycoprotein (MOG). In some embodiments, the second therapeutic molecule is a MBP or a PLP if the first therapeutic molecule is MOG. In some embodiments, the second therapeutic molecule is a MBP or a MOG if the first therapeutic molecule is PLP. In some embodiments, the second therapeutic molecule is a PLP or a MOG if the first therapeutic molecule is MBP. In some embodiments, the second therapeutic molecule is encoded by any one of SEQ ID NOs: 13, 16, 18, 20, 24, 26, 28-30, 32-34, 38-150. In some embodiments, where the second therapeutic molecule is MOG, the second therapeutic molecule is encoded by any one of SEQ ID NOs: 38-92. In some embodiments, where the second therapeutic molecule is PLP, the second therapeutic molecule is encoded by any one of SEQ ID NOs: 100-112, 114-125, and 127-130. In some embodiments, where the second therapeutic molecule is MBP, the second therapeutic molecule is encoded by any one of SEQ ID NOs: 13, 16, 18, 20, 24, 26, 28-30, 32-34, 93, 113, 126, 131-150.

In some embodiments, the MOG, the PLP, and/or the MBP comprises a full-length polypeptide. In some embodiments, the second nucleic acid sequence encodes a polypeptide, a peptide, a ribozyme, a peptide nucleic acid, an siRNA, an RNAi, an antisense oligonucleotide, an antisense polynucleotide, an antibody, an antigen binding fragment, or any combination thereof. In some embodiments, the second nucleic acid sequence encodes a proteolipid protein, a myelin oligodendrocyte, a glycoprotein, a myelin-associated glycoprotein, insulin, an islet-specific glucose-6-phosphatase catalytic subunit-related protein, a Preproinsulin, a glutamic decarboxylase, a tyrosine phosphatase like autoantigen, an insulinoma antigen-2, an Islet cell antigen, a thyroid stimulating hormone (TSH) receptor, a thyrotropin receptor, an Aggrecan, a CD4+ T cell epitope, a porin, or an acetylcholine receptor.

In some embodiments, the second nucleotide sequence or the second autoimmune disease therapeutic molecule of interest is not necessary for the full therapeutic function of the rAAV.

In some embodiments, the polynucleotide encodes a third nucleic acid sequence encoding a third autoimmune disease therapeutic molecule of interest, such as a human myelin basic protein (MBP), proteolipid protein (PLP), or myelin oligodendrocyte glycoprotein (MOG). In some embodiments, the third therapeutic molecule is a MOG, if the first and second therapeutic molecules comprise a MBP and a PLP. In some embodiments, the third therapeutic molecule is a PLP, if the first and second therapeutic molecules comprises a MBP and a MOG. In some embodiments, the third therapeutic molecule is a MBP, if the first and second therapeutic molecule comprises a MOG and a PLP. In some embodiments, the third therapeutic molecule is encoded by any one of SEQ ID NOs: 13, 16, 18, 20, 24, 26, 28-30, 32-34, and 39-93, 100-150. In some embodiments, where the third therapeutic molecule is MOG, the third therapeutic molecule is encoded by any one of SEQ ID NOs: 38-92. In some embodiments, where the third therapeutic molecule is PLP, the third therapeutic molecule is encoded by any one of SEQ ID NOs: 100-112, 114-125, and 127-130. In some embodiments, where the third therapeutic molecule is MBP, the third therapeutic molecule is encoded by any one of SEQ ID NOs: 13, 16, 18, 20, 24, 26, 28-30, 32-34, 93, 113, 126, 131-150. Thus, in some embodiments, the polynucleotide encodes a MOG, a MBP, and a PLP.

In some embodiments, the MOG, the PLP, and/or the MBP comprises a full-length polypeptide. In some embodiments, the third nucleic acid sequence encodes a polypeptide, a peptide, a ribozyme, a peptide nucleic acid, an siRNA, an RNAi, an antisense oligonucleotide, an antisense polynucleotide, an antibody, an antigen binding fragment, or any combination thereof. In some embodiments, the third nucleic acid sequence encodes a proteolipid protein, a myelin oligodendrocyte, a glycoprotein, a myelin-associated glycoprotein, insulin, an islet-specific glucose-6-phosphatase catalytic subunit-related protein, a Preproinsulin, a glutamic decarboxylase, a tyrosine phosphatase like autoantigen, an insulinoma antigen-2, an Islet cell antigen, a thyroid stimulating hormone (TSH) receptor, a thyrotropin receptor, an Aggrecan, a CD4+ T cell epitope, a porin, or an acetylcholine receptor.

In some embodiments, the third nucleotide sequence or the third autoimmune disease therapeutic molecule of interest is not necessary for the full therapeutic function of the rAAV.

Exemplary polynucleotide sequences (e.g., cDNA sequences) and protein sequences that may be encoded by the polynucleotide are provided below. In some embodiments, the transgene comprises a sequence that is at least 80%, 85%, 90%, 91%, 92%, 93%, 94%, 95%, 96%, 97%, 98%, or 99% identical to any one of the cDNA sequences provided below (SEQ ID NOs: 8, 10, 12, 13, 14, 16, 18, 20, 22, 24, 26, 28-30, 32-34, or 38-150). In some embodiments, the transgene comprises a sequence that is any one of the cDNA sequences provided below (SEQ ID NOs: 8, 10, 12, 13, 14, 16, 18, 20, 22, 24, 26, 28-30, 32-34, or 38-150). In some embodiments, the transgene (e.g., a cDNA sequence) is codon-optimized for expression in human cells. In some embodiments, the transgene contains a nucleotide sequence that encodes at least 20, 30, 40, 50, 60, 70, 80, 90, 100, 110, 120, 130, 140, 150, 160, 170, 180, 190, 200, 210, 220, 230, 240 or more contiguous amino acids of any one of the protein sequences provided herein (e.g., any one of SEQ ID NOs: 1, 2, 3, 9, 11, 15, 17, 19, 21, 23, 25, 27, 31, or 35). In some embodiments, the transgene contains a nucleotide sequence that encodes a protein that is at least 80%, 85%, 90%, 91%, 92%, 93%, 94%, 95%, 96%, 97%, 98%, or 99% identical to any one of the protein sequences provided herein (e.g., any one of SEQ ID NOs: 1, 2, 3, 9, 11, 15, 17, 19, 21, 23, 25, 27, 31, or 35). In some embodiments, the transgene contains a nucleotide sequence that encodes any one of the protein sequences provided herein (e.g., any one of SEQ ID NOs: 1, 2, 3, 9, 11, 15, 17, 19, 21, 23, 25, 27, 31, or 35).

Exemplary *Mus musculus* Myelin Oligodendrocyte Glycoprotein (MOG) cDNA

Exemplary *Mus musculus* Proteolipid Protein 1 (PLP) cDNA

```
                                              (SEQ ID NO: 10)
ATGGGCTTGTTAGAGTGTTGTGCTAGATGTCTGGTAGGGGCCCCCTTTG

CTTCCCTGGTGGCCACTGGATTGTGTTTCTTTGGAGTGGCACTGTTCTG

TGGATGTGGACATGAAGCTCTCACTGGTACAGAAAAGCTAATTGAGACC

TATTTCTCCAAAAACTACCAGGACTATGAGTATCTCATTAATGTGATTC

ATGCTTTCCAGTATGTCATCTATGGAACTGCCTCTTTCTTCTTCCTTTA

TGGGGCCCTCCTGCTGGCTGAGGGCTTCTACACCACCGGCGCTGTCAGG

CAGATCTTTGGCGACTACAAGACCACCATCTGCGGCAAGGGCCTGAGCG

CAACGGTAACAGGGGGCCAGAAGGGGAGGGGTTCCAGAGGCCAACATCA

AGCTCATTCTTTGGAGCGGGTGTGTCATTGTTTGGGAAAATGGCTAGGA

CATCCCGACAAGTTTGTGGGCATCACCTATGCCCTGACTGTTGTATGGC

TCCTGGTGTTTGCCTGCTCGGCTGTACCTGTGTACATTTACTTCAATAC

CTGGACCACCTGTCAGTCTATTGCCTTCCCTAGCAAGACCTCTGCCAGT

ATAGGCAGTCTCTGCGCTGATGCCAGAATGTATGGTGTTCTCCCATGGA

ATGCTTTCCCTGGCAAGGTTTGTGGCTCCAACCTTCTGTCCATCTGCAA

AACAGCTGAGTTCCAAATGACCTTCCACCTGTTTATTGCTGCGTTTGTG
```

```
                                              (SEQ ID NO: 8)
  1    atggcctgtt tgtggagctt ctctttgccc agctgcttcc tctcccttct cctcctcctt 61    ctcctccagt tgtcatgcag ctatgcagga caattcagag tgataggacc agggtatccc 121    atccgggctt tagttgggga tgaagcagag ctgccgtgcc gcatctctcc tgggaaaaat 181    gccacgggca tggaggtggg ttggtaccgt tctcccttct caagagtggt tcacctctac 241    cgaaatggca aggaccaaga tgcagagcaa gcacctgaat accggggacg cacagagctt 301    ctgaaagaga ctatcagtga gggaaaggtt acccttagga ttcagaacgt gagattctca 361    gatgaaggag gctacacctg cttcttcaga gaccactctt accaagaaga ggcagcaatg 421    gagttgaaag tggaagatcc cttctattgg gtcaaccccg gtgtgctgac tctcatcgca 481    cttgtgccta cgatcctcct gcaggtctct gtaggccttg tattcctctt cctgcagcac 541    agactgagag gaaaacttcg tgcagaagta gagaatctcc atcggacttt tgatcctcac 601    ttcctgaggg tgccctgctg gaagataaca ctgtttgtta ttgtgcctgt tcttggaccc 661    ctggttgcct tgatcatctg ctacaactgg ctgcaccgaa gactggcagg acagtttctt 721    gaagagctaa gaaaccccct ttga
```

Exemplary *Mus musculus* Myelin-Oligodendrocyte Glycoprotein (MOG) Protein

```
                                              (SEQ ID NO: 9)
  1    maclwsfswp scflslllll llqlscsyag qfrvigpgyp iralvgdeae lpcrispgkn 61    atgmevgwyr spfsrvvhly rngkdqdaeq apeyrgrtel lketisegkv tlriqnvrfs 121    deggytcffr dhsyqeeaam elkvedpfyw vnpgvltlia lvptillqvs vglvflflqh 181    rlrgklraev enlhrtfdph flrvpcwkit lfvivpvlgp lvaliicynw lhrrlagqfl 241    eelrnpf
```

-continued

```
GGTGCTGCGGCCACACTAGTTTCCCTGCTCACCTTCATGATTGCTGCCA

CTTACAACTTCGCCGTCCTTAAACTCATGGGCCGAGGCACCAAGTTCTG

A
```

Exemplary *Mus musculus* Proteolipid Protein 1 (PLP) Protein

```
                                            (SEQ ID NO: 11)
  1    mglleccarc lvgapfaslv atglcffgva lfcgcgheal tgtekliety fsknyqdyey 61    linvihafqy viygtasfff lygalllaeg fyttgavrqi fgdyktticg kglsatvtgg 121    qkgrgsrgqh qahslervch clgkwlghpd kfvgityalt vvwllvfacs avpvyiyfnt 181    wttcqsiafp sktsasigsl cadarmygvl pwnafpgkvc gsnllsickt aefqmtfhlf 241    iaafvgaaat lvslltfmia atynfavlkl mgrgtkf
```

Exemplary *Mus musculus* Myelin Basic Protein (MBP) cDNA

```
                       (SKQ ID NO: 12)
ATGGGAAACCACTCTGGAAAGAGAGAATTATCTGCTGAGAAGGCCAGTA

AGGATGGAGAGATTCACCGAGGAGAGGCTGGAAAGAAGAGAAGCGTGGG

CAAGCTTTCTCAGACGGCCTCAGAGGACAGTGATGTGTTTGGGGAGGCA

GATGCGATCCAGAACAATGGGACCTCGGCTGAGGACACGGCGGTGACAG

ACTCCAAGCACACAGCAGACCCAAAGAATAACTGGCAAGGCGCCCACCC

AGCTGACCCAGGGAACCGCCCCCACTTGATCCGCCTCTTTTCCCGAGAT

GCCCCGGGAAGGGAGGACAACACCTTCAAAGACAGGCCCTCAGAGTCCG

ACGAGCTTCAGACCATCCAAGAAGACCCCACAGCAGCTTCCGGAGGCCT

GGATGTGATGGCATCACAGAAGAGACCCTCACAGCGATCCAAGTACCTG

GCCACAGCAAGTACCATGGACCATGCCAGGCATGGCTTCCTCCCAAGGC

ACAGAGACACGGGCATCCTTGACTCCATCGGGCGCTTCTTTAGCGGTGA

CAGGGGTGCGCCCAAGCGGGGCTCTGGCAAGGTGAGCTCCGAGCCGTAG
```

Exemplary *Mus musculus* Myelin Basic Protein (MBP) Protein

```
                                             (SEQ ID NO: 1)
  1   mgnhsgkrel saekaskdge ihrgeagkkr svgklsqtas edsdvfgead aiqnngtsae 61   dtavtdskht adpknnwqga hpadpgnrph lirlfsrdap gredntfkdr psesdelqti 121   qedptaasgg ldvmasqkrp sqrskylata stmdharhgf lprhrdtgil dsigrffsgd 181   rgapkrgsgk vssep
```

Exemplary *Homo sapiens* Myelin Oligodendrocyte Glycoprotein (MOG) cDNA

```
                                            (SEQ ID NO: 14)
  1    atggcaagct tatcgagacc ctctctgccc agctgcctct gctccttcct cctcctcctc 61    ctcctccaag tgtcttccag ctatgcaggg cagttcagag tgataggacc aagacaccct 121    atccgggctc tggtcgggga tgaagtggaa ttgccatgtc gcatatctcc tgggaagaac 181    gctacaggca tggaggtggg gtggtaccgc cccccttct ctagggtggt tcatctctac
```

```
-continued
241 agaaatggca aggaccaaga tggagaccag gcacctgaat atcggggccg dacagagctg 301 ctgaaagatg ctattggtga gggaaaggtg actctcagga tccggaatgt aaggttctca 361 gatgaaggag gtttcacctg cttcttccga gatcattctt accaagagga ggcagcaatg 421 gaattgaaag tagaagatcc tttctactgg gtgagccctg gagtgctggt tctcctcgcg 481 gtgctgcctg tgctcctcct gcagatcact gttggcctcg tcttcctctg cctgcagtac 541 agactgagag gaaaacttcg agcagagata gagaatctcc accggacttt tgatccccac 601 tttctgaggg tgccctgctg gaagataacc ctgtttgtaa ttgtgccggt tcttggaccc 661 ttggttgcct tgatcatctg ctacaactgg ctacatcgaa gactagcagg gcaattcctt 721 gaagagctac gaaatccctt ctga
```

Exemplary *Homo sapiens* Myelin Oligodendrocyte Glycoprotein (MOG) Protein

```
                                                (SEQ ID NO: 15)
  1 maslsrpslp sclcsfllll llqvsssyag qfrvigprhp iralvgdeve lpcrispgkn 61 atgmevgwyr ppfsrvvhly rngkdqdgdq apeyrgrtel lkdaigegkv tlrirnvrfs 121 deggftcffr dhsyqeeaam elkvedpfyw vspgvlvlla vlpvlllqit vglvflclqy 181 rlrgklraei enlhrtfdph flrvpcwkit lfvivpvlgp lvaliicynw lhrrlagqfl 241 eelrnpf
```

Exemplary *Homo sapiens* Myelin Basic Protein (MBP), Transcript Variant 7, cDNA

```
                                   (SEQ ID NO: 13)
ATGGGAAACCACGCAGGCAAACGAGAATTAAATGCCGAGAAGGCCAGTA

CGAATAGTGAAACTAACAGAGGAGAATCTGAAAAAAAGAGAAACCTGGG

TGAACTTTCACGGACAACCTCAGAGGACAACGAAGTGTTCGGAGAGGCA

GATGCGAACCAGAACAATGGGACCTCCTCTCAGGACACAGCGGTGACTG

ACTCCAAGCGCACAGCGGACCCGAAGAATGCCTGGCAGGATGCCCACCC

AGCTGACCCAGGGAGCCGCCCCCACTTGATCCGCCTCTTTTCCCGAGAT

GCCCCGGGGAGGGAGGACAACACCTTCAAAGACAGGCCCTCTGAGTCCG

ACGAGCTCCAGACCATCCAAGAAGACAGTGCAGCCACCTCCGAGAGCCT

GGATGTGATGGCGTCACAGAAGAGACCCTCCCAGAGGCACGGATCCAAG

TACCTGGCCACAGCAAGTACCATGGACCATGCCAGGCATGGCTTCCTCC

CAAGGCACAGAGACACGGGCATCCTTGACTCCATCGGGCGCTTCTTTGG

CGGTGACAGGGGTGCGCCCAAGCGGGGCTCTGGCAAGGACTCACACCAC

CCGGCAAGAACTGCTCACTACGGCTCCCTGCCCCAGAAGTCACACGGCC

GGACCCAAGATGAAAACCCCGTAGTCCACTTCTTCAAGAACATTGTGAC

GCCTCGCACACCACCCCCGTCGCAGGGAAAGGGGAGAGGACTGTCCCTG

AGCAGATTTAGCTGGGGGGCCGAAGGCCAGAGACCAGGATTTGGCTACG

GAGGCAGAGCGTCCGACTATAAATCGGCTCACAAGGGATTCAAGGGAGT

CGATGCCCAGGGCACGCTTTCCAAAATTTTTAAGCTGGGAGGAAGAGAT

AGTCGCTCTGGATCACCCATGGCTAGACGCTGA
```

Exemplary *Homo sapiens* Myelin Basic Protein (MBP), Transcript Variant 7, Protein

```
                                                (SEQ ID NO: 17)
  1 mgnhagkrel naekastnse tnrgesekkr nlgelsrtts ednevfgead anqnngtssq 61 dtavtdskrt adpknawqda hpadpgsrph lirlfsrdap gredntfkdr psesdelqti 121 qedsaatses ldvmasqkrp sqrhgskyla tastmdharh gflprhrdtg ildsigrffg 181 gdrgapkrgs gkdshhpart ahygslpqks hgrtqdenpv vhffknivtp rtpppsqgkg 241 rglslsrfsw gaegqrpgfg yggrasdyks ahkgfkgvda qgtlskifkl ggrdsrsgsp 301 marr
```

Exemplary *Homo sapiens* Myelin Basic Protein (MBP), Transcript Variant 1, cDNA (SEQ ID NO: 131)
```
ATGGCGTCACAGAAGAGACCCTCCCAGAGGCACGGATCCAAGTACCTGG
CCACAGCAAGTACCATGGACCATGCCAGGCATGGCTTCCTCCCAAGGCA
CAGAGACACGGGCATCCTTGACTCCATCGGGCGCTTCTTTGGCGGTGAC
AGGGGTGCGCCCAAGCGGGGCTCTGGCAAGGTACCCTGGCTAAAGCCGG
GCCGGAGCCCTCTGCCCTCTCATGCCCGCAGCCAGCCTGGGCTGTGCAA
```
-continued
```
CATGTACAAGGACTCACACCACCCGGCAAGAACTGCTCACTACGGCTCC
CTGCCCCAGAAGTCACACGGCCGGACCCAAGATGAAAACCCCGTAGTCC
ACTTCTTCAAGAACATTGTGACGCCTCGCACACCACCCCGTCGCAGGG
AAAGGGGAGAGGACTGTCCCTGAGCAGATTTAGCTGGGGGGCCGAAGGC
CAGAGACCAGGATTTGGCTACGGAGGCAGAGCGTCCGACTATAAATCGG
CTCACAAGGGATTCAAGGGAGTCGATGCCCAGGGCACGCTTTCCAAAAT
TTTTAAGCTGGGAGGAAGAGATAGTCGCTCTGGATCACCCATGGCTAGA
CGCTGA
```

Exemplary *Homo sapiens* Myelin Basic Protein (MBP), Transcript Variant 1, Protein (SEQ ID NO: 19)
```
  1  masqkrpsqr hgskylatas tmdharhgfl prhrdtgild sigrffggdr gapkrgsgkv
 61  pwlkpgrspl psharsqpgl cnmykdshhp artahygslp qkshgrtqde npvvhffkni
121  vtprtpppsq gkgrglslsr fswgaegqrp gfgyggrasd yksahkgfkg vdaqgtlski
181  fklggrdsrs gspmarr
```

Exemplary *Homo sapiens* Myelin Basic Protein (MBP), Transcript Variant 2, cDNA (SEQ ID NO: 137)
```
ATGGCGTCACAGAAGAGACCCTCCCAGAGGCACGGATCCAAGTACCTGG
CCACAGCAAGTACCATGGACCATGCCAGGCATGGCTTCCTCCCAAGGCA
CAGAGACACGGGCATCCTTGACTCCATCGGGCGCTTCTTTGGCGGTGAC
AGGGGTGCGCCCAAGCGGGGCTCTGGCAAGGTACCCTGGCTAAAGCCGG
GCCGGAGCCCTCTGCCCTCTCATGCCCGCAGCCAGCCTGGGCTGTGCAA
CATGTACAAGGACTCACACCACCCGGCAAGAACTGCTCACTACGGCTCC
CTGCCCCAGAAGTCACACGGCCGGACCCAAGATGAAAACCCCGTAGTCC
ACTTCTTCAAGAACATTGTGACGCCTCGCACACCACCCCGTCGCAGGG
AAAGGGGGCCGAAGGCCAGAGACCAGGATTTGGCTACGGAGGCAGAGCG
TCCGACTATAAATCGGCTCACAAGGGATTCAAGGGAGTCGATGCCCAGG
GCACGCTTTCCAAAATTTTTAAGCTGGGAGGAAGAGATAGTCGCTCTGG
ATCACCCATGGCTAGACGCTGA
```

Exemplary *Homo sapiens* Myelin Basic Protein (MBP), Transcript Variant 2, Protein (SEQ ID NO: 21)
```
  1  masqkrpsqr hgskylatas tmdharhgfl prhrdtgild sigrffggdr gapkrgsgkv
 61  pwlkpgrspl psharsqpgl cnmykdshhp artahygslp qkshgrtqde npvvhffkni
121  vtprtpppsq gkgaegqrpg fgyggrasdy ksahkgfkgv daqgtlskif klggrdsrsg
181  spmarr
```

Exemplary *Homo sapiens* Myelin Basic Protein (MBP), Transcript Variant 3, cDNA (SEQ ID NO: 22)
ATGGCGTCACAGAAGAGACCCTCCCAGAGGCACGGATCCAAGTACCTGG

CCACAGCAAGTACCATGGACCATGCCAGGCATGGCTTCCTCCCAAGGCA

CAGAGACACGGGCATCCTTGACTCCATCGGGCGCTTCTTTGGCGGTGAC

AGGGGTGCGCCCAAGCGGGGCTCTGGCAAGGACTCACACCACCCGGCAA

GAACTGCTCACTACGGCTCCCTGCCCCAGAAGTCACACGGCCGGACCCA

AGATGAAAACCCCGTAGTCCACTTCTTCAAGAACATTGTGACGCCTCGC

ACACCACCCCCGTCGCAGGGAAAGGGGAGAGGACTGTCCCTGAGCAGAT

TTAGCTGGGGGCCGAAGGCCAGAGACCAGGATTTGGCTACGGAGGCAG

AGCGTCCGACTATAAATCGGCTCACAAGGGATTCAAGGGAGTCGATGCC

CAGGGCACGCTTTCCAAAATTTTTAAGCTGGGAGGAAGAGATAGTCGCT

CTGGATCACCCATGGCTAGACGCTGA

Exemplary *Homo sapiens* Myelin Basic Protein (MBP), Transcript Variant 3, Protein (SEQ ID NO: 23)
  1 masqkrpsqr hgskylatas tmdharhgfl prhrdtgild sigrffggdr gapkrgsgkd 61 shhpartahy gslpqkshgr tqdenpvvhf fknivtprtp ppsqgkgrgl slsrfswgae 121 gqrpgfgygg rasdyksahk gfkgvdaqgt lskifklggr dsrsgspmar r Exemplary *Homo sapiens* Myelin Basic Protein (MBP), Transcript Variant 4, cDNA (SEQ ID NO: 149)
ATGGCGTCACAGAAGAGACCCTCCCAGAGGCACGGATCCAAGTACCTGG

CCACAGCAAGTACCATGGACCATGCCAGGCATGGCTTCCTCCCAAGGCA

CAGAGACACGGGCATCCTTGACTCCATCGGGCGCTTCTTTGGCGGTGAC

AGGGGTGCGCCCAAGCGGGGCTCTGGCAAGGACTCACACCACCCGGCAA

GAACTGCTCACTACGGCTCCCTGCCCCAGAAGTCACACGGCCGGACCCA

AGATGAAAACCCCGTAGTCCACTTCTTCAAGAACATTGTGACGCCTCGC

ACACCACCCCCGTCGCAGGGAAAGGGGGCCGAAGGCCAGAGACCAGGAT

TTGGCTACGGAGGCAGAGCGTCCGACTATAAATCGGCTCACAAGGGATT

CAAGGGAGTCGATGCCCAGGGCACGCTTTCCAAAATTTTTAAGCTGGGA

GGAAGAGATAGTCGCTCTGGATCACCCATGGCTAGACGCTGA

Exemplary *Homo sapiens* Myelin Basic Protein (MBP), Transcript Variant 4, Protein (SEQ ID NO: 25)
  1 masqkrpsqr hgskylatas tmdharhgfl prhrdtgild sigrffggdr gapkrgsgkd 61 shhpartahy gslpqkshgr tqdenpvvhf fknivtprtp ppsqgkgaeg qrpgfgyggr 121 asdyksahkg fkgvdaqgtl skifklggrd srsgspmarr Exemplary *Homo sapiens* Myelin Basic Protein (MBP), Transcript Variant 8, cDNA (SEQ ID NO: 28)
```
ATGGGAAACCACGCAGGCAAACGAGAATTAAATGCCGAGAAGGCCAGTACG

AATAGTGAAACTAACAGAGGAGAATCTGAAAAAAAGAGAAACCTGGGTGAA

CTTTCACGGACAACCTCAGAGGACAACGAAGTGTTCGGAGAGGCAGATGCG

AACCAGAACAATGGGACCTCCTCTCAGGACACAGCGGTGACTGACTCCAAG

CGCACAGCGGACCCGAAGAATGCCTGGCAGGATGCCCACCCAGCTGACCCA
```

-continued
```
GGGAGCCGCCCCCACTTGATCCGCCTCTTTTCCCGAGATGCCCCGGGGAGG

GAGGACAACACCTTCAAAGACAGGCCCTCTGAGTCCGACGAGCTCCAGACC

ATCCAAGAAGACAGTGCAGCCACCTCCGAGAGCCTGGATGTGATGGCGTCA

CAGAAGAGACCCTCCCAGAGGCACGGATCCAAGTACCTGGCCACAGCAAGT

ACCATGGACCATGCCAGGCATGGCTTCCTCCCAAGGCACAGAGACACGGGC

ATCCTTGACTCCATCGGGCGCTTCTTTGGCGGTGACAGGGGTGCGCCCAAG

CGGGGCTCTGGCAAGGTGAGCTCTGAGGAGTAG
```

Exemplary *Homo sapiens* Myelin Basic Protein (MBP), Transcript Variant 8, Protein (SEQ ID NO: 27)
```
  1 mgnhagkrel naekastnse tnrgesekkr nlgelsrtts ednevfgead anqnngtssq
 61 dtavtdskrt adpknawqda hpadpgsrph lirlfsrdap gredntfkdr psesdelqti
121 qedsaatses ldvmasqkrp sqrhgskyla tastmdharh gflprhrdtg ildsigrffg
181 gdrgapkrgs gkvssee
```

Exemplary *Homo sapiens* Proteolipid Protein 1 (PLP1), Transcript Variant 1, cDNA (SEQ ID NO: 100)
```
ATGGGCTTGTTAGAGTGCTGTGCAAGATGTCTGGTAGGGGCCCCCTTTGCT

TCCCTGGTGGCCACTGGATTGTGTTTCTTTGGGGTGGCACTGTTCTGTGGC

TGTGGACATGAAGCCCTCACTGGCACAGAAAAGCTAATTGAGACCTATTTC

TCCAAAAACTACCAAGACTATGAGTATCTCATCAATGTGATCCATGCCTTC

CAGTATGTCATCTATGGAACTGCCTCTTTCTTCTTCCTTTATGGGGCCCTC

CTGCTGGCTGAGGGCTTCTACACCACCGGCGCAGTCAGGCAGATCTTTGGC

GACTACAAGACCACCATCTGCGGCAAGGGCCTGAGCGCAACGGTAACAGGG

GGCCAGAAGGGGAGGGGTTCCAGAGGCCAACATCAAGCTCATTCTTTGGAG

CGGGTGTGTCATTGTTTGGGAAAATGGCTAGGACATCCCGACAAGTTTGTG

GGCATCACCTATGCCCTGACCGTTGTGTGGCTCCTGGTGTTTGCCTGCTCT

GCTGTGCCTGTGTACATTTACTTCAACACCTGGACCACCTGCCAGTCTATT

GCCTTCCCCAGCAAGACCTCTGCCAGTATAGGCAGTCTCTGTGCTGATGCC

AGAATGTATGGTGTTCTCCCATGGAATGCTTTCCCTGGCAAGGTTTGTGGC

TCCAACCTTCTGTCCATCTGCAAAACAGCTGAGTTCCAAATGACCTTCCAC

CTGTTTATTGCTGCATTTGTGGGGCTGCAGCTACACTGGTTTCCCTGCTC

ACCTTCATGATTGCTGCCACTTACAACTTTGCCGTCCTTAAACTCATGGGC

CGAGGCACCAAGTTCTGA
```

Exemplary *Homo sapiens* Proteolipid Protein 1 (PLP1), Transcript Variant 1, Protein (SEQ ID NO: 11)
```
  1 mglleccarc lvgapfaslv atglcffgva lfcgcgheal tgtekliety fsknyqdyey
 61 linvihafqy viygtasfff lygalllaeg fyttgavrqi fgdyktticg kglsatvtgg
121 qkgrgsrgqh qahslervch clgkwlghpd kfvgityalt vvwllvfacs avpvyiyfnt
```

-continued 181 wttcqsiafp sktsasigsl cadarmygvl pwnafpgkvc gsnllsickt aefqmtfhlf 241 iaafvgaaat lvslltfmia atynfavlkl mgrgtkf Exemplary *Homo sapiens* Proteolipid Protein 1 (PLP1), Transcript Variant 2, cDNA (SEQ ID NO: 107)
ATGGGCTTGTTAGAGTGCTGTGCAAGATGTCTGGTAGGGGCCCCCTTTGCT

TCCCTGGTGGCCACTGGATTGTGTTTCTTTGGGGTGGCACTGTTCTGTGGC

TGTGGACATGAAGCCCTCACTGGCACAGAAAAGCTAATTGAGACCTATTTC

TCCAAAAACTACCAAGACTATGAGTATCTCATCAATGTGATCCATGCCTTC

CAGTATGTCATCTATGGAACTGCCTCTTTCTTCTTCCTTTATGGGGCCCTC

CTGCTGGCTGAGGGCTTCTACACCACCGGCGCAGTCAGGCAGATCTTTGGC

GACTACAAGACCACCATCTGCGGCAAGGGCCTGAGCGCAACGTTTGTGGGC

ATCACCTATGCCCTGACCGTTGTGTGGCTCCTGGTGTTTGCCTGCTCTGCT

GTGCCTGTGTACATTTACTTCAACACCTGGACCACCTGCCAGTCTATTGCC

TTCCCCAGCAAGACCTCTGCCAGTATAGGCAGTCTCTGTGCTGATGCCAGA

ATGTATGGTGTTCTCCCATGGAATGCTTTCCCTGGCAAGGTTTGTGGCTCC

AACCTTCTGTCCATCTGCAAAACAGCTGAGTTCCAAATGACCTTCCACCTG

TTTATTGCTGCATTTGTGGGGGCTGCAGCTACACTGGTTTCCCTGCTCACC

TTCATGATTGCTGCCACTTACAACTTTGCCGTCCTTAAACTCATGGGCCGT

TGGCACCAAGTTCTGA

Exemplary *Homo sapiens* Proteolipid Protein 1 (PLP1), Transcript Variant 2, Protein (SEQ ID NO: 31)
1   mglleccarc lvgapfaslv atglcffgva lfcgcgheal tgtekliety fsknyqdyey 61  linvihafqy viygtasfff lygalllaeg fyttgavrqi fgdyktticg kglsatfvgi 121 tyaltvvwll vfacsavpvy iyfntwttcq siafpsktsa sigslcadar mygvLpwnaf 181 pgkvcgsnll sicktaefqm tfhlfiaafv gaaatlvsll tfmiaatynf avlklmgrgt 241 kf Exemplary *Homo sapiens* Proteolipid Protein 1 (PLP1), Transcript Variant 3, cDNA (SEQ ID NO: 100)
ATGGGCTTGTTAGAGTGCTGTGCAAGATGTCTGGTAGGGGCCCCCTTTGCT

TCCCTGGTGGCCACTGGATTGTGTTTCTTTGGGGTGGCACTGTTCTGTGGC

TGTGGACATGAAGCCCTCACTGGCACAGAAAAGCTAATTGAGACCTATTTC

TCCAAAAACTACCAAGACTATGAGTATCTCATCAATGTGATCCATGCCTTC

CAGTATGTCATCTATGGAACTGCCTCTTTCTTCTTCCTTTATGGGGCCCTC

CTGCTGGCTGAGGGCTTCTACACCACCGGCGCAGTCAGGCAGATCTTTGGC

GACTACAAGACCACCATCTGCGGCAAGGGCCTGAGCGCAACGGTAACAGGG

GGCCAGAAGGGGAGGGGTTCCAGAGGCCAACATCAAGCTCATTCTTTGGAG

CGGGTGTGTCATTGTTTGGGAAAATGGCTAGGACATCCCGACAAGTTTGTG

GGCATCACCTATGCCCTGACCGTTGTGTGGCTCCTGGTGTTTGCCTGCTCT

GCTGTGCCTGTGTACATTTACTTCAACACCTGGACCACCTGCCAGTCTATT

GCCTTCCCCAGCAAGACCTCTGCCAGTATAGGCAGTCTCTGTGCTGATGCC

AGAATGTATGGTGTTCTCCCATGGAATGCTTTCCCTGGCAAGGTTTGTGGC

TCCAACCTTCTGTCCATCTGCAAAACAGCTGAGTTCCAAATGACCTTCCAC

CTGTTTATTGCTGCATTTGTGGGGGCTGCAGCTACACTGGTTTCCCTGCTC

ACCTTCATGATTGCTGCCACTTACAACTTTGCCGTCCTTAAACTCATGGGC

CGAGGCACCAAGTTCTGA

Exemplary *Homo sapiens* Proteolipid Protein 1 (PLP1), Transcript Variant 3, Protein

```
                                                          (SEQ ID NO: 11)
  1  mglleccarc lvgapfaslv atglcffgva lfcgcgheal tgtekliety fsknyqdyey 61  linvihafqy viygtasfff lygalllaeg fyttgavrqi fgdyktticg kglsatvtgg 121  qkgrgsrgqh qahslervch clgkwlghpd kfvgityalt vvwllvfacs avpvyiyfnt 181  wttcqsiafp sktsasigsl cadarmygvl pwnafpgkvc gsnllsickt aefqmtfhlf 241  iaafvgaaat lvslltfmia atynfavlkl mgrgtkf
```

Exemplary *Homo sapiens* Proteolipid Protein 1 (PLP1), Transcript Variant 4, cDNA

```
                            (SEQ ID NO: 120)
ATGGACTATGAGTATCTCATCAATGTGATCCATGCCTTCCAGTATGTCATC

TATGGAACTGCCTCTTTCTTCTTCCTTTATGGGGCCCTCCTGCTGGCTGAG

GGCTTCTACACCACCGGCGCAGTCAGGCAGATCTTTGGCGACTACAAGACC

ACCATCTGCGGCAAGGGCCTGAGCGCAACGGTAACAGGGGGCCAGAAGGGG

AGGGGTTCCAGAGGCCAACATCAAGCTCATTCTTTGGAGCGGGTGTGTCAT

TGTTTGGGAAAATGGCTAGGACATCCCGACAAGTTTGTGGGCATCACCTAT

GCCCTGACCGTTGTGTGGCTCCTGGTGTTTGCCTGCTCTGCTGTGCCTGTG

TACATTTACTTCAACACCTGGACCACCTGCCAGTCTATTGCCTTCCCCAGC

AAGACCTCTGCCAGTATAGGCAGTCTCTGTGCTGATGCCAGAATGTATGGT

GTTCTCCCATGGAATGCTTTCCCTGGCAAGGTTTGTGGCTCCAACCTTCTG

TCCATCTGCAAAACAGCTGAGTTCCAAATGACCTTCCACCTGTTTATTGCT

GCATTTGTGGGGGCTGCAGCTACACTGGTTTCCCTGCTCACCTTCATGATT

GCTGCCACTTACAACTTTGCCGTCCTTAAACTCATGGGCCGAGGCACCAAG

TTCTGA
```

Exemplary *Homo sapiens* Proteolipid Protein 1 (PLP1), Transcript Variant 4, Protein

```
                                                          (SEQ ID NO: 35)
  1  mdyeylinvi hafqyviygt asffflygal llaegfyttg avrqifgdyk tticgkglsa 61  tvtggqkgrg srgqhqahsl ervchclgkw lghpdkfvgi tyaltvvwll vfacsavpvy 121  iyfntwttcq siafpsktsa sigslcadar mygvlpwnaf pgkvcgsnll sicktaefqm 181  tfhlfiaafv gaaativsll tfmiaatynf avlklmgrgt kf
```

In some embodiments, the third nucleotide sequence or the second autoimmune disease therapeutic molecule of interest is not necessary for the full therapeutic function of the rAAV.

In certain embodiments, the nucleic acid segments cloned into the novel rAAV expression vectors described herein will express or encode one or more polypeptides, peptides, ribozymes, peptide nucleic acids, siRNA's, RNAi's, antisense oligonucleotides, antisense polynucleotides, antibodies, antigen binding fragments, or any combination thereof.

As noted herein, the therapeutic agents useful in the present disclosure may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors or one or more uptake inhibitors thereof, serpins, serpin receptors, tumor suppressors, diagnostic molecules, chemotherapeutic agents, cytotoxins, or any combination thereof.

In some embodiments, the second and/or third nucleic acid sequence encodes a polypeptide, a peptide, a ribozyme, a peptide nucleic acid, an siRNA, an RNAi, an antisense oligonucleotide, an antisense polynucleotide, an antibody, an antigen binding fragment, or any combination thereof. In some embodiments, the second and/or third nucleic acid sequence encodes a proteolipid protein, a myelin oligodendrocyte, a glycoprotein, a myelin-associated glycoprotein, a gliadin peptide, a glutenin, insulin, an islet-specific glucose-6-phosphatase catalytic subunit-related protein, a Preproinsulin, a glutamic decarboxylase, a tyrosine phosphatase like autoantigen, an insulinoma antigen-2, an Islet cell antigen, a thyroid stimulating hormone (TSH) receptor, a thyrotropin receptor, an Aggrecan, a CD4+ T cell epitope, a porin, or an acetylcholine receptor.

In related embodiments, the present disclosure further provides populations and pluralities of rAAV nucleic acid vectors, virions, infectious viral particles, or host cells that include one or more nucleic acid segments that encode an autoimmune disease therapeutic agent.

In some embodiments, the rAAV vector is of serotype AAV1, AAV3, AAV4, AAV5, AAV6, AAV7, AAV8, AAV9, AAV10, AAV2-AAV3 hybrid, AAVrh.10, AAVrh.74, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2(Y→F), AAV8(Y733F), AAV2.15, AAV2.4, AAVM41, or AAVr3.45, or a variant thereof. In some embodiments, the rAAV vector is of serotype AAV8. In some embodiments, the rAAV vector is pseudotyped.

Some embodiments contemplate a pharmaceutical composition for treating or ameliorating one or more symptoms of an autoimmune disease in a mammal, that comprises an effective amount of the rAAV vector as described herein.

Some embodiments contemplate a method of treating a mammal in need thereof (e.g., a human subject) comprising systemically administering to the mammal a therapeutically-effective amount of the rAAV vector as described herein or the pharmaceutical composition as described herein.

Some embodiments contemplate a method for preventing an autoimmune disease or inhibiting progression of the disease in a mammal, the method comprising systemically administering to the mammal the rAAV vector as described herein or the pharmaceutical composition as described herein in an amount and for a time sufficient to prevent or inhibit progression of the autoimmune disease in the mammal.

In some embodiments, the mammal (e.g., a human mammal) has, is suspected of having, is at risk for developing, or has been diagnosed with the autoimmune disease. In some embodiments, the autoimmune disease is multiple sclerosis, disseminated sclerosis, encephalomyelitis disseminata, optic neuritis, celiac disease, or an allergic disease. In some embodiments, the mammal is a newborn, an infant, a juvenile, an adult, or a young adult.

In some embodiments, expression of the therapeutic molecule in the mammal reduces CNS inflammation, inhibits demyelination, re-establishes immune tolerance to one or more neuroproteins, stimulates the production of endogenous antigen-specific regulatory T cells, or any combination thereof. In some embodiments, the autoimmune disease is multiple sclerosis. In some embodiments, progression of the autoimmune disease in the mammal is inhibited or reversed for at least 50 days, at least 75 days, at least 100 days, at least 125 days, at least 150 days, at least 175 days, at least 200 days, or more than 200 days after administration of the rAAV vector. In some embodiments, progression of the autoimmune disease in the mammal is inhibited or reversed for at least 150 days after administration of the rAAV vector.

In some embodiments, the rAAV vector or the pharmaceutical composition is able to provide therapeutic results following administration to the mammal after a single injection (e.g., a single systemic injection) of the vector or composition. In particular embodiments, the injection comprises less than $10^{13}$, less than $10^{12}$, or less than $10^{11}$ vector genomes/ml of rAAV vector.

In some embodiments, expression of the therapeutic molecule in the mammal re-establishes immune tolerance to at least two different neuroproteins. In some embodiments, the at least two different neuroproteins comprise multiple different epitopes of a single neuroprotein, e.g. a MOG protein.

In some embodiments, the nucleic acid segment encodes a full-length mammalian MOG operably linked to a hepatocyte-specific promoter, wherein the rAAV vector is of serotype AAV8.

Some embodiments contemplate the use of the rAAV vector as disclosed herein, or the pharmaceutical composition vector as disclosed herein, as a medicament. Some embodiments contemplate the rAAV vector as disclosed herein, or the pharmaceutical composition vector as disclosed herein, for use in treating or ameliorating one or more symptoms of multiple sclerosis in a mammal.

The present disclosure also provides a method of transducing a population of mammalian cells, e.g. human cells. In an overall and general sense, the method includes at least the step of introducing into one or more cells of the population, a composition that comprises an effective amount of one or more of the rAAV nucleic acid vectors disclosed herein.

In some embodiments, the present disclosure also provides isolated nucleic acid segments that encode one or more of the rAAV vector-based gene therapy constructs as described herein, and provides recombinant vectors, virus particles, infectious virions, and isolated host cells that comprise one or more of the rAAV nucleic acid vectors described herein.

Additionally, the present invention provides compositions, as well as therapeutic and/or diagnostic kits that include one or more of the disclosed AAV nucleic acid vector or AAV particle compositions, formulated with one or more additional ingredients, or prepared with one or more instructions for their use.

In one aspect, the present disclosure provides compositions comprising recombinant adeno-associated viral (rAAV) nucleic acid vectors, virions, and viral particles, and pharmaceutical formulations thereof, which are useful in methods for delivering genetic material encoding one or more beneficial or therapeutic product(s) to mammalian cells and tissues. In some embodiments, the compositions and methods of the present disclosure provide a significant advancement in the art through their use in the treatment, prevention, and/or amelioration of symptoms of one or more mammalian inflammatory diseases, including human autoimmune diseases such as MS and the like.

In some embodiments, the present disclosure provides rAAV-based expression constructs that encode one or more therapeutic agent(s) (including, but not limited to, for example, protein(s), polypeptide(s), peptide(s), enzyme(s), antibodies, antigen binding fragments, as well as variants and/or active fragments thereof), for use in the treatment, prophylaxis, and/or amelioration of one or more symptoms of a mammalian disease, dysfunction, injury, and/or disorder.

The improved nucleic acid vectors and expression systems of the present invention may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the rAAV vector at a selected site within the vector.

In further aspects of the present invention, the exogenous polynucleotide(s) that may be delivered into suitable host cells by the rAAV nucleic acid vectors disclosed herein are of mammalian origin, such as polynucleotides encoding one or more polypeptides or peptides of human, non-human primate, porcine, bovine, ovine, feline, canine, equine, epine, caprine, or lupine origin. In particular embodiments, the polynucleotides are of human origin.

The exogenous polynucleotide(s) that may be delivered into host cells by the disclosed viral nucleic acid vectors may, in certain embodiments, encode one or more proteins, one or more polypeptides, one or more peptides, one or more enzymes, or one or more antibodies (or antigen-binding fragments thereof), or alternatively, may express one or more siRNAs, ribozymes, antisense oligonucleotides, PNA molecules, or any combination thereof.

When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent. In some embodiments, a combination of two or more rAAV particles are administered to a mammalian subject to reverse or prevent progression of an autoimmune disease. In some embodiments, the mammalian subject is treated with any one of an rAAV.MOG, rAAV.PLP, rAAV.MBP, or a combination of two or three of these vectors. Such combination therapies, or cocktails, may comprise a composition comprising two or three of these vectors, or two or three compositions each comprising one of these vectors. In some embodiments, the serotype of the rAAV particles (capsids) of the combination therapy are the same (e.g., rAAV8). In some embodiments, the serotypes of the rAAV particles of the combination are different (e.g., rAAV8 and rAAV2).

In other embodiments, the present disclosure also provides rAAV nucleic acid vectors that are comprised within an infectious adeno-associated viral particle or a virion, as well as pluralities of such virions or infectious particles. Such vectors, particles, and virions may be comprised within one or more diluents, buffers, physiological solutions or pharmaceutical vehicles, or formulated for administration to a mammal in one or more diagnostic, therapeutic, and/or prophylactic regimens. The vectors, virus particles, virions, and pluralities thereof of the present invention may also be provided in excipient formulations that are acceptable for veterinary administration to selected livestock, exotics, domesticated animals, and companion animals (including pets and such like), as well as to non-human primates, zoological or otherwise captive specimens, and such like.

The present disclosure also concerns host cells that comprise at least one of the disclosed rAAV nucleic acid expression vectors, or one or more virus particles or virions that comprise such an expression vector. Such host cells are particularly mammalian host cells, such as human liver cells, and may be either isolated, or in cell or tissue culture. In the case of genetically modified animal models, the transformed host cells may even be comprised within the body of a non-human animal itself.

Compositions comprising one or more of the disclosed rAAV nucleic acid vectors, expression systems, infectious rAAV particles, or host cells also form part of the present invention, and particularly those compositions that further comprise at least a first pharmaceutically-acceptable excipient for use in therapy, and for use in the manufacture of medicaments for the treatment of one or more mammalian inflammatory diseases, disorders, dysfunctions, or trauma. Such pharmaceutical compositions may optionally further comprise one or more diluents, buffers, liposomes, a lipid, and/or a lipid complex. Alternatively, the rAAV nucleic acid vectors or rAAV particles of the present invention may be comprised within a plurality of microspheres, nanoparticles, liposomes, or any combination thereof.

Kits comprising one or more of the disclosed rAAV nucleic acid vectors (as well as one or more virions, viral particles, transformed host cells or pharmaceutical compositions comprising such vectors, virions, particle, or host cells) and instructions for using such kits in one or more therapeutic, diagnostic, and/or prophylactic clinical embodiments are also provided by the present invention. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present invention concerns methods of using the disclosed rAAV nucleic acid vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, one or more autoimmune diseases in humans.

Compositions comprising one or more of the disclosed rAAV nucleic acid vectors, expression systems, infectious rAAV particles, and host cells also form part of the present invention, and particularly those compositions that further comprise at least a first pharmaceutically-acceptable excipient for use in the manufacture of medicaments and methods involving therapeutic administration of such rAAV nucleic acid vectors, rAAV particles, and host cells.

Another important aspect of the present invention concerns methods of use of the disclosed nucleic acid vectors, virions, expression systems, compositions, and host cells described herein in the preparation of medicaments for treating or ameliorating the symptoms of various autoimmune diseases, such as MS, in a mammal, and in particular one or more such diseases in a human.

In some embodiments of any one of the method provided, the method further comprises administering an mTOR inhibitor, e.g., rapamycin. In some embodiments, the mTOR inhibitor is rapamycin. In some embodiments, the mTOR inhibitor is a rapalog, such as temsirolimus (CCI-779), everolimus (RAD001), and ridaforolimus (AP-23573).

Manufacture of rAAV Vectors

In some embodiments, the rAAV nucleic acid vector is encapsidated by a rAAV particle as described herein. The rAAV particle may be of any AAV serotype (e.g., 1, 2, 3, 4, 5, 6, 7, 8, 9, or 10), including any variant or derivative (e.g., including non-naturally occurring variants of a serotype) or pseudotype. In some embodiments, the rAAV particle is an AAV8 particle, which may be pseudotyped with AAV2 ITRs. Non-limiting examples of derivatives and pseudotypes include AAV2-AAV3 hybrid, AAVrh.10, AAVrh.74, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45; or a derivative thereof. In some embodiments, the rAAV vector is of serotype AAV8. In some embodiments, the rAAV vector is not of serotype AAV8. In some embodiments, the rAAV vector is pseudotyped. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. 2012 Jan. 24. The AAV vector toolkit: poised at the clinical crossroads. Asokan Al, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV1, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Exemplary rAAV nucleic acid vectors useful according to the disclosure include single-stranded (ss) or self-complementary (sc) AAV nucleic acid vectors, such as single-stranded or self-complementary recombinant viral genomes.

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector sequence may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

In some embodiments, the one or more helper plasmids include a first helper plasmid comprising a rep gene and a cap gene and a second helper plasmid comprising a Ela gene, a E1b gene, a E4 gene, a E2a gene, and a VA gene. In some embodiments, the rep gene is a rep gene derived from AAV2, and the cap gene is a cap gene derived from AAV2 and includes modifications to the gene in order to produce a modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap open reading frames (ORFs) for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a herpes simplex virus (HSV) containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

To express a therapeutic agent in accordance with the present invention one may prepare a tyrosine capsid-modified rAAV particle containing an expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. In some embodiments, the recombinant nucleic acid vector constructs are those that comprise an rAAV nucleic acid vector that contains a therapeutic gene of interest operably linked to one or more promoters that is capable of expressing the gene in one or more selected mammalian cells. Such nucleic acid vectors are described in detail herein.

Pharmaceutical Compositions and Methods of Treatment

The genetic constructs of the present invention may be prepared in a variety of compositions, and may also be formulated in appropriate pharmaceutical vehicles for administration to human or animal subjects. The rAAV molecules of the present invention and compositions comprising them provide new and useful therapeutics for the treatment, control, and amelioration of symptoms of a variety of disorders, diseases, injury, and/or dysfunctions of the mammalian nervous system, and in particular, for the treatment or amelioration of MS. In some embodiments, the rAAV vectors of the present invention are used to treat an autoimmune disease. In some embodiments, the autoimmune disease is selected from multiple sclerosis, disseminated sclerosis, encephalomyelitis disseminata, optic neuritis, celiac disease, and/or an allergic disease. In some embodiments, the autoimmune disease is multiple sclerosis (MS). Thus, some embodiments contemplate a method of treating a mammal in need thereof comprising systemically administering to the mammal a therapeutically-effective amount of an rAAV vector as disclosed herein.

Some embodiments contemplate a method for preventing an autoimmune disease or inhibiting progression of the disease in a mammal, the method comprising systemically administering to the mammal an rAAV vector as disclosed herein in an amount and for a time sufficient to prevent or inhibit progression of the autoimmune disease in the mammal. In some embodiments, the mammal has, is suspected of having, is at risk for developing, or has been diagnosed with the autoimmune disease. In some embodiments, the autoimmune disease is multiple sclerosis, disseminated sclerosis, encephalomyelitis disseminata, optic neuritis, celiac disease, or an allergic disease. In some embodiments, the mammal is a newborn, an infant, a juvenile, an adult, or a young adult. In some embodiments, the mammal is a human.

In some embodiments, the expression of the therapeutic molecule in the mammal reduces CNS inflammation, inhibits demyelination, re-establishes immune tolerance to one or more neuroproteins, stimulates the production of endogenous antigen-specific regulatory T cells, or any combination thereof. In some embodiments, expression of the therapeutic molecule in the mammal re-establishes immune tolerance to at least two different neuroproteins. In some embodiments, the at least two different neuroproteins comprise different epitopes of a single neuroprotein. In some embodiments, the single neuroprotein is a MOG protein. In some embodiments, the at least two different neuroproteins comprise at least one epitope of a MOG protein and at least one epitope of a PLP protein. In some embodiments, the at least two different neuroproteins comprise at least one epitope of a MOG protein and at least one epitope of an MBP protein.

In some embodiments, the autoimmune disease is multiple sclerosis. In some embodiments, the progression of the autoimmune disease in the mammal is inhibited (e.g., the progression of one or more signs or symptoms of the disease is prevented) or reversed (e.g., reverse one or more signs or symptoms of the disease) for at least 50 days, at least 75 days, at least 100 days, at least 125 days, at least 150 days, at least 175 days, at least 200 days, or more than 200 days after administration of the rAAV vector. In some embodiments, progression of the autoimmune disease is inhibited or reversed for at least 180 days, 1 year, 1.25 years, 1.75 years, 2 years, 3 years, 4 years, 5 years, or more than 5 years in a subject (e.g., a human subject) after administration. In particular embodiments, progression of the autoimmune disease in the mammal is inhibited or reversed for at least 2 years after administration of the rAAV vector. In some embodiments, the rAAV vector is administered to the mammal in a single injection.

In some embodiments, this disclosure contemplates using the disclosed vectors to treat pre-existing neurological symptoms (e.g., muscle weakness in humans, or complete tail paralysis in mouse subjects) via the reversal of such symptoms. In some embodiments, the pre-existing neurological symptoms (for example those symptoms associated with the condition comprising MS in humans, or EAE in mice) are induced. In some embodiments, the subject having pre-existing neurological symptoms is treated with an rAAV vector (e.g., one or more rAAV vectors encoding one or more MOG, PLP, and/or MBP proteins, for example AAV8-MOG) as described herein. In some embodiments, the subject treated with an rAAV vector of the disclosure does not exhibit a harmful cytotoxic T cell response.

In some embodiments the subject is a human. In some embodiments, the human has, and/or has been diagnosed as having, one or more diseases or conditions. In some embodiments, the human has one or more symptoms of a disease or condition. In some embodiments, the human has the disease or condition for any length of time (for example recently diagnosed, long term chronic disease, recurring disease, etc.). In some embodiments, the one or more diseases or conditions comprises MS. In some embodiments, the subject is a non-transgenic mouse expressing pre-existing neurological symptoms.

In some embodiments, the subject having pre-existing neurological symptoms exhibits a mean clinical score, calculated as described herein, of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 at the time of the treatment. In some embodiments, the subject having pre-existing neurological symptoms exhibits a mean clinical score of 0.3 or 0.8 at the time of injection.

In some embodiments, the subject having pre-existing neurological symptoms is treated with an rAAV vector of the disclosure for a period of time, for example 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 1 year, 2 years, 3 years, 4 years, 5 years, 10 years, or longer, etc. In some embodiments, the subject having pre-existing neurological symptoms is treated with an rAAV vector of the disclosure every other day per day for a period of time. In some embodiments, the subject having pre-existing neurological symptoms is treated with an rAAV vector of the disclosure once per week for a period of time. In some embodiments, the subject having pre-existing neurological symptoms is treated with an rAAV vector of the disclosure once per day for a period of time. In some embodiments, the subject having pre-existing neurological symptoms is treated with an rAAV vector of the disclosure multiple times per day (for example 2, 3, 4, 5, etc. times per day) for a period of time.

In an exemplary embodiment, the subject having pre-existing neurological symptoms is treated one time with an rAAV vector of the disclosure. In some embodiments, the subject treated one time with an rAAV vector of the disclosure does not exhibit a harmful cytotoxic T cell response. In some embodiments, the subject having pre-existing neurological symptoms that is treated one time with an rAAV vector of the disclosure shows reversal of the pre-existing neurological symptoms. In some embodiments, the subject having pre-existing neurological symptoms that is treated one time with an rAAV vector of the disclosure shows reversal of the pre-existing neurological symptoms for a period of time, for example 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 1 year, 2 years, 3 years, 4 years, 5 years, 10 years, or longer, etc.

In some embodiments, the subject having pre-existing neurological symptoms that is treated one time with an rAAV vector of the present disclosure exhibits complete remission (e.g., the neurological symptoms never return) and regains lost function (e.g., in human subject, muscle strength and/or complete use of musculature, or in mouse subjects, use of hind legs and/or ability to freely ambulate). In some embodiments, all subjects having pre-existing neurological symptoms that are treated one time with an rAAV vector of the present disclosure, and responded to such treatment, regained the ability to freely ambulate.

Methods of Treatment: Pre-Tolerization, Pre-Treatment, and Re-Challenge of Subjects Using the Vectors and Pharmaceutical Compositions of the Disclosure In some embodiments, the disclosure contemplates using the disclosed vectors to prevent disease by, e.g., pre-tolerizing healthy subjects prior to disease onset. In some embodiments, the healthy subjects selected for preventative treatment by, e.g., pre-tolerization are subjects with an established family history of the disease being treated. In some embodiments, the healthy subjects selected for preventative treatment by, e.g., pre-tolerization are subjects who have tested positive for genetic or molecular markers known to be associated with the disease being treated.

In some embodiments, the subject selected for preventative treatment by e.g., pre-tolerization is administered an rAAV vector or pharmaceutical composition comprising an rAAV vector of the disclosure prior to disease onset. In some embodiments, the subject treated with an rAAV vector or pharmaceutical composition comprising an rAAV vector of the disclosure prior to disease onset does not exhibit a harmful cytotoxic T cell response. In some embodiments, the subject selected for preventative treatment by e.g., pre-tolerization is administered an rAAV vector or pharmaceutical composition comprising an rAAV vector of the disclosure one time prior to disease onset. In some embodiments, an rAAV vector or pharmaceutical composition comprising an rAAV vector-MOG is administered to the subject multiple times prior to disease onset (e.g., 1 time, 2 times, 3 times, 4 times, 5 times, 6 times, 7 times, 8 times, 9 times, 10 times, etc.). In some embodiments, the subject selected for preventative treatment by e.g., pre-tolerization who has been administered an rAAV vector or pharmaceutical composition comprising an rAAV vector of the disclosure shows no symptoms (for example genetic, molecular, phenotypic, or any other symptoms) of disease for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 151 days, 152 days, 153 days, 154 days, 155 days, 156 days, 157 days, 158 days, 159 days, 160 days, 161 days, 162 days, 163 days, 164 days, 165 days, 166 days, 167 days, 168 days, 169 days, 170 days, 171 days, 172 days, 173 days, 174 days, 175 days, 176 days, 177 days, 178 days, 179 days, 180 days, 181 days, 182 days, 183 days, 184 days, 185 days, 186 days, 187 days, 188 days, 189 days, 190 days, 191 days, 192 days, 193 days, 194 days, 195 days, 196 days, 197 days, 198 days, 199 days, 200 days, 201 days, 202 days, 203 days, 204 days, 205 days, 206 days, 207 days, 208 days, 209 days, 210 days, 1 year, 2 years, 3 years, 4 years, 5 years, 10 years, or longer, etc. following treatment.

In some embodiments, a state of disease is induced (for example MS, or EAE) in those subjects receiving preventative treatment by e.g., pre-tolerization using the vectors disclosed herein for the purpose of e.g., evaluating vector pre-treatment efficacy. In some embodiments, a subject is pre-treated by e.g., pre-tolerization via a single administration of an rAAV vector or pharmaceutical composition comprising an rAAV vector of the disclosure before disease (for example MS, or EAE) is induced, for example 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 151 days, 152 days, 153 days, 154 days, 155 days, 156 days, 157 days, 158 days, 159 days, 160 days, 161 days, 162 days, 163 days, 164 days, 165 days, 166 days, 167 days, 168 days, 169 days, 170 days, 171 days, 172 days, 173 days, 174 days, 175 days, 176 days, 177 days, 178 days, 179 days, 180 days, 181 days, 182 days, 183 days, 184 days, 185 days, 186 days, 187 days, 188 days, 189 days, 190 days, 191 days, 192 days, 193 days, 194 days, 195 days, 196 days, 197 days, 198 days, 199 days, 200 days, 201 days, 202 days, 203 days, 204 days, 205 days, 206 days, 207 days, 208 days, 209 days, 210 days, 1 year, 2 years, 3 years, 4 years, 5 years, 10 years, or longer etc. before disease is induced. In specific embodiments, a subject is pre-treated by e.g., pre-tolerization via a single administration of an rAAV vector or pharmaceutical composition comprising an rAAV vector of the disclosure 200 days before disease (for example MS, or EAE) is induced.

In some embodiments, the subject pre-treated with an rAAV vector or pharmaceutical composition comprising an rAAV vector of the disclosure does not exhibit a harmful cytotoxic T cell response. In some embodiments, the pre-treatment results in the complete prevention of disease onset (e.g., MS, or EAE). In some embodiments, the pre-treatment results in the complete prevention of disease onset (e.g., MS, or EAE) for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 151 days, 152 days, 153 days, 154 days, 155 days, 156 days, 157 days, 158 days, 159 days, 160 days, 161 days, 162 days, 163 days, 164 days, 165 days, 166 days, 167 days, 168 days, 169 days, 170 days, 171 days, 172 days, 173 days, 174 days, 175 days, 176 days, 177 days, 178 days, 179 days, 180 days, 181 days, 182 days, 183 days, 184 days, 185 days, 186 days, 187 days, 188 days, 189 days, 190 days, 191 days, 192 days, 193 days, 194 days, 195 days, 196 days, 197 days, 198 days, 199 days, 200 days, 201 days, 202 days, 203 days, 204 days, 205 days, 206 days, 207 days, 208 days, 209 days, 210 days, 1 year, 2 years, 3 years, 4 years, 5 years, 10 years, or longer, etc. following the attempted induction (e.g., experimental induction) or expected onset (e.g., expected natural onset) of disease in the subject. In some embodiments, the pre-treatment results in the complete prevention of disease onset (e.g., MS, or EAE) for 30 days following the attempted induction (e.g., experimental induction) or expected onset (e.g., expected natural onset) of disease in the subject. In some embodiments, the pre-treatment results in the complete prevention of disease onset (e.g., MS, or EAE) for 75-120 days following the attempted induction (e.g., experimental induction) or expected onset (e.g., expected natural onset) of disease in the subject.

In some embodiments, the number of rAAV particles administered to a subject may be on the order ranging from $10^6$ to $10^{14}$ particles/ml or $10^3$ to $10^{15}$ particles/ml, or any values therebetween for either range, such as for example, about $10^3$, $10^4$, $10^5$, $10^6$, $10^7$, $10^8$, $10^9$, $10^{10}$, $10^{11}$, $10^{12}$, $10^{13}$, $10^{14}$, or $10^{15}$ particles/ml. In one embodiment, rAAV particles of higher than $10^{13}$ particles/ml may be administered. The rAAV particles can be administered as a single dose, or divided into two or more administrations as may be required to achieve therapy of the particular disease or disorder being treated. In some embodiments, 0.0001 ml to 10 mls, e.g., 0.001 ml, 0.01 ml, 0.1 ml, 1 ml, 2 ml, 5 ml or 10 ml, are delivered to a subject. In some embodiments, the number of rAAV particles administered to a subject may be on the order ranging from $10^6$-$10^{14}$ vgs/kg weight of the subject, or any values therebetween, such as for example, about $10^6$, $10^7$, $10^8$, $10^9$, $10^{10}$, $10^{11}$, $10^{12}$, $10^{13}$, or $10^{14}$ vgs/kg.

In some embodiments, the disclosure provides formulations of one or more viral-based compositions disclosed herein in pharmaceutically acceptable solutions for administration to a cell or an animal, either alone or in combination with one or more other modalities of therapy, and in particular, for therapy of human cells, tissues, and diseases affecting man. Thus some embodiments contemplate a pharmaceutical composition for treating or ameliorating one or more symptoms of an autoimmune disease in a mammal, which composition comprises an effective amount of an rAAV vector as described herein. Some embodiments further contemplate a method of treating a mammal in need thereof, the method comprising systemically administering to the mammal a therapeutically-effective amount of the pharmaceutical composition comprising an effective amount of an rAAV vector as disclosed herein.

Some embodiments contemplate a method for preventing an autoimmune disease or inhibiting progression of the disease in a mammal, the method comprising systemically administering to the mammal the pharmaceutical composition comprising an effective amount of an rAAV vector as disclosed herein in an amount and for a time sufficient to prevent or inhibit progression of the autoimmune disease in the mammal. In some embodiments, the mammal has, is suspected of having, is at risk for developing, or has been diagnosed with the autoimmune disease. In some embodiments, the autoimmune disease is multiple sclerosis, disseminated sclerosis, encephalomyelitis disseminata, optic neuritis, celiac disease, or an allergic disease. Uses of any of the disclosed compositions as a medicament to treat multiple sclerosis, disseminated sclerosis, encephalomyelitis disseminata, optic neuritis, celiac disease, or an allergic disease are als contemplated. In some embodiments, the mammal is a newborn, an infant, a juvenile, an adult, or a young adult. In some embodiments, the mammal is a human.

In some embodiments, the expression of the therapeutic molecule in the mammal reduces CNS inflammation, inhibits demyelination, re-establishes immune tolerance to one or more neuroproteins, stimulates the production of endogenous antigen-specific regulatory T cells, or any combination thereof. In some embodiments, expression of the therapeutic molecule in the mammal re-establishes immune tolerance to at least two different neuroproteins. In some embodiments, the at least two different neuroproteins comprise multiple different epitopes of a single neuroproteins. In some embodiments, the rAAV vector comprises a nucleic acid segment that encodes a full-length mammalian MOG operably linked to a hepatocyte-specific promoter, wherein the rAAV vector is of serotype AAV8. In some embodiments, the pharmaceutical composition comprising an effective amount of an rAAV vector of the disclosure is used as a medicament. In some embodiments, the rAAV vector is contemplated for use in treating or ameliorating one or more symptoms of multiple sclerosis in a mammal.

In some embodiments, the autoimmune disease is multiple sclerosis. In some embodiments, the progression of the autoimmune disease in the mammal is inhibited (e.g., the progression of one or more signs or symptoms of the disease is prevented) and/or reversed (e.g., one or more signs or symptoms of the disease is reversed) for at least 50 days, at least 75 days, at least 100 days, at least 125 days, at least 150 days, at least 175 days, at least 200 days, or more than 200 days after administration of the rAAV vector. In some embodiments, progression of the autoimmune disease in the mammal is inhibited and/or reversed for at least 150 days after administration of the rAAV vector. In some embodiments, the pharmaceutical composition comprising an effective amount of an rAAV vector of the disclosure is administered to the mammal in a single injection.

In some embodiments, this disclosure contemplates using the disclosed vectors to treat certain pre-existing neurological symptoms, which may in some embodiments be associated with the condition comprising MS in humans, or EAE in mice (e.g., muscle weakness in humans, or complete tail paralysis in mouse subjects), via the reversal of such symptoms. In some embodiments, the subject having pre-existing neurological symptoms some embodiments, the pre-existing neurological symptoms (for example those symptoms associated with the condition comprising MS in humans, or EAE in mice) are induced. In some embodiments, the subject having pre-existing neurological symptoms is treated with a pharmaceutical composition comprising an rAAV vector (e.g., one or more rAAV vectors encoding one or more MOG, PLP, and/or MBP proteins, for example AAV8-MOG) as described herein. is treated with a pharmaceutical composition comprising an rAAV vector comprising a polynucleotide (e.g., a cDNA sequence) that is codon-optimized for human expression, for example an AAV8-MOG vector wherein the MOG transgene sequence is codon-optimized for human expression.

In some embodiments, the subject treated with a pharmaceutical composition comprising an rAAV vector of the disclosure does not exhibit a harmful cytotoxic T cell response. In some embodiments, the pharmaceutical composition comprising an rAAV vector of the disclosure provides evasion or abrogation, completely or partially, of a harmful cytotoxic T cell response following administration to liver tissues, e.g., liver tissues in a subject. In some embodiments, the subject having pre-existing neurological symptoms exhibits a mean clinical score, calculated as described elsewhere herein, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 at the time of the treatment. In some embodiments, the subject having pre-existing neurological symptoms exhibits a mean clinical score of 0.3 or 0.8 at the time of injection.

In some embodiments, the subject having pre-existing neurological symptoms is treated with a pharmaceutical composition comprising an rAAV vector of the disclosure for a period of time, for example 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 1 year, 2 years, 3 years, 4 years, 5 years, 10 years, or longer, etc. In some embodiments, the subject having pre-existing neurological symptoms is treated with a pharmaceutical composition comprising an rAAV vector of the disclosure every other day per day for a period of time. In some embodiments, the subject having pre-existing neurological symptoms is treated with a pharmaceutical composition comprising an rAAV vector of the disclosure once per week for a period of time. In some embodiments, the subject having pre-existing neurological symptoms is treated with a pharmaceutical composition comprising an rAAV vector of the disclosure once per day for a period of time. In some embodiments, the subject having pre-existing neurological symptoms is treated with a pharmaceutical composition comprising an rAAV vector of the disclosure multiple times per day (for example 2, 3, 4, 5, etc. times per day) for a period of time.

In an exemplary embodiment, the subject having pre-existing neurological symptoms is treated one time with a pharmaceutical composition comprising an rAAV vector of the disclosure. In some embodiments, the subject treated one time with a pharmaceutical composition comprising an rAAV vector of the disclosure does not exhibit a harmful cytotoxic T cell response. In some embodiments, the subject having pre-existing neurological symptoms that is treated one time with a pharmaceutical composition comprising an rAAV vector of the disclosure shows reversal of the pre-existing neurological symptoms. In some embodiments, the subject having pre-existing neurological symptoms that is treated one time with a pharmaceutical composition comprising an rAAV vector of the disclosure shows reversal of the pre-existing neurological symptoms for a period of time, for example 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 1 year, 2 years, 3 years, 4 years, 5 years, 10 years, or longer, etc.

In some embodiments, the subject having pre-existing neurological symptoms that is treated one time with a pharmaceutical composition comprising an rAAV vector of the disclosure exhibits complete remission (e.g., the neurological symptoms never return) and regains lost function (e.g., in human subjects: muscle strength and/or complete use of musculature; in mouse subjects: use of hind legs and/or ability to freely ambulate). In some embodiments, all subjects having pre-existing neurological symptoms that are treated one time with a pharmaceutical composition comprising an rAAV vector of the disclosure, and responded to such treatment, regained the ability to freely ambulate.

Some embodiments also contemplate the re-challenge (e.g., a second attempt to induce a disease state) of the subjects who were pre-treated by e.g., pre-tolerization, as described elsewhere herein. These embodiments indicate the robustness of the treatment therapies disclosed herein. Thus, in some embodiments, the subject pre-treated by e.g., pre-tolerization via administration of a vector prior to disease onset (as described herein), and who is thus immunized via the vector treatment against the first attempt to induce disease, undergoes a second attempt to induce a disease state. In some embodiments, the induction of disease comprises administering antigenic peptides to the subject. In some embodiments, the antigenic peptides are EAE-inducing antigenic peptides.

In some embodiments, the second attempt at inducing disease onset occurs after the first attempt at inducing disease, for example 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 1 year, 2 years, 3 years, 4 years, 5 years, 10 years, or longer, etc. after the first attempt.

In some embodiments, the pre-treatment by e.g., pre-tolerization using the vector(s) of the instant disclosure results in the complete prevention (e.g., 100% of subjects pre-treated with the vector do not experience symptoms of disease) of disease onset (e.g., MS or EAE). In some embodiments, pre-treatment by e.g., pre-tolerization is administered 200 days before the first attempted induction of disease (e.g., MS or EAE) in the subject. In some embodiments, the pre-treatment of the subject results in complete prevention of disease for 75-120 days, for example 100 days, following the first attempted induction of disease in the subject. In some embodiments, the pre-treatment of the subject results in complete prevention of disease for 75-120 days, for example 100 days, following the first attempted induction of disease in the subject, even after a second attempt ("re-challenge") to induce disease (e.g., the administration of an MS or EAE inducer) is conducted, in some embodiments. In some embodiments, the second attempt to induce disease occurs 84 days after the first attempt.

In some embodiments, subjects pre-treated by e.g., pre-tolerization survive following the attempted onset of disease. In some embodiments, 10%, 20%, 30%, 40%, 50%, 55%, 60%, 65%, 70% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of subjects pre-treated by e.g., pre-tolerization survive following the attempted onset of disease. In some embodiments, more than 75% of subjects receiving the preventative treatment survive for at least 50 days (e.g., for 50 days, 55 days, 60 days, 65 days, 70 days, 75 days, 80 days, 85 days, 90 days, 95 days, 100 days, 105 days, 110 days, 115 days, 120 days, 125 days, 130 days, 135 days, 140 days, 145 days, 150 days, 155 days, 160 days, 165 days, 170 days, 175 days, 180 days, 185 days, 190 days, or 200 days, or longer, up to and including the point in time at which the subject dies from any other unrelated cause) following the attempted onset of disease. In some embodiments, more than 75% of subjects receiving the preventative treatment survive until the point in time at which the subject dies from another, unrelated cause (e.g., old age, traumatic injury, cancer, and/or any other secondary condition which induces death). In an exemplary embodiment, 100% of subjects receiving the preventative treatment survive for at least 150 days (e.g., for 150 days or longer) following the attempted onset of disease.

In some embodiments, the re-administration of the vector induces a full primary immune response in the subject. In some embodiments, the re-administration of the vector induces a recall response in the subject. In an exemplary embodiment, a subject is administered an rAAV vector or pharmaceutical composition comprising an rAAV vector of the disclosure prior to disease onset, disease (e.g., MS or EAE) is induced, and the rAAV vector or pharmaceutical composition comprising an rAAV vector is re-administered to the same subject 84 days after disease onset, inducing a full primary immune response. In some embodiments, the subject administered and re-administered an rAAV vector or pharmaceutical composition comprising an rAAV vector of the disclosure does not exhibit a harmful cytotoxic T cell response.

Thus, in some embodiments, the current disclosure contemplates the use of the vector(s) as disclosed herein to induce the stable expression of an epitope, which in turn induces the in vivo production of antigen-specific Tregs both prior to, and for a period of time (e.g., over 100 days) following, disease onset (for example, MS in humans, or the induction of the EAE condition in a mouse subject). In some embodiments, the antigen-specific Tregs are MOG-specific Tregs. In some embodiments, the amount of anti-specific Tregs in a sample is measured, for example by using an assay. In some embodiments, the assay is an antigen-specific MHC tetramer flow cytometry assay. In some embodiments, the level of antigen-specific Tregs present after vector administration is increased relative to the level of the antigen-specific Tregs present prior to vector administration.

In some embodiments, the first and/or second nucleic acid segments is operably controlled by a promoter to drive its expression. In some embodiments, the promoter is a promoter that drives expression of the nucleic acid segment in the liver of the subject, e.g., a mammalian subject. In some embodiments, the promoter comprises a mammalian cell-specific or a mammalian tissue-specific promoter. In some embodiments, the promoter comprises a hepatocyte-specific promoter.

In some embodiments, the hepatocyte-specific promoter comprises human apolipoprotein E (hapoE). In some embodiments, the hepatocyte-specific promoter comprises a hepatic combinatorial bundle (HCB) promoter. In other embodiments, the hepatocyte-specific promoter comprises an albumin promoter, a human a1-antitrypsin promoter, a transthyretin (TTR) promoter, or an apolipoprotein E (apoE) promoter. In particular embodiments, the promoter is a human apoE promoter, or an HCB promoter.

In some embodiments, the vector is co-administered with an agent that induces immunosuppression. In some embodiments, the induced immunosuppression is transient. In some embodiments, the agent that induces immunosuppression is an mTOR inhibitor. In some embodiments, the mTOR inhibitor is rapamycin.

If desired, rAAV particles described herein may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, so long as the additional agents do not cause a significant adverse effect upon contact with the target cells or host tissues. The rAAV particles of the disclosure may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravitreal, intraocular, intravenous, intranasal, intra-articular, and intramuscular administration and formulation.

Typically, these formulations may contain at least about 0.1% of the therapeutic agent (e.g., an rAAV particle of the disclosure) or more, although the percentage of the active ingredient(s) may, of course, be varied and may conveniently be between about 1 or 2% and about 70% or 80% or more of the weight or volume of the total formulation. Naturally, the amount of therapeutic agent(s) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and, as such, a variety of dosages and treatment regimens may be desirable.

In certain circumstances it will be desirable to deliver rAAV particles in suitably formulated pharmaceutical compositions (as disclosed herein) either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The pharmaceutical forms of the compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil (such as peanut oil, soybean oil, and sesame oil), animal oil, or oil of synthetic origin. Saline solutions and aqueous dextrose and glycerol solutions can also be employed as liquid carriers. Other exemplary carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose.

The compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection. In some embodiments, the composition is administered intravenously, by hepatic artery infusion, portal vein injection, or intrasplenic injection. In some embodiments, the composition comprises a AAV8 rAAV particle comprising a rAAV nucleic acid vector as described herein, and the composition is administered intravenously.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage may occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions may be prepared by incorporating the rAAV particles in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, exemplary methods of preparation are vacuum-drying and freeze-drying techniques which yield a powder of the active ingredient plus any additional desired ingredient from a previously sterile-filtered solution thereof.

The amount of rAAV particle compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of viral particles to provide therapeutic benefit to the patient undergoing such treatment. Alternatively, in some circumstances, it may be desirable to provide multiple and/or successive administrations of the compositions, either over a relatively short, or a relatively prolonged, period of time, as may be determined by the medical practitioner overseeing the administration of such compositions.

The composition may include rAAV particles or nucleic acid vectors either alone, or in combination with one or more additional active ingredients, which may be obtained from natural or recombinant sources or chemically synthesized.

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs), RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, exemplary methods and compositions are described herein. For purposes of the present invention, the following terms are defined below:

The term "subject," as used herein, describes an organism, including mammals such as primates, to which treatment with the compositions according to the present invention can be provided. Mammalian species that can benefit from the disclosed methods of treatment include, but are not limited to, humans; apes; chimpanzees; orangutans; monkeys; domesticated animals such as dogs and cats; livestock such as horses, cattle, pigs, sheep, goats, and chickens; and other animals such as mice, rats, guinea pigs, and hamsters. In some embodiments, the subject has, is suspected of having, is at risk for developing, or has been diagnosed with an autoimmune disease or disorder, such as multiple sclerosis, disseminated sclerosis, or encephalomyelitis disseminata. In some embodiments, the subject has an autoimmune disease or disorder, such as multiple sclerosis, disseminated sclerosis, or encephalomyelitis disseminata. Other exemplary autoimmune diseases include type 1 diabetes, Grave's disease, arthritis (e.g., rheumatoid arthritis or PGIA), autoimmune uveitis, Peripheral Neuropathy, Myasthenia gravis, Lupus, and Crohn's disease. In some embodiments, an autoimmune disease or disorder is associated with an infection (e.g., a microbial or viral infection).

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "effective amount," as used herein, refers to an amount that is capable of treating or ameliorating a disease or condition or otherwise capable of producing an intended therapeutic effect.

The term "promoter," as used herein refers to a region or regions of a nucleic acid sequence that regulates transcription.

The term "vector," as used herein, refers to a nucleic acid molecule (typically comprised of DNA) capable of replication in a host cell and/or to which another nucleic acid segment can be operatively linked so as to bring about replication of the attached segment. A plasmid, a cosmid, or a virus are each exemplary vectors.

The term "substantially corresponds to," "substantially homologous," or "substantial identity," as used herein, denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity. In some embodiments, the selected sequence and reference sequence will have at least about 86, 87, 88, 89, 90, 91, 92, 93, 94, or 95 percent sequence identity. In some embodiments, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, at least about 85%, and/or about 90% or 95% or higher, as readily determined by one or more of the sequence comparison algorithms well-known to those of skill in the art, such as e.g., the FASTA program analysis described by Pearson and Lipman (1988).

The term "operably linked," as used herein, denotes that the nucleic acid sequences being linked are typically contiguous, or substantially contiguous, and, where necessary to join two protein coding regions, are contiguous and in reading frame. However, since enhancers generally function when separated from the promoter by several kilobases and intronic sequences may be of variable lengths, some polynucleotide elements may be operably linked but not contiguous.

The term "biologically active," as used herein, refers to a variant nucleic acid or protein sequence that has substantially the same activity, such as reduction of clinical severity of EAE in a mouse model or induction of T regulatory cells as described in Examples 1-7, below, as a nucleic acid or protein as described herein (e.g., has substantially the same or the same activity as a MOG, PLP, or MBP nucleic acid or protein described herein).

Nucleic Acids, Proteins, and Variants Thereof

The genetic constructs of the present invention may be comprised within an appropriate viral vector, e.g., an rAAV vector. The embodiments of the present disclosure provide for the targeted delivery of certain nucleic acid sequences using viral vector delivery for the treatment of disease. In some embodiments, the nucleic acid sequences encode a therapeutic molecule. In some embodiments the therapeutic molecule comprises a protein. In some embodiments, the therapeutic molecule comprises one of a myelin oligodendrocyte glycoprotein (MOG), a proteolipid protein (PLP), and a myelin basic protein (MBP). In some embodiments, the therapeutic molecule encodes one or more transcript variants of MOG, MBP, and/or PLP.

Some embodiments therefore contemplate the targeted delivery of a nucleic acid segment (or sequence) encoding a MOG protein using viral vector delivery for the treatment of disease. MOGs are myelin proteins of the immunoglobulin superfamily that are expressed at the outermost surface of myelin sheaths and oligodendrocyte membranes, thus making MOGs a potential target of cellular and humoral immune responses in inflammatory demyelinating diseases such as multiple sclerosis (MS). In some embodiments, the nucleic acid sequence encodes a wild-type MOG protein, or a functional fragment thereof. In some embodiments, the nucleic acid sequence encoding the wild-type MOG protein, or a functional fragment thereof, is SEQ ID NO: 38, SEQ ID NO: 39, SEQ ID NO: 40, SEQ ID NO: 41, and/or SEQ ID NO: 42.

In some embodiments, the nucleic acid sequence encodes a MOG protein, or a functional fragment thereof, that has been codon-optimized for human expression. In some embodiments, the nucleic acid sequence has been codon-modified, e.g., mutated to have one or more putative stop codons in non-coding sequences removed. In some embodiments, the nucleic acid sequence is codon-optimized for human expression and/or codon-modified. Accordingly, in some embodiments, the polynucleotide of any of the disclosed rAAV vectors comprises a nucleic acid sequence that is at least 95%, at least 98%, at least 99%, or at least 99.5% identical to any one of the sequences of SEQ ID NOs: 13, 16, 18, 20, 24, 26, 28-30, 32-34, 39-93, and 100-150. In some embodiments, the polynucleotide of any of the disclosed rAAV vectors comprises a nucleic acid sequence that is at least 95%, at least 98%, at least 99%, or at least 99.5% identical to any one of the sequences of SEQ ID NOs: 16, 18, 20, 24, 26, 29, 30, 32-34, 39-93, 101-106, 108-119, 121-130, 132-136, 138-148 and 150. In some embodiments, the nucleic acid of any of the disclosed rAAV vectors comprises a nucleic acid sequence that comprises, or consists of, any one of the sequences of SEQ ID NOs: 13, 16, 18, 20, 24, 26, 28-30, 32-34, 39-93, and 100-150. In particular embodiments, the polynucleotide of any of the disclosed rAAV vectors comprises a nucleic acid sequence that comprises, or consists of, any one of the sequences of SEQ ID NOs: 16, 18, 20, 24, 26, 29, 30, 32-34, 39-93, 101-106, 108-119, 121-130, 132-136, 138-148 and 150.

In some embodiments, the nucleic acid sequence encodes a PLP protein, or a functional fragment thereof, that has been codon-optimized for human expression. In some embodiments, the nucleic acid sequence encodes a MBP protein, or a functional fragment thereof, that has been codon-optimized for human expression.

In some embodiments, the nucleic acid segments of any of the disclosed rAAV vectors encodes more than one codon-optimized neuropeptide-encoding sequence. In some embodiments, vectors are provided that comprise a second peptide-encoding sequence that is codon-optimized for human expression. In some embodiments, vectors are provided that comprise a third peptide-encoding sequence that is codon-optimized for human expression (i.e., comprise in total three codon-optimized neuropeptide-encoding sequences). In some embodiments, vectors are provided that comprise any two of a codon-optimized MOG-encoding peptide, a codon-optimized PLP-encoding peptide, and a codon-optimized MBP-encoding peptide. Provided herein are vectors that comprise each of (i) a codon-optimized MOG-encoding peptide, (ii) a codon-optimized PLP-encoding peptide, and (iii) a codon-optimized MBP-encoding peptide.

Exemplary *Mus musculus* Myelin-Oligodendrocyte Glycoprotein (MOG) Nucleic Acid Sequences of the Disclosure SEQ ID NOs: 38-42 Show the *Homo sapiens* Myelin Oligodendrocyte Glycoprotein:

```
SEQ ID NO: 38 (MOG CDS (GenBank: BC035938.1))
ATGGCAAGCTTATCGAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCGTCTTC

CTCTGCCTGCAGTACAGACTGAGAGGAAAACTTCGAGCAGAGATAGAGAATCTCCACCGGACTTT

TGATCCCCACTTTCTGAGGGTGCCCTGCTGGAAGATAACCCTGTTTGTAATTGTGCCGGTTCTTGGA

CCCTTGGTTGCCTTGATCATCTGCTACAACTGGCTACATCGAAGACTAGCAGGGCAATTCCTTGAA
```

-continued

GAGCTACGTAAGTTCTCTTCTCTCTGTTATAAGCAGAGAATAAAAAGCCAGGAAAGGGAGACAGA

AGCAACAAGAGGAAGAGGCGGGCTATTGAGGGATCACATTCCCAGAGGAAAGGAGGAGCTGGAG

AGCCTGGGTGGAGGGAAGACTCCTCCTGGGAGGTAG

SEQ ID NO: 39:
ATGGCCAGCCTGAGCAGACCTAGCCTGCCCAGCTGCCTGTGCTCATTCCTGCTGCTGCTGCTG

CAGGTGTCCTCTAGCTACGCCGGCCAGTTCAGAGTGATCGGCCCTAGACACCCTATCCGGGCCCTG

GTTGGAGATGAGGTGGAACTGCCTTGTAGAATCAGCCCCGGCAAAAACGCCACAGGCATGGAAGT

GGGCTGGTATAGACCCCCCTTTTCTAGAGTGGTGCACCTGTACAGAAACGGCAAAGACCAGGACG

GCGATCAGGCCCCTGAGTACAGAGGCAGAACAGAGCTGCTGAAGGACGCCATCGGCGAGGGCAA

GGTGACCCTGAGAATCAGAAATGTGCGGTTCAGCGACGAGGGCGGCTTCACCTGCTTCTTCCGGG

ACCACAGCTACCAGGAGGAAGCCGCTATGGAACTGAAAGTGGAAGATCCTTTCTACTGGGTCAGC

CCTGGCGTGCTGGTGCTGCTTGCTGTGCTGCCTGTGCTCTTGCTGCAAATCACCGTGGGTCTTGTGT

TCCTGTGTCTGCAGTACCGGCTGAGAGGCAAGCTGAGAGCCGAGATCGAGAACCTGCACAGAACC

TTCGACCCCCACTTCCTGCGGGTGCCCTGCTGGAAGATCACACTGTTCGTGATAGTTCCAGTGCTG

GGACCTCTGGTCGCCCTGATCATCTGCTACAACTGGCTGCACCGGAGACTGGCCGGACAGTTTCTG

GAAGAACTGAGAAAGTTCAGCAGCCTGTGCTACAAGCAGAGAATCAAGAGCCAGGAGCGGGAAA

CCGAGGCCACCAGAGGCAGAGGAGGCCTGCTCCGCGACCACATCCCCAGAGGCAAGGAAGAGCT

CGAGAGCCTGGGCGGAGGAAAAACACCTCCAGGCAGATGA

SEQ ID NO: 40:
ATGGCAAGCCTCTCACGACCAAGTCTGCCCTCTTGCCTGTGTTCTTTCCTTCTCCTGCTTCTCTTGCA

GGTGTCCTCTAGTTATGCGGGTCAGTTTAGGGTTATTGGTCCTAGACATCCGATACGGGCTTTGGT

AGGTGACGAGGTCGAACTGCCGTGTCGGATAAGTCCTGGTAAGAACGCCACGGGCATGGAAGTTG

GTTGGTACCGCCCGCCATTCTCCAGAGTGGTGCATCTGTACAGGAATGGAAAGGATCAGGACGGT

GATCAAGCACCAGAGTATCGCGGTAGGACCGAACTCCTGAAAGATGCAATAGGGGAAGGAAAGG

TAACTTTGCGCATTCGAAATGTTCGATTTTCAGACGAGGGTGGGTTCACCTGTTTTTTTAGGGATCA

CAGTTATCAGGAAGAAGCAGCTATGGAACTGAAGGTAGAAGATCCGTTTTATTGGGTGTCTCCAG

GCGTCCTGGTTCTCTTGGCAGTACTTCCGGTGCTGTTGTTGCAAATCACCGTAGGTCTCGTCTTTCT

GTGTCTGCAATACAGGCTGCGCGGAAAGCTGCGCGCGGAGATTGAGAACCTGCATAGGACGTTCG

ACCCACACTTCCTGAGGGTTCCCTGCTGGAAGATCACACTCTTTGTTATTGTCCCGGTGCTCGGCCC

CCTTGTTGCTCTTATCATTTGTTATAACTGGCTTCACCGGAGGCTTGCCGGGCAGTTCTTGGAGGAG

CTTAGAAAATTTAGTTCTCTGCTATAAACAGCGGATTAAGTCACAGGAACGCGAGACAGAAGC

GACTAGGGGCAGAGGGGGCCTGCTTAGGGACCATATTCCGAGGGGTAAAGAAGAGCTGGAATCCC

TTGGTGGTGGTAAGACACCTCCAGGAAGGTAG

SEQ ID NO: 41:
ATGGCTTCCCTTTCACGACCGTCCTTGCCTTCTTGCCTGTGCTCCTTCTTGTTGCTCCTTCTTTTGCA

GGTGAGTTCCAGTTATGCTGGTCAATTTAGAGTCATTGGCCCACGCCACCCGATACGCGCGCTGGT

GGGAGATGAGGTAGAGCTCCCCTGCCGCATATCCCCGGGCAAAAATGCGACCGGCATGGAGGTAG

GCTGGTATAGACCGCCGTTCTCCCGAGTGGTACACCTTTATCGCAACGGTAAAGACCAAGACGGG

GATCAGGCCCCAGAATATAGAGGTCGGACGGAACTGCTGAAAGACGCGATTGGAGAAGGCAAAG

TCACACTTAGAATCCGCAACGTCAGATTTTCAGATGAAGGCGGTTTTACCTGCTTTTTCAGAGATC

ACTCTTATCAGGAGGAGGCCGCTATGGAGCTTAAAGTGGAAGACCCTTTTTATTGGGTCTCTCCTG

GCGTGTTGGTTTTGCTTGCTGTCCTTCCGGTTCTTCTGCTCCAGATAACTGTCGGACTTGTTTTTCTG

-continued
```
TGTCTTCAATACCGACTCCGAGGGAAACTCCGAGCTGAAATAGAGAACCTGCATCGGACCTTTGAC

CCTCATTTCCTTCGCGTGCCTTGCTGGAAAATTACCTTGTTTGTAATTGTTCCCGTACTCGGGCCTCT

CGTAGCACTGATCATATGCTATAACTGGCTCCATAGGAGACTCGCGGGGCAATTCTTGGAAGAGCT

TCGGAAGTTTTCTAGTCTCTGTTACAAGCAACGAATCAAGTCCCAAGAAAGGGAAACGGAAGCCA

CGAGAGGACGCGGCGGGCTCCTGAGAGATCATATCCCGAGGGGTAAAGAAGAGCTCGAAAGCCTT

GGTGGAGGTAAGACTCCGCCGGGTCGATAG

SEQ ID NO: 42:
ATGGCGTCTTTGTCACGCCCTTCACTCCCTTCATGCCTGTGCAGCTTCCTTCTGCTCCTGCTCCTTCA

AGTCTCATCCTCATATGCAGGCCAGTTTAGAGTGATCGGACCACGCCACCCAATCCGCGCTCTGGT

TGGCGACGAAGTAGAGTTGCCATGCAGAATTAGCCCCGGCAAAAATGCGACTGGCATGGAAGTAG

GATGGTACCGCCCGCCCTTTTCAAGAGTTGTTCATTTGTATAGAAATGGTAAGGACCAAGATGGCG

ATCAAGCTCCTGAATATCGCGGACGGACCGAGTTGCTTAAGGATGCCATCGGGGAAGGGAAGGTA

ACATTGAGGATTCGGAACGTACGATTTAGTGACGAGGGGGGATTCACATGCTTCTTTCGGGACCAT

TCCTATCAAGAGGAGGCGGCCATGGAGCTTAAAGTTGAGGATCCCTTCTACTGGGTTTCACCCGGA

GTCTTGGTCCTCCTTGCGGTCCTCCCAGTTCTTCTTCTCCAGATAACAGTGGGTCTTGTATTTCTCTG

CCTTCAATATAGGCTTAGAGGAAAACTCAGGGCGGAAATAGAAAATCTGCACCGCACCTTCGACC

CGCATTTCTTGCGGGTACCTTGTTGGAAGATAACGCTCTTCGTCATCGTTCCTGTGCTGGGGCCTTT

GGTTGCGCTGATTATTTGTTATAACTGGCTTCATAGACGGCTGGCAGGACAGTTCCTGGAAGAGCT

TCGCAAGTTCTCCAGTTTGTGCTATAAGCAAAGGATAAAAAGTCAAGAGCGCGAAACCGAAGCTA

CGCGCGGACGAGGCGGTCTGCTTCGAGATCATATTCCAAGAGGGAAGGAGGAGCTGGAGTCTTTG

GGCGGTGGAAAGACTCCACCCGGAAGGTAG
```

In some embodiments, the nucleic acid sequence of any of the disclosed rAAV vectors encodes a MOG variant, or a functional fragment thereof. As used herein, a "variant" refers to a MOG protein, or a functional fragment thereof, that differs from the wild-type MOG protein in its amino acid sequence and/or function, and which is encoded by one of the variant nucleic acid sequences of the present disclosure. In some embodiments, the variant nucleic acid sequence encoding the MOG protein variant, or functional fragment thereof, is transcript variant alpha 1 (mRNA Accession: NM_206809.4, GI: 1519313458). In some embodiments, the variant nucleic acid sequence encoding the MOG protein variant, or functional fragment thereof, is SEQ ID NO: 43, SEQ ID NO: 44, SEQ ID NO: 45, SEQ ID NO: 46, and/or SEQ ID NO: 47.

SEQ ID NOs: 43-47 Show the *Homo sapiens* Myelin Oligodendrocyte Glycoprotein (MOG), Transcript Variant Alpha 1 (mRNA Accession: NM_206809.4, GI: 1519313458):

```
SEQ ID NO: 43:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGATCCCCACTTTCTGAGGGTGCCCTGCTGGAAGATAACCCTGTTTGTAATTGTGCCGGTTCTTGGA

CCCTTGGTTGCCTTGATCATCTGCTACAACTGGCTACATCGAAGACTAGCAGGGCAATTCCTTGAA

GAGCTACGAAATCCCTTCTGA
```

SEQ ID NO: 44:
ATGGCCAGCCTGAGCCGGCCTTCTCTGCCTAGCTGCCTGTGCAGCTTCCTGTTACTGCTGCTGCTGC

AAGTGTCTTCTAGCTACGCCGGACAGTTTAGAGTGATCGGCCCCAGACACCCTATCCGGGCCCTGG

TCGGAGATGAGGTGGAACTGCCTTGCAGAATCAGCCCTGGCAAGAACGCCACAGGCATGGAAGTG

GGCTGGTACAGACCCCCCTTCAGCAGAGTGGTGCACCTGTACCGGAACGGCAAGGACCAGGACGG

CGATCAGGCCCCTGAGTACAGAGGCAGAACCGAGCTGCTTAAAGACGCCATCGGCGAGGGCAAG

GTTACACTGAGAATCAGAAATGTGCGGTTCAGCGACGAGGGCGGCTTCACCTGCTTCTTCCGGGAC

CACAGCTACCAGGAGGAAGCCGCTATGGAACTGAAGGTCGAGGACCCTTTCTACTGGGTGTCCCC

TGGAGTGCTGGTGCTGTTGGCTGTGCTGCCCGTGCTGCTCCTGCAGATCACCGTGGGACTGATCTT

CCTCTGTCTGCAGTACCGGCTGCGGGGCAAACTGAGAGCCGAGATCGAGAACCTGCACCGGACCT

TCGACCCCCACTTCCTGCGGGTGCCTTGTTGGAAGATCACACTGTTCGTGATCGTGCCAGTGCTGG

GCCCTCTGGTGGCCCTGATCATCTGCTACAACTGGCTGCACAGAAGACTGGCCGGCCAGTTCCTGG

AAGAGCTGAGAAACCCCTTCTGA

SEQ ID NO: 45:
ATGGCTAGCCTGAGTAGACCGAGTCTCCCGTCATGTCTGTGTTCATTCCTTCTTCTGCTCCTCCTCC

AGGTAAGTAGTAGCTATGCAGGTCAATTTAGGGTGATAGGTCCCCGACACCCTATTCGAGCGTTGG

TAGGAGATGAAGTAGAACTCCCGTGTCGCATCAGCCCCGGCAAGAACGCCACCGGCATGGAAGTG

GGATGGTATCGACCGCCGTTTTCAAGAGTTGTCCATCTGTATAGGAATGGCAAAGATCAGGACGG

GGACCAAGCACCCGAATACAGGGGACGCACAGAACTTCTTAAAGATGCGATAGGAGAGGGTAAA

GTTACGTTGAGAATTCGCAACGTGCGGTTTAGTGATGAAGGTGGCTTCACGTGCTTCTTCCGCGAT

CACAGTTACCAAGAAGAAGCCGCGATGGAACTCAAGGTCGAAGATCCGTTCTACTGGGTCAGCCC

TGGTGTACTGGTTTTGTTGGCCGTGTTGCCTGTATTGTTGCTTCAAATCACGGTTGGTTTGATTTTTC

TCTGTCTCCAGTACCGACTGAGAGGGAAGTTGCGGGCCGAGATTGAGAACCTCCATAGGACCTTC

GACCCACACTTCCTGCGAGTCCCTTGCTGGAAAATAAACACTCTTCGTCATTGTGCCGGTTTTGGGG

CCCCTGGTAGCTTTGATAATTTGTTACAACTGGCTCCATCGCAGACTGGCAGGCCAATTCCTGGAG

GAACTGCGAAACCCGTTTTGA

SEQ ID NO: 46:
ATGGCGTCTCTGTCACGGCCTTCACTGCCTTCTTGCCTGTGTAGCTTTCTCTTGCTTCTCCTTCTGCA

AGTATCTTCATCCTATGCGGGACAGTTCCGAGTCATTGGACCACGGCACCCGATCCGCGCACTTGT

AGGAGATGAAGTCGAGCTGCCTTGCCGGATCTCCCCTGGGAAAAACGCCACAGGGATGGAAGTGG

GCTGGTACCGCCCCCCCTTCAGCAGGGTCGTCCATCTGTATCGAAACGGGAAAGACCAGGACGGA

GACCAGGCCCCCGAATATCGGGGTAGAACGGAATTGCTCAAGGACGCGATCGGCGAAGGCAAGG

TTACGTTGCGGATAAGGAATGTACGATTTAGTGACGAAGGAGGATTTACCTGCTTTTTTAGGGACC

ATAGTTACCAAGAAGAGGCGGCAATGGAGCTTAAGGTTGAGGACCCATTTTATTGGGTAAGCCCC

GGCGTTCTCGTACTTCTGGCCGTACTCCCAGTGCTCCTCCTTCAGATCACTGTTGGCCTCATATTCC

TGTGTTTGCAGTACCGGCTCCGAGGTAAGCTGCGGGCGGAAATCGAAACTTGCATAGAACCTTC

GATCCCCATTTCCTCCGAGTGCCTTGTTGGAAGATTACTTTGTTCGTCATAGTCCCTGTCCTTGGGC

CTCTTGTAGCATTGATAATCTGCTATAATTGGTTGCATAGGCGCCTTGCCGGACAATTCCTCGAGG

AGCTCCGAAATCCATTCTGA

SEQ ID NO: 47:
ATGGCGTCTCTGTCTCGACCTTCCCTCCCATCATGTCTGTGTTCCTTCCTCCTGCTCCTGCTTCTTCA

AGTTTCCTCTTCTTACGCGGGACAATTTAGAGTGATCGGACCGCGACATCCCATTCGCGCGTTGGT

CGGGGATGAAGTCGAGTTGCCGTGCCGGATCAGTCCCGGTAAAAACGCTACCGGAATGGAAGTGG

```
GTTGGTATCGACCTCCTTTCTCCCGCGTCGTACACCTCTATCGAAATGGTAAAGATCAGGACGGGG

ACCAGGCCCCGAGTATCGCGGAAGAACGGAACTCCTTAAAGATGCTATAGGAGAAGGTAAAGTT

ACGCTTCGGATCAGAAACGTGCGCTTCTCAGATGAGGGGGGATTTACATGCTTCTTTAGGGACCAC

TCTTATCAAGAGGAAGCTGCGATGGAGCTCAAAGTTGAGGACCCATTTTATTGGGTCTCTCCGGGC

GTTTTGGTATTGTTGGCAGTACTCCCTGTTTTGCTTCTCCAAATTACGGTCGGTCTTATATTCCTGTG

TCTGCAGTATCGCTTGCGCGGCAAGTTGAGAGCTGAGATCGAGAACTTGCACAGGACCTTCGACCC

GCACTTTCTGAGGGTACCGTGTTGGAAGATAACACTGTTTGTTATCGTACCTGTTCTCGGACCGCTT

GTAGCCCTCATTATCTGCTATAACTGGCTGCACAGGCGCTTGGCGGGACAATTCTTGGAGGAGTTG

CGAAACCCATTTTGA
```

In some embodiments, the variant nucleic acid sequence encoding the MOG protein variant, or functional fragment thereof, is transcript variant alpha 2 (mRNA Accession: NM_206812.4, GI: 1675035062). In some embodiments, the variant nucleic acid sequence encoding the MOG protein variant, or functional fragment thereof, is SEQ ID NO: 48, SEQ ID NO: 49, SEQ ID NO: 50, SEQ ID NO: 51, and/or SEQ ID NO: 52.

SEQ ID NOs: 48-52 Show the *Homo sapiens* Myelin Oligodendrocyte Glycoprotein (MOG), Transcript Variant Alpha 2 (mRNA Accession: NM_206812.4, GI: 1675035062):

```
SEQ ID NO: 48:
ATGGCAAGCTTATCAAGACCCTCTCTGCCCAGCTGCCTCTGCTCCTTCCTCCTCCTCCTCCTCCTCC

AAGTGTCTTCCAGCTATGCAGGGCAGTTCAGAGTGATAGGACCAAGACACCCTATCCGGCTCTG

GTCGGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGGGCAATTCCTTGAAGAGCTACGAAATCCCTTCTGA

SEQ ID NO: 49:
ATGGCCAGCCTGAGCAGACCCTCTCTGCCTAGCTGCCTGTGCAGCTTCCTGCTGCTGCTGCTGCTTC

AAGTGTCCAGCTCTTACGCCGGCCAGTTCAGAGTGATCGGCCCTAGACACCCCATCCGGGCCCTGG

TGGGCGATGAGGTGGAACTGCCGTGCAGAATCAGCCCCGGCAAAAACGCCACCGGCATGGAAGTG

GGATGGTACAGACCTCCTTTTAGCCGGGTGGTGCACCTGTACAGAAACGGCAAGGACCAGGACGG

CGACCAGGCCCCTGAGTACCGGGGCAGAACCGAGCTGCTTAAAGACGCCATCGGAGAAGGCAAG

GTGACCCTGCGGATCAGAAACGTGCGGTTCAGTGATGAGGGCGGATTCACCTGCTTCTTCCGGGAC

CACAGCTACCAGGAGGAAGCCGCTATGGAACTGAAGGTTGAGGACCCCTTCTACTGGGTCAGCCC

TGGAGTGCTGGTCCTGCTGGCCGTGCTGCCTGTGCTGCTGCTGCAGATCACAGTGGGCCTGATCTT

CCTGTGTCTGCAGTACCGGCTGAGAGGCAAGCTGAGGGCTGAAATCGAGAACCTGCACAGAACAT

TCGGCCAGTTTCTGGAAGAGCTGAGAAATCCTTTCTGA
```

SEQ ID NO: 50:
ATGGCGAGTTTGTCACGGCCCTCTCTGCCATCATGTCTGTGCTCATTCCTTCTGCTGTTGTTGCTTCA

GGTGTCAAGTTCTTACGCCGGTCAGTTCAGGGTAATCGGGCCGAGGCATCCTATAAGAGCCTTGGT

TGGAGATGAAGTGGAGCTTCCTTGCCGCATTTCCCCTGGTAAGAATGCGACGGGAATGGAAGTGG

GATGGTATAGACCTCCATTCTCACGCGTTGTTCATCTCTACAGAAATGGCAAAGACCAAGACGGGG

ACCAGGCCCCCGAGTATCGGGGTCGCACGGAACTCCTTAAAGACGCCATAGGAGAGGGGAAAGTA

ACTTTGAGGATACGCAACGTACGCTTCAGCGATGAAGGTGGGTTTACATGCTTCTTCCGCGATCAT

AGTTACCAGGAGGAGGCGGCGATGGAGCTTAAAGTCGAGGATCCGTTCTACTGGGTGAGCCCAGG

TGTTCTGGTTCTCCTCGCTGTACTGCCTGTGCTGCTTCTTCAGATAACAGTAGGTTTGATTTTTCTGT

GCTTGCAGTACCGGCTGAGAGGCAAATTGCGAGCGGAGATCGAAAACTTGCATCGAACCTTCGGA

CAGTTTTTGGAAGAGCTTAGAAACCCTTTCTGA

SEQ ID NO: 51:
ATGGCATCTCTGAGTCGGCCTAGCCTGCCATCTTGTCTGTGCTCTTTTCTTTTGCTTTTGTTGTTGCA

AGTGTCCTCAAGTTACGCTGGACAATTCAGAGTTATCGGACCCCGCCACCCAATCAGGGCGCTCGT

CGGAGACGAGGTAGAACTTCCGTGTCGCATTTCTCCAGGCAAAAACGCAACGGGGATGGAAGTCG

GTTGGTACAGGCCTCCCTTTTCCCGGGTGGTACATCTTTATAGGAATGGAAAAGACCAAGACGGAG

ACCAAGCACCGGAATATCGAGGCCGGACAGAGCTGCTCAAAGACGCAATCGGGGAGGGGAAGGT

CACTCTGAGGATCCGAAACGTCCGATTCAGCGACGAGGGGGGTTTACATGCTTTTTCAGGGATCA

CAGCTATCAGGAAGAGGCGGCTATGGAATTGAAGGTTGAAGACCCATTTTACTGGGTATCACCCG

GAGTGCTGGTGCTCCTGGCGGTCCTCCCCGTATTGCTCCTGCAAATAACCGTTGGGTTGATTTTCCT

CTGCCTTCAATACCGATTGCGCGGGAAACTGAGGGCAGAAATTGAAAATCTTCATCGGACCTTCGG

GCAGTTTCTGGAAGAGCTTAGAAACCCCTTTTGA

SEQ ID NO: 52:
ATGGCTTCACTTTCACGCCCGTCACTTCCTTCCTGTCTCTGTTCATTCCTTTTGTTGTTGCTCCTCCA

AGTCAGTAGTTCTTACGCAGGTCAATTTAGGGTTATAGGTCCCAGGCATCCCATAAGAGCGTTGGT

GGGAGACGAGGTAGAGCTTCCTTGCAGGATCTCTCCTGGAAAAAATGCCACGGGCATGGAAGTCG

GATGGTATCGACCCCCATTCTCACGCGTGGTTCACCTCTACCGCAACGGAAAGGACCAGGATGGC

GACCAGGCTCCAGAGTATCGCGGCCGAACGGAATTGCTGAAGGACGCGATCGGCGAGGGAAAAG

TGACGCTGAGGATTCGAAATGTTCGATTTTCAGATGAGGGGGTTTCACATGCTTCTTTCGCGACC

ATTCTTATCAGGAGGAGGCTGCCATGGAACTCAAGGTGGAGGACCCTTTTTATTGGGTCAGCCCCG

GCGTACTTGTTCTCTTGGCGGTACTGCCAGTACTTCTGCTCCAGATCACTGTAGGATTGATATTTCT

CTGTCTCCAATATCGACTCAGGGGTAAGCTGCGGGCTGAAATTGAAAATTTGCACAGAACTTTTGG

GCAGTTCCTGGAGGAACTCAGAAACCCTTTCTGA

In some embodiments, the variant nucleic acid sequence encoding the MOG protein variant, or functional fragment thereof, is transcript variant alpha 3 (mRNA Accession: NM_001008228.3, GI: 1675155353). In some embodiments, the variant nucleic acid sequence encoding the MOG protein variant, or functional fragment thereof, is SEQ ID NO: 53, SEQ ID NO: 54, SEQ ID NO: 55, SEQ ID NO: 56, and/or SEQ ID NO: 57.

SEQ ID NOs: 53-57 Show the *Homo sapiens* Myelin Oligodendrocyte Glycoprotein (MOG), Transcript Variant Alpha 3 (mRNA Accession: NM_001008228.3, GI: 1675155353):

SEQ ID NO: 53:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT

-continued

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGAGTCCTTTGGTGTTCTAGGACCCCAGGTTAAGGAACCAAAAAAGACAGGGCAATTCCTTGAAG

AGCTACGAAATCCCTTCTGA

SEQ ID NO: 54:
ATGGCCAGCTTGTCTAGACCTAGCCTGCCCAGCTGCCTGTGCAGCTTCCTGCTGCTGCTGCTGCTGC

AGGTGTCCAGCAGCTACGCCGGCCAGTTCAGAGTGATCGGCCCTAGACACCCCATCCGGGCCCTG

GTGGGCGACGAGGTCGAGCTGCCGTGCAGAATCTCTCCAGGCAAGAACGCCACAGGAATGGAAGT

GGGCTGGTACAGACCCCCCTTCAGCAGAGTGGTGCACCTGTACCGGAACGGCAAGGACCAGGACG

GCGATCAGGCCCCTGAGTACCGAGGAAGAACAGAGCTGCTCAAGGACGCCATCGGCGAGGGCAA

AGTGACACTGAGAATCAGAAACGTGCGGTTCAGTGATGAGGGCGGCTTCACCTGCTTCTTCCGGG

ACCACAGCTACCAGGAGGAAGCCGCTATGGAACTGAAGGTGGAAGATCCTTTCTACTGGGTCAGC

CCTGGCGTGCTGGTCCTGCTGGCCGTGCTGCCTGTGCTGCTGCTGCAAATCACCGTGGGTCTTATCT

TCCTGTGTCTGCAGTACAGACTGAGAGGCAAGCTGAGAGCCGAGATCGAGAACCTGCACAGAACC

TTCGAGAGCTTTGGCGTGCTGGGCCCCCAGGTTAAGGAACCCAAGAAGACCGGACAGTTTCTGGA

AGAGCTGCGGAATCCTTTCTGA

SEQ ID NO: 55:
ATGGCAAGTCTTTCAAGGCCGAGCCTCCCTTCTTGTTTGTGTAGTTTCCTCCTGCTGCTGCTCCTCC

AGGTTTCATCCTCTTACGCTGGACAATTCCGCGTAATCGGCCCTCGGCATCCTATTCGAGCACTCGT

AGGTGATGAAGTTGAGTTGCCGTGTAGAATATCTCCAGGCAAGAACGCGACTGGGATGGAGGTTG

GATGGTATCGCCCCCCATTCTCACGCGTCGTTCATCTTTATAGGAATGGGAAGGATCAGGACGGGG

ATCAAGCACCTGAGTACCGGGGTAGGACTGAGCTCTTGAAGGACGCGATTGGTGAGGGTAAGGTT

ACTCTTAGGATTAGAAATGTACGGTTCTCCGACGAAGGTGGGTTCACTTGCTTCTTCCGCGACCAC

TCATACCAGGAGGAAGCGGCGATGGAATTGAAGGTCGAGGATCCGTTCTACTGGGTGTCACCTGG

TGTCCTGGTCTTGCTTGCAGTTCTCCCAGTTCTCTTGCTGCAGATCACGGTCGGTTTGATCTTCCTCT

GCTTGCAATACCGCCTCCGCGGGAAACTCCGCGCGGAAATCGAAAACCTGCACAGGACATTTGAA

AGTTTCGGGGTACTTGGACCCCAGGTGAAGGAGCCCAAAAAAACGGGACAGTTCTTGGAGGAACT

GCGAAACCCCTTCTGA

SEQ ID NO: 56:
ATGGCCTCTTTGTCTCGGCCGAGTTTGCCATCCTGTCTGTGTTCTTTTCTTCTCCTGCTTCTGCTGCA

GGTAAGCAGTTCATACGCAGGACAGTTCCGGGTTATTGGACCGCGCCATCCAATCCGGGCCTTGGT

AGGTGACGAGGTGGAATTGCCATGCCGCATCAGTCCGGGAAGAACGCGACAGGAATGGAGGTA

GGATGGTACAGACCGCCCTTTTCTCGAGTTGTGCATCTGTACCGCAACGGCAAAGATCAAGACGG

GGACCAAGCACCCGAGTACCGAGGTAGGACTGAGCTTTTGAAAGATGCCATCGGGGAGGGGAAA

GTTACTCTGCGCATCCGAAACGTGCGCTTTTCCGATGAAGGCGGTTTCACTTGTTTCTTTAGAGACC

ATTCCTACCAAGAAGAAGCCGCTATGGAATTGAAAGTAGAAGATCCATTCTATTGGGTTTCTCCAG

GCGTCCTTGTTCTGCTTGCAGTTCTTCCCGTACTCCTGCTTCAAATTACGGTTGGCCTCATATTTCTT

TGTCTCCAATATCGACTTCGGGGCAAACTTCGCGCCGAAATAGAGAATCTCCATAGGACGTTTGAA

```
TCTTTTGGGGTACTCGGGCCGCAGGTGAAAGAGCCAAAAAAGACCGGTCAATTTCTCGAAGAGCT

CAGGAATCCCTTTTGA

SEQ ID NO: 57:
ATGGCGTCCCTTAGCCGGCCTTCCCTTCCTTCCTGCCTCTGTTCCTTTCTGCTTTTGCTTTTGTTGCA

AGTTTCTAGCAGCTATGCTGGACAATTTCGCGTCATCGGCCAAGACACCCAATTAGGGCCCTCGT

CGGGGATGAAGTGGAGCTTCCGTGCAGGATTAGTCCTGGGAAGAACGCTACTGGTATGGAAGTTG

GATGGTATAGGCCCCCGTTCAGCAGGGTCGTCCACCTCTATCGGAACGGGAAAGATCAAGATGGA

GATCAGGCGCCCGAATACAGAGGTCGGACTGAGTTGCTCAAAGATGCAATCGGTGAAGGCAAGGT

CACTCTGAGAATTCGGAACGTGCGATTTTCCGACGAAGGCGGATTTACCTGCTTTTTTAGGGATCA

TTCATATCAGGAAGAGGCGGCGATGGAGCTCAAGGTTGAAGATCCCTTCTATTGGGTTTCTCCGGG

CGTTTTGGTTTTGCTGGCCGTTTTGCCTGTACTCCTTCTCCAGATCACTGTTGGACTGATATTCTTGT

GTCTCCAGTATCGACTGAGAGGTAAACTCCGCGCAGAGATAGAGAATTTGCATAGGACATTCGAG

AGCTTTGGAGTACTTGGCCCTCAGGTCAAAGAACCGAAAAAGACCGGACAGTTCTTGGAAGAGCT

GAGAAATCCCTTCTGA
```

In some embodiments, the variant nucleic acid sequence encoding the MOG protein variant, or functional fragment thereof, is transcript variant alpha 5 (mRNA Accession: NM_206814.6, GI: 1675006674). In some embodiments, the variant nucleic acid sequence encoding the MOG protein variant, or functional fragment thereof, is SEQ ID NO: 58, SEQ ID NO: 59, SEQ ID NO: 60, SEQ ID NO: 61, and/or SEQ ID NO: 62.

SEQ ID NOs: 58-62 Show the *Homo sapiens* Myelin Oligodendrocyte Glycoprotein (MOG), Transcript Variant Alpha 5 (mRNA Accession: NM_206814.6, GI: 1675006674):

```
SEQ ID NO: 58:
ATGGCAAGCTTATCAAGACCCTCTCTGCCCAGCTGCCTCTGCTCCTTCCTCCTCCTCCTCCTCCTCC

AAGTGTCTTCCAGCTATGCAGATCCTTTCTACTGGGTGAGCCCTGGAGTGCTGGTTCTCCTCGCGGT

GCTGCCTGTGCTCCTCCTGCAGATCACTGTTGGCCTCATCTTCCTCTGCCTGCAGTACAGACTGAGA

GGAAAACTTCGAGCAGAGATAGAGAATCTCCACCGGACTTTTGATCCCCACTTTCTGAGGGTGCCC

TGCTGGAAGATAACCCTGTTTGTAATTGTGCCGGTTCTTGGACCCTTGGTTGCCTTGATCATCTGCT

ACAACTGGCTACATCGAAGACTAGCAGGGCAATTCCTTGAAGAGCTACGAAATCCCTTCTGA

SEQ ID NO: 59:
ATGGCCAGCCTGAGCAGACCTAGCCTGCCTTCTTGTCTGTGCAGCTTCCTGCTGCTGCTGCTGCTGC

AGGTGTCCAGCAGCTACGCCGACCCTTTCTACTGGGTGTCTCCAGGCGTGCTGGTGCTGCTCGCCG

TGCTTCCTGTGCTGCTGCTGCAGATCACCGTGGGCCTGATCTTCCTCTGCCTGCAATACAGACTGAG

AGGCAAGCTGCGGGCCGAGATCGAGAACCTGCACAGAACCTTCGACCCCCACTTCCTGAGAGTGC

CGTGCTGGAAGATCACACTGTTCGTGATCGTGCCCGTGCTTGGACCTCTGGTCGCCCTGATCATCT

GCTACAACTGGCTGCACCGGAGACTGGCCGGCCAGTTCCTGGAAGAGCTGCGAAACCCCTTCTGA

SEQ ID NO: 60:
ATGGCGAGTCTCTCAAGGCCGTCTTTGCCGTCTTGTCTTTGCAGCTTTTTGTTGCTTTTGCTGCTCCA

AGTATCATCAAGTTACGCGGACCCTTTTTATTGGGTTTCACCTGGCGTACTTGTGCTGTTGGCGGTC

CTCCCAGTATTGCTGTTGCAAATCACGGTGGGTCTTATATTTCTTTGCTTGCAATACCGCTTGCGGG

GTAAGCTCAGGGCTGAAATAGAAAACTTGCATCGCACATTCGACCCGCATTTTCTCCGCGTGCCGT

GTTGGAAAATTACGCTCTTCGTTATCGTGCCAGTACTTGGACCTCTTGTCGCGCTCATCATCTGCTA

TAACTGGCTTCACCGCCGCCTTGCCGGTCAGTTCCTTGAAGAATTGAGAAATCCCTTTTGA

SEQ ID NO: 61:
ATGGCAAGCCTCAGCAGGCCTAGTTTGCCATCATGCCTTTGTTCTTTTCTCTTGTTGCTGCTGCTCC

AAGTCAGTAGCTCTTATGCAGATCCCTTTTATTGGGTCTCCCCAGGTGTACTTGTTTTGTTGGCGGT
```

-continued

```
GTTGCCGGTTCTGTTGCTGCAAATTACAGTAGGGTTGATATTTCTGTGTTTGCAGTATCGCCTGCGG

GGGAAGCTGAGAGCTGAAATAGAGAACTTGCATAGGACCTTCGATCCACACTTTCTCAGAGTCCCT

TGTTGGAAAATTACGCTGTTCGTTATCGTGCCCGTGCTCGGCCCCTTGGTAGCCTTGATAATTTGCT

ATAACTGGCTTCATCGCAGACTTGCTGGTCAGTTCTTGGAGGAGCTTCGCAATCCTTTTGA

SEQ ID NO: 62:
ATGGCTAGTCTGTCCCGACCTTCCTTGCCAAGTTGCCTGTGTTCTTTTCTCCTGCTGCTTCTCCTCCA

AGTCTCAAGCTCATACGCAGACCCGTTCTACTGGGTGAGCCCCGGCGTACTTGTGCTGTTGGCAGT

TTTGCCGGTACTGCTCCTTCAGATAACAGTCGGGTTGATTTTCCTCTGCCTTCAATACCGCTTGAGA

GGGAAACTCCGCGCCGAGATCGAAAACCTTCACCGGACCTTCGATCCCCACTTTCTTAGGGTACCC

TGCTGGAAGATAACTTTGTTCGTCATTGTACCCGTCCTGGGACCGTTGGTTGCGTTGATTATATGTT

ATAACTGGCTGCACCGCAGGTTGGCGGGACAGTTTCTGGAAGAGCTCCGCAATCCGTTTTGA
```

In some embodiments, the variant nucleic acid sequence encoding the MOG protein variant, or functional fragment thereof, is transcript variant alpha 6 (mRNA Accession: NM_001170418.2, GI: 1676316977). In some embodiments, the variant nucleic acid sequence encoding the MOG protein variant, or functional fragment thereof, is SEQ ID NO: 63, SEQ ID NO: 64, SEQ ID NO: 65, SEQ ID NO: 66, and/or SEQ ID NO: 67.

SEQ ID NOs: 63-67 Show the *Homo sapiens* Myelin Oligodendrocyte Glycoprotein (MOG), Transcript Variant Alpha 6 (mRNA Accession: NM_001170418.2, GI: 1676316977):

```
SEQ ID NO: 63:
ATGGCAAGCTTATCAAGACCCTCTCTGCCCAGCTGCCTCTGCTCCTTCCTCCTCCTCCTCCTCC

AAGTGTCTTCCAGCTATGCAGATCCTTTCTACTGGGTGAGCCCTGGAGTGCTGGTTCTCCTCGCGGT

GCTGCCTGTGCTCCTCCTGCAGATCACTGTTGGCCTCATCTTCCTCTGCCTGCAGTACAGACTGAGA

GGAAAACTTCGAGCAGAGATAGAGAATCTCCACCGGACTTTTGAGTCCTTTGGTGTTCTAGGACCC

CAGGTTAAGGAACCAAAAAAGACAGGGCAATTCCTTGAAGAGCTACGAAATCCCTTCTGA

SEQ ID NO: 64:
ATGGCCAGCTTGTCTAGACCTAGCCTGCCCAGCTGCCTGTGCAGCTTTCTGCTGCTGCTGCTGCTTC

AAGTGTCCAGCAGCTACGCCGATCCTTTCTACTGGGTCAGCCCCGGCGTGCTCGTGCTGCTGGCCG

TGCTGCCTGTGCTGCTGCTGCAGATCACCGTGGGCCTGATCTTCCTGTGTCTGCAATACAGACTGA

GAGGCAAGCTGAGAGCCGAGATCGAGAACCTGCACAGAACCTTCGAGAGCTTCGGCGTGTTGGGC

CCTCAGGTGAAGGAACCCAAGAAGACAGGCCAGTTCCTGGAAGAGCTGCGGAACCCCTTCTGA

SEQ ID NO: 65:
ATGGCTTCCCTCTCAAGACCCAGCCTCCCAAGCTGCCTTTGCTCATTCCTGTTGCTCTTGCTCCTGC

AAGTCTCATCCTCTTACGCTGACCCCTTTTACTGGGTCAGTCCGGGCGTCCTCGTATTGTTGGCCGT

GCTGCCTGTACTCCTTCTTCAAATCACAGTGGGCCTTATATTTCTCTGTCTGCAATACCGGCTCCGA

GGCAAATTGCGGGCCGAGATAGAAAATTTGCACAGGACATTTGAATCATTCGGCGTCCTCGGCCC

ACAGGTGAAAGAGCCCAAAAAAACGGGACAATTTCTCGAGGAATTGAGGAATCCTTTCTGA

SEQ ID NO: 66:
ATGGCAAGTTTGTCACGGCCCTCTCTGCCGAGCTGTTTGTGTAGCTTTCTCCTGTTGTTGCTGTTGC

AGGTTAGCTCCAGCTATGCAGATCCCTTCTATTGGGTTTCACCTGGGGTGCTGGTTCTCCTGGCGGT

GCTTCCTGTTTTGCTGCTCCAGATTACCGTAGGACTGATTTTTCTCTGCCTCCAATACCGGTTGCGA

GGCAAGCTCAGAGCAGAAATTGAGAATCTCCACAGGACATTCGAGTCCTTCGGGGTGCTTGGGCC

TCAGGTCAAGGAACCGAAAAAGACAGGTCAGTTCCTTGAGGAGCTGCGAAATCCTTTTTGA

SEQ ID NO: 67:
ATGGCTAGTCTCAGCCGACCAAGCCTGCCTTCCTGTCTTTGTTCTTTCCTTCTGTTGCTGTTGTTGCA

GGTGTCCAGCTCTTATGCTGATCCTTTTTACTGGGTATCCCCTGGAGTCTTGGTTCTCCTCGCCGTA
```

```
CTTCCGGTGCTCTTGTTGCAGATCACGGTAGGGCTTATATTTCTTTGCTTGCAATACCGATTGCGGG

GCAAACTGCGAGCTGAAATAGAAAACCTCCACAGAACTTTCGAGTCATTTGGCGTGCTCGGACCG

CAGGTCAAGGAGCCTAAGAAAACTGGTCAGTTCCTCGAAGAGCTGCGCAACCCGTTCTGA
```

In some embodiments, the variant nucleic acid sequence encoding the MOG protein variant, or functional fragment thereof, is transcript variant beta 2 (mRNA Accession: NM_001008229.3, GI: 1675167992). In some embodiments, the variant nucleic acid sequence encoding the MOG protein variant, or functional fragment thereof, is SEQ ID NO: 68, SEQ ID NO: 69, SEQ ID NO: 70, SEQ ID NO: 71, and/or SEQ ID NO: 72.

SEQ ID NOs: 68-72 Show the *Homo sapiens* Myelin Oligodendrocyte Glycoprotein (MOG), Transcript Variant Beta 2 (mRNA Accession: NM_001008229.3, GI: 1675167992):

```
SEQ ID NO: 68:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGTCTTCCACCTGGAAGCCCTCTCTGGCTAA

SEQ ID NO: 69:
ATGGCCAGCCTGAGCAGACCTAGCCTGCCATCTTGTCTGTGCAGCTTCCTGCTGCTGCTGCTGCTGC

AGGTGTCCAGCAGCTACGCCGGCCAGTTCCGGGTGATCGGTCCTAGACACCCCATCAGAGCCCTG

GTCGGAGATGAGGTGGAACTGCCGTGCAGAATCAGCCCCGGCAAGAACGCCACAGGCATGGAAG

TGGGCTGGTACCGGCCTCCTTTTAGCAGAGTGGTGCACCTGTACAGAAACGGCAAAGACCAGGAC

GGCGATCAGGCCCCTGAGTACCGGGGCAGAACCGAGCTGCTCAAGGACGCCATCGGCGAGGGCA

AGGTGACCCTGAGAATCCGGAACGTGCGGTTCAGCGACGAGGGCGGATTTACCTGCTTCTTCAGA

GATCACTCTTATCAGGAGGAAGCCGCTATGGAACTGAAGGTTGAGGACCCCTTCTACTGGGTCAGC

CCTGGCGTGCTGGTGCTGCTGGCCGTGCTGCCTGTGCTCCTGCTGCAGATCACAGTGGGCCTGATC

TTCCTGTGTCTGCAATACAGACTGAGAGGCAAGCTGCGGGCCGAGATCGAGAACCTGCACCGGAC

CTTCGTGTTCCACCTGGAAGCTCTGTCCGGCTGA

SEQ ID NO: 70:
ATGGCGAGTCTTAGTCGCCCGAGTCTTCCGTCATGTCTTTGTTCTTTCCTTCTTCTTTTGCTCTTGCA

AGTTAGCTCTAGCTACGCCGGGCAATTCAGGGTTATAGGGCCTAGGCATCCAATACGAGCATTGGT

TGGGGACGAAGTAGAACTGCCGTGTAGGATAAGCCCTGGCAAAAACGCTACTGGGATGGAAGTCG

GGTGGTATCGACCGCCATTCAGCCGAGTTGTGCACCTTTACAGAAACGGAAAAGACCAAGACGGC

GATCAAGCTCCCGAATATAGAGGAAGGACCGAACTGCTGAAGGACGCCATAGGGGAAGGTAAGG

TGACGCTGAGGATCAGAAACGTGAGGTTTAGTGACGAAGGAGGTTTCACGTGCTTTTTTCGGGACC

ATTCTTATCAGGAGGAAGCTGCGATGGAGTTGAAAGTTGAAGACCCGTTTTACTGGGTGAGTCCTG

GGGTGCTCGTTCTCTTGGCGGTCCTCCCGGTACTTCTGTTGCAGATAACCGTCGGTCTCATATTTCT

CTGCCTTCAGTACCGCTTGAGGGGCAAGCTCCGGGCAGAAATAGAGAACTTGCATCGGACGTTTGT

TTTTCATTTGGAGGCGCTGTCTGGATAA
```

SEQ ID NO: 71:
ATGGCTTCTCTTTCTAGACCCTCTTTGCCAAGTTGTCTTTGCTCTTTTCTTCTCCTCCTCCTGCTGCA

GGTTAGCAGCTCCTATGCTGGTCAGTTCCGAGTAATAGGTCCTAGACATCCGATTCGAGCGCTCGT

TGGCGATGAAGTTGAACTTCCCTGTAGAATAAGCCCCGGTAAAAACGCGACAGGCATGGAGGTCG

GGTGGTATCGCCCCCCGTTCTCTAGAGTGGTGCATCTTTATCGGAATGGAAAGGATCAAGATGGTG

ACCAAGCACCTGAGTATAGAGGCCGCACAGAACTCCTCAAAGACGCGATAGGCGAAGGAAAAGT

CACCCTCCGAATACGAAACGTGCGGTTTTCTGATGAAGGTGGTTTCACGTGTTTTTTCAGAGACCA

TAGTTATCAAGAAGAAGCTGCAATGGAGCTCAAGGTTGAAGACCCTTTCTATTGGGTAAGCCCAG

GAGTTTTGGTTCTGCTTGCGGTCCTTCCGGTACTGCTCCTCCAGATTACCGTGGGGCTTATATTCCT

CTGTCTCCAGTATAGGTTGAGGGGCAAGCTCAGAGCAGAAATAGAGAATTTGCATCGCACATTCG

TGTTTCACCTGGAGGCGTTGAGTGGATAA

SEQ ID NO: 72:
ATGGCGAGTCTTTCACGCCCATCTTTGCCTTCCTGCTTGTGTAGTTTCCTGCTCCTTCTTCTGCTTCA

GGTTAGCAGTTCTTATGCAGGGCAATTTCGCGTTATCGGGCCCAGACACCCAATTCGGGCCCTTGT

TGGAGATGAGGTTGAACTCCCGTGCAGGATAAGTCCAGGAAAAAATGCTACGGGGATGGAAGTCG

GATGGTATAGGCCGCCCTTCTCCAGGGTAGTACATCTGTATAGAAACGGCAAGGACCAAGATGGA

GATCAGGCCCCAGAGTACAGGGGGCGCACAGAGCTGCTTAAAGACGCTATTGGAGAGGGCAAAG

TGACCCTTCGGATACGAAATGTACGCTTTAGCGATGAGGGCGGGTTCACCTGTTTCTTTCGCGACC

ACTCTTATCAAGAGGAGGCGGCTATGGAGCTCAAGGTTGAAGACCCTTTCTACTGGGTAAGCCCA

GGCGTGCTTGTTTTGCTGGCTGTCCTGCCCGTGCTTTTGCTCCAGATCACTGTAGGTCTGATATTTC

TCTGTTTGCAATATCGATTGAGAGGGAAACTGCGCGCTGAAATCGAAAACTTGCACCGGACCTTCG

TCTTTCACTTGGAAGCCTTGTCTGGTTAA

In some embodiments, the variant nucleic acid sequence encoding the MOG protein variant, or functional fragment thereof, is transcript variant beta 1 (mRNA Accession: NM_002433.5, GI: 167631981). In some embodiments, the variant nucleic acid sequence encoding the MOG protein variant, or functional fragment thereof, is SEQ ID NO: 73, SEQ ID NO: 74, SEQ ID NO: 75, SEQ ID NO: 76, and/or SEQ ID NO: 77.

SEQ ID NOs: 73-77 Show the *Homo sapiens* Myelin Oligodendrocyte Glycoprotein (MOG), Transcript Variant Beta 1 (mRNA Accession: NM_002433.5, GI: 167631981):

SEQ ID NO: 73:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGATCCCCACTTTCTGAGGGTGCCCTGCTGGAAGATAACCCTGTTTGTAATTGTGCCGGTTCTTGGA

CCCTTGGTTGCCTTGATCATCTGCTACAACTGGCTACATCGAAGACTAGCAGGGCAATTCCTTGAA

GAGCTACTCTTCCACCTGGAAGCCCTCTCTGGCTAA

-continued

SEQ ID NO: 74:
ATGGCCAGCCTGTCTAGACCTAGCCTGCCTTCATGCCTGTGCAGCTTCCTGCTGCTCCTGTTGCTGC

AGGTGTCCAGCTCTTACGCCGGACAGTTCCGGGTGATCGGCCCTAGACACCCCATCAGAGCCCTGG

TGGGCGACGAGGTGGAACTGCCCTGCAGAATCAGCCCTGGAAAGAACGCCACCGGCATGGAAGTG

GGATGGTACCGGCCTCCTTTCAGCAGAGTGGTGCACCTGTACAGAAACGGCAAAGACCAGGACGG

CGATCAGGCCCCTGAGTACCGGGGCAGAACAGAGCTGCTGAAGGACGCCATCGGCGAGGGCAAG

GTGACACTGCGGATCCGGAACGTGCGGTTCAGTGATGAGGGAGGCTTCACCTGCTTCTTCAGAGAT

CACAGCTACCAGGAGGAAGCCGCCATGGAACTGAAAGTCGAGGACCCCTTCTACTGGGTCTCCCC

TGGCGTGCTGGTTCTGCTGGCCGTGCTGCCTGTGCTGCTGCTGCAGATCACCGTGGGCCTGATCTTC

CTGTGTCTGCAATACAGACTGAGAGGCAAGCTGCGGGCCGAGATCGAGAACCTGCACAGAACCTT

CGACCCTCACTTCCTGAGAGTGCCTTGCTGGAAGATCACCCTGTTTGTGATCGTGCCCGTGCTGGG

CCCCCTGGTCGCCCTGATCATCTGCTACAACTGGCTGCACCGGAGACTGGCTGGCCAGTTTCTCGA

GGAACTGCTGTTCCACCTGGAAGCTCTGAGCGGCTGA

SEQ ID NO: 75:
ATGGCGTCATTGTCCCGGCCGAGTCTTCCTAGTTGCCTCTGCAGTTTTCTTTTGCTTCTGCTGTTGCA

AGTCAGCAGCAGCTACGCCGGGCAGTTTAGAGTGATTGGCCCAAGACATCCCATTAGGGCACTGG

TGGGAGACGAGGTCGAACTTCCGTGTAGAATAAGTCCCGGAAAAAACGCTACAGGTATGGAGGTG

GGCTGGTATCGCCCGCCATTCAGTCGCGTAGTGCATCTCTATAGAAACGGCAAGGATCAGGATGG

CGACCAGGCCCCTGAGTACCGAGGCCGGACCGAACTGCTGAAAGACGCAATAGGCGAAGGCAAG

GTAACGCTCAGAATAAGGAACGTGCGGTTTAGCGACGAGGGCGGCTTTACATGCTTTTTCCGCGAT

CATTCATACCAGGAGGAAGCAGCAATGGAGCTTAAAGTCGAAGATCCTTTTTATTGGGTAAGCCC

AGGTGTACTGGTTCTGCTTGCTGTACTTCCGGTTCTCCTGCTTCAAATTACGGTCGGCTTATCTTT

CTCTGCCTTCAATACAGATTGCGAGGAAAACTCAGGGCGGAGATCGAAAACCTTCACCGAACATT

TGACCCGCACTTTCTCAGGGTGCCCTGCTGGAAGATCACACTTTTTGTTATAGTCCCCGTGTTGGGT

CCGCTTGTGGCACTGATAATCTGTTATAACTGGTTGCACAGAAGGCTCGCAGGACAATTCTTGGAG

GAATTGCTTTTCCACCTTGAGGCGTTGTCCGGCTAA

SEQ ID NO: 76:
ATGGCGTCTCTTTCTCGACCAAGCCTTCCTTCATGTCTCTGCAGCTTTTTGCTTCTGCTTCTCCTTCA

GGTCAGCTCATCCTACGCAGGACAGTTTCGCGTGATTGGTCCCAGACACCCAATCCGAGCATTGGT

GGGCGATGAGGTCGAGCTCCCCTGTAGGATCAGCCCTGGAAAAAATGCAACAGGAATGGAAGTAG

GCTGGTATAGGCCGCCATTTTCTCGCGTTGTGCATCTCTACCGCAATGGTAAAGACCAGGATGGAG

ACCAGGCTCCAGAGTACCGAGGGAGGACCGAACTGCTGAAAGATGCCATCGGTGAGGGAAAAGT

TACGCTTAGAATAAGGAATGTCCGATTCTCTGACGAAGGTGGCTTCACCTGCTTCTTTCGAGACCA

TAGTTACCAGGAAGAGGCGGCTATGGAACTCAAAGTTGAAGACCCATTTTACTGGGTCTCTCCGGG

CGTACTCGTATTGCTGGCCGTTCTCCCAGTTCTCCTTCTGCAAATTACAGTTGGGTTGATCTTTTTGT

GTCTCCAATATCGGCTTAGAGGCAAATTGAGAGCAGAGATAGAAACCTTC ACCGGACTTTTGATC

CTCATTTCCTTCGAGTTCCGTGTTGGAAAATTACCCTCTTTGTGATTGTTCCGGTGTTGGGCCCATT

GGTCGCTCTTATTATCTGTTACAATTGGCTGCACAGACGACTGGCAGGTCAGTTCCTGGAAGAACT

GCTGTTCCACCTGGAGGCATTGTCTGGCTAA

SEQ ID NO: 77:
ATGGCTTCATTGTCACGGCCGTCCCTCCCCTCATGTCTTTGTAGTTTTCTTTTGCTGCTTCTTTTGCA

GGTTTCCTCTTCCTACGCAGGACAGTTCCGCGTCATAGGGCCAAGGCACCCGATTCGCGCACTGGT

AGGCGATGAAGTGGAACTCCCGTGCCGGATCTCACCCGGCAAGAACGCCACTGGGATGGAAGTTG

```
GTTGGTATAGGCCCCCGTTTTCTAGGGTGGTACACTTGTACCGCAACGGAAAAGACCAAGATGGC

GACCAGGCACCAGAGTACCGGGGTAGAACTGAACTCCTGAAGGACGCAATAGGGGAGGGTAAGG

TAACGCTGAGGATAAGGAATGTGCGATTCTCAGATGAAGGCGGATTTACTTGTTTCTTTAGGGACC

ACTCCTACCAGGAGGAAGCAGCCATGGAGCTTAAGGTCGAGGACCCCTTCTATTGGGTATCCCCTG

GTGTCCTCGTGCTTCTGGCCGTACTTCCGGTATTGCTCTTGCAAATTACGGTGGGGTTGATTTTCCT

TTGTCTTCAATACAGGCTCCGGGGAAAACTTCGAGCTGAGATCGAGAATTTGCATCGCACTTTTGA

CCCGCACTTTCTCCGAGTGCCATGCTGGAAAATTACACTCTTCGTGATAGTACCTGTCTTGGGCCCA

TTGGTGGCGCTCATTATCTGTTATAATTGGCTGCATAGACGACTCGCCGGGCAGTTTCTCGAAGAG

CTTTTGTTTCACCTTGAAGCCCTGAGCGGCTAA
```

In some embodiments, the variant nucleic acid sequence encoding the MOG protein variant, or functional fragment thereof, is transcript variant beta 3 (mRNA Accession: NM_206811.4, GI: 1675144717). In some embodiments, the variant nucleic acid sequence encoding the MOG protein variant, or functional fragment thereof, is SEQ ID NO: 78, SEQ ID NO: 79, SEQ ID NO: 80, SEQ ID NO: 81, and/or SEQ ID NO: 82.

SEQ ID NOs: 78-82 Show the *Homo sapiens* Myelin Oligodendrocyte Glycoprotein (MOG), Transcript Variant Beta 3 (mRNA Accession: NM_206811.4, GI: 1675144717):

```
SEQ ID NO: 78:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGAGTCCTTTGGTGTTCTAGGACCCCAGGTTAAGGAACCAAAAAAGACAGGGCAATTCCTTGAAG

AGCTACTCTTCCACCTGGAAGCCCTCTCTGGCTAA

SEQ ID NO: 79:
ATGGCCAGCCTGTCTAGACCCAGCCTGCCTAGCTGCCTGTGCAGCTTTCTGCTGCTGCTGCTGCTGC

AGGTGTCTAGCTCTTACGCCGGCCAGTTCCGGGTGATCGGCCCTAGACACCCCATCCGGGCCCTGG

TGGGAGATGAGGTGGAACTGCCGTGCAGAATCAGCCCTGGAAAGAACGCCACAGGCATGGAAGT

GGGCTGGTATAGACCTCCTTTTAGCAGAGTGGTGCACCTGTACAGAAATGGCAAGGATCAGGACG

GCGACCAGGCCCCTGAGTACCGGGGCAGAACCGAGCTGCTGAAGGACGCCATCGGAGAAGGCAA

GGTGACACTGCGGATCAGAAACGTGCGGTTCAGCGACGAGGGCGGCTTCACCTGCTTCTTCAGAG

ATCACAGCTACCAGGAGGAAGCCGCTATGGAACTGAAAGTCGAGGACCCCTTCTACTGGGTGTCC

CCTGGCGTGCTCGTGCTGCTGGCCGTGCTGCCTGTGCTGCTGCTGCAAATCACCGTGGGCCTGATC

TTCCTGTGTCTGCAGTACAGACTGAGAGGCAAACTGAGAGCCGAGATCGAGAACCTGCACCGGAC

CTTCGAGAGCTTCGGCGTGTTGGGCCCCAGGTTAAGGAACCTAAGAAGACCGGCCAGTTTCTGG

AAGAGCTGCTCTTCCACCTGGAAGCTCTGAGCGGCTGA

SEQ ID NO: 80:
ATGGCATCCTTGTCTCGCCCGAGCCTCCCGAGTTGCCTCTGTTCCTTCCTTCTCCTCCTCTTGCTCCA

GGTCAGTTCAAGTTATGCAGGCCAGTTCCGGGTCATCGGACCACGACACCCCATCAGGGCCTTGGT
```

-continued
```
AGGAGACGAAGTAGAGTTGCCATGTCGCATCTCACCTGGTAAAAATGCGACCGGGATGGAAGTCG

GTTGGTATCGACCACCGTTCTCCAGGGTCGTGCATTTGTATAGGAACGGTAAGGATCAGGATGGTG

ACCAGGCCCCAGAGTACAGGGGTCGCACGGAACTCTTGAAAGACGCGATTGGGGAAGGAAAGGT

TACTTTGCGGATCCGGAATGTCAGATTTTCCGATGAGGGAGGCTTTACGTGTTTTTTCGGGATCAC

AGTTACCAGGAAGAAGCGGCAATGGAACTCAAGGTAGAAGACCCCTTTTATTGGGTCTCTCCTGG

AGTATTGGTCCTGCTGGCAGTTCTTCCTGTACTTCTCTTGCAGATCACGGTGGGACTCATTTTTCTG

TGTTTGCAGTATCGACTTCGAGGAAAGCTCCGAGCAGAGATTGAGAATCTTCACCGGACCTTTGAG

AGTTTTGGGGTTCTTGGTCCTCAGGTGAAGGAACCAAAAAAAACGGGGCAATTTCTTGAGGAATT

GCTCTTCCACTTGGAAGCTCTCTCTGGTTAA

SEQ ID NO: 81:
ATGGCAAGTCTTTCAAGACCCTCTCTCCCAAGTTGTCTGTGCTCATTCCTTCTGTTGCTTTTGCTCCA

GGTAAGCTCCAGCTATGCGGGGCAGTTCAGGGTAATTGGCCCCCGACATCCGATTCGAGCACTCGT

TGGCGATGAAGTTGAACTCCCTTGCCGCATAAGCCCCGGTAAAAACGCGACAGGGATGGAAGTCG

GGTGGTATCGGCCTCCGTTTTCAAGGGTTGTTCATCTCTACAGGAACGGTAAGGACCAAGATGGGG

ATCAGGCGCCTGAGTACCGAGGCAGAACCGAACTGCTCAAAGACGCCATCGGAGAAGGGAAGGT

GACACTGCGGATAAGAAATGTTCGGTTCAGTGATGAGGGAGGGTTTACCTGTTTCTTTAGGGATCA

TAGCTACCAAGAAGAGGCAGCCATGGAACTCAAGGTTGAAGATCCGTTCTACTGGGTTTCACCGG

GTGTTCTGGTCCTCTTGGCCGTCCTCCCGGTGTTGCTTCTGCAGATAACTGTCGGTCTCATCTTTCTC

TGTCTTCAATATAGGTTGAGGGGAAAACTTCGCGCCGAAATTGAGAATCTGCATCGCACTTTCGAG

AGTTTCGGGGTTCTCGGGCCGCAAGTGAAAGAGCCTAAGAAGACTGGGCAATTTCTTGAGGAGTT

GCTGTTTCACCTCGAGGCATTGTCAGGATAA

SEQ ID NO: 82:
ATGGCATCTCTCTCTCGCCCGAGCCTTCCATCCTGCTTGTGCTCTTTTCTGCTCCTCCTGCTTCTTCA

AGTGTCTAGCTCATACGCAGGACAGTTTCGGGTTATAGGTCCGAGGCACCCGATCCGAGCCCTCGT

GGGCGATGAGGTCGAACTCCCGTGTCGCATCAGTCCAGGAAAAAACGCGACAGGGATGGAGGTTG

GGTGGTACCGGCCGCCATTCTCAAGAGTAGTTCACCTTTACAGGAATGGCAAAGACCAGGATGGT

GATCAAGCTCCAGAATACCGAGGTAGGACTGAGTTGTTGAAGGATGCGATAGGGGAAGGAAAAG

TGACCCTGCGGATTAGAAACGTGCGATTCAGTGATGAAGGAGGATTCACATGCTTCTTTAGGGATC

ACTCTTACCAAGAGGAAGCCGCGATGGAGTTGAAGGTCGAAGACCCCTTTTATTGGGTTTCTCCTG

GCGTGCTTGTACTGTTGGCAGTCCTTCCAGTCTTGCTGCTTCAGATAACGGTTGGTCTGATATTTCT

TTGTCTTCAATACCGGCTCAGAGGAAAACTGCGCGCTGAGATAGAGAATTTGCACAGAACATTCG

AGTCATTTGGAGTTCTGGGTCCGCAAGTCAAAGAACCCAAGAAAACTGGGCAGTTCCTTGAGGAA

TTGCTCTTTCACCTGGAAGCGCTCTCAGGGTAA
```

In some embodiments, the variant nucleic acid sequence encoding the MOG protein variant, or functional fragment thereof, is transcript variant beta 5 (mRNA Accession: NM_206810.4, GI: 1676439763). In some embodiments, the variant nucleic acid sequence encoding the MOG protein variant, or functional fragment thereof, is SEQ ID NO: 83, SEQ ID NO: 84, SEQ ID NO: 85, SEQ ID NO: 86, and/or SEQ ID NO: 87.

SEQ ID NOs: 83-87 Show the *Homo sapiens* Myelin Oligodendrocyte Glycoprotein (MOG), Transcript Variant Beta 5 (mRNA Accession: NM_206810.4, GI: 1676439763):

```
SEQ ID NO: 83:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT
```

SEQ ID NO: 83 (continued):
GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGGGCAATTCCTTGAAGAGCTACTCTTCCACCTGGAAGCCCTCTCTGGCTAA

SEQ ID NO: 84:
ATGGCCAGCCTGAGCCGGCCTAGCCTGCCCAGCTGCCTGTGCAGCTTCCTGCTGCTGCTGCTGCTG

CAGGTGTCCAGCAGCTACGCCGGACAGTTTAGAGTGATCGGTCCTAGACACCCCATCCGGGCCCTG

GTGGGCGATGAGGTGGAACTGCCGTGCAGAATCAGCCCTGGAAAGAACGCCACCGGCATGGAAGT

GGGATGGTACAGACCCCCCTTTAGCAGAGTGGTGCACCTGTACCGGAACGGCAAGGATCAGGACG

GCGACCAGGCCCCTGAGTACCGGGGCAGAACAGAGCTGCTGAAGGACGCCATCGGCGAGGGCAA

AGTGACACTGCGGATCAGAAACGTGCGGTTCAGCGACGAGGGAGGCTTCACCTGCTTCTTCAGAG

ATCACTCTTATCAGGAGGAAGCCGCTATGGAACTCAAGGTCGAGGACCCCTTCTACTGGGTGTCTC

CTGGCGTGCTGGTCCTGCTGGCCGTGCTGCCTGTGCTGCTGCTTCAAATCACCGTGGGCCTGATCTT

CCTCTGTCTGCAGTACAGACTGAGAGGCAAGCTGAGAGCCGAGATCGAGAACCTGCACAGAACCT

TCGGCCAGTTCCTGGAAGAGCTGCTCTTCCACCTGGAAGCTCTGTCCGGCTGA

SEQ ID NO: 85:
ATGGCATCACTCAGTAGACCCTCTCTGCCATCATGCTTGTGCTCTTTCCTTTTGCTGCTGCTGTTGC

AAGTCTCTTCATCTTATGCGGGCCAGTTTCGGGTAATAGGTCCTAGACACCCCATCCGGGCTCTGG

TGGGCGATGAAGTAGAGTTGCCTTGCCGGATCTCACCGGGAAAAAACGCTACAGGTATGGAGGTG

GGTTGGTATCGGCCGCCGTTCAGCCGCGTTGTGCATCTGTACCGAAATGGTAAAGATCAAGACGGC

GATCAGGCCCCGGAGTACCGGGGTCGCACAGAACTGCTCAAGGACGCTATCGGGGAGGGCAAAGT

CACACTCAGAATACGGAATGTCAGATTCTCTGATGAAGGTGGATTCACCTGTTTCTTTCGAGATCA

TAGTTACCAAGAAGAAGCTGCAATGGAACTGAAGGTCGAAGATCCGTTCTATTGGGTTTCACCGG

GCGTCCTCGTCTTGCTGGCCGTACTGCCAGTATTGTTGCTCCAAATAACGGTTGGTCTCATTTTCTT

GTGTCTCCAATATAGATTGCGGGAAAGCTCCGAGCAGAAATTGAGAACCTCCATAGAACATTCG

GGCAATTCCTCGAAGAACTTCTCTTTCACTTGGAGGCGTTGAGCGGTTAA

SEQ ID NO: 86:
ATGGCGTCTCTTAGTCGCCCTAGCTTGCCTTCCTGTCTGTGCTCATTTCTCCTTCTTCTTCTTTTGCA

GGTGTCTTCTTCTTACGCCGGGCAGTTTAGGGTGATCGGTCCAAGACATCCGATAAGAGCCCTCGT

TGGTGACGAAGTAGAGCTGCCCTGTCGCATCTCCCCAGGAAAAAACGCCACCGGTATGGAGGTTG

GGTGGTACCGACCGCCTTTTAGTCGAGTAGTCCATCTCTACAGAAATGGCAAAGATCAGGATGGG

GATCAAGCCCCTGAATACCGAGGGAGGACAGAGCTTCTCAAGGACGCCATTGGGGAGGGTAAAGT

CACGCTTCGAATCAGGAACGTGAGATTCAGTGATGAGGGCGGATTTACTTGTTTCTTCAGGGATCA

CTCTTATCAGGAAGAAGCCGCCATGGAGCTGAAAGTCGAAGACCCCTTTCTACTGGGTTAGCCCCGG

AGTGCTGGTGCTTCTCGCCGTACTTCCGGTCCTTTTGCTCCAGATAACAGTTGGTCTGATCTTTCTTT

GCCTTCAATATAGGCTCAGGGGAAAATTGCGAGCCGAAATCGAAAATCTTCATAGGACATTCGGA

CAATTCTTGGAAGAATTGCTTTTTCATCTTGAGGCCCTTTCCGGATAA

SEQ ID NO: 87:
ATGGCTTCTCTCAGTCGGCCCTCTCTTCCGTCCTGCCTCTGTTCCTTTCTTTTGCTCTTGCTGCTTCA

GGTGAGTAGCTCATACGCCGGCCAATTCCGGGTCATCGGACCTCGGCATCCAATCAGGGCGTTGGT

TGGAGATGAGGTAGAGTTGCCTTGCAGGATAAGTCCTGGCAAGAATGCGACCGGAATGGAAGTGG

GTTGGTATAGACCCCCTTTTTCACGGGTAGTACACTTGTATAGGAACGGCAAAGACCAGGACGGC

GACCAGGCGCCCGAGTATCGAGGTCGAACCGAATTGCTCAAAGATGCGATCGGAGAGGGAAAAG

TAACCCTTCGCATACGGAATGTGCGGTTCTCTGATGAAGGGGGCTTCACGTGCTTCTTTCGGGACC

ATAGTTATCAGGAAGAGGCCGCAATGGAGCTTAAGGTTGAGGACCCTTTCTACTGGGTATCCCCAG

GCGTATTGGTATTGCTTGCCGTGCTCCCTGTGCTTCTCCTGCAAATTACGGTGGGTCTTATTTTCCTT

TGCCTGCAATACCGGCTTCGCGGGAAACTTAGAGCAGAAATTGAAAATCTGCACCGCACTTTCGGC

CAATTCCTGGAAGAATTGCTGTTTCACCTGGAAGCCCTCTCAGGTTAA

In some embodiments, the variant nucleic acid sequence encoding the MOG protein variant, or functional fragment thereof, is transcript variant 10 (mRNA Accession: NM_001363610.2 GI: 1676319210). In some embodiments, the variant nucleic acid sequence encoding the MOG protein variant, or functional fragment thereof, is SEQ ID NO: 88, SEQ ID NO: 89, SEQ ID NO: 90, SEQ ID NO: 91, and/or SEQ ID NO: 92.

SEQ ID NOs: 88-92 Show the Homo sapiens Myelin Oligodendrocyte Glycoprotein (MOG), Transcript Variant 10 (mRNA Accession: NM_001363610.2 GI: 1676319210):

SEQ ID NO: 88:
ATGGCAAGCTTATCAAGACCCTCTCTGCCCAGCTGCCTCTGCTCCTTCCTCCTCCTCCTCCTCC

AAGTGTCTTCCAGCTATGCAGGGCAGTTCAGAGTGATAGGACCAAGACACCCTATCCGGGCTCTG

GTCGGGGATGAAGTGGAATTGCCATGTCGCATATCTCCTGGGAAGAACGCTACAGGCATGGAGGT

GGGGTGGTACCGCCCCCCCTTCTCTAGGGTGGTTCATCTCTACAGAAATGGCAAGGACCAAGATGG

AGACCAGGCACCTGAATATCGGGGCCGGACAGAGCTGCTGAAAGATGCTATTGGTGAGGGAAAG

GTGACTCTCAGGATCCGGAATGTAAGGTTCTCAGATGAAGGAGGTTTCACCTGCTTCTTCCGAGAT

CATTCTTACCAAGAGGAGGCAGCAATGGAATTGAAAGTAGAAGATCCTTTCTACTGGGTGAGCCC

TGGAGTGCTGGTTCTCCTCGCGGTGCTGCCTGTGCTCCTCCTGCAGATCACTGTTGGCCTCATCTTC

CTCTGCCTGCAGTACAGACTGAGAGGAAAACTTCGAGCAGAGATAGAGAATCTCCACCGGACTTT

TGATCCCCACTTTCTGAGGGTGCCCTGCTGGAAGATAACCCTGTTTGTAATTGTGCCGGTTCTTGGA

CCCTTGGTTGCCTTGATCATCTGCTACAACTGGCTACATCGAAGACTAGCAGGGCAATTCCTTGAA

GAGCTACGTAAGTTCTCTTCTCTGTTATAAGCAGAGAATAAAAAGCCAGGAAAGGGAGACAGA

AGCAACAAGAGGAAGAGGCGGGCTATTGAGGGATCACATTCCCAGAGGAAAGGAGGAGCTGGAG

AGCCTGGGTGGAGGGAAGACTCCTCCTGGGAGGTAG

SEQ ID NO: 89:
ATGGCCAGCTTGTCTAGACCCAGCCTGCCTAGCTGCCTGTGCAGCTTCCTGCTGCTGCTGCTTCTGC

AAGTGTCTTCTAGCTACGCCGGACAGTTCAGAGTTATCGGCCCTAGACACCCCATCCGGGCCCTGG

TCGGCGATGAGGTTGAGCTGCCCTGTAGAATCAGCCCTGGCAAAAACGCCACCGGCATGGAAGTG

GGCTGGTACAGACCTCCTTTTAGCAGAGTGGTGCACCTGTACAGAAACGGCAAGGATCAGGACGG

CGACCAGGCCCCTGAGTACCGGGGCAGAACAGAGCTGCTGAAAGACGCCATCGGAGAAGGCAAG

GTGACCCTGCGGATCAGAAATGTGCGGTTCAGCGACGAGGGCGGCTTCACATGCTTCTTCCGGGAC

CACAGCTACCAGGAGGAAGCTGCTATGGAACTGAAGGTCGAGGACCCTTTCTACTGGGTGTCCCCT

GGAGTGCTGGTGCTGCTGGCCGTGCTGCCTGTGCTGCTGCTGCAGATCACCGTGGGTCTTATCTTCC

TGTGCCTGCAGTACCGGCTGCGGGGCAAGCTGAGAGCCGAGATCGAGAACCTGCACAGAACCTTC

GACCCCCACTTCCTGAGGGTGCCTTGCTGGAAGATCACCCTGTTCGTGATCGTGCCCGTGCTGGGA

CCTCTGGTGGCCCTGATCATCTGCTACAACTGGCTGCACCGGAGACTGGCCGGCCAGTTTCTTGAG

GAACTGAGAAAGTTCAGCAGCCTGTGTTACAAGCAGAGAATCAAGAGCCAGGAGAGAGAGACAG

AGGCCACAAGAGGCCGGGGAGGCCTGCTCAGAGATCACATCCCCAGAGGCAAAGAGGAACTCGA

GAGCCTGGGCGGAGGCAAGACCCCTCCAGGCAGATGA

SEQ ID NO: 90:
ATGGCTTCATTGAGTAGGCCCTCTCTTCCTTCCTGTCTGTGTTCATTTCTGCTGCTTCTTCTCCTCCA

AGTGAGTTCCTCCTATGCGGGCCAATTTCGGGTTATAGGGCCTCGACACCCGATCCGAGCCCTCGT

AGGAGACGAAGTTGAGCTTCCATGTCGCATAAGTCCGGGGAAAAATGCCACAGGAATGGAAGTTG

GATGGTATAGACCTCCTTTTAGCCGCGTTGTGCACCTCTACAGAAACGGAAAAGACCAGGATGGG

GATCAAGCGCCGGAGTATCGAGGTCGGACTGAACTGCTGAAAGATGCAATAGGGGAAGGTAAGG

TCACGCTTAGAATTCGGAATGTGCGCTTCTCCGATGAAGGTGGCTTCACTTGCTTTTTCCGAGACCA

CAGCTACCAGGAGGAGGCAGCGATGGAGCTTAAAGTCGAAGATCCGTTTTACTGGGTATCACCTG

GGGTCTTGGTTCTTCTCGCTGTCCTTCCGGTGCTGTTGCTTCAAATCACCGTCGGATTGATTTTCTT

TGTCTCCAGTACCGCCTCCGCGGCAAGCTCAGAGCTGAAATTGAAAACCTCCATAGGACTTTTGAT

CCCCACTTCCTTCGGGTGCCATGCTGGAAAATAACATTGTTCGTTATCGTTCCGGTGCTTGGCCCGC

TCGTCGCCTTGATTATCTGCTACAACTGGCTGCACAGGCGCCTGGCGGGTCAATTCTTGGAGGAGC

TCAGGAAATTTAGTTCCCTGTGCTACAAGCAAAGGATAAAATCTCAAGAACGGGAGACCGAAGCA

ACACGGGGTCGAGGTGGGCTGTTGCGGGACCATATCCCCAGAGGTAAAGAGGAACTTGAAAGTCT

TGGTGGCGGAAGACACCCCCGGGTAGGTAG

SEQ ID NO: 91:
ATGGCTTCCCTCTCTCGCCCGAGTCTCCCTAGTTGTCTTTGCTCCTTTCTCTTGCTGCTCTTGTTGCA

AGTCTCATCTTCTTACGCCGGGCAGTTTAGGGTAATCGGCCCGCGGCACCCGATACGCGCTCTTGT

TGGGGATGAGGTAGAGTTGCCGTGTAGGATTTCCCCTGGTAAAAACGCTACTGGTATGGAAGTAG

GATGGTATAGACCCCCGTTTAGCCGGGTAGTCCATCTTTACCGAAACGGAAAAGATCAAGATGGT

GACCAAGCGCCGGAATACCGCGGCCGAACTGAGTTGCTGAAAGACGCAATCGGTGAGGGTAAAGT

TACCCTCAGAATTAGAAACGTCAGATTTTCCGATGAGGGGGGCTTCACCTGTTTTTTCAGGGACCA

TAGTTACCAAGAGGAAGCAGCTATGGAGCTGAAGGTAGAAGATCCGTTCTATTGGGTAAGTCCAG

GTGTATTGGTGCTGCTCGCCGTATTGCCTGTTCTCCTCCTCCAAATTACGGTGGGGTTGATATTCTT

GTGCTTGCAGTATAGGTTGCGAGGTAAGCTCCGAGCCGAGATCGAGAATCTCCACAGGACGTTTG

ACCCTCACTTCCTTCGAGTACCATGCTGGAAGATAACCCTCTTCGTTATTGTTCCTGTTTTGGGCCC

CCTCGTCGCTCTCATAATCTGCTACAATTGGCTGCATAGGAGACTTGCTGGGCAGTTCCTGGAAGA

ACTCCGGAAATTTAGCAGTTTGTGTTACAAGCAGAGGATAAAATCTCAAGAGAGGGAGACCGAAG

CAACCAGGGGCCGGGGTGGCCTTTTGAGGGATCACATTCCGCGAGGAAAGAGGAGCTCGAAAGC

CTTGGGGCGGAAAGACCCCGCCGGGTAGATAG

SEQ ID NO: 92:
ATGGCAAGTTTGTCCCGCCCTTCATTGCCTAGCTGTCTGTGTTCTTTTCTCCTTTTGCTGCTTCTTCA

GGTTAGTAGTAGTTACGCCGGGCAGTTTCGCGTGATCGGCCAAGACATCCTATACGCGCATTGGT

AGGTGACGAAGTCGAACTCCCATGCAGAATCTCCCCTGGAAAAAACGCGACCGGGATGGAGGTGG

GCTGGTACCGACCCCCCTTCTCTCGGGTGGTCCATTTGTACCGGAACGGTAAAGACCAAGATGGGG

ACCAGGCTCCCGAGTACCGGGGGCGAACTGAGTTGCTTAAAGACGCAATTGGAGAGGGTAAAGTA

ACGTTGCGGATTAGAAATGTGAGATTTTCCGATGAAGGTGGATTTACGTGTTTCTTTCGAGACCAT

TCCTATCAGGAAGAAGCTGCCATGGAGTTGAAAGTGGAGGATCCATTTTACTGGGTTAGTCCAGGC

```
GTGCTCGTACTTCTGGCTGTTCTGCCCGTACTTCTTCTGCAAATCACCGTAGGTCTTATCTTTCTGTG

TTTGCAGTATAGGCTTCGAGGCAAGCTCAGGGCTGAAATAGAGAATCTCCATAGGACATTTGACCC

TCACTTTCTGCGGGTGCCCTGTTGGAAGATCACCTTGTTCGTAATCGTGCCAGTCCTTGGACCATTG

GTAGCACTCATAATATGTTACAATTGGCTCCATAGGCGACTGGCCGGACAATTCTTGGAGGAACTG

CGCAAGTTCAGCAGCTTGTGTTATAAACAACGAATTAAATCCCAGGAGAGAGAGACGGAAGCAAC

TAGAGGTCGAGGCGGCCTGCTCCGAGATCACATACCGAGAGGTAAAGAAGAATTGGAGTCACTTG

GTGGAGGAAAAACGCCCCCGGGTCGGTAG
```

Some embodiments therefore contemplate the targeted delivery of a nucleic acid sequence encoding a PLP using viral vector delivery for the treatment of disease. In some embodiments, the PLP protein is PLP1. PLP1 is a form of myelin proteolipid protein that is the predominant myelin protein present in the central nervous system (CNS), thus making PLPs a potential target in inflammatory demyelinating diseases such as multiple sclerosis (MS). In some embodiments, the nucleic acid sequence encodes a wild-type PLP1 protein, or a functional fragment thereof. In some embodiments, the nucleic acid sequence encoding the wild-type PLP1 protein, or a functional fragment thereof, is SEQ ID NO: 100, SEQ ID NO: 94, SEQ ID NO: 95, SEQ ID NO: 96, SEQ ID NO: 97, SEQ ID NO: 98, and/or SEQ ID NO: 99.

Exemplary Proteolipid Protein 1 (PLP1) Nucleic Acid Sequences of the Disclosure

SEQ ID NOs: 94-100 Show the *Homo sapiens* Proteolipid Protein 1 (PLP1), RefSeqGene on Chromosome X:

```
SEQ ID NO: 100:
ATGGGCTTGTTAGAGTGCTGTGCAAGATGTCTGGTAGGGGCCCCCTTTGCTTCCCTGGTGGCCACT

GGATTGTGTTTCTTTGGGGTGGCACTGTTCTGTGGCTGTGGACATGAAGCCCTCACTGGCACAGAA

AAGCTAATTGAGACCTATTTCTCCAAAAACTACCAAGACTATGAGTATCTCATCAATGTGATCCAT

GCCTTCCAGTATGTCATCTATGGAACTGCCTCTTTCTTCTTCCTTTATGGGGCCCTCCTGCTGGCTG

AGGGCTTCTACACCACCGGCGCAGTCAGGCAGATCTTTGGCGACTACAAGACCACCATCTGCGGC

AAGGGCCTGAGCGCAACGGTAACAGGGGGCCAGAAGGGGAGGGGTTCCAGAGGCCAACATCAAG

CTCATTCTTTGGAGCGGGTGTGTCATTGTTTGGGAAAATGGCTAGGACATCCCGACAAGTTTGTGG

GCATCACCTATGCCCTGACCGTTGTGTGGCTCCTGGTGTTTGCCTGCTCTGCTGTGCCTGTGTACAT

TTACTTCAACACCTGGACCACCTGCCAGTCTATTGCCTTCCCCAGCAAGACCTCTGCCAGTATAGG

CAGTCTCTGTGCTGATGCCAGAATGTATGGTGTTCTCCCATGGAATGCTTTCCCTGGCAAGGTTTGT

GGCTCCAACCTTCTGTCCATCTGCAAAACAGCTGAGTTCCAAATGACCTTCCACCTGTTTATTGCTG

CATTTGTGGGGGCTGCAGCTACACTGGTTTCCCTGCTCACCTTCATGATTGCTGCCACTTACAACTT

TGCCGTCCTTAAACTCATGGGCCGAGGCACCAAGTTCTGA

SEQ ID NO: 94:
ATGGGACTGCTGGAATGCTGCGCCCGGTGCCTGGTTGGAGCCCCTTTCGCCAGCCTGGTGGCCACA

GGCCTGTGCTTCTTCGGAGTGGCCCTTTTCTGCGGTTGTGGACACGAGGCCCTGACCGGCACGGAA

AAGCTGATCGAGACATATTTCAGCAAGAACTACCAGGACTACGAGTACCTGATCAACGTGATCCA

CGCCTTTCAGTACGTGATCTACGGCACCGCCAGCTTCTTCTTTCTGTACGGCGCCCTGCTGCTGGCC

GAGGGCTTCTACACCACCGGCGCCGTGCGGCAGATCTTCGGCGACTACAAGACCACAATCTGCGG

CAAGGGCCTGAGCGCCACAGTGACCGGCGGCCAGAAAGGCAGAGGCAGCAGAGGACAACACCAG

GCCCACTCTCTCGAGAGAGTGTGCCACTGCCTGGGAAAGTGGCTGGGCCACCCTGATAAGTTCGTG

GGAATCACCTACGCCCTGACCGTGGTGTGGCTGCTGGTGTTCGCTTGTTCTGCTGTTCCTGTGTACA

TCTACTTCAACACCTGGACCACCTGCCAGAGCATCGCCTTCCCCAGCAAAACCAGCGCCTCTATAG

GAAGCCTCTGTGCCGACGCCAGAATGTACGGCGTGCTGCCTTGGAACGCCTTTCCAGGCAAAGTGT

GTGGCAGCAACCTGCTCTCCATCTGCAAGACCGCCGAATTCCAGATGACCTTCCACCTGTTCATCG
```

CCGCTTTTGTGGGCGCTGCCGCTACACTGGTCAGCCTGCTGACATTCATGATCGCCGCCACCTACA

ACTTCGCCGTGCTGAAGCTGATGGGCAGAGGCACAAAGTTCTGA

SEQ ID NO: 95:
ATGGGACTGCTGGAGTGCTGCGCCCGGTGCCTGGTTGGAGCCCCTTTCGCCAGCCTGGTGGCCACA

GGCCTGTGCTTCTTCGGAGTGGCCCTTTTCTGCGGTTGTGGACACGAGGCCCTGACCGGCACGGAA

AAGCTGATCGAGACATATTTCAGCAAGAACTACCAGGACTACGAGTACCTGATCAACGTGATCCA

CGCCTTTCAGTACGTGATCTACGGCACCGCCAGCTTCTTCTTTCTGTACGGCGCCCTGCTGCTGGCC

GAGGGCTTCTACACCACCGGCGCCGTGCGGCAGATCTTCGGCGACTACAAGACCACAATCTGCGG

CAAGGGCCTGAGCGCCACAGTGACCGGCGGCCAGAAAGGCAGAGGCAGCAGAGGACAACACCAG

GCCCACTCTCTCGAGAGAGTGTGCCACTGCCTGGGAAAGTGGCTGGGCCACCCTGATAAGTTCGTG

GGAATCACCTACGCCCTGACCGTGGTGTGGCTGCTGGTGTTCGCTTGTTCTGCTGTTCCTGTGTACA

TCTACTTCAACACCTGGACCACCTGCCAGAGCATCGCCTTCCCCAGCAAAACCAGCGCCTCTATAG

GAAGCCTCTGTGCCGACGCCAGAATGTACGGCGTGCTGCCTTGGAACGCCTTTCCAGGCAAAGTGT

GTGGCAGCAACCTGCTCTCCATCTGCAAGACCGCCGAATTCCAGATGACCTTCCACCTGTTCATCG

CCGCTTTTGTGGGCGCTGCCGCTACACTGGTCAGCCTGCTGACATTCATGATCGCCGCCACCTACA

ACTTCGCCGTGCTGAAGCTGATGGGCAGAGGCACAAAGTTCTGA

SEQ ID NO: 96:
ATGGGGCTCCTTGAGTGTTGCGCGCGATGTCTTGTTGGGGCGCCATTTGCGAGCCTCGTAGCCACG

GGACTCTGCTTTTTCGGCGTGGCACTCTTTTGTGGCTGTGGGCACGAGGCCCTGACTGGCACTGAA

AAGCTCATAGAGACTTATTTCAGCAAGAATTACCAAGACTACGAATACCTCATCAATGTGATTCAC

GCGTTTCAGTATGTTATTTATGGAACCGCGTCCTTTTTCTTTCTGTACGGGGCTTTGCTCCTTGCTGA

AGGCTTTTACACTACGGGGGCTGTCCGGCAGATATTTGGAGACTATAAGACTACCATTTGCGGAAA

GGGATTGAGCGCTACCGTTACAGGGGGCCAGAAAGGGCGAGGATCACGAGGCCAACATCAGGCG

CACTCTCTGGAAAGAGTATGCCATTGCCTGGGTAAGTGGCTGGGACATCCAGATAAATTTGTAGGA

ATAACCTATGCCCTCACTGTTGTGTGGTTGCTTGTTTTTGCCTGTTCTGCCGTACCTGTTTATATCTA

TTTCAACACCTGGACAACTTGCCAATCTATAGCCTTTCCCTCCAAGACATCTGCCAGCATCGGCTCT

CTGTGCGCTGATGCCAGGATGTATGGCGTCTTGCCTTGGAATGCCTTCCCTGGGAAAGTATGTGGG

TCAAACCTTCTGAGCATTTGTAAAACGGCAGAGTTTCAGATGACGTTTCATCTTTTTATAGCGGCGT

TCGTTGGCGCCGCTGCTACGCTCGTTTCCCTTCTCACTTTTATGATAGCTGCAACGTATAATTTTGC

GGTTTTGAAGCTCATGGGCCGAGGCACTAAATTTTGA

SEQ ID NO: 97:
ATGGGTCTCCTTGAGTGTTGTGCTCGGTGTCTTGTCGGTGCACCCTTCGCGTCCTTGGTGGCGACAG

GTCTGTGCTTTTTCGGTGTGGCACTGTTTTGTGGTTGCGGGCACGAGGCTCTGACAGGTACGGAGA

AACTGATCGAGACTTACTTCTCTAAAAATTACCAAGATTACGAGTACCTCATAAACGTAATTCACG

CATTCCAGTACGTCATATACGGGACTGCGTCTTTTTTCTTCTTGTACGGCGCCTTGCTCCTTGCGGA

AGGGTTTTATACTACCGGGGCAGTACGACAGATTTTCGGCGATTACAAAACAACAATCTGCGGAA

AGGGACTGAGTGCAACCGTTACCGGAGGCCAAAAAGGACGGGGTTCAAGAGGCCAACACCAGGC

ACACAGCCTGGAGCGGGTATGCCACTGCTTGGGGAAGTGGCTCGGGCATCCTGACAAGTTTGTTG

GAATAACTTATGCCTTGACCGTCGTCTGGCTGCTCGTCTTTGCCTGTAGCGCAGTTCCAGTGTACAT

CTACTTCAACACATGGACCACTTGCCAGTCCATCGCGTTCCCATCAAAGACAAGCGCGTCAATCGG

GTCACTGTGCGCAGATGCCCGCATGTACGAGTGTTGCCCTGGAACGCCTTCCCCGGGAAAGTATG

CGGAAGCAATCTCTTGTCTATTTGTAAGACAGCGGAATTCCAGATGACATTCCACCTTTTTATCGC

AGCGTTTGTCGGCGCCGCCGCGACGCTTGTCTCTTTGTTGACATTTATGATTGCCGCGACATACAAT

TTTGCTGTGCTGAAGTTGATGGGCAGAGGCACGAAATTCTGA

SEQ ID NO: 98:
ATGGGGCTCTTGGAGTGCTGTGCCAGATGCCTCGTTGGTGCCCCATTTGCAAGCCTGGTGGCAACC

GGACTCTGCTTCTTTGGTGTAGCACTGTTTTGCGGCTGTGGTCATGAGGCTCTCACGGGAACAGAA

AAATTGATCGAAACTTATTTCTCCAAGAATTACCAGGACTATGAGTACCTCATAAACGTCATCCAT

GCATTTCAGTATGTGATTTATGGGACCGCTAGTTTTTTTTTCTTTACGGCGCCCTCCTTCTCGCCGA

AGGATTTTATACGACCGGTGCGGTCCGACAAATCTTCGGAGACTATAAAACTACTATTTGTGGCAA

AGGACTCTCAGCTACCGTTACGGGCGGACAGAAGGGCCGAGGATCCCGCGGGCAACACCAGGCGC

ACTCTTTGGAAAGAGTCTGCCATTGCCTTGGAAAGTGGCTGGGGCACCCAGATAAGTTCGTAGGCA

TAACTTACGCCCTCACTGTAGTATGGTTGCTGGTTTTCGCATGCTCAGCGGTCCCAGTCTACATTTA

TTTTAACACCTGGACTACGTGTCAATCAATAGCCTTTCCGTCCAAAACGTCAGCATCCATAGGTTC

CCTGTGCGCGGACGCGAGAATGTATGGGGTGCTGCCGTGGAACGCTTTTCCTGGTAAGGTTTGCGG

GAGCAATCTGCTCAGCATTTGTAAAACTGCAGAGTTCCAGATGACGTTCCATTTGTTCATCGCTGC

GTTTGTGGGGCGGCAGCGACACTCGTATCCCTGCTCACCTTTATGATTGCCGCAACGTATAACTT

TGCGGTTCTTAAGCTTATGGGCCGGGGGACAAAGTTCTGA

SEQ ID NO: 99:
ATGGGGCTCTTGGAGTGCTGTGCCAGATGCCTCGTTGGTGCCCCATTTGCAAGCCTGGTGGCAACC

GGACTCTGCTTCTTTGGTGTAGCACTGTTTTGCGGCTGTGGTCATGAGGCTCTCACGGGAACAGAA

AAATTGATCGAAACTTATTTCTCCAAGAATTACCAGGACTATGAGTACCTCATAAACGTCATCCAT

GCATTTCAGTATGTGATTTACGGGACCGCTAGTTTTTTTTTCTTTACGGCGCCCTCCTTCTCGCCGA

AGGATTTTATACGACCGGTGCGGTCCGACAAATCTTCGGAGACTATAAAACTACTATTTGTGGCAA

AGGACTCTCAGCTACCGTTACGGGCGGACAGAAGGGCCGAGGATCCCGCGGGCAACACCAGGCGC

ACTCTTTGGAAAGAGTCTGCCATTGCCTTGGAAAGTGGCTGGGGCACCCAGATAAGTTCGTAGGCA

TAACTTACGCCCTCACTGTAGTATGGTTGCTGGTTTTCGCATGCTCAGCGGTCCCAGTCTACATTTA

TTTTAACACCTGGACTACGTGTCAATCAATAGCCTTTCCGTCCAAAACGTCAGCATCCATAGGTTC

CCTGTGCGCGGACGCGAGAATGTATGGGGTGCTGCCGTGGAACGCTTTTCCTGGTAAGGTTTGCGG

GAGCAATCTGCTCAGCATTTGTAAAACTGCAGAGTTCCAGATGACGTTCCATTTGTTCATCGCTGC

GTTTGTGGGGCGGCAGCGACACTCGTATCCCTGCTCACCTTTATGATTGCCGCAACGTATAACTT

TGCGGTTCTTAAGCTTATGGGCCGGGGGACAAAGTTCTGA

In some embodiments, the nucleic acid sequence encodes a PLP1 variant, or a functional fragment thereof. As used herein, a "variant" refers to a PLP1 protein, or a functional fragment thereof, that differs from the wild-type PLP1 protein in its amino acid sequence and/or function, and which is encoded by one of the variant nucleic acid sequences of the present disclosure. In some embodiments, the variant nucleic acid sequence encoding the PLP1 protein variant, or functional fragment thereof, is transcript variant 1. In some embodiments, the variant nucleic acid sequence encoding the PLP1 protein variant, or functional fragment thereof, is SEQ ID NO: 100, SEQ ID NO: 101, SEQ ID NO: 102, SEQ ID NO: 103, SEQ ID NO: 104, SEQ ID NO: 105, and/or SEQ ID NO: 106.

SEQ ID NOs: 100-106 Show the *Homo sapiens* Proteolipid Protein 1 (PLP1), Transcript Variant 1:

SEQ ID NO: 100:
ATGGGCTTGTTAGAGTGCTGTGCAAGATGTCTGGTAGGGGCCCCCTTTGCTTCCCTGGTGGCCACT

GGATTGTGTTTCTTTGGGGTGGCACTGTTCTGTGGCTGTGGACATGAAGCCCTCACTGGCACAGAA

AAGCTAATTGAGACCTATTTCTCCAAAAACTACCAAGACTATGAGTATCTCATCAATGTGATCCAT

GCCTTCCAGTATGTCATCTATGGAACTGCCTCTTTCTTCTTCCTTTATGGGGCCCTCCTGCTGGCTG

AGGGCTTCTACACCACCGGCGCAGTCAGGCAGATCTTTGGCGACTACAAGACCACCATCTGCGGC

AAGGGCCTGAGCGCAACGGTAACAGGGGGCCAGAAGGGGAGGGGTTCCAGAGGCCAACATCAAG

CTCATTCTTTGGAGCGGGTGTGTCATTGTTTGGGAAAATGGCTAGGACATCCCGACAAGTTTGTGG

GCATCACCTATGCCCTGACCGTTGTGTGGCTCCTGGTGTTTGCCTGCTCTGCTGTGCCTGTGTACAT

TTACTTCAACACCTGGACCACCTGCCAGTCTATTGCCTTCCCCAGCAAGACCTCTGCCAGTATAGG

CAGTCTCTGTGCTGATGCCAGAATGTATGGTGTTCTCCCATGGAATGCTTTCCCTGGCAAGGTTTGT

GGCTCCAACCTTCTGTCCATCTGCAAAACAGCTGAGTTCCAAATGACCTTCCACCTGTTTATTGCTG

CATTTGTGGGGCTGCAGCTACACTGGTTTCCCTGCTCACCTTCATGATTGCTGCCACTTACAACTT

TGCCGTCCTTAAACTCATGGGCCGAGGCACCAAGTTCTGA

SEQ ID NO: 101:
ATGGGCCTGCTGGAATGCTGCGCCCGGTGCCTGGTGGGCGCCCCTTTCGCCAGCCTGGTGGCCACA

GGACTGTGCTTCTTCGGCGTGGCCCTGTTCTGCGGCTGCGGCCACGAGGCCCTGACCGGCACAGAG

AAGCTGATCGAGACATATTTCAGCAAGAACTACCAGGACTACGAGTACCTGATCAACGTGATCCA

CGCCTTCCAATACGTGATCTACGGCACCGCCTCTTTTTTCTTCCTGTACGGCGCTCTGCTGCTGGCC

GAGGGCTTCTACACCACCGGCGCCGTGCGGCAGATCTTCGGCGACTACAAGACCACAATCTGCGG

CAAAGGCCTGTCTGCCACCGTTACAGGCGGCCAGAAGGGCAGAGGCAGTAGAGGACAGCACCAG

GCCCACAGCCTGGAAAGAGTGTGCCACTGCCTGGGCAAGTGGCTGGGACATCCTGATAAGTTCGT

GGGCATCACCTACGCCCTGACCGTGGTGTGGCTGCTGGTCTTTGCCTGCAGCGCCGTGCCTGTGTA

CATCTACTTCAACACCTGGACCACCTGTCAGAGCATCGCCTTTCCTAGCAAGACCAGCGCCAGCAT

CGGCAGCCTCTGTGCTGATGCCAGAATGTACGGAGTGCTGCCTTGGAACGCCTTCCCCGGCAAGGT

GTGTGGCAGCAACCTGCTGAGCATTTGTAAAACCGCCGAATTCCAGATGACATTCCACCTGTTTAT

CGCCGCTTTTGTGGGAGCCGCTGCTACACTGGTTTCTCTGCTCACCTTCATGATCGCTGCCACCTAC

AACTTCGCCGTGCTGAAGCTGATGGGAAGAGGCACTAAGTTCTGA

SEQ ID NO: 102:
ATGGGCCTGCTGGAgTGCTGCGCCCGGTGCCTGGTGGGCGCCCCTTTCGCCAGCCTGGTGGCCACA

GGACTGTGCTTCTTCGGCGTGGCCCTGTTCTGCGGCTGCGGCCACGAGGCCCTGACCGGCACAGAG

AAGCTGATCGAGACATATTTCAGCAAGAACTACCAGGACTACGAGTACCTGATCAACGTGATCCA

CGCCTTCCAATACGTGATCTACGGCACCGCCTCTTTTTTCTTCCTGTACGGCGCTCTGCTGCTGGCC

GAGGGCTTCTACACCACCGGCGCCGTGCGGCAGATCTTCGGCGACTACAAGACCACAATCTGCGG

CAAAGGCCTGTCTGCCACCGTTACAGGCGGCCAGAAGGGCAGAGGCAGTAGAGGACAGCACCAG

GCCCACAGCCTGGAAAGAGTGTGCCACTGCCTGGGCAAGTGGCTGGGACATCCTGATAAGTTCGT

GGGCATCACCTACGCCCTGACCGTGGTGTGGCTGCTGGTCTTTGCCTGCAGCGCCGTGCCTGTGTA

CATCTACTTCAACACCTGGACCACCTGTCAGAGCATCGCCTTTCCTAGCAAGACCAGCGCCAGCAT

CGGCAGCCTCTGTGCTGATGCCAGAATGTACGGAGTGCTGCCTTGGAACGCCTTCCCCGGCAAGGT

GTGTGGCAGCAACCTGCTGAGCATTTGTAAAACCGCCGAATTCCAGATGACATTCCACCTGTTTAT

CGCCGCTTTTGTGGGAGCCGCTGCTACACTGGTTTCTCTGCTCACCTTCATGATCGCTGCCACCTAC

AACTTCGCCGTGCTGAAGCTGATGGGAAGAGGCACTAAGTTCTGA

SEQ ID NO: 103:
ATGGGGCTCTTGGAGTGCTGCGCCAGGTGTCTCGTCGGAGCGCCATTTGCCTCCTTGGTGGCAACG

GGACTTTGCTTTTTCGGCGTAGCCCTGTTTTGCGGGTGCGGCCATGAAGCGTTGACCGGCACTGAG

AAGCTGATAGAAACCTATTTCTCAAAAAATTATCAAGACTACGAGTATCTTATCAACGTCATTCAC

GCCTTTCAATATGTGATCTACGGTACGGCTAGCTTCTTTTTCCTGTATGGTGCGCTGTTGCTCGCTG

AAGGATTTTACACGACAGGTGCCGTTCGGCAAATTTTTGGCGATTATAAAACGACAATTTGTGGAA

AAGGCCTCTCAGCTACCGTGACTGGCGGCCAAAAAGGCCGGGGTAGCAGGGGTCAGCATCAAGCA

CATTCCCTCGAACGAGTGTGCCACTGCCTTGGAAAGTGGTTGGGGCACCCCGATAAATTCGTGGGG

ATAACCTACGCTCTTACTGTTGTTTGGCTGCTCGTGTTCGCCTGCTCTGCTGTACCTGTGTATATCTA

CTTTAATACATGGACCACGTGCCAAAGTATTGCCTTTCCTAGTAAGACATCTGCTTCTATTGGATCA

CTCTGCGCTGATGCACGGATGTATGGCGTTTTGCCGTGGAATGCTTTCCCTGGTAAAGTGTGTGGTT

CCAATCTGTTGAGTATTTGTAAAACAGCAGAGTTCCAGATGACGTTCCACCTGTTTATCGCTGCTTT

TGTTGGTGCAGCGGCCACGCTTGTCAGCCTGTTGACTTTTATGATAGCTGCTACCTACAACTTTGCG

GTACTCAAGCTCATGGGGCGAGGCACAAAGTTTTGA

SEQ ID NO: 104:
ATGGGGCTTCTCGAGTGCTGCGCTCGCTGTCTGGTTGGCGCACCTTTTGCAAGCCTTGTAGCGACT

GGCTTGTGTTTTTTCGGTGTGGCATTGTTTTGCGGGTGCGGTCACGAGGCGTTGACAGGTACTGAG

AAGCTGATCGAGACTTACTTCTCTAAAAATTATCAAGATTACGAATACCTGATTAACGTGATACAC

GCTTTCCAGTATGTAATCTACGGCACAGCGAGCTTTTTCTTTCTTTATGGCGCACTGCTGCTCGCGG

AAGGATTCTATACTACTGGGGCGGTTCGGCAGATCTTTGGTGATTACAAAACAACAATTTGCGGTA

AAGGTCTTTCCGCAACAGTCACTGGCGGGCAGAAGGGGCGAGGAAGCCGGGGGCAACATCAGGC

ACACTCCTTGGAAAGAGTATGCCATTGTTTGGGGAAATGGCTGGGCCACCCGGACAAATTTGTCGG

TATCACATACGCGCTTACTGTTGTTTGGTTGTTGGTATTTGCTTGTTCAGCTGTCCCAGTCTATATCT

ATTTTAACACCTGGACCACTTGCCAATCTATCGCATTCCCTTCAAAGACCTCTGCGTCCATAGGCTC

TCTTTGTGCAGATGCTAGAATGTACGGCGTATTGCCTTGGAATGCATTCCCAGGTAAAGTTTGCGG

TAGTAACCTGCTTAGCATTTGCAAGACTGCTGAATTCCAGATGACATTCCACCTCTTTATTGCCGCA

TTTGTAGGTGCTGCTGCCACACTCGTGTCTCTCCTGACTTTTATGATTGCGGCAACGTATAACTTCG

CAGTTTTGAAGCTGATGGGAGGGTACTAAATTCTGA

SEQ ID NO: 105:
ATGGGGCTTCTCGAGTGCTGCGCTCGCTGTCTGGTTGGCGCACCTTTTGCAAGCCTTGTAGCGACT

GGCTTGTGTTTTTTCGGTGTGGCATTGTTTTGCGGGTGCGGTCACGAGGCGTTGACAGGTACTGAG

AAGCTGATCGAGACTTACTTCTCTAAAAATTATCAAGATTACGAATACCTGATTAACGTGATACAC

GCTTTCCAGTATGTAATCTACGGCACAGCGAGCTTTTTCTTTCTTTAcGGCGCACTGCTGCTCGCGG

AAGGATTCTATACTACTGGGGCGGTTCGGCAGATCTTTGGTGATTACAAAACAACAATTTGCGGTA

AAGGTCTTTCCGCAACAGTCACTGGCGGGCAGAAGGGGCGAGGAAGCCGGGGGCAACATCAGGC

ACACTCCTTGGAAAGAGTATGCCATTGTTTGGGGAAATGGCTGGGCCACCCGGACAAATTTGTCGG

TATCACATACGCGCTTACTGTTGTTTGGTTGTTGGTATTTGCTTGTTCAGCTGTCCCAGTCTATATCT

ATTTTAACACCTGGACCACTTGCCAATCTATCGCATTCCCTTCAAAGACCTCTGCGTCCATAGGCTC

TCTTTGTGCAGATGCTAGAATGTACGGCGTATTGCCTTGGAATGCATTCCCAGGTAAAGTTTGCGG

TAGTAACCTGCTTAGCATTTGCAAGACTGCTGAATTCCAGATGACATTCCACCTCTTTATTGCCGCA

TTTGTAGGTGCTGCTGCCACACTCGTGTCTCTCCTGACTTTTATGATTGCGGCAACGTATAACTTCG

CAGTTTTGAAGCTGATGGGAGGGGTACTAAATTCTGA

SEQ ID NO: 106:
ATGGGCCTCCTTGAGTGCTGTGCCAGGTGTCTTGTAGGGGCTCCCTTTGCTTCACTGGTTGCTACGG

GTCTGTGCTTTTTTGGTGTCGCACTGTTTTGCGGGTGTGGACACGA AGCCTTGACTGGTACGGAAA

AGCTCATAGAGACTTATTTCTCCAAAAACTACCAAGACTACGAGTACTTGATAAATGTTATTCACG

CGTTCCAGTATGTTATCTATGGACGGCAAGCTTCTTTTTCCTGTACGGCGCGTTGTTGTTGGCAGA

GGGATTCTACACTACGGGCGCGGTAAGACAGATCTTCGGGGATTATAAGACTACTATTTGCGGGA

-continued

```
AGGGCCTCAGCGCCACCGTTACCGGCGGTCAAAAGGGTAGAGGGTCTCGCGGTCAGCACCAAGCC

CATAGTCTTGAACGGGTCTGTCATTGCCTCGGAAAATGGCTTGGTCACCCAGACAAGTTTGTGGGA

ATTACCTATGCGCTCACTGTGGTATGGCTGCTTGTCTTCGCTTGCTCAGCAGTCCCTGTGTATATCT

ATTTCAACACGTGGACCACATGCCAGAGTATAGCATTCCCAAGTAAGACGAGCGCGTCCATCGGC

AGTTTGTGTGCTGACGCGAGGATGTACGGCGTTCTCCCTTGGAATGCATTTCCGGGAAAAGTGTGT

GGATCAAATTTGCTTAGCATTTGCAAGACAGCGGAATTCCAAATGACATTCCACCTGTTCATTGCG

GCGTTCGTCGGAGCAGCTGCCACCCTTGTTAGTCTTCTGACCTTCATGATCGCCGCTACCTATAACT

TCGCAGTCCTCAAGTTGATGGGCCGGGGTACTAAGTTTTGA
```

In some embodiments, the variant nucleic acid sequence encoding the PLP1 protein variant, or functional fragment thereof, is transcript variant 2. In some embodiments, the variant nucleic acid sequence encoding the PLP1 protein variant, or functional fragment thereof, is SEQ ID NO: 107, SEQ ID NO: 108, SEQ ID NO: 109, SEQ ID NO: 110, SEQ ID NO: 111, and/or SEQ ID NO: 112.

SEQ ID NOs: 107-112 Show the *Homo sapiens* Proteolipid Protein 1 (PLP1), Transcript Variant 2:

```
SEQ ID NO: 107:
ATGGGCTTGTTAGAGTGCTGTGCAAGATGTCTGGTAGGGGCCCCCTTTGCTTCCCTGGTGGCCACT

GGATTGTGTTTCTTTGGGGTGGCACTGTTCTGTGGCTGTGGACATGAAGCCCTCACTGGCACAGAA

AAGCTAATTGAGACCTATTTCTCCAAAAACTACCAAGACTATGAGTATCTCATCAATGTGATCCAT

GCCTTCCAGTATGTCATCTATGGAACTGCCTCTTTCTTCTTCCTTTATGGGGCCCTCCTGCTGGCTG

AGGGCTTCTACACCACCGGCGCAGTCAGGCAGATCTTTGGCGACTACAAGACCACCATCTGCGGC

AAGGGCCTGAGCGCAACGTTTGTGGGCATCACCTATGCCCTGACCGTTGTGTGGCTCCTGGTGTTT

GCCTGCTCTGCTGTGCCTGTGTACATTTACTTCAACACCTGGACCACCTGCCAGTCTATTGCCTTCC

CCAGCAAGACCTCTGCCAGTATAGGCAGTCTCTGTGCTGATGCCAGAATGTATGGTGTTCTCCCAT

GGAATGCTTTCCCTGGCAAGGTTTGTGGCTCCAACCTTCTGTCCATCTGCAAAACAGCTGAGTTCC

AAATGACCTTCCACCTGTTTATTGCTGCATTTGTGGGGGCTGCAGCTACACTGGTTTCCCTGCTCAC

CTTCATGATTGCTGCCACTTACAACTTTGCCGTCCTTAAACTCATGGGCCGAGGCACCAAGTTCTG

A

SEQ ID NO: 108:
ATGGGCCTGCTGGAATGCTGCGCCCGGTGCCTGGTGGGCGCCCCTTTCGCTTCTCTGGTCGCCACC

GGCCTCTGTTTTTTCGGCGTGGCCCTGTTCTGCGGTTGTGGCCACGAGGCCCTGACCGGCACAGAG

AAGCTGATCGAGACATATTTCAGCAAGAACTACCAGGACTACGAGTACCTGATCAACGTGATCCA

CGCCTTCCAATACGTGATCTACGGCACCGCCAGCTTCTTCTTCCTGTACGGCGCTCTGCTGCTGGCC

GAGGGCTTCTACACCACCGGAGCTGTTAGACAGATCTTCGGAGATTACAAGACCACAATCTGCGG

AAAGGGCCTGAGCGCCACATTCGTGGGCATCACCTACGCCCTGACAGTGGTGTGGCTGCTGGTCTT

TGCTTGTAGCGCCGTCCCCGTGTACATCTACTTCAACACCTGGACCACATGCCAGAGCATCGCCTT

CCCCAGCAAGACCAGCGCCTCTATCGGCAGCCTGTGCGCCGACGCCAGAATGTACGGCGTGCTGC

CTTGGAACGCCTTTCCTGGAAAAGTGTGCGGCTCTAATCTGCTCAGCATCTGCAAGACAGCCGAAT

TCCAGATGACCTTCCACCTGTTTATCGCCGCTTTTGTGGGAGCCGCTGCTACACTGGTGTCCCTGCT

GACCTTCATGATCGCCGCCACCTACAACTTCGCCGTGCTGAAGCTGATGGGCAGAGGCACCAAGTT

CTGA
```

SEQ ID NO: 109:
ATGGGCCTGCTGGAgTGCTGCGCCCGGTGCCTGGTGGGCGCCCCTTTCGCTTCTCTGGTCGCCACCG

GCCTCTGTTTTTTCGGCGTGGCCCTGTTCTGCGGTTGTGGCCACGAGGCCCTGACCGGCACAGAGA

AGCTGATCGAGACATATTTCAGCAAGAACTACCAGGACTACGAGTACCTGATCAACGTGATCCAC

GCCTTCCAATACGTGATCTACGGCACCGCCAGCTTCTTCTTCCTGTACGGCGCTCTGCTGCTGGCCG

AGGGCTTCTACACCACCGGAGCTGTTAGACAGATCTTCGGAGATTACAAGACCACAATCTGCGGA

AAGGGCCTGAGCGCCACATTCGTGGGCATCACCTACGCCCTGACAGTGGTGTGGCTGCTGGTCTTT

GCTTGTAGCGCCGTCCCCGTGTACATCTACTTCAACACCTGGACCACATGCCAGAGCATCGCCTTC

CCCAGCAAGACCAGCGCCTCTATCGGCAGCCTGTGCGCCGACGCCAGAATGTACGGCGTGCTGCC

TTGGAACGCCTTTCCTGGAAAAGTGTGCGGCTCTAATCTGCTCAGCATCTGCAAGACAGCCGAATT

CCAGATGACCTTCCACCTGTTTATCGCCGCTTTTGTGGGAGCCGCTGCTACACTGGTGTCCCTGCTG

ACCTTCATGATCGCCGCCACCTACAACTTCGCCGTGCTGAAGCTGATGGGCAGAGGCACCAAGTTC

TGA

SEQ ID NO: 110:
ATGGGTTTGTTGGAGTGCTGCGCTCGGTGCCTGGTGGGGCACCGTTTGCGAGCTTGGTTGCAACC

GGTCTCTGCTTTTTCGGGGTAGCACTTTTTTGCGGGTGTGGACATGAGGCTTTGACCGGAACGGAA

AAACTTATTGAGACCTACTTCAGTAAGAATTATCAGGACTACGAGTATCTGATTAATGTAATTCAC

GCATTTCAGTACGTGATATATGGTACAGCTTCCTTTTTTTTTCTGTACGGAGCATTGCTGTTGGCAG

AAGGATTCTACACGACGGGGCGGTACGACAGATCTTCGGGGACTATAAGACAACCATCTGTGGA

AAAGGCTTGAGTGCTACTTTCGTAGGCATTACTTACGCCTTGACGGTAGTGTGGCTCTTGGTTTCG

CTTGTTCTGCAGTGCCAGTTTACATCTACTTCAATACTTGGACGACGTGTCAATCAATAGCGTTCCC

TAGTAAGACAAGTGCCAGCATTGGTAGTTTGTGCGCGGACGCTCGCATGTACGGAGTTCTCCCTTG

GAACGCCTTTCCCGGCAAGGTCTGTGGGTCTAACCTGCTCAGCATATGTAAGACCGCAGAATTCCA

AATGACATTTCATTTGTTCATCGCTGCCTTTGTGGGTGCCGCTGCCACCCTGGTGTCCCTTCTTACG

TTTATGATAGCAGCAACGTACAATTTTGCAGTATTGAAACTCATGGGCGGGGCACTAAGTTCTGA

SEQ ID NO: 111:
ATGGGGCTCCTTGAGTGCTGTGCCCGGTGCCTGGTCGGTGCTCCCTTCGCTTCACTTGTTGCCACTG

GACTCTGCTTTTTTGGAGTCGCCTTGTTTTGTGGTTGTGGGCACGAGGCGCTCACAGGCACCGAGA

AGCTTATAGAAACTTACTTCAGCAAGAACTATCAAGACTATGAATACCTTATCAATGTTATTCACG

CGTTTCAGTACGTAATTTATGGAACCGCCTCCTTCTTTTTCCTGTACGGGGCCTTGTTGCTTGCTGA

GGGCTTCTACACAACTGGGGCCGTCCGCCAGATCTTCGGTGACTACAAAACGACAATTTGCGGTAA

GGGCCTTTCCGCTACTTTTGTTGGTATCACTTATGCGCTGACAGTCGTATGGCTTCTTGTATTTGCG

TGTAGCGCCGTACCTGTTTATATCTACTTCAACACGTGGACTACCTGCCAATCTATAGCGTTCCCAT

CAAAGACCAGTGCTAGTATCGGGTCCCTGTGTGCTGACGCCAGAATGTACGGTGTACTTCCTTGGA

ATGCTTTCCCAGGTAAAGTATGCGGCTCAAATCTGCTCAGTATATGTAAGACGGCCGAGTTTCAGA

TGACTTTCCATCTGTTCATTGCGGCGTTCGTCGGCGCAGCGGCTACTCTGGTCTCACTTCTGACGTT

TATGATAGCTGCCACTTATAACTTTGCGGTTCTCAAGTTGATGGGTCGCGGTACGAAGTTTTGA

SEQ ID NO: 112:
ATGGGGCTTCTTGAGTGTTGCGCCAGGTGTCTCGTTGGCGCTCCCTTCGCGAGCCTTGTCGCCACCG

GCTTGTGTTTCTTTGGAGTTGCTTTGTTCTGTGGCTGCGGCCATGAGGCTCTTACCGGGACTGAAAA

GCTGATTGAAACGTATTTCAGCAAGAACTACCAAGACTACGAGTACCTGATAAACGTAATCCATG

CGTTTCAGTACGTAATATATGGTACCGCATCTTTCTTCTTCTTGTACGGGGCGCTGCTCCTGGCAGA

GGGATTTTACACTACAGGTGCTGTGCGACAAATTTTCGGAGATTATAAAACAACAATTTGCGGAAA

```
GGGTCTTAGTGCTACGTTCGTTGGGATAACGTACGCGCTGACAGTCGTATGGCTGCTTGTCTTTGC

GTGTAGCGCCGTTCCGGTGTATATATATTTTAATACGTGGACAACGTGTCAATCCATTGCTTTTCCG

AGCAAAACTTCCGCTTCTATCGGATCCCTGTGTGCCGACGCGAGAATGTACGGAGTTCTTCCCTGG

AACGCCTTTCCGGGCAAGGTGTGTGGTTCCAACCTTCTTTCTATATGTAAAACAGCGGAGTTCCAA

ATGACTTTCCATCTTTTTATAGCCGCATTCGTAGGAGCAGCTGCAACTCTGGTTTCCTTGCTGACAT

TCATGATCGCAGCTACTTATAACTTTGCAGTCTTGAAACTTATGGGACGCGGAACTAAATTTTGA
```

In some embodiments, the variant nucleic acid sequence encoding the PLP1 protein variant, or functional fragment thereof, is transcript variant 3. In some embodiments, the variant nucleic acid sequence encoding the PLP1 protein variant, or functional fragment thereof, is SEQ ID NO: 100, SEQ ID NO: 114, SEQ ID NO: 115, SEQ ID NO: 116, SEQ ID NO: 117, SEQ ID NO: 118, and/or SEQ ID NO: 119.

SEQ ID NOs: 100 and 114-119 Show the *Homo sapiens* Proteolipid Protein 1 (PLP1), Transcript Variant 3:

```
SEQ ID NO: 100:
ATGGGCTTGTTAGAGTGCTGTGCAAGATGTCTGGTAGGGGCCCCCTTTGCTTCCCTGGTGGCCACT

GGATTGTGTTTCTTTGGGGTGGCACTGTTCTGTGGCTGTGGACATGAAGCCCTCACTGGCACAGAA

AAGCTAATTGAGACCTATTTCTCCAAAAACTACCAAGACTATGAGTATCTCATCAATGTGATCCAT

GCCTTCCAGTATGTCATCTATGGAACTGCCTCTTTCTTCTTCCTTTATGGGCCCTCCTGCTGGCTG

AGGGCTTCTACACCACCGGCGCAGTCAGGCAGATCTTTGGCGACTACAAGACCACCATCTGCGGC

AAGGGCCTGAGCGCAACGGTAACAGGGGGCCAGAAGGGGAGGGGTTCCAGAGGCCAACATCAAG

CTCATTCTTTGGAGCGGGTGTGTCATTGTTTGGGAAAATGGCTAGGACATCCCGACAAGTTTGTGG

GCATCACCTATGCCCTGACCGTTGTGTGGCTCCTGGTGTTTGCCTGCTCTGCTGTGCCTGTGTACAT

TTACTTCAACACCTGGACCACCTGCCAGTCTATTGCCTTCCCCAGCAAGACCTCTGCCAGTATAGG

CAGTCTCTGTGCTGATGCCAGAATGTATGGTGTTCTCCCATGGAATGCTTTCCCTGGCAAGGTTTGT

GGCTCCAACCTTCTGTCCATCTGCAAAACAGCTGAGTTCCAAATGACCTTCCACCTGTTTATTGCTG

CATTTGTGGGGCTGCAGCTACACTGGTTTCCCTGCTCACCTTCATGATTGCTGCCACTTACAACTT

TGCCGTCCTTAAACTCATGGGCCGAGGCACCAAGTTCTGA

SEQ ID NO: 114:
ATGGGACTGCTGGAATGCTGCGCCCGGTGCCTGGTGGGCGCCCCTTTCGCCAGCCTGGTGGCCACC

GGCCTGTGCTTCTTTGGCGTGGCCCTGTTCTGCGGCTGCGGACACGAGGCCCTGACAGGCACCGAG

AAGCTGATCGAGACATATTTCAGCAAGAACTACCAGGACTACGAGTACCTGATCAACGTGATCCA

CGCCTTTCAGTACGTGATCTACGGAACCGCCAGCTTCTTCTTCCTGTACGGCGCTCTGCTGCTGGCC

GAAGGCTTCTACACCACCGGCGCTGTTAGACAGATCTTCGGCGACTACAAGACAACCATCTGTGG

AAAAGGACTGAGCGCCACCGTGACCGGCGGCCAAAAGGGCCGGGGCTCTAGAGGCCAGCACCAG

GCCCACTCTCTGGAAAGAGTGTGCCACTGCCTGGGCAAATGGCTGGGCCACCCTGATAAGTTCGTG

GGCATCACCTACGCCCTGACCGTGGTGTGGCTGCTTGTTTTCGCCTGCAGCGCCGTGCCAGTGTAC

ATCTACTTCAACACCTGGACCACATGCCAGAGCATCGCCTTTCCTAGCAAGACCAGCGCCTCTATC

GGCAGCCTGTGTGCCGACGCCAGAATGTACGGCGTGCTGCCTTGGAACGCCTTCCCCGGCAAGGT

GTGTGGCAGCAACCTGCTTTCTATCTGCAAGACCGCCGAGTTCCAGATGACCTTCCACCTGTTCAT

CGCCGCTTTTGTGGGAGCCGCCGCCACACTGGTCAGCCTGCTGACCTTCATGATCGCCGCTACATA

CAACTTCGCCGTGCTGAAGCTGATGGGCAGAGGCACCAAGTTCTGA

SEQ ID NO: 115:
ATGGGACTGCTGGAGTGCTGCGCCCGGTGCCTGGTGGGCGCCCCTTTCGCCAGCCTGGTGGCCACC

GGCCTGTGCTTCTTTGGCGTGGCCCTGTTCTGCGGCTGCGGACACGAGGCCCTGACAGGCACCGAG
```

-continued
AAGCTGATCGAGACATATTTCAGCAAGAACTACCAGGACTACGAGTACCTGATCAACGTGATCCA

CGCCTTTCAGTACGTGATCTACGGAACCGCCAGCTTCTTCTTCCTGTACGGCGCTCTGCTGCTGGCC

GAAGGCTTCTACACCACCGGCGCTGTTAGACAGATCTTCGGCGACTACAAGACAACCATCTGTGG

AAAAGGACTGAGCGCCACCGTGACCGGCGGCCAAAAGGGCCGGGGCTCTAGAGGCCAGCACCAG

GCCCACTCTCTGGAAAGAGTGTGCCACTGCCTGGGCAAATGGCTGGGCCACCCTGATAAGTTCGTG

GGCATCACCTACGCCCTGACCGTGGTGTGGCTGCTTGTTTTCGCCTGCAGCGCCGTGCCAGTGTAC

ATCTACTTCAACACCTGGACCACATGCCAGAGCATCGCCTTTCCTAGCAAGACCAGCGCCTCTATC

GGCAGCCTGTGTGCCGACGCCAGAATGTACGGCGTGCTGCCTTGGAACGCCTTCCCCGGCAAGGT

GTGTGGCAGCAACCTGCTTTCTATCTGCAAGACCGCCGAGTTCCAGATGACCTTCCACCTGTTCAT

CGCCGCTTTTGTGGGAGCCGCCGCCACACTGGTCAGCCTGCTGACCTTCATGATCGCCGCTACATA

CAACTTCGCCGTGCTGAAGCTGATGGGCAGAGGCACCAAGTTCTGA

SEQ ID NO: 116:
ATGGGACTTTTGGAGTGTTGCGCCAGATGCCTGGTCGGTGCCCCGTTTGCAAGCCTTGTTGCCACT

GGCTTGTGCTTCTTCGGTGTAGCATTGTTCTGCGGGTGTGGCCATGAGGCTCTGACAGGTACAGAG

AAGTTGATTGAAACATACTTTTCCAAGAACTACCAAGACTACGAATATCTGATTAACGTTATACAT

GCCTTCCAATATGTAATCTATGGGACCGCTAGCTTTTTCTTCCTTTATGGAGCTTTGCTCCTGGCCG

AGGGTTTTTACACGACGGGTGCGGTTCGACAGATTTTTGGAGACTATAAGACTACGATTTGTGGTA

AAGGACTCAGCGCGACCGTGACGGGTGGACAAAAAGGTCGCGGTTCTCGGGGTCAACACCAAGCT

CACTCTCTTGAACGAGTTTGTCACTGTTTGGGAAAATGGCTCGGCCATCCCGATAAATTGTGGGC

ATAACTTACGCTCTTACGGTGGTATGGCTCCTGGTCTTTGCGTGCTCCGCTGTCCCCGTATATATCT

ATTTCAACACATGGACTACGTGCCAATCCATCGCTTTTCCCAGCAAGACGAGTGCGTCTATAGGTT

CACTTTGCGCTGATGCGAGGATGTACGGCGTGCTCCCCTGGAATGCTTTTCCTGGCAAAGTTTGTG

GTTCTAATCTTCTGAGTATTTGCAAAACAGCAGAATTTCAGATGACCTTCCATTTGTTTATAGCCGC

TTTTGTGGGTGCAGCTGCTACACTCGTGAGCCTTCTTACGTTCATGATTGCTGCAACATACAATTTT

GCTGTACTCAAACTCATGGGCAGAGGCACCAAATTCTGA

SEQ ID NO: 117:
ATGGGTCTCCTTGAGTGCTGCGCCAGGTGCCTTGTTGGAGCTCCGTTCGCCAGTCTGGTAGCCACT

GGGTTGTGCTTCTTCGGCGTCGCCTTGTTCTGCGGATGTGGGCACGAGGCGCTTACTGGTACCGAG

AAATTGATCGAGACATACTTTTCAAAGAATTATCAAGACTATGAATACCTGATAAATGTGATTCAC

GCATTTCAATACGTGATATACGGCACAGCCTCTTTCTTTTTTCTGTACGGGGCTCTCCTTCTCGCTG

AAGGCTTCTACACGACTGGGGCAGTCAGACAAATCTTTGGCGATTACAAGACGACTATATGTGGG

AAGGGCCTGTCAGCCACCGTGACCGGGGGCAGAAGGGCAGGGGCTCAAGAGGGCAGCATCAAG

CTCATTCACTTGAGCGGGTTTGCCATTGCTTGGGGAAATGGCTGGGCCATCCAGATAAATTCGTCG

GTATCACTTATGCTCTTACAGTAGTGTGGCTGCTTGTATTCGCTTGTAGTGCAGTCCCCGTGTACAT

TTATTTCAACACCTGGACCACCTGTCAGTCTATCGCGTTTCCCTCCAAGACGTCAGCATCCATCGGG

AGTCTGTGTGCGGACGCAAGAATGTACGGCGTTTTGCCCTGGAATGCGTTTCCGGGCAAAGTGTGC

GGGTCTAATTTGCTTTCTATTTGCAAGACCGCTGAGTTCCAGATGACTTTTCACTTGTTTATTGCGG

CCTTTGTGGGGGCTGCCGCGACGCTGGTCTCTTTGCTCACATTTATGATAGCAGCTACGTATAATTT

CGCGGTCTTGAAACTGATGGGGAGAGGCACGAAATTCTGA

SEQ ID NO: 118:
ATGGGCTTGCTCGAATGTTGTGCGAGGTGCCTCGTTGGCGCTCCATTTGCATACTTGTAGCAACA

GGCCTCTGTTTTTTTGGTGTCGCGCTCTTTTGTGGCTGTGGACATGAAGCGCTCACGGGTACAGAG

```
                                  -continued
AAGCTCATAGAAACCTACTTCAGCAAAAATTACCAGGATTACGAATACCTGATCAACGTCATCCAC

GCCTTTCAATACGTGATCTATGGGACCGCGAGCTTTTTCTTCCTTTATGGGCGCTTCTGCTCGCGG

AAGGTTTTTACACTACGGGCGCGGTCCGACAGATATTCGGTGACTATAAGACGACAATATGTGGA

AAAGGTCTTTCAGCCACAGTCACAGGGGGCCAAAAGGGCCGAGGGTCAAGGGGTCAGCACCAGG

CCCATTCACTTGAACGGGTATGTCATTGTTTGGGCAAGTGGTTGGGGCACCCAGATAAGTTTGTCG

GCATAACCTATGCTCTGACGGTTGTTTGGCTCCTGGTTTTCGCTTGTTCTGCGGTCCCGGTTTATAT

CTACTTTAACACCTGGACAACCTGTCAATCTATAGCATTTCCAAGTAAGACGTCAGCTAGCATCGG

TTCCCTGTGTGCTGACGCCAGAATGTACGGTGTTTTGCCCTGGAACGCCTTTCCTGGAAAAGTCTGT

GGTTCTAATCTGTTGTCAATTTGCAAGACAGCGGAGTTCCAGATGACGTTCCATCTCTTTATTGCCG

CCTTCGTTGGGCGGCGGCGACCTTGGTTTCTCTTCTGACCTTTATGATAGCTGCAACTTATAACTT

TGCCGTACTGAAACTGATGGGAAGGGGGACCAAATTCTGA

SEQ ID NO: 119:
ATGGGCTTGCTCGAATGTTGTGCGAGGTGCCTCGTTGGCGCTCCATTTGCATCACTTGTAGCAACA

GGCCTCTGTTTTTTGGTGTCGCGCTCTTTTGTGGCTGTGGACATGAAGCGCTCACGGGTACAGAG

AAGCTCATAGAAACCTACTTCAGCAAAAATTACCAGGATTACGAATACCTGATCAACGTCATCCAC

GCCTTTCAATACGTGATCTAcGGGACCGCGAGCTTTTTCTTCCTTTATGGGCGCTTCTGCTCGCGG

AAGGTTTTTACACTACGGGCGCGGTCCGACAGATATTCGGTGACTATAAGACGACAATATGTGGA

AAAGGTCTTTCAGCCACAGTCACAGGGGGCCAAAAGGGCCGAGGGTCAAGGGGTCAGCACCAGG

CCCATTCACTTGAACGGGTATGTCATTGTTTGGGCAAGTGGTTGGGGCACCCAGATAAGTTTGTCG

GCATAACCTATGCTCTGACGGTTGTTTGGCTCCTGGTTTTCGCTTGTTCTGCGGTCCCGGTTTATAT

CTACTTTAACACCTGGACAACCTGTCAATCTATAGCATTTCCAAGTAAGACGTCAGCTAGCATCGG

TTCCCTGTGTGCTGACGCCAGAATGTACGGTGTTTTGCCCTGGAACGCCTTTCCTGGAAAAGTCTGT

GGTTCTAATCTGTTGTCAATTTGCAAGACAGCGGAGTTCCAGATGACGTTCCATCTCTTTATTGCCG

CCTTCGTTGGGCGGCGGCGACCTTGGTTTCTCTTCTGACCTTTATGATAGCTGCAACTTATAACTT

TGCCGTACTGAAACTGATGGGAAGGGGGACCAAATTCTGA
```

In some embodiments, the variant nucleic acid sequence encoding the PLP1 protein variant, or functional fragment thereof, is transcript variant 4. In some embodiments, the variant nucleic acid sequence encoding the PLP1 protein variant, or functional fragment thereof, is SEQ ID NO: 120, SEQ ID NO: 121, SEQ ID NO: 122, SEQ ID NO: 123, SEQ ID NO: 124, and/or SEQ ID NO: 125.

SEQ ID NOs: 120-125 Show the *Homo sapiens* Proteolipid Protein 1 (PLP1), Transcript Variant 4:

```
SEQ ID NO: 120:
ATGGACTATGAGTATCTCATCAATGTGATCCATGCCTTCCAGTATGTCATCTATGGAACTGCCTCTT

TCTTCTTCCTTTATGGGCCCTCCTGCTGGCTGAGGGCTTCTACACCACCGGCGCAGTCAGGCAGA

TCTTTGGCGACTACAAGACCACCATCTGCGGCAAGGGCCTGAGCGCAACGGTAACAGGGGGCCAG

AAGGGGAGGGGTTCCAGAGGCCAACATCAAGCTCATTCTTTGGAGCGGGTGTGTCATTGTTTGGG

AAAATGGCTAGGACATCCCGACAAGTTTGTGGGCATCACCTATGCCCTGACCGTTGTGTGGCTCCT

GGTGTTTGCCTGCTCTGCTGTGCCTGTGTACATTTACTTCAACACCTGGACCACCTGCCAGTCTATT

GCCTTCCCCAGCAAGACCTCTGCCAGTATAGGCAGTCTCTGTGCTGATGCCAGAATGTATGGTGTT

CTCCCATGGAATGCTTTCCCTGGCAAGGTTTGTGGCTCCAACCTTCTGTCCATCTGCAAAACAGCTG

AGTTCCAAATGACCTTCCACCTGTTTATTGCTGCATTTGTGGGGGCTGCAGCTACACTGGTTTCCCT

GCTCACCTTCATGATTGCTGCCACTTACAACTTTGCCGTCCTTAAACTCATGGGCCGAGGCACCAA

GTTCTGA
```

-continued

SEQ ID NO: 121:
ATGGACTACGAGTACCTGATCAACGTGATCCACGCCTTTCAGTACGTGATCTACGGCACCGCCTCC

TTCTTCTTCCTGTACGGCGCCCTGCTGCTGGCCGAGGGCTTCTACACCACCGGCGCTGTGCGGCAG

ATCTTCGGCGACTACAAGACCACAATCTGCGGCAAGGGCCTGTCTGCCACAGTGACCGGCGGCCA

GAAAGGCAGAGGCTCTAGAGGCCAACACCAGGCCCACTCTCTGGAAAGAGTGTGCCACTGCCTGG

GCAAATGGCTGGGCCACCCTGATAAGTTCGTGGGCATCACATACGCCCTGACCGTGGTGTGGCTGC

TCGTGTTCGCCTGCAGCGCCGTCCCCGTGTACATCTACTTCAACACCTGGACCACCTGTCAGAGCA

TCGCCTTCCCCAGCAAGACAAGCGCCAGCATCGGCAGCCTGTGCGCCGACGCCAGAATGTACGGC

GTGCTGCCTTGGAACGCCTTTCCTGGCAAGGTGTGTGGCAGCAACCTGCTGAGCATTTGCAAGACC

GCCGAGTTCCAGATGACCTTCCACCTGTTCATCGCCGCCTTCGTGGGAGCCGCTGCCACCCTGGTG

TCCCTGCTGACATTCATGATCGCCGCTACATACAACTTCGCCGTGCTGAAGCTGATGGGCAGAGGG

ACCAAGTTCTGA

SEQ ID NO: 122:
ATGGATTACGAATACCTTATTAACGTCATTCACGCCTTCCAATATGTCATTTATGGAACTGCTTCCT

TCTTTTTCTTGTATGGGGCACTGTTGTTGGCTGAGGGGTTTTATACGACGGGCGCGGTTAGGCAAA

TCTTTGGCGATTATAAAACAACAATCTGTGGTAAGGGGTTGAGTGCAACAGTAACTGGAGGTCAA

AAAGGCAGAGGTTCTCGCGGTCAGCATCAAGCGCACTCCCTGGAGCGCGTTTGTCATTGCTTGGGG

AAATGGCTCGGCCACCCTGATAAATTTGTAGGTATTACCTACGCACTGACAGTTGTTTGGCTTCTG

GTTTTCGCTTGTAGCGCAGTGCCCGTCTATATCTACTTCAACACATGGACTACTTGCCAGAGTATAG

CTTTTCCCTCTAAGACTTCCGCTTCTATTGGTTCTTTGTGCGCGGACGCCAGAATGTATGGGGTGCT

CCCGTGGAATGCATTCCCGGGCAAAGTTTGCGGGTCAAACTTGTTGTCAATTTGTAAGACCGCTGA

GTTTCAGATGACATTCCACCTGTTCATCGCTGCTTTCGTGGGTGCTGCCGCCACATTGGTAAGCCTC

CTGACTTTCATGATTGCTGCTACCTACAACTTTGCAGTTCTGAAACTTATGGGGCGCGGAACCAAG

TTCTGA

SEQ ID NO: 123:
ATGGATTACGAATACTTGATAAATGTAATTCATGCGTTCCAGTATGTGATATACGGAACGGCGAGC

TTTTTCTTTCTTTATGGGGCGTTGCTGTTGGCTGAGGGCTTTTATACTACCGGCGCTGTGCGCCAGA

TTTTTGGGGATTACAAGACGACTATCTGCGGAAAAGGTCTTTCAGCCACTGTCACGGGAGGCCAGA

AAGGTAGAGGCTCCAGAGGCCAGCACCAAGCTCATTCACTGGAGCGAGTTTGTCATTGTTTGGGC

AAATGGCTTGGTCACCCGGATAAGTTCGTCGGTATCACCTATGCGCTTACCGTAGTCTGGCTTTTG

GTCTTCGCTTGTAGTGCGGTACCTGTTTATATTTATTTCAATACCTGGACCACATGTCAGTCAATAG

CGTTCCCCTCTAAGACTTCTGCGTCCATTGGCAGCCTTTGTGCTGACGCCCGCATGTATGGTGTCTT

GCCATGGAACGCATTTCCAGGCAAGGTTTGTGGGTCCAATCTCCTCTCAATCTGTAAAACCGCCGA

GTTTCAAATGACGTTTCACCTTTTCATAGCGGCATTTGTTGGTGCGGCGGCGACACTCGTGTCTCTG

CTCACATTTATGATTGCCGCCACTTACAACTTCGCCGTACTGAAGTTGATGGGCGCGGAACCAAA

TTTTGA

SEQ ID NO: 124:
ATGGATTACGAATACTTGATAAATGTAATTCATGCGTTCCAGTATGTGATATACGGAACGGCGAGC

TTTTTCTTTCTTTACGGGGCGTTGCTGTTGGCTGAGGGCTTTTATACTACCGGCGCTGTGCGCCAGA

TTTTTGGGGATTACAAGACGACTATCTGCGGAAAAGGTCTTTCAGCCACTGTCACGGGAGGCCAGA

AAGGTAGAGGCTCCAGAGGCCAGCACCAAGCTCATTCACTGGAGCGAGTTTGTCATTGTTTGGGC

AAATGGCTTGGTCACCCGGATAAGTTCGTCGGTATCACCTATGCGCTTACCGTAGTCTGGCTTTTG

GTCTTCGCTTGTAGTGCGGTACCTGTTTATATTTATTTCAATACCTGGACCACATGTCAGTCAATAG

-continued

CGTTCCCCTCTAAGACTTCTGCGTCCATTGGCAGCCTTTGTGCTGACGCCCGCATGTATGGTGTCTT

GCCATGGAACGCATTTCCAGGCAAGGTTTGTGGGTCCAATCTCCTCTCAATCTGTAAAACCGCCGA

GTTTCAAATGACGTTTCACCTTTTCATAGCGGCATTTGTTGGTGCGGCGGCGACACTCGTGTCTCTG

CTCACATTTATGATTGCCGCCACTTACAACTTCGCCGTACTGAAGTTGATGGGGCGCGGAACCAAA

TTTTGA

SEQ ID NO: 125:
ATGGATTACGAATACTTGATCAACGTAATCCATGCCTTTCAATACGTTATATACGGTACGGCATCA

TTCTTTTTTTGTATGGCGCCCTCCTCCTTGCTGAAGGTTTCTACACAACGGGTGCTGTGAGGCAGA

TATTTGGGGATTACAAAACCACCATTTGTGGCAAAGGACTCTCAGCAACGGTGACCGGGGGTCAG

AAAGGTCGCGGCTCTCGGGGACAACACCAGGCTCACAGTCTCGAAAGAGTTTGTCACTGCCTCGG

GAAGTGGCTTGGTCACCCCGATAAGTTTGTTGGAATAACGTATGCGCTCACCGTCGTATGGCTGTT

GGTCTTCGCATGTTCAGCGGTCCCAGTGTATATATACTTCAATACCTGGACCACCTGCCAGTCTATA

GCATTCCCTTCCAAGACCTCCGCGTCCATAGGGTCACTCTGTGCTGATGCTCGAATGTACGGGGTT

CTTCCGTGGAATGCTTTTCCTGGGAAAGTGTGCGGGTCTAACCTGCTCTCAATCTGCAAGACAGCC

GAGTTTCAGATGACATTCCATCTGTTCATCGCCGCGTTCGTTGGCGCCGCGGCAACATTGGTGTCTT

TGTTGACATTTATGATAGCCGCAACCTACAACTTTGCTGTCTTGAAGCTCATGGGTCGGGCACGA

AGTTCTGA

SEQ ID NOs: 11 and 127-130 Show the *Homo sapiens* Proteolipid Protein 1 (PLP1), RefSeq Protein:

SEQ ID NO: 11 (ORG protein sequence):
MGLLECCARCLVGAPFASLVATGLCFFGVALFCGCGHEALTGTEKLIETYFSKNYQDYEYLINVIHAFQ

YVIYGTASFFFLYGALLLAEGFYTTGAVRQIFGDYKTTICGKGLSATVTGGQKGRGSRGQHAHSLER

VCHCLGKWLGHPDKFVGITYALTVVWLLVFACSAVPVYIYFNTWTTCQSIAFPSKTSASIGSLCADAR

MYGVLPWNAFPGKVCGSNLLSICKTAEFQMTFHLFIAAFVGAAATLVSLLTFMIAATYNFAVLKLMGR

GTKF

SEQ ID NO: 127:
ATGGGACTGCTTGAGTGCTGCGCCCGGTGCCTGGTGGGCGCCCCTTTCGCCTCTCTGGTTGCCACC

GGCCTGTGTTTTTTCGGCGTGGCCCTGTTCTGCGGTTGTGGACACGAGGCCCTGACCGGCACAGAG

AAGCTGATCGAGACATATTTCAGCAAGAACTACCAGGACTACGAGTACCTGATCAACGTGATCCA

CGCCTTTCAGTACGTGATCTACGGCACCGCCAGCTTCTTCTTCCTGTACGGCGCCCTGCTGCTGGCC

GAAGGCTTCTACACCACCGGCGCTGTTAGACAGATCTTCGGAGATTATAAGACCACAATCTGCGGC

AAAGGCCTGAGCGCCACCGTGACAGGCGGACAGAAGGGCCGGGGCAGTAGAGGCCAGCACCAGG

CCCACAGCCTGGAAAGAGTGTGCCACTGCCTGGGCAAGTGGCTGGGACATCCTGATAAGTTCGTG

GGCATCACCTACGCCCTTACAGTGGTGTGGCTGCTGGTGTTCGCCTGCAGCGCCGTGCCCGTGTAC

ATCTACTTCAACACCTGGACCACCTGCCAGAGCATCGCCTTCCCCAGCAAGACCAGCGCCAGCATC

GGCTCTCTGTGCGCCGACGCCAGAATGTACGGCGTGCTGCCTTGGAACGCCTTTCCAGGAAAGGTG

TGTGGCAGCAACCTGTTGTCTATTTGTAAAACCGCCGAGTTCCAGATGACCTTCCACCTGTTTATCG

CCGCTTTTGTGGGCGCCGCTGCTACACTGGTCAGCCTGCTGACATTCATGATCGCCGCCACCTACA

ACTTCGCCGTGCTGAAGCTGATGGGCAGAGGCACCAAGTTC

SEQ ID NO: 128:
ATGGGCCTGCTTGAGTGTTGTGCAAGGTGTCTGGTCGGAGCACCTTTTGCGTCTCTGGTTGCGACG

GGCTTGTGCTTCTTCGGGGTGGCGTTGTTCTGTGGGTGTGGGCACGAAGCCCTCACGGGTACTGAG

AAGCTGATAGAAACCTATTTCAGTAAAAACTATCAAGATTATGAGTATCTCATTAACGTCATCCAC

GCGTTTCAATATGTTATCTACGGGACGGCGAGCTTTTTCTTCCTCTATGGAGCCCTTTTGCTGGCTG

AGGGCTTTTATACAACCGGTGCTGTCAGGCAGATCTTCGGCGATTACAAGACGACAATCTGCGGG

AAAGGTCTGTCCGCTACTGTAACAGGAGGGCAAAAGGGGCGGGGTAGTCGCGGACAACACCAGG

CGCATTCCCTGGAGCGCGTATGTCACTGCCTGGGCAAGTGGCTTGGACACCCAGACAAGTTCGTAG

GAATCACGTACGCTTTGACAGTGGTGTGGCTTCTGGTATTCGCGTGCAGCGCCGTGCCTGTCTACA

TATACTTCAATACGTGGACTACTTGTCAGTCCATAGCTTTCCCTAGTAAGACCTCTGCGAGCATAG

GCTCCCTTTGTGCAGATGCAAGAATGTATGGGGTACTCCCTTGGAATGCGTTTCCTGGGAAAGTAT

GTGGTAGTAATCTTCTCAGTATATGTAAAACAGCGGAGTTCCAGATGACGTTTCATCTCTTTATTGC

TGCTTTTGTAGGTGCAGCTGCAACACTCGTGTCCCTCCTTACGTTTATGATCGCTGCTACCTACAAT

TTCGCCGTATTGAAACTTATGGGGCGGGGCACAAAATTT

SEQ ID NO: 129:
ATGGGCCTCCTGGAGTGCTGCGCCAGGTGCCTCGTAGGAGCACCCTTTGCTTCCTTGGTTGCTACA

GGCTTGTGCTTTTTCGGGGTTGCATTGTTTTGCGGATGTGGGCACGAGGCTTTGACCGGGACGGAA

AAGTTGATTGAAACTTATTTCTCAAAAAATTACCAGGACTATGAATATCTGATAAACGTAATACAT

GCATTCCAGTATGTGATCTACGGTACTGCATCATTCTTTTTTCTGTACGGTGCCCTCCTTCTGGCTG

AGGGCTTTTATACAACTGGAGCCGTGCGACAAATTTTTGGAGATTACAAGACCACGATTTGCGGAA

AAGGGCTGTCCGCTACTGTGACAGGAGGCCAGAAGGGGCGAGGCTCTCGCGGACAACACCAGGC

ACATAGCTTGGAACGAGTATGTCACTGCCTCGGCAAATGGCTTGGGCACCCCGATAAGTTTGTTGG

GATCACGTATGCACTGACGGTCGTCTGGCTTCTGGTATTTGCCTGTTCAGCGGTGCCAGTATATATA

TACTTTAATACCTGGACTACCTGTCAGTCTATCGCCTTTCCGAGTAAGACGAGTGCCTCAATCGGCT

CACTCTGCGCTGATGCTCGAATGTACGGGGTTCTGCCGTGGAACGCCTTTCCGGGCAAGGTTTGTG

GTTCAAACTTGCTTTCTATTTGTAAAACAGCAGAATTCCAGATGACATTTCATCTTTTCATCGCTGC

TTTTGTGGGCGCCGCGGCGACATTGGTATCTCTGTTGACATTCATGATAGCTGCAACATATAACTTC

GCCGTTCTGAAGTTGATGGGACGGGGAACAAAGTTC

SEQ ID NO: 130:
ATGGGACTCCTTGAATGCTGCGCGCGGTGCCTCGTCGGTGCACCGTTCGCTTCACTGGTTGCAACC

GGCCTCTGTTTCTTTGGCGTTGCATTGTTCTGCGGGTGTGGGCATGAAGCTTTGACTGGCACGGAG

AAGCTCATTGAAACCTATTTTAGCAAGAACTATCAGGACTACGAGTACCTTATAAACGTGATTCAC

GCCTTCCAATACGTTATATACGGAACCGCTTCTTTTTTTTCCTTTATGGTGCGCTTTTGTTGGCCGA

GGGCTTCTATACAACCGGTGCAGTACGCCAAATCTTCGGCGATTATAAGACGACGATCTGTGGCAA

GGGGCTGAGTGCAACCGTGACTGGCGGCCAAAAAGGCCGCGGTAGTCGGGGACAACATCAAGCA

CATAGTCTGGAACGAGTATGTCACTGTCTCGGCAAGTGGTTGGGACATCCTGATAAGTTCGTTGGT

ATTACATATGCCCTGACAGTCGTTTGGCTCCTCGTCTTTGCTTGTAGTGCTGTGCCGGTGTACATCT

ATTTCAATACCTGGACGACGTGTCAGTCTATCGCGTTCCCGTCAAAAACGTCCGCAAGCATAGGTT

CACTTTGTGCCGATGCTAGGATGTACGGAGTTTTGCCATGGAATGCGTTTCCTGGGAAAGTGTGTG

GCTCCAACCTTCTCTCAATCTGTAAGACCGCCGAATTCCAAATGACATTCCATCTCTTTATCGCAGC

CTTTGTCGGTGCCGCCGCTACCCTCGTGAGTCTTTTGACATTCATGATCGCGGCCACATACAACTTC

GCAGTCCTTAAGCTCATGGGCAGGGGCACTAAATTC

In some aspects, the targeted delivery of a nucleic acid segment (or sequence) encoding a MBP using viral vector delivery for the treatment of disease is disclosed. MBP is a major constituent of the myelin sheath of oligodendrocytes and Schwann cells in the nervous system, and MBP-related transcripts are also present in the bone marrow and the immune system, thus making MBPs a potential target in inflammatory demyelinating diseases such as multiple sclerosis (MS). In some embodiments, the nucleic acid sequence encodes a wild-type MBP protein, or a functional fragment thereof.

In some embodiments, the nucleic acid sequence encodes a MBP variant, or a functional fragment thereof. As used herein, a "variant" refers to a MBP protein, or a functional fragment thereof, that differs from the wild-type MBP protein in its amino acid sequence and/or function, and which is encoded by one of the variant nucleic acid sequences of the present disclosure. In some embodiments, the variant nucleic acid sequence encoding the MBP protein variant, or functional fragment thereof, is transcript variant 1. In some embodiments, the variant nucleic acid sequence encoding the MBP protein variant, or functional fragment thereof, is SEQ ID NO: 131, SEQ ID NO: 132, SEQ ID NO: 133, SEQ ID NO: 134, SEQ ID NO: 135, and/or SEQ ID NO: 136.

Exemplary Myelin Basic Protein 1 (MBP) Nucleic Acid Sequences of the Disclosure

SEQ ID NOs: 131-136 Show the *Homo sapiens* Myelin Basic Protein (MBP), Transcript Variant 1, mRNA:

```
SEQ ID NO: 131:
ATGGCGTCACAGAAGAGACCCTCCCAGAGGCACGGATCCAAGTACCTGGCCACAGCAAGTACCAT

GGACCATGCCAGGCATGGCTTCCTCCCAAGGCACAGAGACACGGGCATCCTTGACTCCATCGGGC

GCTTCTTTGGCGGTGACAGGGGTGCGCCCAAGCGGGGCTCTGGCAAGGTACCCTGGCTAAAGCCG

GGCCGGAGCCCTCTGCCCTCTCATGCCCGCAGCCAGCCTGGGCTGTGCAACATGTACAAGGACTCA

CACCACCCGGCAAGAACTGCTCACTACGGCTCCCTGCCCCAGAAGTCACACGGCCGGACCCAAGA

TGAAAACCCCGTAGTCCACTTCTTCAAGAACATTGTGACGCCTCGCACACCACCCCGTCGCAGGG

AAAGGGGAGAGGACTGTCCCTGAGCAGATTTAGCTGGGGGGCCGAAGGCCAGAGACCAGGATTT

GGCTACGGAGGCAGAGCGTCCGACTATAAATCGGCTCACAAGGGATTCAAGGGAGTCGATGCCCA

GGGCACGCTTTCCAAAATTTTTAAGCTGGGAGGAAGAGATAGTCGCTCTGGATCACCCATGGCTAG

ACGCTGA

SEQ ID NO: 132:
ATGGCCTCTCAGAAGCGGCCCAGCCAGCGGCACGGTTCTAAGTACCTGGCCACAGCTAGCACCAT

GGACCACGCCAGACACGGCTTCCTGCCAAGACACAGAGATACCGGCATCCTGGACAGCATCGGCC

GCTTCTTCGGCGGAGATAGAGGCGCCCCTAAGAGAGGCTCAGGCAAGGTGCCCTGGCTGAAGCCT

GGCAGAAGCCCTCTGCCTAGCCACGCCAGAAGCCAGCCTGGCCTGTGCAATATGTACAAGGACAG

CCACCACCCCGCCAGAACAGCCCACTACGGCAGCCTGCCTCAGAAAAGCCACGGCCGGACACAGG

ATGAAAACCCCGTCGTGCACTTCTTCAAGAACATCGTGACCCCTAGAACCCCTCCACCTTCCCAAG

GAAAAGGCAGAGGCCTGTCCCTCAGCAGATTCAGCTGGGGAGCTGAGGGCCAGAGACCTGGATTT

GGCTACGGCGGACGGGCCAGCGACTATAAGTCCGCCCATAAGGGCTTTAAGGGCGTGGACGCCCA

GGGCACCCTGAGCAAGATCTTCAAACTGGGCGGCCGGGACTCTAGATCTGGCAGCCCCATGGCTA

GGCGGTGA

SEQ ID NO: 133:
ATGGCGTCACAGAAGCGACCTTCTCAGAGGCACGGAAGCAAGTATCTCGCGACGGCCAGTACCAT

GGATCACGCCAGGCATGGCTTCTTGCCTAGACACCGAGATACTGGGATTCTTGACTCTATAGGTCG

GTTTTTTGGTGGCGACCGCGGTGCTCCAAAAAGAGGTAGCGGTAAGGTACCCTGGCTGAAACCGG

GTAGATCCCCACTGCCGAGCCATGCCAGGTCCCAACCTGGCCTGTGCAACATGTATAAAGACTCTC

ATCATCCCGCTCGCACTGCCCATTACGGGAGCCTTCCCCAAAAATCACACGGTCGCACTCAAGACG

AAAACCCGGTTGTACACTTTTTCAAAAATATAGTGACCCCTCGGACTCCCCCACCGTCCCAGGGGA

AAGGGAGAGGCCTTTCACTTTCAAGATTTAGCTGGGGCGCGGAAGGCCAACGCCCGGGTTTTGGA

TACGGTGGAGGGCCTCTGATTACAAATCCGCCCACAAAGGCTTCAAAGGGGTGGATGCCCAAGG

CACCCTTTCCAAAATATTTAAGCTCGGAGGACGGGACTCTAGGTCTGGGTCTCCTATGGCGCGACG

CTGA
```

-continued

SEQ ID NO: 134:
ATGGCTTCACAAAAACGCCCAAGTCAACGGCACGGCAGCAAATACCTGGCGACAGCTTCCACTAT

GGATCATGCGCGACATGGATTTCTTCCCAGGCATAGGGATACAGGTATCCTTGACAGTATCGGAAG

ATTCTTCGGCGGTGATCGGGGAGCCCCTAAGAGAGGGAGTGGTAAAGTACCCTGGCTGAAACCTG

GCCGGAGTCCCCTTCCTAGTCACGCCAGGTCTCAACCTGGGTTGTGTAATATGTACAAGGATAGTC

ATCACCCCGCTCGAACCGCCCACTACGGCTCTTTGCCGCAAAAGTCACACGGCCGGACTCAGGAC

GAAAACCCTGTCGTGCACTTCTTTAAAAACATCGTCACGCCAAGAACACCACCACCAAGTCAAGG

AAAGGGGCGCGGTCTCAGCCTGTCTCGATTCTCATGGGGGGCCGAGGGGCAGCGACCCGGCTTCG

GCTACGGGGTCGGGCATCCGATTATAAGTCCGCCCACAAAGGGTTTAAGGGGGTGGACGCCCAA

GGCACTCTGTCCAAAATCTTTAAATTGGGTGGGCGAGATTCCCGAAGCGGTTCCCCGATGGCGAGA

AGGTGA

SEQ ID NO: 135:
ATGGCGAGTCAAAAAAGACCGTCACAGCGACATGGGTCCAAGTATCTCGCTACTGCTTCCACAAT

GGACCATGCGAGGCATGGGTTCCTCCCGAGACATCGAGATACCGGGATACTCGATTCAATAGGCA

GGTTTTTTGGCGGCGATAGGGGCGCTCCGAAACGAGGATCTGGAAAAGTGCCTTGGTTGAAACCG

GGGAGATCCCCCTTGCCGTCTCACGCACGCTCTCAACCCGGTCTTTGCAATATGTATAAGGACTCT

CATCACCCAGCAAGGACCGCCCACTACGGCTCCCTCCCGCAAAAAAGCCACGGACGGACCCAGGA

CGAGAATCCTGTCGTACACTTTTTCAAAAACATTGTGACACCTCGGACGCCACCTCCCTCCCAGGG

AAAGGGTCGAGGCCTCTCTCTCTCCCGATTCTCCTGGGGGGCAGAGGGTCAGAGACCGGGTTTTGG

TTATGGTGGACGGGCATCCGATTACAAGTCAGCGCACAAAGGATTCAAAGGGGTGGACGCTCAAG

GCACGCTGTCAAAAATTTTTAAACTGGGAGGACGCGACAGTAGAAGTGGTAGCCCCATGGCAAGG

CGCTGA

SEQ ID NO: 136:
ATGGCGAGTCAAAAAAGACCGTCTCAGAGGCACGGGAGCAAGTACCTGGCGACAGCCTCCACAAT

GGACCACGCCAGACACGGCTTCTTGCCCAGACACCGAGATACCGGTATATTGGACTCAATCGGAA

GATTTTTCGGGGGCGACAGAGAAGCGCCTAAGCGGGGGTCCGGAAAAGTTCCTTGGCTCAAACCC

GGACGGAGCCCACTTCCTAGTCACGCACGGAGTCAACCTGGGCTGTGTAATATGTACAAAGACTC

ACATCACCCTGCGCGGACAGCCCACTACGGAAGTCTTCCACAGAAGTCTCACGGGCGCACCCAAG

ACGAAAATCCCGTGGTCCACTTCTTCAAGAATATCGTTACCCCAAGAACCCCGCCACCATCTCAAG

GGAAAGGGAGAGGTCTGTCCCTTTCTCGATTCAGTTGGGGTGCAGAAGGTCAGAGACCAGGATTT

GGCTATGGTGGACGCGCTTCTGATTACAAATCCGCCCATAAAGGGTTTAAGGGTGTGGACGCGCA

AGGTACGCTCTCAAAGATCTTCAAATTGGGTGGACGCGATTCAAGATCAGGAAGTCCTATGGCGA

GGCGCTGA

In some embodiments, the variant nucleic acid sequence encoding the MBP protein variant, or functional fragment thereof, is transcript variant 2. In some embodiments, the variant nucleic acid sequence encoding the MBP protein variant, or functional fragment thereof, is SEQ ID NO: 137, SEQ ID NO: 138, SEQ ID NO: 139, SEQ ID NO: 140, SEQ ID NO: 141, and/or SEQ ID NO: 142.

SEQ ID NOs: 137-142 Show the *Homo sapiens* Myelin Basic Protein (MBP), Transcript Variant 2, mRNA:

SEQ ID NO: 137:
ATGGCGTCACAGAAGAGACCCTCCCAGAGGCACGGATCCAAGTACCTGGCCACAGCAAGTACCAT

GGACCATGCCAGGCATGGCTTCCTCCCAAGGCACAGAGACACGGGCATCCTTGACTCCATCGGGC

GCTTCTTTGGCGGTGACAGGGGTGCGCCCAAGCGGGGCTCTGGCAAGGTACCCTGGCTAAAGCCG

GGCCGGAGCCCTCTGCCCTCTCATGCCCGCAGCCAGCCTGGGCTGTGCAACATGTACAAGGACTCA

CACCACCCGGCAAGAACTGCTCACTACGGCTCCCTGCCCCAGAAGTCACACGGCCGGACCCAAGA

TGAAAACCCCGTAGTCCACTTCTTCAAGAACATTGTGACGCCTCGCACACCACCCCGTCGCAGGG

AAAGGGGGCCGAAGGCCAGAGACCAGGATTTGGCTACGGAGGCAGAGCGTCCGACTATAAATCG

GCTCACAAGGGATTCAAGGGAGTCGATGCCCAGGGCACGCTTTCCAAAATTTTTAAGCTGGGAGG

AAGAGATAGTCGCTCTGGATCACCCATGGCTAGACGCTGA

SEQ ID NO: 138:
ATGGCTAGCCAGAAGAGACCTAGCCAGAGACATGGCAGCAAGTACCTGGCCACCGCCAGCACCAT

GGACCACGCCAGACACGGCTTTCTGCCTAGACACCGGGACACCGGCATCCTGGACAGCATCGGCA

GATTCTTCGGCGGAGATAGAGGCGCCCCTAAGCGGGGCTCTGGCAAAGTGCCTTGGCTGAAGCCC

GGCCGGAGCCCCCTGCCCAGCCACGCCAGGTCCCAACCTGGCCTGTGCAATATGTACAAGGACAG

CCACCACCCCGCCAGAACCGCCCACTACGGCAGCCTCCCTCAGAAAAGCCACGGCAGAACACAGG

ACGAGAACCCCGTGGTCCACTTCTTCAAGAACATCGTGACACCTCGGACACCTCCACCTTCTCAGG

GAAAAGGCGCTGAAGGCCAGCGGCCTGGCTTCGGCTACGGAGGACGGGCCTCTGATTATAAGTCC

GCCCACAAGGGATTTAAGGGCGTGGACGCTCAGGGCACCCTGTCTAAGATCTTCAAGCTGGGCGG

AAGAGATAGCAGAAGCGGCTCCCCAATGGCCCGCAGATGA

SEQ ID NO: 139:
ATGGCTAGCCAAAAACGGCCAAGCCAACGACATGGGTCAAAATATCTGGCAACTGCTTCAACCAT

GGATCACGCCCGACATGGATTTTTGCCCAGACATCGAGACACCGGGATTCTCGATAGCATAGGCC

GATTCTTCGGCGGTGACCGAGGCGCTCCAAAACGCGGTTCTGGTAAGGTTCCCTGGTTGAAGCCGG

GTCGCTCACCTCTTCCATCCCACGCACGCTCCCAACCCGGTCTGTGTAATATGTATAAGGATTCAC

ATCACCCTGCACGCACGGCGCATTATGGAAGCCTGCCACAGAAGTCCCACGGACGAACACAAGAC

GAGAATCCTGTGGTCCATTTCTTCAAGAATATCGTGACGCCAAGAACACCCCCTCCTAGTCAGGGC

AAAGGTGCCGAAGGGCAGCGGCCTGGATTCGGGTATGGTGGGAGAGCTTCTGACTACAAGTCCGC

TCACAAGGATTTAAGGGCGTGGATGCCCAAGGCACACTTTCTAAGATTTTTAAATTGGGGGCCG

CGACTCCCGCTCTGGATCACCGATGGCACGCCGCTGA

SEQ ID NO: 140:
ATGGCCTCTCAAAAACGACCAAGTCAGAGGCATGGTAGCAAATACCTCGCCACAGCTAGTACGAT

GGACCACGCTAGGCATGGTTTCCTTCCTCGCCACCGGGATACAGGAATCCTTGACAGTATAGGTCG

GTTCTTTGGCGGAGATAGAGGTGCCCCTAAACGCGGTTCAGGGAAGGTCCCCTGGTTGAAGCCCG

GCCGGTCTCCCCTGCCCAGTCACGCTCGAAGTCAGCCGGGGTTGTGCAACATGTACAAGGACAGC

CATCATCCGGCACGCACGGCACATTATGGCTCTCTCCCTCAGAAATCCCATGGCCGAACTCAGGAT

GAAAATCCAGTAGTACATTTTTTTAAGAACATAGTAACGCCTAGAACTCCCCGCCGTCCCAAGGT

AAAGGGGCCGAGGGGCAAAGACCCGGCTTTGGTTACGGAGGACGAGCGAGCGATTACAAATCAG

CCCATAAGGGATTCAAGGGCGTAGATGCACAAGGGACGCTTAGCAAAATTTTCAAACTTGGAGGA

AGAGACAGTAGATCAGGGTCTCCAATGGCTCGAAGATGA

SEQ ID NO: 141:
ATGGCTAGCCAAAAGAGACCATCACAAAGACACGGTTCAAAATATCTCGCAACGGCGTCTACTAT

GGACCACGCCCGCCACGGGTTTCTGCCTCGCCATCGAGATACAGGAATTCTCGATTCCATAGGTAG

ATTCTTCGGCGGGGATAGAGGCGCACCAAAGCGAGGAAGCGGGAAAGTACCATGGCTGAAACCA

GGAAGAAGTCCCTTGCCGAGCCACGCCAGAAGTCAGCCCGGCCTTTGCAATATGTATAAGGATAG

TCATCATCCTGCCCGCACGGCACACTACGGGAGTCTCCCGCAGAAGTCTCACGGCCGAACCCAAG

ACGAAAACCCCGTTGTTCACTTTTTCAAAAATATAGTCACACCGCGCACTCCTCCCCCAAGCCAAG

-continued
```
GAAAGGGGGCTGAAGGCCAGAGGCCTGGCTTTGGATACGGCGGCAGAGCCTCCGACTACAAAAGT

GCCCATAAGGGTTTCAAAGGGGTAGATGCTCAGGGAACACTTTCCAAGATATTCAAGCTGGGCGG

GCGAGACAGTCGATCTGGAAGCCCGATGGCACGACGGTGA

SEQ ID NO: 142:
ATGGCGAGTCAAAAGAGACCTAGCCAGAGACACGGCTCAAAATATCTCGCCACAGCATCAACGAT

GGACCACGCCAGGCACGGGTTTCTCCCGAGACACCGCGACACCGGGATACTGGATAGCATTGGTC

GATTTTTTGGAGGAGACCGCGGTGCTCCTAAGCGCGGGTCAGGTAAAGTTCCCTGGCTCAAACCCG

GCAGGAGTCCATTGCCGTCCCATGCACGCTCTCAGCCTGGCCTCTGTAATATGTATAAGGACTCAC

ATCACCCGGCTCGGACCGCCCATTACGGCAGTCTTCCGCAGAAGAGTCACGGTCGGACTCAAGAT

GAGAACCCTGTAGTCCATTTTTTCAAGAACATTGTCACTCCGCGGACACCTCCCCCAAGCCAGGGA

AAGGGAGCCGAAGGGCAAAGACCCGGTTTTGGCTATGGCGGGCGAGCATCAGACTATAAGTCAGC

TCACAAAGGTTTTAAGGGCGTCGACGCCCAAGGGACTCTTAGTAAAATTTTCAAACTGGGAGGGC

GAGACAGTCGCAGTGGATCACCTATGGCCCGACGATGA
```

In some embodiments, the variant nucleic acid sequence encoding the MBP protein variant, or functional fragment thereof, is transcript variant 3. In some embodiments, the variant nucleic acid sequence encoding the MBP protein variant, or functional fragment thereof, is SEQ ID NO: 143, SEQ ID NO: 144, SEQ ID NO: 145, SEQ ID NO: 146, SEQ ID NO: 147, and/or SEQ ID NO: 148.

SEQ ID NOs: 143-148 Show the *Homo sapiens* Myelin Basic Protein (MBP), Transcript Variant 3, mRNA:

```
SEQ ID NO: 143:
ATGGCGTCACAGAAGAGACCCTCCCAGAGGCACGGATCCAAGTACCTGGCCACAGCAAGTACCAT

GGACCATGCCAGGCATGGCTTCCTCCCAAGGCACAGAGACACGGGCATCCTTGACTCCATCGGGC

GCTTCTTTGGCGGTGACAGGGGTGCGCCCAAGCGGGGCTCTGGCAAGGACTCACACCACCCGGCA

AGAACTGCTCACTACGGCTCCCTGCCCCAGAAGTCACACGGCCGGACCCAAGATGAAAACCCCGT

AGTCCACTTCTTCAAGAACATTGTGACGCCTCGCACACCACCCCCGTCGCAGGGAAAGGGGAGAG

GACTGTCCCTGAGCAGATTTAGCTGGGGGCCGAAGGCCAGAGACCAGGATTTGGCTACGGAGGC

AGAGCGTCCGACTATAAATCGGCTCACAAGGGATTCAAGGGAGTCGATGCCCAGGGCACGCTTTC

CAAAATTTTTAAGCTGGGAGGAAGAGATAGTCGCTCTGGATCACCCATGGCTAGACGCT GA

SEQ ID NO: 144:
ATGGCTTCTCAGAAAAGACCTAGCCAAAGACACGGCAGCAAGTACCTGGCCACCGCCTCCACCAT

GGACCACGCCAGACACGGCTTTCTGCCAAGACACCGGGACACCGGCATCCTGGACAGCATCGGCC

GCTTCTTTGGTGGAGATAGAGGCGCCCCTAAGCGGGGATCTGGCAAGGACAGCCACCACCCCGCC

AGAACCGCTCACTACGGCTCCCTGCCTCAGAAGTCCCACGGAAGAACCCAGGACGAGAACCCCGT

GGTCCACTTCTTCAAGAACATCGTGACACCCAGAACACCTCCTCCATCTCAGGGCAAAGGCAGGG

GCCTGAGCCTCAGCCGGTTCAGCTGGGGCGCTGAAGGCCAGCGGCCTGGCTTCGGCTACGGCGGA

CGGGCCAGCGATTATAAGAGCGCCCATAAGGGCTTCAAAGGCGTGGACGCCCAGGGAACACTGTC

TAAGATCTTCAAGCTGGGCGGCAGAGATAGCAGAAGCGGCAGCCCTATGCCCGGA GATGA

SEQ ID NO: 145:
ATGGCAAGTCAGAAGCGCCCGTCCCAAAGGCACGGAAGTAAGTACCTCGCTACAGCTTCAACCAT

GGATCATGCAAGACACGGCTTTCTCCCAAGACATCGCGACACTGGTATCCTCGATAGCATAGGAC

GATTTTCGGGGGTGACAGAGGGGCGCCCAAAAGAGGTTCTGGCAAAGACTCACATCACCCTGCA

AGAACAGCTCACTATGGGAGCCTGCCTCAAAAGAGCCACGGAAGGACACAGGACGAAAATCCAG

TGGTGCATTTCTTTAAAAATATAGTGACACCACGAACCCCACCGCCTTCACAGGGAAAAGGTCGG

GGCCTTTCACTCTCAAGATTTTCTTGGGGAGCGGAGGGCCAGCGCCCAGGGTTTGGATACGGAGGC
```

-continued
CGCGCTAGTGATTATAAGTCCGCACACAAAGGTTTCAAAGGTGTAGATGCCCAAGGTACTTTGAGC

AAAATCTTTAAATTGGGCGGGCGCGACTCAAGGAGCGGCTCCCCTATGGCACGCAGATG A

SEQ ID NO: 146:
ATGGCAAGCCAGAAGCGCCCTTCCCAGCGCCACGGGAGTAAATATCTCGCAACAGCAAGTACTAT

GGATCATGCTCGCCACGGCTTTCTGCCCCGACACCGCGACACAGGAATTTTGGACTCCATCGGCCG

CTTTTTTGGTGGGGACAGAGGAGCACCCAAGCGCGGTAGTGGCAAGGACTCTCACCACCCCGCAA

GAACCGCTCACTATGGTAGCCTTCCTCAAAAATCTCATGGCCGGACGCAGGATGAAAATCCAGTA

GTGCATTTCTTCAAGAATATCGTAACGCCAAGAACCCCGCCGCCTTCTCAAGGAAAGGGCGAGG

TCTGTCTCTTAGCCGCTTCAGCTGGGGTGCCGAAGGACAGAGGCCGGGCTTTGGATATGGGGG GA

GAGCTTCAGACTATAAGAGCGCCCACAAAGGTTTTAAGGGTGTGGACGCCCAAGGTACTCTCTCA

AAAATCTTCAAACTGGGGGACGCGATAGTCGGTCCGGCAGCCCCATGGCCCGAAGATGA

SEQ ID NO: 147:
ATGGCAAGCCAGAAGAGACCGAGCCAGAGACATGGAAGTAAGTATTTGGCTACAGCGAGCACCA

TGGATCATGCCCGCCACGGATTCCTCCCGAGACATAGAGACACGGGGATCCTCGACTCTATAGGCC

GGTTCTTTGGGGGAGATAGGGGTGCCCCCAAGCGGGGTAGCGGAAAAGATAGCCATCATCCGGCC

CGCACTGCGCATTACGGCTCCCTTCCACAAAAGTCACACGGGCGGACCCAAGACGAGAATCCGGT

GGTTCATTTTTTTAAGAACATAGTCACGCCTAGGACACCACCGCCGAGTCAAGGAAAAGGACGGG

GACTCAGCCTTAGTCGGTTTTCCTGGGGAGCTGAGGGGCAAAGGCCGGGCTTTGGCTATGGCGGTC

GAGCTTCAGATTACAAGAGTGCACATAAAGGGTTTAAGGGAGTTGATGCTCAAGGAACCCTCAGT

AAAATCTTCAAGTTGGGTGGGCGGGATTCCAGGTCAGGATCACCCATGGCCAGGAG GTGA

SEQ ID NO: 148:
ATGGCTTCTCAGAAGCGCCCTAGCCAACGCCACGGCTCCAAGTACTTGGCAACGGCTTCTACCATG

GACCACGCTAGGCATGGCTTTTTGCCTAGACACCGAGACACGGGGATTCTCGATTCTATAGGGAGG

TTCTTTGGGGGGACCGGGGTGCTCCCAAGCGGGGGTCCGGAAAGGATAGCCACCACCCGGCTAG

GACGGCTCATTATGGTAGCTTGCCGCAAAAGAGTCATGGTCGCACTCAGGATGAGAATCCCGTAG

TCCACTTTTTTAAGAACATCGTCACACCACGGACGCCCCGCCTTCACAAGGGAAAGGTAGGGGCC

TCTCACTCTCTCGGTTCAGCTGGGGTGCCGAGGGACAACGACCTGGTTTTGGTTACGGAGGGCGGG

CTAGTGATTATAAGTCTGCGCATAAAGGCTTTAAGGGTGTGGACGCGCAAGGCACACTTTCAAAG

ATTTTTAAGCTCGGAGGTCGAGATTCTCGATCAGGTAGCCCTATGGCAAGACGCTGA

In some embodiments, the variant nucleic acid sequence encoding the MBP protein variant, or functional fragment thereof, is transcript variant 4. In some embodiments, the variant nucleic acid sequence encoding the MBP protein variant, or functional fragment thereof, is SEQ ID NO: 149, SEQ ID NO: 150, SEQ ID NO: 93, SEQ ID NO: 113, and/or SEQ ID NO: 126.

SEQ ID NOs: 149, 150, 93, 113, and 126 Show the *Homo sapiens* Myelin Basic Protein (MBP), Transcript Variant 4, mRNA:

SEQ ID NO: 149:
ATGGCGTCACAGAAGAGACCCTCCCAGAGGCACGGATCCAAGTACCTGGCCACAGCAAGTACCAT

GGACCATGCCAGGCATGGCTTCCTCCCAAGGCACAGAGACACGGGCATCCTTGACTCCATCGGGC

GCTTCTTTGGCGGTGACAGGGGTGCGCCCAAGCGGGGCTCTGGCAAGGACTCACACCACCCGGCA

AGAACTGCTCACTACGGCTCCCTGCCCCAGAAGTCACACGGCCGGACCCAAGATGAAAACCCCGT

AGTCCACTTCTTCAAGAACATTGTGACGCCTCGCACACCACCCCCGTCGCAGGGAAAGGGGGCCG

AAGGCCAGAGACCAGGATTTGGCTACGGAGGCAGAGCGTCCGACTATAAATCGGCTCACAAGGGA

TTCAAGGGAGTCGATGCCCAGGGCACGCTTTCCAAAATTTTTAAGCTGGGAGGAAGAGATAGTCG

CTCTGGATCACCCATGGCTAGACGCTGA

SEQ ID NO: 150:
ATGGCTTCCCAAAAGCGGCCTTCTCAGCGGCACGGCAGCAAGTACCTGGCCACAGCCAGCACAAT

GGACCACGCCAGACACGGCTTCCTGCCCCGGCACCGGGACACCGGCATCCTGGACTCCATCGGCA

GATTCTTCGGCGGAGATAGAGGAGCCCCTAAGAGAGGCTCCGGAAAGGACAGCCACCACCCCGCC

AGAACCGCCCACTACGGCTCTCTGCCACAGAAAAGCCACGGCCGGACCCAGGACGAGAACCCCGT

GGTGCACTTCTTTAAGAACATCGTGACCCCTAGAACCCCTCCACCTAGCCAGGGCAAGGGTGCTGA

AGGCCAGAGACCTGGCTTTGGCTACGGCGGAAGGGCCTCTGATTATAAGAGCGCCCATAAGGGCT

TCAAAGGCGTCGACGCCCAGGGAACACTGAGCAAAATCTTCAAGCTGGGCGGCAGAGATAGCAG

AAGCGGCAGCCCTATGGCTCGCAGATGA

SEQ ID NO: 93:
ATGGCATCACAAAAAAGACCCAGTCAGCGCCACGGCAGTAAGTACCTGGCTACAGCGAGTACGAT

GGATCACGCTCGACACGGGTTCTTGCCGCGGCATCGAGACACAGGCATTTTGGATTCTATCGGGAG

GTTTTTCGGTGGGGACCGAGGTGCTCCGAAGCGCGGCAGCGGCAAGGACAGTCATCATCCGGCGA

GAACCGCGCACTATGGCAGTTTGCCGCAAAAAAGTCACGGTAGAACCCAAGACGAGAATCCTGTT

GTTCACTTTTTCAAAAACATTGTGACGCCACGAACACCACCCCCGTCTCAAGGGAAGGGTGCGGA

AGGCCAGCGCCCTGGTTTCGGATACGGAGGCCGGGCTTCAGATTACAAATCCGCTCATAAAGGGT

TCAAGGGTGTGGATGCCCAGGGGACTTTGTCTAAAATTTTCAAATTGGGAGGACGGGATTCAAGA

TCAGGCTCCCCAATGGCCCGACGGTGA

SEQ ID NO: 113:
ATGGCATCACAGAAGAGGCCTAGTCAAAGGCACGGTTCTAAATATCTTGCCACAGCATCTACTATG

GACCACGCACGACACGGCTTTTTGCCACGACACAGGGATACGGGGATCTTGGACTCCATTGGTCG

ATTTTTCGGCGGTGATAGAGGAGCGCCCAAAAGAGGTTCCGGAAAAGATAGCCACCATCCCGCAA

GGACTGCCCATTATGGAAGCCTTCCTCAGAAAAGCCACGGGAGGACTCAGGACGAAAACCCAGTT

GTTCACTTCTTTAAGAATATAGTGACGCCACGGACCCCTCCGCCGAGCCAAGGGAAGGGCGCAGA

GGGCCAACGACCAGGATTTGGGTATGGCGGCAGAGCAAGTGACTATAAGAGCGCTCATAAGGGCT

TCAAAGGCGTCGACGCGCAGGGGACCTTGTCTAAAATCTTTAAGTTGGGTGGAAGAGATAGCCGG

TCTGGCAGTCCGATGGCTCGGCGCTGA

SEQ ID NO: 126:
ATGGCTTCTCAAAAACGACCCTCACAACGCCACGGTTCAAAATACCTGGCGACGGCCAGCACCAT

GGATCATGCACGGCATGGCTTCTTGCCAAGGCATCGGGACACCGGCATTCTCGACTCAATTGGAAG

GTTTTTTGGAGGGGATCGAGGCGCCCCCAAGCGCGGATCTGGGAAGGACTCCCATCACCCTGCCC

GCACCGCTCACTATGGCTCTTTGCCACAAAAATCCCATGGCCGCACCCAAGATGAAAATCCAGTGG

TCCATTTTTTAAGAACATAGTGACGCCCCGAACCCCCCCACCGTCCCAAGGTAAAGGAGCAGAA

GGCCAACGACCAGGATTCGGATACGGGGGTCGGGCAAGTGATTATAAGTCTGCCCATAAGGGTTT

TAAGGGGGTAGACGCTCAAGGTACGCTGAGCAAAATTTTTAAACTTGGTGGCCGCGATTCTAGGA

GCGGGTCACCGATGGCGAGGAGGTGA

In some embodiments, the variant nucleic acid sequence encoding the MBP protein variant, or functional fragment thereof, is transcript variant 7. In some embodiments, the variant nucleic acid sequence encoding the MBP protein variant, or functional fragment thereof, is SEQ ID NO: 13, SEQ ID NO: 16, SEQ ID NO: 18, SEQ ID NO: 20, SEQ ID NO: 24, and/or SEQ ID NO: 26.

SEQ ID NOs: 13, 16, 18, 20, 24, and 26 Show the *Homo sapiens* Myelin Basic Protein (MBP), Transcript Variant 7, mRNA:

SEQ ID NO: 13:
ATGGGAAACCACGCAGGCAAACGAGAATTAAATGCCGAGAAGGCCAGTACGAATAGTGAAACTA

ACAGAGGAGAATCTGAAAAAAAGAGAAACCTGGGTGAACTTTCACGGACAACCTCAGAGGACAA

```
CGAAGTGTTCGGAGAGGCAGATGCGAACCAGAACAATGGGACCTCCTCTCAGGACACAGCGGTGA

CTGACTCCAAGCGCACAGCGGACCCGAAGAATGCCTGGCAGGATGCCCACCCAGCTGACCCAGGG

AGCCGCCCCCACTTGATCCGCCTCTTTTCCCGAGATGCCCCGGGGAGGGAGGACAACACCTTCAAA

GACAGGCCCTCTGAGTCCGACGAGCTCCAGACCATCCAAGAAGACAGTGCAGCCACCTCCGAGAG

CCTGGATGTGATGGCGTCACAGAAGAGACCCTCCCAGAGGCACGGATCCAAGTACCTGGCCACAG

CAAGTACCATGGACCATGCCAGGCATGGCTTCCTCCCAAGGCACAGAGACACGGGCATCCTTGAC

TCCATCGGGCGCTTCTTTGGCGGTGACAGGGGTGCGCCCAAGCGGGGCTCTGGCAAGGACTCACA

CCACCCGGCAAGAACTGCTCACTACGGCTCCCTGCCCCAGAAGTCACACGGCCGGACCCAAGATG

AAAACCCCGTAGTCCACTTCTTCAAGAACATTGTGACGCCTCGCACACCACCCCGTCGCAGGGAA

AGGGGAGAGGACTGTCCCTGAGCAGATTTAGCTGGGGGGCCGAAGGCCAGAGACCAGGATTTGGC

TACGGAGGCAGAGCGTCCGACTATAAATCGGCTCACAAGGGATTCAAGGGAGTCGATGCCCAGGG

CACGCTTTCCAAAATTTTTAAGCTGGGAGGAAGAGATAGTCGCTCTGGATCACCCATGGCTAGACG

CTGA

SEQ ID NO: 16:
ATGGGCAACCACGCCGGTAAGAGAGAACTGAACGCCGAAAAGGCCTCTACAAACTCCGAGACAA

ATAGAGGAGAAAGCGAGAAGAAGCGGAACCTGGGCGAGCTGAGCAGAACCACATCTGAAGATAA

CGAGGTGTTCGGCGAAGCCGACGCCAACCAGAACAACGGCACAAGCAGCCAAGATACAGCCGTC

ACCGACTCCAAGAGAACAGCTGACCCCAAGAATGCCTGGCAGGACGCCCACCCCGCCGATCCAGG

GAGCCGGCCCCACCTGATCAGACTGTTCTCCCGGGATGCCCCTGGCAGAGAGGACAATACCTTCA

AGGACAGACCTTCTGAGTCTGATGAACTCCAGACCATTCAGGAGGACAGCGCTGCTACCAGCGAG

AGCCTGGACGTGATGGCCAGCCAGAAACGGCCTAGCCAAAGACACGGCTCCAAGTACCTGGCCAC

CGCTAGCACCATGGACCACGCCAGACACGGCTTTCTGCCCAGACATAGAGACACCGGCATCCTGG

ACAGCATCGGCAGGTTCTTCGGAGGCGACCGGGGCGCTCCTAAGCGGGGATCTGGAAAAGACAGC

CACCACCCTGCTAGAACCGCCCACTACGGCAGCCTGCCTCAGAAGTCCCACGGCCGGACCCAGGA

TGAGAACCCCGTGGTGCACTTCTTTAAAAACATCGTGACCCCTCGGACCCCACCTCCTAGCCAGGG

CAAGGGCCGCGGACTGAGCCTGAGCAGATTCAGCTGGGGCGCCGAGGGCCAGAGACCCGGCTTTG

GCTATGGCGGCAGAGCCAGCGACTACAAGAGCGCCCATAAGGGCTTCAAAGGCGTGGACGCCCAG

GGAACACTGTCTAAGATCTTCAAGCTGGGCGGAAGAGATTCTCGGAGCGGCAGCCCTATG

GCCCGTAGATGA

SEQ ID NO: 18:
ATGGGGAATCATGCTGGTAAGCGCGAGCTGAATGCTGAAAAAGCAAGTACAAACTCCGAAACCAA

TCGAGGAGAGAGTGAAAAGAAACGAAACCTTGGTGAACTGAGTCGGACCACCTCCGAGGATAAC

GAGGTTTTCGGCGAGGCGGACGCGAATCAAAACAATGGTACTTCATCACAGGACACGGCGGTCAC

TGATTCCAAACGAACGGCAGACCCGAAGAATGCCTGGCAAGATGCACATCCGGCTGATCCCGGTA

GCCGGCCCCACCTGATAAGGCTTTTCTCCCGAGACGCGCCGGGCAGGGAGGACAATACATTTAAA

GATCGCCCTAGCGAAAGTGACGAGTTGCAGACCATACAAGAAGATTCAGCAGCAACCAGTGAATC

CCTGGATGTTATGGCATCTCAGAAGAGGCCGAGCCAGCGACACGGTAGCAAATACCTCGCGACGG

CGAGTACGATGGACCATGCACGCCATGGCTTTCTTCCTCGCCATAGGACACAGGTATACTCGATT

CCATAGGACGATTCTTTGGAGGGGATCGGGGTGCTCCTAAACGAGGTTCTGGTAAAGATTCCCATC

ACCCTGCTCGCACCGCACATTACGGGAGCCTCCCGCAAAGTCACACGGACGCACCCAGGATGAG

AACCCCGTCGTGCATTTCTTTAAAAATATAGTTACTCCACGAACTCCACCACCGAGTCAAGGCAAA
```

-continued

GGCAGGGGCCTTAGCCTGTCAAGATTCAGCTGGGGTGCTGAGGGCCAGAGACCAGGATTTGGATA

TGGAGGTAGGGCGTCTGATTACAAGTCCGCCCACAAGGGTTTCAAAGGGGTGGATGCTCAAGGGA

CATTGTCAAAAATTTTCAAGTTGGGCGGACGGGACTCTCGAAGCGGATCCCCAATGGCCCGAC

GATGA

SEQ ID NO: 20:
ATGGGAAATCACGCTGGAAAACGGGAGTTGAACGCCGAAAAAGCCTCTACCAATAGCGAAACCA

ATCGCGGAGAGTCAGAGAAAAGAGAAACCTGGGTGAGCTGAGTCGCACTACGAGTGAAGATAA

CGAAGTCTTCGGTGAGGCGGACGCGAATCAAAATAATGGGACTAGCAGCCAAGACACGGCCGTCA

CAGATAGCAAACGCACAGCAGATCCCAAGAATGCTTGGCAAGACGCACATCCGGCCGACCCCGGG

TCTAGACCCCACCTGATTCGGCTCTTTAGCCGCGACGCACCTGGAAGGGAGGATAACACCTTTAAG

GATCGGCCTAGTGAATCTGATGAGCTTCAGACCATACAAGAAGACAGCGCCGCCACCTCAGAATC

ACTTGACGTCATGGCTTCACAAAAGCGCCCCTCACAAAGGCATGGCTCCAAATACTTGGCTACAGC

AAGCACGATGGACCATGCTCGGCACGGCTTCCTTCCCCGCCACCGGGACACCGGCATACTCGACA

GCATAGGGCGCTTTTTCGGTGGAGACAGGGGAGCTCCCAAGCGGGGTAGTGGTAAGGATTCTCAT

CATCCCGCCCGAACCGCGCACTATGGATCACTTCCTCAGAAATCCCATGGCAGGACTCAAGACGA

AAACCCGGTTGTGCACTTTTTCAAGAACATTGTAACCCCTCGGACTCCGCCGCCGAGCCAGGGTAA

AGGACGAGGCTTGTCCCTCTCAAGATTCTCATGGGGGGCAGAGGGACAGCGCCCGGGGTTTGGCT

ACGGGGGTCGGGCGAGCGACTACAAATCAGCCCACAAAGGGTTTAAGGGGGTGGATGCACAGGG

AACCTTGTCAAAAATTTTTAAACTCGGAGGACGAGACAGTAGGAGCGGTTCTCCCATGGCGCGGC

GATGA

SEQ ID NO: 24:
ATGGGCAATCACGCCGGCAAGCGAGAACTGAACGCGGAGAAGGCTTCTACTAATTCCGAAACTAA

CAGGGGCGAGTCAGAAAAGAAACGGAATCTCGGGGAGTTGTCAAGGACGACGAGCGAGGACAAC

GAAGTCTTCGGCGAGGCAGACGCCAACCAGAATAACGGTACGTCAAGCCAAGACACGGCCGTCAC

TGATTCCAAACGAACTGCCGATCCAAAGAACGCATGGCAGGATGCACATCCTGCGGATCCTGGCA

GTCGACCGCATCTTATTCGCCTGTTCTCAAGAGATGCCCCAGGAAGAGAAGATAATACATTTAAGG

ATCGACCGTCCGAGTCTGATGAGCTGCAGACGATCCAAGAAGACAGCGCGGCAACGTCTGAGTCT

CTCGACGTGATGGCTTCTCAAAAACGGCCCTCACAAAGGCATGGTTCTAAATACCTCGCTACTGCG

AGCACGATGGATCACGCTAGACATGGGTTCCTTCCCCGGCATAGAGACACAGGAATTCTGGATAG

TATAGGCAGGTTCTTCGGCGGCGATAGAGGTGCGCCAAAGAGGGGCTCTGGAAAGGATTCTCACC

ACCCGGCCCGGACAGCTCACTATGGTAGTTTGCCCCAGAAGTCACATGGTAGGACGCAAGACGAA

AACCCCGTAGTTCATTTTTTAAAAACATCGTCACTCCCAGGACCCCACCGCCGTCACAAGGAAAA

GGACGGGGCCTGTCTCTTTCTAGATTCTCTTGGGGGGCAGAGGGGCAACGCCCTGGCTTTGGGTAC

GGTGGGCGAGCTTCTGACTACAAGTCCGCTCATAAGGGTTTCAAAGGGGTCGATGCTCAGGGCAC

GCTGTCAAAGATATTCAAGCTGGGAGGACGGGACAGTCGCTCTGGCAGCCCTATGGCACGAA

GGTGA

SEQ ID NO: 26:
ATGGGCAATCATGCAGGGAAACGCGAACTGAACGCAGAAAAAGCCTCCACAAACAGTGAGACTA

ATCGAGGAGAAAGCGAGAAGAAGCGAAACTTGGGCGAATTGTCACGAACCACATCAGAGGACAA

TGAAGTATTCGGGGAAGCTGACGCCAACCAGAACAACGGCACCTCCAGCCAAGATACAGCTGTAA

CCGATTCTAAACGGACAGCAGACCCAAAGAATGCTTGGCAAGATGCACACCCTGCCGACCCAGGG

TCTAGACCACACCTCATTAGACTTTTCTCCCGAGATGCGCCTGGGCGAGAGGATAATACCTTTAAA

-continued
```
GACCGACCCTCCGAATCCGACGAGCTGCAAACAATTCAGGAGGACAGTGCGGCGACCAGTGAGTC

ACTCGACGTGATGGCCTCTCAAAAGCGGCCATCACAGCGACATGGATCCAAATATCTTGCAACCG

CGTCTACCATGGACCATGCTCGACATGGTTTTTTGCCTCGCCATAGGGACACAGGGATTCTTGACT

CAATAGGGCGGTTTttcGGGGGCGACAGAGGGGCACCTAAACGAGGCTCAGGTAAAGACAGTCATC

ATCCGGCACGAACTGCGCACTACGGCTCCCTGCCACAAAAGTCTcacGGCCGAACACAAGACGAAA

ACCCAGTGGTGCACTTCTTTAAAAATATCGTTACCCCCCGAACGCCACCGCCATCACAAGGTAAGG

GACGAGGCTTGTCACTGTCACGCTTCAGCTGGGGGGCAGAAGGGCAACGCCCCGGTTTCGGATAT

GGTGGAAGAGCATCAGACTATAAAAGCGCGCACAAAGGATTCAAAGGTGTCGACGCCCAGGGGA

CACTCTCTAAGATCTTTAAGCTGGGAGGTCGGGATTCACGATCAGGATCCCCTATGGCACGGAG

ATGA
```

In some embodiments, the variant nucleic acid sequence encoding the MBP protein variant, or functional fragment thereof, is transcript variant 8. In some embodiments, the variant nucleic acid sequence encoding the MBP protein variant, or functional fragment thereof, is SEQ ID NO: 28, SEQ ID NO: 29, SEQ ID NO: 30, SEQ ID NO: 32, SEQ ID NO: 33, and/or SEQ ID NO: 34.

SEQ ID NOs: 28-30 and 32-34 Show the *Homo sapiens* Myelin Basic Protein (MBP), Transcript Variant 8, mRNA:

```
SEQ ID NO: 28:
ATGGGAAACCACGCAGGCAAACGAGAATTAAATGCCGAGAAGGCCAGTACGAATAGTGAAACTA

ACAGAGGAGAATCTGAAAAAAAGAGAAACCTGGGTGAACTTTCACGGACAACCTCAGAGGACAA

CGAAGTGTTCGGAGAGGCAGATGCGAACCAGAACAATGGGACCTCCTCTCAGGACACAGCGGTGA

CTGACTCCAAGCGCACAGCGGACCCGAAGAATGCCTGGCAGGATGCCCACCCAGCTGACCCAGGG

AGCCGCCCCCACTTGATCCGCCTCTTTTCCCGAGATGCCCCGGGGAGGGAGGACAACACCTTCAAA

GACAGGCCCTCTGAGTCCGACGAGCTCCAGACCATCCAAGAAGACAGTGCAGCCACCTCCGAGAG

CCTGGATGTGATGGCGTCACAGAAGAGACCCTCCCAGAGGCACGGATCCAAGTACCTGGCCACAG

CAAGTACCATGGACCATGCCAGGCATGGCTTCCTCCCAAGGCACAGAGACACGGGCATCCTTGAC

TCCATCGGGCGCTTCTTTGGCGGTGACAGGGGTGCGCCCAAGCGGGGCTCTGGCAAGGTGAGCTCT

GAGGAGTAG

SEQ ID NO: 29:
ATGGGCAACCACGCCGGCAAGCGCGAGCTGAACGCCGAGAAGGCCTCTACAAACAGCGAAACCA

ATAGAGGCGAATCCGAAAAAAAGCGGAACCTGGGCGAGCTGAGCAGAACCACCTCCGAAGATAA

CGAGGTGTTCGGCGAGGCCGATGCTAATCAGAACAACGGCACCTCTAGCCAAGATACAGCCGTCA

CCGACAGCAAGAGAACAGCCGACCCCAAGAACGCCTGGCAGGACGCTCATCCTGCTGATCCTGGC

AGCAGACCCCACCTGATCAGACTGTTCAGCCGGGACGCCCCTGGAAGAGAGGACAACACCTTCAA

GGACCGGCCATCTGAAAGCGACGAGCTCCAGACCATCCAGGAGGACAGCGCCGCTACATCTGAGA

GCCTGGACGTGATGGCCAGCCAGAAGAGGCCTAGCCAGCGGCACGGCAGCAAGTACCTGGCCACA

GCCAGCACCATGGACCACGCCAGACACGGCTTCCTGCCCAGACACAGAGATACCGGCATCCTGGA

TAGCATCGGCAGATTTTTCGGAGGCGACAGAGGAGCCCCTAAGCGGGGATCTGGCAAAGTGTCCA

GCGAGGAATGA

SEQ ID NO: 30:
ATGGGGAACCATGCGGGTAAAAGGGAGTTGAACGCCGAAAAAGCGTCCACAAACTCTGAAACTA

ATCGGGGTGAGTCAGAGAAAAAAAGGAATCTGGGCGAACTTTCTAGAACAACAAGCGAAGACAA

CGAAGTTTTCGGCGAAGCGGATGCGAATCAGAACAACGGGACCTCTTCTCAGGATACTGCAGTAA

CGGATAGCAAGCGCACAGCCGATCCGAAGAATGCCTGGCAAGACGCCCACCCAGCCGATCCTGGG

TCACGCCCACACCTCATTAGACTGTTCAGCCGCGATGCGCCAGGCCGAGAGGATAATACCTTTAAG
```

-continued

```
GATCGACCCTCCGAGAGCGATGAGTTGCAAACAATCCAGGAGGATAGCGCGGCAACGTCAGAGTC

TCTCGATGTAATGGCCTCTCAGAAGAGACCTTCACAACGACATGGAAGCAAGTATCTCGCCACAG

CGAGCACTATGGATCACGCGCGACATGGCTTCCTTCCCAGGCACAGGGATACCGGAATACTCGAT

AGCATTGGAAGGTTTTTTGGTGGGGATAGGGGTGCCCCAAAACGGGGTTCCGGTAAGGTTTCCTCC

GAAGAATAG

SEQ ID NO: 32:
ATGGGTAATCACGCAGGGAAGCGGGAGCTGAATGCGGAGAAAGCCTCTACTAACTCTGAAACGAA

CAGAGGAGAGAGCGAAAAAAAACGCAACCTGGGAGAGCTGTCTAGGACGACGTCTGAGGACAAT

GAAGTCTTTGGTGAGGCCGACGCTAATCAAAATAACGGTACTTCCAGCCAGGATACTGCGGTAAC

CGATTCCAAGCGGACTGCCGATCCAAAAAACGCTTGGCAGGACGCACACCCAGCAGACCCTGGCT

CCCGCCCACACCTTATCCGACTCTTTTCTCGGGACGCACCAGGACGGGAAGACAACACTTTCAAAG

ATCGACCATCTGAGTCCGACGAGCTGCAAACTATCCAGGAAGATTCCGCGGCCACGTCTGAGTCA

CTGGACGTTATGGCCTCACAAAAGAGGCCAAGTCAAAGACATGGGTCCAAATATCTTGCTACAGC

GTCAACTATGGATCATGCCCGCCATGGTTTTTTGCCGCGCCATCGAGATACCGGGATTCTTGACAG

TATCGGTCGCTTTTTTGGAGGAGACCGGGGTGCTCCTAAGAGAGGATCTGGCAAAGTCTCCAGTGA

GGAATAG

SEQ ID NO: 33:
ATGGGCAACCACGCTGGAAAACGGGAGTTGAACGCCGAGAAAGCGTCTACAAACAGTGAAACCA

ACCGGGGCGAATCAGAAAAGAAGCGCAACCTTGGCGAACTTTCCCGGACGACTTCTGAGGATAAT

GAAGTATTCGGGGAAGCAGATGCTAATCAAAATAACGGGACTAGCTCACAAGACACTGCCGTCAC

CGACAGCAAACGCACTGCGGACCCAAAGAATGCTTGGCAAGACGCACACCCTGCAGACCCTGGGA

GCAGGCCTCACTTGATTAGGCTTTTCTCTCGGGACGCGCCAGGCCGAGAAGACAATACGTTCAAAG

ACAGACCTAGTGAAAGCGATGAGCTTCAAACCATTCAGGAAGACTCTGCGGCTACCAGTGAGAGC

CTTGATGTAATGGCATCCCAGAAAAGGCCATCTCAGAGGCACGGTTCAAAATACCTGGCCACTGC

ATCTACAATGGACCATGCTAGACATGGGTTCCTCCCGAGGCATAGAGACACTGGAATACTCGATTC

TATAGGGCGGTTCTTTGGAGGTGACCGCGGCGCACCTAAGCGGGGTTCCGGGAAGGTCTCAAGTG

AGGAGTAG

SEQ ID NO: 34:
ATGGGAAACCACGCAGGAAAGCGGGAACTTAACGCCGAGAAAGCTTCCACTAACTCTGAAACGA

ATCGGGGTGAGTCCGAGAAAAAGCGGAACCTCGGTGAGCTGAGTAGGACCACCTCCGAAGATAAC

GAAGTCTTCGGGGAGGCGGACGCAAACCAGAATAACGGAACCTCAAGCCAGGATACTGCGGTTAC

AGATAGCAAACGCACAGCGGATCCCAAGAACGCCTGGCAAGACGCGCATCCGGCAGATCCGGGC

AGTCGGCCTCATCTTATACGACTTTTCAGTCGCGACGCCCAGGGCGAGAAGACAATACGTTCAAG

GACCGCCCTTCCGAGTCCGACGAACTTCAGACTATTCAAGAAGACAGTGCTGCCACTTCCGAATCC

CTCGACGTTATGGCCTCACAGAAGAGACCGAGTCAAAGACATGGATCAAAGTATCTTGCTACGGC

AAGTACGATGGATCACGCGAGACATGGATTTCTCCCCAGGCATCGCGATACGGGCATATTGGACT

CTATTGGCCGGTTTTTTGGGGGTGATAGGGGGGCTCCGAAACGCGGGTCCGGCAAGGTGTCTTCAG

AAGAGTGA
```

In some embodiments, the rAAV virions, particles and pharmaceutical compositions comprising any of the rAAV vectors of the disclosure do not comprise a MOG peptide-, MBP peptide-, or PLP neuropeptide-encoding sequence that has not been codon-optimized or codon-modified. In some embodiments, the rAAV vectors of the disclosure do not comprise a MOG, MBP, or PLP neuropeptide-encoding sequence that is not codon-optimized for human expression. In some embodiments, the rAAV vectors of the disclosure comprise a sequence that is codon-optimized for expression in mammals (or mammalian tissues) other than humans, such as canines. In some embodiments, the rAAV vectors of the disclosure comprise a sequence encoding a neuropeptide, wherein the sequence does not comprise, or consist of, any one of SEQ ID NOs: 8, 10, 12-14, 22, 28, 100, 107, 120, 131, 137, and 149. In some embodiments, the rAAV vectors of the disclosure comprise a sequence encoding a neuropeptide, wherein the sequence does not comprise, or consist of, any one of SEQ ID NOs: 1, 2, 3, 9, 11, 15, 17, 19, 21, 23, 25, 27, 31, or 35.

In some embodiments, the AAV particles of the disclosure do not comprise an AAV8 capsid. In some embodiments, the AAV particles of the disclosure do not comprise a capsid selected from AAVrh.10 or AAVrh.74. In some embodiments, an AAV particle of the disclosure does not comprise a capsid selected from AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2(Y→F), AAV8 (Y733F), AAV2.15, AAV2.4, AAVM41, or AAVr3.45.

In various embodiments, any of the rAAV particles, compositions, and methods of treatment of the disclosure are intended for use in treatment of multiple sclerosis. In some embodiments, any of the rAAV particles, compositions, and methods of treatment are intended for use in treatment of a disease other than multiple sclerosis. In some embodiments, any of the disclosed particles and compositions are intended for use in treatment of disseminated sclerosis, an encephalomyelitis, or an allergic disease.

In some embodiments, any of the rAAV particles, compositions, and methods of treatment of the disclosure induce tolerization in a manner that bypasses T helper cells. In some embodiments, any of the rAAV particles, compositions, and methods of treatment of the disclosure induce tolerization in a manner that raises the amount or activity of Treg cells. In other embodiments, any of the rAAV particles, compositions, and methods of treatment of the disclosure induce tolerization in a manner that bypasses activity of Treg cells.

In some embodiments of the methods of treatment provided herein, the methods do not comprise the co-administration of an agent with the rAAV particle (or vector). For instance, in some embodiments, the methods of treatment provided may not comprise the administration of an mTOR inhibitor. In some embodiments, the methods of treatment provided may not comprise the administration of a sphingosine-1-phosphate receptor modulator or inhibitor, such as fingolimod. In some embodiments, the methods of treatment may not comprise the administration of a glucocorticoid, such as prednisolone.

EXAMPLES

The following examples are included to demonstrate embodiments of the present disclosure. It should be appreciated by those of skill in the art that the techniques disclosed in the examples that follow represent techniques discovered by the inventor to function well in the practice of the present disclosure, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the present disclosure.

Example 1—Re-Establishing Immune Tolerance to Neuroantigens by AAV Gene Therapy

The inventor has demonstrated that hepatocyte-restricted expression of an AAV-delivered neuroantigen establishes persistent immunological tolerance mediated by antigen-specific Tregs capable of preventing and reversing EAE in mice. This example describes the development of a protocol that persistently induces Tregs in vivo and prevents disease development in a murine model of MS. The example also determines if tolerance can induce remission of pre-existing EAE disease and substantially reduce clinical and tissue-associated pathology.

Neurodegenerative disease such as Multiple sclerosis (MS) is characterized by chronic infiltration of the CNS by pathogenic autoreactive lymphocytes that recognize neuroantigens. Functional defects in the endogenous regulatory T cells (Tregs) leading to a failure of central and/or peripheral mechanisms required for maintaining immunological tolerance combined with T cells recognizing myelin protein peptides are implicated in the pathogenesis of the disease. In C57BL/6 mice, experimental autoimmune encephalomyelitis (EAE) induced by myelin oligodendrocyte glycoprotein (MOG) produces a CD4 T cell-mediated inflammatory CNS disease that serves as a relevant model for MS (FIGS. 1, 2A and 2B).

Hepatic gene transfer with AAV vectors containing liver specific promoters can produce stable transgene expression and induce a robust antigen-specific immune tolerance to a variety of therapeutic proteins. It has been reported that induced Tregs not only suppress cellular immune responses against the transgene product but can also suppress humoral responses. Importantly, it has been shown that immune tolerance established by antigen expression in the liver is maintained even when the antigen was subsequently expressed in a highly immunogenic manner in other organs, such as skeletal muscle or intravenously.

The development of protocols that stimulate an increase in Treg numbers and/or their function has become a focus in treating autoimmune disease. Many of the beneficial effects of currently approved immunomodulators used in the treatment of MS are associated with restoring Treg homeostasis. This example demonstrates that liver-directed AAV gene therapy represents a novel approach to halt disease progression by restoring normal Treg function at disease onset.

Figure 7A:
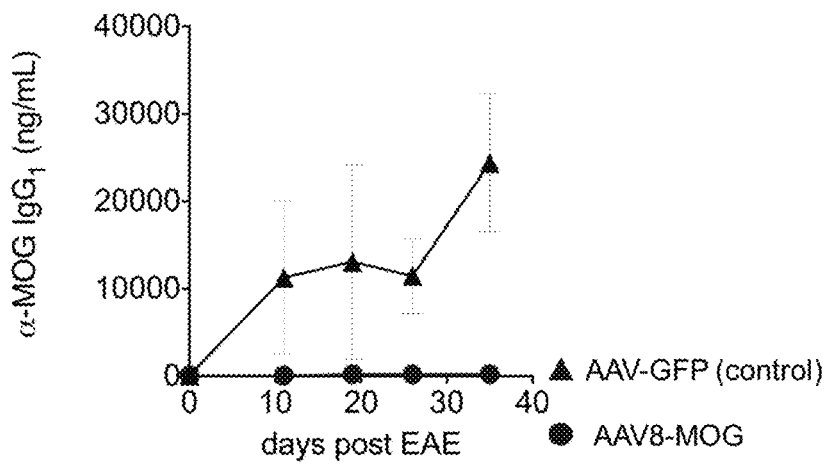
FIG. 7A, FIG. 7B, and FIG. 7C show that AAV8-vectored gene therapy prevents the onset of EAE in the animal model of MS.
Figure 7B:
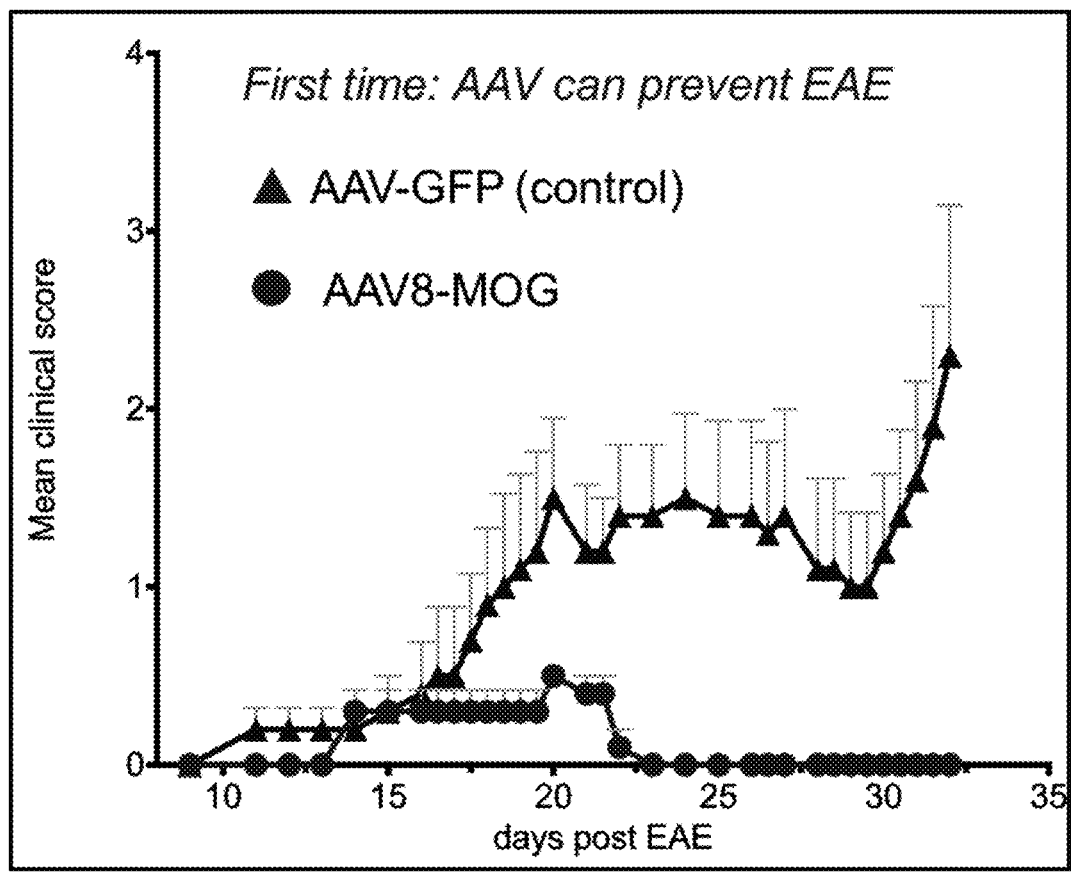
Figure 7C:
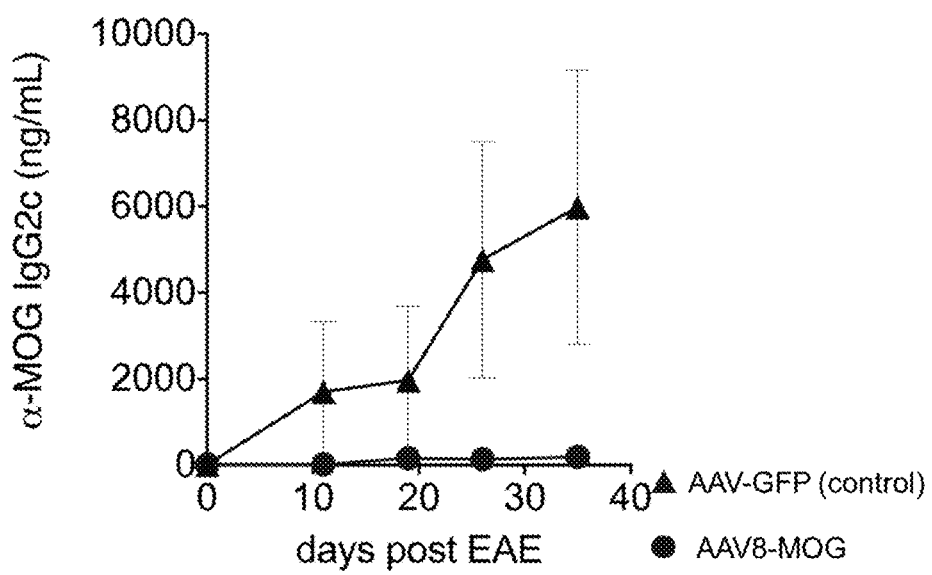
Figure 8:
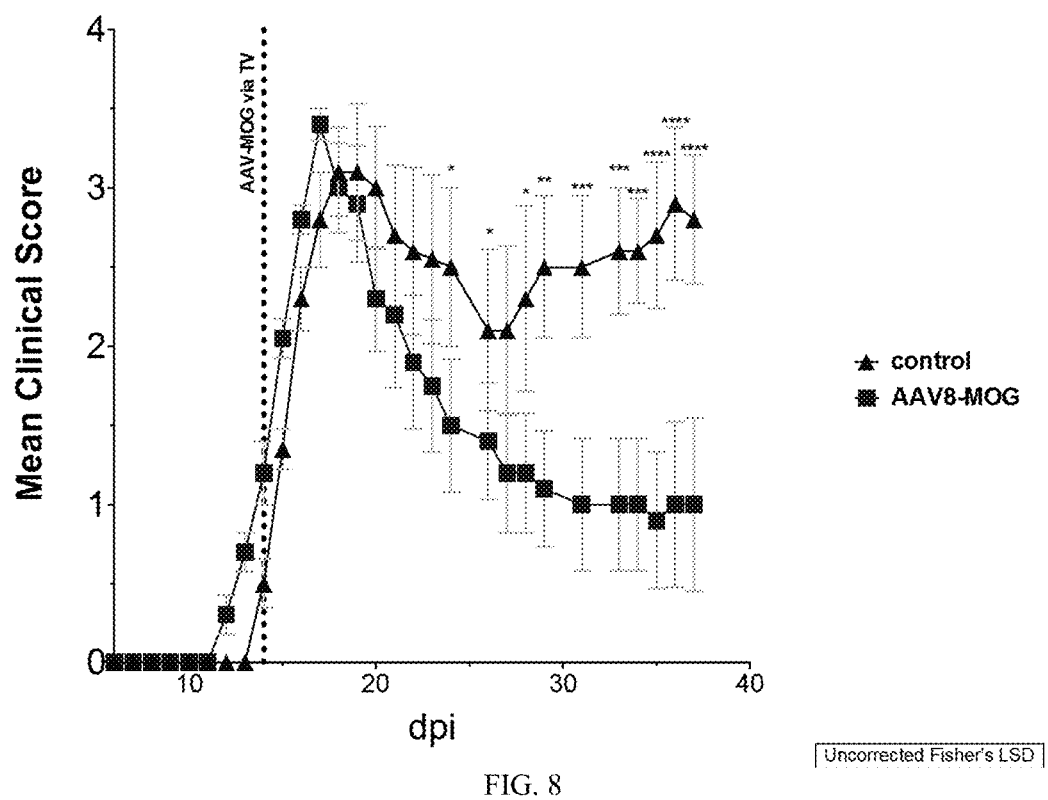
FIG. 8 shows that AAV8-MOG ameliorated the disease in the animal model of MS.
Figure 9:
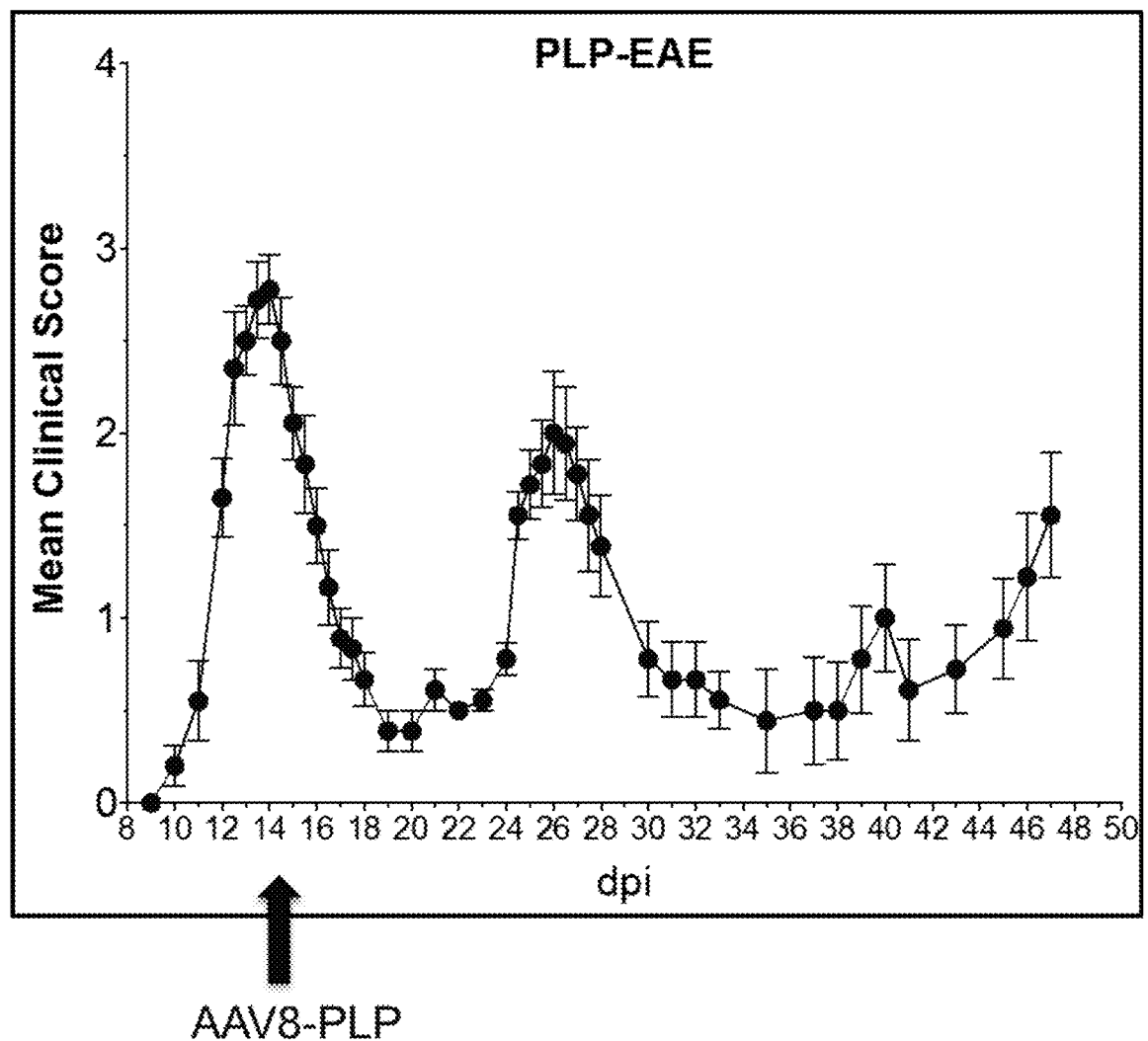
FIG. 9 shows a PLP-induced EAE naive control group to demonstrate disease progression.
Figure 10:
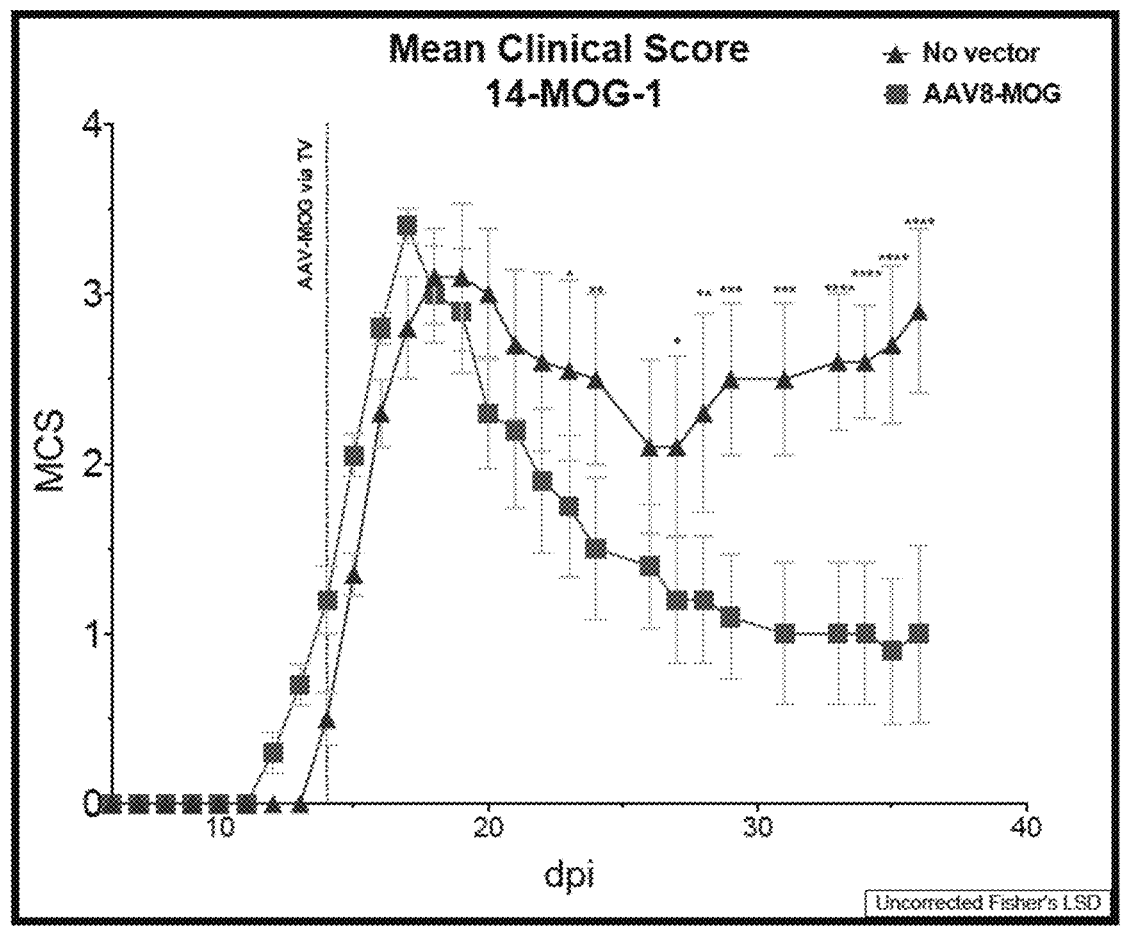
FIG. 10 shows effective suppression of pre-existing disease using the AAV8-vectored MOG treatment.

First, an AAV8-MOG vector was generated, and hepatic expression of the transgene in mice was validated by western blot and qPCR analysis (FIG. 4). Next, to determine if hepatic expression of MOG can provide protection against the development of EAE mice were injected with either AAV8-MOG or -GFP vector. 2 weeks later EAE was induced and the mice were monitored and scored according to the classic scale for clinical signs of EAE. Plasma was obtained at 0-, 7-, and 14-days post EAE or at 0, 11-, 19-, 26-, and 35-days post EAE. The results revealed that mice receiving AAV8-MOG were clearly protected from developing EAE. Furthermore, these mice also did not produce any anti-MOG IgG1 or IgG2c autoantibodies. In contrast, those mice receiving the control vector developed severe EAE with elevated antibody titers (FIGS. 7 and 8).

Example 2—Therapeutic Molecules for AAV-Based Gene Therapy of MS

This example shows that liver directed gene transfer using an AAV vector expressing a neuro-antigen is capable of suppressing inflammation in the CNS and preventing EAE. Importantly, using AAV to express a full-length neuroprotein will enable greater applicability across MS-associated HLA haplotypes. Ongoing plans are to evaluate reversal of pre-existing EAE and functional analysis of the interplay of effector (Th1/Th17) cells and Tregs.

Using the following sequences for full length proteins, HLA/MHC restrictions were avoided.

MBP sequence in vector:
(SEQ ID NO: 1)
MGNHSGKRELSAEKASKDGEIHRGEAGKKRSVGKLSQTASEDSDVFGEADA

IQNNGTSAEDTAVTDSKHTADPKNNWQGAHPADPGNRPHLIRLFSRDAPGR

EDNTFKDRPSESDELQTIQEDPTAASGGLDVMASQKRPSQRSKYLATASTM

DHARHGFLPRHRDTGILDSIGRFFSGDRGAPKRGSGKVSSEP*

PLP sequence in vector:
(SEQ ID NO: 2)
MGLLECCARCLVGAPFASLVATGLCFFGVALFCGCGHEALTGTEKLIETYF

SKNYQDYEYLINVIHAFQYVIYGTASFFFLYGALLLAEGFYTTGAVRQIFG

DYKTTICGKGLSATVTGGQKGRGSRGQHQAHSLERVCHCLGKWLGHPDKFV

GITYALTVVWLLVFACSAVPVYIYFNTWTTCQSIAFPSKTSASIGSLCADA

RMYGVLPWNAFPGKVCGSNLLSICKTAEFQMTFHLFIAAFVGAA

MOG sequence in vector:
(SEQ ID NO: 3)
MACLWSFSLPSCFLSLLLLLLQLSCSYAGQFRVIGPGYPIRALVGDEAEL

PCRISPGKNATGMEVGWYRSPFSRVVHLYRNGKDQDAEQAPEYRGRTELLK

ETISEGKVTLRIQNVRFSDEGGYTCFFRDHSYQEEAAMELKVEDPFYWVNP

GVLTLIALVPTILLQVSVGLVFLFLQHRLRGKLRAEVENLHRTFDPHFLRV

PCWKITLFVIVPVLGPLVALIICYNWLHRRLAGQFLEELRNPL

EAE inducing peptide in SJL mice PLP$_{139-151}$:
(SEQ ID NO: 4)
HCLGKWLGHPDKF.

EAE inducing peptide in C57BL mice:
(SEQ ID NO: 5)
NTWTCQSIAFP
or

PLP$_{178-191}$:
(SEQ ID NO: 37)
NTWTTCQSIAFPSK.

C57BL: MOG$_{35-55}$:
(SEQ ID NO: 6)
MEVGWYRSPFSRVVHLYRNGK.

SJL: MOG$_{92-106}$:
(SEQ ID NO: 7)
DEGGYTCFFRDHSYQ.

Example 3—RAAV8 Vectors for Gene Therapy of MS

AAV8 vectors can stably express a neuro-protein in hepatocytes. AAV8-MOG can prevent the development of EAE, and AAV8-MOG can abrogate clinical symptoms of established EAE.

This example describes the development of a (pre)clinically relevant therapy using viral gene transfer that will result in the induction and expansion of antigen-specific T cells, re-establishing immunological tolerance as a treatment for multiple sclerosis. The approach has broad application as it uses full length myelin oligodendrocyte glycoprotein (MOG) protein and thus abrogates the need to identify HLA/MHC specific epitopes for inducing antigen specific Tregs. The knowledge gained from the work presented here will have the potential of creating a new line of treatment protocols for patients with MS as well as advance the research for both the MS and gene therapy fields.

Collectively, there is clear rationale for therapeutic approaches that are multifactorial. The present invention provides a novel therapy that not only focuses on reducing $CD4^+$ T cells, but that can also target the effect of $CD8^+$ T cells, B cells, and B cell derived components of the immune system.

Experimental Methods

Prevention of EAE: C57Bl/6 mice will be injected with AAV8-MOG or control vector for hepatocyte-specific expression. At 4 weeks after gene transfer, induction of EAE will begin. Mice will be monitored daily and neurological impairment will be recorded on a detailed clinical scale. Weekly, blood/serum will be collected and analyzed for frequency of activated CD4, CD8, and Tregs by flow cytometric analysis, and α-MOG antibody formation will be quantified via ELISA. Upon termination, histology of harvested tissues will be evaluated for transgene expression (liver), magnitude and phenotype of infiltration of inflammatory cells, demyelination, and white matter damage (CNS). Establishing a baseline correlation of histology to clinical score (especially in control mice) will be essential for identifying success in subsequent aims.

Reversal of EAE: In this disclosure, induction of EAE in mice is first performed. Upon the first signs of EAE, mice will be randomly selected to receive hepatic gene transfer using AAV8-MOG or control vector. A detailed clinical assessment will be recorded daily. At various time points, blood/serum will be collected and analyzed as above. Upon sacrificing, liver and CNS tissue will be harvested and preserved for pathological and histochemical analysis.

Ex vivo functional analysis of tolerogenic Tregs: To determine if the AAV8-MOG induced Tg-specific Tregs are immunosuppressive, $GFP^+$Tregs isolated by FACS from transgenic mice ("$Foxp3^{EGFP}$," B6.Cg-$Foxp3^{tm2Tch}$/J) that received vector 4 weeks earlier will be co-cultured with allogeneic splenocytes obtained from 2D2-TCR mice (MOG specific TCR) in the presence of MOG peptide. Cells and culture supernatant will be analyzed for activation, apoptosis, Th1/Th2/Th17 cytokines, or CTL activity via specific assays.

In vivo adoptive transfer of Tregs: To test whether the immunosuppressive function of Tg-specific Tregs is able to attenuate disease progression, $GFP^+$Tregs, isolated as above, will be adoptively transferred into (a) naive mice that will subjected to EAE induction 24 hours later and (b) mice that have undergone MOG-induced EAE. At various time points, blood/serum will be collected, and liver and CNS tissue will be harvested and analyzed as above.

The overall theme of the present invention is the development of a gene therapy-based method for in vivo induction of endogenous antigen (Ag)-specific regulatory T-cells (Tregs) using liver-directed Adeno-associated virus (AAV) gene therapy, as a novel treatment strategy for autoimmune diseases, e.g., multiple sclerosis (MS).

As noted above, MS is an autoimmune neurodegenerative disease of the central nervous system (CNS) in which the etiology is not well understood. Although auto-aggressive $CD4^+$ T cells play a central role, the breakdown of immune tolerance mechanisms that permit activation of naive myelin-specific T cells is considered an initial step in the pathogenesis of MS. A number of pivotal studies in rodent models have substantiated that Ag-specific Tregs have a significant role in modulating autoimmune CNS disease and can be highly effective at treating MS.[1-5] Consequentially, there has been a major focus in developing protocols that stimulate Treg numbers and their function. Unfortunately, successful therapeutic use of Tregs has been limited by the lack of safe and effective Ag-specific protocols for isolation and expansion that are suitable for translation.

Using the AAV gene transfer platform, it has been clearly demonstrated that hepatocyte-restricted transgene expression from an optimized AAV vector can reliably induce immune tolerance to various therapeutic proteins, including coagulation factor IX (F.IX), α-1-antitrypsin, erythropoietin, and lysosomal storage enzymes, among others.[6] Tolerance induction after hepatic gene transfer involves a combination of mechanisms. Importantly, AAV induced tolerance is mediated by Ag-specific CD4+CD25+FoxP3+ Tregs, which is critically dependent on achieving and maintaining adequate hepatocyte-restricted transgene expression.[7-9] It has also been demonstrated that AAV induced Tregs can actively suppress antibody formation and cytotoxic CD8+ T cell responses against the transgene product.[7,10,11] Tolerized animals fail to form antibodies to the transgene even after subsequent attempts to immunize with protein formulated in adjuvant.[10-12] Efficient hepatic gene transfer induces a TGF-β dependent CD4+CD25+FoxP3+ Treg response that confers a dominant state of Ag-specific immune tolerance that is maintained even when the antigen was later introduced in other tissues in a highly immunogenic manner.[7,12] Induction of programmed cell death of effector T cells further tilts the balance toward tolerance, which is effectively enforced by induced Treg.[13,14] Published data have demonstrated that hepatic AAV tolerance can also reverse pre-existing immune responses to F.IX in a hemophilia B mouse model.[15] These now well-established concepts have been further supported by results from other laboratories and have led to the development of several immune tolerance protocols for genetic diseases.[16-37]

Over 400,000 people in the United States currently are living with MS, and 10,000 new cases are diagnosed each year. With a 1:600-800 lifetime risk of developing the disease, MS is the most common cause of neurologic disability in young adults between 18 and 45 years of age. This demographic represents the majority of the adult workforce in the United States; therefore, the direct and indirect costs of health care for this population currently are estimated at $12 billion annually.[38]

Multiple sclerosis (MS) is a protracted, immune-mediated disease of the CNS. MS is a neuroinflammatory autoimmune disease in which T cell-driven inflammation leads to demyelination and damage of axons. Although the exact pathogenesis of MS remains unknown, it is believed that myelin-specific CD4+ T cells play a central role in initiating and orchestrating CNS inflammation. A failure of central and peripheral mechanisms (particularly Tregs) to maintain self-tolerance and control potentially pathogenic auto-reactive lymphocytes is thought to be a key event in the development and pathogenesis of MS.[4,39-41] Several studies using in vitro suppression assays have documented functional impairments of Tregs from MS patients.[42,43] Experiments in mice using adoptive transfer of myelin-specific Tregs or Treg depletion have also provided evidence that Tregs can control the development and severity of experimental autoimmune encephalomyelitis (EAE) and accumulate within the CNS during the recovery.[44] It has also been shown that transgenic mice expressing myelin basic protein (MBP) could prevent the onset of EAE disease in mice in a Treg dependent process.[45,46] In fact, the mechanism-of-action for several of the currently approved immune-modulators used in the treatment of MS are associated with restoring Treg homeostasis.[39,47,48]

Cumulatively, the literature clearly supports the concept that Treg cells influence the susceptibility and progression of disease. Recent advances have led to the recognition that Ag-specific Tregs represent an ideal form of cell therapy for MS. However, Tregs are still among the least understood T cell subsets, and consequently the most difficult to use for therapeutic applications.

Gene therapy with AAV vectors induces antigen-specific immune tolerance. Gene therapy continues to be a proven and powerful new tool for the treatment of a broad spectrum of diseases.[49] AAV vectors specifically have had great successes with in vivo gene transfer to a variety of target tissues.[12] For example, AAV gene transfer to retinal epithelial cells restores vision in children with Leber Congenital Amaurosis (LCA) and with Choroideremia.[50,51] An AAV vector for treatment of lipoprotein lipase is the first gene therapy drug approved in the Western world ("Glybera").[52] Gene therapy by hepatic AAV administration has resulted in sustained expression of factor IX (F.IX) at levels of >5% of normal in hemophilia B patients, changing their bleeding phenotype from severe to mild.[48] Hepatic AAV gene transfer promotes tolerance via induction of transgene product-specific Treg, a phenomenon that can be exploited for the treatment of MS.[6, 21, 34, 35, 49, 53]

Effective therapy for established EAE needs to consider induction of multiple direct and indirect (cross-tolerance) regulatory mechanisms, including the induction of antigen (Ag)-specific CD4+CD25+FoxP3+ Tregs across multiple endogenous myelin epitopes (epitope spreading). Neutralization of epitope spreading remains one of the most elusive aspects of developing effective MS treatments. See Zhang et al., *J. Immunol.*, 184:6629-6636 (2010), herein incorporated by reference.

The literature supports the idea that Tregs are potent suppressors of EAE, and essential to establish disease remission. However, very few studies have addressed how to generate such Ag-specific Tregs in a manner that is both reliable and translatable. The present disclosure demonstrates that hepatic gene transfer using AAV8 vectors to express full-length myelin-associated proteins will induce Ag-specific Tregs across multiple endogenous epitopes in a manner that has been shown to be safe, feasible, and long lasting. This disclosure is innovative in several respects: (i) This is the first time a clinically proven AAV vector technique is used to re-establish immunological tolerance in the context of an autoimmune disease; (ii) exemplary AAV8 vectors have been designed to express a full-length neuroprotein (myelin oligodendrocyte glycoprotein (MOG) or proteolipid proteins (PLP)), thus abrogating the need for identifying HLA/MHC specific epitopes and enhancing the potential for success; and (iii) Based on published data, incorporating transient immune modulation using the FDA approved mTOR inhibitor rapamycin should provide a synergistic effect, facilitating tolerance induction to neuroantigens by further tipping the balance from Teff to Treg in vivo.[54-56]

The inventor has shown that AAV8 liver gene transfer of a neural protein (PLP or MOG) induces activation of Ag-specific Tregs, and is sufficient to re-establish immune tolerance and abrogate disease progression in the CNS of a murine model for MS.

Hepatic gene transfer with AAV vectors can reliably induce a robust antigen-specific immune tolerance in experimental animals to a variety of therapeutic proteins.[7, 9,13, 54,57] Here, tolerance was characterized by lack of antibody formation, helper T cell response, or CTL response to the transgene product, even after subsequent challenge with protein in adjuvant. Using mice transgenic for a T cell receptor, evidence of anergy and deletion of transgene product-specific CD4 T cells was found.

That immune tolerance established by hepatic transgene expression is maintained even when the antigen was subsequently expressed in a highly immunogenic manner in other organs, such as skeletal muscle, or even delivered intravenously.[7] These results revealed that liver directed gene therapy could abrogate potential cytotoxic CD8 T cell responses, indicating that the range of immune tolerance extends beyond the level of antigen expression initially achieved by hepatic gene transfer.

Hepatic AAV gene transfer efficiently and rapidly reversed pre-existing high antibodies titers and provided long-term correction of haemostasis in a murine hemophilia B model.[15,56] High levels of transgene protein suppressed memory B cells and increased Treg induction, indicating direct and indirect mechanisms of suppression of inhibitor formation. There is an increasing body of evidence that B cells and autoantibodies may play a pathogenic role in demyelinating disease.[58,59]

Immune tolerance induction by hepatic AAV gene transfer does not require protein to be secreted. Although hepatic expression is crucial for tolerance induction, secretion from hepatocytes for systemic delivery of the transgene product is not required. Expression of a cytoplasmic a neo-antigen in as few as 3% of the hepatocytes is sufficient to induce Tregs and provide long-term suppression of inflammatory responses.[57]

Results

Successfully establishing multiple models of EAE induction: EAE is a widely accepted experimental mouse model of multiple sclerosis that is induced in susceptible animals by immunization with central nervous system antigens. EAE is an autoimmune disease that is mediated by $CD4^+$ T helper 1 ($T_H1$) cells and interleukin-17 producing $T_H17$ cells that are reactive to components of the myelin sheath. The cells infiltrate the nervous parenchyma, release pro-inflammatory cytokines and chemokines, promote leukocyte infiltration and contribute to demyelination.

EAE can be induced in various strains of mice using different neuro-proteins emulsified in complete Freud's adjuvant (CFA). Disease progression and pathology manifests differently with each combination. For example, EAE induced by MOG produces encephalitogenic T-cells and demyelinating autoantibodies in C57BL/6 mice. The resulting disease is a chronic-progressive disease characterized by axonal demyelination and white matter lesions in the spinal cord, and is generally considered to be a relevant model for human immune-mediated demyelinating disease.[60] EAE can also be induced in SJL (H-2s) mice using the major encephalitogenic PLP peptide ($PLP_{139-151}$). Here the disease is characterized by a relapsing-remitting course of paralysis, which allows assessment of the efficacy of various immune regulatory strategies in a re-occurring disease setting.

Figure 5A:
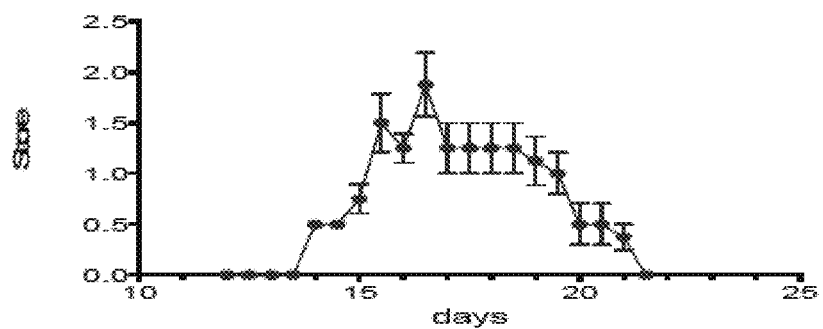
FIG. 5A and FIG. 5B show the mean clinical score of EAE mice.
Figure 5B:
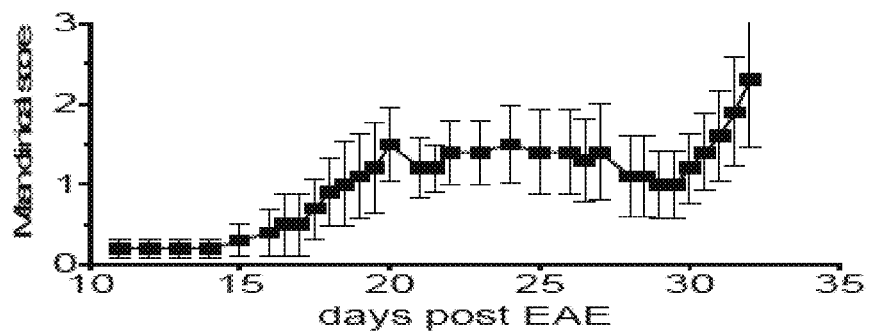

In this disclosure, the inventor demonstrates the timeline and clinical scoring for successful induction of EAE disease in two different mouse strains. In one experiment, 8-week-old female mice were injected subcutaneously with 200 µg myelin peptide emulsified in CFA containing 4 mg/ml *Mycobacterium tuberculosis*. Clinical signs of EAE began 12 days later at which time mice were evaluated twice daily. Mice were scored according to the severity of the clinical signs (FIG. 5A). In a similar experiment, EAE was induced in C57BL/6 mice (n=5) using MOG in order to develop a chronic progressive EAE disease (FIG. 5B)

Novel AAV8 vectors transduce mouse hepatocytes efficiently and express the delivered neural protein: AAV is a non-pathogenic single stranded DNA parvovirus with a genome size of approximately 4.7 kb. Serotypes with distinct tissue tropisms have been isolated from multiple vertebrate species, including humans. Viral vectors derived from AAV are devoid of viral genes and instead contain an expression cassette for the gene of interest, which is limited to ~5 kb in length. In this disclosure, an AAV8 serotype vector was chosen because it has strong natural tropism for hepatocytes after peripheral vein administration, avoiding the need for an invasive procedure. Additionally, it fails to transduce professional antigen presenting cells (APCs). The engineered vector constructs include a strong and highly hepatocyte-specific promoter.[10]

Figure 4A:
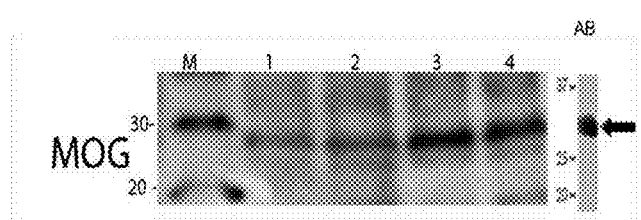
FIG. 4A and FIG. 4B show the AAV8 expression of MOG.
Figure 4B:
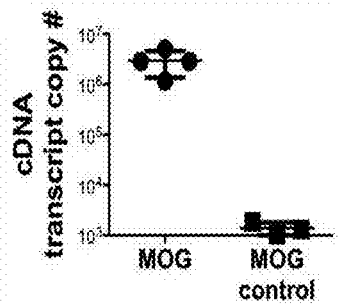

The newly synthesized vectors were evaluated for transduction efficiency. To demonstrate efficacy, the inventor assessed whether mouse hepatocytes could be transduced and express the neuro-protein transgene following tail vein injection. A group of mice was injected with $1 \times 10^{11}$ vector particles of AAV8-ApoE/hAAT-MOG. Two weeks later, using liver lysates, evidence of hepatic expression of MOG was probed by both western blot and qPCR analysis. The results demonstrate the ability of this novel vector to stably produce hepatic expression of the neuro-antigen after liver gene transfer (FIG. 4A and FIG. 4B).

AAV8-MOG produces hepatic transgene expression that can prevent the establishment of EAE: Previously, others have shown that ectopic expression of a myelin-associated protein using various transient methodologies promoted resistance to EAE.[18, 28, 45, 61] Unfortunately, these prior approaches have not developed into practical therapies for human autoimmune disease. Prior to this invention, the ability of AAV liver gene transfer to induce antigen specific suppression of autoimmune disease went untested in the scientific community.

Figure 6A:
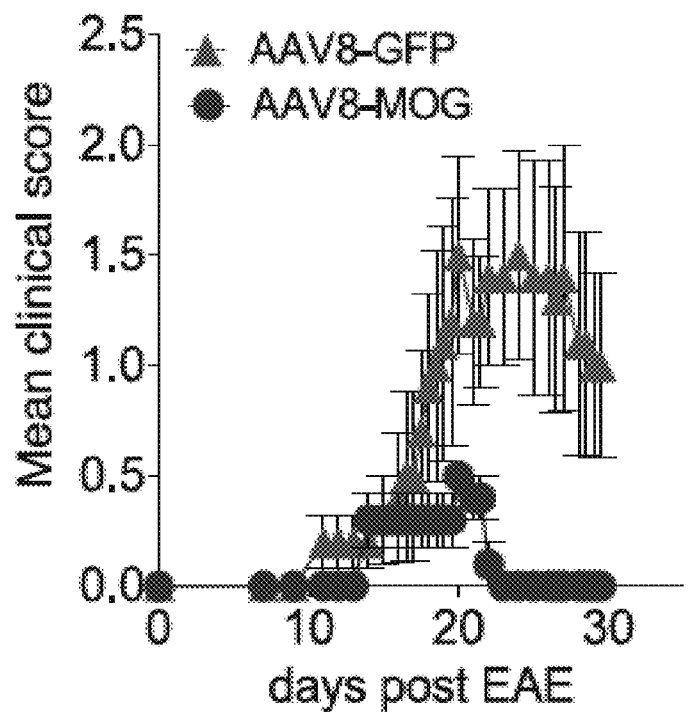
FIG. 6A, FIG. 6B, and FIG. 6C show AAV8-MOG prevented development of EAE in C57BL/6 mice. C57BL/6 mice (n=5) were injected with AAV8-MOG or control. EAE was induced 2 weeks later.
Figure 6B:
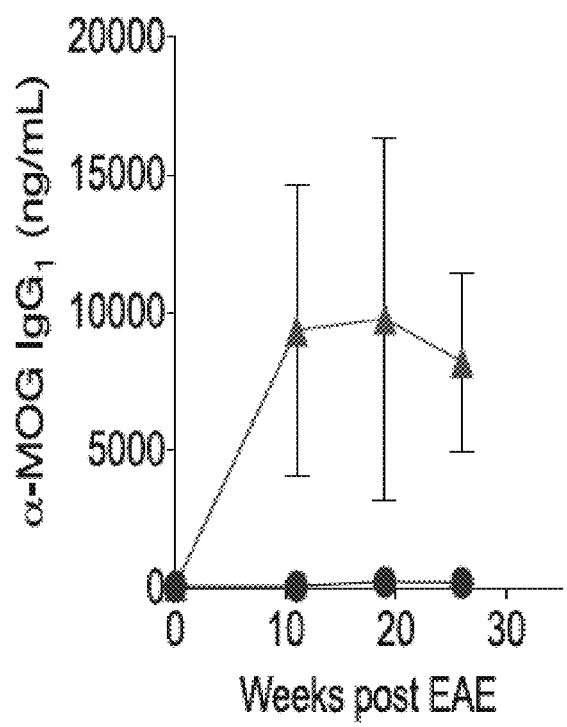
Figure 6C:
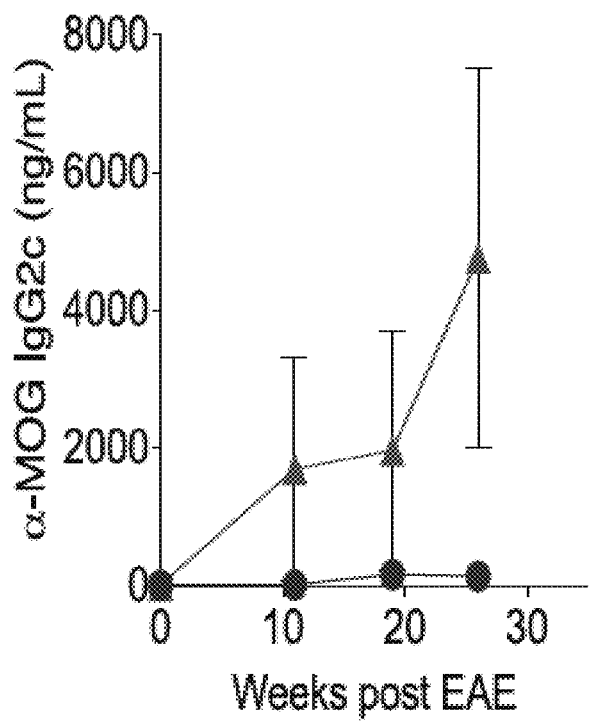

To further support this invention, a pilot study was performed. A small number of mice (n=5) were intravenously injected with $10^{11}$ vector particles via the tail vein with either AAV8-MOG or AAV8-GFP (control) vector. Two weeks later, EAE was induced using MOG in CFA as previously performed. Plasma samples were obtained at 0-, 7- and 14-days post EAE induction or at 0, 11-, 19-, 26-, and 35-days post EAE induction. The mice that received AAV8-MOG were essentially protected from developing EAE (FIG. 6A, FIG. 6B, and FIG. 6C). In contrast, those mice receiving the control vector developed severe EAE with elevated antibody titers. This data indicates that the vectors described herein not only express in the liver, but also had an immune modulatory effect.

Active suppression by Tregs plays a key role in the control of auto-reactive T cells and the induction of peripheral tolerance in vivo. In particular, the significance of Ag-specific Tregs in conferring resistance to organ-specific autoimmunity and in limiting autoimmune tissue damage has been documented in many disease models, including MS.[44] However, a safe and clinically feasible method for sustained expansion of endogenous Tregs has yet been identified.[41, 44, 60, 63] a treatment protocol based on liver-directed AAV gene therapy can durably induce Ag-specific tolerance, thus having the potential of blocking the pathogenic autoimmune response present in MS and inhibiting disease activity; while avoiding the severe side effects associated with many of the currently used immunotherapies. Based on these and related studies, AAV8-liver gene transfer can restore immunological tolerance against myelin-sheath antigens, such as MOG and PLP, by inducing Ag-specific Tregs in vivo.

Experimental approach and methods of analyses: This set of experiments tests vector constructs in order to verify efficiency of liver transduction and hepatic expression without adverse effects. Groups of (i) C57BL/6 or (ii) SJL/J mice (7-8 weeks old) will be injected with the $10^{11}$ vector particles (vp) (effective dose of vector as previously determined) of (i) AAV8-MOG or (ii) AAV8-PLP (respectively), or control (irrelevant transgene, GFP) intravenously via the tail vein. Beginning on day 0, blood will be collected every 2 weeks and analyzed for the frequency of various T cell populations using standard markers of T cell phenotype (including, but not limited to, CD4, CD8, FoxP3, CD25, CD62L, CD44). Humoral immune responses (e.g., α-IgG1, -IgG2a, -IgG2c responses) may be determined via antigen specific ELISA. At 14 days post gene transfer, half of the mice from each group may be randomly selected and humanely euthanized. Tissues (blood, liver, spleen, and CNS (brain/spinal cord)) may be harvested for analysis. Hepatic transgene expression levels may be determined at the mRNA level using real-time quantitative PCR. Absolute and relative hepatic protein levels of the transgene will also be determined via western blot using liver lysates. At 90 days post injection, the remainder of the mice may be processed similarly to establish sustained transgene expression. Additionally, some mice may be subjected to EAE induction at various time points after vector administration and evaluated for prevention of disease, as described in preliminary data. Aliquots of the collected tissue samples may be archived as a reference material.

In vitro functional suppression analysis of Ag-specific Tregs induced by AAV8 hepatic gene transfer. Splenic Tregs (CD4$^+$CD25$^+$) may be magnetically sorted from mice that received (i) AAV8-MOG or (ii) AAV8-PLP or AAV8-GFP (control) vector and co-cultured with graded numbers of CFSE labeled cells obtained from 2D2-TCR mice (this C57Bl/6 mouse line expresses a TCR which recognize MOG$_{35-55}$ in the context of H-2 IA$^b$) or splenocytes harvested and labeled from SJL mice that have been previously immunized with PLP/adjuvant in the presence of anti-CD3/CD28 coated beads (provides APC independent/non-specific activation of Teff). Treg mediated suppression of proliferating effector cells may be determined by flow cytometry. Cell-culture supernatants may be analyzed for Th1/Th2/Th17 cytokines via specific assays. Results may be compared with data from naïve and EAE induced mice (in which many CD4$^+$CD25$^+$ cells should represent activated effector rather than Treg). This disclosure demonstrates Ag-specific functional suppression from the vector induced Tregs compared to controls.

Based on the initial data and published studies, maximal transgene expression may occur by 2 weeks, which remains fairly unchanged over time, thus indicating stable transduction of hepatocytes.[10] Since the vector constructs have been purposely designed to express full length MOG or PLP and include a strong hepatocyte promoter, it is also expected that AAV8 vector-mediated expression may be constrained to the hepatocytes and not secreted. Sequestering the transgene will constrain pathological consequences of freely circulating AAV-derived neuroantigen. Lastly, the inventor does not expect inflammatory responses in any tissues and analysis of liver enzymes (ALT/AST) should demonstrate an absence of hepatotoxicity. Furthermore, based on pilot studies, it is expected that vector administration prior to EAE induction will prevent disease development. A positive outcome would also be the absence/significant reduction in antigen specific antibody responses. Lastly, results from the Treg suppression assays are expected to show that suppression induced by hepatic transgene expression is facilitated by activation of Ag-specific Tregs.

Even though the literature overwhelmingly supports the idea that Tregs are potent suppressors of EAE and are the driving force to switch from disease progression to remission, very few studies in the past have addressed a method by which to generate such Ag-specific Tregs that is both safe and effective.[64] In theory, this could be achieved by two approaches. The first would be to isolate Tregs, expand their numbers ex vivo, and then reintroduce them, with the idea that an increase in overall frequency of polyclonal Tregs might influence ongoing disease. In 2004, Bluestone's group in a type-1 diabetes model provided initial proof of principle for this approach.[65] More recently, others have further shown that using expanded Tregs from myelin-specific transgenic TCR mice is more effective.[64] The second approach is to administer a suitable treatment that promotes the expansion of Treg numbers and/or function in vivo. Recent reports have described the use of various compounds (e.g., nano-particles/small molecules) to enhance Treg function in EAE, while others try to augment antigen presentation in order to generate Tregs.[64,66] In the end, a reliable and translatable method for induction of the disease relevant Ag-specific Tregs is still lacking—until now. This proposal presents a methodology that will provide a durable method for the continued in vivo induction of endogenous Ag-specific Tregs. Based on previous work, hepatic gene transfer using AAV8 vectors expressing full-length MOG or PLP should induce Ag-specific Tregs across multiple endogenous myelin epitopes in a manner that has been shown to be safe, feasible, and long-lasting.

Experimental approach and methods of analyses. Here, mice will first undergo active induction of EAE using either (i) MOG or (ii) PLP. At the first clinical signs of EAE, in MOG-induced chronic-progressive mice, or at the peak of disease, in PLP-induced relapsing-remitting mice, AAV8-MOG or AAV8-PLP vector (respectively) or AAV8-GFP for control mice may be given. Mice may be clinically scored by weight and neurological deficit 2× daily. Blood may be collected and analyzed for humoral (IgG) responses as before. At ~45 days, each cohort of mice may be perfused and randomly subdivided into 2 groups. Group 1 will have brain, spinal cord, and liver tissues harvested and preserved for histopathological and immunofluorescent analysis. Infiltrating lymphocytes may be isolated from the brain and spinal cords from mice in Group 2 (as previously described[67]). The frequency of various T cell populations may be analyzed using standard markers of T cells (including, but not limited to, CD4, CD8, FoxP3, CD25, CD62L, CD44, CTLA-4, CD103). Liver tissue may be subjected to transcriptional and protein analysis as shown. Results may be compared to control mice and reference material. Portions of the tissue may also be archived for future studies.

It is expected that therapeutic treatment with a single injection of AAV8-MOG or -PLP vector at the onset or peak of the disease will result in a dramatic remission in clinical impairment. There should be a concurrent reduction in antibody titers and/or frequency of B cell responses to the EAE inducing peptide, as compared to control-vector treated mice. CNS inflammation is characteristic of EAE, and the degree of lymphocyte infiltration correlates with disease progression; whereas, the presence of Tregs in the CNS during EAE has been associated with diminished inflammation and resolution of clinical disease.[68] Hence, it is expected that a significant reduction of inflammatory infiltrates in the CNS of vector-treated mice will be observable upon histopathological analysis. This would suggest that the induced Ag-specific Tregs migrating to the site of CNS damage are protective and are capable limiting damage mediated by effector T cells. Additionally, the natural relapsing-remitting nature of PLP-induced EAE may be exploited by timing the injection of the AAV8-PLP vector so that the peak effects of induced tolerance correspond to when the disease is relatively quiescent (remitting).

On the other hand, mice that receive MOG for EAE induction begin showing neurological impairments after ~12 days, which progressively escalate. In this scenario, it is possible that some level of inflammation will still be present, although the phenotypic analysis of the T cell populations show that absolute numbers of T cells infiltrating the CNS is lower, with a greater Treg:Teff ratio.

Transient immunosuppression using rapamycin. Rapamycin readily crosses the BBB thus exerting direct effects within the CNS. Blocking the activation of the mTOR pathway, rapamycin prevents activation of T cells by inhibiting their response to IL-2 thus preventing Ag-induced proliferation of Teff, while selectively allowing expansion of functional $CD4^+CD25^+FoxP3^+$ Tregs. In EAE, rapamycin is effective in preventing the onset of disease; however, suppression of established disease is only maintained with continued use.[69] In a further series of experiments, vector-treated mice are transiently immunosuppressed. Groups of mice are then injected with AAV8-MOG, -PLP, -GFP or PBS at specific time-points that correspond to either initial onset or peak of disease. Concurrently, mice receive intraperitoneal rapamycin (1 mg/kg), or PBS (sham control) daily for 14 consecutive days.[69] At specific time points corresponding to pre- and post-treatment and significant changes in clinical scoring, tissues and lymphocytes may be harvested from the CNS and spleen from randomly selected mice. Histopathological changes within the tissues can then be identified. Isolated cells are then phenotyped and the frequency of Tregs and Teffs from the different compartments may be determined and compared to control groups to validate the efficacy of rapamycin co-treatment.

Regardless of AAV8 administration, treatment with rapamycin alone is expected to transiently produce a rapid reduction in the clinical presentation of EAE because it selectively inhibits Teff proliferation.[69] However, when used in conjunction with AAV8 liver gene transfer, rapamycin treatment has a synergistic effect that results in an increase in vector induced Ag-specific $FoxP3^+$ Tregs (since they are less sensitive to mTOR signaling inhibition) with a corresponding decrease in effector T cells.[70] The shift to tolerance is further potentiated by the fact Tregs have been shown to mediate selective inhibition of antigen-specific Th1 cells in the CNS of EAE.[71]

The data clearly supports the ability of AAV liver gene transfer to induce Ag-specific Tregs and invoke immune tolerance. Because accumulation of Tregs in the CNS during the recovery phase of EAE has been a consistent finding in actively induced models, it seems unlikely that the present therapy would not have, at least to some degree, a clinical or pathological benefit.[3,64,71,72]

Therapeutic Regimens

The therapeutic regimens presented herein address an unmet need by providing an effective treatment for diseases such as MS using a gene therapy approach. Using the AAV vector platform disclosed herein to deliver full-length proteins offers a superior HLA-independent approach for Ag-specific Treg induction compared to other ex vivo or epitope-restricted Treg mediated therapies. Additionally, AAV gene transfer results in continuous Treg generation because of the long-term hepatocyte expression of transgene.[73]

In some embodiments, progression of an autoimmune disease (e.g., multiple sclerosis) in the mammal is inhibited or reversed for at least 50 days, at least 100 days, at least 150 days, at least 175 days, at least 200 days, or more than 200 days after administration of any of the disclosed rAAV particles or compositions comprising any of the disclosed rAAV nucleic acid vectors to the mammal. In particular embodiments, progression of the autoimmune disease in the mammal is inhibited or reversed for at least 125-150 days. In some embodiments, the mammal is an experimental animal, such as a rodent. In some embodiments, the mammal is a human.

In some embodiments, progression of an autoimmune disease (e.g., multiple sclerosis) in a mammal at risk of developing symptoms is prevented, either partially or completely. In some embodiments, progression is prevented for at least 50 days, at least 100 days, at least 150 days, at least 175 days, at least 200 days, or more than 200 days after administration of any of the disclosed rAAV particles or compositions comprising any of the disclosed rAAV nucleic acid vectors to the mammal.

In some embodiments, the composition or particle comprising the rAAV nucleic acid vector is administered to a mammal diagnosed with and/or suffering from an autoimmune disease such as multiple sclerosis (MS). In some embodiments, the mammal suffers from symptoms of the disease. In some embodiments, the mammal suffers from an early stage of the disease. In some embodiments, the mammal suffers from a late stage of the disease.

In some embodiments, the composition or particle comprising the rAAV nucleic acid vector is administered to the mammal in a single injection. In some embodiments, the particle is administered in two or more injections in a single doctor's (physician) visit. In some embodiments, the particle is administered in two or more injections among multiple doctor's visits, or throughout the course of a therapeutic regimen.

In some embodiments, the therapeutically-effective amount of the rAAV nucleic acid vector in any of the disclosed compositions is an amount of between $10^6$ and $10^{14}$ vector genomes (vgs)/kg of the subject. In some embodiments, the therapeutically-effective amount is greater than $10^{14}$ vector genomes (vgs)/kg subject. In some embodiments, the therapeutically-effective amount is about $10^{11}$ vector genomes (vgs)/kg. In some embodiments, the therapeutically-effective amount is $10^6$, $10^7$, $10^8$, $10^9$, $10^{10}$, $10^{11}$, $10^{12}$, $10^{13}$, or $10^{14}$ vgs/kg.

In some embodiments, progression of the autoimmune disease in the mammal is inhibited or reversed for at least 150 days in a subject suffering therefrom that is refractory to other MS therapies, such as one or more standard-of-care MS therapies. In some embodiments, progression of the autoimmune disease in the mammal is inhibited or reversed for at least 150 days, in a subject that is refractory to a small-molecule MS therapy, such as a BTK inhibitor or a pyrimidine synthesis inhibitor. In some embodiments, the subject is human. In some embodiments, the composition or particle comprising the rAAV nucleic acid vector is administered to the subject in a single injection.

In some embodiments, progression of relapse-remitting forms of MS in the mammal is inhibited or reversed for at least 50 days, at least 100 days, at least 150 days, at least 175 days, at least 200 days, or more than 200 days after administration of any of the disclosed rAAV particles or compositions comprising any of the disclosed rAAV nucleic acid vectors to the subject suffering therefrom.

Example 4—Further Data from EAE Mouse Model and Assessment of Other Proteins

Figure 11:
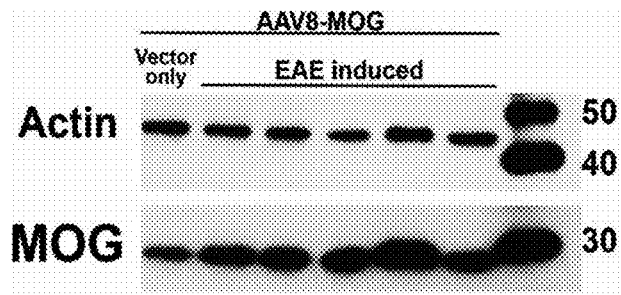
FIG. 11 shows hepatic transgene expression of MOG. Western blot analysis from protein extracted from liver of MOG induced EAE mice injected with AAV8-MOG.

Animals were injected intravenously via tail vein with $10^{11}$ vector particles of AAV8-apoE/hAAT-MOG. The MOG sequence used was murine MOG. It was shown that MOG transgene was expressed in the liver as evidenced by increased amounts of MOG protein (FIG. 11) in samples from the liver.

Figure 12:
FIG. 12 shows Luxol Fast Blue (LFB) staining of spinal cords from mice that received AAV8-GFP and had EAE induced (left) or not (right).

To ensure that AAV did not interfere with the development or progression of EAE in the mouse model described in the other Examples, control AAV8-GFP was injected intravenously into mice. Two weeks later, EAE was induced or not induced. The AAV control vector did not appear to interfere with development or progression of EAE (FIG. 12).

Figure 13B:
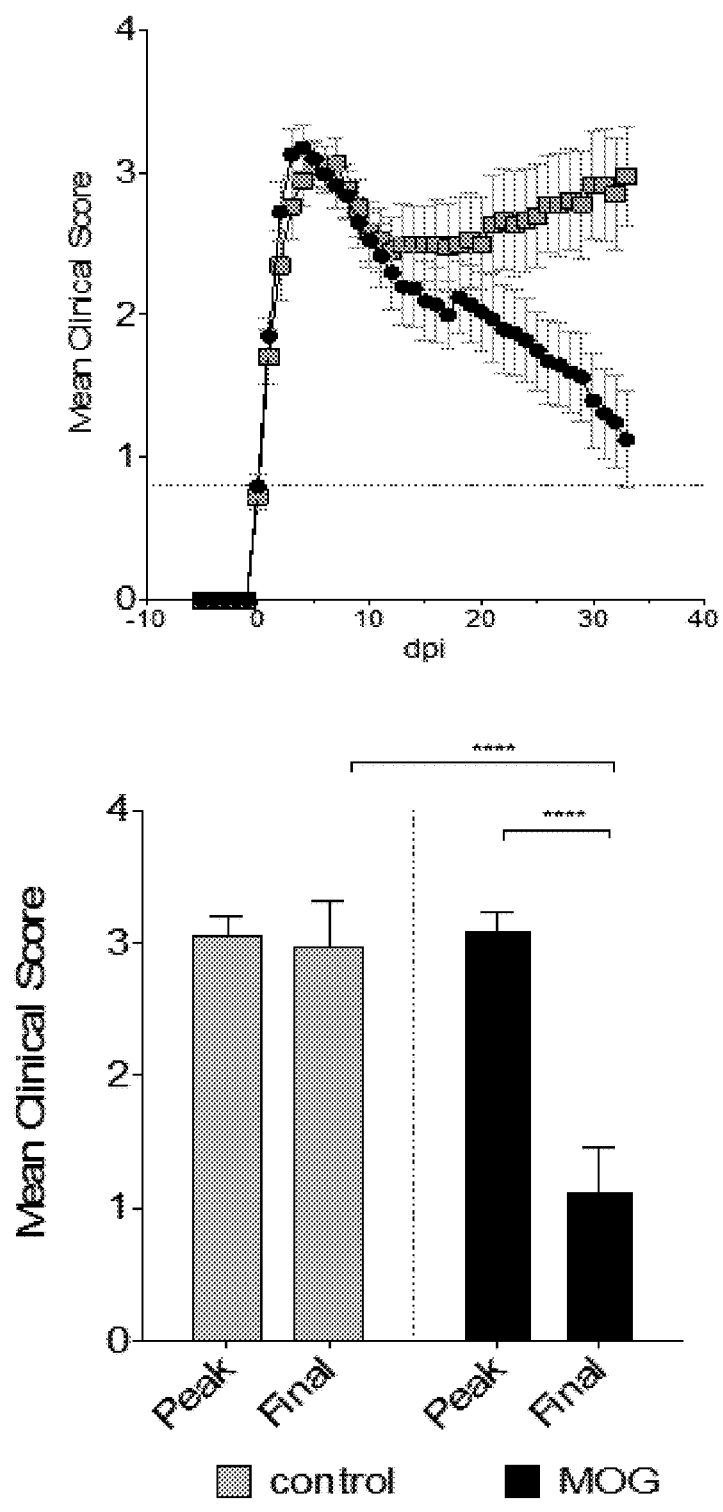

In another study, EAE was induced in C57BL/6 mice. At various times of neurological deficit of mean clinical score (MCS) ~0.3, ~0.8, or ~1.3, mice received AAV8-MOG or control vector. Mean clinical score was recorded. Even at increasing disease pathology, AAV-MOG vector had significantly reduced neurological deficit compared to control vector treated mice (FIGS. 13A-13C). Bar graphs show statistical significance between final scores and peak-to-final scores.

In a further study, serial sections of spinal cord were taken from an EAE-induced female mouse ~35 days after receiving control vector (MCS=4.0). Hematoxylin and eosin stain showed areas of high inflammatory infiltration (FIG. 14A). Luxol fast blue stain showed areas of demyelination (FIG. 14B). In contrast, serial sections of spinal cord from an EAE-induced female mouse ~35 days after receiving AAV-MOG vector (MCS=1.25) showed suppression of inflammation. Hematoxylin and eosin stain showed diminished infiltration (FIG. 15A). Luxol fast blue stain appeared to have less areas of demyelination as a result of the suppression of the inflammation (FIG. 15B).

Figure 16A:
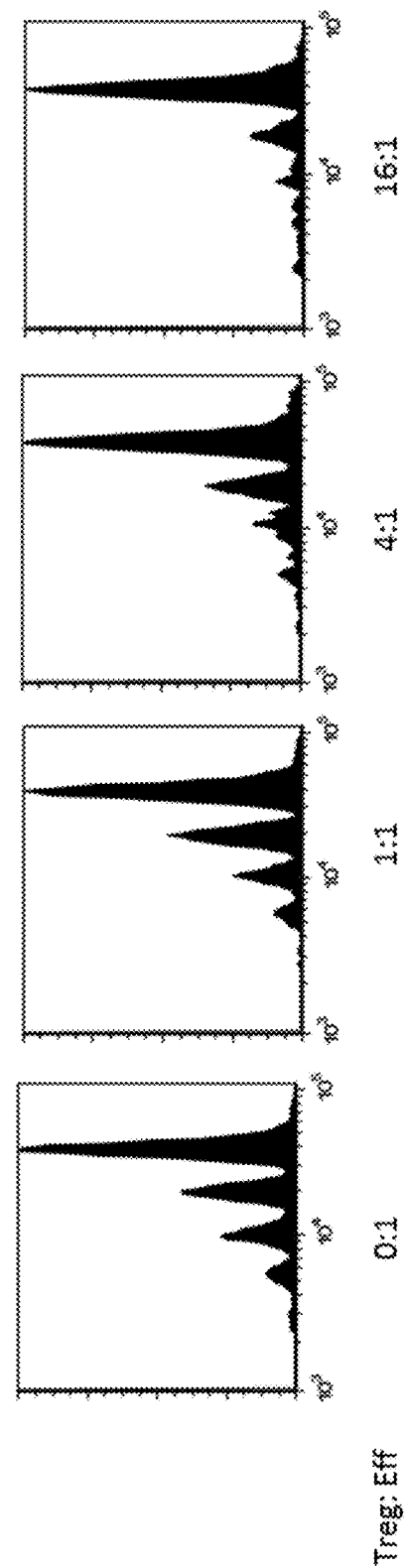
FIG. 16A and FIG. 16B show that Tregs isolated from spleens of AAV-MOG treated mice are functionally suppressive.
Figure 16B:
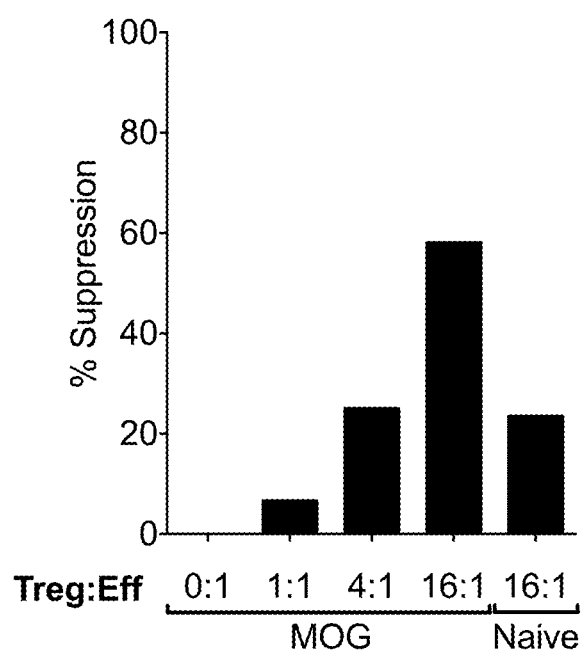
Figure 17A:
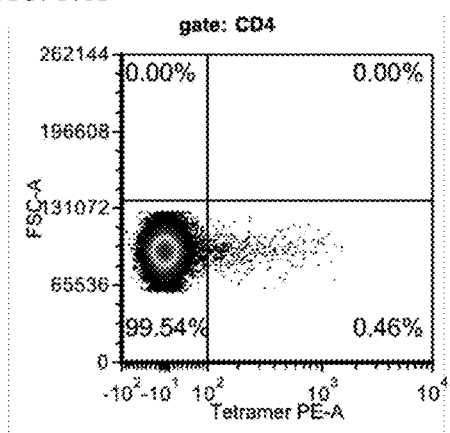
FIG. 17A, FIG. 17B, FIG. 17C and FIG. 17D show that AAV-MOG vector induces antigen specific Tregs. Splenocytes from mice injected with AAV-MOG vector 8 weeks prior showed an increase in frequencies of I-Ab $MOG_{35-55}$ Tetramer positive CD4+ (FIG. 17A) and Treg+ (FIG. 17C) compared to control tetramer positive CD+ (FIG. 17B) and Treg+ (FIG. 17D).
Figure 17B:
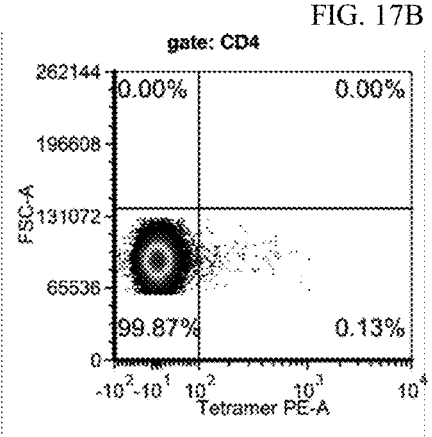
Figure 17C:
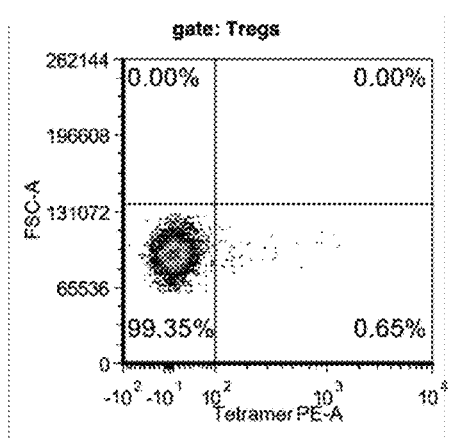
Figure 17D:
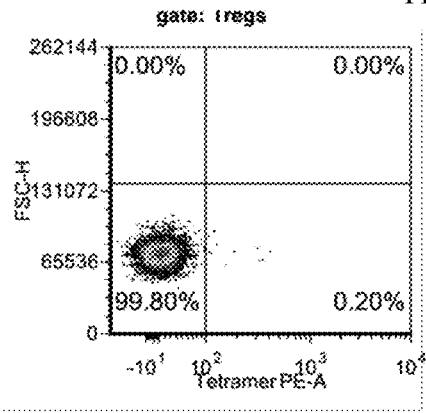

In another study, regulatory T cell (Treg)-mediated suppression was measured by CFDA-SE Cell Tracer. Effector T cells (Teff) were isolated from C57BL/6 mice and labeled with CFDA. Cells were cultured either alone or in the presence of Tregs at a various Treg:Teff ratios. After 72 hours, proliferation was determined by CFDA dilution and flow cytometric analysis. Tregs isolated from spleens of AAV-MOG treated mice were found to be functionally suppressive (FIGS. 16A and 16B).

In a further study, the ability of AAV-MOG to induce antigen specific Tregs was assessed. Splenocytes from mice injected with AAV-MOG vector 8 weeks prior showed an increase in frequencies of I-Ab $MOG_{35-55}$ Tetramer positive CD4+ and Treg+ compared to control tetramer (FIGS. 17A-17D), indicating that AAV-MOG vector induced antigen-specific Tregs.

Figure 18:
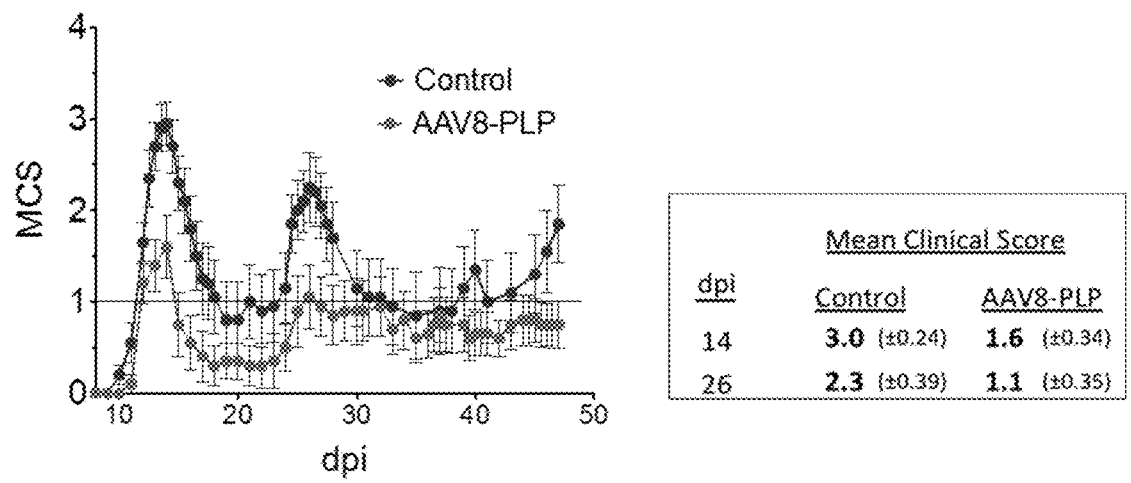
FIG. 18 shows that AAV8-PLP reduces clinical severity in mice with PLP-induced relapsing-remitting EAE.

Next, a PLP vector was tested. AAV8-PLP was used for this part of the study. The PLP used was murine PLP. This initial proof-of-concept experiment demonstrated the timeline and clinical scoring for successful induction of PLP/EAE and the potential therapeutic benefit of liver gene transfer. Female SJL mice were injected with AAV8-PLP or control 2 weeks before immunization with 200 μg PLP emulsified in CFA containing 4 mg/ml *Mycobacterium tuberculosis*. Clinical signs of EAE began ~10 days later, at which time mice were evaluated twice daily. Mice were scored according to the severity of the clinical signs (FIG. 2). Clearly, mice receiving AAV8-PLP vector had a significant reduction in disease at the peak of onset (FIG. 18). There was also a significant decrease in MCS during relapse (day 26) with fewer relapses overall (FIG. 18). These results show that AAV8-PLP reduced clinical severity in mice with PLP-induced relapsing-remitting EAE. Increased reduction or complete prevention is anticipated with optimization of vector dose and timing.

Figure 19A:
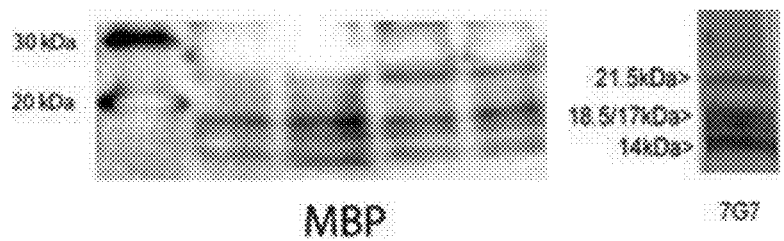
FIG. 19A and FIG. 19B show testing of a MBP vector.
Figure 19B:
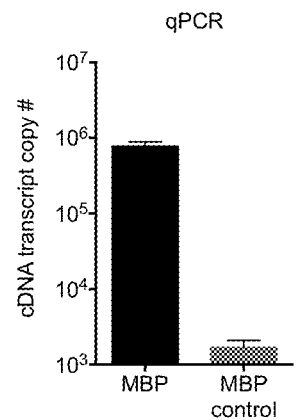

Lastly, a MBP vector was tested. AAV8-MBP was used for this part of the study. The MBP used was murine MBP. Western blot analysis from protein extracted from liver of mice injected with AAV8-MBP showed an increase in MBP expression (FIG. 19A), which was consistent with an increase in mRNA levels (FIG. 19B).

Example 5—Gene Therapy-Induced Antigen-Specific Tregs Inhibit Neuroinflammation and Reverse Disease in a Mouse Model of Multiple Sclerosis The devastating neurodegenerative disease multiple sclerosis (MS) could substantially benefit from an adeno-associated virus (AAV) immunotherapy designed to restore a robust and durable antigen-specific tolerance. However, developing a sufficiently potent and lasting immune-regulatory therapy that can intervene in ongoing disease is a major challenge and has thus been elusive. This problem was addressed herein by developing a highly effective and robust tolerance-inducing in vivo gene therapy. Using a pre-clinical animal model, a liver-targeting gene transfer vector that expresses full-length myelin oligodendrocyte glycoprotein (MOG) in hepatocytes was designed. It is shown here that by harnessing the tolerogenic nature of the liver, this powerful gene immunotherapy restores immune tolerance by inducing functional MOG-specific regulatory T cells (Tregs) in vivo, independent of major histocompatibility complex (MHC) restrictions. It is demonstrated herein that mice treated prophylactically are protected from developing disease and neurological deficits. More importantly, it is also demonstrated herein that when given to mice with preexisting disease, ranging from mild neurological deficits to severe paralysis, the gene immunotherapy abrogated CNS inflammation and significantly reversed clinical symptoms of disease. This specialized approach for inducing antigen-specific immune tolerance has significant therapeutic potential for treating MS and other autoimmune disorders.

Introduction

Multiple sclerosis (MS) is a complex T cell-driven autoimmune disease of the CNS for which there is no known cure. Although the exact etiology is unknown, the disease is thought to result from peripheral activation of myelin-reactive CD4+ effector T cells that have escaped immune-regulatory mechanisms.[39-41,4,74]

Active suppression by regulatory T cells (Tregs) plays a key role in the control of self-antigen-reactive T cells and the induction of peripheral tolerance in vivo.[40] Unfortunately, abnormalities in the frequency or suppressive function of peripheral CD4+CD25+FOXP3+ Tregs have been observed in various autoimmune diseases, including MS.[75,76]

An attractive therapeutic strategy for restoring self-tolerance and controlling disease is to selectively induce autoantigen-specific CD4+CD25+FOXP3+ Tregs. Numerous studies have demonstrated the power of Treg-based immunotherapies.[75,77,78] For example, it has been shown that adoptive transfer of polyclonal CD4+CD25+ Tregs can temporarily prevent or reduce the neurological symptoms of experimental autoimmune encephalomyelitis (EAE), the murine model of MS.[79] Recent clinical studies have reported that injection of CD4+CD25+ Tregs appears to be a safe and effective cellular treatment in patients with type 1 diabetes and graft-versus-host disease.[80,81] In an attempt to generate sufficient cells, several ex vivo approaches for expanding CD4+CD25+ Tregs or in vitro induction of Tregs have been explored.[78] Polyclonal and in vitro antigen-specific Treg expansion are two well-known methods that have been used to generate an adequate amount of CD4+CD25+ Tregs. Unfortunately, there are several obstacles blocking the development of large-scale ex vivo or in vitro antigen-specific Treg expansion techniques.[82]

An alternative and efficient in vivo approach for inducing Ag-specific tolerance is through ectopic expression of an antigen in the liver.[46,83] Leveraging the tolerogenic nature of the liver, hepatic gene transfer has successfully been used to induce robust transgene tolerance in large- and small-animal disease models.[6,84] Viral vectors such as adeno-associated virus (AAV) have emerged as an effective vehicle for in vivo delivery of therapeutic genes to various tissues and are currently being used in multiple phase I/II clinical trials (see ClinicalTrials.gov).

In this disclosure, it was demonstrated that hepatic gene therapy with an AAV vector containing the full DNA coding sequence for the neuroprotein, myelin oligodendrocyte glycoprotein (MOG), can prevent development of and reverse preexisting EAE. The vector therapy resulted in the induction/expansion of antigen-specific FOXP3+ Tregs. When vector is administered prophylactically, mice were protected from developing EAE disease. When administered to mice exhibiting mild-to-moderate neurological deficits, vector alone was effective at reversing both clinical and pathological signs of disease. When combined with a short course of immune suppression, the AAV immunotherapy can rescue mice from fatal end-stage EAE disease and restore mobility after exhibiting severe paralysis.

Experimental Methods

Animal Strains. Female (9- to 12-week-old) inbred C57BL/6 and C57BL/6-Tg (Tcra2D2,Tcrb2D2), 1Kuch/J (MOGTCR 2D2), and B6.129(Cg)-Foxp3tm3(DTR/GFP) Ayr/J (FOXP3gfp+) mice were purchased from Jackson Laboratories (Bar Harbor, ME, USA). All procedures involving animals were carried out in accordance with the guidelines of the University of Florida Institutional Animal Care and Use Committee (IACUC).

Vector Production. A recombinant AAV8 vector expressing full-length MOG under a hepatocyte-specific promoter was produced by the method of transfection using anionic liposomes as a transfection reagent into human embryonic kidney (HEK293) cells, below passage 50. Two plasmid DNAs—recombinant construct flanked by the AAV inverted terminal repeats (iTRs), pAAV-Apolipoprotein E (ApoE)/hAAT-MOG, and a helper plasmid for AAV8 serotype (pDG8) mixed in equimolar amount—totaling 90 µg per 15 cm plate were added to each plate containing ~1×10⁷ cells. Virus was recovered from both cells and medium. Medium was collected on days 2 and 4 post-transfection, with consequent virus precipitation with 40% polyethylene glycol (PEG)8000/2.5 M NaCl solution. Cells were resuspended in 20 mM Tris/HCl (pH 8.5)/15 mM NaCl lysis buffer, 10 mL per 1-2×10⁸ cells. Cells were lysed by one-time freeze/thaw cycle and three rounds, 1 min each, of sonication on ice. Virus pelleted by PEG/NaCl was processed similarly to the virus recovered from the cells and combined. Clarified lysates ran on a step iodixanol density gradient[85] and dialyzed/concentrated on Apollo 20 spinning devices. The titer of each preparation was estimated using a dot-blot assay.

Induction of EAE. Mice were immunized by subcutaneous injection of $MOG_{35-55}$ in CFA (Hooke Labs, Lawrence, MA, USA). Pertussis toxin (PT) 200 ng (Hooke Labs, Lawrence, MA, USA) was injected intraperitoneally (i.p.) 6 and 24 hr later. The clinical symptoms of EAE were checked daily and graded on a clinical score of 0-5: 0, no clinical signs; 0.5, partially limp tail; 1.0, paralyzed tail; 2.0, loss of coordinated movement and hind-limb paresis; 2.5, one hind limb paralyzed; 3.0, both hind limbs paralyzed; 3.5, hind limbs paralyzed and weakness in forelimbs; 4.0, forelimbs paralyzed (quadriplegia); and 5.0, moribund. Mice had to reach inclusion criteria of an MCS ≥2.0 to be included in the study group. Mice would be euthanized if an MCS ≥4.0 was maintained for 48 hr, as per IACUC policy.

Vector Administration. To examine the prophylactic effect of vector administration, 7- to 9-week-old female C57BL/6 mice were injected with 10¹¹ vector genomes (vg) of AAV8.MOG or control vector. Two weeks later, EAE was induced. To evaluate the therapeutic effect of vector administration, EAE was induced first in 9- to 11-week-old mice before the administration of vectors. As mice reached the targeted/indicated severity of disease they were injected with 10¹¹ vg of AAV8.MOG or control vector (scAAV.GFP or sham/PBS) via the tail vein. Rapamycin (LC Laboratories, Woburn, MA, USA) was dissolved in a vehicle solution containing (0.2% w/v) carboxymethyl-cellulose sodium salt (C-5013) and (0.25% v/v) polysorbate-80 (P-8074) (Sigma, St. Louis, MO, USA) in distilled water and stored at 4° C. protected from light according to the manufacturer's instructions. Rapamycin (5 mg/kg) was given i.p. as indicated for a total of three and five doses beginning on the day of vector administration.

Gene Expression. Messenger RNA was isolated from 30 mg of liver samples harvested from mice that had received vector 2 weeks earlier using the RNeasy kit (QIAGEN, Valencia, CA, USA). Real-time qPCR was performed in duplicate using RT2 qPCR Primer Assay for Mouse MOG (QIAGEN) according to the manufacturer's protocols. A MyIQ iCycler fluorescent detection system with iQ5 operating software Version 2.0 (Bio-Rad Laboratories, Hercules, CA, USA) was used to generate and analyze data. All gene expression was compared with that of glyceraldehyde-3-phosphate dehydrogenase.[86]

Flow Cytometry. Peripheral blood cells or splenocytes harvested from mice and processed to produce single-cell suspensions were stained with antibodies to CD3 (145-2C11), CD4 (RM4-5), CD25 (PC61), CD8 (53-6.7), B220 (RA3-6B2), CD44 (IM7), and CD62L (MEL14) (BD Biosciences, San Jose, CA, USA). Class II MHC tetramers included $MOG_{38-49}$/I-Ab class II MHC (GWYR-SPFSRVVH) and h.CLIP87-101 (PVSKMRMATPLL-MQA), and were provided by the NIH Tetramer Core (Emory University, Atlanta, GA, USA). Red blood cell lysis was performed with VersaLyse (Beckman Coulter, Brea, CA, USA). Intracellular staining for FOXP3 was performed using the FOXP3 staining kit (eBioscience, San Diego, CA, USA). Samples were analyzed on an LSR-II flow cytometer (BD Biosciences) and post-analyzed using FCS Express 4 (Denovo Software, Los Angeles, CA, USA).

In Vitro Suppression Assay. Spleens from FOXP3gfp+ mice that received vector no less than 2 weeks earlier were homogenized and enriched for CD4+ T cells by magnetic depletion of non-target cells over an LS column (Miltenyi Biotec, San Diego, CA, USA). GFP+ cells, representing the Treg population of CD4+ T cells (~10%), were further isolated using the FACSAria II cell sorter (BD Biosciences). Splenocytes isolated from 2D2-MOGTCR mice were labeled with CellTrace Violet (Invitrogen, Carlsbad, CA, USA) according to the manufacturer's protocol. CD4+ FOXP3GFP+ Tregs and CellTrace Violet-labeled responder splenocytes were seeded at the indicated effector/responder ratios in complete 5% RPMI media containing 1 µg/mL $MOG_{35-55}$ peptide for 72 hr at 37° C. Cells were resuspended and stained with anti-CD4 antibody to assess proliferation of responder CD4+ T cells. GFP was used to discriminate between responder cells and Tregs. Proliferation was determined by quantitating CellTrace Violet fluorescence intensity relative to the parent population of unstimulated responder cells (0% proliferation) and stimulated cells incubated without Tregs (100% proliferation). Percentage of CD4+ responder T cell proliferation was determined using FCS Express 4.

Analysis of Plasma Samples. Plasma was analyzed for anti-MOG IgG1 and IgG2c by ELISA as previously described.[12]

Western Blot. Protein was extracted from liver tissue using T-PER Tissue Extraction Reagent (Thermo) in the presence of Halt Protease Inhibitor (Thermo). Total protein concentration was measured using the bicinchoninic acid protein assay (Pierce). Samples were separated on 4%-20% Mini-PROTEAN TGX gels (Bio-Rad) and transferred to polyvinylidene fluoride (PVDF) membrane following standard protocols. After blocking, the membrane was incubated for 1 hr at room temperature with antibody against MOG or β-actin in 1% fat-free dry milk in 1× tris-buffered saline with tween (TBST). HRP-conjugated secondary antibody was used for signal detection with the ECL 2 Western Blotting Substrate (Pierce).

Histopathology. For histopathological analysis of the spinal cord, formalin-fixed, paraffin-embedded, 5 µm sections were stained with Luxol Fast Blue or H&E by standard procedures.

Statistical Analysis. Results are reported in figure legends as mean±SEM, unless otherwise stated. Statistical significance was determined using GraphPad Prism software (La Jolla, CA, USA). The p values are reported as indicated.

Study Approval. All studies were in accordance with protocols approved by IACUC at the University of Florida, Gainesville.

Results

Hepatic Gene Transfer with AAV8.MOG Induces Immunosuppressive MOG-Specific Tregs.

Figure 20A:
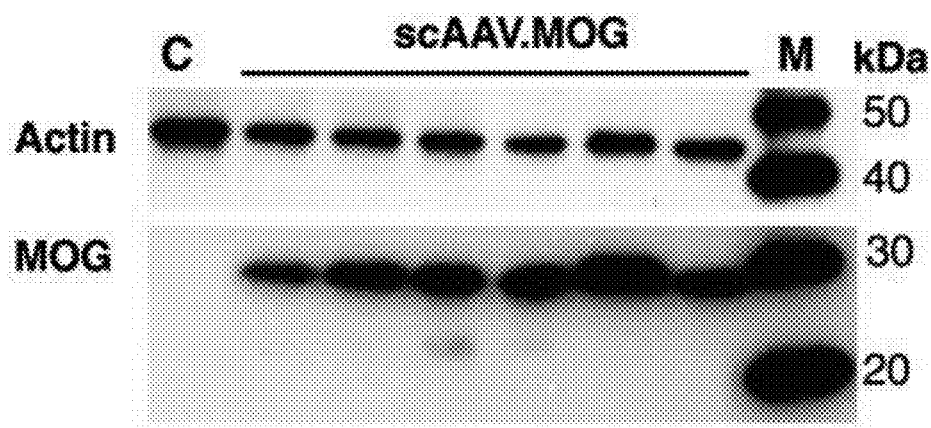
FIG. 20A, FIG. 20B, FIG. 20C, FIG. 20D, FIG. 20E, and FIG. 20F show that functional Ag-specific Tregs are induced following AAV8.MOG injection. C56Bl/6 mice were injected with $10^{11}$ vg of AAV8-MOG via tail vein.
Figure 20B:
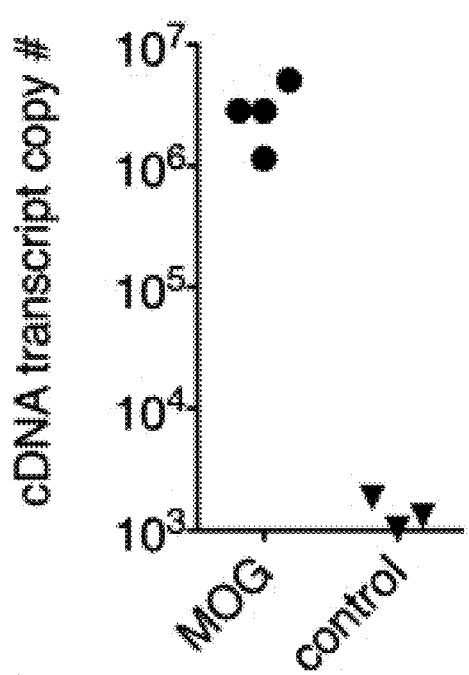

To study the ability of the liver to induce immune tolerance to a transgene protein, an AAV8 vector was engineered to contain the full coding sequence (CDS) of the neuroprotein MOG, which was placed under control of a liver-specific promoter. To establish that AAV8.MOG can transduce hepatocytes and will stably express the non-secreted neuroprotein, C57BL/6 mice were systemically injected with a single dose of the vector ($10^{11}$ vector genomes). Western blot and real-time qPCR analysis of liver lysates from tissue harvested 2 weeks later confirmed vector transduction and hepatocyte expression of MOG (FIGS. 20A and 20B).

Figure 20C:
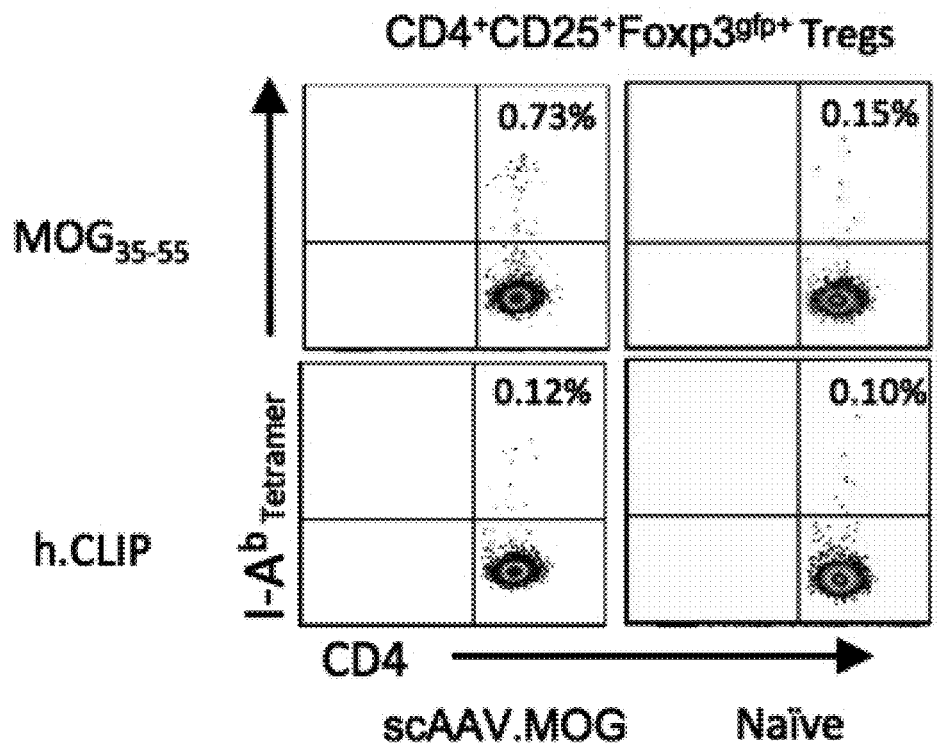
Figure 20D:
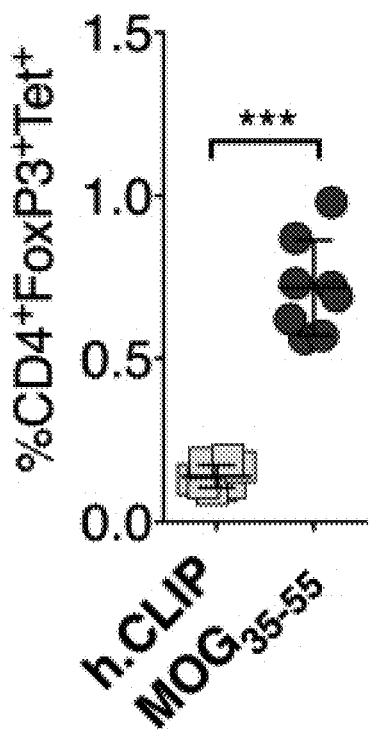
Figure 25:
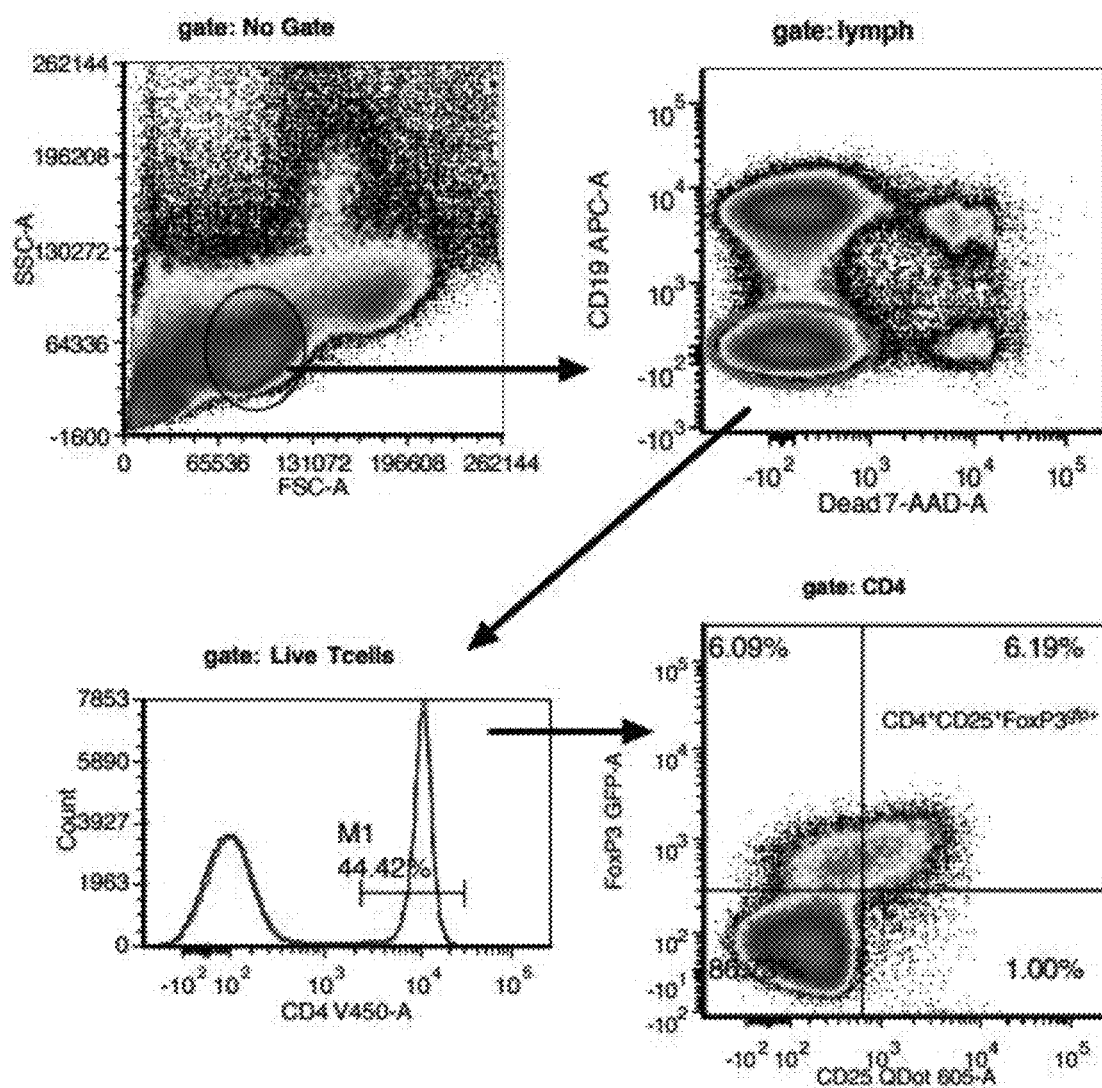
FIG. 25 shows a gating scheme to identify live CD4$^+$CD25$^+$FoxP3$^{gfp+}$ cells.

Although MOG protein accounts for only 0.05%-0.1% of total myelin proteins, it is reported to induce a more potent T cell response than other myelin antigens in patients with MS.[87,88] To complicate matters, a loss of immune tolerance because of deficits in either Treg numbers or their function has been observed in autoimmune and inflammatory diseases, including MS.[74] Previously, in a model used for protein replacement therapy, the notion that hepatocyte expression induces transgene (Tg)-specific Tregs could only be indirectly established.[1] Here, an experimental system was developed that allowed for direct determination of the frequency of MOG-specific FOXP3+ Tregs. Using a transgenic C57BL/6 Foxp3-EGFP reporter mouse that expresses EGFP under the control of the mouse Foxp3 promoter (FOXP3-gfp+), in combination with a $MOG_{38-49}$/I-Ab major histocompatibility complex (MHC) tetramer, allowed for the direct identification of AAV8.MOG-induced Tg-specific CD4+ Tregs (FIGS. 20C and 20D). To do so, freshly isolated splenocytes from mice that had previously received AAV8.MOG vector were chosen for analysis. This allowed for the determination of the real-time frequency of tetramer-specific cells as opposed to values amplified by ex vivo restimulation.[72] Multi-parametric flow cytometry revealed a significantly higher I-Ab MOG35-55 tetramer+ frequency from CD4+CD25+FOXP3-gfp+ gated cells compared with the control (h.CLIP/I-Ab) tetramer (p<0.0001) (FIGS. 20C and 20D; FIG. 25). Similarly, age-matched naive reporter mice failed to bind either tetramer at levels above that of control mice, ruling out potential non-specific binding (FIG. 20C). These findings provide direct and unambiguous evidence that liver-directed AAV induces transgene-specific Tregs in mice, further confirming that hepatic expression of a full-length transmembrane neuroprotein can indeed drive in vivo induction of antigen-specific Tregs.

Figure 20E:
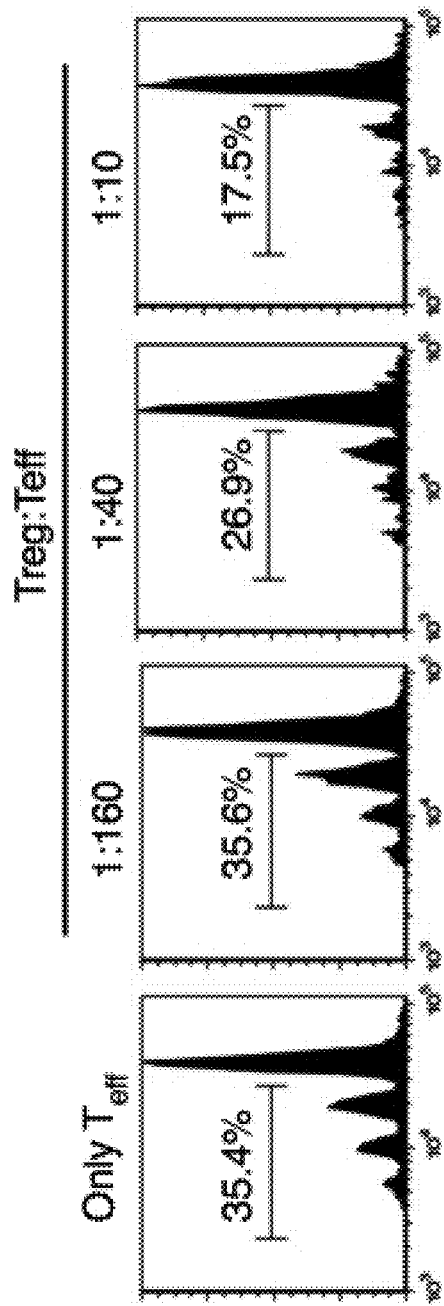
Figure 20F:
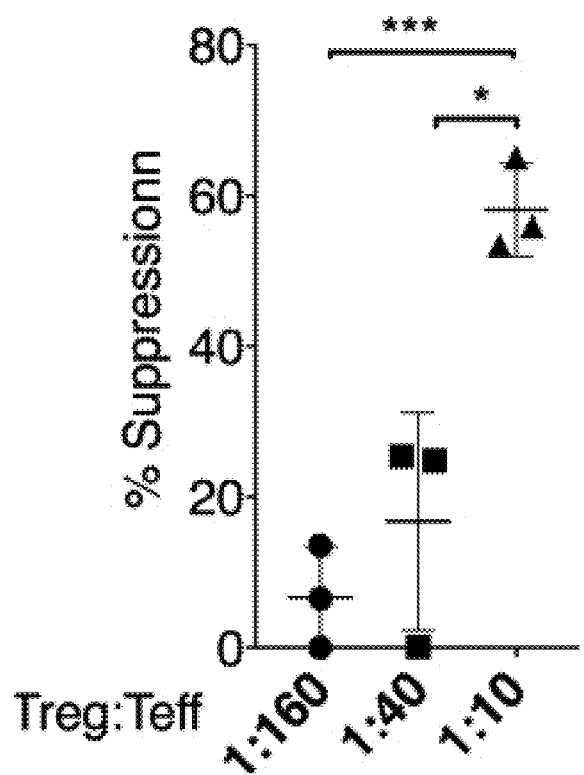

Next, to test whether the vector-induced MOG-specific Tregs were functional, the capacity of FAC-sorted CD4+ FOXP3gfp+ Tregs harvested from the spleens of AAV8.MOG tolerized mice, or age-matched naive mice, to suppress the proliferation of MOG-specific effector T cells was assessed when co-cultured in the presence of the immunodominant $MOG_{35-55}$ peptide. Indeed, at a 1:10 Treg/effector T cell (Teff) ratio, the vector-induced Tregs suppressed 58% of the effector cell proliferation. This was nearly three times more effective than naive polyclonal Tregs (FIGS. 20E and 20F). These results demonstrate that hepatocyte expression of a non-secreted transmembrane neuroprotein delivered by an AAV8 vector induces functionally suppressive MOG-specific Tregs in vivo.

Pre-Treatment with AAV8.MOG Vector Prevents EAE Induction.

Figure 21A:
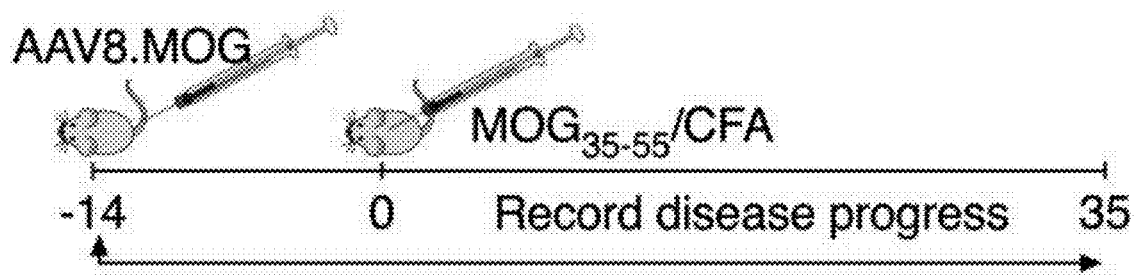
FIG. 21A, FIG. 21B, FIG. 21C, FIG. 21D, FIG. 21E and FIG. 21F show that the prophylactic administration of AAV8.MOG protects mice from EAE. C57BL/6 mice (9 weeks old) were intravenously injected with $10^{11}$ vg/mouse via the tail vein with either AAV8.MOG or AAV8.GFP/control vector (day −14). Two weeks later (day 0), EAE was induced with MOG$_{35-55}$/CFA.
Figure 21B:
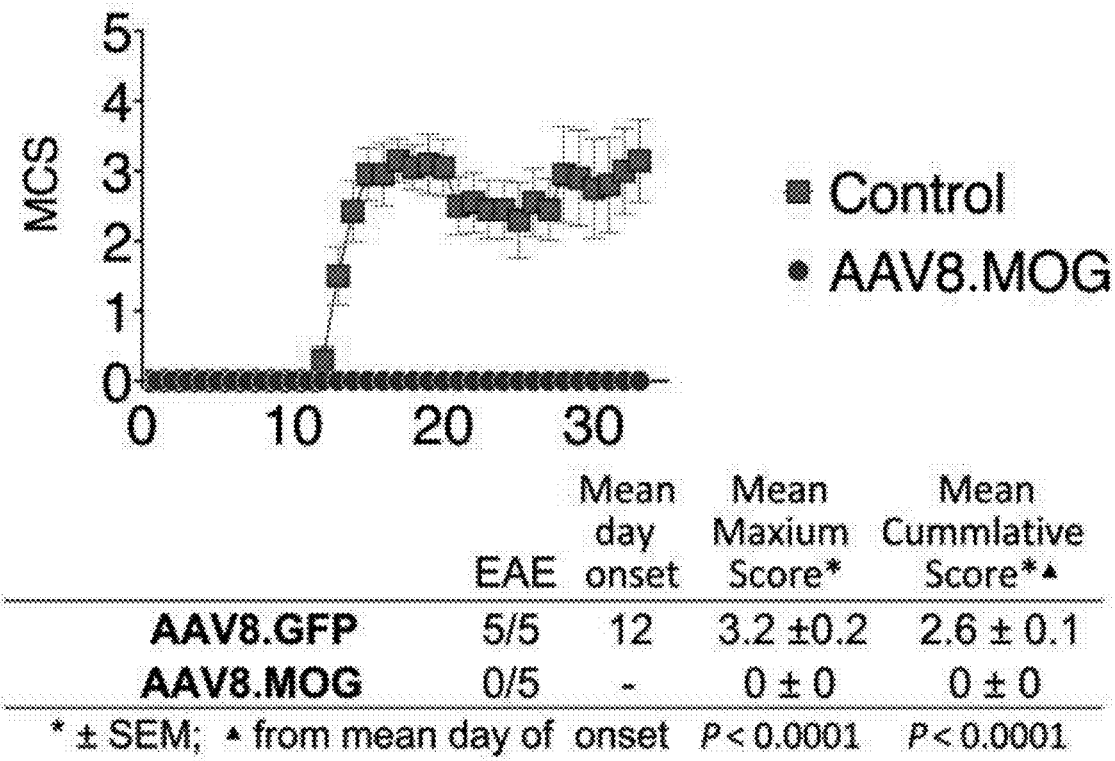
Figure 21C:
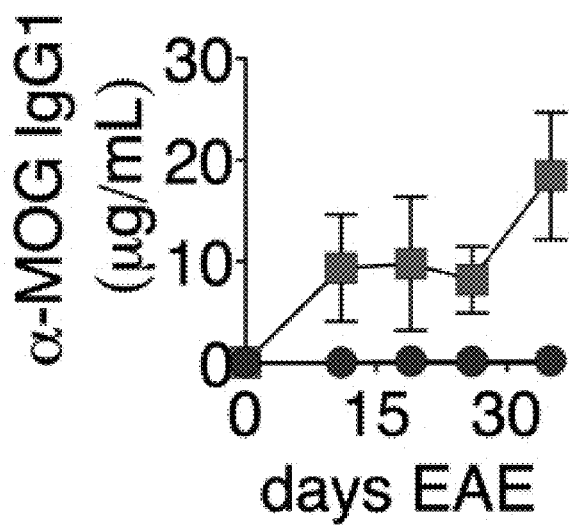
Figure 21D:
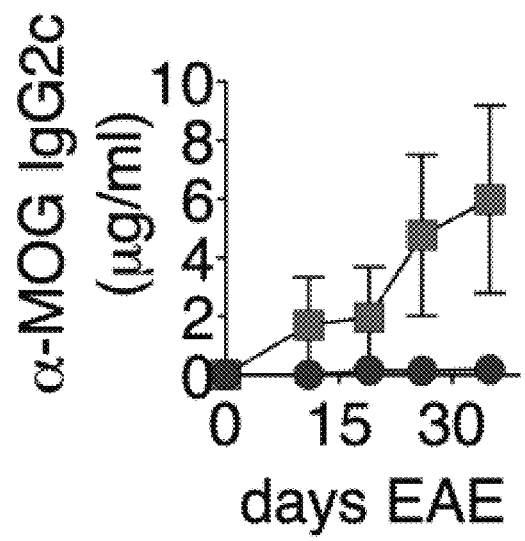

Next, experiments were conducted to examine whether pre-treatment with AAV8.MOG would induce transgene-specific immune tolerance and protect susceptible mice from developing EAE (FIG. 21A). AAV8.MOG or AAV8.GFP (irrelevant transgene control) vector was administered to cohorts of mice. Two weeks later, mice were immunized with $MOG_{35-55}$ emulsified in complete Freund's adjuvant (CFA) to induce EAE. Mice were monitored for signs of neurological deficits using a five-point scale as described (Table 1). Beginning 10 days after EAE induction, mice receiving control vector developed severe neurological impairments (maximum mean clinical score [MCS]: 3.15±0.2) (FIG. 21B). Disease progression was also associated with increasing anti-$MOG_{35-55}$ immunoglobulin (Ig) G1 and IgG2c antibody titers (FIGS. 21C and 21D). In contrast, mice that received AAV8.MOG were protected and failed to develop clinical signs of EAE or produce MOG35-55-specific antibody responses (FIGS. 21B-21D). Notably, neurological deficits in control mice continued to increase in terms of both maximum and cumulative EAE scores until they developed severe paralysis and needed to be humanely euthanized.

Figure 21E:
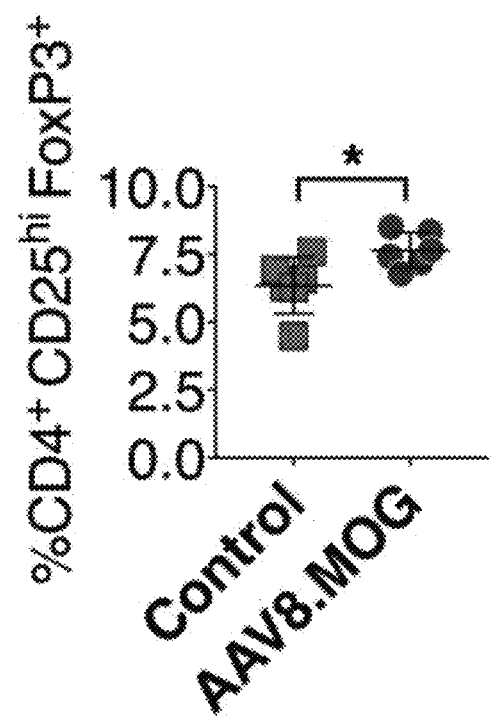

Next, the frequency of FOXP3+ Tregs in peripheral blood mononuclear cells was evaluated. Flow cytometry analysis results showed that mice treated with AAV8.MOG had a small but significant increased frequency of CD4+ CD25hiFOXP3+ Tregs in peripheral blood mononuclear cells (PBMCs) compared with control mice (FIG. 21E), further supporting that AAV hepatic gene therapy administration selectively expands FOXP3+ Treg populations and induces tolerance to the encoded transgene antigen.[6]

Figure 21F:
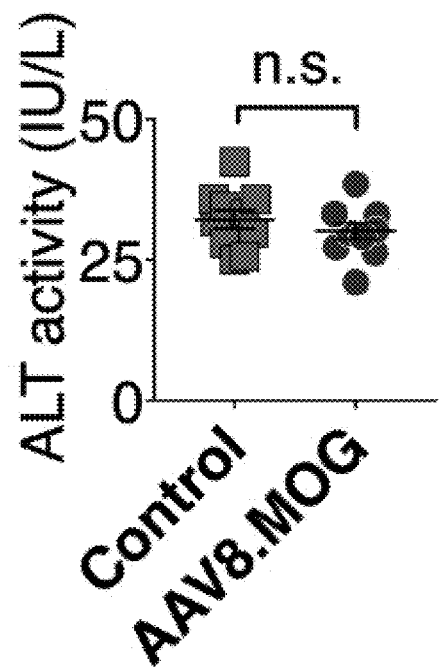

Although various proteins have been safely expressed in the liver following AAV gene transfer,[89] evaluating the long-term stability of MOG expression in hepatocytes in the context of induced EAE was of interest. Elevations in serum/plasma alanine aminotransferase (ALT) enzyme level are routinely used in the clinic to screen for liver disease and cell-mediated immunity directed against AAV-transduced hepatocytes.[90,91] Analysis of plasma ALT activity in mice ~4 months after receiving gene transfer revealed no significant difference between AAV8.MOG-treated and age-matched naive C57BL6 mice, indicating that AAV8.MOG did not induce chronic liver disease (FIG. 21F). Additionally, hepatocyte expression of MOG persisted in the mice that received AAV8.MOG until termination of experiment at 200 days after EAE induction (FIG. 20A). Notably, throughout this protracted timeline, mice never developed any observable signs of neurological disability or general distress, suggesting that hepatocyte expression of MOG does not provoke any deleterious immune responses. Collectively, these data demonstrate that prophylactic administration of liver-directed AAV8.MOG produces long-term stable hepatocyte expression of MOG that has an immuno-suppressive effect capable of preventing the development of EAE.

TABLE 1

Description of the Mean Clinical Score (MCS) five-point scale

| Score | Clinical Presentation |
| --- | --- |
| 0.0 | no clinical signs |
| 0.5 | partial paralysis/limp tail |
| 1.0 | paralyzed tail |
| 1.5 | impaired coordination/balance |
| 2.0 | hind-limb paresis |
| 2.5 | one hind limb paralyzed |
| 3.0 | hind-limb paralysis (paraplegia) |
| 3.5 | hind limbs paralyzed and forelimb paresis |
| 4.0 | hind-limb and forelimb paralysis (quadriplegia) |
| 5.0 | moribund/dead* |

*Mice euthanized or found deceased were recorded as 5 for remainder of time.

The Immune Tolerance Induced by AAV8.MOG is Robust.

Figure 22A:
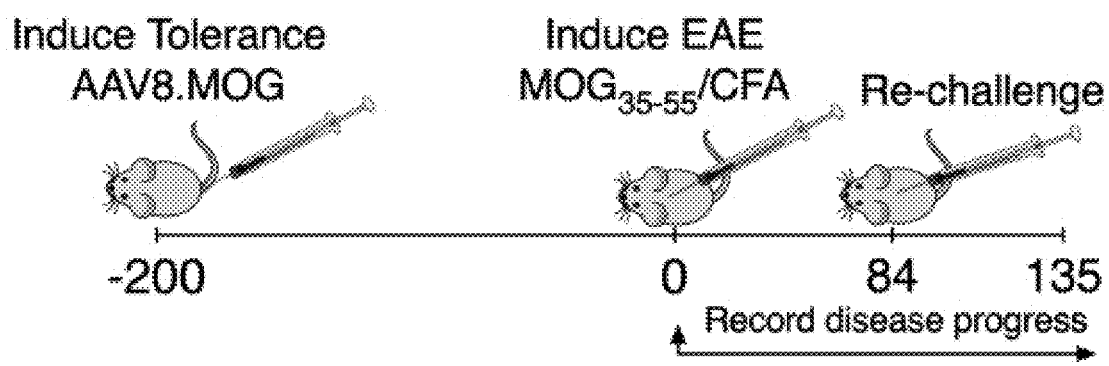
FIG. 22A, FIG. 22B, FIG. 22C and FIG. 22D show that AAV8.MOG-induced immune tolerance is robust. Age-matched C57BL/6 mice (9-10 weeks old) were intravenously injected with $10^{11}$ vg/mouse via the tail vein with either AAV8.MOG or PBS/control vector. EAE was induced with MOG$_{35-55}$/CFA 200 days later and re-challenged after 84 more days.
Figure 22B:
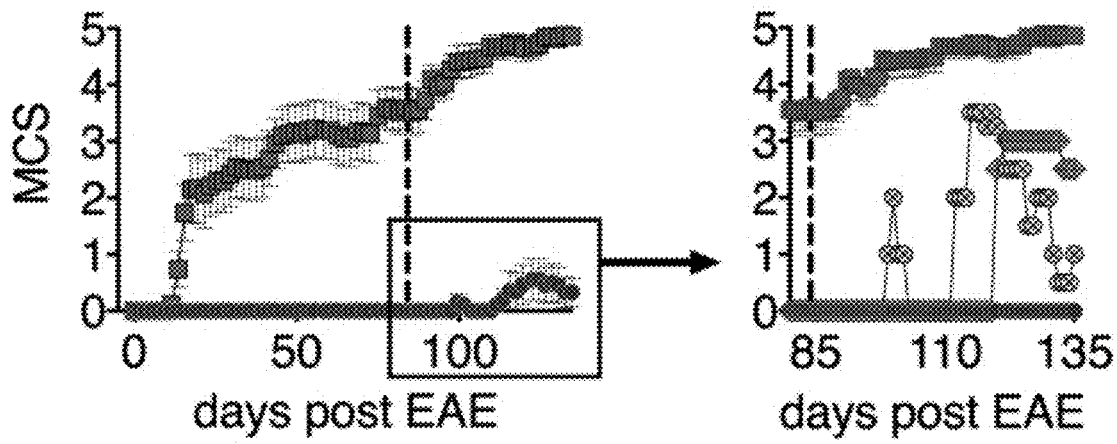
Figure 22C:
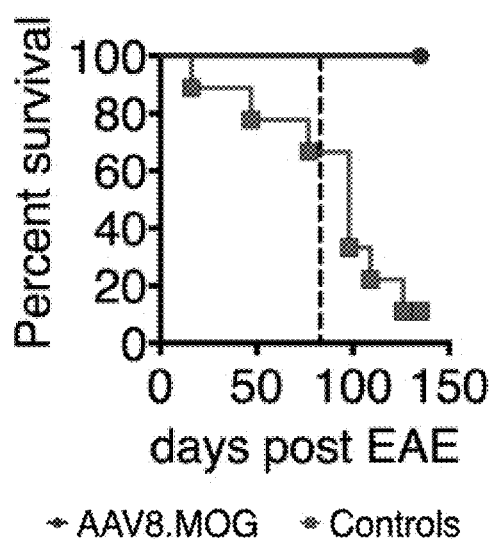

Next, the possibility that a single vector injection could provide long-term hepatic transgene expression and still induce immune tolerance was evaluated. Two cohorts of mice were injected, intravenously, with either AAV8.MOG or PBS/sham (FIG. 22A). EAE was induced in both cohorts of animals ~200 days later with $MOG_{35-55}$/CFA. Mice were then monitored daily, and collections of plasma and lymphocytes were obtained every 2 weeks for analysis and Treg staining. Even though vector was given over 7 months earlier, mice that received AAV8.MOG failed to develop any signs of EAE disease, whereas the age-matched control mice began exhibiting neurological deficits at day 14, which rapidly increased in severity (FIG. 22B), and began to succumb to disease as early as 16 days after EAE induction (FIG. 22C). These results demonstrate that vector-induced immune tolerance is stable and can be maintained long term.

Figure 22D:
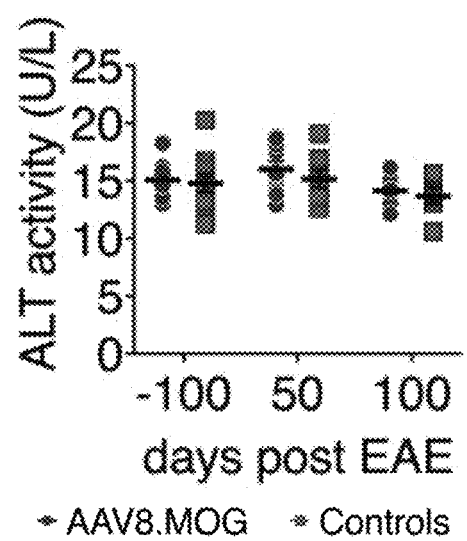

In EAE[92-95] and other models of protein replacement gene therapy,[6,15] long-term induction of tolerance is often confirmed by re-challenging the mice. To further demonstrate the robustness of the immunotherapy described herein, the ability of the AAV8.MOG treatment to maintain tolerance and prevent disease following a second attempt to induce MOG-specific EAE was evaluated. Almost 3 months after the initial EAE induction (9.5 months from AAV8.MOG induction of tolerance), both groups of mice were re-challenged with MOG35-55 and monitored for development of or change in clinical signs. In the control mice, disease escalation occurred rapidly (FIG. 22B). Within 15 days, half of the re-challenged control mice succumbed to disease, whereas 100% of the AAV8.MOG-treated mice survived (FIG. 22C). However, at 16 and 37 days after secondary challenge, two mice developed a slow relapsing-remitting disease (FIG. 22B, right). Nonetheless, 80% of the mice that received AAV8.MOG vector months earlier showed absolutely no signs of EAE or liver disease over the course of the experiment (FIG. 22B-22D). The disease escalation in the control mice confirmed that vector-treated mice were indeed tolerized and not simply protected via a vaccination mechanism. Thus, these data clearly demonstrated that AAV8.MOG protection is indeed stable and robust.

AAV8.MOG Immunotherapy Reverses Established EAE Disease.

Figure 23A:
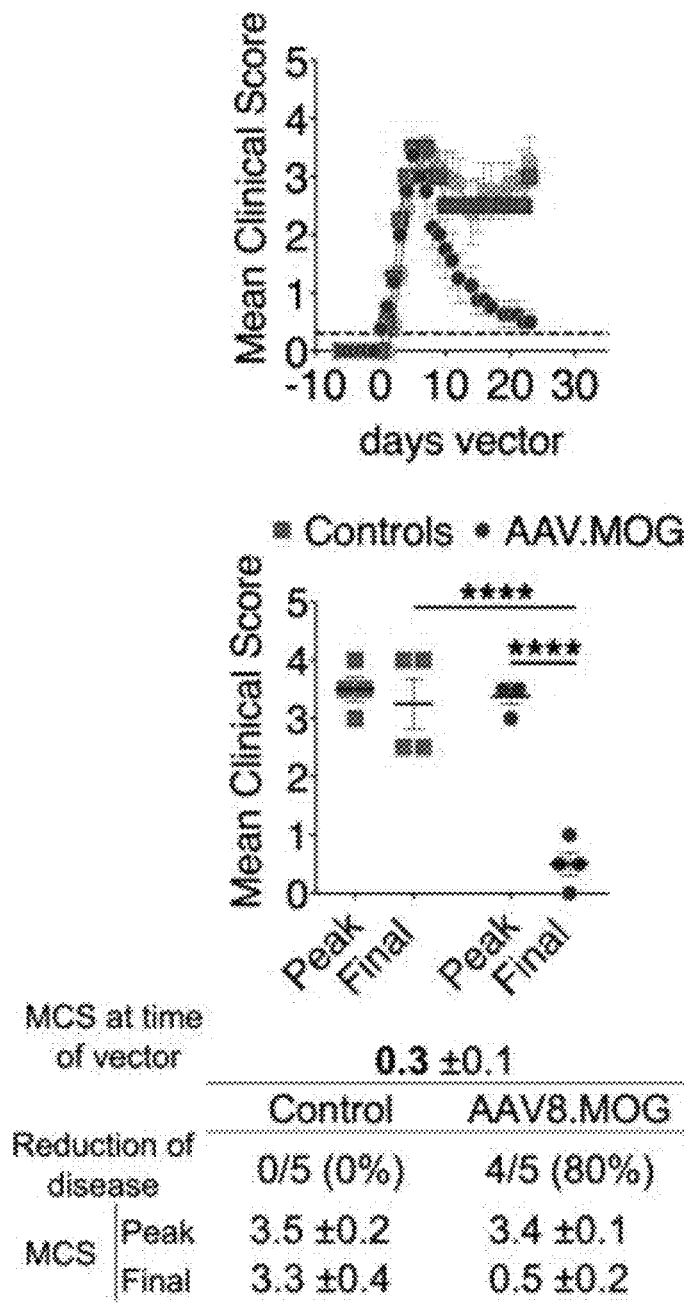
FIG. 23A, FIG. 23B, FIG. 23C and FIG. 23D show that AAV8.MOG induces clinical and pathological remission of EAE. EAE was induced in 9-week-old female C57BL/6 mice using MOG$_{35-55}$ in CFA. MCS (mean±SEM) was recorded, and as mice developed increasing neurological symptoms, was recorded as increasing MCS. Mice were intravenously injected with either $10^{11}$ vector genomes (vg) AAV8.MOG or control via the tail vein in an alternating fashion.
Figure 23B:
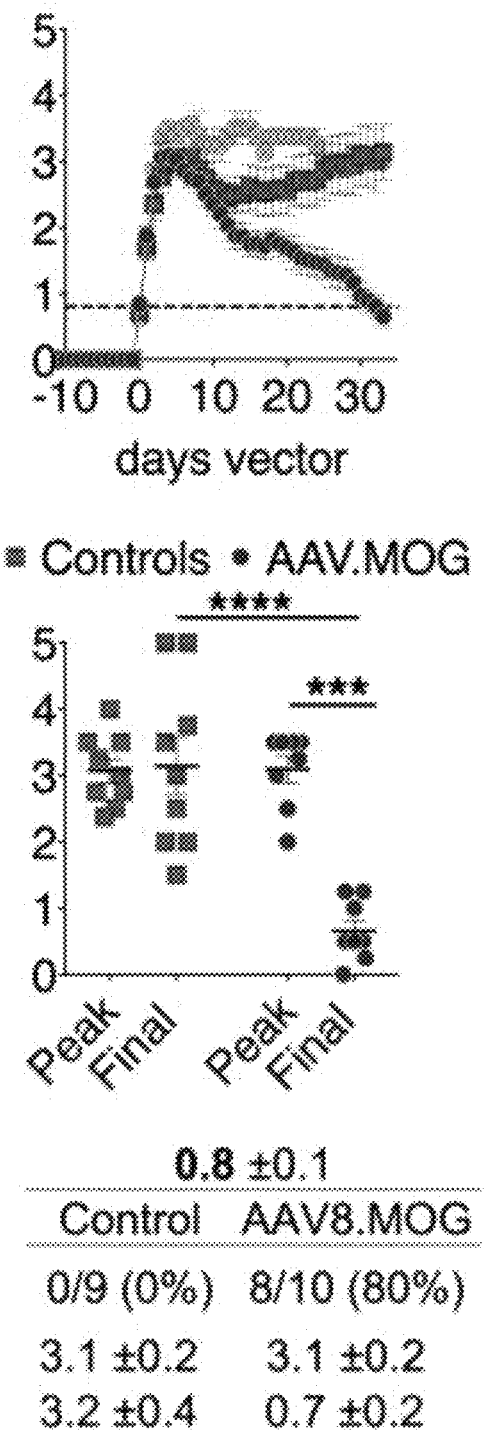
Figure 23C:
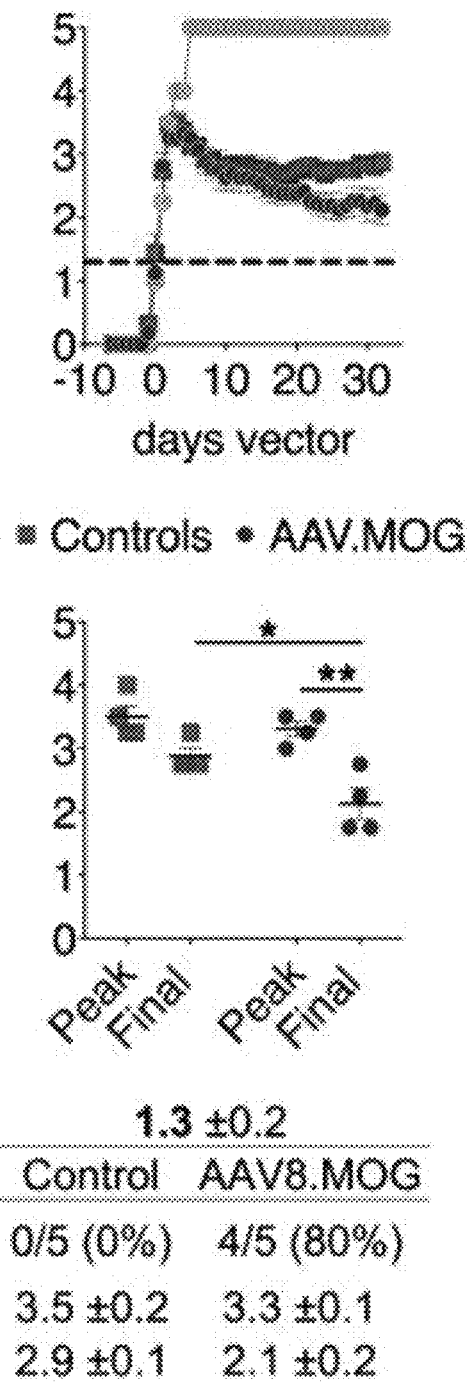

The early symptoms of MS are often minor and overlooked. Diagnosis is usually made after the first clinically isolated syndrome (CIS), which is defined as an episode of neurological deficit that lasts at least 24 hours and is caused by inflammation or demyelination.[96] In terms of rate and severity of disability, disease progression is highly variable and difficult to predict, which often results in a diagnosis well after disease has been established. Therefore, experiments were conducted to investigate whether induction of Ag-specific tolerance following AVV8.MOG immunotherapy would be effective in diminishing or reversing disease in mice during progressive stages of neurological impairment. In this series of experiments, EAE was induced in age-matched mice before being treated with vector. As the mice developed signs of neurological impairment, they were divided in an alternating fashion into two different groups so that the baseline clinical scores would be comparable between the groups (referred to as rolling enrollment). As mice reached the target MCS, they were injected with either AAV8.MOG or PBS/sham vector (FIGS. 23A-23C). In the first cohort, mice received treatment early in the disease process as they began to lose tail tonality (FIG. 23A). Both groups of mice continued to develop severe paralyzing EAE by day 7 (peak MCS: ~3.5). Strikingly, beginning around day 8, all but one mouse that was treated with a single injection of AAV8.MOG began to exhibit a significant reversal of clinical symptoms (final MCS: 0.5±0.3). In contrast, control mice proceeded to develop severe neurological disabilities (final MCS: 3.3±0.4). In the next iteration, the ability of AAV8.MOG immunotherapy to reverse moderate disease was evaluated by withholding treatment until mice exhibited complete tail paralysis (MCS: ~1). Like before, both groups of mice rapidly developed severe EAE with hind-leg paralysis (FIG. 23B). After a brief remission, control mice relapsed and developed severe ascending paralysis (final MCS: 3.2±0.4). In contrast, AAV8.MOG-treated mice went into a nearly complete remission and regained use of their hind legs (final MCS: 0.7±0.2) (FIG. 23B).

Lastly, the ability of AAV8.MOG to induce tolerance and abrogate disease in mice with even more advanced preexisting disease was further probed. Following induction of EAE, AAV8.MOG immunotherapy was withheld until disease advanced and mice presented with complete tail paralysis with hind-leg inhibition and loss of fine motor coordination that affected their gait and balance (combined MCS: 1.3±0.2) (FIG. 23C). Mice continued to develop severe EAE with hind-leg paralysis, which critically impeded their ability to freely move around the cage and obtain food (peak MCS: ≥3.3). By day 30, mice that received AAV8.MOG immunotherapy had a significantly greater reduction in clinical scores compared to control mice (p=0.0412). Although not as robust as previously seen, these results have substantial clinical relevance. Notably, all the mice that responded to the gene immunotherapy regained the ability to freely ambulate, whereas control mice continued to have hind-leg paralysis.

Inflammation in the Spinal Cord of Treated Mice.

Figure 23D:
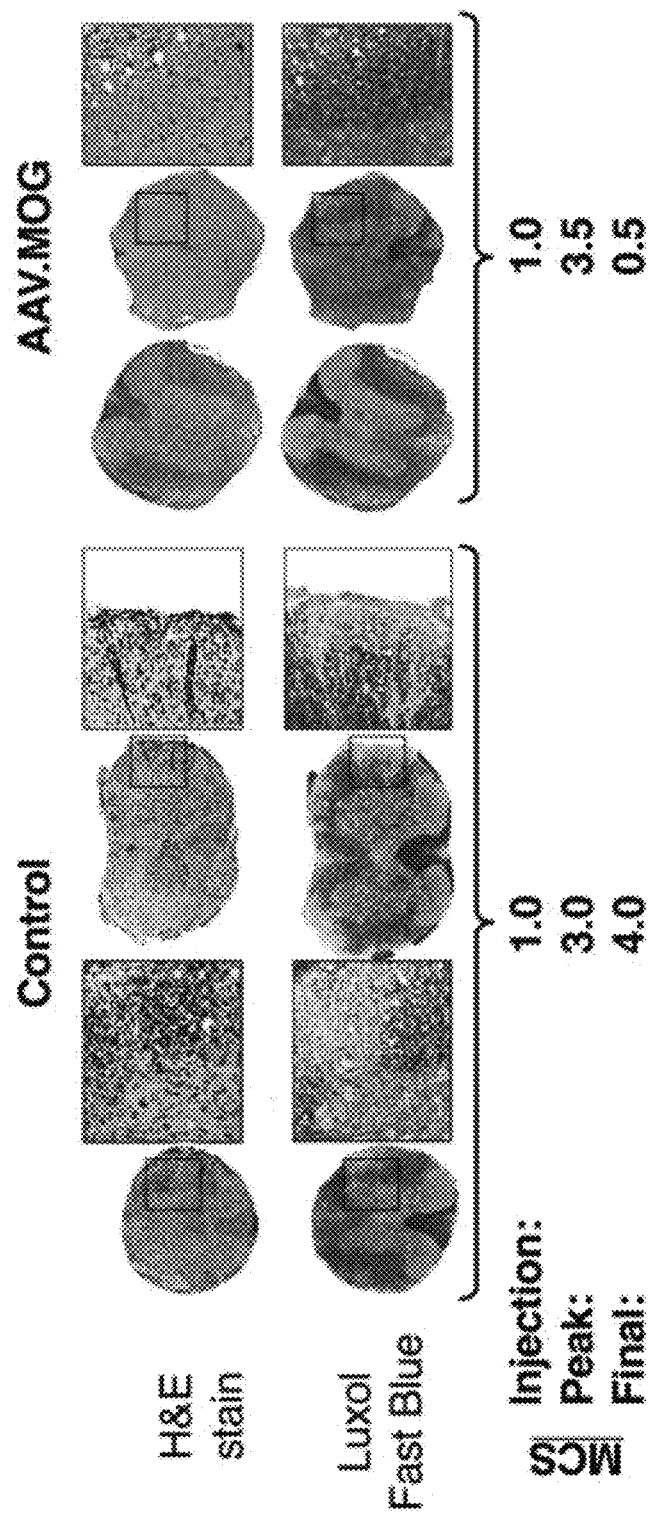

In EAE, the spinal cord is the primary site of encephalitogenic effector cells and demyelination, and the degree of neurological impairment is related to the magnitude of inflammation during the early stages of the disease.[1] To determine whether the amelioration of neurological deficits was associated with a reduction in encephalitogenic inflammation and/or demyelination, serial sections from multiple regions of spinal cords from mice that received AAV8.MOG were compared to control mice for pathological differences 35 days after receiving vector. Histological examination showed that non-tolerized control mice had numerous foci of cellular infiltrates that were co-localized to areas of demyelination within the white matter (FIG. 23D). In contrast, there was an absence of inflammatory lesions within the spinal cord of the mice treated with AAV8.MOG. These findings were consistent across the other treatment groups, as well as with prior literature.[46,97] These results suggest that AAV gene immunotherapy reverses the clinical symptoms associated with EAE disease through a mechanism that suppresses tissue-specific inflammation.

Transient Immune Suppression Enhances AAV8.MOG Immunotherapy in EAE.

It has been shown in an EAE model that Tregs may accumulate in the target tissue but are non-suppressive.[72] The failure to suppress the effector response is believed to be associated with the localized inflammation causing a Th1/Th17 microenvironment within the CNS. As suggested by the diminished impact of AAV8.MOG treatment in mice with delayed treatment seen in FIG. 23C, this pro-inflammatory microenvironment may limit the effectiveness of the induced Tregs, especially at the height of inflammation. To overcome this limitation, it was hypothesized that successful treatment may require adjunct immune suppression to modulate the pro-inflammatory environment within the CNS.[98,99] To address this, the immunosuppressive drug rapamycin was investigated. Rapamycin has been used to suppress graft refection in organ transplantation, and its safety and efficacy have been evaluated for use in humans with MS.[69] In general terms, rapamycin has a potent anti-proliferative effect on antigen-stimulated effector T cells, while simultaneously allowing expansion of CD4+CD25+ FOXP3+ Tregs, making it an ideal choice.[100,101]

Figure 24A:
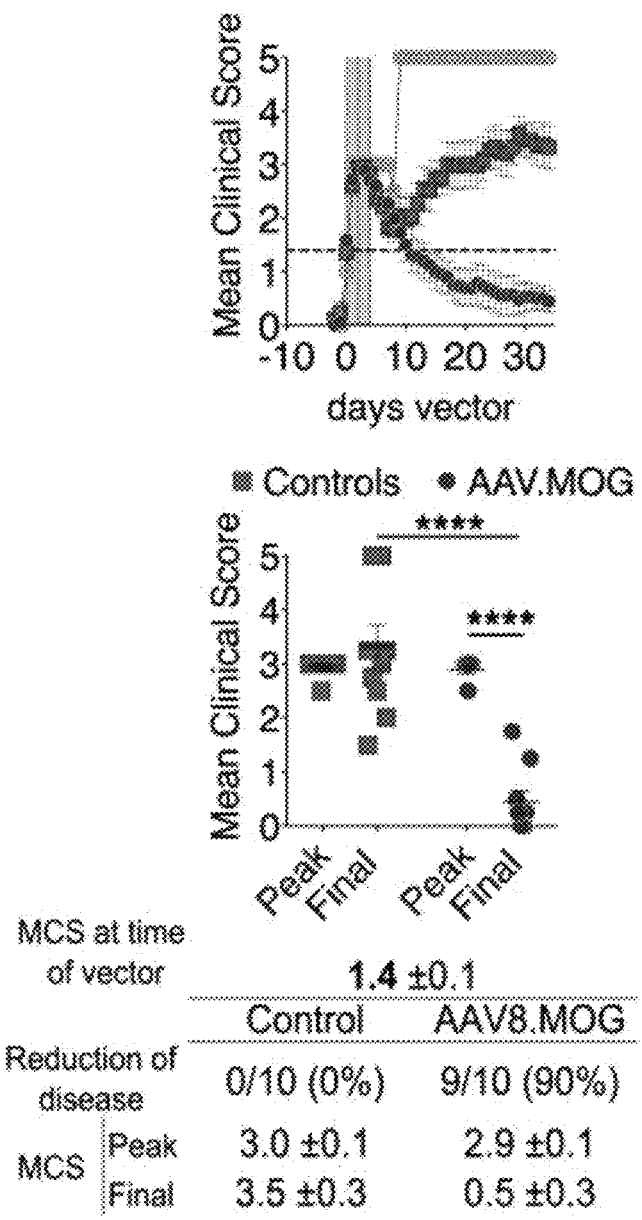
FIG. 24A, FIG. 24B, FIG. 24C, FIG. 24D, FIG. 24E, FIG. 24F, FIG. 24G, and FIG. 24H show that therapeutic effects of therapy are enhanced following transient rapamycin immunosuppression. EAE was induced as in FIGS. 23A-23D.
Figure 26:
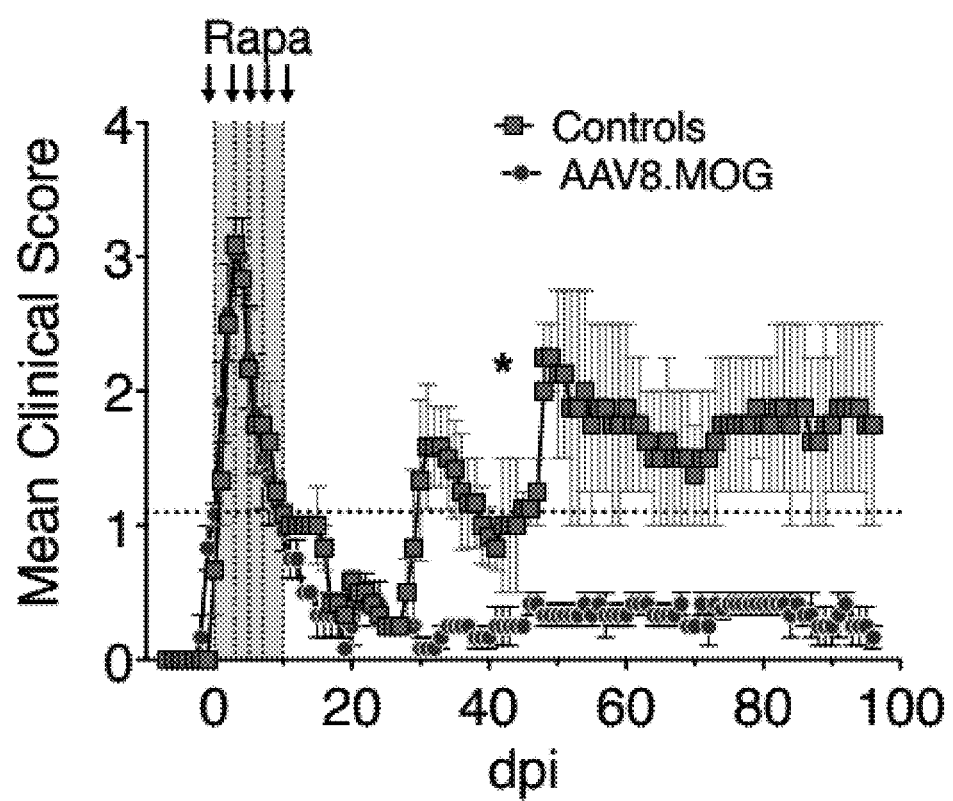
FIG. 26 shows that AAV8.MOG/Rapamycin co-treatment reverses clinical signs of pre-existing disease. EAE was induced as previously described. As mice developed neurological symptoms and presented with complete tail paralysis, they were intravenously injected with either AAV8.MOG/rapamycin or rapamycin alone (control). Clinical scores (mean±SEM) were recorded. Dashed line indicates MCS at time of treatment. Arrows indicate time of vector and rapamycin injections. (n=3/group).

To test the hypothesis, the experimental parameters that previously produced the smallest degree of disease reversal were reestablished (FIG. 23C). EAE was induced and AAV8.MOG treatment was withheld until mice developed complete tail paralysis with hind-leg paresis (MCS: 1.4±0.1, combined). Immediately after being treated with either AAV8.MOG or PBS/control, all mice received an intraperitoneal injection of rapamycin (5 mg/kg). Subsequently, mice received two additional doses of rapamycin (5 mg/kg) 48 hr apart (FIG. 24). As expected, EAE disease progressed quickly and both groups of mice developed severe neurological deficits and paralysis (peak MCS: 2.9-3.0) (FIG. 24A). Within 72 hr of receiving the rapamycin, both AAV8.MOG-treated and control mice responded to the immunosuppression and displayed signs of remission (a sustained reduction in MCS≥1).[69] However, by day 10, 100% of the control mice had relapsed and rapidly developed end-stage EAE disease (final MCS: 3.5±0.3). In contrast, neurological deficits in AAV8.MOG-treated mice continued to decrease, and all but one animal (90%) achieved complete remission (final MCS: 0.5±0.3) (FIG. 24A). Additionally, in a separate experiment, mice that received the AAV8.MOG vector/rapamycin combination remained symptom free (final MCS: 0.2±0.1) until termination of the experiment at ~100 days after EAE (FIG. 26).

Figure 24B:
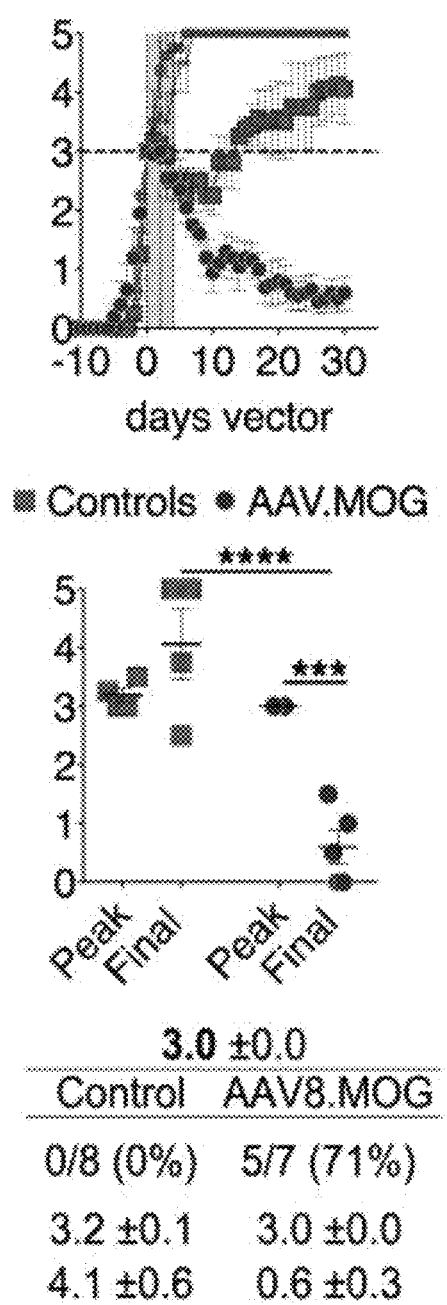
Figure 24C:
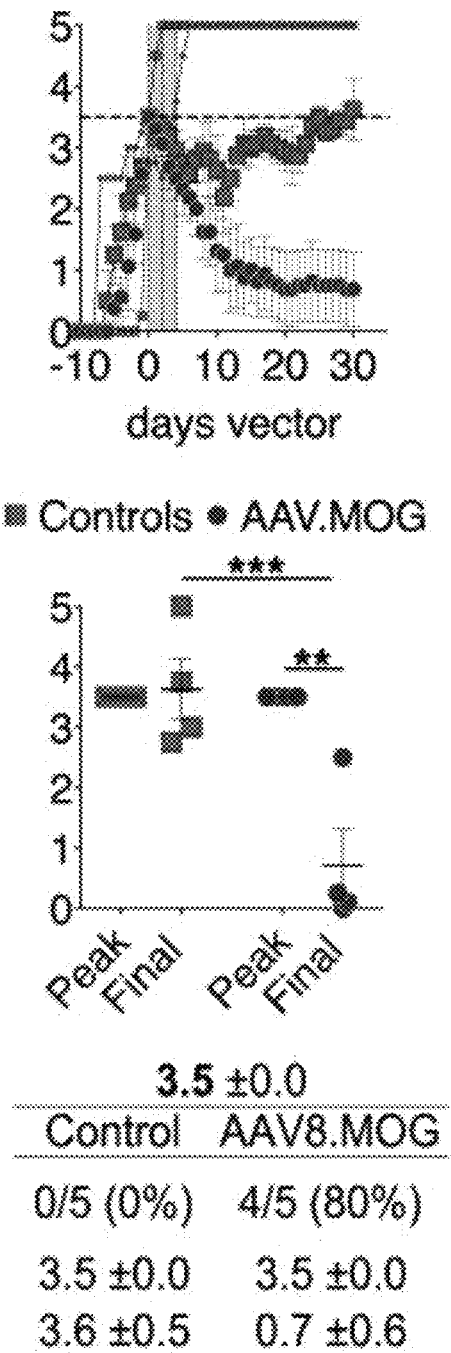

Next, the effectiveness of the combined immunotherapy in late and end-stage EAE disease was tested. In these cohorts, EAE disease was induced as before and allowed to develop until the mice began exhibiting complete tail and hind-limb paralysis (MCS: 3.0±0.0) (FIG. 24B) or borderline quadriplegia (hind-limb paralysis with forearm paresis that prevents the mouse from righting itself when placed on its back) (MCS: 3.5±0.0) (FIG. 24C) before AAV8.MOG/rapamycin treatment was administered. Remarkably, mice that received the AAV8.MOG/rapamycin immunotherapy, 71% (FIG. 24B) and 80% (FIG. 24C), respectively, responded to the treatment and went into near-complete remission (MCS: >1) by day ~30. In contrast, after transiently responding to the rapamycin, the control mice relapsed into severe paralyzing or fatal EAE disease (FIGS. 24B and 24C). Notably, in both groups, a limited number of the animals failed to respond to rapamycin immunosuppression, suggesting the disease process was beyond the point of rescue.

Hepatocyte Expression of MOG in Combination with Rapamycin Promotes Treg Expansion of Peripheral Tregs and Reverses EAE.

Figure 24D:
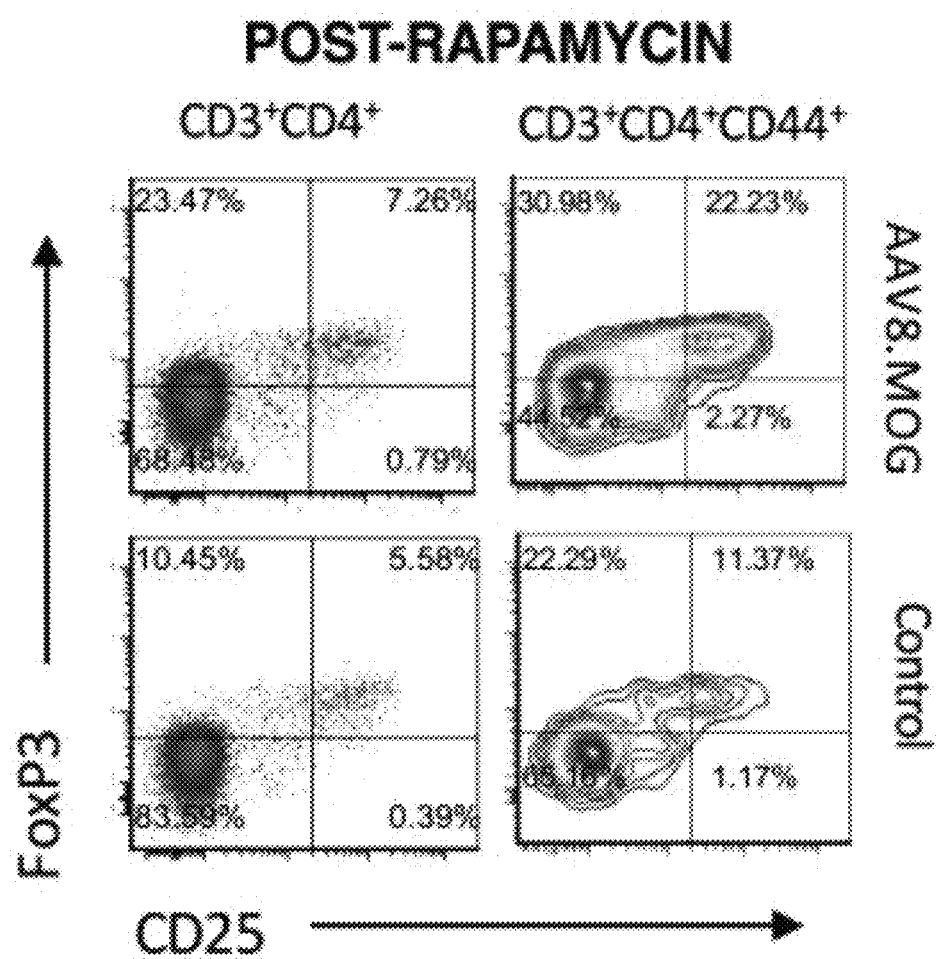
Figure 24E:
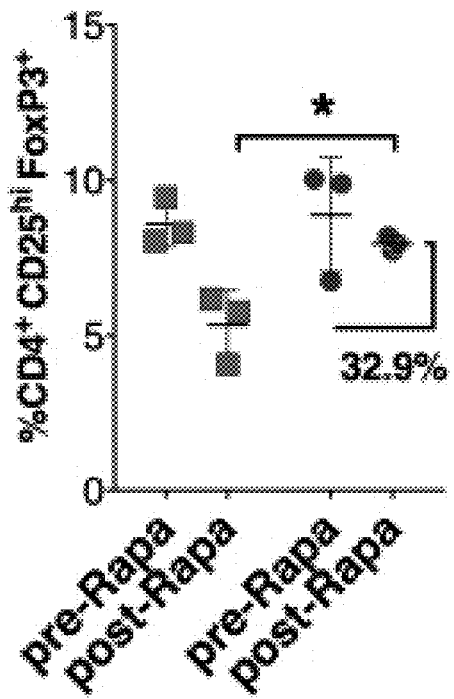
Figure 24F:
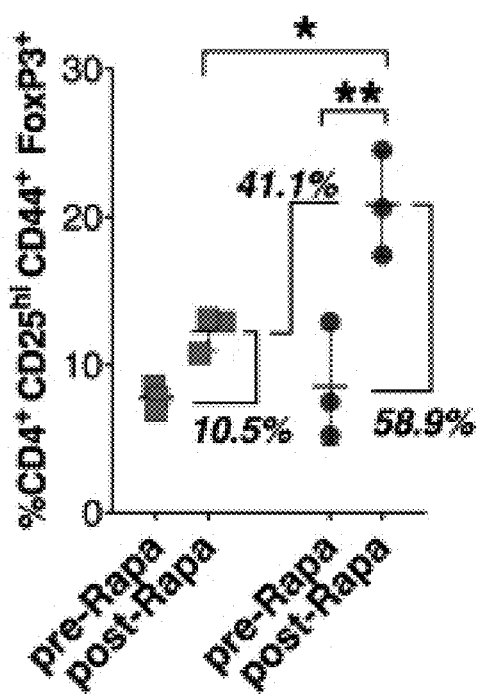

Rapamycin blocks the activation of a serine/threonine protein kinase called mammalian target of rapamycin (mTOR), which has a potent anti-proliferative effect on antigen-stimulated effector T and B cells. This results in selective reduction of T helper (Th) 1, Th2, and Th17 cells while simultaneously allowing the expansion of Ag-specific Tregs.[100] To determine whether rapamycin treatment enhanced the induction of tolerance and cellular responses during AAV8.MOG immunotherapy, the frequency of Tregs from AAV8.MOG/rapamycin-treated mice was compared with rapamycin-only control mice (FIGS. 24D-24F). Phenotypic analysis revealed no significant difference in the percentage of total CD4+CD25hiFOXP3+ Tregs obtained from peripheral blood of AAV8.MOG tolerized mice, compared with that of control mice before rapamycin treatment. In contrast, when analyzed after the final rapamycin dose on day 10, there was an ~33% difference in total Tregs between control mice receiving rapamycin alone and AAV8.MOG-treated animals (FIGS. 24D and 24E).

CD44 is a cell-surface glycoprotein involved in cell-to-cell interactions that are important in activation, migration, and apoptosis. Its relative expression has been associated with FOXP3 expression and Treg function, and can be used to identify activated Tregs.[102,103] Similar to activated effector or memory CD4+ T cells, activated Tregs also express high levels CD44.[103] Restricting the analysis to activated Tregs (CD4+CD44+ CD25hiFOXP3+) revealed a 58.9% increase in Tregs in mice that received rapamycin and AAV8.MOG immunotherapy (FIGS. 24D and 24F). In contrast, only a 10.5% increase was seen in rapamycin-only-treated mice.

Figure 24G:
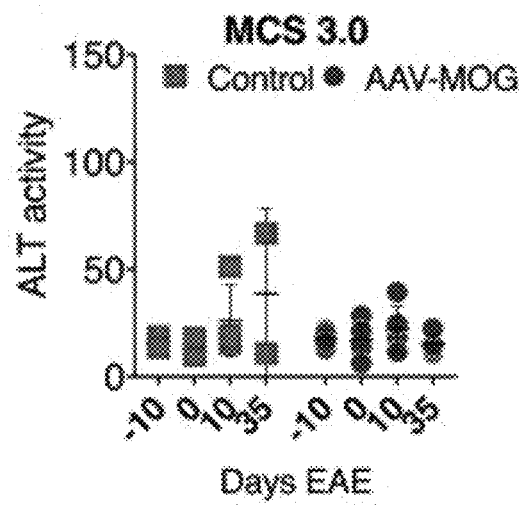
Figure 24H:
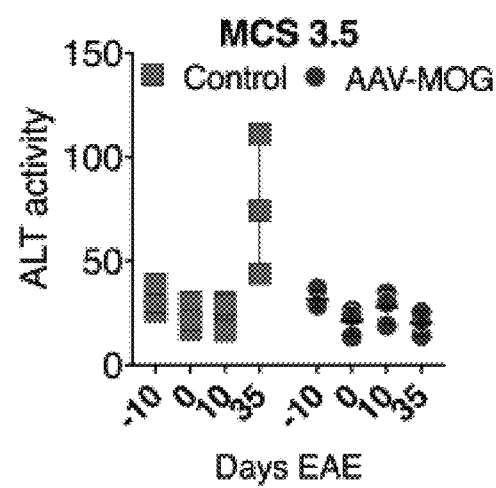

Plasma ALT levels were also monitored as an indicator of liver damage and failure of therapy. As reported above, the level of ALT activity detected in AAV8.MOG-treated mice and control mice was unremarkable throughout the rapamycin treatment window (FIGS. 24G and 24H). However, at 35 days post-treatment the control mice had a significant increase in plasma ALT levels that corresponded with an increase in clinical score (MCS: 3.6±0.5, final). Based on the profound level of neurological impairment the control mice were experiencing, the significant rise in ALT is indicative of liver toxicity associated with end-stage organ failure (FIGS. 24B and 24C).

Collectively, these findings demonstrate that transient immunosuppression with rapamycin has a synergistic effect on AAV8.MOG immunotherapy that selectively induces in vivo expansion of Tregs and restores tolerance in an antigen-dependent manner.[100]

MS is a complex autoimmune disease that has no cure. Early diagnosis and aggressive treatment with immunomodulating agents can lower the relapse rate and slow progression. However, these treatments are generally non-specific and risk significant side effects with long-term use.[104] Newer disease-modifying therapies that target specific immune responses or target specific CNS antigens have shown potential, but various experimental limitations have prevented clinical translation.[77,105,106]

Tregs are an essential component in preventing autoimmunity and controlling responses to alloantigens. A disruption in the homeostasis of tolerance in a variety of autoimmune diseases, including MS, may result from a substantial decrease in the number or functional impairment of Tregs.[76,107] Using the EAE model, studies have shown that adoptive transfer of polyclonal Tregs is able to attenuate the development of autoimmune diseases.[79] In contrast, disease was exacerbated when CD4+CD25+ Tregs were depleted.[3] Additionally, adoptive transfer of autologous ova-specific ex vivo-expanded Tregs has been evaluated in a clinical trial for Crohn's disease.[108] Although the treatment was well tolerated and showed efficacy, the results were only transient, lasting about 5 weeks, which is supported by in vivo and in vitro data suggesting that ova-Tregs have a limited survival capacity upon chronic activation.[108] Other difficulties with ex vivo expansion of antigen-specific Tregs include proper identification of antigens, long culture times, and overall expense.

Although the mechanism is not yet elucidated, various in vivo techniques, such as transgenic expression, liver-targeting nanoparticles, and lentivirus (LV)-mediated gene transfer, have been shown to leverage the natural ability of the liver to induce specific tolerance to an ectopically expressed autoantigen.[46,83,84,7,12,66,64] However, even though these and other studies have provided mechanistic insight, their clinical value is currently being evaluated. Rather, an approach is needed that is translatable to the clinic and achieves robust in vivo induction of a durable Treg response, capable of reversing established autoimmune disease.

Addressing these requirements, the liver-directed AAV immunotherapy procedure presented here is based on the clinically tested AAV gene therapy platform. Overall, it provides a less complex approach for inducing antigen-specific Tregs in vivo.[6,109] It is shown herein that a single dose of vector established a durable source of antigen needed for sustained induction and activation of autoreactive Tregs. Additionally, having engineered the vector to include the full coding sequence of MOG, it is likely to induce multiple immunodominant and sub-dominant antigen-specific Tregs, independent of MHC restrictions and without compromising long-term immune homeostasis. This is supported by previous work in a hemophilia model where an AAV vector expressing clotting factor IX was used to induce tolerance to the same transgene in multiple strains of mice.[15,12,110,10]

As explained above, Treg immunotherapy for MS has to be capable of reversing established disease in order to be clinically feasible. The data presented clearly demonstrate that AAV.MOG immunotherapy not only prevents induction of the autoimmune disease, but more importantly clearly reverses preexisting disease if administered during early onset. However, AAV immunotherapy alone was not sufficient to fully reverse end-stage EAE disease. However, when augmented with transient immunosuppression, a potent synergistic effect was revealed that rescued mice with rapidly progressing paralysis. The use of rapamycin was specifically chosen because it induces de novo expression of FOXP3 and expands functional FOXP3+ Tregs from naive cells in vivo, while inhibiting the proliferation and trafficking of conventional CD4+ and CD8+ T cells.[101,111,112,54] Rapamycin has also been shown to be effective at modulating EAE. Esposito et al.[69] demonstrated that continuous rapamycin monotherapy can effectively inhibit the induction and the progression of established disease; however, upon withdrawal of the drug, mice rapidly developed a relapsing-remitting form of EAE. Clearly, mitigating the inflammation in the CNS was necessary for the AAV8.MOG immunotherapy to be maximally effective.

In summary, a novel immunotherapy has been developed herein that reverses debilitating paralysis in an animal model of MS that is superior to the traditional non-specific immunosuppression therapies currently available. Accordingly, in some embodiments, this approach is used as a clinical therapy for treating MS and/or other human autoimmune diseases.

Example 6—Evaluation Against Challenge with Multiple Immunogenic Epitopes

Data provided herein demonstrates that a single administration of any pf the vectors described herein can provide protection against multiple epitopes, including de novo epitopes that are presented during disease progression through epitope spreading.

Neutralization of epitope spreading remains one of the most elusive aspects of developing effective MS treatments. In 2010, it was shown that, after an initial challenge in the relapsing-remitting EAE mouse with the proteolipid protein epitope PLP139_151, a second antigenic epitope, $PLP_{178-191}$, was revealed to immune cells during the following relapse. See Zhang et al., J. Immunol., 184:6629-6636 (2010). Subsequently, a third epitope was revealed during subsequent relapses in the EAE model against a myelin basic protein epitope. In particular, Zhang stated that, "upon transfer into SJL/J mice, [$PLP_{139-151}$-specific induced Tregs] undergo [antigen]-driven proliferation and are effective at suppressing induction of experimental autoimmune encephalomyelitis induced by the cognate $PLP_{139-151}$ peptide, but not $_{PLP78-191}$ or a mixture of the two peptides." Tregs specific to the $PLP_{139-151}$ epitope were unable to provide bystander or cross-suppression against effector T cells specific for $PLP_{178-191}$. Thus, there is substantial difficulty in reversing the EAE phenotype when EAE-induced mice are challenged with multiple immunogenic epitopes simultaneously. That a single administration of this vector could provide the efficacy of this kind without an adverse response indicates the safety and feasibility of this therapy.

The data in Examples 6 and 7 relate to mixed epitope disease induction, wherein the presence of primary and secondary (and tertiary, etc.) epitopes activate autoimmune conditions. For example, in various embodiments of the mouse models described herein, disease (EAE) is induced using either MOG, PLP, MBP, or a combination of the three and subsequently treated with any one of AAV.MOG, AAV.PLP, AAV.MBP, or a combination of two or three of these vectors. In some embodiments, disease is induced using either MOG, PLP, or both, and subsequently treated with AAV.MOG, AAV.PLP, or both. The data in these Examples, presented below, indicate that each the AAV.MOG, AAV.PLP, AAV.MBP are not restricted to neutralization of epitope of the MOG, PLP, and MBP transgenes, respectively, but rather show cross-reaction and cross-suppression of EAE induced by epitopes that do not share identity with the transgene. Relatedly, data presented in Example 7 suggests the existence of bystander cross-suppression effects. Bystander cross-suppression is suppression of disease activated by an epitope that does not share identity with the transgene encoded in the vector, i.e. is non-antigen restricted.

For example, in the C57BL/6, SJL, DB-1A and related mouse models, an experimental autoimmune encephalomyelitis (EAE) condition can be induced by injection of any one of three protein antigens—MOG, proteolipid protein (PLP), and myelin basic protein (MBP). Induction by one of these antigens produces CD4+ T cell-mediated inflammation in the central nervous system that serves as a relevant model for MS in humans (see, e.g., FIGS. 1, 2A, and 2B). Each of these three proteins presents different immunogenic epitopes to immune cells.

Figure 27A:
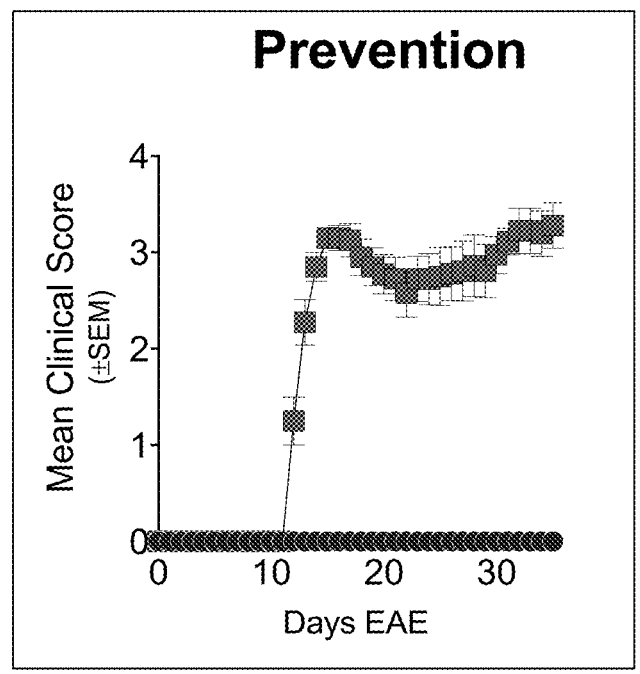
FIG. 27A and FIG. 27B show that AAV.MOG is able to prevent (FIG. 27A) and reverse (FIG. 27B) disease even when induced with multiple immunogenic epitopes simultaneously ($MOG_{35-55}+MOG_{119-132}$). AAV.MOG is capable of preventing and reversing EAE induced by multiple MOG epitopes simultaneously. EAE was induced by injecting $MOG_{35-55}+MOG_{119-132}$/CFA. Mean clinical scores reported as mean±SEM. Clinical symptoms were either prevented or significantly lower in the treated group as compared to the control group.
Figure 27B:
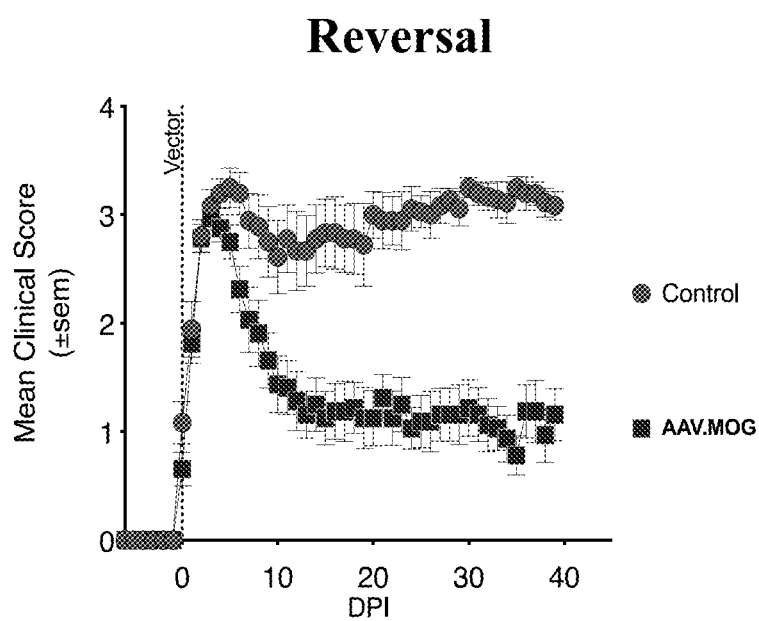

It is demonstrated herein that a single injection of the claimed AAV-MOG vector confers protection against secondary endogenous myelin epitopes (FIGS. 27A and 27B). This finding has major implications for treatment of MS, in which multiple epitope antigens are presented simultaneously in a phenomenon known as epitope spreading. This secondary protection was shown to both prevent and reverse disease conditions in EAE mice, including in relapsing-remitting MS models.

Figure 28A:
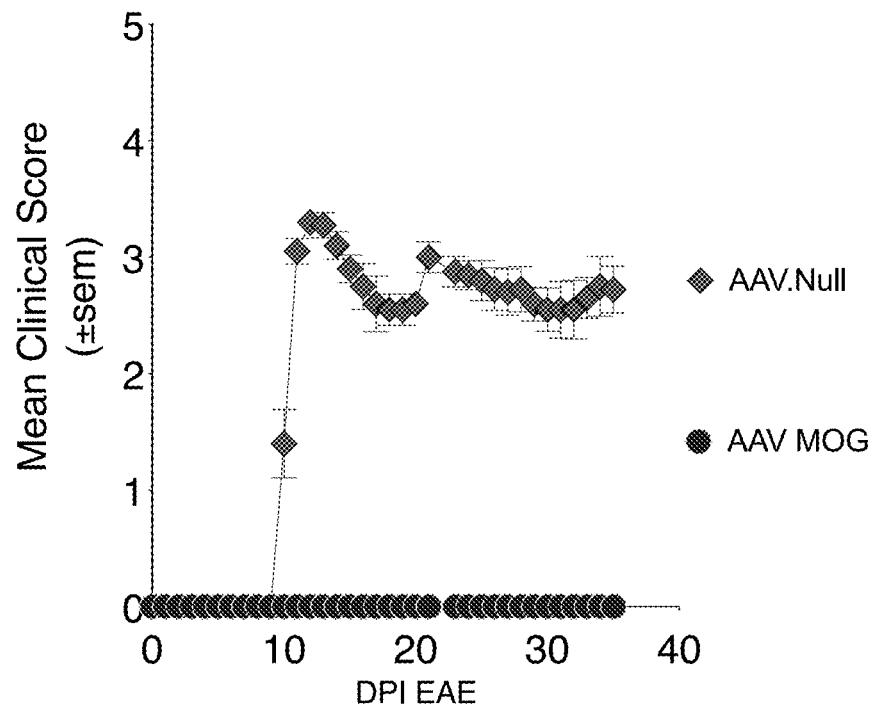
FIG. 28A, FIG. 28B, FIG. 28C and FIG. 28D show that the same AAV.MOG vector is effective in genetically diverse strains of mice with different immunodominant epitopes. AAV.MOG vector is thus effective in mice of a different genetic background. Using DBA-1 ($H-2^q$) mice, AAV8.MOG vector was administered two weeks prior to EAE induction using $MOG_{79-96}$ (FIG. 28A) or given after early disease onset (FIG. 28C). Treatment both prevented and reversed clinical symptoms as control mice developed severe EAE and had to be euthanized (FIG. 28B). Compared to control mice, mice administered treatment remained symptom free (FIG. 28A) or quickly recovered (FIG. 28C).
Figure 28B:
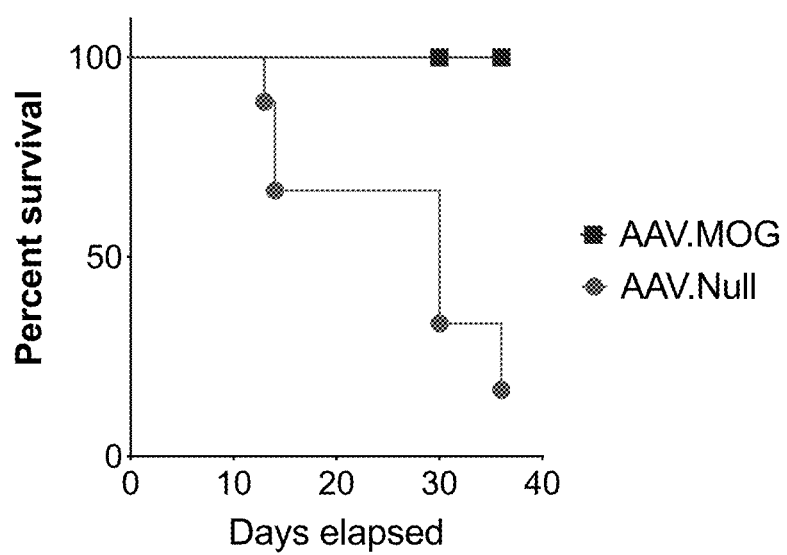
Figure 28C:
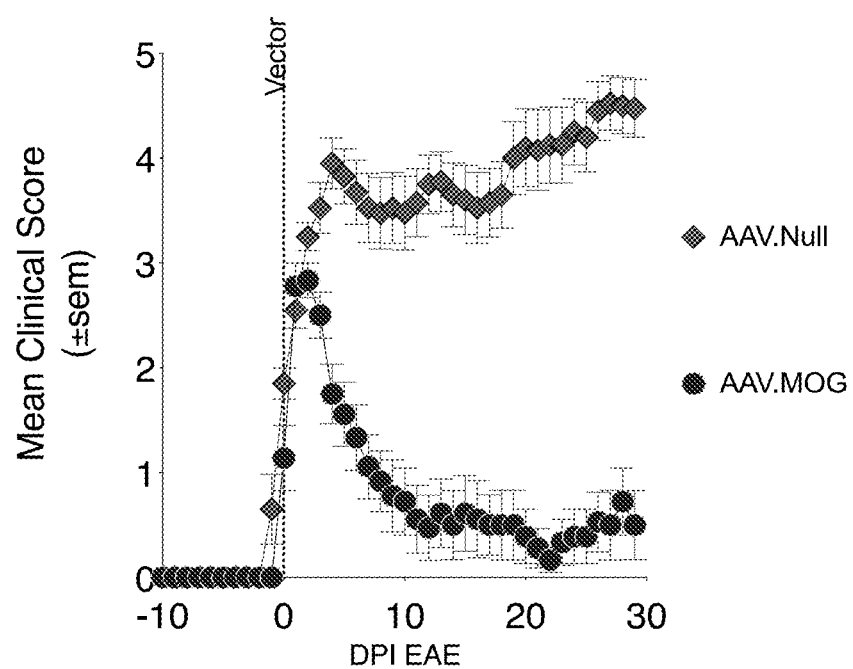
Figure 28D:
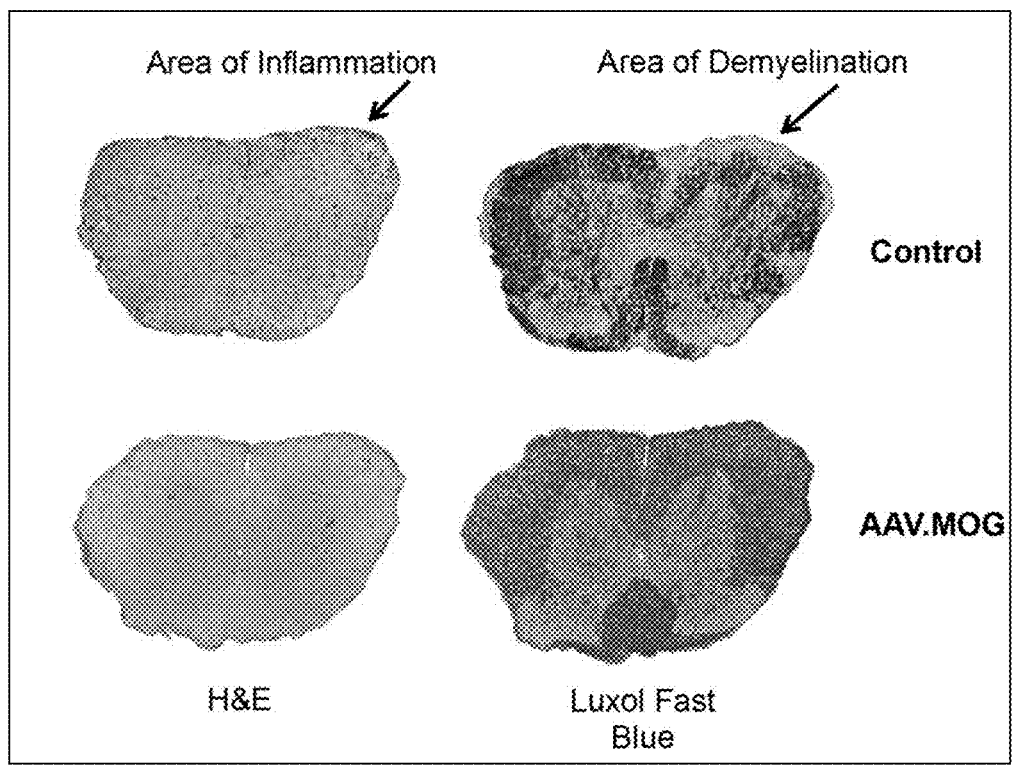

In particular, AAV8-MOG administration to mice prevented EAE (FIG. 27A) and abrogated (FIG. 27B) pre-existing EAE induced by multiple immunogenic MOG epitopes simultaneously. EAE was induced by injecting simultaneously the $MOG_{35-55}$ and $MOG_{119-132}$ epitopes suspended in complete Freund's adjuvant (CFA). EAE symptoms were either prevented or substantially lowered in the treated group as compared to an untreated group of mice. And FIGS. 28A-28D shows that a single administration of AAV-MOG is effective at both reversing pre-existing EAE and preventing EAE onset in mice having different immunogenic epitope backgrounds. AAV8-MOG was administered to genetically diverse DBA-1 mice two weeks prior to EAE induction by the $MOG_{79-96}$ epitope (FIG. 28A). Vector administration prevented EAE in treated mice, while control mice developed severe EAE (FIG. 28B). AAV8-MOG was also administered to DBA-1 mice in which early EAE onset had been triggered. These mice recovered rapidly (FIG. 28C).

Similar EAE reversal and EAE prevention patterns are evaluated and demonstrated with an AAV8 particle comprising a MOG-encoding sequence that has been codon-optimized for human expression.

This data represents the first known demonstration that delivery of a Treg-inducing AAV vector is capable both of preventing and reversing MS disease phenotypes in vivo after conferring protection against multiple simultaneously-presented MOG epitopes and in mice having different immunogenic backgrounds. It establishes robust results in both chronic-progressive and relapsing-remitting models of EAE. This data indicates that the ability of the AAV-MOG vector of the claims to induce tolerance to clinically relevant epitopes in a subject is comprehensive. Additional data demonstrates that AAV-MOG administration in SJL mice did not cause any appreciable liver inflammation. The conferral of protection against multiple epitopes is contemplated herein.

Accordingly, presented herein are rAAV vectors and compositions and particles comprising these rAAV vectors, that provide expression of an encoded therapeutic molecule in the mammal that re-establishes immune tolerance to at least two different neuroproteins. In some embodiments, these at least two different neuroproteins comprise different epitopes of a single neuroprotein, such as MOG, MBP, or PLP. In various embodiments, the encoded therapeutic molecule is a full-length MOG, full-length MBP, or full-length PLP. In some embodiments, the encoded therapeutic molecule has a length that is less than a full-length MOG, full-length MBP, or full-length PLP.

In various embodiments, the sequence encoding the therapeutic molecule is codon-optimized for expression in human cells, tissues, and/or subjects. In some embodiments, the sequence encoding the therapeutic molecule is a MOG, MBP, or PLP-encoding sequence that has been codon-optimized for human expression.

Example 7—Multiple Types of Gene-Immunotherapy are Capable of Preventing and Reversing Severe Disease in a Mouse Model of Multiple Sclerosis AAV Gene Immunotherapy (AAV.MOG) Reverses MS-Like Disease in Genetically Diverse Mice An autoimmune disease like Multiple Sclerosis (MS) is caused by a breakdown of tolerance against endogenous proteins. Regulatory T cells (Tregs) maintain homeostasis between immune activation and suppression; however, in MS the mechanisms dependent on thymically produced Treg cells appear insufficient to prevent the initial priming of encephalithogenic T cells. Using the experimental autoimmune encephalomyelitis (EAE) model of MS, it was previously shown that neuroinflammation and clinical symptoms can be prevented or completely ameliorated, even in preexisting disease, by extrathymically induced antigen (Ag)-specific Tregs. Historically, Ag-specific therapies have remained elusive due to genetic differences and the various encephalitogenic epitopes present. Thus, a treatment must be capable of overcoming such barriers in order to provide the most effective therapy for patients suffering from MS.

To address this, a powerful gene-immunotherapy capable of dynamically adjusting to the unique Ag-specific requirements needed to restore tolerance through de novo-induced Treg was developed. Here, the effectiveness of an adeno-associated virus (AAV) geneimmunotherapy (AAV.MOG) to prevent and/or ameliorate pre-existing EAE disease induced with multiple antigenic epitopes of myelin oligodendrocyte glycoprotein ($MOG_{35-55}$, $MOG_{79-96}$, $MOG_{92-106}$, or $MOG_{1-125}$) is demonstrated. Moreover, it is shown that the same hepatocyte-directed MOG-expressing AAV vector is therapeutically effective in genetically diverse mice (C57BL*H-2$^b$; DBA/1*H-2$^q$; SJL*H-2$^s$).

To demonstrate prevention of disease, mice were given AAV.MOG (or AAV.Null) vector 2-weeks before EAE was induced. In all scenarios, multiple strains of mice receiving the AAV.MOG gene-immunotherapy showed virtually no signs of disease onset nor cellular infiltration or demyelination within the CNS (hallmarks of EAE) (FIGS. 38, 39, 40A, 41A, and 42). In striking contrast, controls developed severe demyelinating EAE.

Figure 40A:
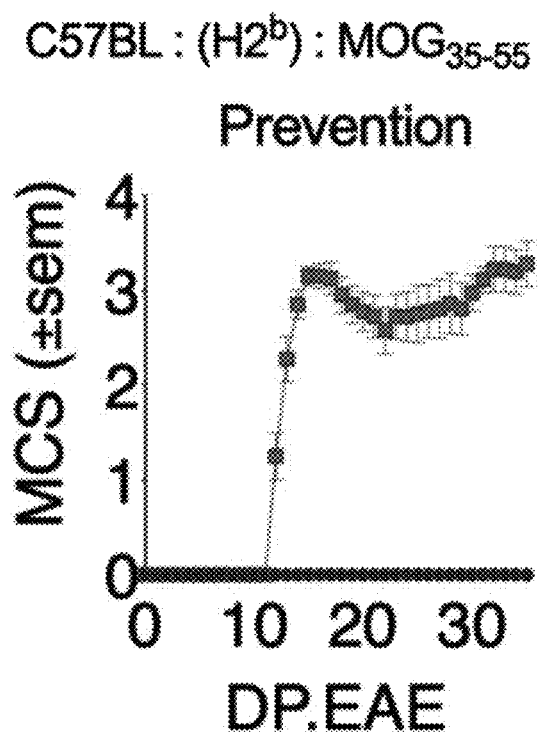
FIG. 40A and FIG. 40B show the prevention and reversal of symptoms using AAV.MOG gene-immunotherapy ($MOG_{35-55}$). C57BL ($H2^b$) mice receiving the AAV.MOG gene-immunotherapy ($MOG_{35-55}$) had significant reductions in neurological impairment (clinical disease score) (p<0.05), cellular infiltration, and demyelination as compared to controls receiving AAV.null.
Figure 40B:
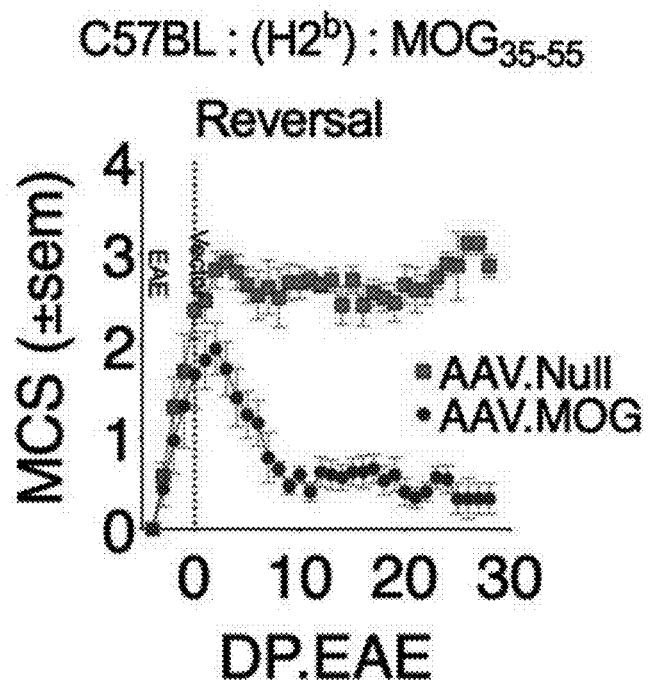
Figure 41A:
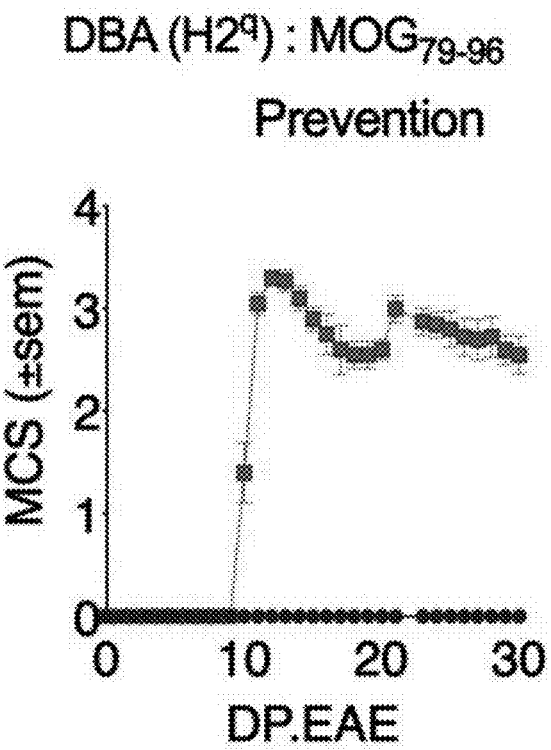
FIG. 41A and FIG. 41B show the prevention and reversal of symptoms using AAV.MOG gene-immunotherapy ($MOG_{79-96}$).

As shown in FIG. 40A, C57BL (H$2^b$) mice receiving the AAV.MOG gene-immunotherapy (MOG$_{35-55}$) showed virtually no signs of disease onset nor cellular infiltration or demyelination within the CNS (hallmarks of EAE) when compared to mice receiving AAV.null (FIG. 40A). C57BL (H$2^b$) mice receiving the AAV.MOG gene-immunotherapy (MOG$_{35-55}$) had significant reductions in neurological impairment (MCS), cellular infiltration, and demyelination as compared to controls receiving AAV.null (FIG. 40B). And as shown in FIG. 41A, DBA (H$2^q$) mice receiving the AAV.MOG gene-immunotherapy (MOG$_{79-96}$) showed virtually no signs of disease onset nor cellular infiltration or demyelination within the CNS when compared to mice receiving AAV.null (FIG. 40A). DBA (H$2^q$) mice receiving the AAV.MOG gene-immunotherapy (MOG$_{79-96}$) had significant reductions in neurological impairment, cellular infiltration, and demyelination as compared to controls receiving AAV.null.

Figure 41B:
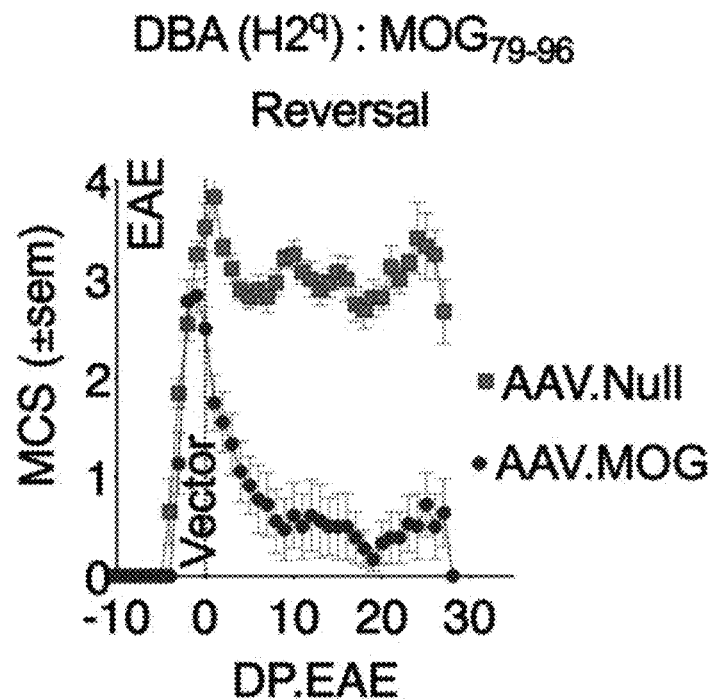

To show the therapeutic effectiveness of the immunotherapy to ameliorate/reverse active pre-existing disease, EAE was induced using one or more immunogenic epitopes, prior to administering treatment at a predetermined disease severity. Remarkably, after an initial increase in disease severity, mice receiving AAV.MOG had significant reductions in neurological impairment (clinical disease score) (p<0.05), cellular infiltration, and demyelination as compared to controls (FIGS. 40B and 41B).

Similar EAE reversal and EAE prevention patterns are evaluated and demonstrated with an rAAV particle comprising a MOG-encoding sequence that has been codon-optimized for human expression. Administration of these particles comprising codon-optimized MOG sequences are currently undergoing evaluation in C57BL/6×SJL, C57BL*H-$2^b$, DBA/1*H-$2^q$, and SJL*H-$2^s$ mice.

Figure 31A:
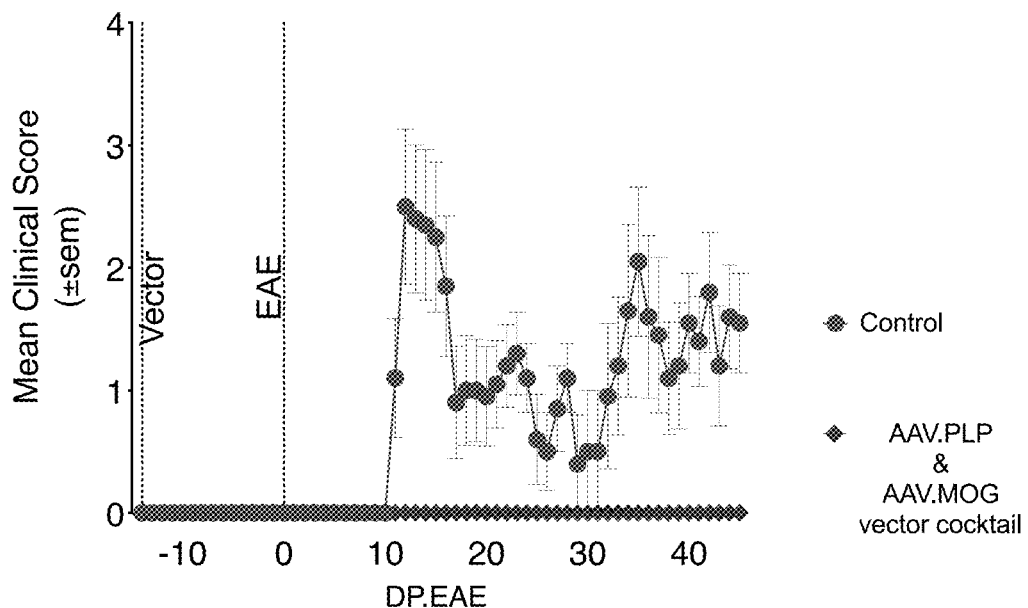
FIG. 31A and FIG. 31B show the prevention of EAE disease and absence of liver damage in the presence of multiple vectors.
Figure 31B:
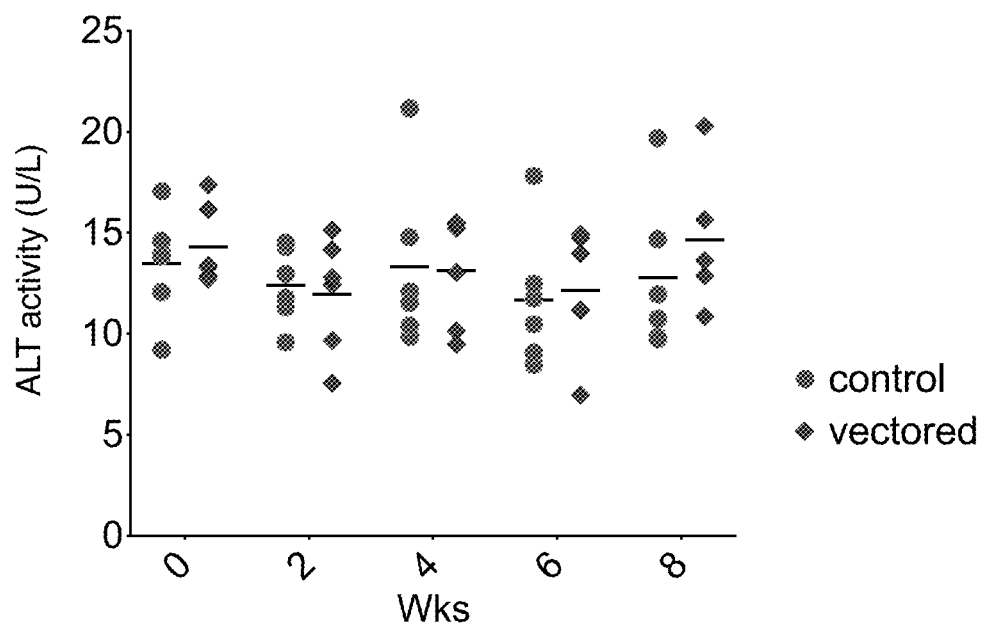
Figure 42:
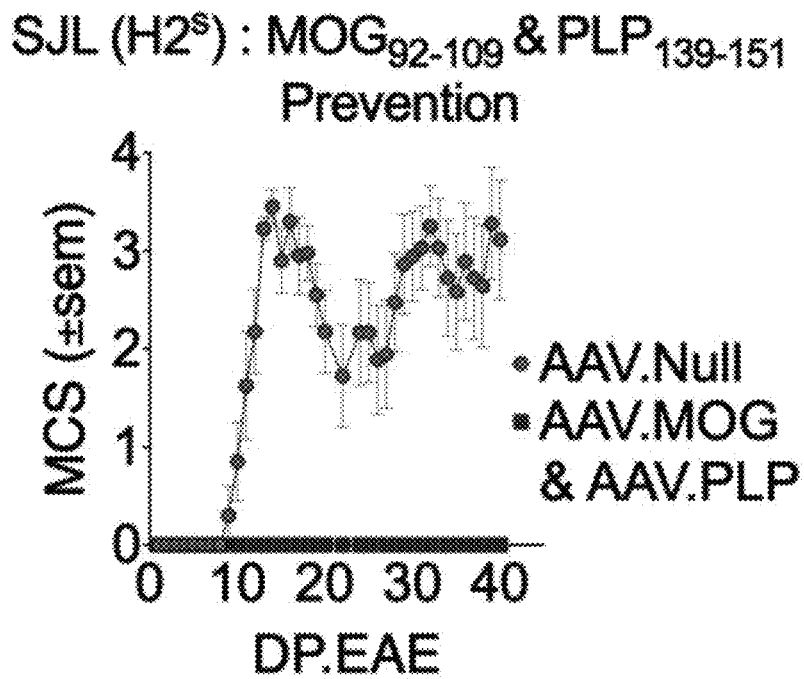
FIG. 42 shows that SJL ($H2^s$) mice receiving the AAV.MOG gene-immunotherapy ($MOG_{35-55}$ & $PLP_{139-151}$) showed virtually no signs of disease onset nor cellular infiltration or demyelination within the CNS (hallmarks of EAE) when compared to mice receiving AAV.null.

Lastly, to further demonstrate the strength and effectiveness of this gene-immunotherapy on disease, a cocktail of vectors encoding two different neuroproteins (AAV.MOG & AAV.PLP) was administered. At 14 days post-injection, disease was induced using both dominant immunogenic EAE inducing epitopes (MOG$_{35-55}$ & PLP$_{139-151}$). Amazingly, the mice receiving the immunotherapy failed to develop disease, whereas the control mice quickly developed a severe relapsing-remitting or (relapse-remitting) EAE disease, as shown in FIGS. 31A, 31B and 42. Female SJL (H-$2^s$) mice were injected with a mixture of AAV.MOG and AAV.PLP vectors to see if there were any adverse reactions or toxicity. No significant differences were determined between mice receiving the mixture of vectors and the control mice. Thus, these results demonstrate vector efficacy and indicate that there was no adverse response to the administration of multiple vectors.

Suppression of EAE with Secondary Immunogenic Epitopes of MOG

Figure 32:
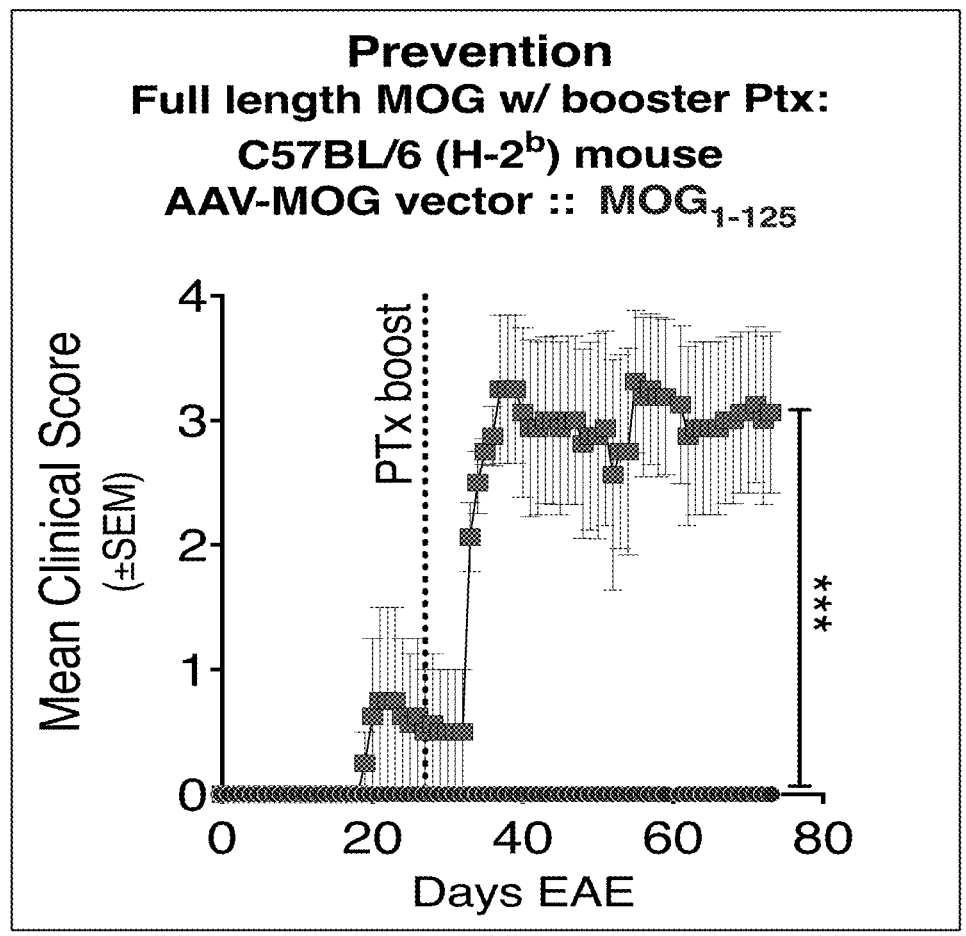
FIG. 32 shows that AAV.MOG is capable of preventing EAE induced by full-length $MOG_{1-125}$. Female C57BL/6 mice were intravenously injected with AAV.MOG or control. Two weeks later, EAE was induced by injecting $MOG_{1-125}$/CFA. Mean clinical scores are reported as mean±SEM; $p \leq 0.0001$.

As shown in FIG. 32, AAV.MOG was capable of preventing EAE induced by full-length MOG$_{1-125}$. Female C57BL/6 mice were intravenously injected with AAV.MOG or control. Two weeks later, EAE was induced by injecting MOG$_{1-125}$ in CFA. At ~30 days post EAE, a pertussis toxin booster was given in order to promote increased disease development. FIG. 32 thus demonstrates that AAV.MOG is protective against initial disease development and reactivation.

Figure 33A:
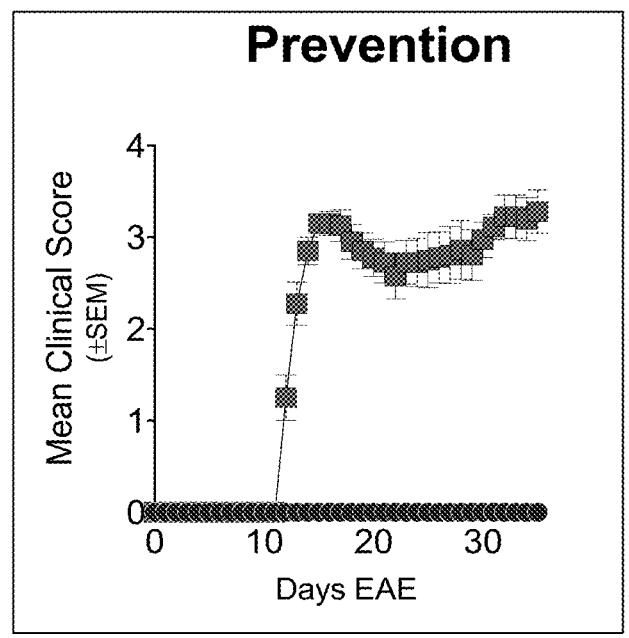
FIG. 33A and FIG. 33B show that AAV.MOG is able to prevent (FIG. 33A) and reverse (FIG. 33B) disease even when induced with multiple immunogenic epitopes simultaneously ($MOG_{35-55}+MOG_{119-132}$). EAE was induced by injecting $MOG_{35-55}+MOG_{119-132}$/CFA. Mean clinical scores are reported as mean±SEM.
Figure 33B:
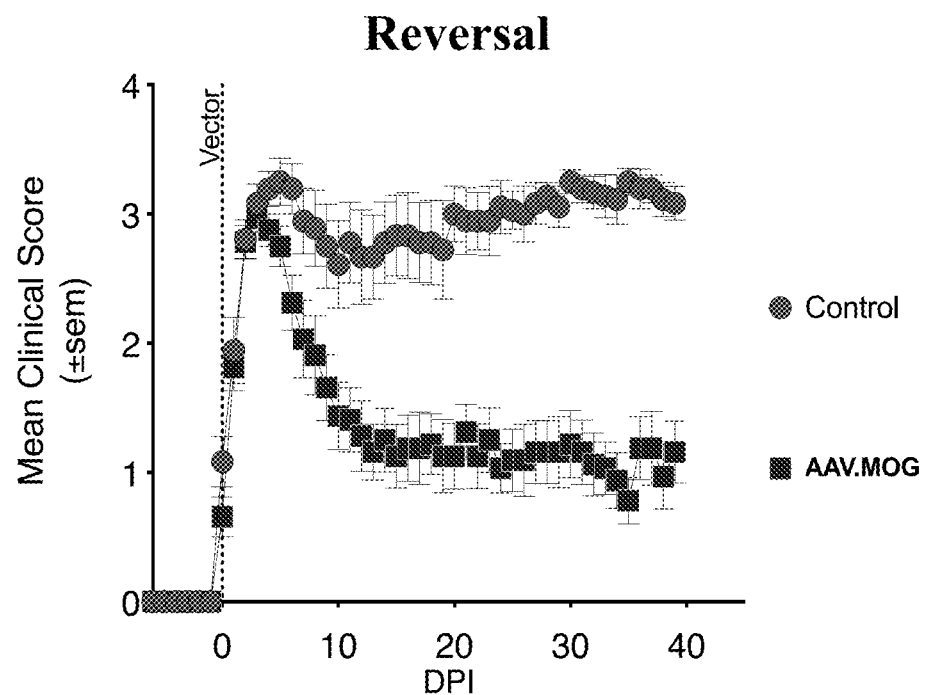

As shown in FIGS. 33A and 33B, AAV.MOG was able to prevent and reverse disease even when induced with multiple immunogenic epitopes simultaneously (MOG$_{35-55}$+ MOG$_{119-132}$). EAE was induced by injecting MOG$_{35-55}$+ MOG$_{119-132}$ in CFA. Clinical symptoms were either prevented or significantly lower in the treated group as compared to the control group.

Figure 34A:
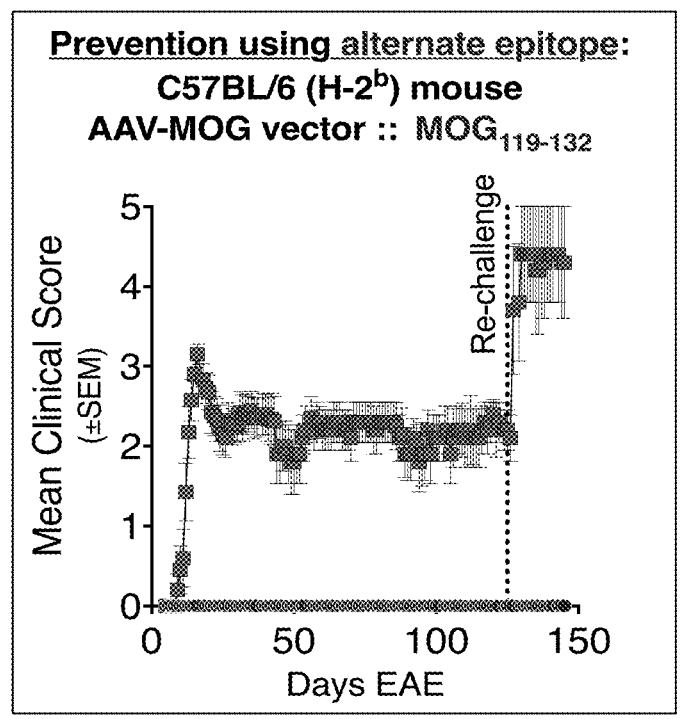
FIG. 34A and FIG. 34B show that AAV8.MOG is capable of preventing EAE induced with transmembrane MOG epitope in C57BL/6 mice. At ~120 days post EAE induction, mice were re-challenged (FIG. 34A). Following re-challenge, mice in the treated group remained disease free, whereas in control mice disease increased (FIG. 34B). Mean clinical scores reported as mean±SEM.
Figure 34B:
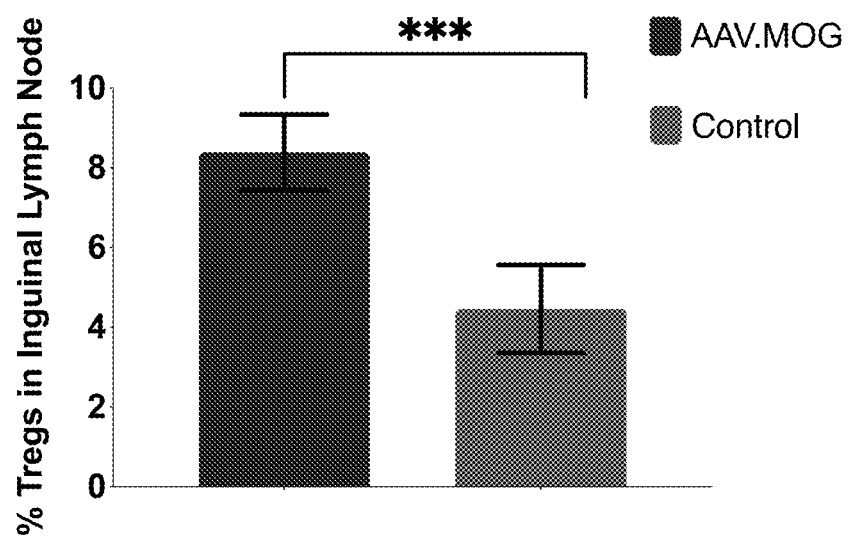

As shown in FIGS. 34A and 34B, AAV8.MOG was capable of preventing EAE induced with transmembrane MOG epitope. C57BL/6 mice were intravenously injected with AAV8.MOG or control at ~8 weeks of age. EAE was induced by injecting MOG$_{119-132}$ in CFA at ~10 weeks. At ~120 days post EAE induction, mice were re-challenged (FIG. 34A). Following re-challenge, mice in the treated group remained disease free, whereas in control mice disease increased (FIG. 34B). Significant increase in Tregs isolated from mice treated with AAV.MOG was observed compared to control mice.

Figure 35:
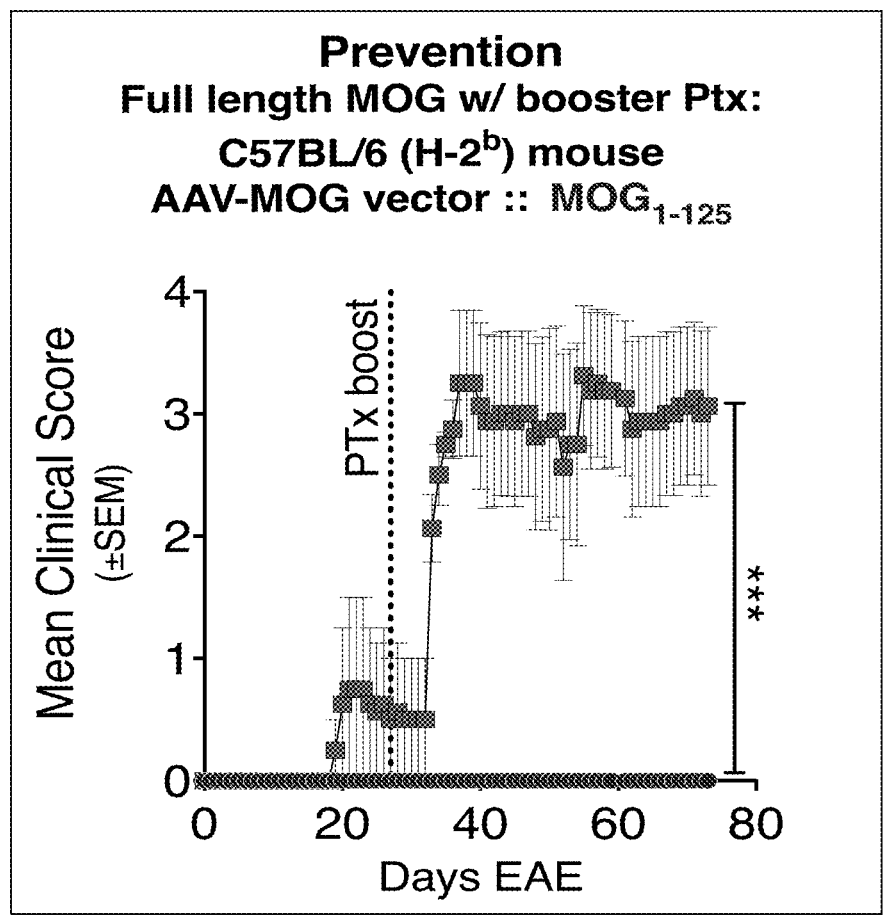
FIG. 35 shows that AAV8.MOG is capable of preventing EAE induced by full-length MOG in female C57BL/6 mice. The depicted plot shows mean clinical scores of treated (n=5) and control (n=5) mice. Mean clinical scores reported as mean±SEM; $p \leq 0.0001$.

As shown in FIG. 35, AAV8.MOG was capable of preventing EAE induced by full-length MOG. Female C57BL/6 mice were intravenously injected with $1 \times 10^{11}$ vector genomes of AAV8.MOG or control at ~8 weeks of age. EAE was induced by injecting MOG$_{1-125}$ emulsified in CFA s.c. at ~10 weeks of age. PTX booster was given ~30 days post EAE. Mice were monitored daily for clinical signs of EAE.

Figure 36:
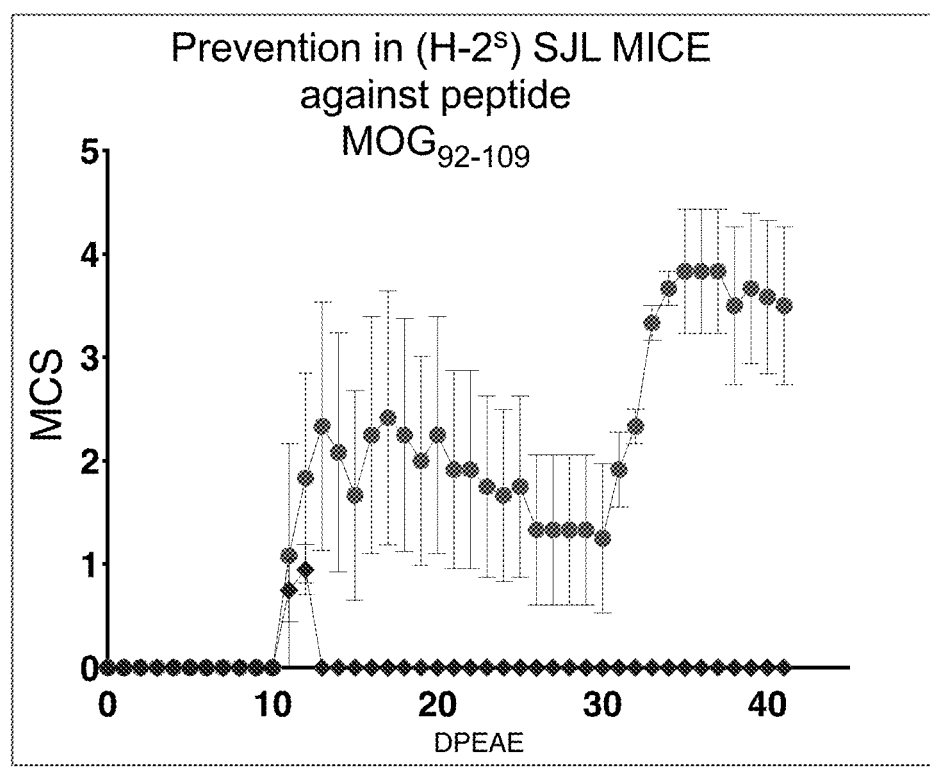
FIG. 36 shows disease prevention in SJL ($H-2^s$) mice using an alternate MOG epitope. SJL were treated with AAV8.MOG or Null vector. Two weeks later, EAE was induced with an alternate epitope, $MOG_{92-109}$.

As shown in FIG. 36, EAE onset was prevented in SJL (H-$2^s$) mice for which EAE was induced with an alternate MOG epitope, MOG$_{92-109}$. SJL were treated with AAV8.MOG or Null vector. Two weeks later, EAE was induced with MOG$_{92-109}$. Mice receiving therapeutic vector were protected from developing EAE for at least 40 days.

Figure 37:
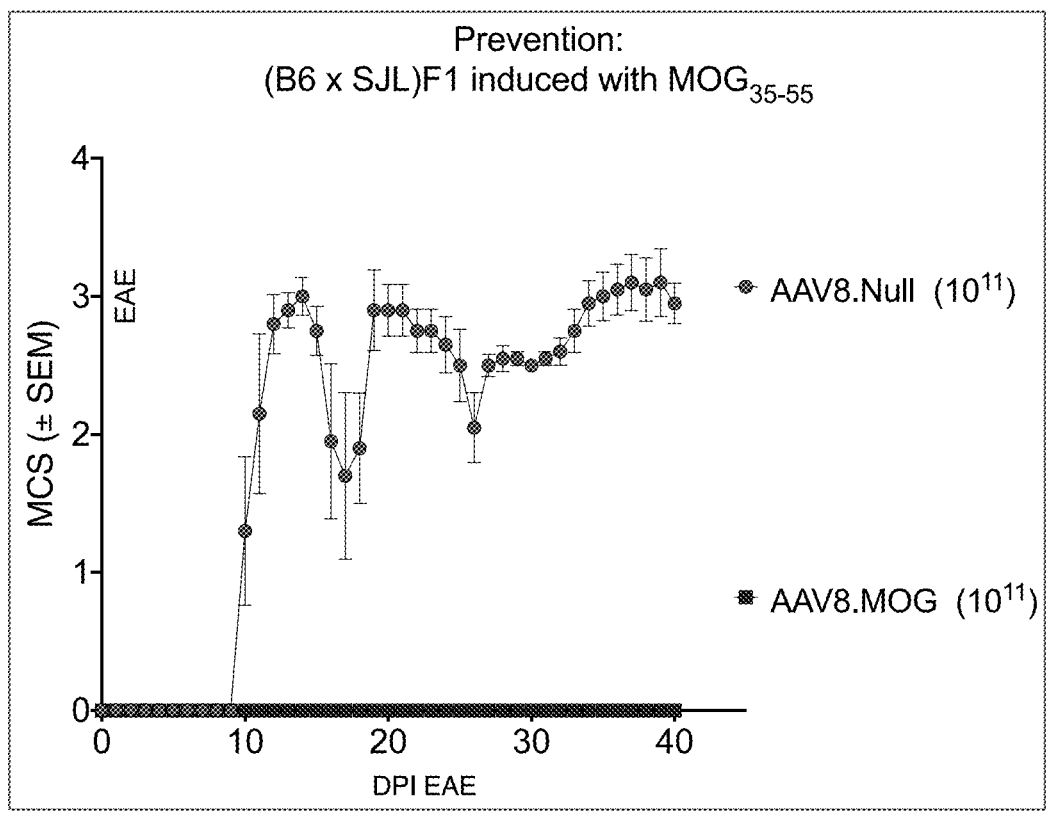
FIG. 37 shows disease prevention in cross-bred mice that were induced with alternate epitope $MOG_{35-55}$.
Figure 38:
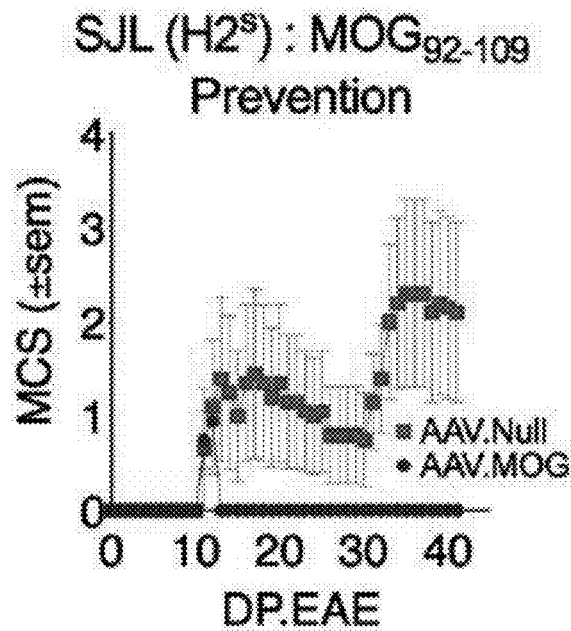
FIG. 38 shows that SJL ($H2^s$) mice receiving the AAV.MOG gene-immunotherapy ($MOG_{92-109}$) showed virtually no signs of disease onset nor cellular infiltration or demyelination within the CNS (hallmarks of EAE) when compared to mice receiving AAV.null.
Figure 39:
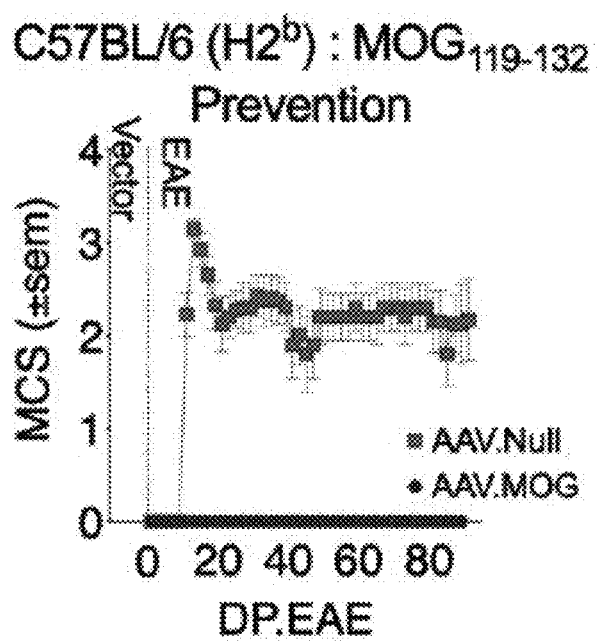
FIG. 39 shows that C57BL/6 ($H2^b$) mice receiving the AAV.MOG gene-immunotherapy ($MOG_{119-132}$) showed virtually no signs of disease onset nor cellular infiltration or demyelination within the CNS (hallmarks of EAE) when compared to mice receiving AAV.null.

As shown in FIG. 37, EAE onset was prevented in cross-bred mice for which EAE was induced with an alternate MOG epitope, MOG$_{35-55}$. The first-generation offspring of a cross of B6 and SJL mice were treated with AAV8.MOG or Null vector. Two weeks later, EAE was induced with MOG$_{35-55}$ Mice receiving therapeutic vector were protected from developing EAE for at least 40 days.

These results establish a novel gene immunotherapy platform for treating MS that is universally applicable and superior to the traditional non-specific immunosuppression therapies currently available.

AAV.PLP Stops Disease and Prevents Epitope Spreading in a Model of Relapsing-Remitting Multiple Sclerosis In autoimmune diseases like MS there is a failure of thymically derived regulatory T cells (Tregs) to maintain tolerance, and antigen-specific therapies have remained elusive due to the genetic diversity of multiple unknown encephalitogenic epitopes present in patients. To address this, relevant AAV-based geneimmunotherapies that can restore tolerance in order prevent or reverse clinical symptoms and neuroinflammation in preexisting disease by inducing antigen specific Tregs in the experimental autoimmune encephalomyelitis (EAE) model have been developed.

Given that 85% of MS patients are diagnosed with relapsing-remitting (RR) MS, demonstrating the therapeutic efficacy of this novel gene-immunotherapy in models that closely resemble clinical disease is an essential step toward a cure. Proteolipid protein (PLP)-induced EAE presents with an initial relapsing-remitting disease (RR-EAE), followed by a secondary progressive stage in SJL mice and is similar to that of human MS disease.

Using a hepatocyte-directed AAV vector expressing mouse PLP (AAV.PLP), antigen-specific tolerance to multiple epitopes of PLP and abrogated disease has been effectively induced/restored. To initially test if the gene-immunotherapy vector could prevent disease, AAV.PLP or Null vector was given 14 days prior to EAE induction. EAE was then induced in SJL (H-2$^s$) mice by immunization using PLP$_{139-151}$ in adjuvant.

Figure 29A:
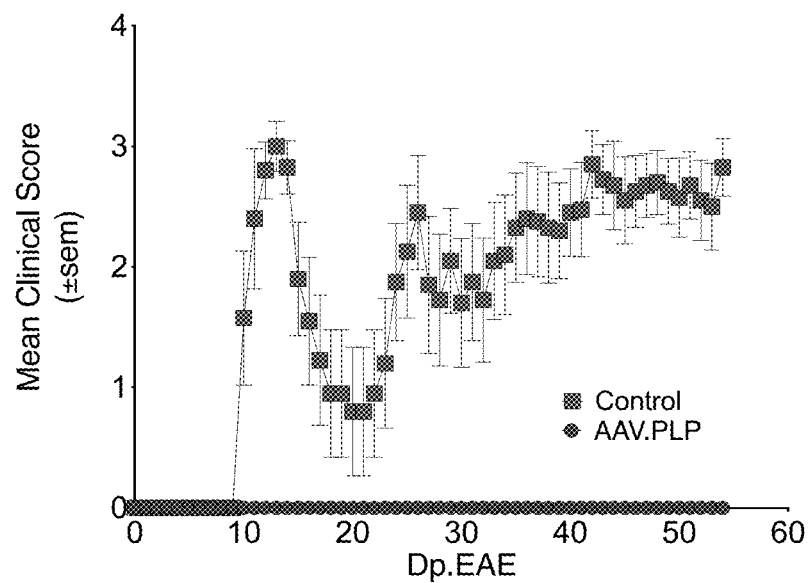
FIG. 29A, FIG. 29B, FIG. 29C, FIG. 29D, FIG. 29E, and FIG. 29F show the prevention and reversal of relapsing-remitting disease that was induced with immunodominant epitope $PLP_{139-151}$. Disease was induced in female SJL ($H-2^s$) mice using the immunodominant epitope of PLP mapping to an intracellular region of the native protein ($PLP_{139-151}$). AAV.PLP vector or control was administered either 10 days before (FIG. 29A), ~10 days after (FIG. 29E), or ~18 days after EAE was induced (FIG. 29F).
Figure 29B:
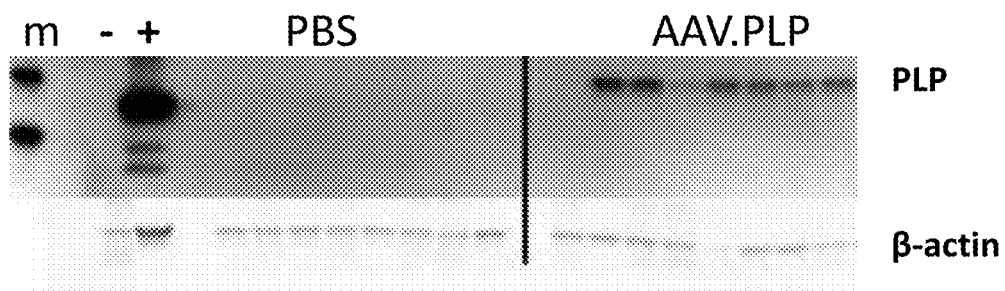
Figure 29C:
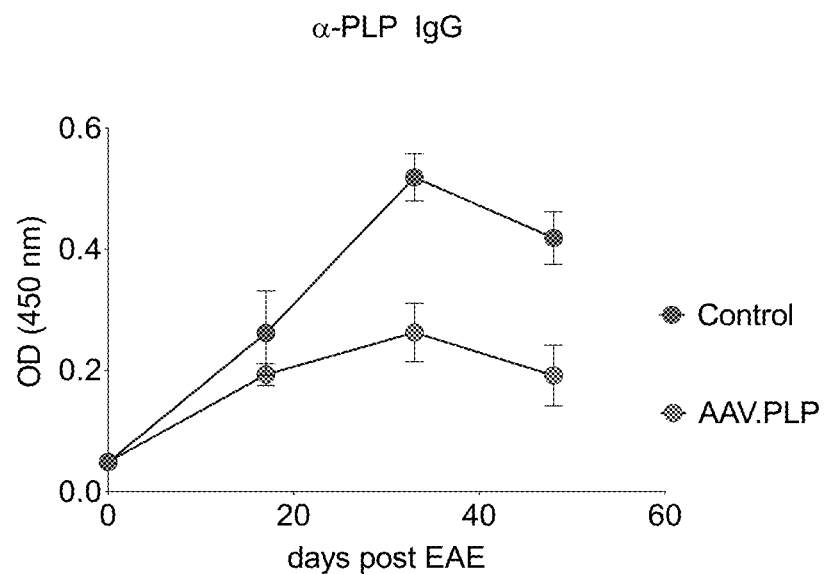
Figure 29D:
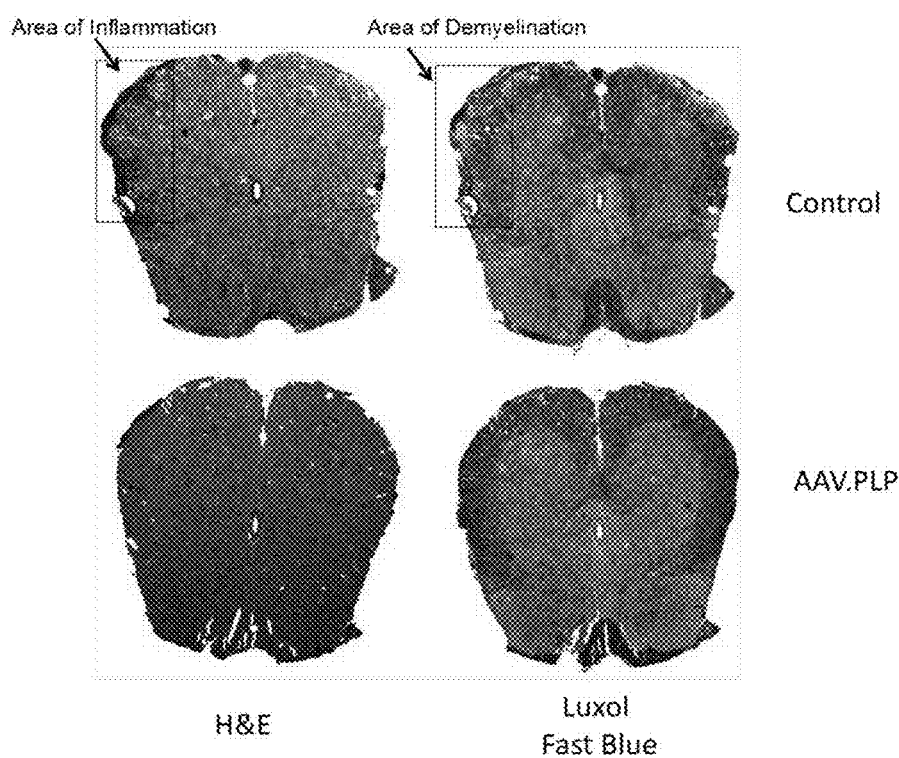
Figure 29E:
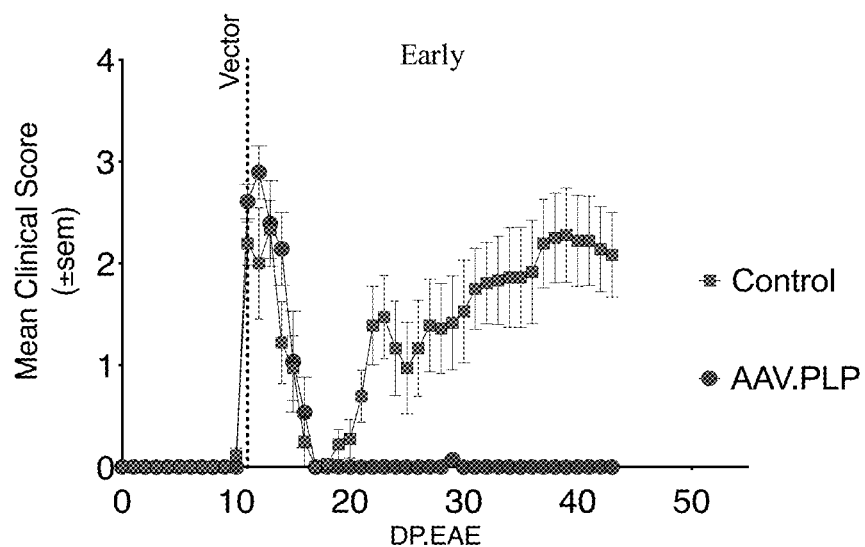
Figure 29F:
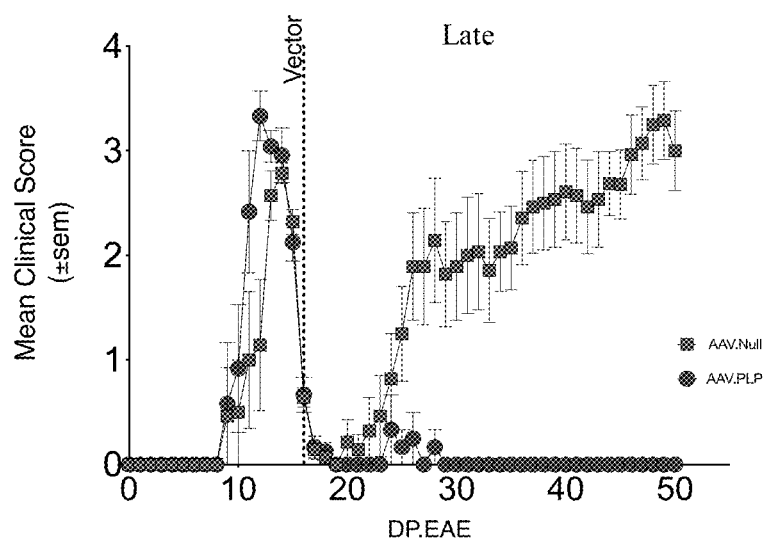

Beginning 10 days later, all control mice quickly developed severe RR-EAE. Remarkably, the AAV.PLP treated mice were protected and never developed any signs of neurological disease (FIG. 29A). For therapeutic reversal of pre-existing disease, immunotherapy treatment was administered after the first appearance of symptoms (early reversal) or during the first remission (late reversal) (FIGS. 29E and 29F). Again, following the initial response, AAV.PLP completely blocked or ameliorated clinical disease, reduced cellular infiltration, and suppressed demyelination in PLP$_{139-151}$ immunized mice, regardless of treatment timing.

Figure 30A:
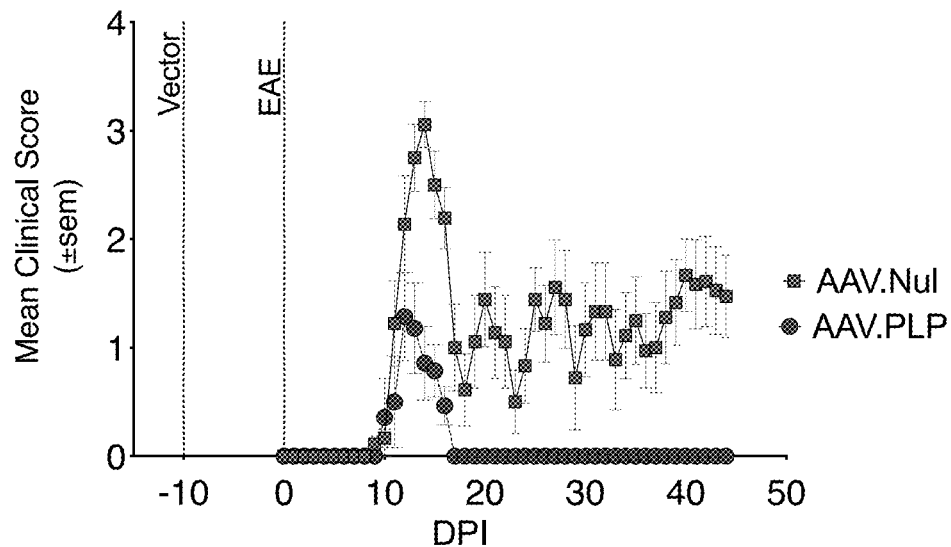
FIG. 30A and FIG. 30B show the prevention and reversal of relapsing-remitting disease induced with a secondary epitope $PLP_{178-191}$. Disease was induced in female SJL (H-T) mice using an alternate epitope of PLP mapping to an extracellular region of the native protein ($PLP_{178-191}$) either 10 days after (FIG. 30A) or ~10 days before (FIG. 30B) AAV.PLP vector was administered. In both timelines, AAV.PLP was able to establish overt protection and prevented disease relapse after initial onset.
Figure 30B:
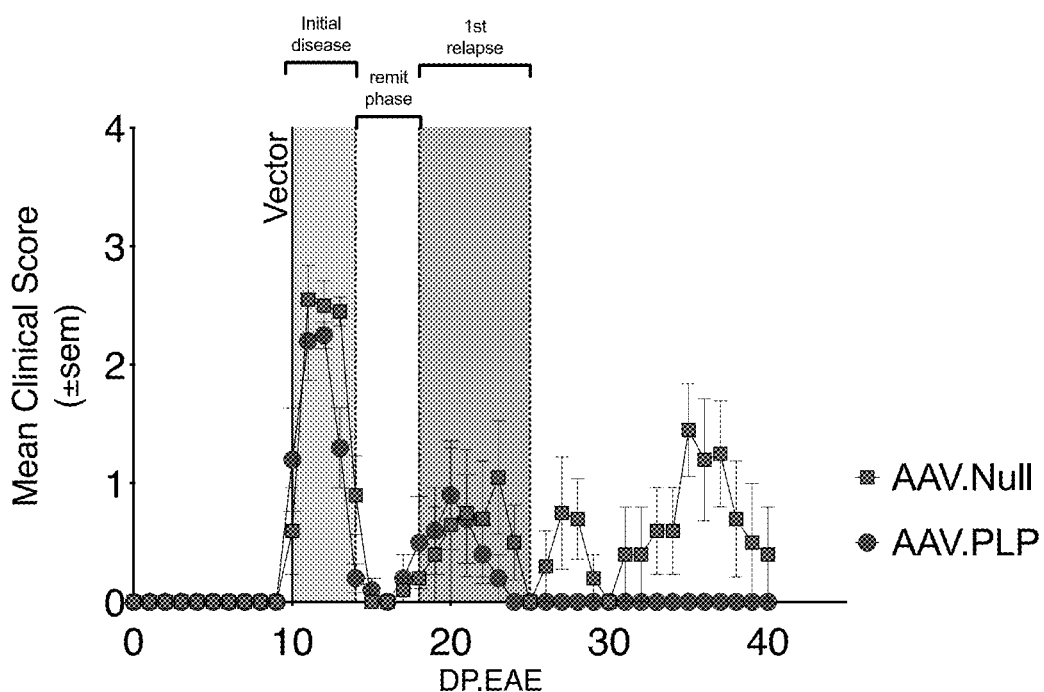
Figure 43:
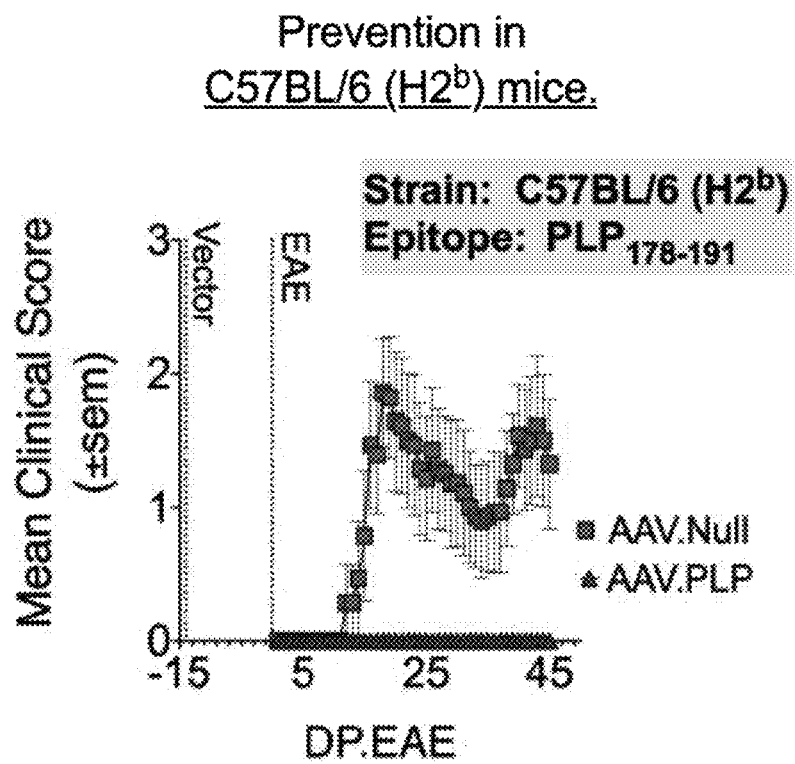
FIG. 43 shows that that AAV.PLP can adjust to genetic diversity (MHC-unrestricted). EAE was induced in a cohort of C57BL/6 ($H2^b$) (IAb) mice using AAV.PLP gene-immunotherapy ($PLP_{178-191}$). The AAV.PLP gene-immunotherapy completely prevented disease.

To demonstrate that AAV.PLP is not restricted to a specific epitope, the vector was tested using a secondary immunogenic PLP epitope (PLP$_{178-191}$) that results from the epitope spreading process occurring in SJL mice induced with PLP$_{139-151}$. Remarkably, in both prevention and reversal experiments, disease was significantly reduced or resolved in AAV.PLP treated mice (FIGS. 30A and 30B). In contrast, 100% of the control mice relapsed after the initial remission phase. Lastly, to show that AAV.PLP can adjust to genetic diversity (MHC-unrestricted), EAE was induced in a cohort of C57BL (IAb) mice using PLP$_{178-191}$. As before, the AAV.PLP gene-immunotherapy completely prevented disease (FIG. 43).

Similar RR-EAE reversal and RR-EAE prevention patterns are evaluated and demonstrated with an rAAV particle comprising a PLP-encoding sequence that was codon-optimized for human expression. Administration of these particles comprising codon-optimized PLP sequences are currently undergoing evaluation in SJL and C57BL mice, as well as cross-bred C57BL/6×SJL mice.

For the first time, definitive evidence is provided showing that AAV directed gene-immunotherapy not only efficiently prevents the development of MS-like disease, but can also abrogate active pre-existing disease and relapses in a murine model of RRMS. The data further supports that treatment simultaneously provides protection against intramolecular epitope spreading. Clinical translation of this novel gene therapy could result in prevention of the early inflammatory responses, thus stopping the transition into secondary progressive MS and significantly improving the quality of life for MS patients.

MBP-Specific Gene-Immunotherapy (AAV.MBP) Prevents and Reverses Severe Disease in a Mouse Model of Multiple Sclerosis Multiple sclerosis (MS) is an autoimmune of the central nervous system that results from a loss of tolerance to specific neuroproteins. It is the most prevalent non-traumatic neurological disorder incapacitating adults. Currently, approved therapies are based upon generalized immune suppression which become less effective with disease progression and are associated with significant adverse effects. Antigen-specific gene-immunotherapies capable of suppressing and reversing severe experimental autoimmune encephalomyelitis (EAE) induced with multiple neuroproteins, regardless of the epitope or genetic haplotype of the mouse, have recently been developed.

Adding to the platform described herein, viral vector AAV.MBP was designed to provide immune tolerance to myelin basic protein (MBP), a well-characterized autoantigen highly associated with MS and linked to epitope spread in the CNS of patients, has been engineered. Here, the preventative and therapeutic potential of this novel gene therapy is demonstrated using cohorts of (SJL×PL) F1 mice immunized with the immunogenic MBP$_{Ac1-9}$ epitope located within the N-terminal portion of the MBP protein.

Figure 44:
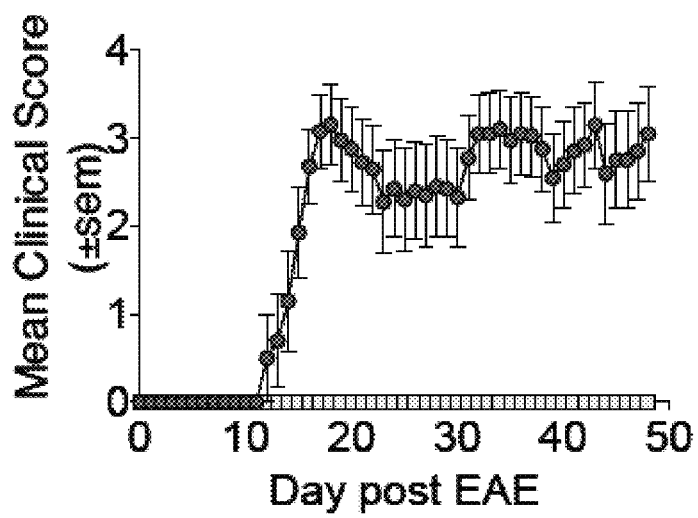
FIG. 44 shows the use of AAV.MBP to prevent EAE induction in mice. AAV.MBP or AAV.Null vector ($10^{11}$ vg/mouse; intravenous injection) was given to two groups of mice (n=10/group) 2-weeks prior to being immunized with the MBP epitope emulsified in CFA in order to prophylactically induce tolerance to MBP. Beginning on day 10 post-EAE induction, the control mice developed severe EAE with bilateral hindlimb paralysis that persisted for >50 days. None of the mice that received AAV.MBP showed any signs of EAE throughout the entire course of the study (MCS peak of 3.2±0.5 versus 0±0; P<0.001)
Figure 46:
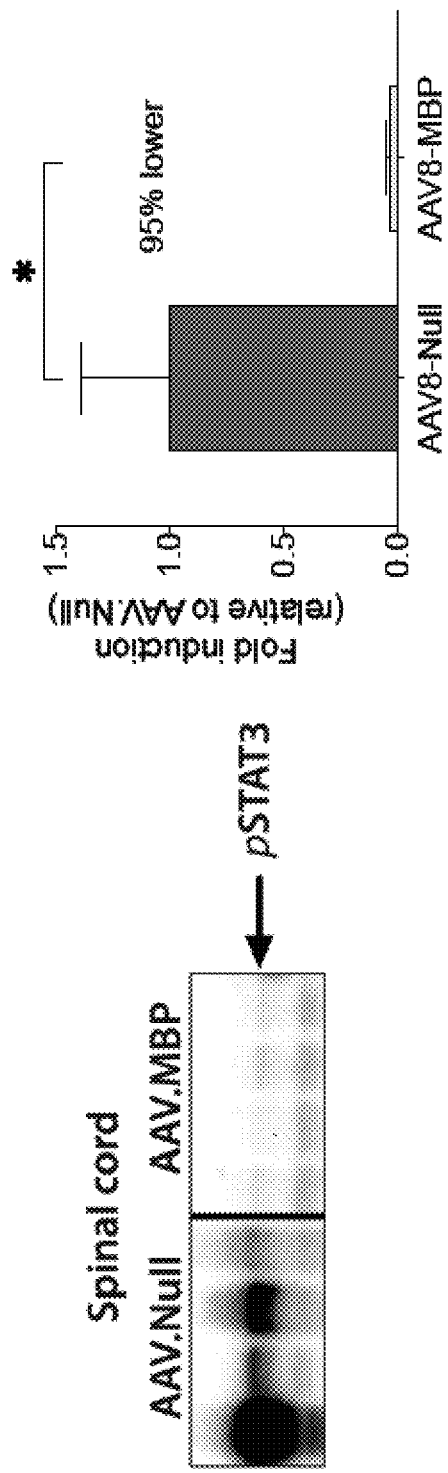
FIG. 46 shows that, at endpoint, AAV.MBP mice had 95% less phosphorylated STAT-3 in the spinal cord compared to the control mice (P<0.05).

To demonstrate prevention of disease, AAV.MBP or AAV.Null vector ($10^{11}$ vg/mouse; intravenous injection) was given to two groups of mice (n=10/group) 2-weeks prior to being immunized with the MBP epitope emulsified in CFA in order to prophylactically induce tolerance to MBP. Beginning on day 10 post-EAE induction, the control mice developed severe EAE with bilateral hindlimb paralysis that persisted for >50 days. In stark contrast, none of the mice that received AAV.MBP showed any signs of EAE throughout the entire course of the study (MCS peak of 3.2±0.5 versus 0±0; P<0.001) (FIG. 44). At endpoint, AAV.MBP mice had 95% less phosphorylated STAT3 in the spinal cord compared to the control mice (P<0.05). This is notable because it has also been shown that development of pathogenic Th17 cells in vivo is dependent on STAT3 signaling (FIG. 46).

Figure 45:
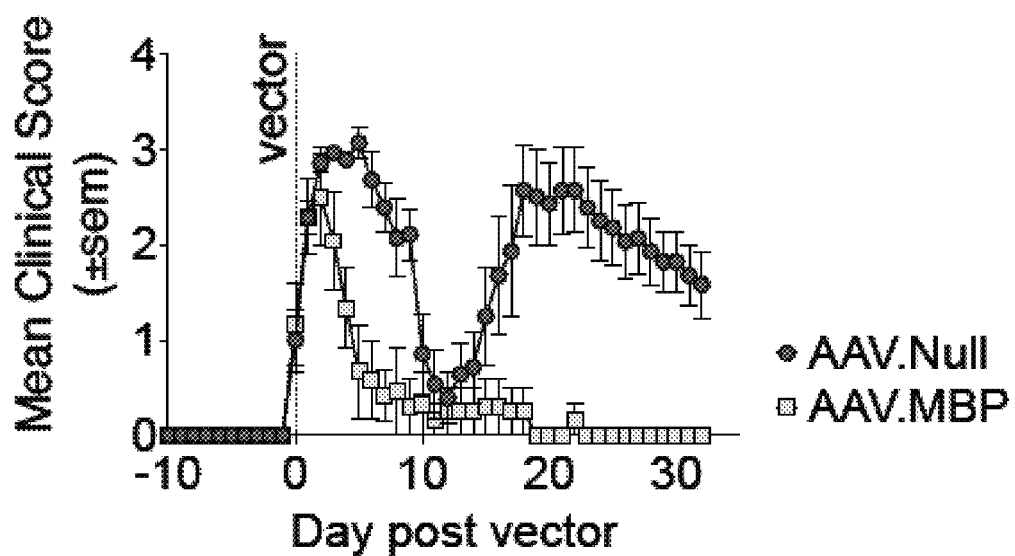
FIG. 45 shows that the gene-immunotherapy can also reverse active-pre-existing disease. EAE was induced using the immunogenic $MBP_{Ac1-9}$ epitope emulsified in CFA. At disease onset, AAV.MBP (or AAV.Null) vector was given. AAV.MBP mice reached a similar MCS peak to that of control (2.5±0.5 versus 2.9±0.1; not significant).

Next, it is demonstrated that the gene-immunotherapy can also reverse active-pre-existing disease. This time EAE was induced first using the immunogenic MBP$_{Ac1-9}$ epitope emulsified in CFA. At disease onset, AAV.MBP (or AAV.Null) vector was given. AAV.MBP mice reached a similar MCS peak to that of control (as shown in FIG. 45). Notably, AAV.MBP mice started recovering as early as 3 days post-vector delivery, whereas clinical disease continued to worsen until day 6 post-injection in AAV.Null-treated mice. Furthermore, by day 9 post-vector delivery, AAV.MBP mice regained significant motor function (lower MCS) compared to the control mice (Ps<0.05). At day 12 post-vector injection, mice from both groups almost completely recovered; however, disease in mice that received AAV.Null quickly relapsed and remained significantly disabled until the end of the experiment (Ps<0.05). In contrast, after the initial response, the AAV.MBP treated mice remained stable and free of clinical disease symptoms.

Similar EAE reversal and EAE prevention patterns are evaluated and demonstrated with an rAAV particle comprising an MBP-encoding sequence that was codon-optimized for human expression. Administration of these particles comprising codon-optimized sequences are currently undergoing evaluation in (SJL×PL) F1 mice, as well as C57BL/6×SJL mice.

These results clearly demonstrate the ability of the present AAV gene-immunotherapy to suppress autoimmune response against MBP, a known MS related antigen.

Additional Experiments Involving Mixed Immunogenic Peptide Induction of EAE

Figure 47:
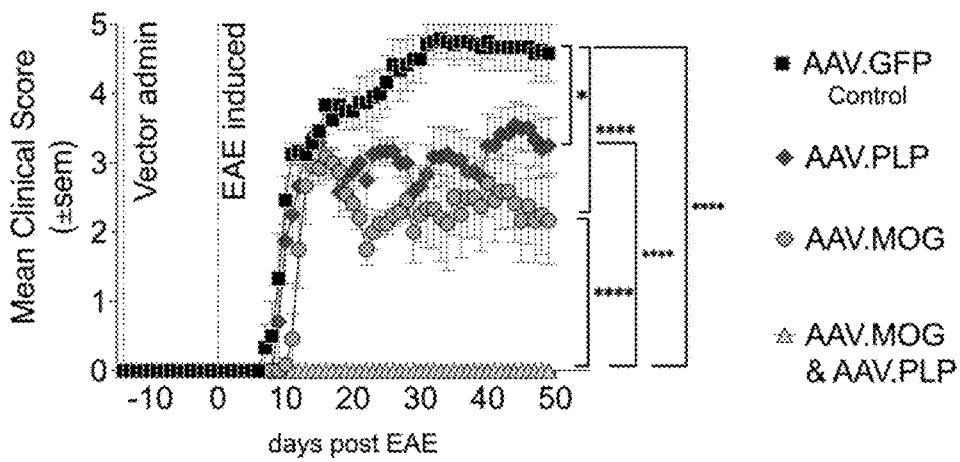
FIG. 47 shows the results of a study of EAE suppression (prevention) by a combination of two myelin peptide-encoding rAAV vectors in a cross-bred, genetically diverse mouse strain. Female C57Bl/6 mice were crossed with male SJL/J mice to produce an F1 generation model (C57Bl/6× SJL/J)F1 which received either AAV.MOG, AAV.PLP, a cocktail of AAV.MOG & AAV.PLP, or AAV.GFP control vector. Two weeks later, EAE was induced using a mixture of $MOG_{35-55}$ & $PLP_{139-151}$. Statistical analysis was performed using ordinary one-way ANOVA.

Induction of demyelinating EAE disease is usually limited to a single protein or peptide emulsified in adjuvant. To overcome this single antigen limitation, a hybrid mouse system was developed by crossing female C57BL/6 mice with male SJL/J mice that allows for the induction and development of EAE disease using a mixture of immunogenic peptide epitopes such as MOG$_{35-55}$ and PLP$_{139-151}$. The first-generation (F1) offspring were used to evaluate the therapeutic efficacy of the AAV immunotherapy vectors in a more complex multiple epitope system. In a first experiment evaluating EAE suppression, cohorts of (C57BL/6×SJL)F1 mice received i) AAV.MOG, ii) AAV.PLP, iii) AAV.GFP control vector, or iv) a cocktail of AAV.MOG & AAV.PLP two weeks before EAE was induced using a mixture of MOG$_{35-55}$ & PLP$_{139-151}$ emulsified in adjuvant to determine if the vector cocktail could prevent EAE disease from developing. The data demonstrates that the single AAV.PLP vector prevented PLP$_{139-151}$ induced diseased and the single AAV.MOG vector prevented MOG$_{35-55}$ induced EAE disease compared to the high clinical scored control mice. More importantly, the cocktail of vectors completely prevented the dual peptide-induced disease (FIG. 47).

Figure 48:
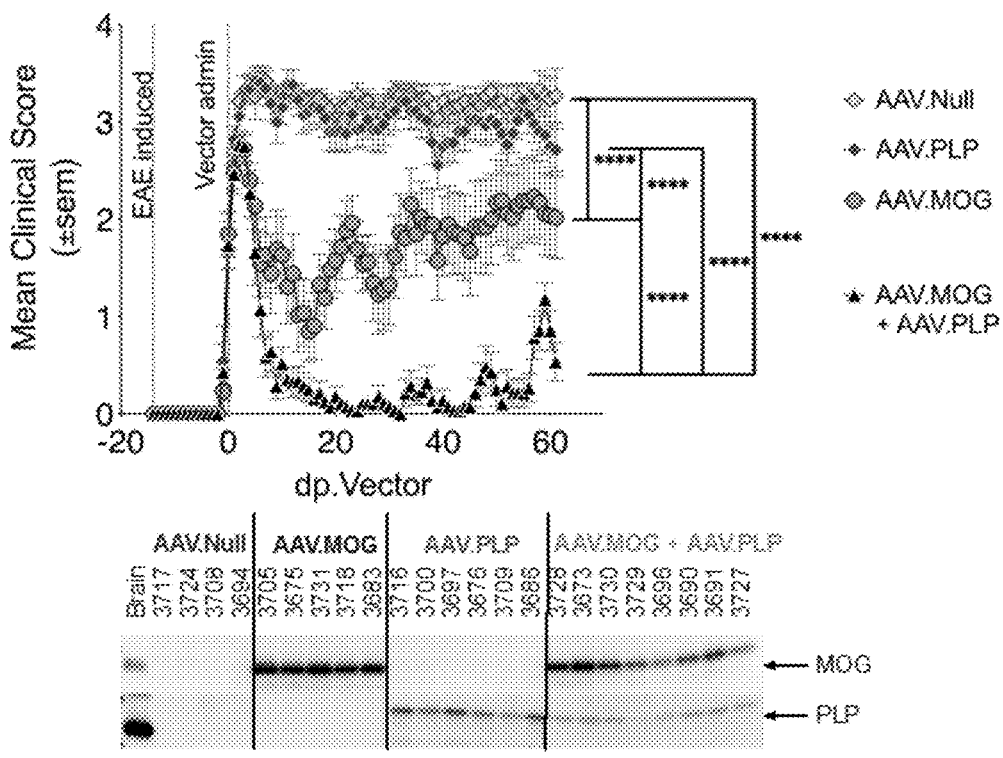
FIG. 48 shows the results of a study evaluating EAE reversal in the (C57Bl/6×SJL/J)F1 dual vector model by the rAAV vector combination. EAE in C57Bl/6×SJL/J mice was induced using a mixture of $MOG_{35-55}$ & $PLP_{139-151}$. Mice having MCS of ~2.0 received either AAV.MOG, AAV.PLP, cocktail of AAV.MOG & AAV.PLP, or AAV.GFP control. Statistical analysis: Ordinary one-way ANOVA. A representative Western blot indicating expression of the myelin-associated peptides in each mouse subject is shown.

An experiment designed to evaluate if the same cocktail of vectors could reverse preexisting diseasing was performed. In this study, MOG$_{35-55}$ & PLP$_{139-151}$ was used to induce EAE prior to therapy. As mice subjects developed, cohorts of mice with a clinical score of MCS ~2.0 were administered either AAV.MOG, AAV.PLP, AAV.GFP control vector, or the cocktail of AAV.MOG & AAV.PLP. Remarkably, administration of the cocktail of vectors produced similar results as the suppression experiment above (FIG. 48). Expression of PLP and MOG was validated in samples taken from each mouse subject. A representative Western blot is shown in FIG. 48.

Figure 49:
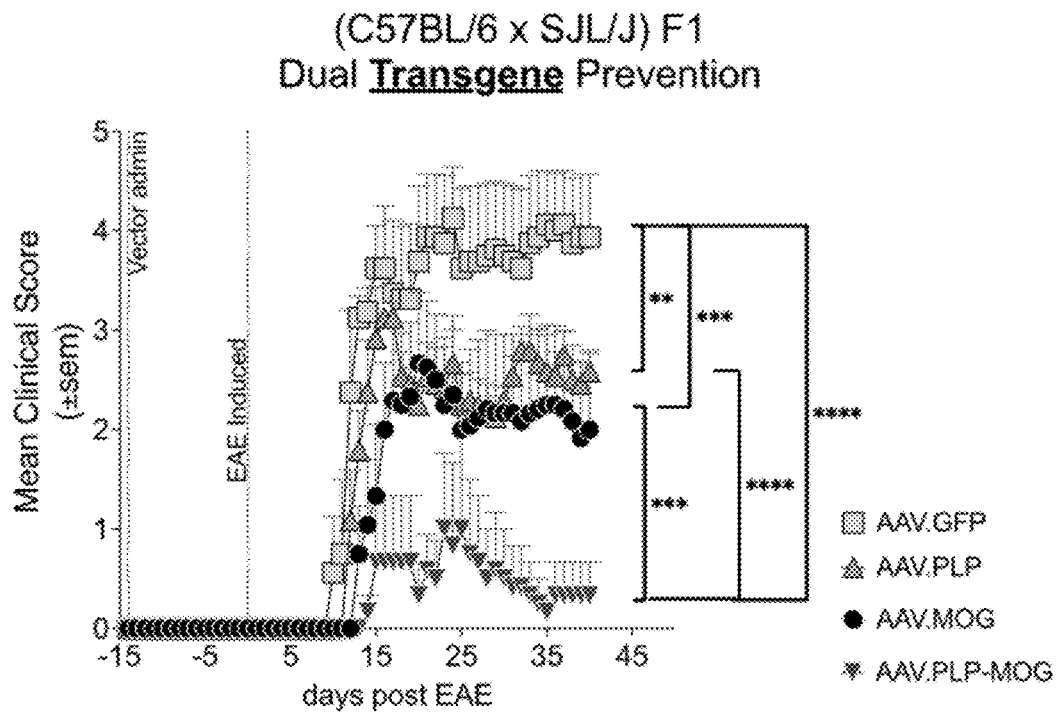
FIG. 49 shows the results of a study of EAE suppression by an AAV vector encoding both PLP and MOG in the (C57Bl/6×SJL/J)F1 model. C57Bl/6×SJL/J mice received either AAV.MOG, AAV.PLP, AAV.GFP control, or a single AAV vector encoding PLP and MOG. Two weeks later, EAE was induced using a mixture of $MOG_{35-55}$ & $PLP_{139-151}$. Statistical analysis: Ordinary one-way ANOVA.

In a second EAE suppression experiment performed in (C57BL/6×SJL)F1, a single vector engineered to express both myelin-associated proteins (AAV.PLP-MOG) was evaluated for ability to prevent the same MOG$_{35-55}$ & PLP$_{139-151}$ induced EAE disease. The protocol of the first EAE suppression experiment (FIG. 47) was repeated, except that the AAV.PLP-MOG dual peptide-expressing vector was administered to a cohort of mice, while other cohorts received either AAV.MOG, AAV.PLP, or AAV.GFP control vector. Remarkably, the data demonstrated that a single, dual peptide vector can indeed significantly can prevent disease caused by two immunogenic antigens (FIG. 49).

Figure 50:
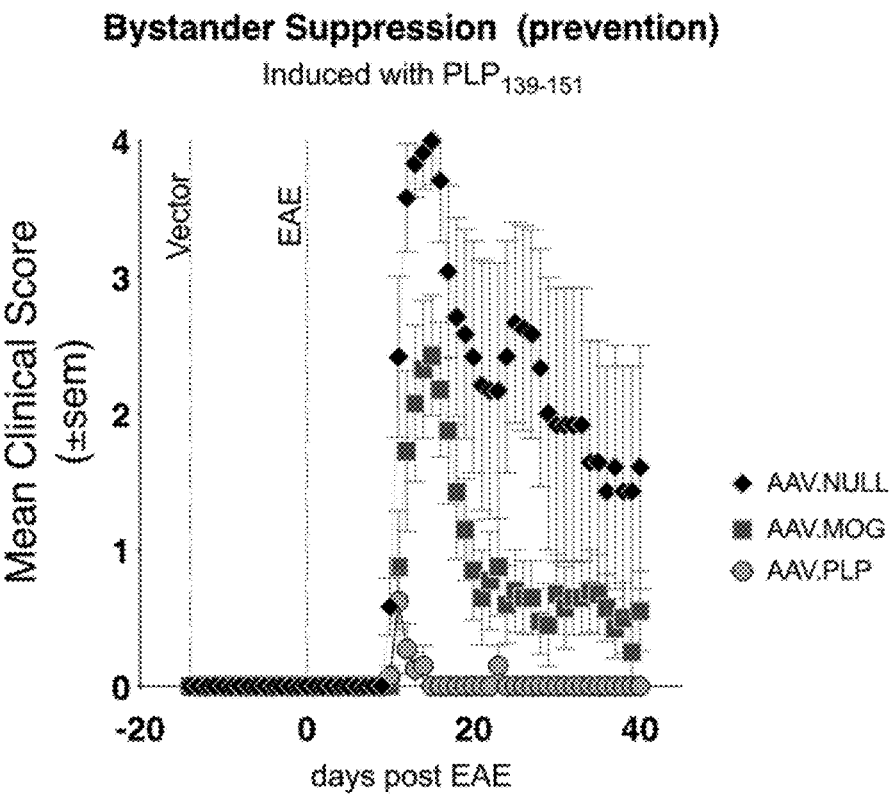
FIG. 50 shows the results of an experiment indicating the bystander EAE suppression provided by AAV.MOG. Female SJL mice were intravenously injected with AAV.MOG, AAV.PLP, or AAV.Null control at ~8 weeks of age. EAE was induced by injecting $PLP_{139-151}$ in CFA at ~10 weeks of age.

As shown in FIG. 50, data indicates that one vector (AAV.MOG) may be protective against EAE via bystander (i.e., non-antigen specific immune suppression). Female SJL mice were i.v. injected with AAV.MOG, AAV.PLP, or AAV.Null control at ~8 weeks of age. EAE was induced with PLP$_{139-151}$ in CFA at ~10 weeks of age. Mice were monitored daily for clinical signs of EAE. Mean clinical scores of AAV.MOG, AAV.PLP, and control mice. Mean clinical scores reported as mean±SEM. The reduced scores of the mice treated with AAV.MOG suggests that a vector targeting a different protein could provided some bystander or non-specific immune suppression. These results indicate that the Tregs that are induced (or activated) by the AAV.MOG can play a role and be suppressive in PLP-induced EAE, even as PLP and MOG do not share identity.

Dual peptide AAV vectors comprising each of a MOG-encoding sequence codon-optimized for human expression and a PLP-encoding sequence codon-optimized for human expression are currently evaluated in their ability to confer EAE protection (and bystander protection). Administration of particles comprising codon-optimized sequences are currently evaluated in C57BL/6×SJL mice.

These findings further indicate the strength of the disclosed vectors in providing a solution to the elusive problem of epitope spreading in MS.

REFERENCES

The following references, to the extent that they provide exemplary procedural or other details supplementary to those set forth herein, are specifically incorporated herein by reference:

1. Kohm A P, Carpentier P A, Anger H A, Miller S D. Cutting edge: CD4+CD25+ regulatory T cells suppress antigen-specific autoreactive immune responses and central nervous system inflammation during active experimental autoimmune encephalomyelitis. Journal of Immunology (Baltimore, MD). 169(9):4712-4716 (2002).
2. Zhang G-X, Yu S, Gran B, Li J, Calida D, Ventura E, Chen X, Rostami A. T cell and antibody responses in remitting-relapsing experimental autoimmune encephalomyelitis in (C57BL/6×SJL) F1 mice. Journal of Neuroimmunology. 2004; 148(1-2):1-10.
3. McGeachy M J, Stephens L A, Anderton S M. Natural recovery and protection from autoimmune encephalomyelitis: contribution of CD4+CD25+ regulatory cells within the central nervous system. Journal of Immunology (Baltimore, MD), 2005; 175(5):3025-3032.
4. Paust S, Cantor H. Regulatory T cells and autoimmune disease. Immunological reviews. 2005; 204:195-207.
5. Marusić S, Tonegawa S. Tolerance induction and autoimmune encephalomyelitis amelioration after administration of myelin basic protein-derived peptide. Journal of Experimental Medicine. 1997; 186(4):507-515.
6. LoDuca P A, Hoffman B E, Herzog R W. Hepatic gene transfer as a means of tolerance induction to transgene products. Current gene therapy. 2009; 9(2):104-14.
7. Hoffman B, Dobrzynski E, Wang L, Hirao L, Mingozzi F, Cao O, Herzog R W. Muscle as a Target for Supplementary Factor IX Gene Transfer 2007; 18(7):603-13.
8. Dobrzynski E, Fitzgerald J C, Cao O, Mingozzi F, Wang L, Herzog R W. Prevention of cytotoxic T lymphocyte responses to factor IX-expressing hepatocytes by gene transfer-induced regulatory T cells. Proceedings of the National Academy of Sciences of the United States of America. 2006; 103(12):4592-7.
9. Dobrzynski E, Herzog R W. Tolerance induction by viral in vivo gene transfer. Clinical medicine & research. 2005; 3(4):234-40.
10. Cooper M, Nayak S, Hoffman B E, Terhorst C, Cao O, Herzog R W. Improved induction of immune tolerance to factor IX by hepatic AAV-8 gene transfer. Human gene therapy. 2009; 20(7):767-76.
11. Cao O, Furlan-Freguia C, Arruda V R, Herzog R W. Emerging role of regulatory T cells in gene transfer. Curr Gene Ther. 2007; 7(5):381-90.
12. Hoffman B E, Martino A T, Sack B K, Cao O, Liao G, Terhorst C, Herzog R W. Nonredundant roles of IL-10 and TGF-beta in suppression of immune responses to hepatic AAV-factor IX gene transfer. Molecular therapy: the journal of the American Society of Gene Therapy. 2011; 19(7):1263-72.
13. Mingozzi F, Liu Y L, Dobrzynski E, Kaufhold A, Liu J H, Wang Y, Arruda V R, High K A, Herzog R W. Induction of immune tolerance to coagulation factor IX antigen by in vivo hepatic gene transfer. The Journal of clinical investigation. 2003; 111(9):1347-56. doi: 10.1172/JCI16887. PMID: 12727926.
14. Faust S M, Bell P, Zhu Y, Sanmiguel J, Wilson J M. The role of apoptosis in immune hyporesponsiveness following AAV8 liver gene transfer. Molecular therapy: the journal of the American Society of Gene Therapy. 2013; 21(12):2227-35.
15. Markusic D M, Hoffman B E, Perrin G Q, Nayak S, Wang X, LoDuca P A, High K A, Herzog R W. Effective gene therapy for hemophilic mice with pathogenic factor IX antibodies. EMBO Molecular Medicine. 2013:1-12.
16. Annoni A, Brown B D, Cantore A, Sergi L S, Naldini L, Roncarolo M G. In vivo delivery of a microRNA-regulated transgene induces antigen-specific regulatory T cells and promotes immunologic tolerance. Blood. 2009; 114 (25):5152-61.

17. Breous E, Somanathan S, Vandenberghe L H, Wilson J M. Hepatic regulatory T cells and Kupffer cells are crucial mediators of systemic T cell tolerance to antigens targeting murine liver. Hepatology. 2009; 50(2):612-21.
18. Matrai J, Cantore A, Bartholomae C C, Annoni A, Wang W, Acosta-Sanchez A, Samara-Kuko E, De Wade L, Ma L, Genovese P, Damo M, Arens A, Goudy K, Nichols T C, von Kalle C, M K L C, Roncarolo M G, Schmidt M, Vandendriessche T, Naldini L. Hepatocyte-targeted expression by integrase-defective lentiviral vectors induces antigen-specific tolerance in mice with low genotoxic risk. Hepatology. 2011; 53(5):1696-707.
19. Mingozzi F, Hasbrouck N C, Basner-Tschakarjan E, Edmonson S A, Hui D J, Sabatino D E, Zhou S, Wright J F, Jiang H, Pierce G F, Arruda V R, High K A. Modulation of tolerance to the transgene product in a nonhuman primate model of AAV-mediated gene transfer to liver. Blood. 2007; 110(7):2334-41.
20. Sun B, Kulis M D, Young S P, Hobeika A C, Li S, Bird A, Zhang H, Li Y, Clay T M, Burks W, Kishnani P S, Koeberl D D Immunomodulatory gene therapy prevents antibody formation and lethal hypersensitivity reactions in murine pompe disease. Molecular therapy: the journal of the American Society of Gene Therapy. 2010; 18(2): 353-360.
21. Miao C H, Harmeling B R, Ziegler S F, Yen B C, Torgerson T, Chen L, Yau R J, Peng B, Thompson A R, Ochs H D, Rawlings D J. CD4+FOXP3+ regulatory T cells confer long-term regulation of factor VIII-specific immune responses in plasmid-mediated gene therapy-treated hemophilia mice. Blood. 2009; 114(19):4034-44.
22. Brown B D, Cantore A, Annoni A, Sergi L S, Lombardo A, Della Valle P, D'Angelo A, Naldini L. A microRNA-regulated lentiviral vector mediates stable correction of hemophilia B mice. Blood. 2007; 110(13):4144-52.
23. Brown B D, Venneri M A, Zingale A, Sergi L, Naldini L. Endogenous microRNA regulation suppresses transgene expression in hematopoietic lineages and enables stable gene transfer. Nature medicine. 2006; 12(5):585-91.
24. Cerullo V, McCormack W, Seiler M, Mane V, Cela R, Clarke C, Rodgers J R, Lee B. Antigen-specific tolerance of human alpha1-antitrypsin induced by helper-dependent adenovirus. Human gene therapy. 2007; 18(12):1215-24.
25. Follenzi A, Battaglia M, Lombardo A, Annoni A, Roncarolo M G, Naldini L. Targeting lentiviral vector expression to hepatocytes limits transgene-specific immune response and establishes long-term expression of human antihemophilic factor IX in mice. Blood. 2004; 103(10): 3700-9.
26. Franco L M, Sun B, Yang X, Bird A, Zhang H, Schneider A, Brown T, Young S P, Clay T M, Amalfitano A, Chen Y T, Koeberl D D. Evasion of immune responses to introduced human acid alpha-glucosidase by liver-restricted expression in glycogen storage disease type II. Molecular therapy: the journal of the American Society of Gene Therapy. 2005; 12(5):876-84.
27. Koeberl D D, Kishnani P S. Immunomodulatory gene therapy in lysosomal storage disorders. Curr Gene Ther. 2009; 9(6):503-10.
28. Luth S, Huber S, Schramm C, Buch T, Zander S, Stadelmann C, Bruck W, Wraith D C, Herkel J, Lohse A W. Ectopic expression of neural autoantigen in mouse liver suppresses experimental autoimmune neuroinflammation by inducing antigen-specific Tregs. The Journal of clinical investigation. 2008; 118(10):3403-10.
29. Matsui H, Hegadorn C, Ozelo M, Burnett E, Tuttle A, Labelle A, McCray P B, Jr., Naldini L, Brown B, Hough C, Lillicrap D. A microRNA-regulated and GP64-pseudotyped lentiviral vector mediates stable expression of FVIII in a murine model of Hemophilia A. Molecular therapy: the journal of the American Society of Gene Therapy. 2011; 19(4):723-30.
30. Matsui H, Shibata M, Brown B, Labelle A, Hegadorn C, Andrews C, Chuah M, VandenDriessche T, Miao C H, Hough C, Lillicrap D. A murine model for induction of long-term immunologic tolerance to factor VIII does not require persistent detectable levels of plasma factor VIII and involves contributions from Foxp3+ T regulatory cells. Blood. 2009; 114(3):677-85.
31. McEachern K A, Nietupski J B, Chuang W L, Armentano D, Johnson J, Hutto E, Grabowski G A, Cheng S H, Marshall J. AAV8-mediated expression of glucocerebrosidase ameliorates the storage pathology in the visceral organs of a mouse model of Gaucher disease. Journal of Gene Medicine, 2006; 8(6):719-29.
32. Nietupski J B, Hurlbut G D, Ziegler R J, Chu Q, Hodges B L, Ashe K M, Bree M, Cheng S H, Gregory R J, Marshall J, Scheule R K. Systemic administration of AAV8-alpha-galactosidase A induces humoral tolerance in nonhuman primates despite low hepatic expression. Molecular therapy: the journal of the American Society of Gene Therapy. 2011; 19(11):1999-2011.
33. Passini M A, Bu J, Fidler J A, Ziegler R J, Foley J W, Dodge J C, Yang W W, Clarke J, Taksir T V, Griffiths D A, Zhao M A, O'Riordan C R, Schuchman E H, Shihabuddin L S, Cheng S H. Combination brain and systemic injections of AAV provide maximal functional and survival benefits in the Niemann-Pick mouse. Proceedings of the National Academy of Sciences of the United States of America. 2007; 104(22):9505-10.
34. Sharland A, Logan G J, Bishop A, Alexander I E. Liver-directed gene expression using recombinant AAV 2/8 vectors—a tolerogenic strategy for gene delivery? Discovery medicine. 2010; 9(49):519-27.
35. Somanathan S, Breous E, Bell P, Wilson J M. AAV vectors avoid inflammatory signals necessary to render transduced hepatocyte targets for destructive T cells. Molecular therapy: the journal of the American Society of Gene Therapy. 2010; 18(5):977-82.
36. Sun B, Bird A, Young S P, Kishnani P S, Chen Y T, Koeberl D D. Enhanced response to enzyme replacement therapy in Pompe disease after the induction of immune tolerance. American journal of human genetics. 2007; 81(5):1042-9.
37. Ziegler R J, Lonning S M, Armentano D, Li C, Souza D W, Cherry M, Ford C, Barbon C M, Desnick R J, Gao G, Wilson J M, Peluso R, Godwin S, Carter B J, Gregory R J, Wadsworth S C, Cheng S H. AAV2 vector harboring a liver-restricted promoter facilitates sustained expression of therapeutic levels of alpha-galactosidase A and the induction of immune tolerance in Fabry mice. Molecular therapy: the journal of the American Society of Gene Therapy. 2004; 9(2):231-40.
38. Moses H, Picone M A, Smith V. An In-Depth Overview: Consensus Medical Communications; 2012.
39. Gonsette R E. Self-tolerance in multiple sclerosis. Acta neurologica Belgica. 2012; 112(2):133-40
40. Viglietta V, Baecher-Allan C, Weiner H L, Hafler D A. Loss of functional suppression by CD4+CD25+ regulatory T cells in patients with multiple sclerosis. J Exp Med. 2004; 199(7):971-9

41. Zozulya A L, Wiendl H. The role of regulatory T cells in multiple sclerosis. Nature Clinical Practice Neurology. 2008; 4(7):384-98.
42. Buckner J H. Mechanisms of impaired regulation by CD4(+)CD25(+)FOXP3(+) regulatory T cells in human autoimmune diseases. Nature Reviews Immunology. 2010; 10(12):849-59. doi: 10.1038/nri2889.
43. Buc M. Role of Regulatory T Cells in Pathogenesis and Biological Therapy of Multiple Sclerosis. Mediators of Inflammation. 2013; 2013(6):1-11.
44. Costantino C M, Baecher-Allan C, Hafler D A. Multiple Sclerosis and Regulatory T Cells. Journal of Clinical Immunology. 2008; 28(6):697-706.
45. Hoffman B E, Herzog R W. Coaxing the liver into preventing autoimmune disease in the brain. The Journal of clinical investigation. 2008; 118(10):3271-3.
46. Lüth S, Huber S, Schramm C, Buch T, Zander S, Stadelmann C, Brück W, Wraith D C, Herkel J, Lohse A W. Ectopic expression of neural autoantigen in mouse liver suppresses experimental autoimmune neuroinflammation by inducing antigen-specific Tregs. The Journal of clinical investigation. 2008; 118(10):3403-10.
47. Haas J, Korporal M, Balint B, Fritzsching B, Schwarz A, Wildemann B Glatiramer acetate improves regulatory T-cell function by expansion of naive CD4(+)CD25(+) FOXP3(+)CD31(+) T-cells in patients with multiple sclerosis. J Neuroimmunol. 2009; 216(1-2):113-7.
48. Nathwani A C, Tuddenham E G, Rangarajan S, Rosales C, McIntosh J, Linch D C, Chowdary P, Riddell A, Pie A J, Harrington C, O'Beirne J, Smith K, Pasi J, Glader B, Rustagi P, Ng C Y, Kay M A, Zhou J, Spence Y, Morton C L, Allay J, Coleman J, Sleep S, Cunningham J M, Srivastava D, Basner-Tschakarjan E, Mingozzi F, High K A, Gray J T, Reiss U M, Nienhuis A W, Davidoff A M. Adenovirus-associated virus vector-mediated gene transfer in hemophilia B. The New England journal of medicine. 2011; 365(25):2357-65.
49. Herzog R W, Cao O, Srivastava A. Two decades of clinical gene therapy—success is finally mounting. Discovery medicine. 2010; 9(45):105-11. Epub 2010/03/03.
50. Mingozzi F, High K A. Therapeutic in vivo gene transfer for genetic disease using AAV: progress and challenges. Nat Rev Genet. 2011; 12(5):341-55.
51. Maclaren R E, Groppe M, Barnard A R, Cottriall C L, Tolmachova T, Seymour L, Clark K R, During M J, Cremers F P, Black G C, Lotery A J, Downes S M, Webster A R, Seabra M C. Retinal gene therapy in patients with choroideremia: initial findings from a phase 1/2 clinical trial. Lancet. 2014. Epub 2014/01/21.
52. Bryant L M, Christopher D M, Giles A R, Hinderer C, Rodriguez J L, Smith J B, Traxler E A, Tycko J, Wojno A P, Wilson J M. Lessons learned from the clinical development and market authorization of Glybera. Human gene therapy Clinical development. 2013; 24(2):55-64.
53. Byrne B J, Falk D J, Pacak C A, Nayak S, Herzog R W, Elder M E, Collins S W, Conlon T J, Clement N, Cleaver B D, Cloutier D A, Porvasnik S L, Islam S, Elmallah M K, Martin A, Smith B K, Fuller D D, Lawson L A, Mah C S. Pompe disease gene therapy. Human molecular genetics. 2011; 20(R1):R61-R68.
54. Moghimi B, Sack B K, Nayak S, Markusic D M, Mah C S, Herzog R W. Induction of tolerance to factor VIII by transient co-administration with rapamycin. Journal of thrombosis and haemostasis: JTH. 2011; 9(8):1524-1533.
55. Nayak S, Cao O, Hoffman B E, Cooper M, Zhou S, Atkinson M A, Herzog R W. Prophylactic immune tolerance induced by changing the ratio of antigen-specific effector to regulatory T cells. Journal of thrombosis and haemostasis: JTH. 2009; 7(9):1523-1532.
56. Nayak S, Sarkar D, Perrin G Q, Moghimi B, Hoffman B E, Zhou S, Byrne B J, Herzog R W. Prevention and Reversal of Antibody Responses Against Factor IX in Gene Therapy for Hemophilia B. Frontiers in Microbiology. 2011; 2.
57. Martino A T, Nayak S, Hoffman B E, Cooper M, Liao G, Markusic D M, Byrne B J, Terhorst C, Herzog R W. Tolerance induction to cytoplasmic beta-galactosidase by hepatic AAV gene transfer: implications for antigen presentation and immunotoxicity. PloS one. 2009; 4(8): e6376.
58. Lalive P H, Molnarfi N, Benkhoucha M, Weber M S, Santiago-Raber M L. Antibody response in MOG$_{(35-55)}$ induced EAE. J Neuroimmunol. 2011; 240-241:28-33. doi: 10.1016/j.jneuroim.2011.09.005.
59. Mann M K, Ray A, Basu S, Karp C L, Dittel B N. Pathogenic and regulatory roles for B cells in experimental autoimmune encephalomyelitis. Autoimmunity. 2012; 45(5):388-399.
60. Miller S D, Karpus W J, Davidson T S. Experimental autoimmune encephalomyelitis in the mouse. Current protocols in immunology/edited by John E Coligan [et al]. 2010; Chapter 15: Unit 15.1.
61. Ko H J, Chung J Y, Nasa Z, Chan J, Siatskas C, Toh B H, Alderuccio F. Targeting MOG expression to dendritic cells delays onset of experimental autoimmune disease. Autoimmunity. 2011; 44(3):177-87.
62. Dobrzynski E, Mingozzi F, Liu Y L, Bendo E, Cao O, Wang L, Herzog R W. Induction of antigen-specific CD4+ T-cell anergy and deletion by in vivo viral gene transfer. Blood. 2004; 104(4):969-77.
63. Fissolo N, Costa C, Nurtdinov R N, Bustamante M F, Llombart V, Mansilla M J, Espejo C, Montalban X, Comabella M. Treatment with MOG-DNA vaccines induces CD4+CD25+FoxP3+ regulatory T cells and upregulates genes with neuroprotective functions in experimental autoimmune encephalomyelitis. Journal of neuroinflammation. 2012; 9:139.
64. O'Connor R A, Anderton S M. Foxp3+ regulatory T cells in the control of experimental CNS autoimmune disease. J Neuroimmunol. 2008; 193(1-2):1-11.
65. Tang Q, Henriksen K J, Bi M, Finger E B, Szot G, Ye J, Masteller E L, McDevitt H, Bonyhadi M, Bluestone J A. In vitro-expanded antigen-specific regulatory T cells suppress autoimmune diabetes. J Exp Med. 2004; 199(11): 1455-65.
66. Chen X, Oppenheim J J, Winkler-Pickett R T, Ortaldo J R, Howard O M. Glucocorticoid amplifies IL-2-dependent expansion of functional FoxP3(+)CD4(+)CD25(+) T regulatory cells in vivo and enhances their capacity to suppress EAE. European journal of immunology. 2006; 36(8):2139-49.
67. Oleszak E L, *Hoffman B E, Chang J R, Zaczynska E, Gaughan J, Katsetos C D, Platsoucas C D, Harvey N. Apoptosis of infiltrating T cells in the central nervous system of mice infected with Theiler's murine encephalomyelitis virus. Virology. 2003; 315(1):110-23. Epub 2003/11/01.
68. Selvaraj R K, Geiger T L. Mitigation of experimental allergic encephalomyelitis by TGF-beta induced Foxp3+ regulatory T lymphocytes through the induction of anergy and infectious tolerance. Journal of immunology. 2008; 180(5):2830-8.
69. Esposito M, Ruffini F, Bellone M, Gagliani N, Battaglia M, Martino G, Furlan R. Rapamycin inhibits relapsing experimental autoimmune encephalomyelitis by both effector and regulatory T cells modulation. J. Neuroimmunol., 2010; 220(1-2):52-63.

70. Bensinger S J, Walsh P T, Zhang J, Carroll M, Parsons R, Rathmell J C, Thompson C B, Burchill M A, Farrar M A, Turka L A. Distinct IL-2 receptor signaling pattern in CD4+CD25+ regulatory T cells. Journal of immunology. 2004; 172(9):5287-96.

71. O'Connor R A, Malpass K H, Anderton S M. The inflamed central nervous system drives the activation and rapid proliferation of Foxp3+ regulatory T cells. Journal of immunology. 2007; 179(2):958-66.

72. Korn T, Reddy J, Gao W, Bettelli E, Awasthi A, Petersen T R, Backstrom B T, Sobel R A, Wucherpfennig K W, Strom T B, Oukka M, Kuchroo V K. Myelin-specific regulatory T cells accumulate in the CNS but fail to control autoimmune inflammation. Nature medicine. 2007; 13(4):423-31.

73. Niemeyer G P, Herzog R W, Mount J, Arruda V R, Tillson D M, Hathcock J, van Ginkel F W, High K A, Lothrop C D, Jr. Long-term correction of inhibitor-prone hemophilia B dogs treated with liver-directed AAV2-mediated factor IX gene therapy. Blood. 2009 113(4):797-806.

74. Dalla Libera D., Di Mitri D., Bergami A., Centonze D., Gasperini C., Grasso M. G., Galgani S., Martinelli V., Comi G., Avolio C. T regulatory cells are markers of disease activity in multiple sclerosis patients. PLoS ONE. 2011; 6:e21386.

75. Carbone F., De Rosa V., Carrieri P. B., Montella S., Bruzzese D., Porcellini A., Procaccini C., La Cava A., Matarese G. Regulatory T cell proliferative potential is impaired in human autoimmune disease. Nat. Med. 2014; 20:69-74.

76. Vila J., Isaacs J. D., Anderson A. E. Regulatory T cells and autoimmunity. Curr. Opin. Hematol. 2009; 16:274-279.

77. MacDonald K. G., Hoeppli R. E., Huang Q., Gillies J., Luciani D. S., Orban P. C., Broady R., Levings M. K. Alloantigen-specific regulatory T cells generated with a chimeric antigen receptor. J. Clin. Invest. 2016; 126:1413-1424.

78. Rossetti M., Spreafico R., Saidin S., Chua C., Moshref M., Leong J. Y., Tan Y. K., Thumboo J., van Loosdregt J., Albani S. Ex vivo-expanded but not in vitro-induced human regulatory T cells are candidates for cell therapy in autoimmune diseases thanks to stable demethylation of the FOXP3 regulatory T cell-specific demethylated region. J. Immunol. 2015; 194:113-124.

79. Beyersdorf N., Gaupp S., Balbach K., Schmidt J., Toyka K. V., Lin C. H., Hanke T., Hünig T., Kerkau T., Gold R. Selective targeting of regulatory T cells with CD28 superagonists allows effective therapy of experimental autoimmune encephalomyelitis. J. Exp. Med. 2005; 202:445-455.

80. Thomas H. R., Gitelman S E Altering the course of type 1 diabetes: an update on prevention and new-onset clinical trials. Pediatr. Diabetes. 2013; 14:311-321.

81. Trzonkowski P., Bieniaszewska M., Juścińska J., Dobyszuk A., Krzystyniak A., Marek N., Myśliwska J., Hellmann A First-in-man clinical results of the treatment of patients with graft versus host disease with human ex vivo expanded CD4+CD25+CD127− T regulatory cells. Clin. Immunol. 2009; 133:22-26.

82. Safinia N., Sagoo P., Lechler R., Lombardi G. Adoptive regulatory T cell therapy: challenges in clinical transplantation. Curr. Opin. Organ Transplant. 2010; 15:427-434.

83. Akbarpour M., Goudy K. S., Cantore A., Russo F., Sanvito F., Naldini L., Annoni A., Roncarolo M. G. Insulin B chain 9-23 gene transfer to hepatocytes protects from type 1 diabetes by inducing Ag-specific FoxP3+ Tregs. Sci. Transl. Med. 2015; 7:289ra81.

84. Sack B. K., Herzog R. W., Terhorst C., Markusic D. M. Development of gene transfer for induction of antigen-specific tolerance. Mol. Ther. Methods Clin. Dev. 2014; 1:14013.

85. Zolotukhin S., Potter M., Zolotukhin I., Sakai Y., Loiler S., Fraites T. J., Jr., Chiodo V. A., Phillipsberg T., Muzyczka N., Hauswirth W. W. Production and purification of serotype 1, 2, and 5 recombinant adeno-associated viral vectors. Methods. 2002; 28:158-167.

86. Martino A. T., Suzuki M., Markusic D. M., Zolotukhin I., Ryals R. C., Moghimi B., Ertl H. C., Muruve D. A., Lee B., Herzog R. W. The genome of self-complementary adeno-associated viral vectors increases Toll-like receptor 9-dependent innate immune responses in the liver. Blood. 2011; 117:6459-6468.

87. Kerlero de Rosbo N., Milo R., Lees M. B., Burger D., Bernard C. C., Ben-Nun A. Reactivity to myelin antigens in multiple sclerosis. Peripheral blood lymphocytes respond predominantly to myelin oligodendrocyte glycoprotein. J. Clin. Invest. 1993; 92:2602-2608.

88. Varrin-Doyer M., Shetty A., Spencer C. M., Schulze-Topphoff U., Weber M. S., Bernard C. C., Forsthuber T., Cree B. A., Slavin A. J., Zamvil S. S. MOG transmembrane and cytoplasmic domains contain highly stimulatory T-cell epitopes in M S. Neurol. Neuroimmunol. Neuroinflamm. 2014; 1:e20.

89. Cao O., Dobrzynski E., Wang L., Nayak S., Mingle B., Terhorst C., Herzog R. W. Induction and role of regulatory CD4+CD25+ T cells in tolerance to the transgene product following hepatic in vivo gene transfer. Blood. 2007; 110:1132-1140.

90. Mingozzi F., High K. A. Immune responses to AAV vectors: overcoming barriers to successful gene therapy. Blood. 2013; 122:23-36.

91. Kim W. R., Flamm S. L., Di Bisceglie A. M., Bodenheimer H. C., Public Policy Committee of the American Association for the Study of Liver Disease Serum activity of alanine aminotransferase (ALT) as an indicator of health and disease. Hepatology. 2008; 47:1363-1370.

92. Pedotti R., Mitchell D., Wedemeyer J., Karpuj M., Chabas D., Hattab E. M., Tsai M., Galli S. J., Steinman L. An unexpected version of horror autotoxicus: anaphylactic shock to a self-peptide. Nat. Immunol. 2001; 2:216-222.

93. Zhang L., Guo Y., Xia C. Q. Infusion of sulfosuccinimidyl-4-[N-maleimidomethyl]cyclohexane-1-carboxylate-conjugated $MOG_{35-55}$-coupled spleen cells effectively prevents and reverses experimental autoimmune encephalomyelitis in mice. J. Immunol. Res. 2015; 2015:129682.

94. Tse H. Y., Li J., Zhao X., Chen F., Ho P. P., Shaw M. K. Lessons learned from studies of natural resistance in murine experimental autoimmune encephalomyelitis. Curr. Trends Immunol. 2012; 13:1-12.

95. Raine C. S., Traugott U., Stone S. H. Applications of chronic relapsing experimental allergic encephalomyelitis to the study of multiple sclerosis. In: Bauer H. J., Poser S., Ritter G., editors. Progress in Multiple Sclerosis Research. Springer Berlin Heidelberg; 1980. pp. 3-10.

96. Marcus J. F., Waubant E. L. Updates on clinically isolated syndrome and diagnostic criteria for multiple sclerosis. Neurohospitalist. 2013; 3:65-80.

97. Berard J. L., Wolak K., Fournier S., David S. Characterization of relapsing-remitting and chronic forms of experimental autoimmune encephalomyelitis in C57BL/6 mice. Glia. 2010; 58:434-445.
98. Bluestone J. A., Bour-Jordan H., Cheng M., Anderson M. T cells in the control of organ-specific autoimmunity. J. Clin. Invest. 2015; 125:2250-2260.
99. Nie H., Zheng Y., Li R., Guo T. B., He D., Fang L., Liu X., Xiao L., Chen X., Wan B. Phosphorylation of FOXP3 controls regulatory T cell function and is inhibited by TNF-α in rheumatoid arthritis. Nat. Med. 2013; 19:322-328.
100. Biswas M., Sarkar D., Kumar S. R., Nayak S., Rogers G. L., Markusic D. M., Liao G., Terhorst C., Herzog R. W. Synergy between rapamycin and FLT3 ligand enhances plasmacytoid dendritic cell-dependent induction of CD4+CD25+FoxP3+ Treg. Blood. 2015; 125:2937-2947.
101. Battaglia M., Stabilini A., Roncarolo M. G. Rapamycin selectively expands CD4+CD25+FoxP3+ regulatory T cells. Blood. 2005; 105:4743-4748.
102. Liu T., Soong L., Liu G., Konig R., Chopra A. K. CD44 expression positively correlates with Foxp3 expression and suppressive function of CD4+ Treg cells. Biol. Direct. 2009; 4:40.
103. Li M. O., Rudensky A. Y. T cell receptor signalling in the control of regulatory T cell differentiation and function. Nat. Rev. Immunol. 2016; 16:220-233.
104. Lallana E. C., Fadul C. E. Toxicities of immunosuppressive treatment of autoimmune neurologic diseases. Curr. Neuropharmacol. 2011; 9:468-477.
105. Gregori S., Passerini L., Roncarolo M. G. Clinical outlook for type-1 and FOXP3(+) T regulatory cell-based therapy. Front. Immunol. 2015; 6:593.
106. Brunstein C. G., Blazar B. R., Miller J. S., Cao Q., Hippen K. L., McKenna D. H., Curtsinger J., McGlave P. B., Wagner J. E. Adoptive transfer of umbilical cord blood-derived regulatory T cells and early viral reactivation. Biol. Blood Marrow Transplant. 2013; 19:1271-1273.
107. Josefowicz S. Z., Lu L. F., Rudensky A. Y. Regulatory T cells: mechanisms of differentiation and function. Annu. Rev. Immunol. 2012; 30:531-564.
108. Desreumaux P., Foussat A., Allez M., Beaugerie L., Hébuterne X., Bouhnik Y., Nachury M., Brun V., Bastian H., Belmonte N. Safety and efficacy of antigen-specific regulatory T-cell therapy for patients with refractory Crohn's disease. Gastroenterology. 2012; 143:1207-1217. e1-e2.
109. Hoffman B. E., Ertl H. C., Terhorst C., High K. A., Herzog R. W. Gene therapy research at the frontiers of viral immunology. Front. Microbiol. 2012; 3:182.
110. Cao O., Hoffman B. E., Moghimi B., Nayak S., Cooper M., Zhou S., Ertl H. C., High K. A., Herzog R. W. Impact of the underlying mutation and the route of vector administration on immune responses to factor IX in gene therapy for hemophilia B. Mol. Ther. 2009; 17:1733-1742.
111. Chapman N. M., Chi H. mTOR signaling, Tregs and immune modulation. Immunotherapy. 2014; 6:1295-1311.
112. Battaglia M., Stabilini A., Migliavacca B., Horejs-Hoeck J., Kaupper T., Roncarolo M. G. Rapamycin promotes expansion of functional CD4+CD25+FOXP3+ regulatory T cells of both healthy subjects and type 1 diabetic patients. J. Immunol. 2006; 177:8338-8347.

It should be understood that the examples and embodiments described herein are for illustrative purposes only and that various modifications or changes in light thereof may be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the present disclosure using terms such as "comprising", "having", "including" or "containing" with reference to an element or elements is intended to provide support for a similar aspect or embodiment of the present disclosure that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the method described herein without departing from the concept, spirit and scope of the present disclosure. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the present disclosure as defined by the appended claims.

What is claimed is:

1. A recombinant adeno-associated viral (rAAV) vector comprising a polynucleotide that comprises a first nucleic acid segment that is at least 95% identical to any one of the sequences of SEQ ID NOs: 16, 18, 20, 24, 26, 29, 30, 32-34, 39-42, 44-47, 49-52, 54-57, 59-62, 64-67, 69-72, 74-77, 79-82, 84-87, 89-99, 101-106, 108-113, 115-119, 121-130, 132-136, 138-142, 144-148, and 150.

2. The rAAV vector of claim 1, wherein the first nucleic acid segment encodes a first therapeutic molecule that comprises a neuropeptide selected from a myelin basic protein (MBP), a myelin oligodendrocyte glycoprotein (MOG), and a proteolipid protein (PLP).

3. The rAAV vector of claim 2, wherein the first nucleic acid segment is operably linked to a promoter that is capable of expressing the first therapeutic molecule in a mammalian liver cell.

4. The rAAV vector of claim 3, wherein the promoter is a hepatocyte-specific promoter.

5. The rAAV vector of claim 4, wherein the hepatocyte-specific promoter comprises an albumin promoter, a human $\alpha_1$-antitrypsin promoter, a transthyretin (TTR) promoter, a hepatic combinatorial bundle (HCB) promoter, or an apolipoprotein E (apoE) promoter.

6. The rAAV vector of claim 1, wherein the polynucleotide further comprises an enhancer, a post-transcriptional regulatory sequence, a polyadenylation signal, or any combination thereof, operably linked to the first nucleic acid segment.

7. The rAAV vector of claim 1, wherein the polynucleotide comprises AAV2 inverted terminal repeat sequences (ITRs).

8. The rAAV vector of claim 2, wherein the polynucleotide comprises a second nucleic acid sequence encoding a second therapeutic molecule.

9. The rAAV vector of claim 8, wherein:
   (a) the second therapeutic molecule is a MBP or a PLP if the first therapeutic molecule is MOG;
   (b) the second therapeutic molecule is a MBP or a MOG if the first therapeutic molecule is PLP; or
   (c) the second therapeutic molecule is a PLP or a MOG if the first therapeutic molecule is MBP.

10. The rAAV vector of claim 8, wherein the polynucleotide comprises a third nucleic acid segment encoding a third therapeutic molecule; wherein
    (a) the third therapeutic molecule is a MOG, if the first and second therapeutic molecules comprise a MBP and a PLP;
    (b) the third therapeutic molecule is a PLP, if the first and second therapeutic molecules comprises a MBP and a MOG; or
    (c) the third therapeutic molecule is a MBP, if the first and second therapeutic molecule comprises a MOG and a PLP.

11. The rAAV vector of claim 8, wherein the second nucleic acid segment encodes a polypeptide, a peptide, a ribozyme, an siRNA, an RNAi, an antisense oligonucleotide, an antisense polynucleotide, an antibody, an antigen binding fragment, or any combination thereof.

12. The rAAV nucleic acid vector of claim 11, wherein the second nucleic acid segment encodes a proteolipid protein, a myelin oligodendrocyte glycoprotein, a glycoprotein, a myelin-associated glycoprotein, a gliadin peptide, a glutenin, insulin, an islet-specific glucose-6-phosphatase catalytic subunit-related protein, a Preproinsulin, a glutamic decarboxylase, a tyrosine phosphatase like autoantigen, an insulinoma antigen-2, an Islet cell antigen, a thyroid stimulating hormone (TSH) receptor, a thyrotropin receptor, an Aggrecan, a CD4+ T cell epitope, a porin, or an acetylcholine receptor.

13. The rAAV vector of claim 1, wherein the rAAV vector is of serotype AAV1, AAV3, AAV4, AAV5, AAV6, AAV7, AAV8, AAV9, AAV10, AAV2-AAV3 hybrid, AAVrh.10, AAVrh.74, AAVhu.14, AAV3a/3b, AAVrh32.33, AAV-HSC15, AAV-HSC17, AAVhu.37, AAVrh.8, CHt-P6, AAV2.5, AAV6.2, AAV218, AAV-HSC15/17, AAVM41, AAV9.45, AAV6 (Y445F/Y731F), AAV2.5T, AAV-HAE1/2, AAV clone 32/83, AAVShHIO, AAV2 (Y→F), AAV8 (Y733F), AAV2.15, AAV2.4, AAVM41, or AAVr3.45; or a variant thereof.

14. A pharmaceutical composition for treating or ameliorating one or more symptoms of an autoimmune disease in a mammal, that comprises an effective amount of the rAAV vector of claim 1.

* * * * *

UNITED STATES PATENT AND TRADEMARK OFFICE
CERTIFICATE OF CORRECTION

| | | |
|---|---|---|
| PATENT NO. | : 12,297,444 B2 | Page 1 of 1 |
| APPLICATION NO. | : 17/229790 | |
| DATED | : May 13, 2025 | |
| INVENTOR(S) | : Brad E. Hoffman | |

It is certified that error appears in the above-identified patent and that said Letters Patent is hereby corrected as shown below:

In the Claims

In Claim 13, Column 296, Line 44, the text:
"AAV2.5, AAV6.2, AAV218,"
Should read:
--AAV2.5, AAV6.2, AAV2i8,--

Signed and Sealed this
Twenty-second Day of July, 2025

Coke Morgan Stewart
*Acting Director of the United States Patent and Trademark Office*